United States Patent
Trzoss et al.

(10) Patent No.: US 11,890,275 B2
(45) Date of Patent: Feb. 6, 2024

(54) THERAPEUTIC COMPOUNDS

(71) Applicant: CELGENE QUANTICEL RESEARCH, INC., San Diego, CA (US)

(72) Inventors: Lynnie Trzoss, San Diego, CA (US); Juan Manuel Betancort, San Diego, CA (US); Toufike Kanouni, Rancho Sante Fe, CA (US); Michael Brennan Wallace, San Diego, CA (US); Amogh Boloor, San Diego, CA (US)

(73) Assignee: Celgene Quanticel Research, Inc.

( * ) Notice: Subject to any disclaimer, the term of this patent is extended or adjusted under 35 U.S.C. 154(b) by 0 days.

(21) Appl. No.: 17/201,190

(22) Filed: Mar. 15, 2021

(65) Prior Publication Data

US 2021/0205284 A1    Jul. 8, 2021

Related U.S. Application Data

(60) Division of application No. 16/773,143, filed on Jan. 27, 2020, now Pat. No. 11,020,380, which is a continuation of application No. 15/956,434, filed on Apr. 18, 2018, now Pat. No. 10,617,680.

(60) Provisional application No. 62/486,894, filed on Apr. 18, 2017, provisional application No. 62/657,456, filed on Apr. 13, 2018.

(51) Int. Cl.

| C07D 413/04 | (2006.01) |
| A61K 31/4412 | (2006.01) |
| A61P 37/00 | (2006.01) |
| A61P 35/00 | (2006.01) |
| A61P 29/00 | (2006.01) |

(52) U.S. Cl.
CPC .......... *A61K 31/4412* (2013.01); *A61P 29/00* (2018.01); *A61P 35/00* (2018.01); *A61P 37/00* (2018.01)

(58) Field of Classification Search
CPC ........................... C07D 413/04; A61K 31/443
USPC ........................................ 546/271.4; 514/340
See application file for complete search history.

(56) References Cited

U.S. PATENT DOCUMENTS

| 5,847,218 | A | 12/1998 | Ohsawa et al. |
| 8,071,595 | B2 | 12/2011 | Ripka et al. |
| 8,809,372 | B2* | 8/2014 | Smith ................. C07D 417/14 546/256 |
| 9,034,900 | B2 | 5/2015 | Bennett et al. |
| 9,115,114 | B2 | 5/2015 | Bennett et al. |
| 9,598,372 | B2 | 3/2017 | Boloor |
| 9,670,221 | B2* | 6/2017 | Amans ................ C07D 519/00 |
| 10,202,360 | B2 | 2/2019 | Bennett et al. |
| 10,617,680 | B2* | 4/2020 | Trzoss ................ C07D 409/14 |
| 11,020,380 | B2 | 6/2021 | Trzoss et al. |
| 2005/0049274 | A1 | 3/2005 | Wall et al. |
| 2009/0054434 | A1 | 2/2009 | Hu et al. |
| 2010/0227846 | A1 | 9/2010 | Ito et al. |
| 2012/0309739 | A1 | 12/2012 | Bell et al. |
| 2013/0109652 | A1 | 5/2013 | Imogai et al. |
| 2014/0179648 | A1 | 6/2014 | Liu et al. |
| 2015/0111885 | A1 | 4/2015 | Bennett et al. |
| 2015/0183784 | A1 | 7/2015 | Bennett et al. |
| 2016/0016966 | A1 | 1/2016 | Amans et al. |
| 2017/0298040 | A1 | 10/2017 | Bennett et al. |
| 2018/0296543 | A1 | 10/2018 | Trzoss et al. |
| 2020/0163946 | A1 | 5/2020 | Trzoss et al. |

FOREIGN PATENT DOCUMENTS

| AR | 111479 A1 | 7/2019 |
| EP | 0 154 190 A1 | 9/1985 |
| EP | 1221444 | 7/2002 |
| EP | 1604988 | 12/2005 |
| EP | 1 896 434 B1 | 12/2008 |
| EP | 3445750 A1 | 2/2019 |
| EP | 3612522 A1 | 2/2020 |
| JP | 61-010557 A | 1/1986 |
| JP | 2007-123269 A | 5/2007 |
| JP | 2007-538035 A | 12/2007 |
| JP | 2009-507758 A | 2/2009 |
| JP | 2011-526282 A | 10/2011 |
| JP | 2012-515800 A | 7/2012 |
| JP | 2013-517244 A | 5/2013 |
| JP | 2014-122161 A | 7/2014 |
| JP | 2016-500661 A | 1/2016 |
| JP | 2016-507496 A | 3/2016 |
| JP | 2016-533397 A | 10/2016 |

(Continued)

OTHER PUBLICATIONS

European Search Report received for European Patent Application No. 17786389.1, dated Oct. 25, 2019, 9 pages.
International Preliminary Report on Patentability issued in International Application No. PCT/US2018/028097, dated Oct. 31, 2019, 27 pages.
Aurora Fine Chmicals, "5-[4-amino-6-(methylthio)-1,3,5-triazin-2-yl]-2(1H)-pyridinone", Database accession No. 1549330-12-2, XP002794784, Feb. 19, 2014, 1 page.
Li, et al., "Discovery of Highly Potent 2-Sulfonyl-Pyrimidinyl Derivatives for Apoptosis Inhibition and Ischemia Treatment", ACS Medicinal Chemistry Letters, vol. 8, No. 4, Mar. 2017, pp. 407-412.
Mele, et al., "BET bromodomain inhibition suppresses TH 17—mediated pathology", Journal of Experimental Medicine, vol. 210, No. 11, Oct. 21, 2013, pp. 2181-2190.
Mu, et al., "Understanding DP receptor antagonism using a CoMSIA approach", Bioorganic & Medicinal Chemistry Letters 21, vol. 21, Issue 1, Jan. 2011, pp. 66-75.

(Continued)

*Primary Examiner* — Charanjit Aulakh
(74) *Attorney, Agent, or Firm* — Wiley Rein LLP

(57) ABSTRACT

The present embodiments relate to substituted heterocyclic derivative therapeutic compounds, compositions comprising said compounds, and the use of said compounds and compositions for epigenetic regulation by inhibition of bromodomain-mediated recognition of acetyl lysine regions of proteins, such as histones. Said compositions and methods are useful for the treatment of diseases mediated by aberrant cell signalling, such as inflammatory disorders, cancer and neoplastic disease. Particular compounds described herein exhibit selective inhibitory activity against CBP compared with BRD4.

44 Claims, No Drawings

(56) References Cited

FOREIGN PATENT DOCUMENTS

| | | |
|---|---|---|
| JP | 2019-513804 A | 5/2019 |
| JP | 2020-516672 A | 6/2020 |
| TW | 201739744 A | 11/2017 |
| TW | 201841900 A | 12/2018 |
| WO | 96/36617 | 11/1996 |
| WO | 97/01551 A1 | 1/1997 |
| WO | 02/078626 A2 | 10/2002 |
| WO | 2005095384 | 10/2005 |
| WO | 2006/137465 A1 | 12/2006 |
| WO | 2007/026950 A1 | 3/2007 |
| WO | 2007/040208 A1 | 4/2007 |
| WO | 2007/139150 A1 | 12/2007 |
| WO | 2008/039882 A1 | 4/2008 |
| WO | 2008/150446 A1 | 12/2008 |
| WO | 2009/028543 A1 | 3/2009 |
| WO | 2009/158393 A1 | 12/2009 |
| WO | 2010/085805 A1 | 7/2010 |
| WO | 2011/086085 A1 | 7/2011 |
| WO | 2012101654 A3 | 1/2012 |
| WO | 2012/020786 A1 | 2/2012 |
| WO | 2012/101654 A2 | 8/2012 |
| WO | 2013/180183 A1 | 12/2013 |
| WO | 2013/188381 A1 | 12/2013 |
| WO | 2013180183 A1 | 12/2013 |
| WO | 2014/055548 A1 | 4/2014 |
| WO | 2014/096965 A2 | 6/2014 |
| WO | 2014/157569 A1 | 10/2014 |
| WO | 2014/165143 A1 | 10/2014 |
| WO | 2014/177524 A1 | 11/2014 |
| WO | 2014177524 A1 | 11/2014 |
| WO | 2015/058160 A1 | 4/2015 |
| WO | 2015/104653 A1 | 7/2015 |
| WO | 2015/153683 A1 | 10/2015 |
| WO | 2015/187089 A1 | 12/2015 |
| WO | 2016/044662 A1 | 3/2016 |
| WO | 2016/047678 A1 | 3/2016 |
| WO | 2016/146738 A1 | 9/2016 |
| WO | 2016/168682 A2 | 10/2016 |
| WO | 2017/009798 A1 | 1/2017 |
| WO | WO 2017-009806 A1 * | 1/2017 | ........... C07D 413/14 |
| WO | 2017/026516 A1 | 2/2017 |
| WO | 2017/053243 A1 | 3/2017 |
| WO | 2017/184462 A1 | 10/2017 |
| WO | 2018/014802 A1 | 1/2018 |
| WO | 2018/195155 A1 | 10/2018 |

OTHER PUBLICATIONS

Ukrorgsyntez Ltd, "6-[4-amino-6-(methylthio)-I,3,5-triazin-2-yl]-3(2H)-pyridazinone", Database accession No. 1696972-65-2, XP002794783, May 3, 2015, 1 page.

International Search Report and Written Opinion, dated Jul. 17, 2018, by International Bureau of WIPO in related to International Patent Application No. PCT/US2018/28097.

PU BC HEM CID 50966644, Mar. 19, 2011, pp. 1-7 7 (online), [retrieved on Jun. 5, 2018], Retrieved from the Internet <URL:http://pubcl1em.ncbi.nlm.nih.gov/compound/50966644#section=Top>; p. 2.

Pubchem CID 2811805, May 28, 2009, pp. 1-7 [online] retrieved from the internet <: http://pubchem.ncbi.nih.gov/compound/28811805#section=Top>; p. 2.

Pubchem CID 20370616, Dec. 5, 2007, pp. 1-7 [online] [retrieved on Jun. 051, 2018 Retrieved from the Internet <: http:/pubchem.ncbi.nih gov/compound/20370616#section=Top>; p. 2.

Pubchem CID 68049058, Nov. 30, 2012, pp. 1-7 [online] [retrieved on Jun. 5, 2018] retrieved from the internet <: http://pubchem.ncbi.nih.gov/compound/68049058#section=Top>; p. 3.

Pubchem CID 90329854, Feb. 13, 2015, pp. 1-6 [online] [Retrieved on Jun. 5, 2018]; retrieved from the internet <: http :!/pubchem.ncbi.nih.gov/compound/90329854>; p. 2.

Hay, Da et al, "Discovery and Optimization of Small-Molecule ligands for the CBP/p300 Bromodomains", Journal of the American Chemical Society, vol. 136, Jun. 19, 2014, pp. 9308-9319; abstract.

Chaikuad, A et al., "Structure-Based Identification of Inhibitory Fragments Targeting the p300/CBP-Associated Factor Bromodomain", Journal of Medicinal Chemistry,vol. 59, Jan. 5, 2016, pp. 1648-1653, p. 1648, col. 1, paragraph 2; p. 1652, col. paragraph 1.

Invitation pursuant to Rule 63(1) EPC for European Patent Application No. 17786389.1, mailed Jan. 18, 2021.

Hudkins, et al., 4-Phenoxypiperidine pyridazin-3-one histamine H3 receptor inverse agonists demonstrating potent and robust wake promoting activity, Biorganic & Medicinal Chemistry Letters 2012, vol. 22, No. 4 , pp. 1504-1509, XP028398203.

Extended European Search Report received for European Patent Application No. 18787518.2, dated Jun. 7, 2021, 7 pages.

International Search Report and Written Opinion issued in International Application No. PCT/US2017/027815, dated Jul. 20, 2017, 9 pages.

Hudkins et al., 4-Phenoxypiperidine pyridazin-3-one histamine H3 receptor inverse agonists demonstrating potent and robust wake promoting activity, Biorganic & Medicinal Chemistry Letters, Jan. 13, 2021.

Chaikuad, Apirat et al., Structure-Based Identification of Inhibitory Fragments Targeting the p300 CBP Associated Factor Bromodomain, Journal of Medicinal Chemistry, Jan. 5, 2016.

Office Action received for Japanese Patent Application Serial No. 2019556274 dated Mar. 2, 2022, 16 pages (Including English Translation).

Vidler, et al., "Discovery of Novel Small-Molecule Inhibitors of BRD4 Using Structure-Based Virtual Screening", Journal of Medicinal Chemistry, 2013, vol. 56, No. 20, pp. 8073-8088, 2013.

PUBCHEM. 5-(5-Methyl-1H-Pyrazol-4-YI)-2H-Isoquinolin-1-One. Jun. 10, 2016, pp. 1-6 [online], 40 [retrieved on Jun. 5, 2018]. Retrieved from the Internet <URL: https://pubchem.ncbi.nlm.nih.gov/compound/119085399#section=IUPAC-Name>; p. 2.

Office Action received for Japanese Patent Application No. 2018-554572, dated Mar. 29, 2021 (11 Pages (6 pages of English Translation and 5 pages of Official Copy Only).

1 Office Action received for Taiwan Patent Application Serial No. 107113171 dated Apr. 6, 2022 6 pages.

European Office Action dated Jan. 5, 2023 received in European Patent Application No. 18 787 518.2-1110 —three pages.

Hamaguchi, et al., "Addressing Phototoxicity Observed in a Novel Series of Biaryl Derivatives: Discovery of Potent, Selective and Orally Active Phosphodiesterase 10A Inhibitor ASP9436", Bioorganic & Medicinal Chemistry, vol. 23, 2015, pp. 3351-3367.

* cited by examiner

THERAPEUTIC COMPOUNDS

CROSS REFERENCE

This application is a divisional application of U.S. application Ser. No. 16/773,143, filed Jan. 27, 2020, which is a continuation of U.S. application Ser. No. 15/956,434 (now U.S. Pat. No. 10,617,680), filed Apr. 18, 2018, which claims the benefit of U.S. Provisional Application No. 62/486,894, filed Apr. 18, 2017, and U.S. Provisional Application No. 62/657,456, filed Apr. 13, 2018, the contents of which are hereby incorporated by reference in their entireties.

FIELD

The embodiments described herein provide compositions, formulations, and methods for treating cancers, neoplastic diseases, inflammatory or immune disorders.

BACKGROUND

A need exists for effective treatments of diseases and disorders mediated by aberrant histone deacetylation, such as inflammatory disorders, cancers, and neoplastic diseases.

BRIEF SUMMARY OF THE INVENTION

Provided herein are substituted heterocyclic derivative therapeutic compounds and pharmaceutical compositions comprising said compounds. The substituted heterocyclic derivative compounds described herein are based upon pyridones and related heterocyclic structures, generally, these pyridones are substituted at the 4- and 5-positions. In particular, the pyridone is substituted at the 5-position with an optionally substituted N-containing heteroaryl, such as oxazole, pyrazole, or triazole.

The subject compounds and compositions are useful for epigenetic regulation by inhibition of bromodomain-mediated recognition of acetyl lysine regions of proteins, such as histones, associated with aberrant cell signaling. More specifically, at least some of the embodiments herein provide for selective inhibition of cyclic AMP-responsive element-binding protein (CREB) binding protine (CBP or CREBBP) activity as compared with inhibition of bromain domain 4 (BRD4) activity. Furthermore, the subject compounds and compositions are useful for the treatment of diseases mediated by aberrant cell signalling, such as inflammatory disorders, and cancer, such as prostate cancer, breast cancer, bladder cancer, lung cancer, melanoma, and the like.

At least one embodiment provides a compound having the structure of Formula I:

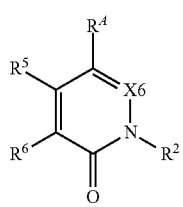

Formula I wherein the compound of Formula I is optionally a pharmaceutically acceptable salt thereof, and wherein:
X6 is N or $CR^7$, wherein $R^7$ is hydrogen, halogen, alkyl, or alkoxy;

$R^2$ is hydrogen, alkyl, aryl, aralkyl, cycloalkyl, cycloalkylalkyl, heterocyclyl, heterocyclylalkyl, heteroaryl, or heteroarylalkyl;

$R^5$ is hydrogen, halogen, —CN, —$N(R^{22})_2$, —$NH(R^{22})$, —$N(R^{22})SO_2R^{21}$, —$N(R^{22})SO_2N(R^{22})_2$, —$N(R^{22})CO(R^{22})$, —$N(R^{22})CO_2R^{21}$, —$N(R^{22})CON(R^{22})_2$, —$OC(O)N(R^{22})_2$, —$C(O)N(R^{22})_2$, —OW, —NW, —SW, —$SO_2W$, or optionally substituted alkyl, aryl, aralkyl, heteroaryl, heteroarylalkyl, cycloalkyl, cycloalkylalkyl, heterocyclyl, or heterocyclylalkyl, wherein
  W is at least one hydrogen, —$N(R^{22})_2$, or optionally substituted alkyl, aryl, aralkyl, cycloalkyl, cycloalkylalkyl, heterocyclyl, heterocyclylalkyl, heteroaryl or heteroarylalkyl;

$R^6$ is hydrogen, halogen, —CN, alkyl, cycloalkyl, cycloalkylalkyl, aryl, aralkyl, heteroaryl, heteroarylalkyl, heterocyclyl, heterocyclylalkyl, —$OR^{22}$, or —$N(R^{22})_2$;

or $R^5$ and $R^6$ taken together form an optionally substituted 5- or 6-membered ring;

$R^4$ is optionally substituted N-containing heteroaryl;

wherein each $R^{22}$ is independently selected from hydrogen, alkyl, cycloalkyl, cycloalkylalkyl, aryl, aralkyl, heterocyclyl, heterocyclylalkyl, heteroaryl, or heteroarylalkyl.

In at least one embodiment, X6 is CH. In at least one embodiment, X6 is CF. In at least one embodiment, $R^2$ is methyl. In at least one embodiment, $R^6$ is hydrogen.

In at least one embodiment, $R^4$ is an optionally substituted five-membered N-containing heteroaryl. In at least one embodiment, $R^4$ is an optionally substituted pyrazole. In at least one embodiment, $R^4$ is an optionally substituted piperidinylpyrazole. In at least one embodiment, $R^4$ is cyclopentylpyrazole. In at least one embodiment, $R^4$ is an optionally substituted imidazole. In at least one embodiment, $R^4$ is an optionally substituted oxazole. In at least one embodiment, $R^4$ is an optionally substituted isoxazole. In at least one embodiment, $R^4$ is an optionally substituted triazole.

In at least one embodiment, $R^4$ is selected from:

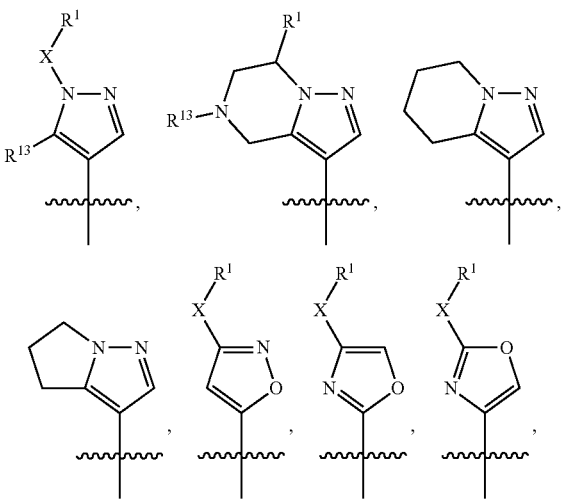

-continued

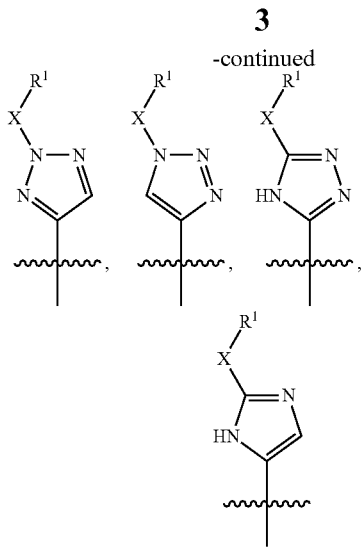

wherein X is a bond, CH$_2$, CHR, or CRR';
  wherein R and R' are independently halogen, halide or alkyl;
R$^1$ is hydrogen, alkyl, aryl, aralkyl, alkoxy, cycloalkyl, cycloalkylalkyl, heterocyclyl, heterocyclylalkyl, heteroaryl, or heteroarylalkyl; and
R$^{13}$ is Y—Z, in which
  Y is a bond or CH(C$_1$-C$_4$alkyl) and
  Z is hydrogen, halogen, alkyl, aryl, CF$_2$, CO$_2$R$^{22}$, N(R$^{22}$), or N(R$^{22}$)CO(R$^{22}$), wherein R$^{22}$ is hydrogen or alkyl.
In some embodiments, R$^A$ is

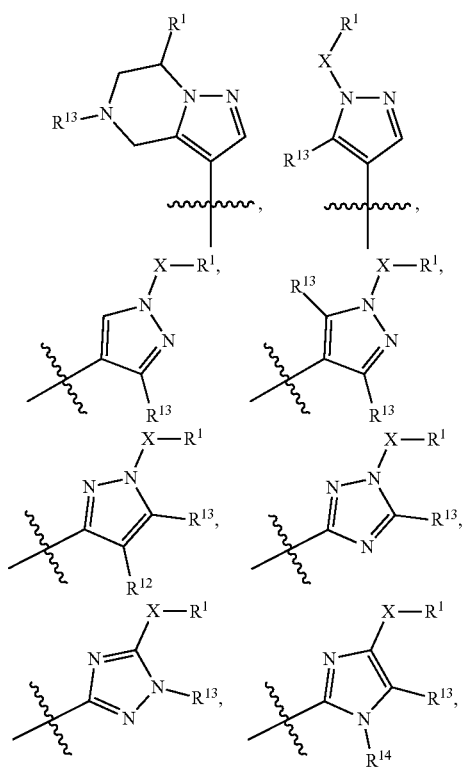

-continued

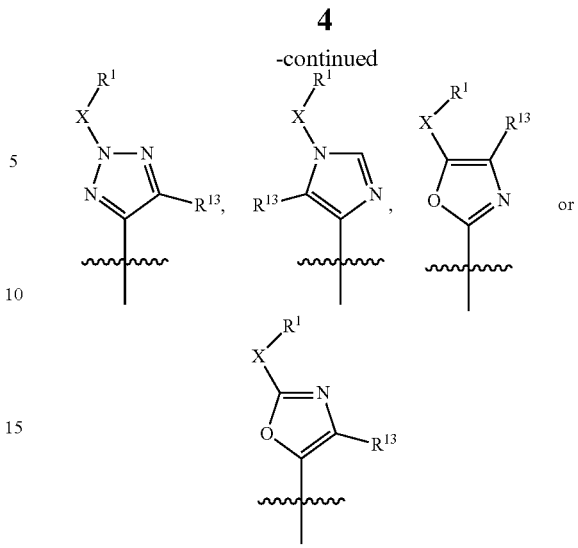

wherein
X is a bond, CH$_2$, CHR, or CRR'; in which
R and R' are independently halogen, halide, alkyl, cycloalkyl, cycloalkylalkyl, aryl, aralkyl, heterocyclyl, heterocyclylalkyl, heteroaryl, heteroarylalkyl, —SO$_2$R$^{21}$, —N(R$^{22}$)SO$_2$R$^{21}$;
R$^1$ is hydrogen, alkyl, aryl, aralkyl, alkoxy, cycloalkyl, cycloalkylalkyl, heterocyclyl, heterocyclylalkyl, heteroaryl, or heteroarylalkyl;
R$^{12}$ is hydrogen, halogen, —CN, alkyl, cycloalkyl, or alkoxy;
each R$^{13}$ is independently Y—Z, in which
  Y is a bond or CH(C$_1$-C$_4$alkyl) and
  Z is hydrogen, halogen, alkyl, aryl, —CF$_2$, —NO$_2$, —CO$_2$R$^{22}$, —N(R$^{22}$), or —N(R$^{22}$)CO(R$^{22}$), —SO$_2$R$^{21}$, —N(R$^{22}$)SO$_2$R$^{21}$, —SO$_2$N(R$^{22}$)$_2$, —N(R$^{22}$)SO$_2$N(R$^{22}$)$_2$, —CON(R$^{22}$)$_2$, —N(R$^{22}$)CO$_2$R$^{21}$, —N(R$^{22}$)CON(R$^{22}$)$_2$, —OC(O)N(R$^{22}$)$_2$, —OSO$_2$N(R$^{22}$)$_2$, or —N(R$^{22}$)SO$_3$R$^{21}$; wherein
    each R$^{21}$ is independently selected from alkyl, cycloalkyl, cycloalkylalkyl, aryl, aralkyl, heterocyclyl, heterocyclylalkyl, heteroaryl, or heteroarylalkyl; and
    each R$^{22}$ is independently selected from hydrogen, alkyl, cycloalkyl, cycloalkylalkyl, aryl, aralkyl, heterocyclyl, heterocyclylalkyl, heteroaryl, or heteroarylalkyl; and
R$^{14}$ is hydrogen, —CN, alkyl, cycloalkyl, or alkoxy.
In at least one embodiment, R$^A$ is a heteroaryl selected from

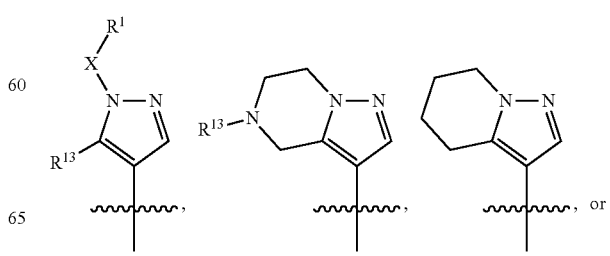

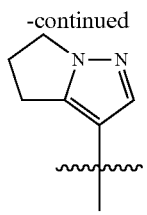

wherein X, $R^1$, and $R^{13}$ are as described above.

Another aspect of the present embodiments provides a compound of Formula I that exhibits selective inhibition of CBP as compared with BRD4. In one embodiment, the activity of CBP is inhibiting by contacting it with a compound of Formula I.

At least one embodiment provides a pharmaceutical composition comprising a compound of Formula I and a pharmaceutically acceptable excipient.

Another aspect of the embodiments described herein relates to a method of treating an inflammatory or immune disorder in a patient in need thereof, comprising administering to the patient a compound of Formula I or a pharmaceutic composition comprising Formula I.

Another aspect of the embodiments described herein relates to a method of treating a neoplastic disease or cancer in a patient in need thereof, comprising administering to the patient a compound of Formula I or a pharmaceutical composition comprising Formula I.

DETAILED DESCRIPTION

All patents and other publications identified are expressly incorporated herein by reference for the purpose of describing and disclosing, for example, the methodologies described in such publications that might be used in connection with the present embodiments. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents are based on the information available to the applicants and does not constitute any admission as to the correctness of the dates or contents of these documents.

As used herein and in the claims, the singular forms include the plural reference and vice versa unless the context clearly indicates otherwise. Throughout this specification, unless otherwise indicated, "comprise," "comprises" and "comprising" are used inclusively rather than exclusively, so that a stated integer or group of integers may include one or more other non-stated integers or groups of integers. The term "or" is inclusive unless modified, for example, by "either." When ranges are used herein for physical properties, such as molecular weight, or chemical properties, such as chemical formulae, all combinations and sub-combinations of ranges and specific embodiments therein are intended to be included. Other than in the operating examples, or where otherwise indicated, all numbers expressing quantities of ingredients or reaction conditions used herein should be understood as modified in all instances by the term "about." The term "about" when referring to a number or a numerical range means that the number or numerical range referred to is an approximation within experimental variability (or within statistical experimental error), and thus the number or numerical range may vary between 1% and 15% of the stated number or numerical range, as will be readily recognized by context.

Unless otherwise defined, scientific and technical terms used in connection with the formulations described herein shall have the meanings that are commonly understood by those of ordinary skill in the art. The terminology used herein is for the purpose of describing particular embodiments only, and is not intended to limit the scope of the present embodiments, which is defined solely by the claims.

Definitions

As used herein, "alkyl" generally refers to a straight or branched hydrocarbon chain consisting solely of carbon and hydrogen atoms, fully saturated, containing no unsaturation double- or triple-bonded carbons, having from one to fifteen carbon atoms (e.g., $C_1$-$C_{15}$ alkyl). In certain embodiments, an alkyl comprises two carbon atoms (e.g., $C_2$alkyl), e.g., ethyl. In certain embodiments, an alkyl comprises one carbon atom, e.g., methyl. In other embodiments, the alkyl group is selected from methyl, ethyl, 1-propyl (n-propyl), 1-methylethyl (iso-propyl), 1-butyl (n-butyl), 1-methylpropyl (sec-butyl), 2-methylpropyl (iso-butyl), 1,1-dimethylethyl (tert-butyl), 1-pentyl (n-pentyl). An alkyl group is attached to the rest of the molecule by single bonds. Unless stated otherwise, an alkyl group is optionally substituted with at least one substituent, such as halogen, hydroxy, cyano, nitro, oxo, thioxo, imino, oximo, —$OR^a$, —$SR^a$, —OC(O)—$R^a$, —$N(R^a)_2$, —C(O)$R^a$, —C(O)O$R^a$, —C(O)N($R^a)_2$, —N($R^a$)C(O)O$R^a$, —OC(O)—N($R^a)_2$, —N($R^a$)C(O)$R^a$, —N($R^a$)S(O)$_t R^a$ (where t is 1 or 2), —S(O)$_t$O$R^a$ (where t is 1 or 2), —S(O)$_t R^a$ (where t is 1 or 2) and —S(O)$_t$N($R^a)_2$ (where t is 1 or 2) where each $R^a$ is independently hydrogen, alkyl, fluoroalkyl, carbocyclyl, carbocyclylalkyl, aryl, aralkyl, heterocyclyl, heterocyclylalkyl, heteroaryl, or heteroarylalkyl, and wherein $R^a$ is itself optionally substituted as described above. In some embodiments, $R^a$ is substituted with, for example, halogen, hydroxy, methoxy, or trifluoromethyl. These and other substituents are known in the art. See, e.g., WO 2014089364, WO 2014100463, WO 2014100818, WO 2014164708, WO 2014151945, WO 2014151106, WO 2015058160, WO 2015089192, WO 2015168466, WO 2015200709, WO 2015200843, WO 2016004105, WO 2016003917, WO 2016037005, WO 2016044342, WO 2016044138, WO 2016044429, WO 2016168682, WO 2016172618.

"Alkoxy" refers generally to a moiety bonded through an oxygen atom of the formula —O-alkyl, where alkyl is an alkyl as defined above; and unless stated otherwise, a moiety comprising an alkoxy group is optionally substituted as described for alkyl.

"Alkenyl" generally refers to a straight or branched hydrocarbon chain group consisting solely of carbon and hydrogen atoms, containing at least one carbon-carbon double bond and having from two to twelve carbon atoms. In certain embodiments, an alkenyl comprises two to eight carbon atoms. In other embodiments, an alkenyl comprises two to four carbon atoms. The alkenyl is attached to the rest of the molecule by a single bond, for example, ethenyl (i.e., vinyl), prop-1-enyl (i.e., allyl), but-1-enyl, pent-1-enyl, penta-1,4-dienyl, and the like. Unless stated otherwise, a moiety comprising an alkenyl group is optionally substituted as described for alkyl.

"Alkynyl" refers to a straight or branched hydrocarbon chain radical group consisting solely of carbon and hydrogen atoms, containing at least one carbon-carbon triple bond, having from two to twelve carbon atoms. In certain embodiments, an alkynyl comprises two to eight carbon atoms. In other embodiments, an alkynyl has two to four carbon atoms. The alkynyl is attached to the rest of the molecule by a single bond, for example, ethynyl, propynyl, butynyl, pentynyl, hexynyl, and the like. Unless stated otherwise, a group containing an alkynyl group is optionally substituted as described for alkyl.

"Alkylene chain" "alkylene linker" or "alkyl linker" refers to a straight or branched divalent hydrocarbon chain linking the rest of the molecule to a radical group, consisting solely of carbon and hydrogen, containing no unsaturation and having from one to twelve carbon atoms. Reference to alkyl may refer to such chains or linkers, as indicated by context. Similarly, "alkynylene chain" refers to a straight or branched divalent hydrocarbon chain linking the rest of the molecule to a radical group, consisting solely of carbon and hydrogen, containing at least one carbon-carbon triple bond and having from two to twelve carbon atoms. These hydrocarbon chains are optionally substituted as described for alkyl.

"Aryl" refers to an aromatic (unsaturated) monocyclic or multicyclic hydrocarbon ring system where at least one of the rings in the ring system is fully unsaturated, i.e., it contains a cyclic, delocalized (4n+2) π-electron system in accordance with the Hückel theory. Generally, the aromatic monocyclic or multicyclic hydrocarbon ring system contains only hydrogen and carbon from five to eighteen carbon atoms. Example aryl groups include benzene, fluorene, indane, indene, tetralin and naphthalene. Unless stated otherwise, the term "aryl," the prefix "ar-" (such as in "aralkyl"), or "Phe" in a structure, includes aryl radicals optionally substituted by one or more substituents independently selected from halo, cyano, nitro; or optionally substituted alkyl, alkenyl, alkynyl, fluoroalkyl, aryl, aralkyl, aralkenyl, aralkynyl, carbocyclyl, carbocyclylalkyl, heterocyclyl, heterocyclylalkyl, heteroaryl or heteroarylalkyl; or —$R^b$—$OR^a$, —$R^b$—OC(O)—$R^a$, —$R^b$—OC(O)—$OR^a$, —$R^b$—OC(O)—N($R^a$)$_2$, —$R^b$—N($R^a$)$_2$, —$R^b$—C(O)$R^a$, —$R^b$—C(O)$OR^a$, —$R^b$—C(O)N($R^a$)$_2$, —$R^b$—O—$R^c$—C(O)N($R^a$)$_2$, —$R^b$—N($R^a$)C(O)$OR^a$, —$R^b$—N($R^a$)C(O)$R^a$, —$R^b$—N($R^a$)S(O)$_t$$R^a$, —$R^b$—S(O)$_t$$R^a$, —$R^b$—S(O)$_t$$OR^a$, or —$R^b$—S(O)$_t$N($R^a$)$_2$, wherein t is 1 or 2, wherein each $R^a$ is independently hydrogen or alkyl, fluoroalkyl, cycloalkyl, cycloalkylalkyl, aryl, aralkyl, heterocyclyl, heterocyclylalkyl, heteroaryl, or heteroarylalkyl, each of which is optionally substituted with halogen, hydroxy, methoxy, or trifluoromethyl, wherein each $R^b$ is independently a bond or a straight or branched alkyl or alkenylene chain, and wherein $R^c$ is a straight or branched alkyl or alkenylene chain. These and other substituents are known in the art. See, e.g., WO 2014089364, WO 2014100463, WO 2014100818, WO 2014164708, WO 2014151945, WO 2014151106, WO 2015058160, WO 2015089192, WO 2015168466, WO 2015200709, WO 2015200843, WO 2016004105, WO 2016003917, WO 2016037005, WO 2016044342, WO 2016044138, WO 2016044429, WO 2016168682, WO 2016172618.

"Aralkyl" refers generally to a moiety of the formula —$R^c$-aryl where $R^c$ is an alkyl, alkyl chain, or alkylene chain, and $R^c$ may also refer to alkenylene chain or alkynylene chain unless the latter are specified or clear by context. The alkyl chain part of the aralkyl moiety is optionally substituted as described above for an alkyl. The aryl part of the aralkyl radical is optionally substituted as described above for an aryl group.

"Aralkoxy" refers to a aralkyl group bonded through an oxygen atom. The aryl or alkyl part of the aralkoxyl group is optionally substituted as described above for an aryl or alkyl group.

"Carbocyclyl" refers to a stable non-aromatic (saturated) monocyclic, bicyclic, or polycyclic hydrocarbon group consisting solely of carbon and hydrogen atoms, which generally includes fused or bridged ring systems, having from three to fifteen carbon atoms. In certain embodiments, a carbocyclyl comprises three to ten carbon atoms. In other embodiments, a carbocyclyl comprises three to seven carbon atoms. The carbocyclyl is attached to the rest of the molecule by single bond(s). A carbocyclyl group may be fully saturated or partially saturated. A fully saturated carbocyclyl group may also refer to a "cycloalkyl." Example monocyclic cycloalkyls include cyclopropyl, cyclobutyl, cyclopentyl, cyclohexyl, cycloheptyl, and cyclooctyl. An unsaturated carbocyclyl may also refer to a "cycloalkenyl." Example monocyclic cycloalkenyls include cyclopentenyl, cyclohexenyl, cycloheptenyl, and cyclooctenyl. Polycyclic carbocyclyls include, for example, adamantyl, norbornyl (i.e., bicyclo[2.2.1]heptanyl), norbornenyl, decalinyl, 7,7-dimethylbicyclo[2.2.1]-heptanyl, and the like. Unless otherwise stated, the term "carbocyclyl" includes carbocyclyls that are optionally substituted by one or more substituents independently selected, for example, as described above for aryl.

"Carbocyclylalkyl" refers to a group of the formula —$R^c$-carbocyclyl, wherein $R^c$ is an alkyl chain. The carbocyclyl is optionally substituted as described above for aryl, and the alkyl is optionally substituted as described for alky. Similarly, carbocyclylalkynyl" refers to a group of the formula —$R^c$-carbocyclyl (where $R^c$ is an alkynylene chain), optionally substituted, as defined above. In some embodiments the carbocyclyl group is a cycloalkyl group, in which the alkynylene chain part of the carbocyclylalkynyl is optionally substituted as defined above for an alkyl chain.

"Carbocyclylalkoxy" refers to a group bonded through an oxygen atom, having the formula —O—$R^c$-carbocyclyl where $R^c$ is an alkyl chain, optionally substituted, as defined for carbocyclyl and alkyl.

As used herein, "carboxylic acid bioisostere" refers to a functional group or moiety that exhibits similar physical, biological and/or chemical properties as a carboxylic acid moiety. Examples of carboxylic acid bioisosteres include, but are not limited to:

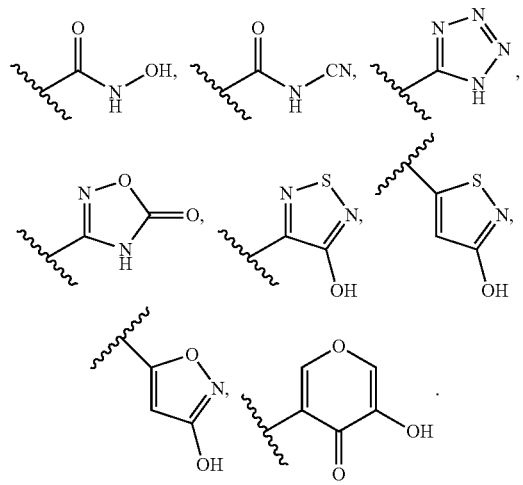

"Halo" or "halogen" refers to bromo, chloro, fluoro, or iodo substituents. "Halide" refers to a binary compound of which one part is a halogen atom and the other part is an element or radical that is less electronegative (or more electropositive) than the halogen, such as fluoride, chloride, bromide, or iodide.

"Fluoroalkyl" refers to an alkyl substituted with one or more fluoro substituents, as defined above, for example, trifluoromethyl, difluoromethyl, fluoromethyl, 2,2,2-trifluoroethyl, 1-fluoromethyl-2-fluoroethyl, and the like. The alkyl part of the fluoroalkyl may be optionally substituted as defined above for an alkyl group.

"Heterocyclyl" refers to a stable three- to eighteen-membered non-aromatic ring group that comprises, generally, two to twelve carbon atoms and one to six heteroatoms selected from nitrogen, oxygen and sulfur. Unless stated otherwise, the heterocyclyl radical is a monocyclic, bicyclic, tricyclic, or tetracyclic ring system, and may include fused or bridged ring systems. The heteroatoms in the heterocyclyl radical may be optionally oxidized. One or more nitrogen atoms, if present, are optionally quaternized. A heterocyclyl is typically fully saturated. A heterocyclyl group may be attached to the rest of the molecule through any atom of the ring(s), or by another atom or group. Examples heterocyclyl groups include azocainyl, azonanyl, aziridinyl, azaspironon-enonyl, azetidinlyl, thienyl[1,3]dithianyl, 1,4-dioxanyl, hydantionyl, imidazolidinyl, morpholinyl, octahydroindolyl, octahydroisoindolyl, 2-oxopiperidinyl, piperidinyl, 2-oxopyrrolidinyl, oxapanenyl, 1-oxaspiro[4,5]decanyl, 1,6-dioxaspiro[3,4]octanyl, 1,4-dioxa-7-azaspiro[4.4]nonanyl, 2-oxa-7-azaspiro[3,5]nonanyl, 2,9-diazaspiro[5,5]undecan-1-one, oxetanyl, 1-oxaspiro[4,4]nonan-2onyl, 1,3,8-trazaspiro[4,5]decan-4-one, 1,4-dithia-7-azaspiro[4,4]nonane, oxathiolanyl, oxazolidonyl, piperazinyl, 4-piperidonyl, pyrrolidinyl, pyrrolizidinyl, decahydroquinolinyl, decahydroisoquinolinyl, succinimidyl, sulfolanyl, thietanyl, thiazolidinyl, tetrahydrofuryl, tetrahydropyranyl, tetrahydrothiophenenyl, tetrafuranyl, tetrahydropyranyl, thiomorpholinyl, dioxothiomorpholinyl, 1-oxothiomorpholinyl, thiepinyl, thiamorpholinyl, thiazolidinedionyl, thicanyl, or 1,3,5 trithianyl. Unless stated otherwise, the term "heterocyclyl" includes optionally substituted heterocyclyls, with substituents, for example, as described for aryl.

"N-heterocyclyl" or "N-attached heterocyclyl" refers to a heterocyclyl containing at least one nitrogen (N-containing) in which the point of attachment of the heterocyclyl radical to the rest of the molecule is through a nitrogen atom in the heterocyclyl radical. A N-heterocyclyl is optionally substituted as described herein. Examples of N-heterocyclyls include 1-morpholinyl, 1-piperidinyl, 1-piperazinyl, 1-pyrrolidinyl, pyrazolyl, pyrazolidinyl, pyrinodyl, pyrrolyl, morpholinyl, imidazolinyl, and imidazolidinyl.

"C-heterocyclyl" or "C-attached heterocyclyl" refers to a heterocyclyl containing at least one heteroatom in which the point of attachment of the heterocyclyl to the rest of the molecule is through a carbon atom in the heterocyclyl radical. A C-heterocyclyl radical is optionally substituted as described herein. Examples of C-heterocyclyls include 2-morpholinyl, 2- or 3- or 4-piperidinyl, 2-piperazinyl, 2- or 3-pyrrolidinyl, and the like.

"Heterocyclylalkyl" refers to group of the formula —$R^c$-heterocyclyl where $R^c$ is an alkyl chain as defined above. If the heterocyclyl is a nitrogen-containing heterocyclyl, the heterocyclyl is optionally attached to the alkyl radical at the nitrogen atom. The alkyl chain of the heterocyclylalkyl and the heterocyclyl part of the heterocyclylalkyl group may each be optionally substituted as defined above.

"Heterocyclylalkoxy" refers to a group bonded through an oxygen atom of the formula —O—$R^c$-heterocyclyl where $R^c$ is an alkyl chain as defined above. If the heterocyclyl is a nitrogen-containing heterocyclyl, the heterocyclyl is optionally attached to the alkyl at the nitrogen atom. The alkyl chain of the heterocyclylalkoxy is optionally substituted as defined above for an alky chain; and the heterocyclyl part of the heterocyclylalkoxy is optionally substituted as defined above for a heterocyclyl group.

"Heteroaryl" refers to a moiety derived from a three- to eighteen-membered aromatic ring that generally comprises two to seventeen carbon atoms and from one to six heteroatoms selected from nitrogen, oxygen and sulfur, wherein at least one of the rings in the ring system is fully unsaturated, i.e., it contains a cyclic, delocalized (4n+2) π-electron system in accordance with the Hückel theory. The heteroaryl may be a monocyclic, bicyclic, tricyclic or tetracyclic ring system, and includes fused or bridged ring systems. The heteroatom(s) in the heteroaryl group is optionally oxidized. One or more nitrogen atoms, if present, are optionally quaternized. The heteroaryl can be attached to the rest of the molecule through any atom of the ring(s). Unless stated otherwise, heteroaryls are optionally substituted with one or more substituents as described, for example, for aryl.

Examples of heteroaryls include azepinyl, acridinyl, benzimidazolyl, benzindolyl, 1,3-benzodioxolyl, benzofuranyl, benzooxazolyl, benzo[d]thiazolyl, benzothiadiazolyl, benzo[b][1,4]dioxepinyl, benzo[b][1,4]oxazinyl, 1,4-benzodioxanyl, benzonaphthofuranyl, benzoxazolyl, benzodioxolyl, benzodioxinyl, benzopyranyl, benzopyranonyl, benzofuranyl, benzofuranonyl, benzothienyl (benzothiophenyl), benzothieno[3,2-d]pyrimidinyl, benzotriazolyl, benzo[4,6]imidazo[1,2-a]-pyridinyl, carbazolyl, cinnolinyl, cyclopenta[d]pyrimidinyl, 6,7-dihydro-5H-cyclopenta[4,5]thieno-[2,3-d]pyrimidinyl, 5,6-dihydrobenzo[h]quinazolinyl, 5,6-dihydrobenzo[h]cinnolinyl, 6,7-dihydro-5H-benzo[6,7]cyclohepta[1,2-c]pyridazinyl, dibenzofuranyl, dibenzothiophenyl, furanyl, furanonyl, furo[3,2-c]pyridinyl, 5,6,7,8,9,10-hexa-hydrocycloocta[d]pyrimidinyl, 5,6,7,8,9, 10-hexahydrocyclo-octa[d]pyridazinyl, 5,6,7,8,9,10-hexahydrocycloocta[d]pyridinyl, isothiazolyl, imidazolyl, indazolyl, indolyl, indazolyl, isoindolyl, indolinyl, isoindolinyl, isoquinolyl, indolizinyl, isoxazolyl, 5,8-methano-5,6,7,8-tetrahydroquinazolinyl, naphthyridinyl, 1,6-naphthyridinonyl, oxadiazolyl, 2-oxoazepinyl, oxazolyl, oxiranyl, 5,6, 6a,7,8,9,10,10a-octahydrobenzo[h]quinazolinyl, 1-phenyl-1H-pyrrolyl, phenazinyl, phenothiazinyl, phenoxazinyl, phthalazinyl, pteridinyl, purinyl, pyrrolyl, pyrazolyl, pyrazolo[3,4-d]-pyrimidinyl, pyridinyl, pyrido[3,2-d]pyrimidinyl, pyrido[3,4-d]pyrimidinyl, pyrazinyl, pyrimidinyl, pyridazinyl, pyrrolyl, quinazolinyl, quinoxalinyl, quinolinyl, isoquinolinyl, tetrahydroquinolinyl, 5,6,7,8-tetrahydroquinazolinyl, 5,6,7,8-tetrahydrobenzo[4,5]thieno[2,3-d]-pyrimidinyl, 6,7,8,9-tetrahydro-5H-cyclohepta[4,5]thieno[2,3-d]-pyrimidinyl, 5,6,7,8-tetrahydropyrido-[4,5-c]pyridazinyl, thiazolyl, thiadiazolyl, triazolyl, tetrazolyl, triazinyl, thieno[2,3-d]-pyrimidinyl, thieno[3,2-d]pyrimidinyl, thieno[2,3-c]pridinyl, and thiophenyl.

"N-heteroaryl" refers to a heteroaryl as defined above containing at least one nitrogen, in which the point of attachment of the heteroaryl to the rest of the molecule is through a nitrogen atom in the heteroaryl ring. An N-heteroaryl radical is optionally substituted as described for aryl.

"C-heteroaryl" refers to a heteroaryl wherein the point of attachment of the heteroaryl to the rest of the molecule is through a carbon atom in the heteroaryl group. A C-heteroaryl radical is optionally substituted as described for aryl.

"Heteroarylalkyl" refers to a of the formula —R$^c$-heteroaryl, where R$^c$ is defined above. If the heteroaryl is a nitrogen-containing heteroaryl, the heteroaryl is optionally attached to the alkyl radical at the nitrogen atom. The alkyl chain of the heteroarylalkyl is optionally substituted as defined above for an alkyl chain; and the heteroaryl part of the heteroarylalkyl group is optionally substituted as defined above for heteroaryl.

"Heteroarylalkoxy" refers to a group bonded through an oxygen atom, and has the formula —O—R$^c$-heteroaryl, where R$^c$ is an alkyl chain. If the heteroaryl is a nitrogen-containing heteroaryl, the heteroaryl is optionally attached to the alkyl at the nitrogen atom. The alkylene chain of the heteroarylalkoxy is optionally substituted as defined above for an alkyl chain. The heteroaryl part of the heteroarylalkoxy is optionally substituted as defined above for a heteroaryl group.

"Optional" or "optionally" means that a subsequently described event or circumstance may or may not occur and that the description includes instances when the event or circumstance occurs and instances in which it does not. For example, "optionally substituted aryl" means that the aryl group may or may not be substituted and that the description includes both substituted aryl radicals and aryl radicals having no substitution. In a list of moieties, radical, or substitutents, the use of "optionally substituted" at the beginning of the list indicates and all member of the list are optionally substituted. In general, unless context or explicit language indicates otherwise, chemical groups or radicals described herein are optionally substituted.

The pyrazole pyridone compounds described herein may contain one or more asymmetric centers and may thus give rise to enantiomers, diastereomers, and other stereoisomeric forms that may be defined, in terms of absolute stereochemistry, as (R)— or (S)—. Unless stated otherwise, all stereoisomeric forms of these compounds are contemplated by this disclosure. When the compounds described herein contain alkene double bonds, and unless specified otherwise, reference to the compound includes a "geometric isomer" both E and Z geometric isomers (e.g., cis or trans). Likewise, all possible isomers, as well as their racemic and optically pure forms, and all tautomeric forms are included. The term "positional isomer" refers to structural isomers around a central ring, such as ortho-, meta-, and para-isomers around a phenyl ring. Stereoisomers can be separated by means and methods known in the art, such as chiral HPLC. Hence, the compounds provided herein encompass various stereoisomers and mixtures thereof, and includes "enantiomers," which refers to two stereoisomers whose molecular structures are non-superimposable mirror images of one another.

"Tautomer" refers to a molecule wherein a proton shift from one atom of a molecule to another atom of the same molecule is possible. The compounds presented herein may, in certain embodiments, exist as tautomers. In circumstances where tautomerization is possible, a chemical equilibrium of the tautomers may exist, but the exact ratio of the tautomers depends on factors such as physical state, temperature, solvent, and pH. Some examples of tautomeric equilibrium include:

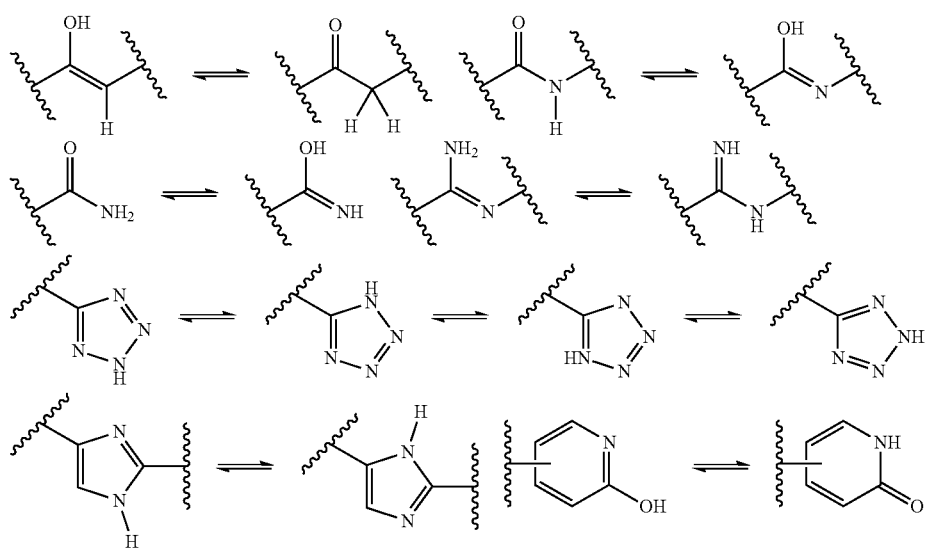

Further, in some embodiments, pyrazole pyridone compounds contain unnatural proportions of atomic isotopes or include compounds that include isotopically enriched atoms. Isotopic substitution with $^2$H, $^3$H, $^{11}$C, $^{13}$C, $^{14}$C, $^{15}$C, $^{12}$N, $^{13}$N, $^{15}$N, $^{16}$N, $^{16}$O, $^{17}$O, $^{14}$F, $^{15}$F, $^{16}$F, $^{17}$F, $^{18}$F, $^{33}$S, $^{34}$S, $^{35}$S, $^{36}$S, $^{35}$Cl, $^{37}$Cl, $^{79}$Br, $^{81}$Br, $^{125}$I are contemplated. All isotopic variations of the present compounds whether radioactive or not, are encompassed within the scope of the present embodiments. In certain embodiments, the compounds disclosed herein have some or all of the $^1$H atoms replaced with $^2$H atoms. The methods of synthesis for deuterium-containing compounds are known in the art. Deuterated starting materials are readily available and are subjected to the synthetic methods described herein to provide for the synthesis of deuterium-containing substituted heterocyclic derivative compounds. Deuterium-containing reagents are available commerically from chemical vendors (e.g., Aldrich Chemical Co.). Deuterium-transfer reagents suitable for use in nucleophilic substitution reactions, such as iodomethane-d3 (CD3I), are readily available and can be employed to transfer a deuterium-substituted carbon atom under nucleophilic substitution reaction conditions to the reaction substrate. Additionally, lithium aluminum deuteride (LiAlD$_4$), can be employed to transfer deuterium under reducing conditions to the reaction substrate. Deuterium gas and palladium catalyst can be employed to reduce unsaturated carbon-carbon linkages and to perform a reductive substitution of aryl carbon-halogen bonds. Accordingly, in one embodiment, a compound described herein contains at least one deuterium atom, such as one, two, three, four, five, or six deuterium atoms. In another embodiment, a compound disclosed herein is fully substituted with deuterium atoms and contains no non-exchangeable $^1$H atoms.

Further, the pyrazole pyridone compounds described herein may be produced or formulated as a "prodrug." Prodrugs are compounds that may be inactive when administered, but are converted under physiological conditions or by hydrolysis (i.e., in vivo) to a biologically active compound; thus prodrugs are pharmaceutically acceptable precursors of a biologically active compound. Prodrug compounds may offer advantages of solubility, tissue compatibility, or delayed release in a subject. Prodrugs also refer to use of covalently bonded carriers that release the active compound in vivo when such prodrug is administered to the subject. Prodrugs of an active compound may be prepared by modifying functional groups present in the active compound in such a way that the modifications are cleaved, either in routine manipulation or in vivo, to the parent active compound. For example, prodrugs include compounds in which a hydroxy, amino, or mercapto group is bonded to any group that, when the prodrug of the active compound is administered to a mammalian subject, cleaves to form a free hydroxy, free amino, or free mercapto group, respectively. Examples of prodrugs include acetate, carboxylate, formate, and benzoate derivatives of alcohol or amine functional groups in the active compounds. See, e.g., Bundgard, DESIGN OF PRODRUGS, at 7-9, 21-24 (Elsevier, Amsterdam, 1985); Higuchi et al., *Pro drugs as Novel Delivery Systems,* 14 A.C.S. Symposium Series; BIOREVERSIBLE CARRIERS IN DRUG DESIGN (Roche (Ed.), Am. Pharm. Assoc. and Pergamon Press; 1987).

Additionally, the pyrazole pyridone compounds described herein may be produced or provided as a pharmaceutically acceptable salt. A pharmaceutically acceptable salt of any one of these compounds is intended to encompass any and all pharmaceutically suitable salt forms, including pharmaceutically acceptable salts such as acid and base addition salts, as are well-known in the art. See, e.g., WO 2014089364, WO 2014100463, WO 2014100818, WO 2014164708, WO 2014151945, WO 2014151106, WO 2015058160, WO 2015089192, WO 2015168466, WO 2015200709, WO 2015200843, WO 2016004105, WO 2016003917, WO 2016037005, WO 2016044342, WO 2016044138, WO 2016044429, WO 2016168682, WO 2016172618.

Accordingly, and as used herein, a reference to a pyrazole pyridone compound of Formula I includes within that reference a pharmaceutically acceptable salt, hydrate, solvate, N-oxide, stereoisomer, tautomer, radioisotopically enriched or deuterated version, or prodrug thereof.

The pyrazole pyridone compounds of the present embodiments can be prepared according to general synthetic routes herein and more specifically as described in the Examples herein. Typically, a pyrazole pyridone compound provided herein is produced in substantially pure form, in that it contains less than about 5%, or less than about 1%, or less than about 0.1%, of other organic small molecules, such as unreacted intermediates or synthesis by-products that are created, for example, in one or more of the steps of synthesis.

In certain embodiments, the pyrazole pyridone compound may be administered as a pure compound. In other embodiments and in general, the pyrazole pyridone compound is combined with a pharmaceutically acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice. See, e.g., REMINGTON: SCI. & PRACTICE OF PHARM. 21st Ed. (Gennaro (Ed.) Mack Pub. Co., Easton, Pa., US, 2005).

As used herein, "treatment" or "treating," or "palliating" or "ameliorating" are used interchangeably herein. These terms refers to an approach for obtaining beneficial or desired results including but not limited to therapeutic benefit or a prophylactic benefit. By "therapeutic benefit" is meant eradication or amelioration of the underlying disorder being treated. Also, a therapeutic benefit is achieved with the eradication or amelioration of one or more of the physiological symptoms associated with the underlying disorder such that an improvement is observed in the patient, notwithstanding that the patient may still be afflicted with the underlying disorder. For prophylactic benefit, the compositions may be administered to a patient at risk of developing a particular disease, or to a patient reporting one or more of the physiological symptoms of a disease, even though a diagnosis of this disease may not have been made.

Substituted pyrazole pyridone compounds are described herein that are inhibitors of abharent cell growth regulatory pathways associated with maladies such as neoplastic growth, cancers, or inflammatory conditions. These compounds, and compositions comprising these compounds, are useful for the treatment of cancer and neoplastic disease. The compounds described herein may, therefore, be useful for treating cancers such as bladder cancer, breast cancer, Burkitts lymphoma, lung cancer, NUT midline carcinoma, melanoma, or prostate cancer.

One embodiment provides a compound of Formula I,

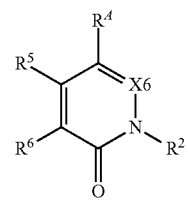

Formula I wherein a compound of Formula I is optionally a pharmaceutically acceptable salt thereof, and wherein:
X6 is CH or C—F;
$R^2$ is hydrogen, or alkyl;
$R^5$ is hydrogen or optionally substituted alkyl, cycloalkyl, heterocyclyl, heterocycloalkyl, aryl, heteroaryl, —OW, —NW, —SW, or —SO$_2$W wherein
  W is optionally substituted alkyl, cycloalkyl, heterocycyl, heterocycloalkyl, aryl, aralkyl, heteroaryl, or heteroaralkyl;
$R^6$ is hydrogen, halogen, halide, or optionally substituted alkyl or alkyloxy; and
$R^4$ is optionally substituted heteroaryl.
In at least one embodiment, X6 is CH.
In at least one embodiment, $R^6$ is hydrogen. In at least one embodiment, $R^6$ is methyl.
In at least one embodiment, $R^2$ is alkyl such as methyl.

In at least one embodiment R$^5$ is optionally substituted aryl. In some embodiments, R$^5$ is unsubstituted phenyl.

In at least one embodiment, R$^5$ is optionally substituted heteroaryl, such as isoxazolyl pyrrolyl, morpholinyl or tetrahydropyranyl. In some embodiments, R$^5$ is optionally substituted N-pyrrolyl. In particular embodiments, R$^5$ is unsubstituted N-pyrrolyl. In particular embodiments, R$^5$ is N-pyrrolyl substituted with methylacetimide.

In some embodiments, R$^5$ is substituted heterocyclyl, in which the substituent may be carboxylic acid, methylacetate, methylsulfonyl, propylacetamide, sulfonyl, methylacetamide, or dimethylacetamide.

In at least one embodiment, R$^5$ is optionally substituted alkyl, such as methyl. In some embodiments, R$^5$ is substituted alkyl, in which the substituent may be, for example, methylacetate, methylsulfonyl, propylacetamide, sulfonyl, methylacetamide, or dimethylacetamide.

In at least one embodiment, R$^5$ is optionally substituted cycloalkyl such as cyclobutyl or cyclopropyl.

In at least one embodiment, R$^5$ is —OW, in which W is optionally substituted alkyl, such as ethyl. In some embodiments, W is substituted alkyl in which the substitution is carboxylic acid, cyano, hydroxy, or pyridinyl.

In at least one embodiment, R$^5$ is —SW, in which W may be optionally substituted alkyl, phenyl, carboxylic acid, alkylacetamide.

In at least one embodiment, R$^5$ is —SO$_2$W, in which W is alkyl.

In at least one embodiment, R$^4$ is optionally substituted five-membered N-containing heteroaryl. In at least one embodiment, R$^4$ is optionally substituted pyrazolyl. In at least one embodiment, R$^4$ is an optionally substituted piperidinylpyrazole. In at least one embodiment, R$^4$ is cyclopentylpyrazole. In at least one embodiment, R$^4$ is optionally substituted imidazole. In at least one embodiment, R$^4$ is optionally substituted oxazole. In at least one embodiment, R$^4$ is an optionally substituted isoxazole. In at least one embodiment, R$^4$ is an optionally substituted triazole.

In some embodiments, R$^4$ is:

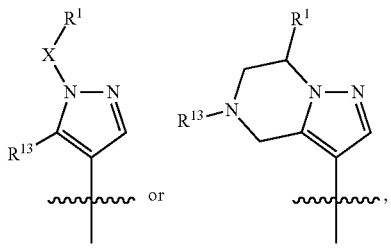

wherein X is a bond, CH$_2$, CHR, or CRR', wherein
  R and R' are independently hydrogen, halogen, or optionally substituted alkyl;
R$^1$ is hydrogen or optionally substituted, alkyl, aryl, aralkyl, alkoxy, cycloalkyl, cycloalkylalkyl, heterocyclyl, heterocyclylalkyl, heteroaryl, heteroarylalkyl, or —SO$_2$W; and
R$^{13}$ is —Y—Z, wherein
  Y is selected from a bond or CH(C$_1$-C$_4$ alkyl), and
  Z is selected from hydrogen, halogen, alkyl, aryl, —CF$_2$, —CO$_2$R$^{22}$, —N(R$^{22}$), or —N(R$^{22}$)CO(R$^{22}$), wherein R$^{22}$ is hydrogen or alkyl.

In at least one embodiment, X is CHR, in which R is C$_1$-C$_5$ alkyl such as ethyl, methyl, or cyclopropyl.

In at least one embodiment of R$^{13}$, Y is a bond and Z is hydrogen. In at least one embodiment of R$^{13}$, Y is a bond and Z is methyl.

In at least one embodiment, R$^1$ is —SO$_2$Me or methylacetamide.

In at least one embodiment, R$^1$ is optionally substituted aryl such as benzyl or phenyl. In at least one embodiment, R$^1$ is substituted benzyl or phenyl. In some embodiments, R$^1$ is benzyl or phenyl substituted with halo, such as bromo, chloro, fluoro, difluoro; benzyl or phenyl substituted with haloalkyl, such as difluoromethyl; benzyl or phenyl substituted with C$_1$-C$_5$ alkyl such as ethyl, methyl, propyl, isopropyl, or cyclopropyl; benzyl or phenyl substituted with cyanyl; benzyl or phenyl substituted with alkoxy such as methoxy; benzyl or phenyl substituted with carboxylate such that R$^1$ is benzoate; or benzyl or phenyl substituted with optionally substituted heteroaryl such as pyrazolyl or methylpyrazolyl.

In at least one embodiment, R$^1$ is optionally substituted cyclyl moiety such as cyclohexyl or cyclopropyl. In embodiments in which R$^1$ is substituted cyclyl moiety, the substitution may by amino, cyano, dimethylamino, halo such as difluoro, hydroxy, methoxy, methyl.

In at least one embodiment, R$^1$ is optionally substituted heterocyclyl such as morpholinyl or tetrahydropyranyl.

In at least one embodiment, R$^1$ is optionally substituted heteroaryl, such as optionally substituted pyridinyl. In at least one embodiment, R$^1$ is optionally substituted heteroarylalkyl, such as pyridinylethyl, or piperidinyl. In some embodiments, R$^1$ is substituted heteroarylalkyl, in which the substitution is, for example, methylsulfonyl or sulfonyl.

In some embodiments, R$^1$ is optionally substituted C$_1$-C$_5$ alkyl such as isobutyl, ethyl, methyl, propyl, cyclopropyl, cyclopropylmethyl, isopropyl.

In some embodiments, R$^1$ is substituted C$_1$-C$_5$ alkyl, in which the substitution may be, for example methylacetate, methylsulfonyl, propylacetamide, sulfonyl, methylacetamide, or dimethylacetamide.

In some embodiments, R$^4$ is selected from:

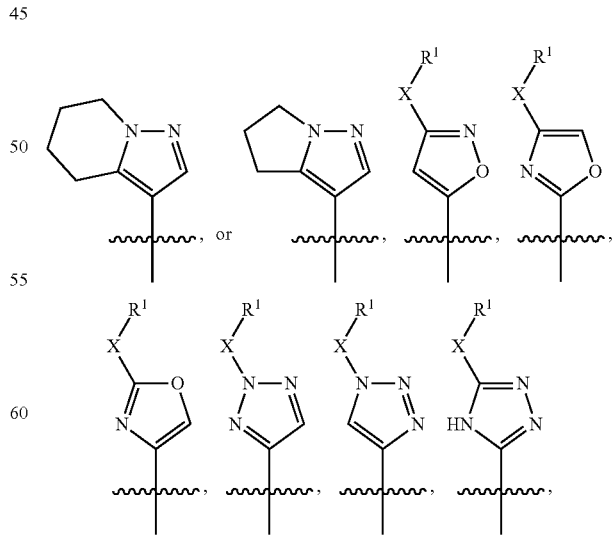

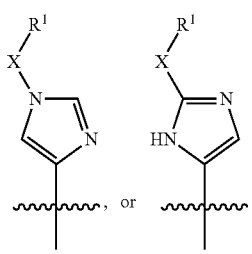

wherein
X is a bond, CH$_2$, CHR, or CRR', wherein
R and R' are independently hydrogen, halogen, or optionally substituted alkyl; and
R$^1$ is hydrogen or optionally substituted, alkyl, aryl, aralkyl, alkoxy, cycloalkyl, cycloalkylalkyl, heterocyclyl, heterocyclylalkyl, heteroaryl, heteroarylalkyl, or —SO$_2$W, wherein W is C$_1$-C$_4$ alkyl, and wherein R$^1$ is as described above.

In at least one embodiment of a compound of Formula I, X6 is CH, R$^2$ is methyl, R$^6$ is H, R$^5$ is N-pyrrolyl, and R$^4$ is benzylpyrazolyl; in a specific embodiment, this compound is 5-(1-benzyl-1H-pyrazol-4-yl)-1-methyl-4-(1H-pyrrol-1-yl)pyridin-2(1H)-one.

In at least one embodiment of a compound of Formula I, X6 is CH, R$^2$ is methyl, R$^6$ is H, R$^5$ is isopropoxy, and R$^4$ is phenylethylpyrazolyl.

In at least one embodiment of a compound of Formula I, in which X6 is CH, R$^2$ is methyl, R$^6$ is H, R$^5$ is H, and R$^4$ is:

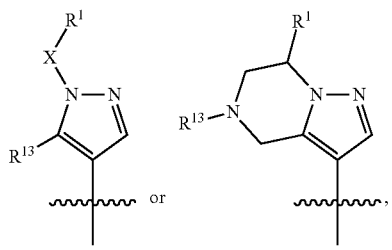

wherein X is CHR, in which R$^{13}$ is methyl; and R$^1$ is chlorobenzyl. In at least one embodiment of a compound of Formula I, in which X6 is CH, R$^2$ is methyl, R$^6$ is H, R$^5$ is H, and R$^4$ is cyclopropyl(phenyl)methylpyrazolyl.

In particular embodiments, a compound of Formula I is a compound of Table 1:

TABLE 1

| Example | Structure | Name |
|---|---|---|
| 1 | 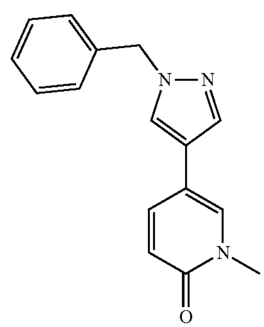 | 5-(1-benzyl-1H-pyrazol-4-yl)-1-methylpyridin-2(1H)-one |
| 2 | 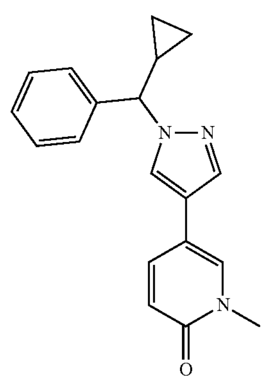 | 5-(1-(cyclopropyl(phenyl)ethyl)-1H-pyrazol-4-yl)-1-methylpyridin-2(1H)-one |

TABLE 1-continued

| Example | Structure | Name |
|---|---|---|
| 3 | 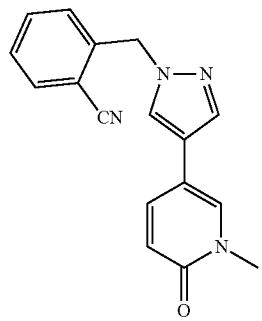 [SMILES: Cn1cc(-c2cnn(Cc3ccccc3C#N)c2)ccc1=O] | 2-((4-(1-methyl-6-oxo-1,6-dihydropyridin-3-yl)-1H-pyrazol-1-yl)methyl)benzonitrile |
| 4 | 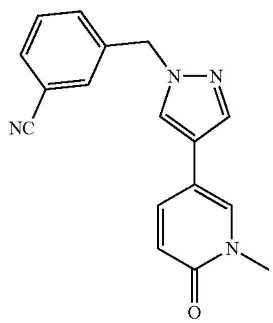 [SMILES: Cn1cc(-c2cnn(Cc3cccc(C#N)c3)c2)ccc1=O] | 3-((4-(1-methyl-6-oxo-1,6-dihydropyridin-3-yl)-1H-pyrazol-1-yl)methyl)benzonitrile |
| 5 | 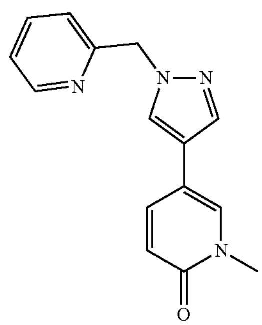 [SMILES: Cn1cc(-c2cnn(Cc3ccccn3)c2)ccc1=O] | 1-methyl-5-(1-(pyridin-2-ylmethyl)-1H-pyrazol-4-yl)pyridin-2(1H)-one |
| 6 | 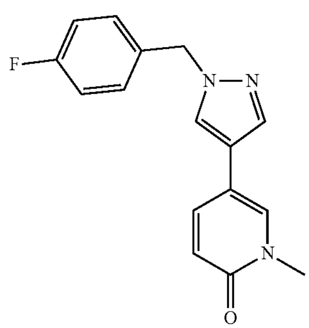 [SMILES: Cn1cc(-c2cnn(Cc3ccc(F)cc3)c2)ccc1=O] | 5-(1-(4-fluorobenzyl)-1H-pyrazol-4-yl)-1-methylpyridin-2(1H)-one |
| 7 | 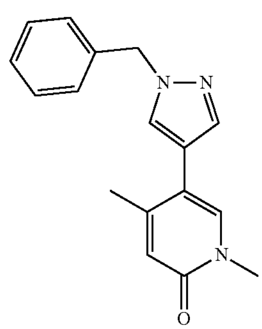 [SMILES: Cc1cc(=O)n(C)cc1-c1cnn(Cc2ccccc2)c1] | 5-(1-benzyl-1H-pyrazol-4-yl)-1,4-dimethylpyridin-2(1H)-one |

TABLE 1-continued

| Example | Structure | Name |
|---|---|---|
| 8 | 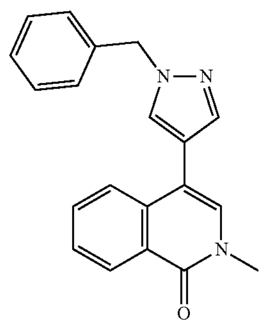 | 4-(1-benzyl-1H-pyrazol-4-yl)-2-methylisoquinolin-1(2H)-one |
| 9 | 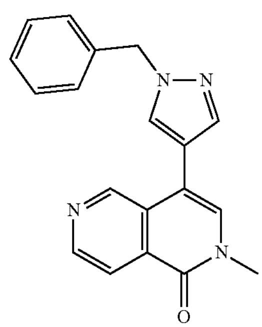 | 4-(1-benzyl-1H-pyrazol-4-yl)-2-methyl-2,6-naphthyridin-1(2H)-one |
| 10 | 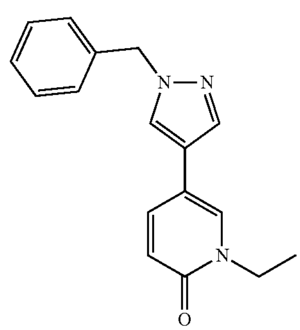 [SMILES: CCn1cc(-c2cnn(Cc3ccccc3)c2)ccc1=O] | 5-(1-benzyl-1H-pyrazol-4-yl)-1-ethylpyridin-2(1H)-one |
| 11 | 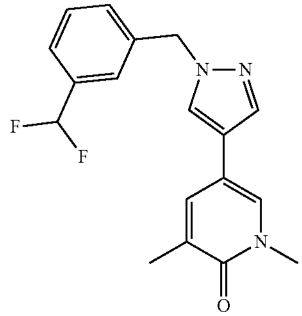 [SMILES: Cc1cc(-c2cnn(Cc3cccc(C(F)F)c3)c2)cn(C)c1=O] | 5-(1-(1-(3-(difluoromethyl)phenyl)ethyl)-1H-pyrazol-4-yl)-1,3-dimethylpyridin-2(1H)-one |

TABLE 1-continued

| Example | Structure | Name |
| --- | --- | --- |
| 12 | 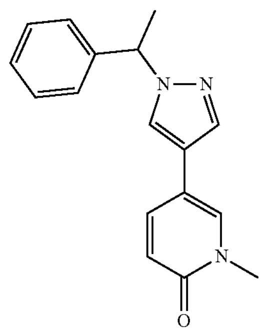 | 1-methyl-5-(phenyl(1-methyl)ethyl)-1H-pyrazol-4-yl)pyridin-2(1H)-one |
| 13 | 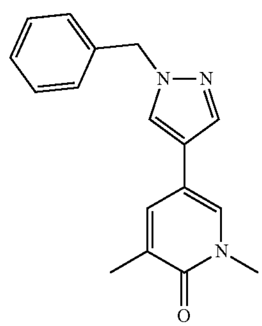 [SMILES: Cc1cc(-c2cnn(Cc3ccccc3)c2)cn(C)c1=O] | 5-(1-benzyl-1H-pyrazol-4-yl)-1,3-dimethyl-pyridin-2(1H)-one |
| 14 | 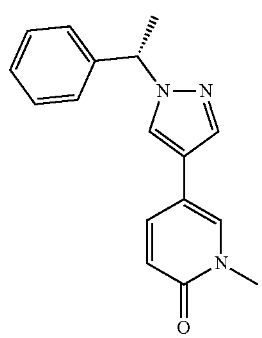 [SMILES: C[C@@H](c1ccccc1)n1cc(-c2ccc(=O)n(C)c2)cn1] | (S)-1-methyl-5-(1-(1-phenylethyl)-1H-pyrazol-4-yl)pyridin-2(1H)-one |
| 15 | 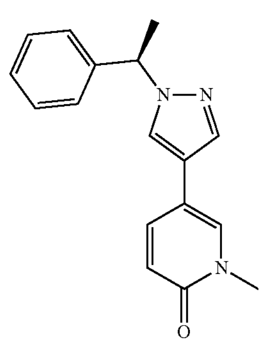 [SMILES: C[C@H](c1ccccc1)n1cc(-c2ccc(=O)n(C)c2)cn1] | (R)-1-methyl-5-(1-(1-phenylethyl)-1H-pyrazol-4-yl)pyridin-2(1H)-one |

TABLE 1-continued

| Example | Structure | Name |
|---|---|---|
| 16 | 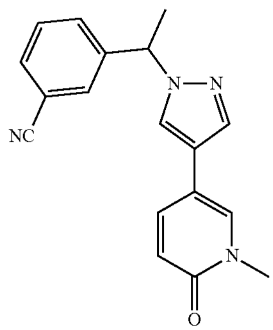 [SMILES: CC(c1cccc(C#N)c1)n1cc(-c2ccc(=O)n(C)c2)cn1] | 3-(1-(4-(1-methyl-6-oxo-1,6-dihydropyridin-3-yl)-1H-pyrazol-1-yl)ethyl)benzonitrile |
| 17 | 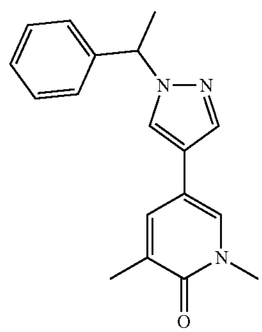 | 1,3-dimethyl-5-(1-(1-phenylethyl)-1H-pyrazol-4-yl)pyridin-2(1H)-one |
| 18 | 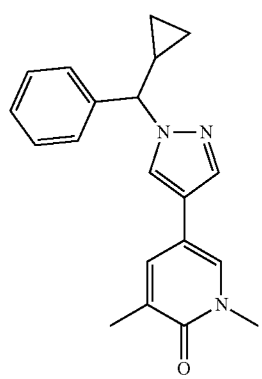 [SMILES: Cc1cc(-c2cnn(C(c3ccccc3)C3CC3)c2)cn(C)c1=O] | 5-(1-(cyclopropyl(phenyl)methyl)-1H-pyrazol-4-yl)-1,3-dimethylpyridin-2(1H)-one |
| 19 | 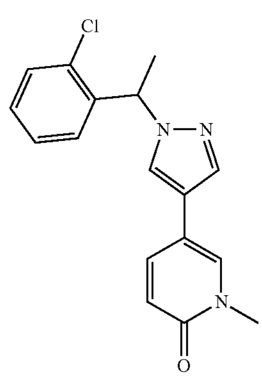 [SMILES: CC(c1ccccc1Cl)n1cc(-c2ccc(=O)n(C)c2)cn1] | 5-(1-(1-(2-chlorophenyl)ethyl)-1H-pyrazol-4-yl)-1-methylpyridin-2(1H)-one |

TABLE 1-continued

| Example | Structure | Name |
|---|---|---|
| 20 | 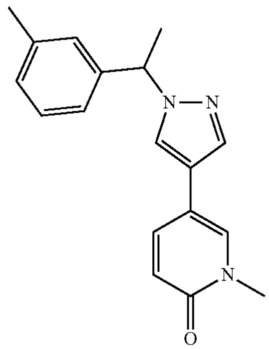 | 1-methyl-5-(1-(1-(m-tolyl)ethyl)-1H-pyrazol-4-yl)pyridin-2(1H)-one |
| 21 | 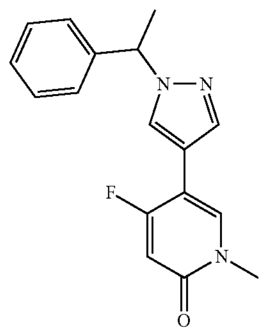 | 4-fluoro-1-methyl-5-(1-(1-phenylethyl)-1H-pyrazol-4-yl)pyridin-2(1H)-one |
| 22 | 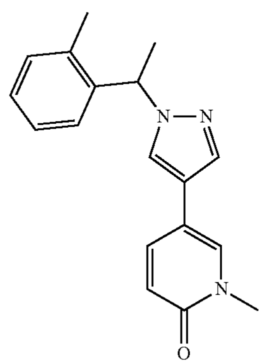 [SMILES: Cc1ccccc1C(C)n1cc(-c2ccc(=O)n(C)c2)cn1] | 1-methyl-5-(1-(1-(o-tolyl)ethyl)-1H-pyrazol-4-yl)pyridin-2(1H)-one |
| 23 | 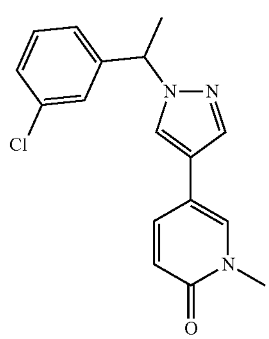 [SMILES: CC(c1cccc(Cl)c1)n1cc(-c2ccc(=O)n(C)c2)cn1] | 5-(1-(1-(3-chlorophenyl)ethyl)-1H-pyrazol-4-yl)-1-methylpyridin-2(1H)-one |

TABLE 1-continued

| Example | Structure | Name |
|---|---|---|
| 24 | 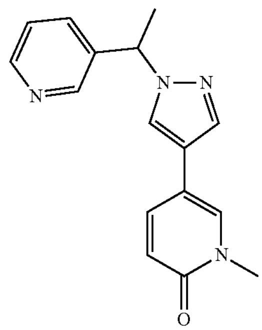 [SMILES: CC(c1cccnc1)n1cc(-c2ccc(=O)n(C)c2)cn1] | 1-methyl-5-(1-(1-(pyridin-3-yl)ethyl)-1H-pyrazol-4-yl)pyridin-2(1H)-one |
| 25 | 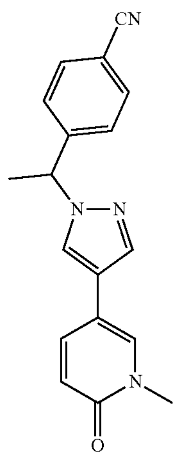 [SMILES: CC(c1ccc(C#N)cc1)n1cc(-c2ccc(=O)n(C)c2)cn1] | 4-(1-(4-(1-methyl-6-oxo-1,6-dihydropyridin-3-yl)-1H-pyrazol-1-yl)ethyl)benzonitrile |
| 26 | 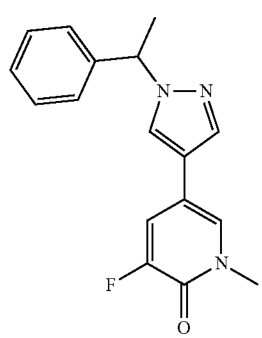 [SMILES: CC(c1ccccc1)n1cc(-c2cc(F)c(=O)n(C)c2)cn1] | 3-fluoro-1-methyl-5-(1-(1-phenylethyl)-1H-pyrazol-4-yl)pyridin-2(1H)-one |
| 27 | 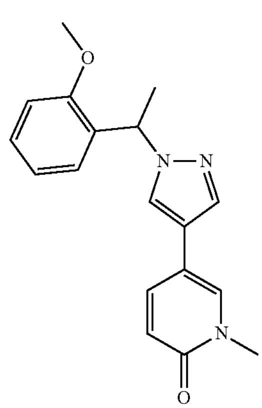 [SMILES: COc1ccccc1C(C)n1cc(-c2ccc(=O)n(C)c2)cn1] | 5-(1-(1-(2-methoxyphenyl)ethyl)-1H-pyrazol-4-yl)-1-methylpyridin-2(1H)-one |

TABLE 1-continued

| Example | Structure | Name |
|---|---|---|
| 28 | 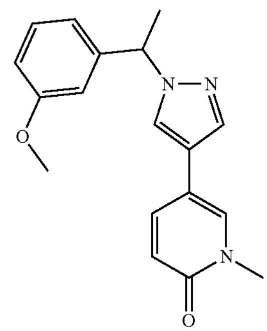 [SMILES: COc1cccc(C(C)n2cc(-c3ccc(=O)n(C)c3)cn2)c1] | 5-(1-(1-(3-methoxyphenyl)ethyl)-1H-pyrazol-4-yl)-1-methylpyridin-2(1H)-one |
| 29 | 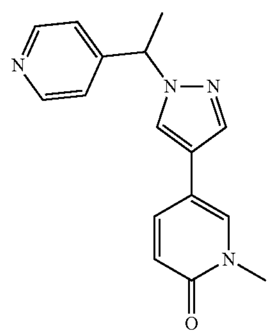 [SMILES: CC(c1ccncc1)n1cc(-c2ccc(=O)n(C)c2)cn1] | 1-methyl-5-(1-(1-(pyridin-4-yl)ethyl)-1H-pyrazol-4-yl)pyridin-2(1H)-one |
| 30 | 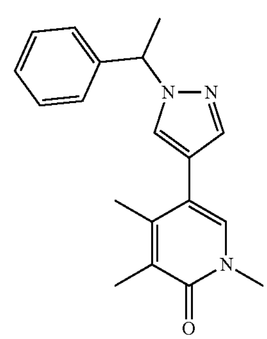 [SMILES: Cc1c(-c2cnn(C(C)c3ccccc3)c2)cn(C)c(=O)c1C] | 1,3,4-trimethyl-5-(1-(1-phenylethyl)-1H-pyrazol-4-yl)pyridin-2(1H)-one |
| 31 | 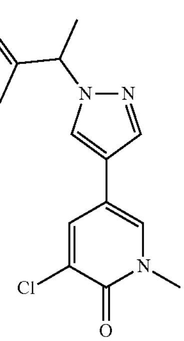 | 3-chloro-1-methyl-5-(1-(1-phenylethyl)-1H-pyrazol-4-yl)pyridin-2(1H)-one |

TABLE 1-continued

| Example | Structure | Name |
| --- | --- | --- |
| 32 | 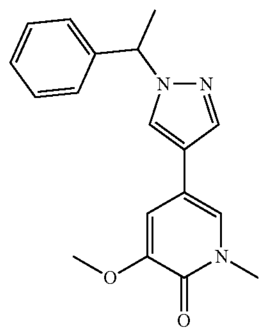 [SMILES: COc1cc(-c2cnn(C(C)c3ccccc3)c2)cn(C)c1=O] | 3-methoxy-1-methyl-5-(1-(1-phenylethyl)-1H-pyrazol-4-yl)pyridin-2(1H)-one |
| 33 | 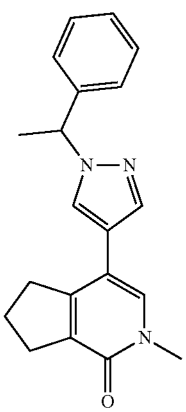 [SMILES: CC(c1ccccc1)n1cc(-c2cn(C)c(=O)c3c2CCC3)cn1] | 2-methyl-4-(1-(1-phenylethyl)-1H-pyrazol-4-yl)-2,5,6,7-tetrahydro-1H-cyclopenta[c]pyridin-1-one |
| 34 | 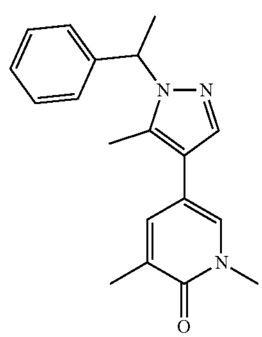 [SMILES: Cc1cc(-c2cnn(C(C)c3ccccc3)c2C)cn(C)c1=O] | 1,3-dimethyl-5-(5-methyl-1-(1-phenylethyl)-1H-pyrazol-4-yl)pyridin-2(1H)-one |
| 35 | 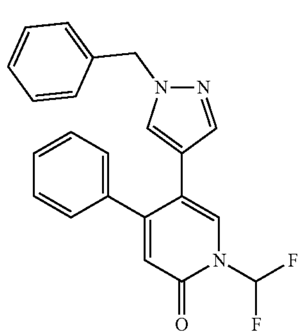 [SMILES: O=c1cc(-c2ccccc2)c(-c2cnn(Cc3ccccc3)c2)cn1C(F)F] | 5-(1-benzyl-1H-pyrazol-4-yl)-1-(difluoromethyl)-4-phenylpyridin-2(1H)-one |

TABLE 1-continued

| Example | Structure | Name |
|---|---|---|
| 36 | 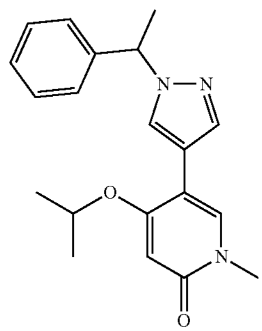 [SMILES: CC(C)Oc1cc(=O)n(C)cc1-c1cnn(C(C)c2ccccc2)c1] | 4-isopropoxy-1-methyl-5-(1-(1-phenylethyl)-1H-pyrazol-4-yl)pyridin-2(1H)-one |
| 37 | 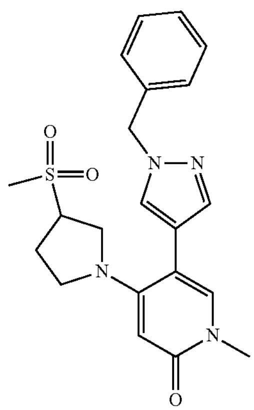 | 5-(1-Benzyl-1H-pyrazol-4-yl)-4-(3-methanesulfonyl-pyrrolidin-1-yl)-1-methyl-1H-pyridin-2-one |
| 38 | 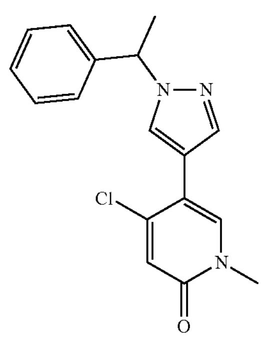 [SMILES: CC(c1ccccc1)n1cc(-c2cn(C)c(=O)cc2Cl)cn1] | 4-chloro-1-methyl-5-(1-(1-phenylethyl)-1H-pyrazol-4-yl)pyridin-2(1H)-one |
| 39 | 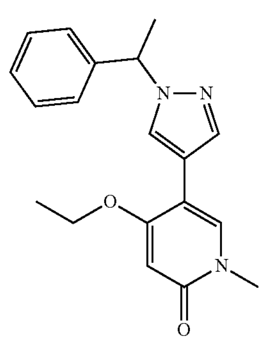 [SMILES: CCOc1cc(=O)n(C)cc1-c1cnn(C(C)c2ccccc2)c1] | 4-ethoxy-1-methyl-5-(1-(1-phenylethyl)-1H-pyrazol-4-yl)pyridin-2(1H)-one |

TABLE 1-continued

| Example | Structure | Name |
|---|---|---|
| 40 | 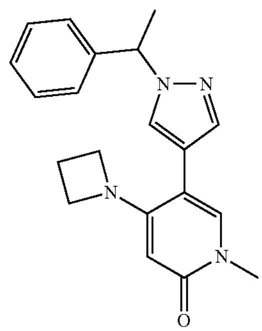 [SMILES: CC(c1ccccc1)n1cc(-c2cn(C)c(=O)cc2N2CCC2)cn1] | 4-(azetidin-1-yl)-1-methyl-5-(1-(1-phenylethyl)-1H-pyrazol-4-yl)pyridin-2(1H)-one |
| 41 | 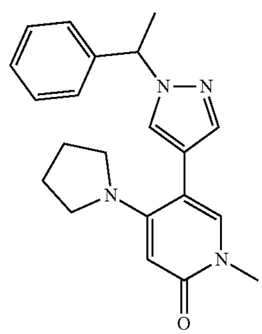 [SMILES: CC(c1ccccc1)n1cc(-c2cn(C)c(=O)cc2N2CCCC2)cn1] | 1-methyl-5-(1-(1-phenylethyl)-1H-pyrazol-4-yl)-4-(pyrrolidin-1-yl)pyridin-2(1H)-one |
| 42 | 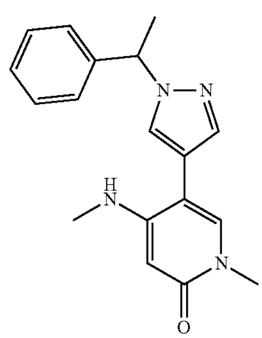 [SMILES: CNc1cc(=O)n(C)cc1-c1cnn(C(C)c2ccccc2)c1] | 1-methyl-4-(methylamino)-5-(1-(1-phenylethyl)-1H-pyrazol-4-yl)pyridin-2(1H)-one |
| 43 | 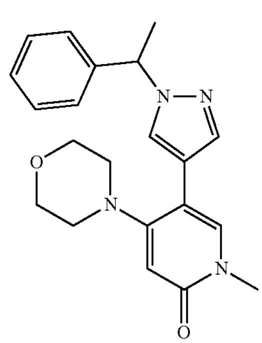 [SMILES: CC(c1ccccc1)n1cc(-c2cn(C)c(=O)cc2N2CCOCC2)cn1] | 1-methyl-4-morpholino-5-(1-(1-phenylethyl)-1H-pyrazol-4-yl)pyridin-2(1H)-one |

TABLE 1-continued

| Example | Structure | Name |
|---|---|---|
| 44 | 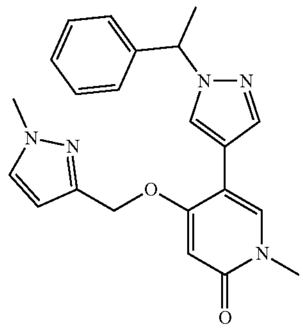 [SMILES: CC(c1ccccc1)n1cc(-c2cn(C)c(=O)cc2OCc2ccn(C)n2)cn1] | 1-methyl-4-((1-methyl-1H-pyrazol-3-yl)methoxy)-5-(1-(1-phenylethyl)-1H-pyrazol-4-yl)pyridin-2(1H)-one |
| 45 | 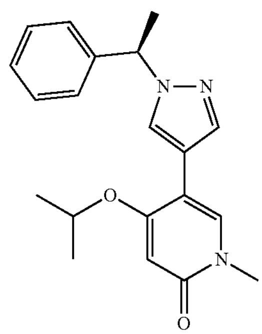 [SMILES: CC(C)Oc1cc(=O)n(C)cc1-c1cnn([C@H](C)c2ccccc2)c1] | (R)-4-isopropoxy-1-methyl-5-(1-(1-phenylethyl)-1H-pyrazol-4-yl)pyridin-2(1H)-one |
| 46 | 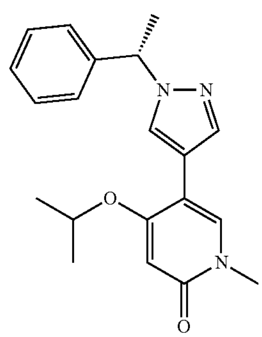 [SMILES: CC(C)Oc1cc(=O)n(C)cc1-c1cnn([C@@H](C)c2ccccc2)c1] | (S)-4-isopropoxy-1-methyl-5-(1-(1-phenylethyl)-1H-pyrazol-4-yl)pyridin-2(1H)-one |
| 47 | 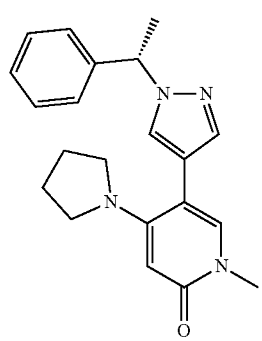 [SMILES: C[C@@H](c1ccccc1)n1cc(-c2cn(C)c(=O)cc2N2CCCC2)cn1] | (S)-1-methyl-5-(1-(1-phenylethyl)-1H-pyrazol-4-yl)-4-(pyrrolidin-1-yl)pyridin-2(1H)-one |

TABLE 1-continued
| Example | Structure | Name |
|---|---|---|
| 48 | 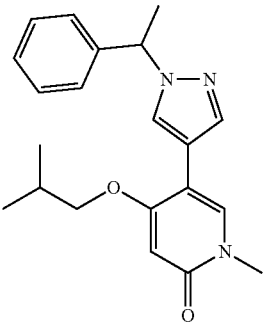 [SMILES: CC(C)COc1cc(=O)n(C)cc1-c1cnn(C(C)c2ccccc2)c1] | 4-isobutoxy-1-methyl-5-(1-(1-phenylethyl)-1H-pyrazol-4-yl)pyridin-2(1H)-one |
| 49 | 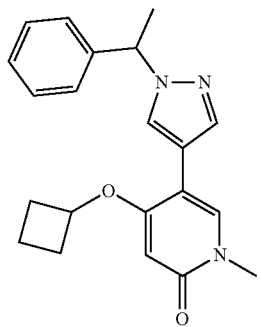 [SMILES: CC(c1ccccc1)n1cc(-c2cn(C)c(=O)cc2OC2CCC2)cn1] | 4-cyclobutoxy-1-methyl-5-(1-(1-phenylethyl)-1H-pyrazol-4-yl)pyridin-2(1H)-one |
| 50 | 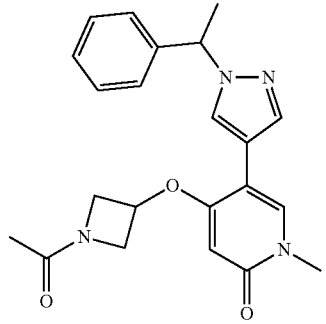 [SMILES: CC(=O)N1CC(Oc2cc(=O)n(C)cc2-c2cnn(C(C)c3ccccc3)c2)C1] | 4-((1-acetylazetidin-3-yl)oxy)-1-methyl-5-(1-(1-phenylethyl)-1H-pyrazol-4-yl)pyridin-2(1H)-one |
| 51 | 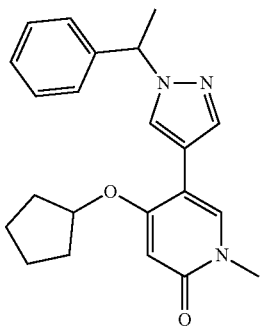 [SMILES: CC(c1ccccc1)n1cc(-c2cn(C)c(=O)cc2OC2CCCC2)cn1] | 4-(cyclopentyloxy)-1-methyl-5-(1-(1-phenylethyl)-1H-pyrazol-4-yl)pyridin-2(1H)-one |

TABLE 1-continued

| Example | Structure | Name |
|---|---|---|
| 52 | 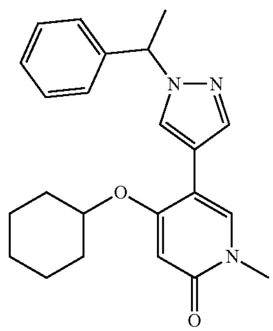 [SMILES: CC(c1ccccc1)n1cc(-c2cn(C)c(=O)cc2OC2CCCCC2)cn1] | 4-(cyclohexyloxy)-1-methyl-5-(1-(1-phenylethyl)-1H-pyrazol-4-yl)pyridin-2(1H)-one |
| 53 | 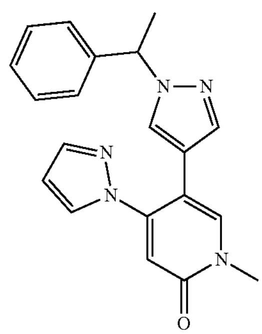 [SMILES: CC(c1ccccc1)n1cc(-c2cn(C)c(=O)cc2-n2cccn2)cn1] | 1-methyl-5-(1-(1-phenylethyl)-1H-pyrazol-4-yl)-4-(1H-pyrazol-1-yl)pyridin-2(1H)-one |
| 54 | 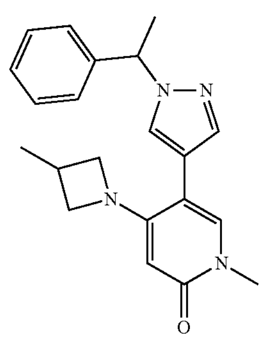 [SMILES: CC1CN(c2cc(=O)n(C)cc2-c2cnn(C(C)c3ccccc3)c2)C1] | 1-methyl-4-(3-methylazetidin-1-yl)-5-(1-(1-phenylethyl)-1H-pyrazol-4-yl)pyridin-2(1H)-one |
| 55 | 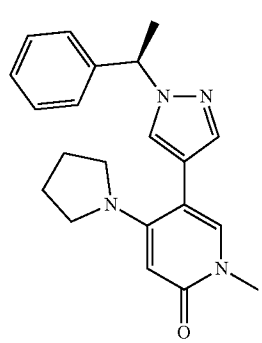 [SMILES: C[C@H](c1ccccc1)n1cc(-c2cn(C)c(=O)cc2N2CCCC2)cn1] | (R)-1-methyl-5-(1-(1-phenylethyl)-1H-pyrazol-4-yl)-4-(pyrrolidin-1-yl)pyridin-2(1H)-one |

TABLE 1-continued
| Example | Structure | Name |
|---|---|---|
| 56 | 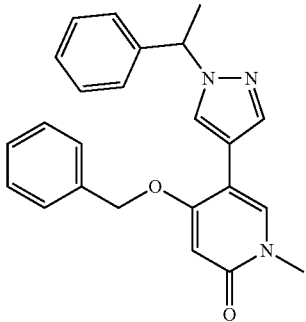 [SMILES: CC(c1ccccc1)n1cc(-c2cn(C)c(=O)cc2OCc2ccccc2)cn1] | 4-(benzyloxy)-1-methyl-5-(1-(1-phenylethyl)-1H-pyrazol-4-yl)pyridin-2(1H)-one |
| 57 | 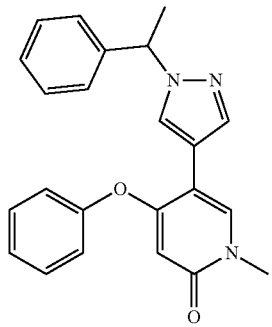 [SMILES: CC(c1ccccc1)n1cc(-c2cn(C)c(=O)cc2Oc2ccccc2)cn1] | 1-methyl-4-phenoxy-5-(1-(1-phenylethyl)-1H-pyrazol-4-yl)pyridin-2(1H)-one |
| 58 | 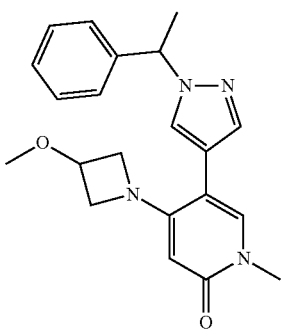 | 4-(3-methoxyazetidin-1-yl)-1-methyl-5-(1-(1-phenylethyl)-1H-pyrazol-4-yl)pyridin-2(1H)-one |
| 59 | 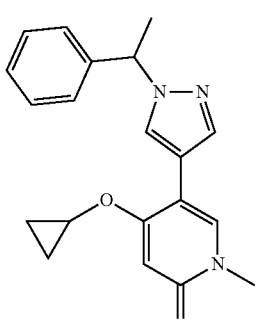 | 4-cyclopropoxy-1-methyl-5-(1-(1-phenylethyl)-1H-pyrazol-4-yl)pyridin-2(1H)-one |

TABLE 1-continued

| Example | Structure | Name |
|---|---|---|
| 60 | 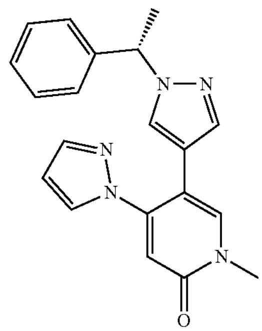 [SMILES: C[C@@H](c1ccccc1)n1cc(-c2cn(C)c(=O)cc2-n2cccn2)cn1] | (S)-1-methyl-5-(1-(1-phenylethyl)-1H-pyrazol-4-yl)-4-(1H-pyrazol-1-yl)pyridin-2(1H)-one |
| 61 | 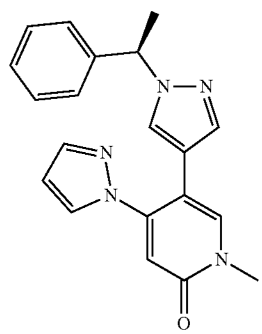 [SMILES: C[C@H](c1ccccc1)n1cc(-c2cn(C)c(=O)cc2-n2cccn2)cn1] | (R)-1-methyl-5-(1-(1-phenylethyl)-1H-pyrazol-4-yl)-4-(1H-pyrazol-1-yl)pyridin-2(1H)-one |
| 62 | 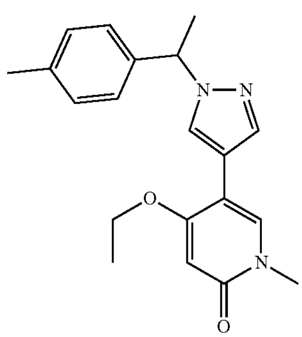 | 4-ethoxy-1-methyl-5-(1-(1-(p-tolyl)ethyl)-1H-pyrazol-4-yl)pyridin-2(1H)-one |
| 63 | 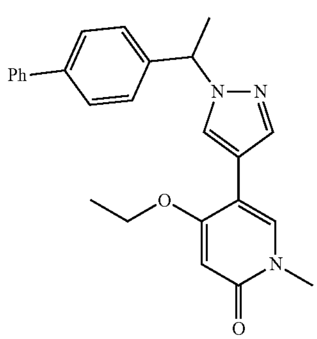 [SMILES: CCOc1cc(=O)n(C)cc1-c1cnn(C(C)c2ccc(-c3ccccc3)cc2)c1] | 5-(1-(1-([1,1'-biphenyl]-4-yl)ethyl)-1H-pyrazol-4-yl)-4-ethoxy-1-methylpyridin-2(1H)-one |

TABLE 1-continued

| Example | Structure | Name |
|---|---|---|
| 64 | 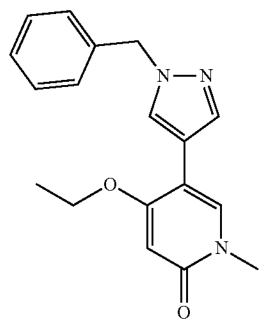 [SMILES: CCOc1cc(=O)n(C)cc1-c1cnn(Cc2ccccc2)c1] | 5-(1-benzyl-1H-pyrazol-4-yl)-4-ethoxy-1-methylpyridin-2(1H)-one |
| 65 | 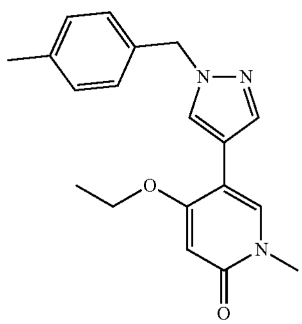 | 4-ethoxy-1-methyl-5-(1-(4-methylbenzyl)-1H-pyrazol-4-yl)pyridin-2(1H)-one |
| 66 | 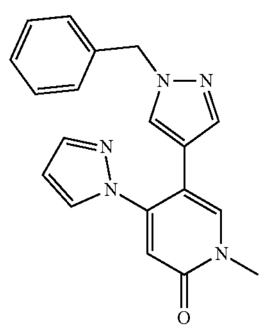 [SMILES: Cn1cc(-c2cnn(Cc3ccccc3)c2)c(-n2cccn2)cc1=O] | 5-(1-benzyl-1H-pyrazol-4-yl)-1-methyl-4-(1H-pyrazol-1-yl)-pyridin-2(1H)-one |
| 67 | 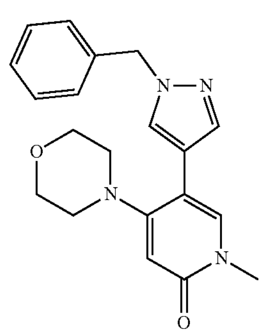 [SMILES: Cn1cc(-c2cnn(Cc3ccccc3)c2)c(N2CCOCC2)cc1=O] | 5-(1-benzyl-1H-pyrazol-4-yl)-1-methyl-4-morpholinopyridin-2(1H)-one |

TABLE 1-continued

| Example | Structure | Name |
| --- | --- | --- |
| 68 | 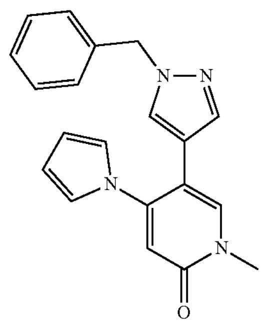 [SMILES: Cn1cc(-c2cnn(Cc3ccccc3)c2)c(-n2cccc2)cc1=O] | 5-(1-benzyl-1H-pyrazol-4-yl)-1-methyl-4-(1H-pyrrol-1-yl)pyridin-2(1H)-one |
| 69 | 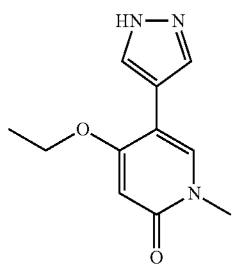 [SMILES: CCOc1cc(=O)n(C)cc1-c1cn[nH]c1] | 4-ethoxy-1-methyl-5-(1H-pyrazol-4-yl)pyridin-2(1H)-one |
| 70 | 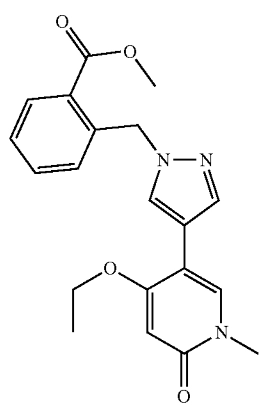 [SMILES: CCOc1cc(=O)n(C)cc1-c1cnn(Cc2ccccc2C(=O)OC)c1] | methyl-2-((4-(4-ethoxy-1-methyl-6-oxo-1,6-dihydropyridin-3-yl)-1H-pyrazol-1-yl)methyl)benzoate |
| 71 | 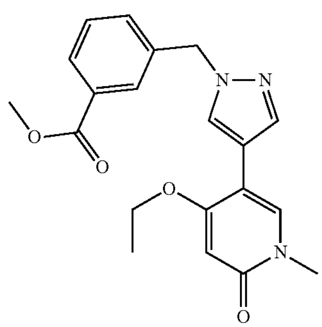 | methyl 3-((4-(4-ethoxy-1-methyl-6-oxo-1,6-dihydropyridin-3-yl)-1H-pyrazol-1-yl)methyl)benzoate |

TABLE 1-continued

| Example | Structure | Name |
|---|---|---|
| 72 | 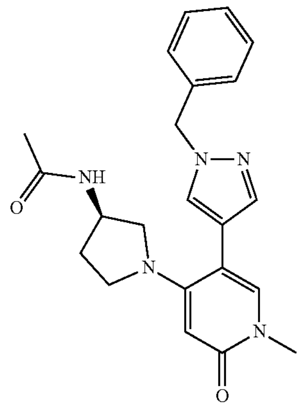 [SMILES: CC(=O)N[C@@H]1CCN(c2cc(=O)n(C)cc2-c2cnn(Cc3ccccc3)c2)C1] | (R)-N-(1-(5-(1-benzyl-1H-pyrazol-4-yl)-1-methyl-2-oxo-1,2-dihydropyridin-4-yl)pyrrolidin-3-yl)acetamide |
| 73 | 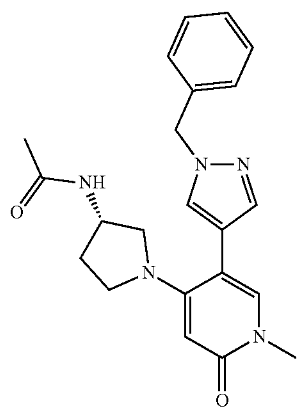 [SMILES: CC(=O)N[C@H]1CCN(c2cc(=O)n(C)cc2-c2cnn(Cc3ccccc3)c2)C1] | (S)-N-(1-(5-(1-benzyl-1H-pyrazol-4-yl)-1-methyl-2-oxo-1,2-dihydropyridin-4-yl)pyrrolidin-3-yl)acetamide |
| 74 | 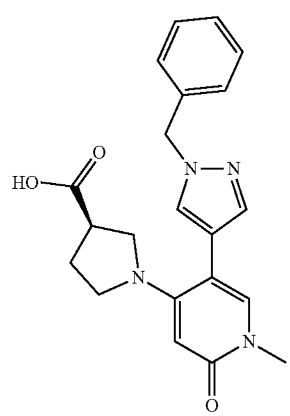 [SMILES: Cn1cc(-c2cnn(Cc3ccccc3)c2)c(N2CC[C@@H](C(=O)O)C2)cc1=O] | (R)-1-(5-(1-benzyl-1H-pyrazol-4-yl)-1-methyl-2-oxo-1,2-dihydropyridin-4-yl)pyrrolidine-3-carboxylic acid |

TABLE 1-continued

| Example | Structure | Name |
| --- | --- | --- |
| 75 | 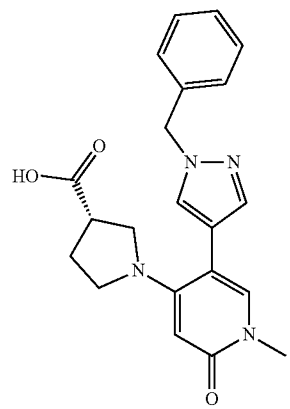 [SMILES: Cn1cc(-c2cnn(Cc3ccccc3)c2)c(N2CC[C@H](C(=O)O)C2)cc1=O] | (S)-1-(5-(1-benzyl-1H-pyrazol-4-yl)-1-methyl-2-oxo-1,2-dihydropyridin-4-yl)pyrrolidine-3-carboxylic acid |
| 76 | 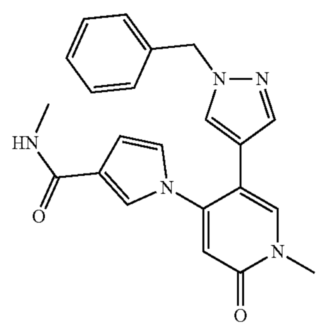 [SMILES: CNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-1H-pyrrole-3-carboxamide |
| 77 | 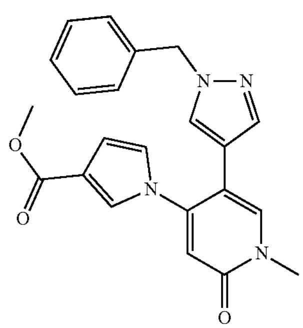 [SMILES: COC(=O)c1ccn(-c2cc(=O)n(C)cc2-c2cnn(Cc3ccccc3)c2)c1] | methyl 1-(5-(1-benzyl-1H-pyrazol-4-yl)-1-methyl-2-oxo-1,2-dihydropyridin-4-yl)-1H-pyrrole-3-carboxylate |
| 78 | 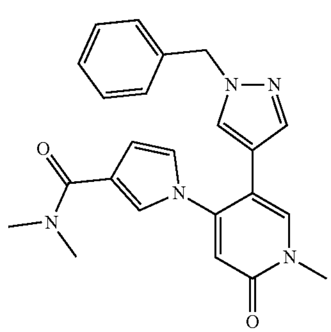 | 1-(5-(1-benzyl-1H-pyrazol-4-yl)-1-methyl-2-oxo-1,2-dihydropyridin-4-yl)-N,N-dimethyl-1H-pyrrole-3-carboxamide |

TABLE 1-continued

| Example | Structure | Name |
|---|---|---|
| 79 | 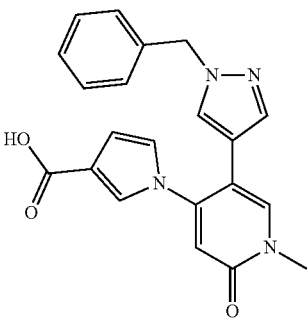 [SMILES: Cn1cc(-c2cnn(Cc3ccccc3)c2)c(-n2ccc(C(=O)O)c2)cc1=O] | 1-(5-(1-benzyl-1H-pyrazol-4-yl)-1-methyl-2-oxo-1,2-dihydropyridin-4-yl)-1H-pyrrole-3-carboxylic acid |
| 80 | 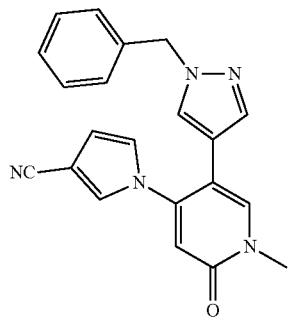 | 1-(5-(1-benzyl-1H-pyrazol-4-yl)-1-methyl-2-oxo-1,2-dihydropyridin-4-yl)-1H-pyrrole-3-carbonitrile |
| 81 | 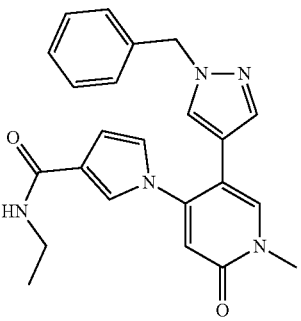 [SMILES: CCNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-N-ethyl-1H-pyrrole-3-carboxamide |
| 82 | 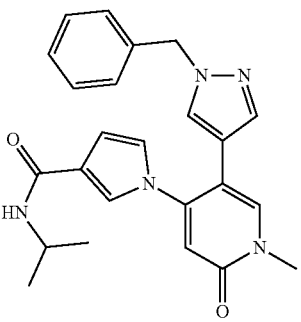 [SMILES: CC(C)NC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-N-isopropyl-1H-pyrrole-3-carboxamide |
| 83 | 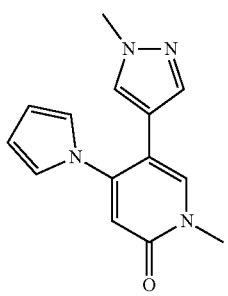 [SMILES: Cn1cc(-c2cn(C)c(=O)cc2-n2cccc2)cn1] | 1-methyl-5-(1-methyl-1H-pyrazol-4-yl)-4-(1H-pyrrol-1-yl)pyridin-2(1H)-one |

TABLE 1-continued

| Example | Structure | Name |
|---|---|---|
| 84 | 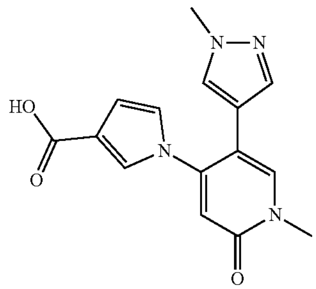 [SMILES: Cn1cc(-c2cn(C)c(=O)cc2-n2ccc(C(=O)O)c2)cn1] | 1-(1-methyl-5-(1-methyl-1H-pyrazol-4-yl)-2-oxo-1,2-dihydropyridin-4-yl)-1H-pyrrole-3-carboxylic acid |
| 85 | 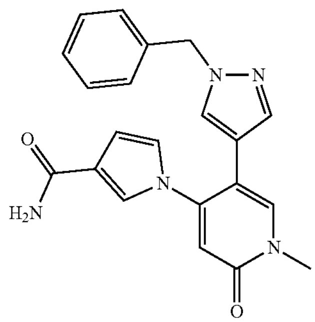 [SMILES: Cn1cc(-c2cnn(Cc3ccccc3)c2)c(-n2ccc(C(N)=O)c2)cc1=O] | 1-(5-(1-benzyl-1H-pyrazol-4-yl)-1-methyl-2-oxo-1,2-dihydropyridin-4-yl)-1H-pyrrole-3-carboxamide |
| 86 | 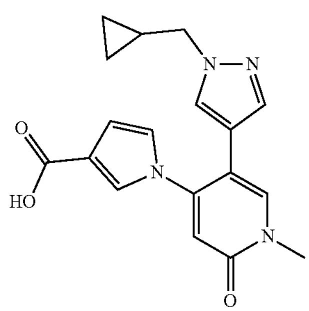 [SMILES: Cn1cc(-c2cnn(CC3CC3)c2)c(-n2ccc(C(=O)O)c2)cc1=O] | 1-(5-(1-(cyclopropylmethyl)-1H-pyrazol-4-yl)-1-methyl-2-oxo-1,2-dihydropyridin-4-yl)-1H-pyrrole-3-carboxylic acid |
| 87 | 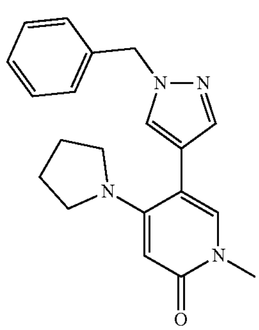 [SMILES: Cn1cc(-c2cnn(Cc3ccccc3)c2)c(N2CCCC2)cc1=O] | 5-(1-Benzyl-1H-pyrazol-4-yl)-1-methyl-4-pyrrolidin-1-yl-1H-pyridin-2-one |

TABLE 1-continued

| Example | Structure | Name |
|---|---|---|
| 88 | 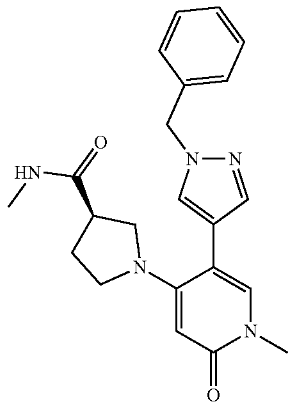 | N-{2-[5-(1-Benzyl-1H-pyrazol-4-yl)-1-methyl-2-oxo-1,2-dihydro-pyridin-4-yl]-cyclopentyl}-acetamide |
| 89 | 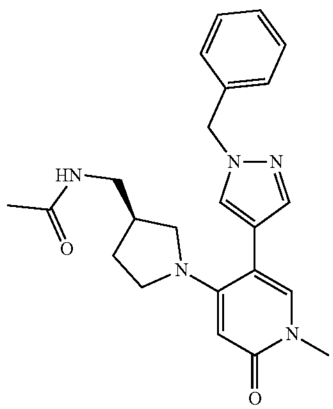 [SMILES: CC(=O)NC[C@@H]1CCN(c2cc(=O)n(C)cc2-c2cnn(Cc3ccccc3)c2)C1] | N-{1-[5-(1-Benzyl-1H-pyrazol-4-yl)-1-methyl-2-oxo-1,2-dihydro-pyridin-4-yl]-pyrrolidin-3-ylmethyl}-acetamide |
| 90 | 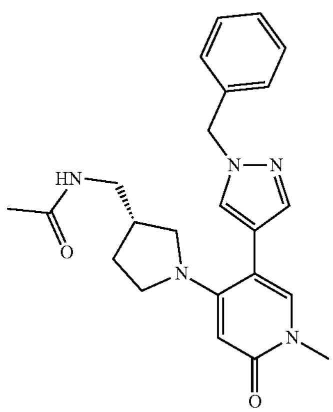 [SMILES: CC(=O)NC[C@H]1CCN(c2cc(=O)n(C)cc2-c2cnn(Cc3ccccc3)c2)C1] | N-{1-[5-(1-Benzyl-1H-pyrazol-4-yl)-1-methyl-2-oxo-1,2-dihydro-pyridin-4-yl]-pyrrolidin-3-ylmethyl}-acetamide |
| 91 | 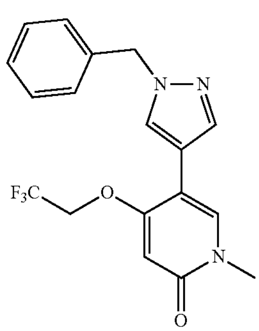 [SMILES: Cn1cc(-c2cnn(Cc3ccccc3)c2)c(OCC(F)(F)F)cc1=O] | 5-(1-benzyl-1H-pyrazol-4-yl)-1-methyl-4-(2,2,2-trifluoroethoxy)pyridin-2(1H)-one |

TABLE 1-continued

| Example | Structure | Name |
|---|---|---|
| 92 | 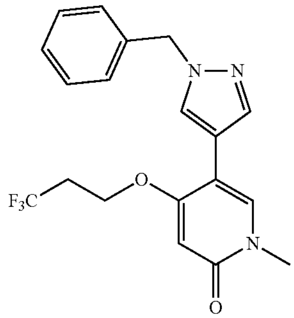 [SMILES: Cn1cc(-c2cnn(Cc3ccccc3)c2)c(OCCC(F)(F)F)cc1=O] | 5-(1-benzyl-1H-pyrazol-4-yl)-1-methyl-4-(3,3,3-trifluoropropoxy)pyridin-2(1H)-one |
| 93 | 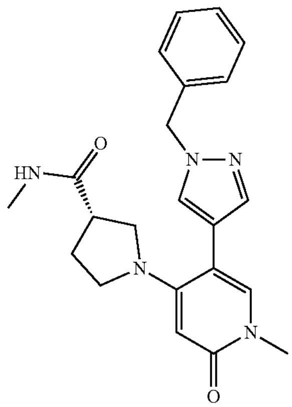 | 1-[5-(1-Benzyl-1H-pyrazol-4-yl)-1-methyl-2-oxo-1,2-dihydro-pyridin-4-yl]-pyrrolidine-3-methylacetamide |
| 94 | 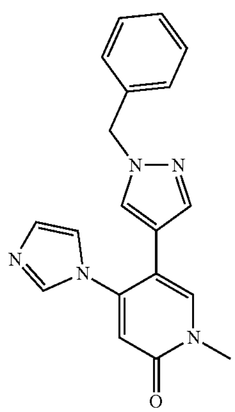 [SMILES: Cn1cc(-c2cnn(Cc3ccccc3)c2)c(-n2ccnc2)cc1=O] | 5-(1-benzyl-1H-pyrazol-4-yl)-4-(1H-imidazol-1-yl)-1-methylpyridin-2(1H)-one |
| 95 | 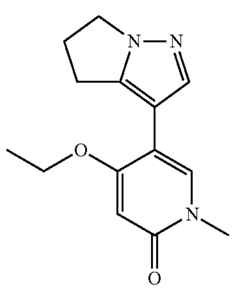 [SMILES: CCOc1cc(=O)n(C)cc1-c1cnn2c1CCC2] | 5-(5,6-dihydro-4H-pyrrolo[1,2-b]pyrazol-3-yl)-4-ethoxy-1-methylpyridin-2(1H)-one |

TABLE 1-continued

| Example | Structure | Name |
|---|---|---|
| 96 | 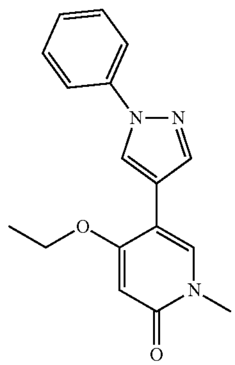 | 4-ethoxy-1-methyl-5-(1-phenyl-1H-pyrazol-4-yl)pyridin-2(1H)-one |
| 97 | 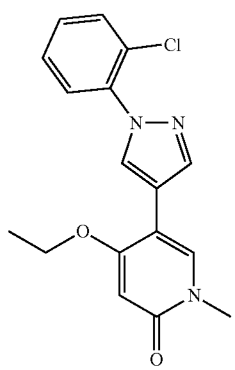 | 5-(1-(2-chlorophenyl)-1H-pyrazol-4-yl)-4-ethoxy-1-methylpyridin-2(1H)-one |
| 98 | 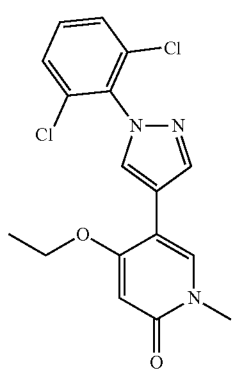 [SMILES: CCOc1cc(=O)n(C)cc1-c1cnn(-c2c(Cl)cccc2Cl)c1] | 5-(1-(2,6-dichlorophenyl)-1H-pyrazol-4-yl)-4-ethoxy-1-methylpyridin-2(1H)-one |
| 99 | 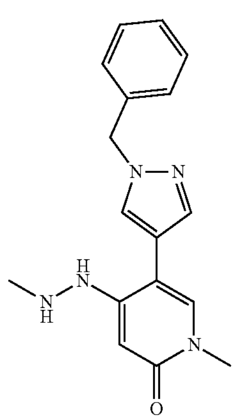 | 5-(1-benzyl-1H-pyrazol-4-yl)-1-methyl-4-(2-methylhydrazinyl)pyridin-2(1H)-one |

TABLE 1-continued

| Example | Structure | Name |
|---|---|---|
| 100 | 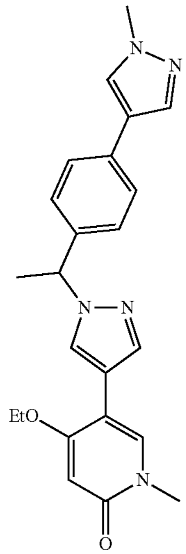 [SMILES: CCOc1cc(=O)n(C)cc1-c1cnn(C(C)c2ccc(-c3cnn(C)c3)cc2)c1] | 4-ethoxy-1-methyl-5-(1-{1-[4-(1-methyl-1H-pyrazol-4-yl)-phenyl]-ethyl}-1H-pyrazol-4-yl)-1H-pyridin-2-one |
| 101 | 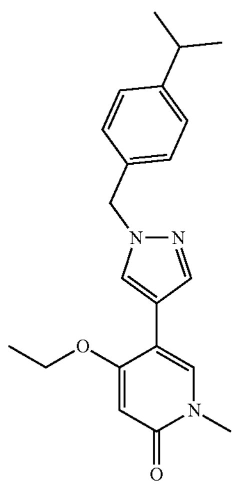 [SMILES: CCOc1cc(=O)n(C)cc1-c1cnn(Cc2ccc(C(C)C)cc2)c1] | 4-Ethoxy-5-[1-(4-isopropyl-benzyl)-1H-pyrazol-4-yl]-1-methyl-1H-pyridin-2-one |
| 102 | 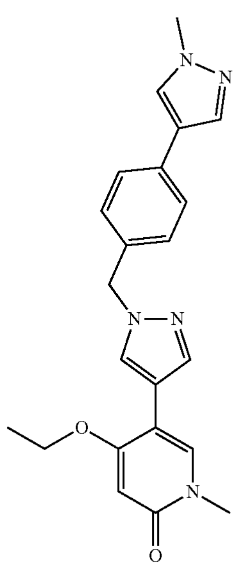 [SMILES: CCOc1cc(=O)n(C)cc1-c1cnn(Cc2ccc(-c3cnn(C)c3)cc2)c1] | 4-ethoxy-1-methyl-5-(1-(4-(1-methyl-1H-pyrazol-4-yl)benzyl)-1H-pyrazol-4-yl)pyridin-2(1H)-one |

TABLE 1-continued

| Example | Structure | Name |
| --- | --- | --- |
| 103 | 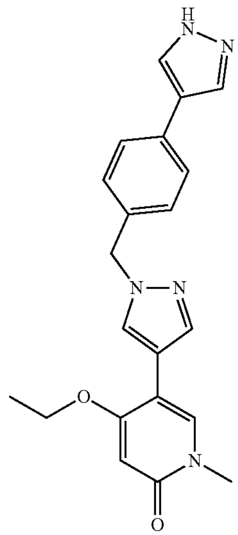 [SMILES: CCOc1cc(=O)n(C)cc1-c1cnn(Cc2ccc(-c3cn[nH]c3)cc2)c1] | 5-(1-(4-(1H-pyrazol-4-yl)benzyl)-1H-pyrazol-4-yl)-4-ethoxy-1-methylpyridin-2(1H)-one |
| 104 | 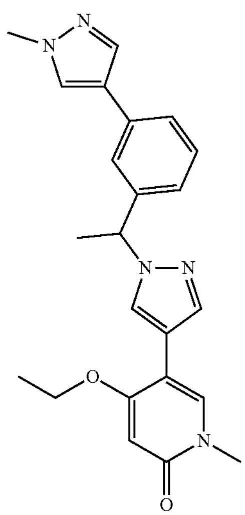 | 4-ethoxy-1-methyl-5-(1-(1-(3-(1-methyl-1H-pyrazol-4-yl)phenyl)ethyl)-1H-pyrazol-4-yl)pyridin-2(1H)-one |
| 105 | 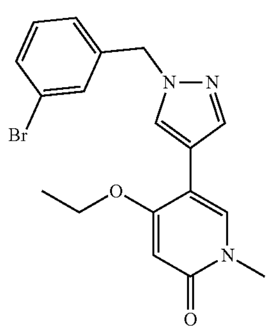 [SMILES: CCOc1cc(=O)n(C)cc1-c1cnn(Cc2cccc(Br)c2)c1] | 5-(1-(3-bromobenzyl)-1H-pyrazol-4-yl)-4-ethoxy-1-methylpyridin-2(1H)-one |

TABLE 1-continued

| Example | Structure | Name |
| --- | --- | --- |
| 106 | 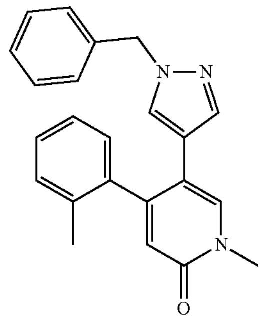 [SMILES: Cc1ccccc1-c1cc(=O)n(C)cc1-c1cnn(Cc2ccccc2)c1] | 5-(1-benzyl-1H-pyrazol-4-yl)-1-methyl-4-(o-tolyl)pyridin-2(1H)-one |
| 107 | 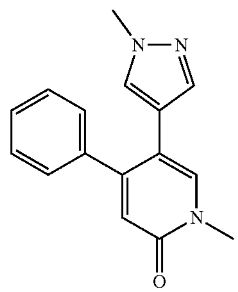 [SMILES: Cn1cc(-c2cn(C)c(=O)cc2-c2ccccc2)cn1] | 1-methyl-5-(1-methyl-1H-pyrazol-4-yl)-4-phenylpyridin-2(1H)-one |
| 108 | 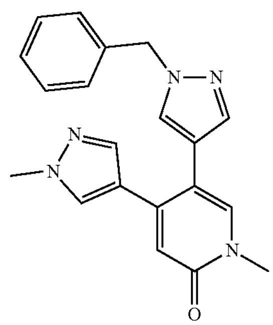 | 5-(1-benzyl-1H-pyrazol-4-yl)-1-methyl-4-(1-methyl-1H-pyrazol-4-yl)pyridin-2(1H)-one |
| 109 | 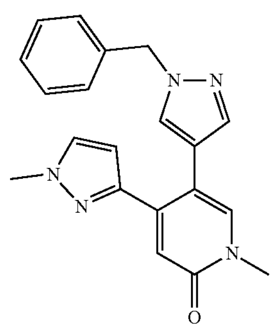 | 5-(1-benzyl-1H-pyrazol-4-yl)-1-methyl-4-(1-methyl-1H-pyrazol-3-yl)pyridin-2(1H)-one |
| 110 | 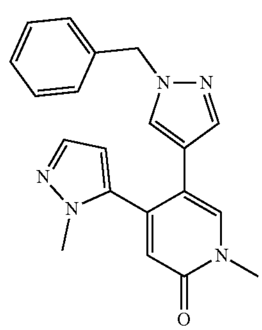 [SMILES: Cn1nccc1-c1cc(=O)n(C)cc1-c1cnn(Cc2ccccc2)c1] | 5-(1-benzyl-1H-pyrazol-4-yl)-1-methyl-4-(1-methyl-1H-pyrazol-5-yl)pyridin-2(1H)-one |

TABLE 1-continued
| Example | Structure | Name |
|---|---|---|
| 111 | 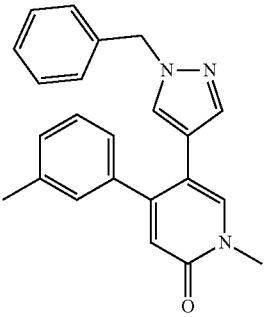 | 5-(1-benzyl-1H-pyrazol-4-yl)-1-methyl-4-(m-tolyl)pyridin-2(1H)-one |
| 112 | 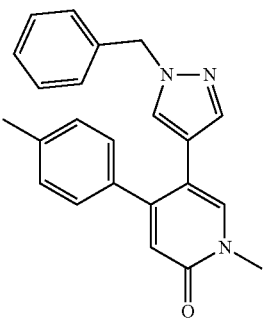 | 5-(1-benzyl-1H-pyrazol-4-yl)-1-methyl-4-(p-tolyl)pyridin-2(1H)-one |
| 113 | 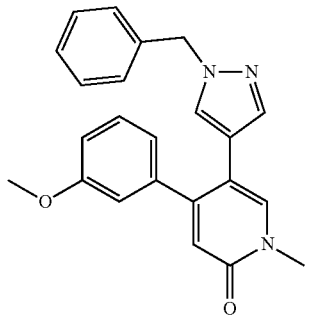 | 5-(1-benzyl-1H-pyrazol-4-yl)-4-(3-methoxyphenyl)-1-methylpyridin-2(1H)-one |
| 114 | 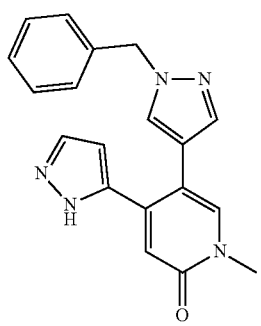 | 5-(1-benzyl-1H-pyrazol-4-yl)-1-methyl-4-(1H-pyrazol-5-yl)pyridin-2(1H)-one |

TABLE 1-continued

| Example | Structure | Name |
|---|---|---|
| 115 | 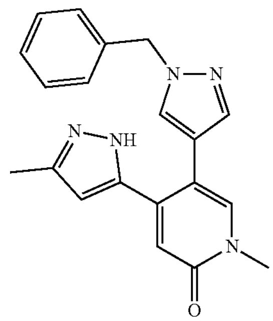 | 5-(1-benzyl-1H-pyrazol-4-yl)-1-methyl-4-(3-methyl-1H-pyrazol-5-yl)pyridin-2(1H)-one |
| 116 | 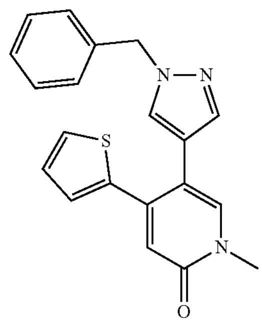 [SMILES: Cn1cc(-c2cnn(Cc3ccccc3)c2)c(-c2cccs2)cc1=O] | 5-(1-benzyl-1H-pyrazol-4-yl)-1-methyl-4-(thiophen-2-yl)pyridin-2(1H)-one |
| 117 | 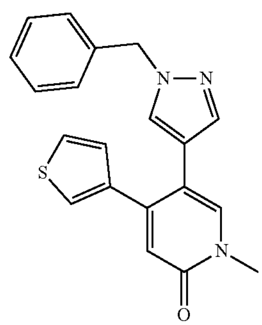 | 5-(1-benzyl-1H-pyrazol-4-yl)-1-methyl-4-(thiophen-3-yl)pyridin-2(1H)-one |
| 118 | 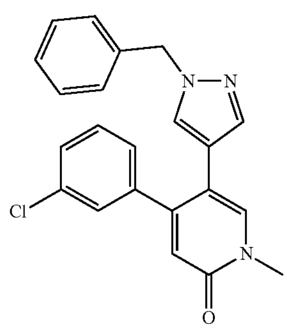 [SMILES: Cn1cc(-c2cnn(Cc3ccccc3)c2)c(-c2cccc(Cl)c2)cc1=O] | 5-(1-benzyl-1H-pyrazol-4-yl)-4-(3-chlorophenyl)-1-methylpyridin-2(1H)-one |
| 119 | 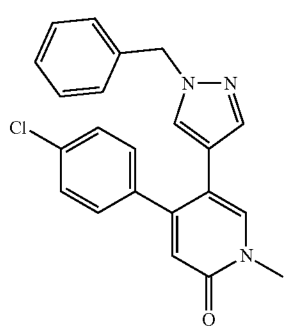 [SMILES: Cn1cc(-c2cnn(Cc3ccccc3)c2)c(-c2ccc(Cl)cc2)cc1=O] | 5-(1-benzyl-1H-pyrazol-4-yl)-4-(4-chlorophenyl)-1-methylpyridin-2(1H)-one |

TABLE 1-continued

| Example | Structure | Name |
|---|---|---|
| 120 | 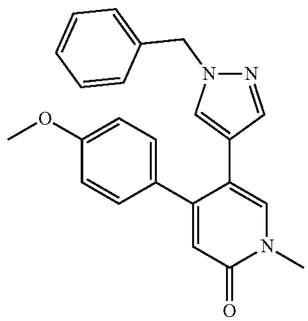 | 5-(1-benzyl-1H-pyrazol-4-yl)-4-(4-methoxyphenyl)-1-methylpyridin-2(1H)-one |
| 121 | 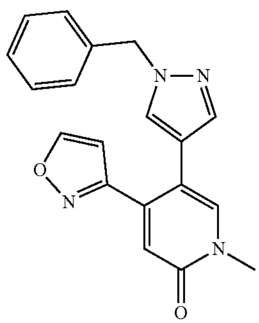 [SMILES: Cn1cc(-c2cnn(Cc3ccccc3)c2)c(-c2ccon2)cc1=O] | 5-(1-benzyl-1H-pyrazol-4-yl)-4-(isoxazol-3-yl)-1-methylpyridin-2(1H)-one |
| 122 | 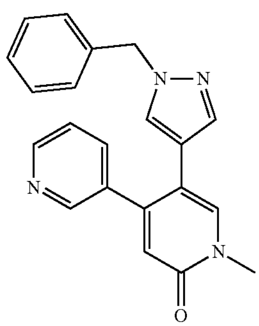 [SMILES: Cn1cc(-c2cnn(Cc3ccccc3)c2)c(-c2cccnc2)cc1=O] | 5'-(1-benzyl-1H-pyrazol-4-yl)-1'-methyl-[3,4'-bipyridin]-2'(1'H)-one |
| 123 | 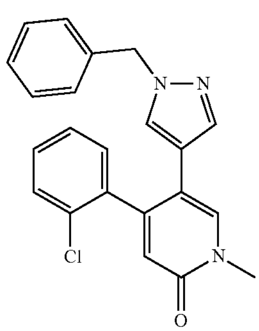 [SMILES: Cn1cc(-c2cnn(Cc3ccccc3)c2)c(-c2ccccc2Cl)cc1=O] | 5-(1-benzyl-1H-pyrazol-4-yl)-4-(2-chlorophenyl)-1-methylpyridin-2(1H)-one |

TABLE 1-continued

| Example | Structure | Name |
|---|---|---|
| 124 | 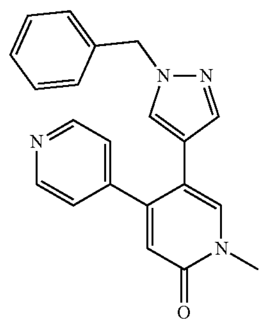 [SMILES: Cn1cc(-c2cnn(Cc3ccccc3)c2)c(-c2ccncc2)cc1=O] | 5-(1-benzyl-1H-pyrazol-4-yl)-1-methyl-[4,4'-bipyridin]-2(1H)-one |
| 125 | 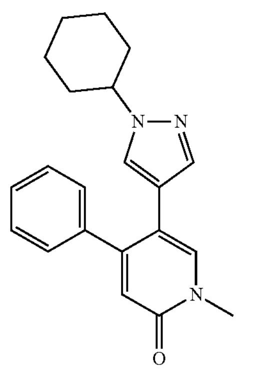 [SMILES: Cn1cc(-c2cnn(C3CCCCC3)c2)c(-c2ccccc2)cc1=O] | 5-(1-cyclohexyl-1H-pyrazol-4-yl)-1-methyl-4-phenylpyridin-2(1H)-one |
| 126 | 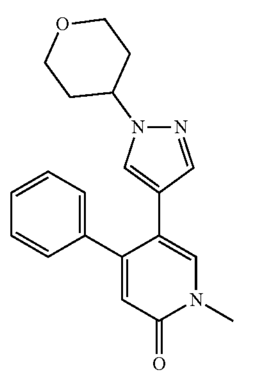 [SMILES: Cn1cc(-c2cnn(C3CCOCC3)c2)c(-c2ccccc2)cc1=O] | 1-methyl-4-phenyl-5-(1-(tetrahydro-2H-pyran-4-yl)-1H-pyrazol-4-yl)pyridin-2(1H)-one |
| 127 | 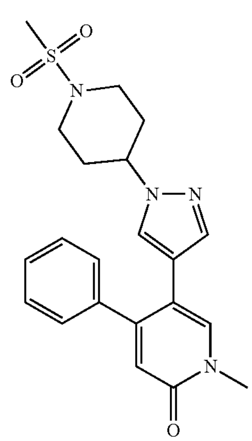 [SMILES: Cn1cc(-c2cnn(C3CCN(S(C)(=O)=O)CC3)c2)c(-c2ccccc2)cc1=O] | 1-methyl-5-(1-(1-(methylsulfonyl)piperidin-4-yl)-1H-pyrazol-4-yl)-4-phenylpyridin-2(1H)-one |

TABLE 1-continued

| Example | Structure | Name |
|---|---|---|
| 128 | 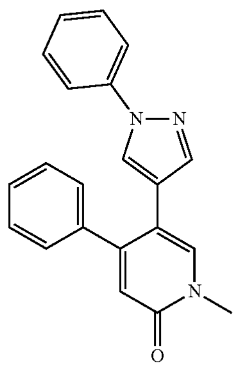 [SMILES: Cn1cc(-c2cnn(-c3ccccc3)c2)c(-c2ccccc2)cc1=O] | 1-methyl-4-phenyl-5-(1-phenyl-1H-pyrazol-4-yl)pyridin-2(1H)-one |
| 129 | 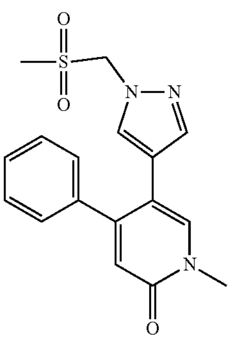 [SMILES: Cn1cc(-c2cnn(CS(C)(=O)=O)c2)c(-c2ccccc2)cc1=O] | 1-methyl-5-(1-((methylsulfonyl)methyl)-1H-pyrazol-4-yl)-4-phenylpyridin-2(1H)-one |
| 130 | 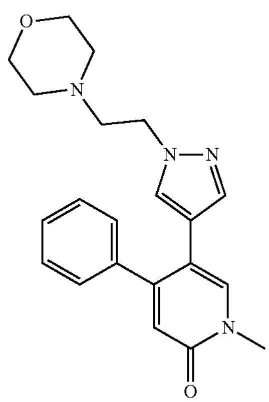 [SMILES: Cn1cc(-c2cnn(CCN3CCOCC3)c2)c(-c2ccccc2)cc1=O] | 1-methyl-5-(1-(2-morpholinoethyl)-1H-pyrazol-4-yl)-4-phenylpyridin-2(1H)-one |
| 131 | 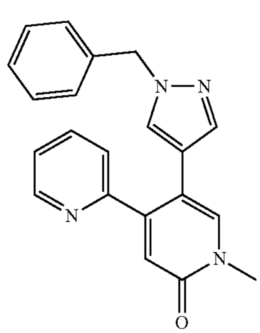 [SMILES: Cn1cc(-c2cnn(Cc3ccccc3)c2)c(-c2ccccn2)cc1=O] | 5'-(1-benzyl-1H-pyrazol-4-yl)-1'-methyl-[2,4'-bipyridin]-2'(1'H)-one |

TABLE 1-continued

| Example | Structure | Name |
|---|---|---|
| 132 | 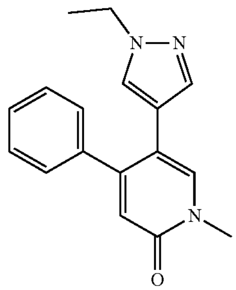 | 5-(1-ethyl-1H-pyrazol-4-yl)-1-methyl-4-phenylpyridin-2(1H)-one |
| 133 | 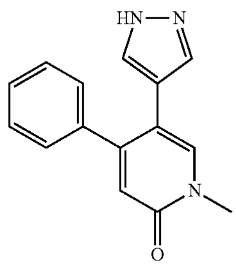 [SMILES: Cn1cc(-c2cn[nH]c2)c(-c2ccccc2)cc1=O] | 1-methyl-4-phenyl-5-(1H-pyrazol-4-yl)pyridin-2(1H)-one |
| 134 | 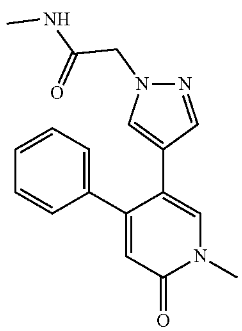 | N-methyl-2-(4-(1-methyl-6-oxo-4-phenyl-1,6-dihydro-pyridin-3-yl)-1H-pyrazol-1-yl)acetamide |
| 135 | 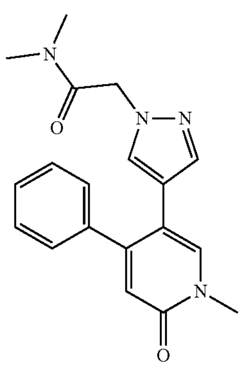 | N,N-dimethyl-2-(4-(1-methyl-6-oxo-4-phenyl-1,6-dihydropyridin-3-yl)-1H-pyrazol-1-yl)acetamide |
| 136 | 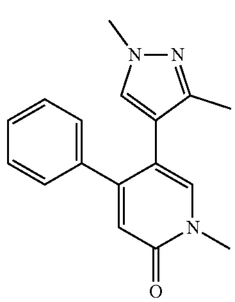 [SMILES: Cc1nn(C)cc1-c1cn(C)c(=O)cc1-c1ccccc1] | 5-(1,3-dimethyl-1H-pyrazol-4-yl)-1-methyl-4-phenylpyridin-2(1H)-one |

TABLE 1-continued

| Example | Structure | Name |
|---|---|---|
| 137 | 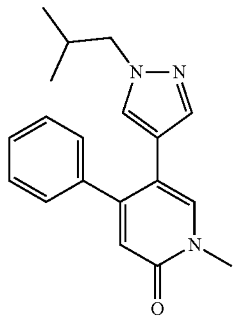 [SMILES: CC(C)Cn1cc(-c2cn(C)c(=O)cc2-c2ccccc2)cn1] | 5-(1-isobutyl-1H-pyrazol-4-yl)-1-methyl-4-phenylpyridin-2(1H)-one |
| 138 | 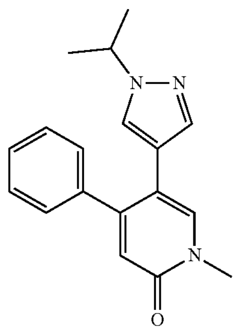 [SMILES: CC(C)n1cc(-c2cn(C)c(=O)cc2-c2ccccc2)cn1] | 5-(1-isopropyl-1H-pyrazol-4-yl)-1-methyl-4-phenylpyridin-2(1H)-one |
| 139 | 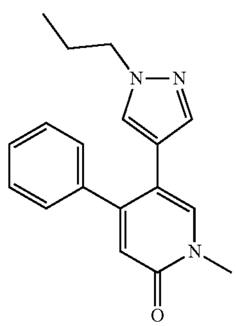 [SMILES: CCCn1cc(-c2cn(C)c(=O)cc2-c2ccccc2)cn1] | 1-methyl-4-phenyl-5-(1-propyl-1H-pyrazol-4-yl)pyridin-2(1H)-one |
| 140 | 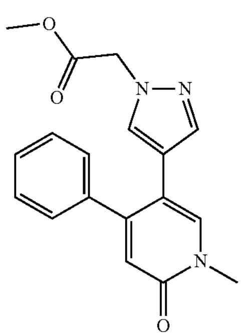 | methyl 2-(4-(1-methyl-6-oxo-4-phenyl-1,6-dihydropyridin-3-yl)-1H-pyrazol-1-yl)acetate |

TABLE 1-continued
| Example | Structure | Name |
|---|---|---|
| 141 | 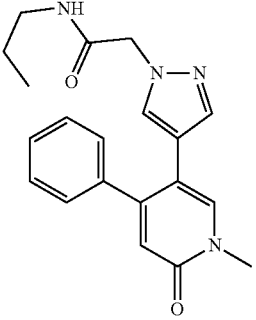 [SMILES: CCCNC(=O)Cn1cc(-c2cn(C)c(=O)cc2-c2ccccc2)cn1] | 2-(4-(1-methyl-6-oxo-4-phenyl-1,6-dihydropyridin-3-yl)-1H-pyrazol-1-yl)-N-propylacetamide |
| 142 | 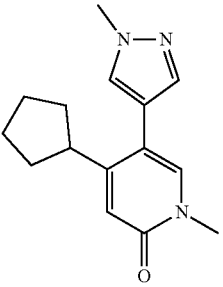 [SMILES: Cn1cc(-c2cn(C)c(=O)cc2C2CCCC2)cn1] | 4-cyclopentyl-1-methyl-5-(1-methyl-1H-pyrazol-4-yl)pyridin-2(1H)-one |
| 143 | 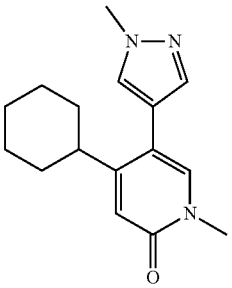 [SMILES: Cn1cc(-c2cn(C)c(=O)cc2C2CCCCC2)cn1] | 4-cyclohexyl-1-methyl-5-(1-methyl-1H-pyrazol-4-yl)pyridin-2(1H)-one |
| 144 | 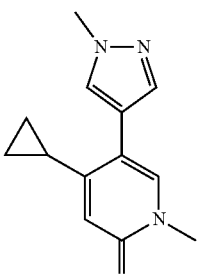 | 4-cyclopropyl-1-methyl-5-(1-methyl-1H-pyrazol-4-yl)pyridin-2(1H)-one |
| 145 | 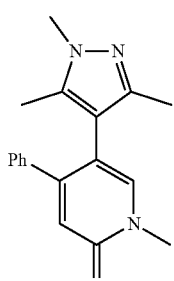 | 1-methyl-4-phenyl-5-(1,3,5-trimethyl-1H-pyrazol-4-yl)pyridin-2(1H)-one |

TABLE 1-continued

| Example | Structure | Name |
|---|---|---|
| 146 | 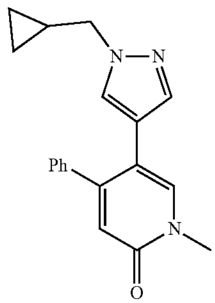 [SMILES: Cn1cc(-c2cnn(CC3CC3)c2)c(-c2ccccc2)cc1=O] | 5-(1-(cyclopropylmethyl)-1H-pyrazol-4-yl)-1-methyl-4-phenylpyridin-2(1H)-one |
| 147 | 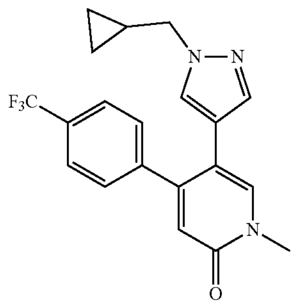 [SMILES: Cn1cc(-c2cnn(CC3CC3)c2)c(-c2ccc(C(F)(F)F)cc2)cc1=O] | 5-(1-Cyclopropylmethyl-1H-pyrazol-4-yl)-1-methyl-4-(4-trifluoromethyl-phenyl)-1H-pyridin-2-one |
| 148 | 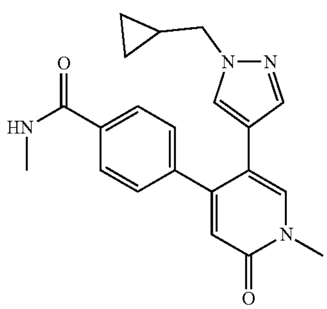 [SMILES: CNC(=O)c1ccc(-c2cc(=O)n(C)cc2-c2cnn(CC3CC3)c2)cc1] | 4-[5-(1-Cyclopropylmethyl-1H-pyrazol-4-yl)-1-methyl-2-oxo-1,2-dihydro-pyridin-4-yl]-N-methyl-benzamide |
| 149 | 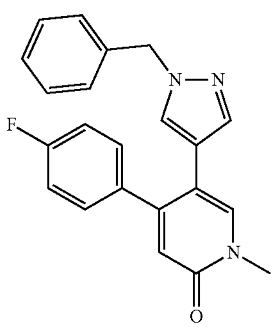 [SMILES: Cn1cc(-c2cnn(Cc3ccccc3)c2)c(-c2ccc(F)cc2)cc1=O] | 5-(1-benzyl-1H-pyrazol-4-yl)-4-(4-fluorophenyl)-1-methylpyridin-2(1H)-one |
| 150 | 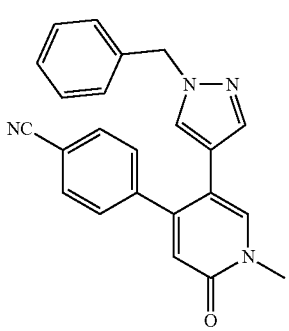 [SMILES: Cn1cc(-c2cnn(Cc3ccccc3)c2)c(-c2ccc(C#N)cc2)cc1=O] | 4-(5-(1-benzyl-1H-pyrazol-4-yl)-1-methyl-2-oxo-1,2-dihydropyridin-4-yl)benzonitrile |

TABLE 1-continued

| Example | Structure | Name |
|---|---|---|
| 151 | 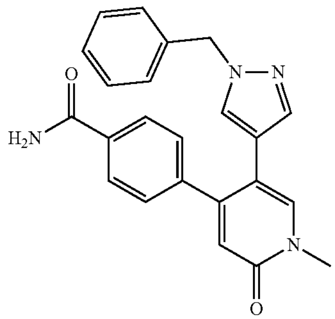 [SMILES: Cn1cc(-c2cnn(Cc3ccccc3)c2)c(-c2ccc(C(N)=O)cc2)cc1=O] | 4-(5-(1-benzyl-1H-pyrazol-4-yl)-1-methyl-2-oxo-1,2-dihydropyridin-4-yl)benzamide |
| 152 | 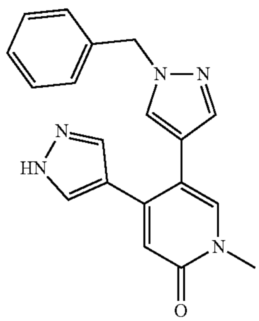 [SMILES: Cn1cc(-c2cnn(Cc3ccccc3)c2)c(-c2cn[nH]c2)cc1=O] | 5-(1-benzyl-1H-pyrazol-4-yl)-1-methyl-4-(1H-pyrazol-4-yl)pyridin-2(1H)-one |
| 153 | 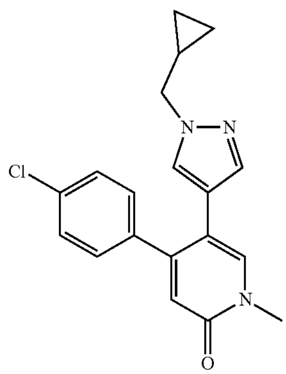 [SMILES: Cn1cc(-c2cnn(CC3CC3)c2)c(-c2ccc(Cl)cc2)cc1=O] | 4-(4-Chloro-phenyl)-5-(1-cyclopropylmethyl-1H-pyrazol-4-yl)-1-methyl-1H-pyridin-2-one |
| 154 | 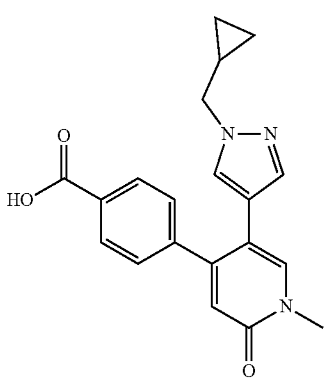 [SMILES: Cn1cc(-c2cnn(CC3CC3)c2)c(-c2ccc(C(=O)O)cc2)cc1=O] | 4-[5-(1-Cyclopropylmethyl-1H-pyrazol-4-yl)-1-methyl-2-oxo-1,2-dihydro-pyridin-4-yl]-benzoic acid |

TABLE 1-continued

| Example | Structure | Name |
|---|---|---|
| 155 | 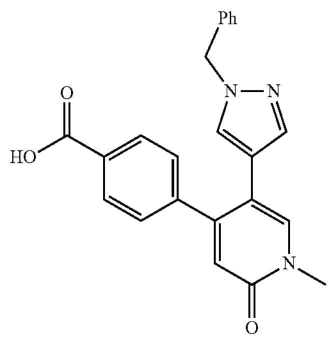 [SMILES: Cn1cc(-c2cnn(Cc3ccccc3)c2)c(-c2ccc(C(=O)O)cc2)cc1=O] | 4-(5-(1-benzyl-1H-pyrazol-4-yl)-1-methyl-2-oxo-1,2-dihydropyridin-4-yl)benzoic acid |
| 156 | 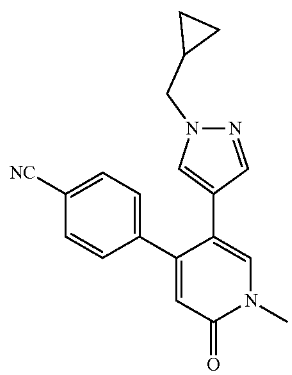 [SMILES: Cn1cc(-c2cnn(CC3CC3)c2)c(-c2ccc(C#N)cc2)cc1=O] | 4-[5-(1-Cyclopropylmethyl-1H-pyrazol-4-yl)-1-methyl-2-oxo-1,2-dihydro-pyridin-4-yl]-benzonitrile |
| 157 | 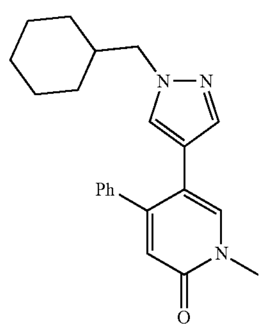 [SMILES: Cn1cc(-c2cnn(CC3CCCCC3)c2)c(-c2ccccc2)cc1=O] | 5-(1-(cyclohexylmethyl)-1H-pyrazol-4-yl)-1-methyl-4-phenylpyridin-2(1H)-one |
| 158 | 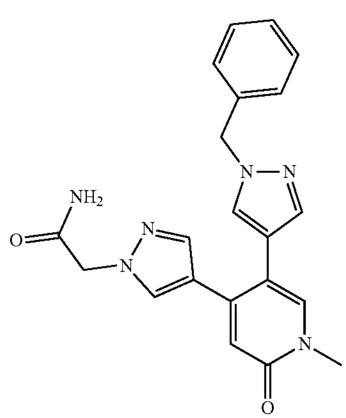 [SMILES: Cn1cc(-c2cnn(Cc3ccccc3)c2)c(-c2cnn(CC(N)=O)c2)cc1=O] | 2-(4-(5-(1-benzyl-1H-pyrazol-4-yl)-1-methyl-2-oxo-1,2-dihydropyridin-4-yl)-1H-pyrazol-1-yl)acetamide |

TABLE 1-continued

| Example | Structure | Name |
|---|---|---|
| 159 | 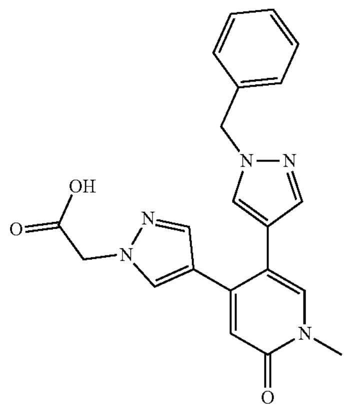 | 2-(4-(5-(1-benzyl-1H-pyrazol-4-yl)-1-methyl-2-oxo-1,2-dihydropyridin-4-yl)-1H-pyrazol-1-yl)acetic acid |
| 160 | 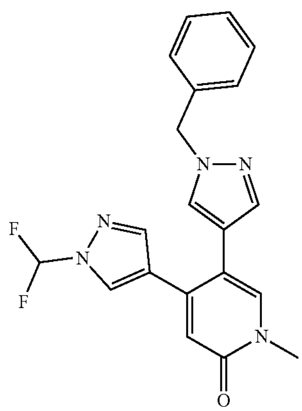 [SMILES: Cn1cc(-c2cnn(Cc3ccccc3)c2)c(-c2cnn(C(F)F)c2)cc1=O] | 5-(1-benzyl-1H-pyrazol-4-yl)-4-(1-(difluoromethyl)-1H-pyrazol-4-yl)-1-methylpyridin-2(1H)-one |
| 161 | 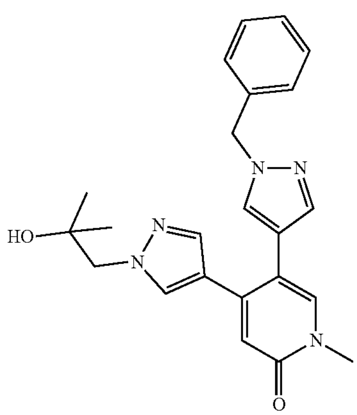 [SMILES: Cn1cc(-c2cnn(Cc3ccccc3)c2)c(-c2cnn(CC(C)(C)O)c2)cc1=O] | 5-(1-benzyl-1H-pyrazol-4-yl)-4-(1-(2-hydroxy-2-methylpropyl)-1H-pyrazol-4-yl)-1-methylpyridin-2(1H)-one |
| 162 | 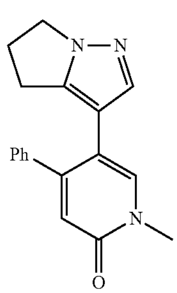 [SMILES: Cn1cc(-c2cnn3c2CCC3)c(-c2ccccc2)cc1=O] | 5-(5,6-dihydro-4H-pyrrolo[1,2-b]pyrazol-3-yl)-1-methyl-4-phenylpyridin-2(1H)-one |

TABLE 1-continued

| Example | Structure | Name |
|---|---|---|
| 163 | 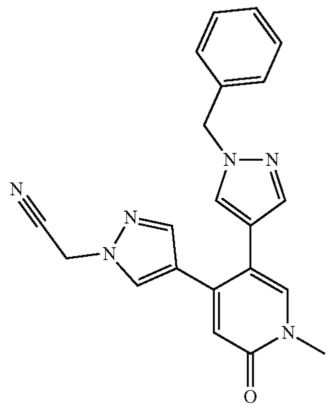 [SMILES: Cn1cc(-c2cnn(Cc3ccccc3)c2)c(-c2cnn(CC#N)c2)cc1=O] | 2-(4-(5-(1-benzyl-1H-pyrazol-4-yl)-1-methyl-2-oxo-1,2-dihydropyridin-4-yl)-1H-pyrazol-1-yl)acetonitrile |
| 164 | 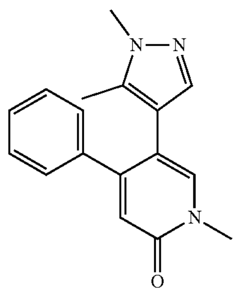 [SMILES: Cc1c(-c2cn(C)c(=O)cc2-c2ccccc2)cnn1C] | 5-(1,5-dimethyl-1H-pyrazol-4-yl)-1-methyl-4-phenylpyridin-2(1H)-one |
| 165 | 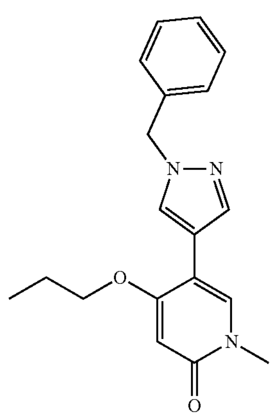 [SMILES: CCCOc1cc(=O)n(C)cc1-c1cnn(Cc2ccccc2)c1] | 5-(1-Benzyl-1H-pyrazol-4-yl)-1-methyl-4-propoxy-1H-pyridin-2-one |
| 166 | 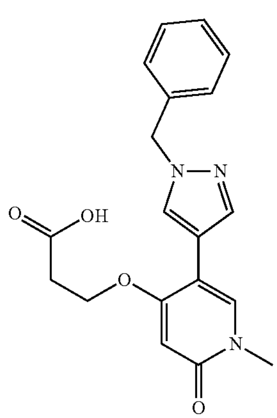 [SMILES: Cn1cc(-c2cnn(Cc3ccccc3)c2)c(OCCC(=O)O)cc1=O] | 3-[5-(1-Benzyl-1H-pyrazol-4-yl)-1-methyl-2-oxo-1,2-dihydro-pyridin-4-yloxy]-propionic acid |

TABLE 1-continued

| Example | Structure | Name |
|---|---|---|
| 167 | 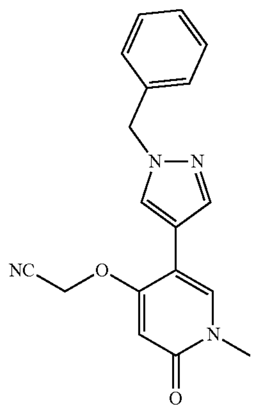 [SMILES: Cn1cc(-c2cnn(Cc3ccccc3)c2)c(OCC#N)cc1=O] | [5-(1-Benzyl-1H-pyrazol-4-yl)-1-methyl-2-oxo-1,2-dihydro-pyridin-4-yloxy]-acetonitrile |
| 168 | 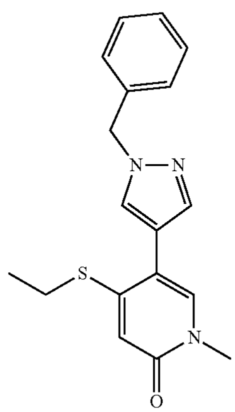 [SMILES: CCSc1cc(=O)n(C)cc1-c1cnn(Cc2ccccc2)c1] | 5-(1-Benzyl-1H-pyrazol-4-yl)-4-ethylsulfanyl-1-methyl-1H-pyridin-2-one |
| 169 | 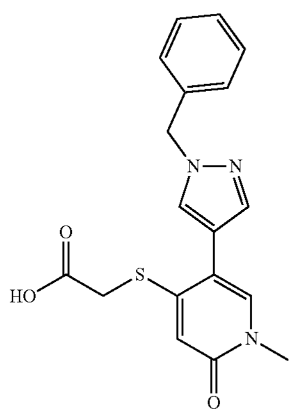 [SMILES: Cn1cc(-c2cnn(Cc3ccccc3)c2)c(SCC(=O)O)cc1=O] | [5-(1-Benzyl-1H-pyrazol-4-yl)-1-methyl-2-oxo-1,2-dihydro-pyridin-4-ylsulfanyl]-acetic acid |
| 170 | 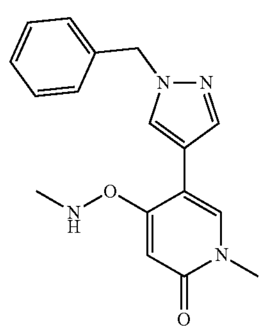 [SMILES: CNOc1cc(=O)n(C)cc1-c1cnn(Cc2ccccc2)c1] | 5-(1-benzyl-1H-pyrazol-4-yl)-1-methyl-4-((methylamino)oxy)pyridin-2(1H)-one |

TABLE 1-continued

| Example | Structure | Name |
|---|---|---|
| 171 | 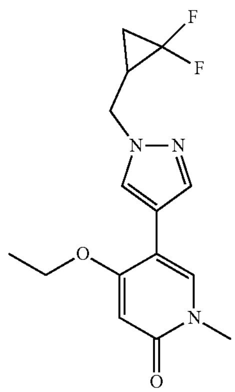 [SMILES: CCOc1cc(=O)n(C)cc1-c1cnn(CC2CC2(F)F)c1] | 5-[1-(2,2-Difluoro-cyclopropylmethyl)-1H-pyrazol-4-yl]-4-ethoxy-1-methyl-1H-pyridin-2-one |
| 172 | 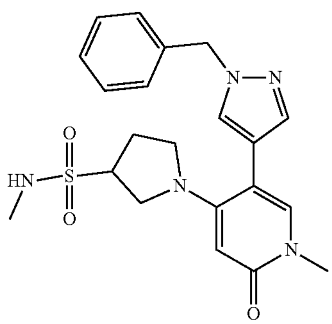 | 1-(5-(1-benzyl-1H-pyrazol-4-yl)-1-methyl-2-oxo-1,2-dihydropyridin-4-yl)-N-methylpyrrolidine-3-sulfonamide |
| 173 | 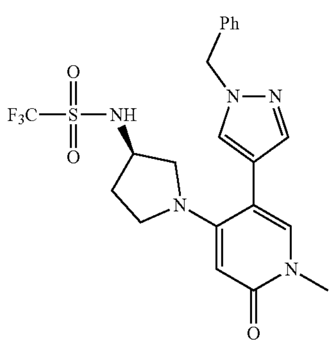 [SMILES: Cn1cc(-c2cnn(Cc3ccccc3)c2)c(N2CC[C@@H](NS(=O)(=O)C(F)(F)F)C2)cc1=O] | (R)-N-(1-(5-(1-benzyl-1H-pyrazol-4-yl)-1-methyl-2-oxo-1,2-dihydropyridin-4-yl)pyrrolidin-3-yl)-1,1,1-trifluoromethanesulfonamide |
| 174 | 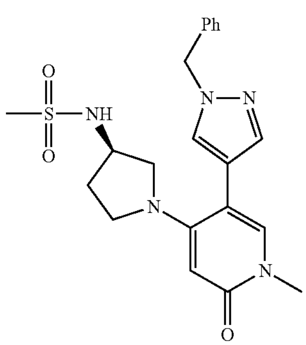 | (R)-N-(1-(5-(1-benzyl-1H-pyrazol-4-yl)-1-methyl-2-oxo-1,2-dihydropyridin-4-yl)pyrrolidin-3-yl)methanesulfonamide |

TABLE 1-continued

| Example | Structure | Name |
|---|---|---|
| 175 | 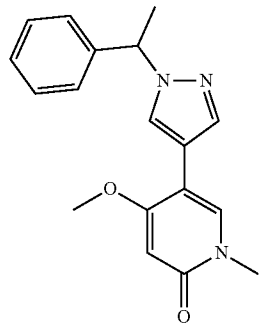 [SMILES: COc1cc(=O)n(C)cc1-c1cnn(C(C)c2ccccc2)c1] | 4-methoxy-1-methyl-5-(1-(1-phenylethyl)-1H-pyrazol-4-yl)pyridin-2(1H)-one |
| 176 | 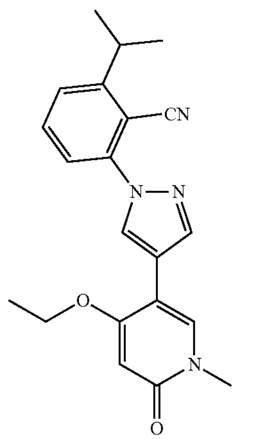 [SMILES: CCOc1cc(=O)n(C)cc1-c1cnn(-c2cccc(C(C)C)c2C#N)c1] | 2-[4-(4-Ethoxy-1-methyl-6-oxo-1,6-dihydro-pyridin-3-yl)-pyrazol-1-yl]-6-isopropyl-benzonitrile |
| 177 | 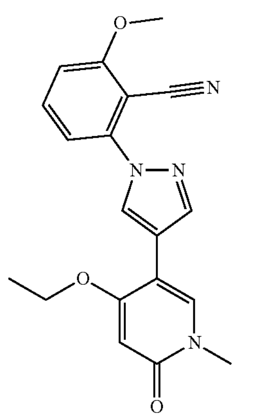 [SMILES: CCOc1cc(=O)n(C)cc1-c1cnn(-c2cccc(OC)c2C#N)c1] | 2-[4-(4-Ethoxy-1-methyl-6-oxo-1,6-dihydro-pyridin-3-yl)-pyrazol-1-yl]-6-methoxy-benzonitrile |
| 178 | 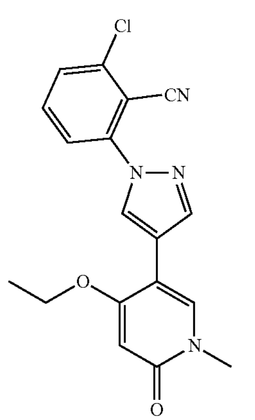 [SMILES: CCOc1cc(=O)n(C)cc1-c1cnn(-c2cccc(Cl)c2C#N)c1] | 2-Chloro-6-[4-(4-ethoxy-1-methyl-6-oxo-1,6-dihydro-pyridin-3-yl)-pyrazol-1-yl]-benzonitrile |

TABLE 1-continued

| Example | Structure | Name |
|---|---|---|
| 179 | 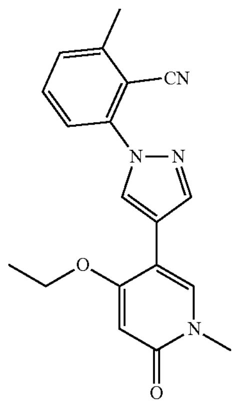 [SMILES: CCOc1cc(=O)n(C)cc1-c1cnn(-c2cccc(C)c2C#N)c1] | 2-[4-(4-Ethoxy-1-methyl-6-oxo-1,6-dihydro-pyridin-3-yl)-pyrazol-1-yl]-6-methyl-benzonitrile |
| 180 | 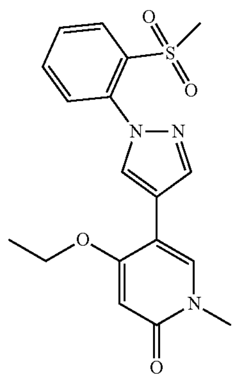 [SMILES: CCOc1cc(=O)n(C)cc1-c1cnn(-c2ccccc2S(C)(=O)=O)c1] | 4-Ethoxy-5-[1-(2-methanesulfonyl-phenyl)-1H-pyrazol-4-yl]-1-methyl-1H-pyridin-2-one |
| 181 | 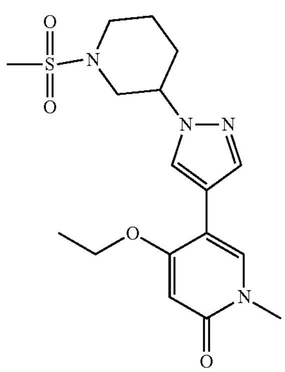 | 4-ethoxy-1-methyl-5-(1-(1-(methylsulfonyl)piperidin-3-yl)-1H-pyrazol-4-yl)pyridin-2(1H)-one |
| 182 | 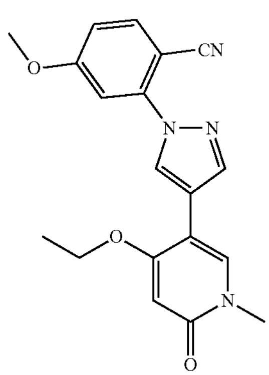 | 2-[4-(4-Ethoxy-1-methyl-6-oxo-1,6-dihydro-pyridin-3-yl)-pyrazol-1-yl]-4-methoxy-benzonitrile |

TABLE 1-continued

| Example | Structure | Name |
|---------|-----------|------|
| 183 | 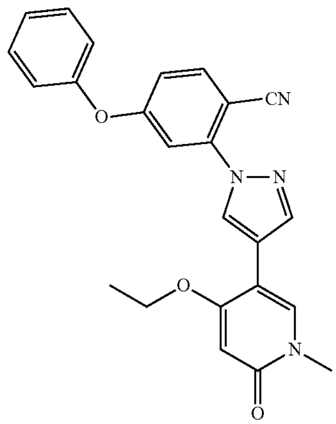 [SMILES: CCOc1cc(=O)n(C)cc1-c1cnn(-c2cc(Oc3ccccc3)ccc2C#N)c1] | 2-[4-(4-Ethoxy-1-methyl-6-oxo-1,6-dihydro-pyridin-3-yl)-pyrazol-1-yl]-4-phenoxy-benzonitrile |
| 184 | 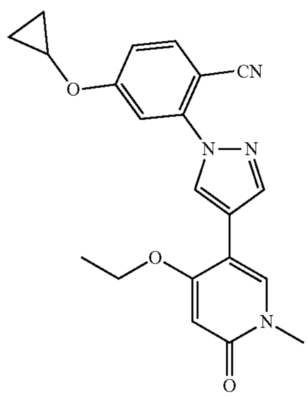 [SMILES: CCOc1cc(=O)n(C)cc1-c1cnn(-c2cc(OC3CC3)ccc2C#N)c1] | 4-Cyclopropoxy-2-[4-(4-ethoxy-1-methyl-6-oxo-1,6-dihydro-pyridin-3-yl)-pyrazol-1-yl]-benzonitrile |
| 185 | 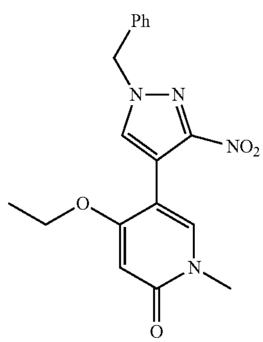 | 5-(1-benzyl-3-nitro-1H-pyrazol-4-yl)-4-ethoxy-1-methylpyridin-2(1H)-one |
| 186 | 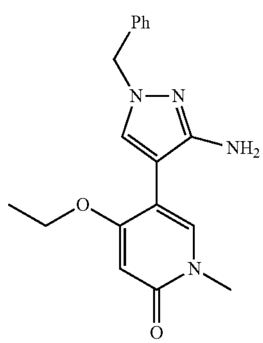 | 5-(3-amino-1-benzyl-1H-pyrazol-4-yl)-4-ethoxy-1-methylpyridin-2(1H)-one |

TABLE 1-continued

| Example | Structure | Name |
|---|---|---|
| 187 | 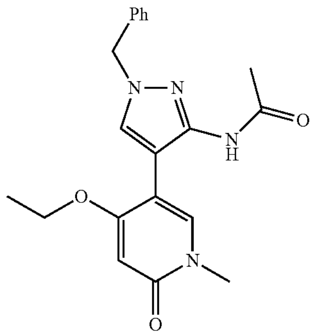 [SMILES: CCOc1cc(=O)n(C)cc1-c1cn(Cc2ccccc2)nc1NC(C)=O] | N-[1-Benzyl-4-(4-ethoxy-1-methyl-6-oxo-1,6-dihydro-pyridin-3-yl)-1H-pyrazol-3-yl]-acetamide |
| 188 | 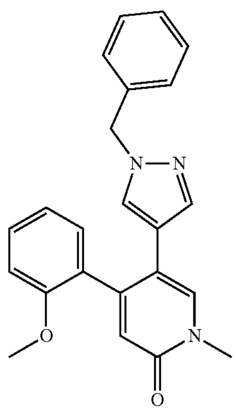 [SMILES: COc1ccccc1-c1cc(=O)n(C)cc1-c1cnn(Cc2ccccc2)c1] | 5-(1-Benzyl-1H-pyrazol-4-yl)-4-(2-methoxy-phenyl)-1-methyl-1H-pyridin-2-one |
| 189 | 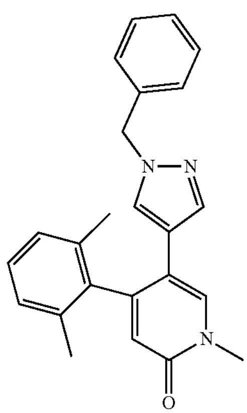 [SMILES: Cc1cccc(C)c1-c1cc(=O)n(C)cc1-c1cnn(Cc2ccccc2)c1] | 5-(1-Benzyl-1H-pyrazol-4-yl)-4-(2,6-dimethyl-phenyl)-1-methyl-1H-pyridin-2-one |
| 190 | 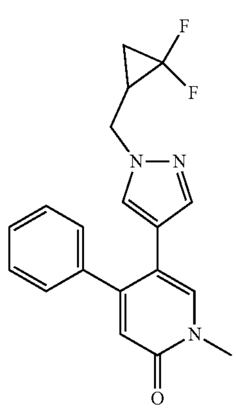 [SMILES: Cn1cc(-c2cnn(CC3CC3(F)F)c2)c(-c2ccccc2)cc1=O] | 5-[1-(2,2-Difluoro-cyclopropylmethyl)-1H-pyrazol-4-yl]-1-methyl-4-phenyl-1H-pyridin-2-one |

TABLE 1-continued

| Example | Structure | Name |
|---|---|---|
| 191 | 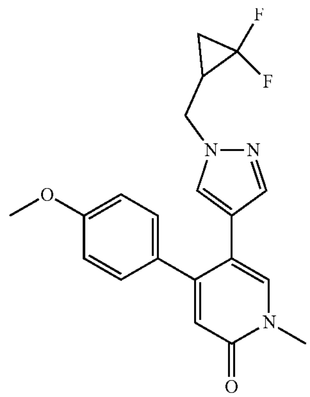 | 5-[1-(2,2-Difluoro-cyclopropylmethyl)-1H-pyrazol-4-yl]-4-(4-methoxy-phenyl)-1-methyl-1H-pyridin-2-one |
| 192 | 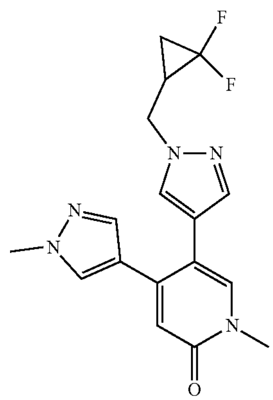 | 5-[1-(2,2-Difluoro-cyclopropylmethyl)-1H-pyrazol-4-yl]-1-methyl-4-(1-methyl-1H-pyrazol-4-yl)-1H-pyridin-2-one |
| 193 | 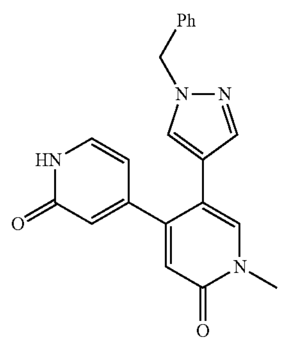 [SMILES: Cn1cc(-c2cnn(Cc3ccccc3)c2)c(-c2cc[nH]c(=O)c2)cc1=O] | 5-(1-Benzyl-1H-pyrazol-4-yl)-1-methyl-1H,1'H-[4,4']bipyridinyl-2,2'-dione |
| 194 | 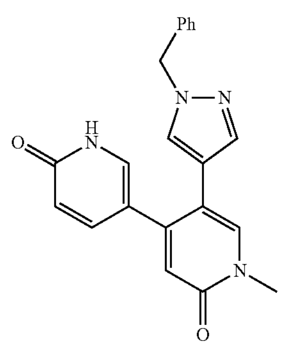 [SMILES: Cn1cc(-c2cnn(Cc3ccccc3)c2)c(-c2ccc(=O)[nH]c2)cc1=O] | 5'-(1-Benzyl-1H-pyrazol-4-yl)-1'-methyl-1H,1'H-[3,4']bipyridinyl-6,2'-dione |

TABLE 1-continued

| Example | Structure | Name |
|---|---|---|
| 195 | 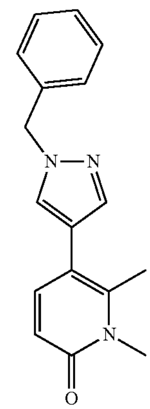 [SMILES: Cc1c(-c2cnn(Cc3ccccc3)c2)ccc(=O)n1C] | 5-(1-Benzyl-1H-pyrazol-4-yl)-1,6-dimethyl-1H-pyridin-2-one |
| 196 | 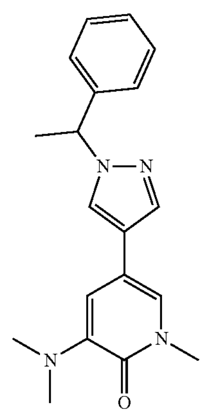 | 3-Dimethylamino-1-methyl-5-[1-(1-phenyl-ethyl)-1H-pyrazol-4-yl]-1H-pyridin-2-one |
| 197 | 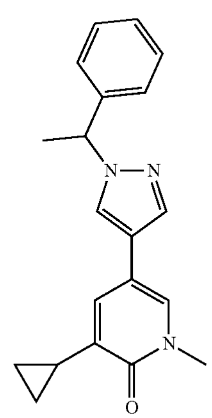 [SMILES: CC(c1ccccc1)n1cc(-c2cc(C3CC3)c(=O)n(C)c2)cn1] | 3-Cyclopropyl-1-methyl-5-[1-(1-phenyl-ethyl)-1H-pyrazol-4-yl]-1H-pyridin-2-one |
| 198 | 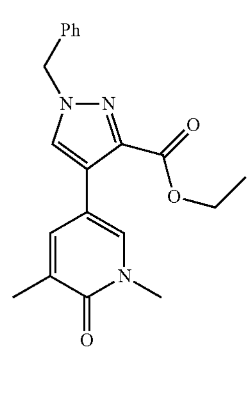 [SMILES: CCOC(=O)c1nn(Cc2ccccc2)cc1-c1cc(C)c(=O)n(C)c1] | 1-Benzyl-4-(1,5-dimethyl-6-oxo-1,6-dihydro-pyridin-3-yl)-1H-pyrazole-3-carboxylic acid ethyl ester |

TABLE 1-continued

| Example | Structure | Name |
|---|---|---|
| 199 | 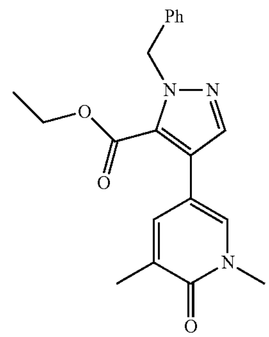 [SMILES: CCOC(=O)c1c(-c2cc(C)c(=O)n(C)c2)cnn1Cc1ccccc1] | 2-Benzyl-4-(1,5-dimethyl-6-oxo-1,6-dihydro-pyridin-3-yl)-2H-pyrazole-3-carboxylic acid ethyl ester |
| 200 | 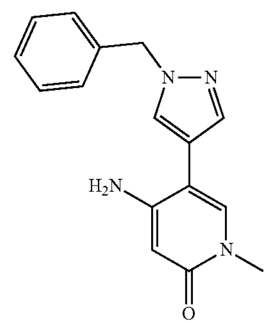 [SMILES: Cn1cc(-c2cnn(Cc3ccccc3)c2)c(N)cc1=O] | 4-amino-5-(1-benzyl-1H-pyrazol-4-yl)-1-methylpyridin-2(1H)-one |
| 201 | 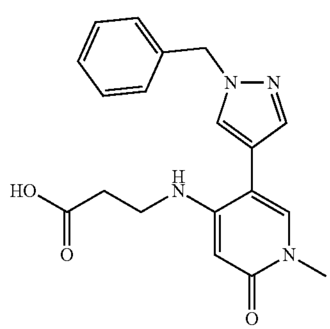 [SMILES: Cn1cc(-c2cnn(Cc3ccccc3)c2)c(NCCC(=O)O)cc1=O] | 3-((5-(1-benzyl-1H-pyrazol-4-yl)-1-methyl-2-oxo-1,2-dihydropyridin-4-yl)amino)propanoic acid |
| 202 | 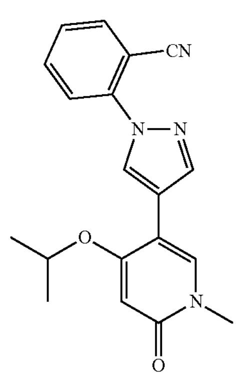 [SMILES: CC(C)Oc1cc(=O)n(C)cc1-c1cnn(-c2ccccc2C#N)c1] | 2-[4-(4-Isopropoxy-1-methyl-6-oxo-1,6-dihydro-pyridin-3-yl)-pyrazol-1-yl]-benzonitrile |

TABLE 1-continued

| Example | Structure | Name |
|---|---|---|
| 203 | 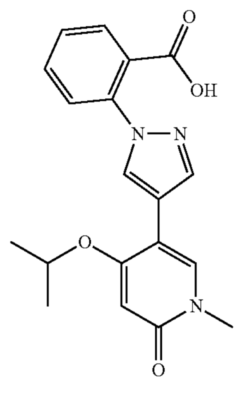 [SMILES: CC(C)Oc1cc(=O)n(C)cc1-c1cnn(-c2ccccc2C(=O)O)c1] | 2-[4-(4-Isopropoxy-1-methyl-6-oxo-1,6-dihydro-pyridin-3-yl)-pyrazol-1-yl]-benzoic acid |
| 204 | 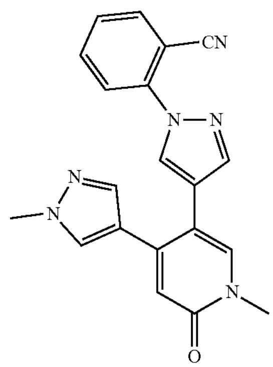 | 2-{4-[1-Methyl-4-(1-methyl-1H-pyrazol-4-yl)-6-oxo-1,6-dihydro-pyridin-3-yl]-pyrazol-1-yl}-benzonitrile |
| 205 | 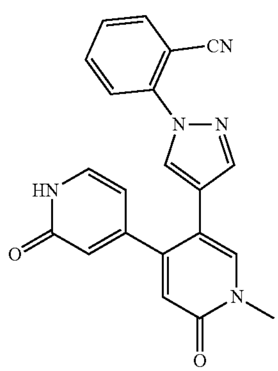 [SMILES: Cn1cc(-c2cnn(-c3ccccc3C#N)c2)c(-c2cc[nH]c(=O)c2)cc1=O] | 2-[4-(1-Methyl-6,2'-dioxo-1,6,1',2'-tetrahydro-[4,4']bipyridinyl-3-yl)-pyrazol-1-yl]-benzonitrile |
| 206 | 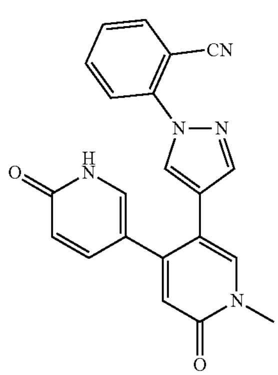 [SMILES: Cn1cc(-c2cnn(-c3ccccc3C#N)c2)c(-c2ccc(=O)[nH]c2)cc1=O] | 2-[4-(1'-Methyl-6,6'-dioxo-1,6,1',6'-tetrahydro-[3,4']bipyridinyl-3'-yl)-pyrazol-1-yl]-benzonitrile |

TABLE 1-continued

| Example | Structure | Name |
|---|---|---|
| 207 | 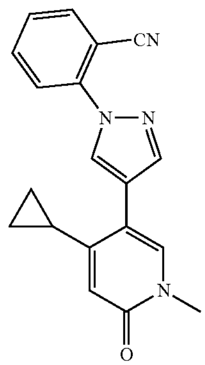 [SMILES: Cn1cc(-c2cnn(-c3ccccc3C#N)c2)c(C2CC2)cc1=O] | 2-[4-(4-Cyclopropyl-1-methyl-6-oxo-1,6-dihydro-pyridin-3-yl)-pyrazol-1-yl]-benzonitrile |
| 208 | 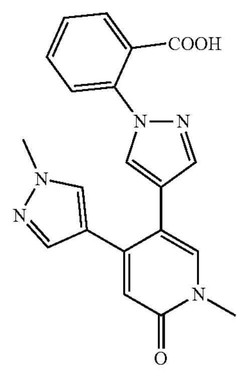 [SMILES: Cn1cc(-c2cc(=O)n(C)cc2-c2cnn(-c3ccccc3C(=O)O)c2)cn1] | 2-{4-[1-Methyl-4-(1-methyl-1H-pyrazol-4-yl)-6-oxo-1,6-dihydro-pyridin-3-yl]-pyrazol-1-yl}-benzoic acid |
| 209 | 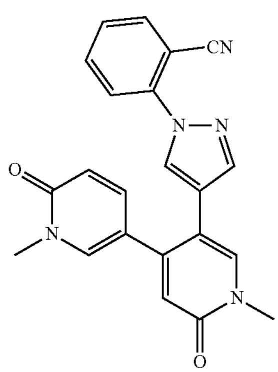 | 2-[4-(1,1'-Dimethyl-6,6'-dioxo-1,6,1',6'-tetrahydro-[3,4']bipyridinyl-3'-yl)-pyrazol-1-yl]-benzonitrile |
| 210 | 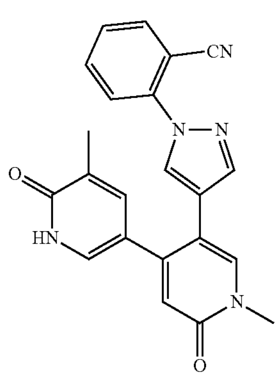 [SMILES: Cc1cc(-c2cc(=O)n(C)cc2-c2cnn(-c3ccccc3C#N)c2)c[nH]c1=O] | 2-[4-(5,1'-Dimethyl-6,6'-dioxo-1,6,1',6'-tetrahydro-[3,4']bipyridinyl-3'-yl)-pyrazol-1-yl]-benzonitrile |

TABLE 1-continued

| Example | Structure | Name |
|---------|-----------|------|
| 211 | 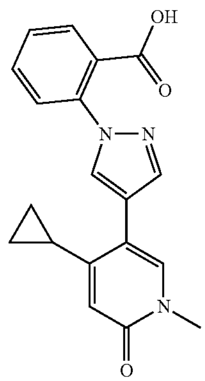 [SMILES: Cn1cc(-c2cnn(-c3ccccc3C(=O)O)c2)c(C2CC2)cc1=O] | 2-[4-(4-Cyclopropyl-1-methyl-6-oxo-1,6-dihydro-pyridin-3-yl)-pyrazol-1-yl]-benzoic acid |
| 212 | 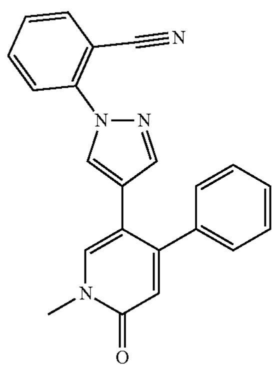 [SMILES: Cn1cc(-c2cnn(-c3ccccc3C#N)c2)c(-c2ccccc2)cc1=O] | 2-[4-(1-Methyl-6-oxo-4-phenyl-1,6-dihydro-pyridin-3-yl)-pyrazol-1-yl]-benzonitrile |
| 213 | 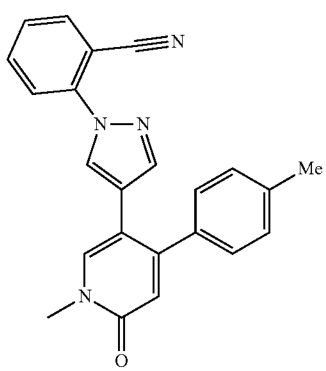 [SMILES: Cc1ccc(-c2cc(=O)n(C)cc2-c2cnn(-c3ccccc3C#N)c2)cc1] | 2-[4-(1-Methyl-6-oxo-4-p-tolyl-1,6-dihydro-pyridin-3-yl)-pyrazol-1-yl]-benzonitrile |
| 214 | 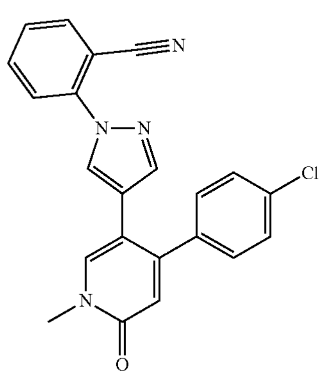 [SMILES: Cn1cc(-c2cnn(-c3ccccc3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-benzonitrile |

TABLE 1-continued

| Example | Structure | Name |
|---|---|---|
| 215 | 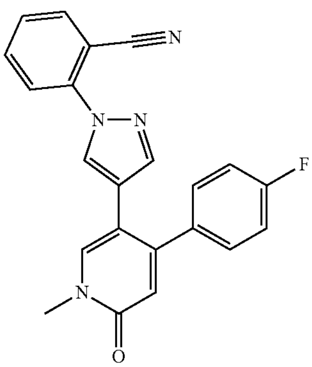 [SMILES: Cn1cc(-c2cnn(-c3ccccc3C#N)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzonitrile |
| 216 | 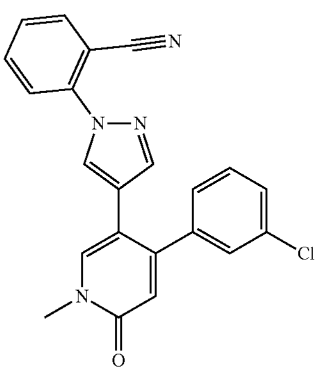 [SMILES: Cn1cc(-c2cnn(-c3ccccc3C#N)c2)c(-c2cccc(Cl)c2)cc1=O] | 2-{4-[4-(3-Chloro-phenyl)-1-methyl-6-oxo-1,6-dihydro-pyridin-3-yl]-pyrazol-1-yl}-benzonitrile |
| 217 | 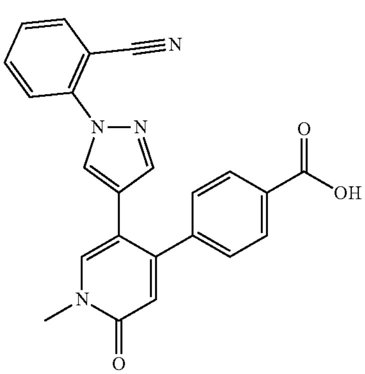 [SMILES: Cn1cc(-c2cnn(-c3ccccc3C#N)c2)c(-c2ccc(C(=O)O)cc2)cc1=O] | 4-{5-[1-(2-Cyano-phenyl)-1H-pyrazol-4-yl]-1-methyl-2-oxo-1,2-dihydro-pyridin-4-yl}-benzoic acid |
| 218 | 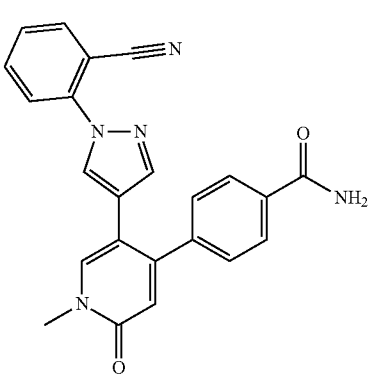 [SMILES: Cn1cc(-c2cnn(-c3ccccc3C#N)c2)c(-c2ccc(C(N)=O)cc2)cc1=O] | 4-{5-[1-(2-Cyano-phenyl)-1H-pyrazol-4-yl]-1-methyl-2-oxo-1,2-dihydro-pyridin-4-yl}-benzamide |

TABLE 1-continued

| Example | Structure | Name |
|---|---|---|
| 219 | 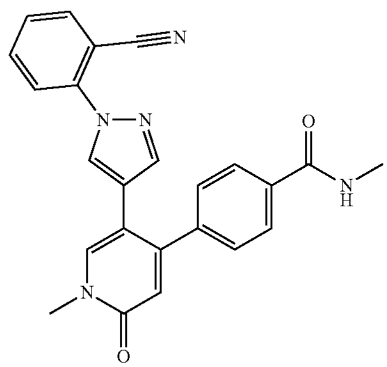 [SMILES: CNC(=O)c1ccc(-c2cc(=O)n(C)cc2-c2cnn(-c3ccccc3C#N)c2)cc1] | 4-{5-[1-(2-Cyano-phenyl)-1H-pyrazol-4-yl]-1-methyl-2-oxo-1,2-dihydro-pyridin-4-yl}-N-methyl-benzamide |
| 220 | 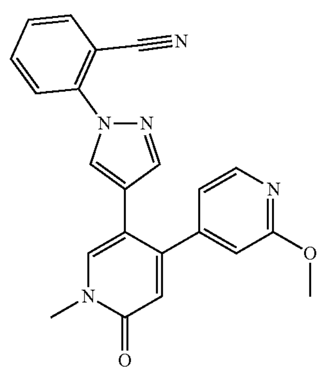 [SMILES: COc1cc(-c2cc(=O)n(C)cc2-c2cnn(-c3ccccc3C#N)c2)ccn1] | 2-[4-(2'-Methoxy-1-methyl-6-oxo-1,6-dihydro-[4,4']bipyridinyl-3-yl)-pyrazol-1-yl]-benzonitrile |
| 221 | 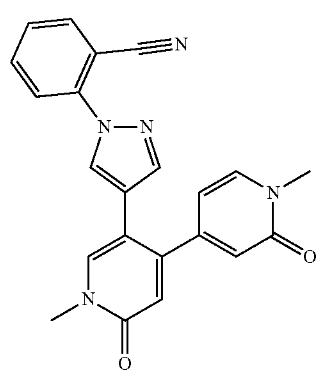 [SMILES: Cn1ccc(-c2cc(=O)n(C)cc2-c2cnn(-c3ccccc3C#N)c2)cc1=O] | 2-[4-(1,1'-Dimethyl-6,2'-dioxo-1,6,1',2'-tetrahydro-[4,4']bipyridinyl-3-yl)-pyrazol-1-yl]-benzonitrile |
| 222 | 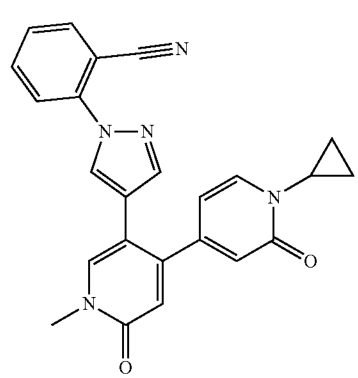 [SMILES: Cn1cc(-c2cnn(-c3ccccc3C#N)c2)c(-c2ccn(C3CC3)c(=O)c2)cc1=O] | 2-[4-(1'-Cyclopropyl-1-methyl-6,2'-dioxo-1,6,1',2'-tetrahydro-[4,4']bipyridinyl-3-yl)-pyrazol-1-yl]-benzonitrile |

TABLE 1-continued

| Example | Structure | Name |
|---|---|---|
| 223 | 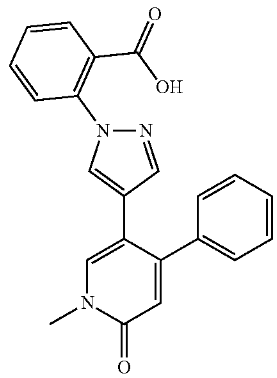 [SMILES: Cn1cc(-c2cnn(-c3ccccc3C(=O)O)c2)c(-c2ccccc2)cc1=O] | 2-[4-(1-Methyl-6-oxo-4-phenyl-1,6-dihydro-pyridin-3-yl)-pyrazol-1-yl]-benzoic acid |
| 224 | 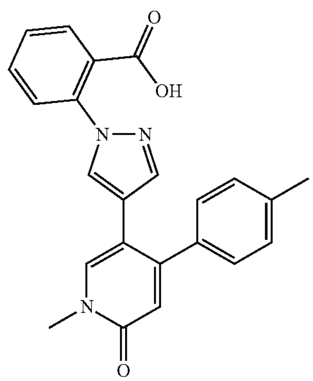 [SMILES: Cc1ccc(-c2cc(=O)n(C)cc2-c2cnn(-c3ccccc3C(=O)O)c2)cc1] | 2-[4-(1-Methyl-6-oxo-4-p-tolyl-1,6-dihydro-pyridin-3-yl)-pyrazol-1-yl]-benzoic acid |
| 225 | 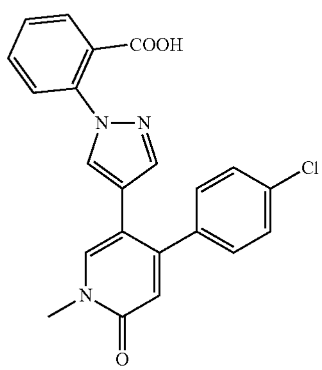 [SMILES: Cn1cc(-c2cnn(-c3ccccc3C(=O)O)c2)c(-c2ccc(Cl)cc2)cc1=O] | 2-(4-(4-(4-chlorophenyl)-1-methyl-6-oxo-1,6-dihydropyridin-3-yl)-1H-pyrazol-1-yl)benzoic acid |
| 226 | 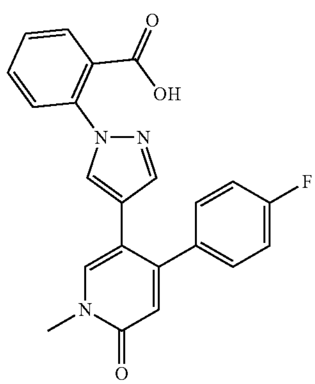 [SMILES: Cn1cc(-c2cnn(-c3ccccc3C(=O)O)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzoic acid |

TABLE 1-continued

| Example | Structure | Name |
|---|---|---|
| 227 | 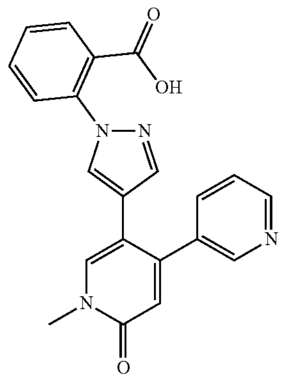 [SMILES: Cn1cc(-c2cnn(-c3ccccc3C(=O)O)c2)c(-c2cccnc2)cc1=O] | 2-[4-(1'-Methyl-6'-oxo-1',6'-dihydro-[3,4']bipyridinyl-3'-yl)-pyrazol-1-yl]-benzoic acid |
| 228 | 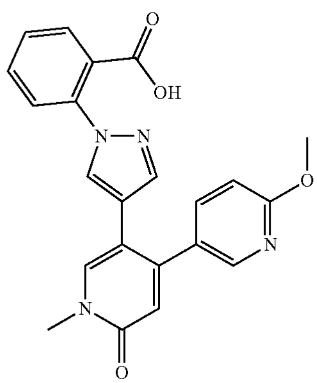 [SMILES: COc1ccc(-c2cc(=O)n(C)cc2-c2cnn(-c3ccccc3C(=O)O)c2)cn1] | 2-[4-(6-Methoxy-1'-methyl-6'-oxo-1',6'-dihydro-[3,4']bipyridinyl-3'-yl)-pyrazol-1-yl]-benzoic acid |
| 229 | 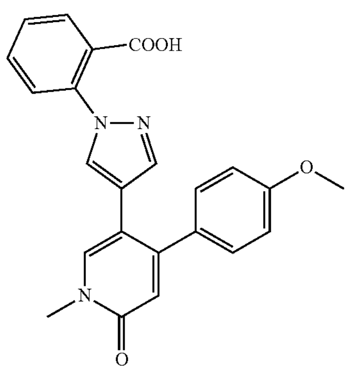 [SMILES: COc1ccc(-c2cc(=O)n(C)cc2-c2cnn(-c3ccccc3C(=O)O)c2)cc1] | 2-{4-[4-(4-Methoxy-phenyl)-1-methyl-6-oxo-1,6-dihydro-pyridin-3-yl]-pyrazol-1-yl}-benzoic acid |
| 230 | 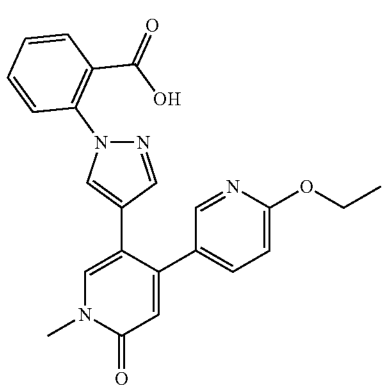 [SMILES: CCOc1ccc(-c2cc(=O)n(C)cc2-c2cnn(-c3ccccc3C(=O)O)c2)cn1] | 2-[4-(6-Ethoxy-1'-methyl-6'-oxo-1',6'-dihydro-[3,4']bipyridinyl-3'-yl)-pyrazol-1-yl]-benzoic acid |

TABLE 1-continued

| Example | Structure | Name |
|---|---|---|
| 231 | 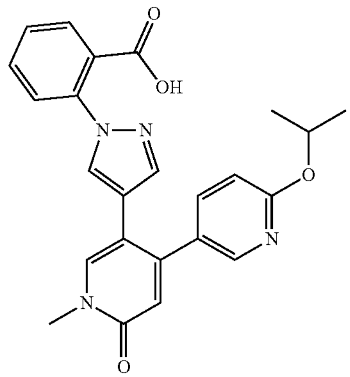 [SMILES: CC(C)Oc1ccc(-c2cc(=O)n(C)cc2-c2cnn(-c3ccccc3C(=O)O)c2)cn1] | 2-[4-(6-Isopropoxy-1'-methyl-6'-oxo-1',6'-dihydro-[3,4']bipyridinyl-3'-yl)-pyrazol-1-yl]-benzoic acid |
| 232 | 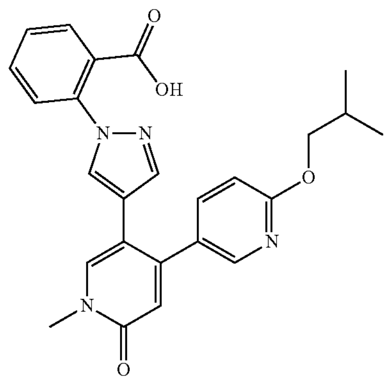 [SMILES: CC(C)COc1ccc(-c2cc(=O)n(C)cc2-c2cnn(-c3ccccc3C(=O)O)c2)cn1] | 2-[4-(6-Isobutoxy-1'-methyl-6'-oxo-1',6'-dihydro-[3,4']bipyridinyl-3'-yl)-pyrazol-1-yl]-benzoic acid |
| 233 | 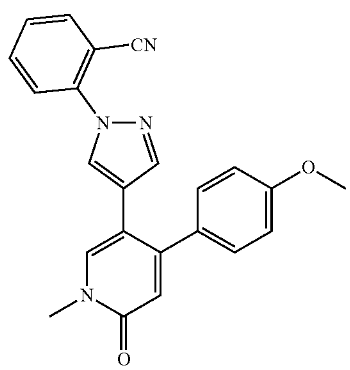 [SMILES: COc1ccc(-c2cc(=O)n(C)cc2-c2cnn(-c3ccccc3C#N)c2)cc1] | 2-{4-[4-(4-Methoxy-phenyl)-1-methyl-6-oxo-1,6-dihydro-pyridin-3-yl]-pyrazol-1-yl}-benzonitrile |
| 234 | 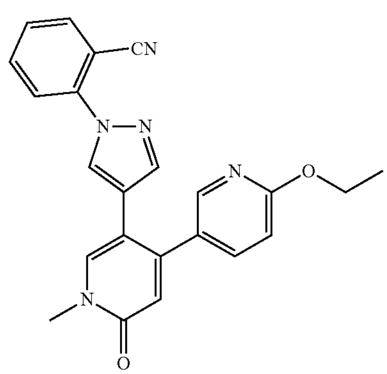 [SMILES: CCOc1ccc(-c2cc(=O)n(C)cc2-c2cnn(-c3ccccc3C#N)c2)cn1] | 2-[4-(6-Ethoxy-1'-methyl-6'-oxo-1',6'-dihydro-[3,4']bipyridinyl-3'-yl)-pyrazol-1-yl]-benzonitrile |

TABLE 1-continued

| Example | Structure | Name |
|---|---|---|
| 235 | 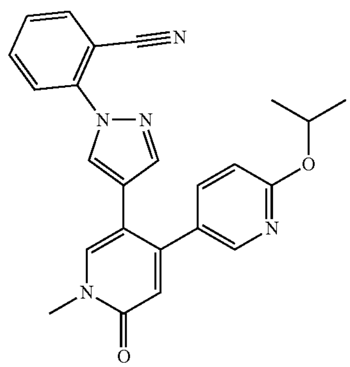 [SMILES: CC(C)Oc1ccc(-c2cc(=O)n(C)cc2-c2cnn(-c3ccccc3C#N)c2)cn1] | 2-[4-(6-Isopropoxy-1'-methyl-6'-oxo-1',6'-dihydro-[3,4']bipyridinyl-3'-yl)-pyrazol-1-yl]-benzonitrile |
| 236 | 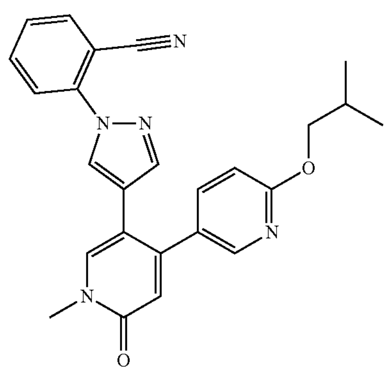 [SMILES: CC(C)COc1ccc(-c2cc(=O)n(C)cc2-c2cnn(-c3ccccc3C#N)c2)cn1] | 2-[4-(6-Isobutoxy-1'-methyl-6'-oxo-1',6'-dihydro-[3,4']bipyridinyl-3'-yl)-pyrazol-1-yl]-benzonitrile |
| 237 | 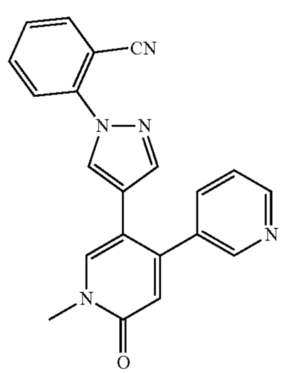 [SMILES: Cn1cc(-c2cnn(-c3ccccc3C#N)c2)c(-c2cccnc2)cc1=O] | 2-[4-(1'-Methyl-6'-oxo-1',6'-dihydro-[3,4']bipyridinyl-3'-yl)-pyrazol-1-yl]-benzonitrile |
| 238 | 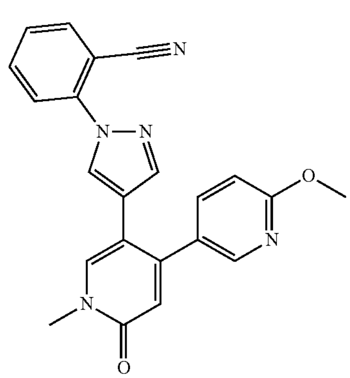 | 2-(4-(6-methoxy-1'-methyl-6'-oxo-1',6'-dihydro-[3,4'-bipyridin]-3'-yl)-1H-pyrazol-1-yl)benzonitrile |

TABLE 1-continued

| Example | Structure | Name |
| --- | --- | --- |
| 239 | 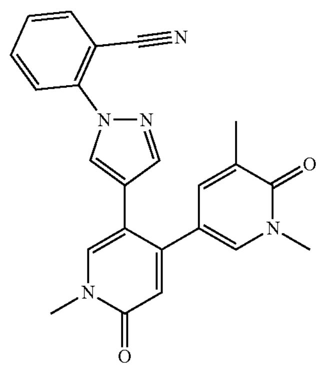 [SMILES: Cc1cc(-c2cc(=O)n(C)cc2-c2cnn(-c3ccccc3C#N)c2)cn(C)c1=O] | 2-(4-(1,1',5-trimethyl-6,6'-dioxo-1,1',6,6'-tetrahydro-[3,4'-bipyridin]-3'-yl)-1H-pyrazol-1-yl)benzonitrile |
| 240 | 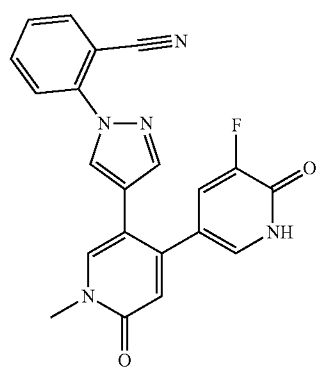 [SMILES: Cn1cc(-c2cnn(-c3ccccc3C#N)c2)c(-c2c[nH]c(=O)c(F)c2)cc1=O] | 2-(4-(5-fluoro-1'-methyl-6,6'-dioxo-1,1',6,6'-tetrahydro-[3,4'-bipyridin]-3'-yl)-1H-pyrazol-1-yl)benzonitrile |
| 241 | 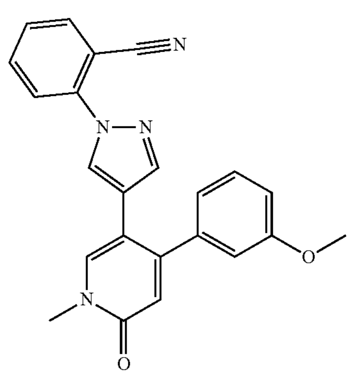 [SMILES: COc1cccc(-c2cc(=O)n(C)cc2-c2cnn(-c3ccccc3C#N)c2)c1] | 2-{4-[4-(3-Methoxy-phenyl)-1-methyl-6-oxo-1,6-dihydro-pyridin-3-yl]-pyrazol-1-yl}-benzonitrile |
| 242 | 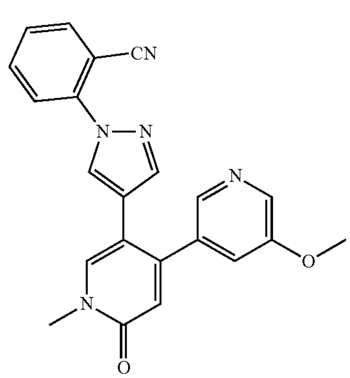 [SMILES: COc1cncc(-c2cc(=O)n(C)cc2-c2cnn(-c3ccccc3C#N)c2)c1] | 2-(4-(5-methoxy-1'-methyl-6'-oxo-1',6'-dihydro-[3,4'-bipyridin]-3'-yl)-1H-pyrazol-1-yl)benzonitrile |

TABLE 1-continued

| Example | Structure | Name |
|---|---|---|
| 243 | 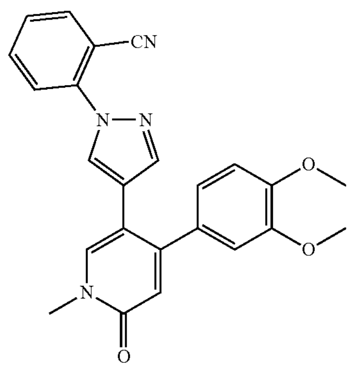 [SMILES: COc1ccc(-c2cc(=O)n(C)cc2-c2cnn(-c3ccccc3C#N)c2)cc1OC] | 2-(4-(4-(3,4-dimethoxyphenyl)-1-methyl-6-oxo-1,6-dihydropyridin-3-yl)-1H-pyrazol-1-yl)benzonitrile |
| 244 | 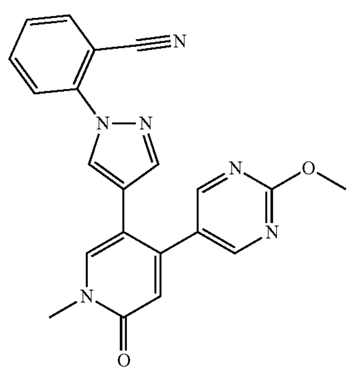 | 2-{4-[4-(2-Methoxy-pyrimidin-5-yl)-1-methyl-6-oxo-1,6-dihydro-pyridin-3-yl]-pyrazol-1-yl}-benzonitrile |
| 245 | 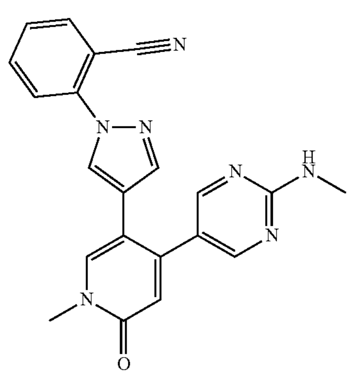 | 2-(4-(1-methyl-4-(2-(methylamino)pyrimidin-5-yl)-6-oxo-1,6-dihydropyridin-3-yl)-1H-pyrazol-1-yl)benzonitrile |
| 246 | 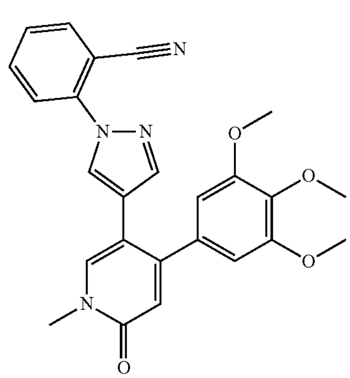 [SMILES: COc1cc(-c2cc(=O)n(C)cc2-c2cnn(-c3ccccc3C#N)c2)cc(OC)c1OC] | 2-{4-[1-Methyl-6-oxo-4-(3,4,5-trimethoxy-phenyl)-1,6-dihydro-pyridin-3-yl]-pyrazol-1-yl}-benzonitrile |

TABLE 1-continued

| Example | Structure | Name |
|---|---|---|
| 247 | 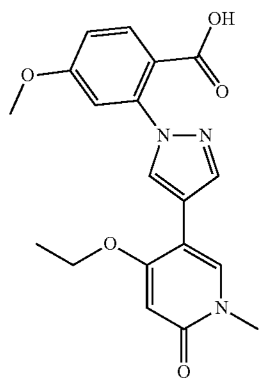 | 2-[4-(4-Ethoxy-1-methyl-6-oxo-1,6-dihydro-pyridin-3-yl)-pyrazol-1-yl]-4-methoxy-benzoic acid |
| 248 | 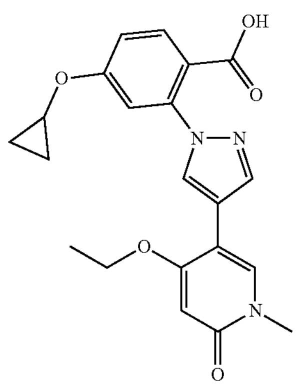 [SMILES: CCOc1cc(=O)n(C)cc1-c1cnn(-c2cc(OC3CC3)ccc2C(=O)O)c1] | 4-Cyclopropoxy-2-[4-(4-ethoxy-1-methyl-6-oxo-1,6-dihydro-pyridin-3-yl)-pyrazol-1-yl]-benzoic acid |
| 249 | 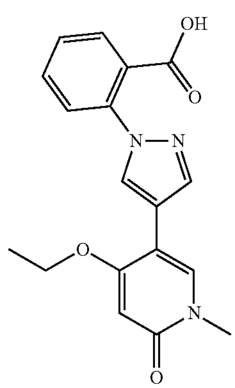 [SMILES: CCOc1cc(=O)n(C)cc1-c1cnn(-c2ccccc2C(=O)O)c1] | 2-(4-(4-ethoxy-1-methyl-6-oxo-1,6-dihydropyridin-3-yl)-1H-pyrazol-1-yl)benzoic acid |
| 250 | 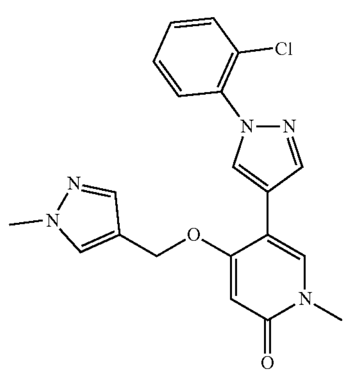 | 5-(1-(2-chlorophenyl)-1H-pyrazol-4-yl)-1-methyl-4-((1-methyl-1H-pyrazol-4-yl)methoxy)pyridin-2(1H)-one |

TABLE 1-continued

| Example | Structure | Name |
|---|---|---|
| 251 | 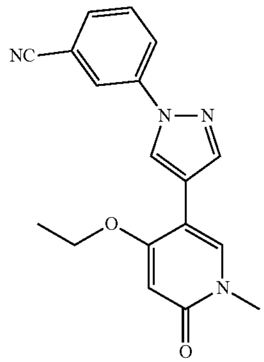 [SMILES: CCOc1cc(=O)n(C)cc1-c1cnn(-c2cccc(C#N)c2)c1] | 3-(4-(4-ethoxy-1-methyl-6-oxo-1,6-dihydropyridin-3-yl)-1H-pyrazol-1-yl)benzonitrile |
| 252 | 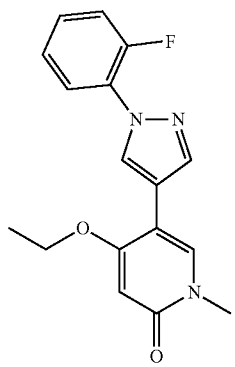 [SMILES: CCOc1cc(=O)n(C)cc1-c1cnn(-c2ccccc2F)c1] | 4-ethoxy-5-(1-(2-fluorophenyl)-1H-pyrazol-4-yl)-1-methylpyridin-2(1H)-one |
| 253 | 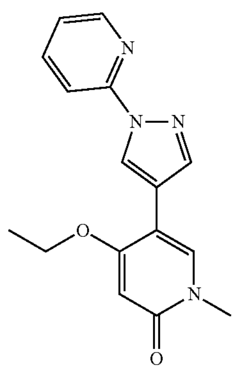 [SMILES: CCOc1cc(=O)n(C)cc1-c1cnn(-c2ccccn2)c1] | 4-ethoxy-1-methyl-5-(1-(pyridin-2-yl)-1H-pyrazol-4-yl)pyridin-2(1H)-one |
| 254 | 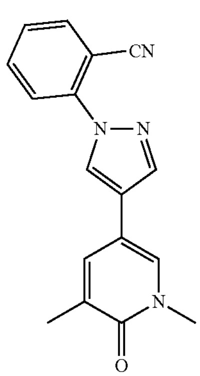 [SMILES: Cc1cc(-c2cnn(-c3ccccc3C#N)c2)cn(C)c1=O] | 2-[4-(1,5-Dimethyl-6-oxo-1,6-dihydro-pyridin-3-yl)-pyrazol-1-yl]-benzonitrile |

TABLE 1-continued

| Example | Structure | Name |
|---|---|---|
| 255 | 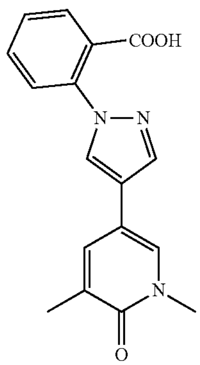 [SMILES: Cc1cc(-c2cnn(-c3ccccc3C(=O)O)c2)cn(C)c1=O] | 2-[4-(1,5-Dimethyl-6-oxo-1,6-dihydro-pyridin-3-yl)-pyrazol-1-yl]-benzoic acid |
| 256 | 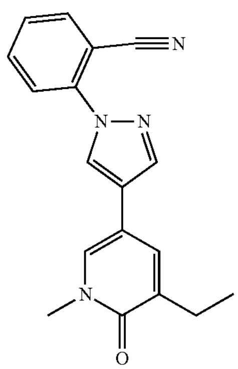 [SMILES: CCc1cc(-c2cnn(-c3ccccc3C#N)c2)cn(C)c1=O] | 2-[4-(5-Ethyl-1-methyl-6-oxo-1,6-dihydro-pyridin-3-yl)-pyrazol-1-yl]-benzonitrile |
| 257 | 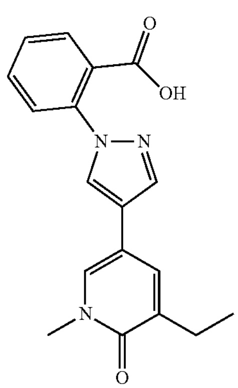 [SMILES: CCc1cc(-c2cnn(-c3ccccc3C(=O)O)c2)cn(C)c1=O] | 2-[4-(5-Ethyl-1-methyl-6-oxo-1,6-dihydro-pyridin-3-yl)-pyrazol-1-yl]-benzoic acid |
| 258 | 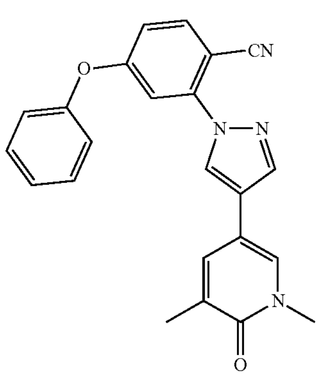 [SMILES: Cc1cc(-c2cnn(-c3cc(Oc4ccccc4)ccc3C#N)c2)cn(C)c1=O] | 2-[4-(1,5-Dimethyl-6-oxo-1,6-dihydro-pyridin-3-yl)-pyrazol-1-yl]-4-phenoxy-benzonitrile |

TABLE 1-continued

| Example | Structure | Name |
|---|---|---|
| 259 | 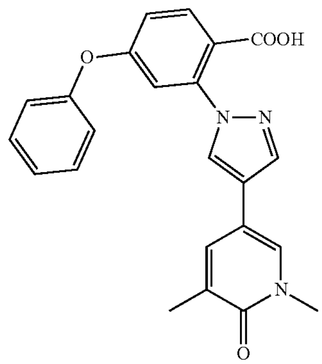 [SMILES: Cc1cc(-c2cnn(-c3cc(Oc4ccccc4)ccc3C(=O)O)c2)cn(C)c1=O] | 2-[4-(1,5-Dimethyl-6-oxo-1,6-dihydro-pyridin-3-yl)-pyrazol-1-yl]-4-phenoxy-benzoic acid |
| 260 | 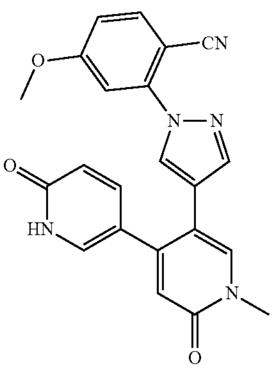 [SMILES: COc1ccc(C#N)c(-n2cc(-c3cn(C)c(=O)cc3-c3ccc(=O)[nH]c3)cn2)c1] | 4-Methoxy-2-[4-(1'-methyl-6,6'-dioxo-1,6,1',6'-tetrahydro-[3,4']bipyridinyl-3'-yl)-pyrazol-1-yl]-benzonitrile |
| 261 | 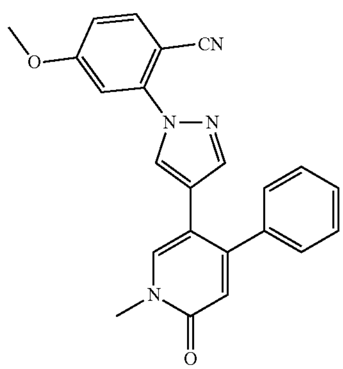 [SMILES: COc1ccc(C#N)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzonitrile |
| 262 | 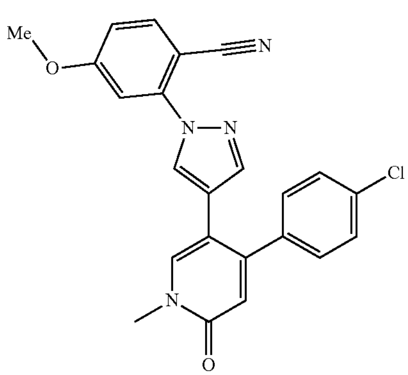 [SMILES: COc1ccc(C#N)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzonitrile |

TABLE 1-continued

| Example | Structure | Name |
| --- | --- | --- |
| 263 | 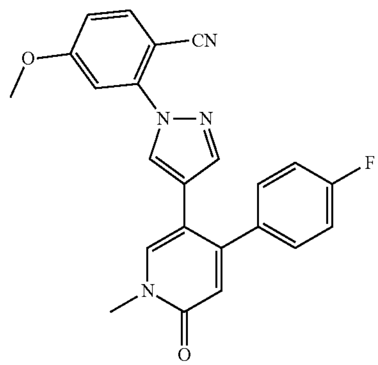 [SMILES: COc1ccc(C#N)c(-n2cc(-c3cn(C)c(=O)cc3-c3ccc(F)cc3)cn2)c1] | 2-{4-[4-(4-Fluoro-phenyl)-1-methyl-6-oxo-1,6-dihydro-pyridin-3-yl]-pyrazol-1-yl}-4-methoxy-benzonitrile |
| 264 | 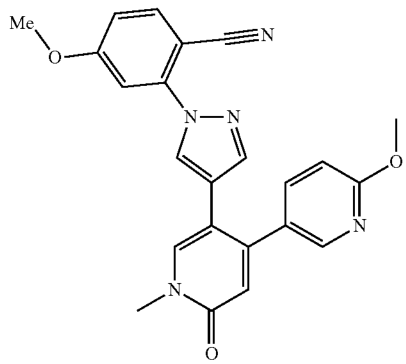 [SMILES: COc1ccc(C#N)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzonitrile |
| 265 | 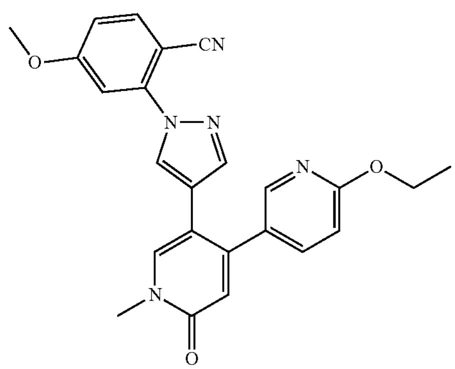 [SMILES: CCOc1ccc(-c2cc(=O)n(C)cc2-c2cnn(-c3cc(OC)ccc3C#N)c2)cn1] | 2-[4-(6-Ethoxy-1'-methyl-6'-oxo-1',6'-dihydro-[3,4']bipyridinyl-3'-yl)-pyrazol-1-yl]-4-methoxy-benzonitrile |
| 266 | 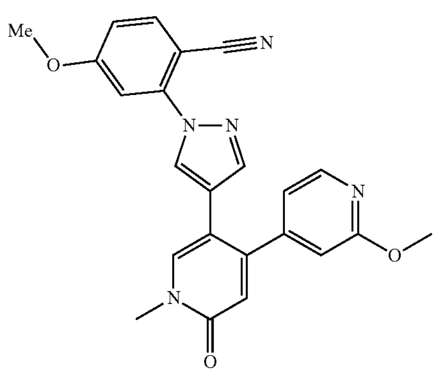 [SMILES: COc1ccc(C#N)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzonitrile |

TABLE 1-continued

| Example | Structure | Name |
|---|---|---|
| 267 | 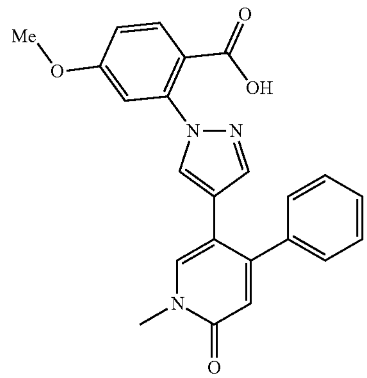 [SMILES: COc1ccc(C(=O)O)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzoic acid |
| 268 | 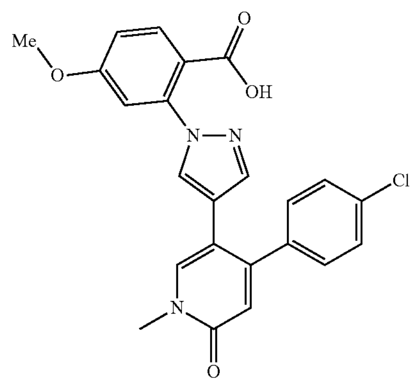 [SMILES: COc1ccc(C(=O)O)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzoic acid |
| 269 | 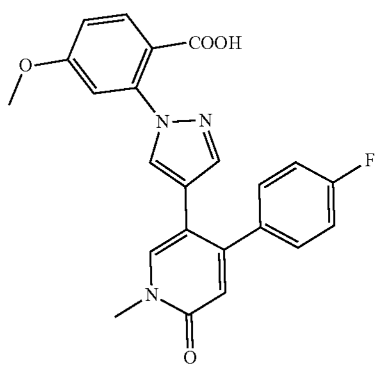 [SMILES: COc1ccc(C(=O)O)c(-n2cc(-c3cn(C)c(=O)cc3-c3ccc(F)cc3)cn2)c1] | 2-{4-[4-(4-Fluoro-phenyl)-1-methyl-6-oxo-1,6-dihydro-pyridin-3-yl]-pyrazol-1-yl}-4-methoxy-benzoic acid |
| 270 | 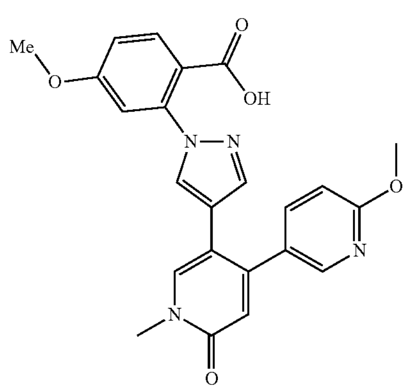 [SMILES: COc1ccc(C(=O)O)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzoic acid |

TABLE 1-continued

| Example | Structure | Name |
|---|---|---|
| 271 | 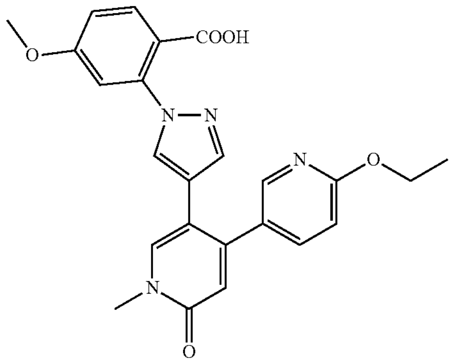 [SMILES: CCOc1ccc(-c2cc(=O)n(C)cc2-c2cnn(-c3cc(OC)ccc3C(=O)O)c2)cn1] | 2-[4-(6-Ethoxy-1'-methyl-6'-oxo-1',6'-dihydro-[3,4']bipyridinyl-3'-yl)-pyrazol-1-yl]-4-methoxy-benzoic acid |
| 272 | 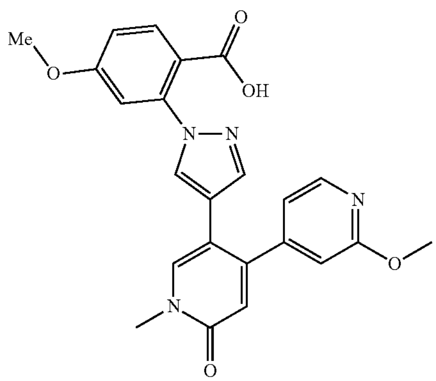 [SMILES: COc1ccc(C(=O)O)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzoic acid |
| 273 | 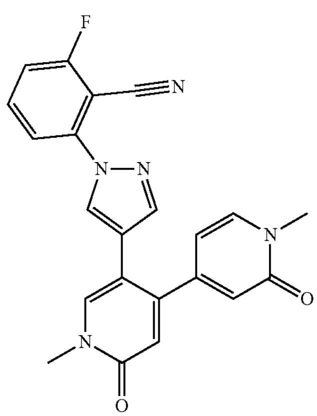 [SMILES: Cn1ccc(-c2cc(=O)n(C)cc2-c2cnn(-c3cccc(F)c3C#N)c2)cc1=O] | 2-[4-(1,1'-Dimethyl-6,2'-dioxo-1,6,1',2'-tetrahydro-[4,4']bipyridinyl-3-yl)-pyrazol-1-yl]-6-fluoro-benzonitrile |
| 274 | 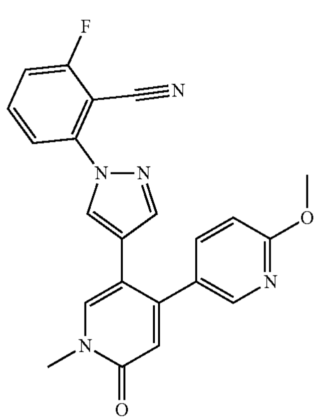 [SMILES: COc1ccc(-c2cc(=O)n(C)cc2-c2cnn(-c3cccc(F)c3C#N)c2)cn1] | 2-Fluoro-6-[4-(6-methoxy-1'-methyl-6'-oxo-1',6'-dihydro-[3,4']bipyridinyl-3'-yl)-pyrazol-1-yl]-benzonitrile |

TABLE 1-continued

| Example | Structure | Name |
|---|---|---|
| 275 | 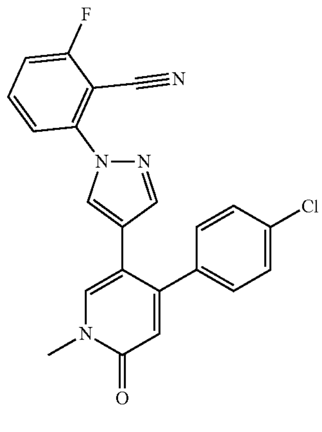 [SMILES: Cn1cc(-c2cnn(-c3cccc(F)c3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-6-fluoro-benzonitrile |
| 276 | 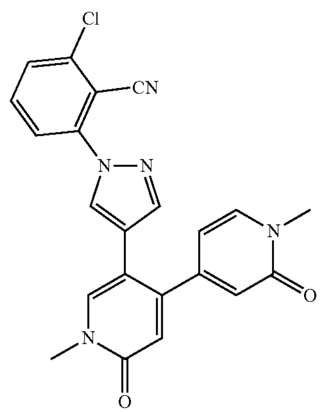 [SMILES: Cn1ccc(-c2cc(=O)n(C)cc2-c2cnn(-c3cccc(Cl)c3C#N)c2)cc1=O] | 2-Chloro-6-[4-(1,1'-dimethyl-6,2'-dioxo-1,6,1',2'-tetrahydro-[4,4']bipyridinyl-3-yl)-pyrazol-1-yl]-benzonitrile |
| 277 | 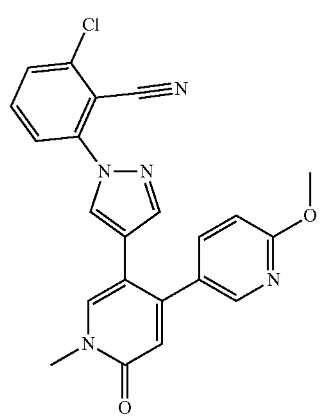 [SMILES: COc1ccc(-c2cc(=O)n(C)cc2-c2cnn(-c3cccc(Cl)c3C#N)c2)cn1] | 2-Chloro-6-[4-(6-methoxy-1'-methyl-6'-oxo-1',6'-dihydro-[3,4']bipyridinyl-3'-yl)-pyrazol-1-yl]-benzonitrile |

TABLE 1-continued

| Example | Structure | Name |
|---|---|---|
| 278 | 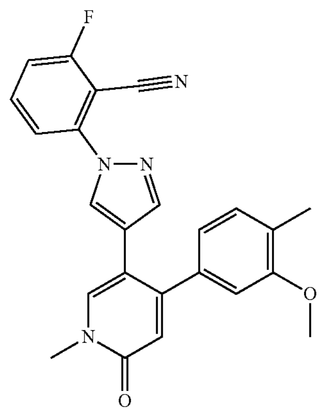 [SMILES: COc1cc(-c2cc(=O)n(C)cc2-c2cnn(-c3cccc(F)c3C#N)c2)ccc1C] | 2-fluoro-6-(4-(4-(3-methoxy-4-methylphenyl)-1-methyl-6-oxo-1,6-dihydropyridin-3-yl)-1H-pyrazol-1-yl)benzonitrile |
| 279 | 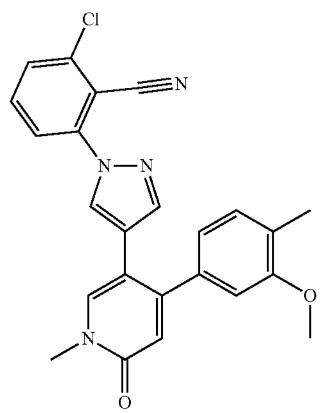 | 2-chloro-6-(4-(4-(3-methoxy-4-methylphenyl)-1-methyl-6-oxo-1,6-dihydropyridin-3-yl)-1H-pyrazol-1-yl)benzonitrile |
| 280 | 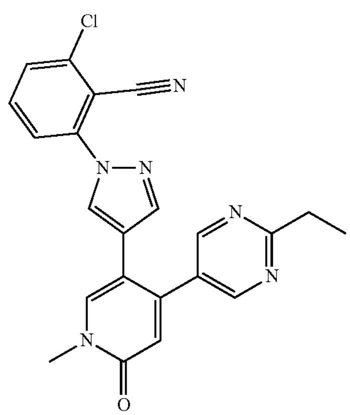 [SMILES: CCc1ncc(-c2cc(=O)n(C)cc2-c2cnn(-c3cccc(Cl)c3C#N)c2)cn1] | 2-chloro-6-(4-(4-(2-ethylpyrimidin-5-yl)-1-methyl-6-oxo-1,6-dihydropyridin-3-yl)-1H-pyrazol-1-yl)benzonitrile |
| 281 | 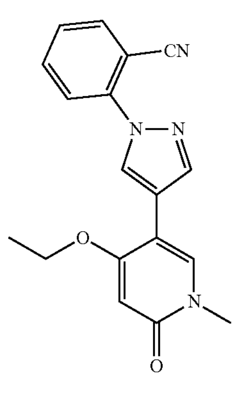 [SMILES: CCOc1cc(=O)n(C)cc1-c1cnn(-c2ccccc2C#N)c1] | 2-(4-(4-ethoxy-1-methyl-6-oxo-1,6-dihydropyridin-3-yl)-1H-pyrazol-1-yl)benzonitrile |

TABLE 1-continued

| Example | Structure | Name |
|---|---|---|
| 282 | 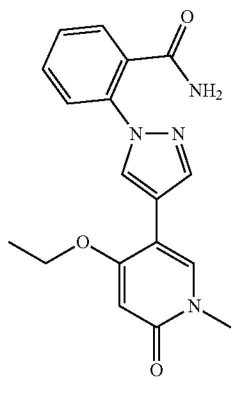 [SMILES: CCOc1cc(=O)n(C)cc1-c1cnn(-c2ccccc2C(N)=O)c1] | 2-(4-(4-ethoxy-1-methyl-6-oxo-1,6-dihydropyridin-3-yl)-1H-pyrazol-1-yl)benzamide |
| 283 | 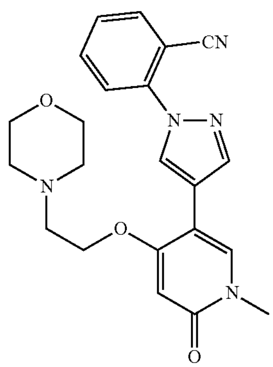 [SMILES: Cn1cc(-c2cnn(-c3ccccc3C#N)c2)c(OCCN2CCOCC2)cc1=O] | 2-(4-(1-methyl-4-(2-morpholinoethoxy)-6-oxo-1,6-dihydropyridin-3-yl)-1H-pyrazol-1-yl)benzonitrile |
| 284 | 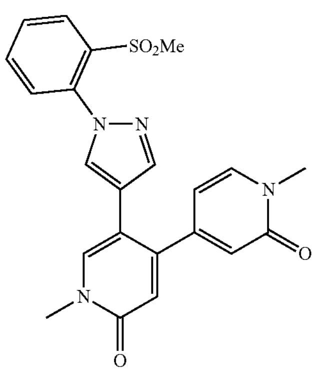 [SMILES: Cn1ccc(-c2cc(=O)n(C)cc2-c2cnn(-c3ccccc3S(C)(=O)=O)c2)cc1=O] | 5-[1-(2-Methanesulfonyl-phenyl)-1H-pyrazol-4-yl]-1,1'-dimethyl-1H,1'H-[4,4']bipyridinyl-2,2'-dione |
| 285 | 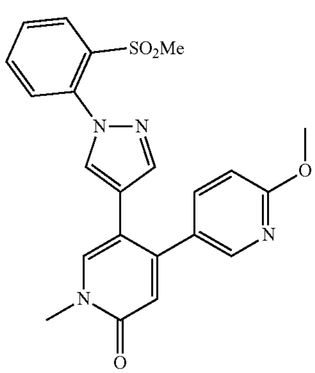 [SMILES: COc1ccc(-c2cc(=O)n(C)cc2-c2cnn(-c3ccccc3S(C)(=O)=O)c2)cn1] | 5'-[1-(2-Methanesulfonyl-phenyl)-1H-pyrazol-4-yl]-6-methoxy-1'-methyl-1'H-[3,4']bipyridinyl-2'-one |

TABLE 1-continued
| Example | Structure | Name |
|---|---|---|
| 286 | 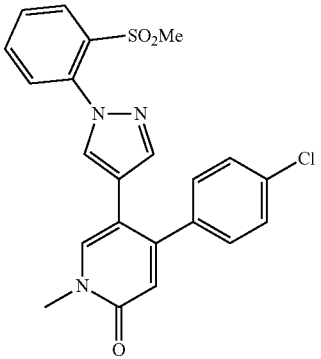 [SMILES: Cn1cc(-c2cnn(-c3ccccc3S(C)(=O)=O)c2)c(-c2ccc(Cl)cc2)cc1=O] | 4-(4-Chloro-phenyl)-5-[1-(2-methanesulfonyl-phenyl)-1H-pyrazol-4-yl]-1-methyl-1H-pyridin-2-one |
| 287 | 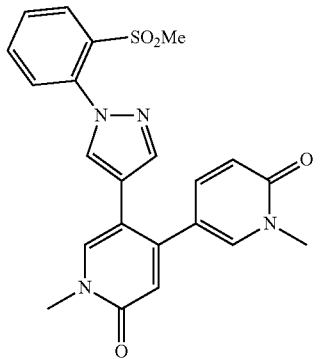 [SMILES: Cn1cc(-c2cc(=O)n(C)cc2-c2cnn(-c3ccccc3S(C)(=O)=O)c2)ccc1=O] | 5'-[1-(2-Methanesulfonyl-phenyl)-1H-pyrazol-4-yl]-1,1'-dimethyl-1H,1'H-[3,4']bipyridinyl-6,2'-dione |
| 288 | 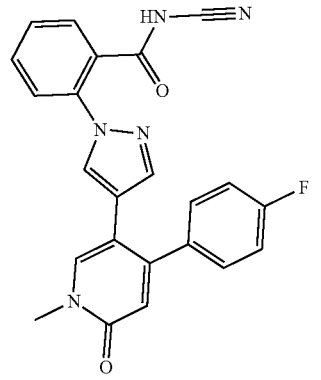 [SMILES: Cn1cc(-c2cnn(-c3ccccc3C(=O)NC#N)c2)c(-c2ccc(F)cc2)cc1=O] | N-cyano-2-(4-(4-(4-fluorophenyl)-1-methyl-6-oxo-1,6-dihydropyridin-3-yl)-1H-pyrazol-1-yl)benzamide |
| 289 | 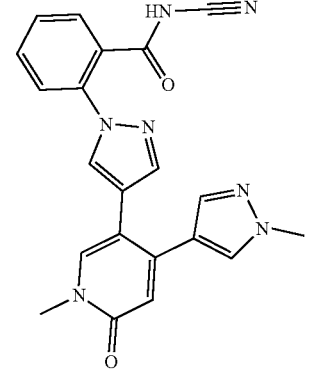 [SMILES: Cn1cc(-c2cc(=O)n(C)cc2-c2cnn(-c3ccccc3C(=O)NC#N)c2)cn1] | N-cyano-2-(4-(1-methyl-4-(1-methyl-1H-pyrazol-4-yl)-6-oxo-1,6-dihydropyridin-3-yl)-1H-pyrazol-1-yl)benzamide |

TABLE 1-continued

| Example | Structure | Name |
| --- | --- | --- |
| 290 | 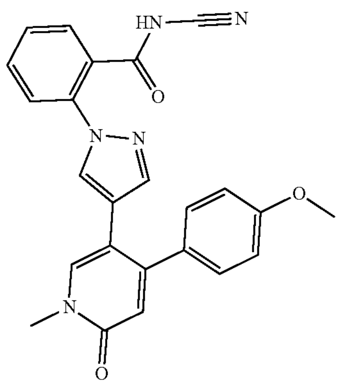 [SMILES: COc1ccc(-c2cc(=O)n(C)cc2-c2cnn(-c3ccccc3C(=O)NC#N)c2)cc1] | N-cyano-2-(4-(4-(4-methoxyphenyl)-1-methyl-6-oxo-1,6-dihydropyridin-3-yl)-1H-pyrazol-1-yl)benzamide |
| 291 | 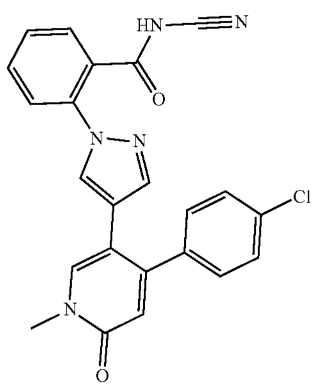 [SMILES: Cn1cc(-c2cnn(-c3ccccc3C(=O)NC#N)c2)c(-c2ccc(Cl)cc2)cc1=O] | 2-(4-(4-(4-chlorophenyl)-1-methyl-6-oxo-1,6-dihydropyridin-3-yl)-1H-pyrazol-1-yl)-N-cyanobenzamide |
| 292 | 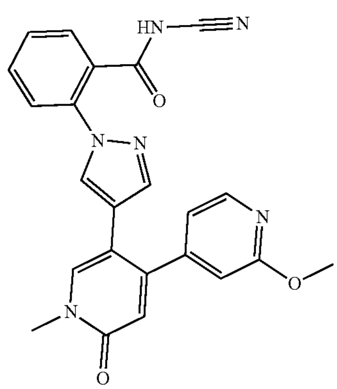 [SMILES: COc1cc(-c2cc(=O)n(C)cc2-c2cnn(-c3ccccc3C(=O)NC#N)c2)ccn1] | N-cyano-2-(4-(2'-methoxy-1-methyl-6-oxo-1,6-dihydro-[4,4'-bipyridin]-3-yl)-1H-pyrazol-1-yl)benzamide |
| 293 | 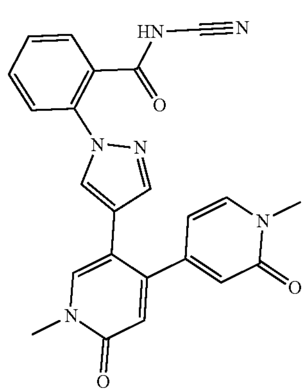 [SMILES: Cn1ccc(-c2cc(=O)n(C)cc2-c2cnn(-c3ccccc3C(=O)NC#N)c2)cc1=O] | N-cyano-2-(4-(1,1'-dimethyl-2',6-dioxo-1,1',2',6-tetrahydro-[4,4'-bipyridin]-3-yl)-1H-pyrazol-1-yl)benzamide |

TABLE 1-continued

| Example | Structure | Name |
|---|---|---|
| 294 | 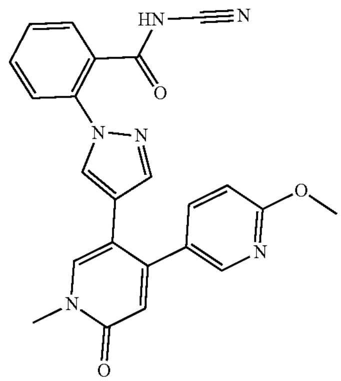 [SMILES: COc1ccc(-c2cc(=O)n(C)cc2-c2cnn(-c3ccccc3C(=O)NC#N)c2)cn1] | N-cyano-2-(4-(6-methoxy-1'-methyl-6'-oxo-1',6'-dihydro-[3,4'-bipyridin]-3'-yl)-1H-pyrazol-1-yl)benzamide |
| 295 | 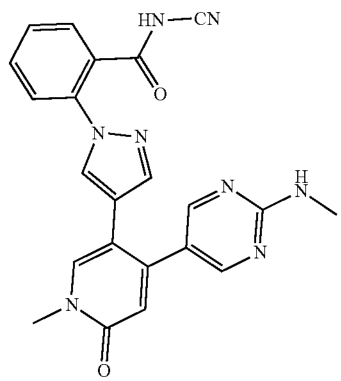 [SMILES: CNc1ncc(-c2cc(=O)n(C)cc2-c2cnn(-c3ccccc3C(=O)NC#N)c2)cn1] | N-cyano-2-(4-(1-methyl-4-(2-(methylamino)pyrimidin-5-yl)-6-oxo-1,6-dihydropyridin-3-yl)-1H-pyrazol-1-yl)benzamide |
| 296 | 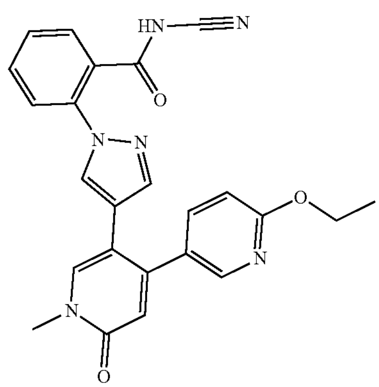 [SMILES: CCOc1ccc(-c2cc(=O)n(C)cc2-c2cnn(-c3ccccc3C(=O)NC#N)c2)cn1] | N-cyano-2-(4-(6-ethoxy-1'-methyl-6'-oxo-1',6'-dihydro-[3,4'-bipyridin]-3'-yl)-1H-pyrazol-1-yl)benzamide |
| 297 | 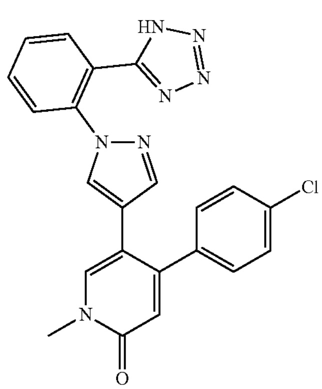 [SMILES: Cn1cc(-c2cnn(-c3ccccc3-c3nnn[nH]3)c2)c(-c2ccc(Cl)cc2)cc1=O] | 5-(1-(2-(1H-tetrazol-5-yl)phenyl)-1H-pyrazol-4-yl)-4-(4-chlorophenyl)-1-methylpyridin-2(1H)-one |

TABLE 1-continued

| Example | Structure | Name |
|---|---|---|
| 298 | 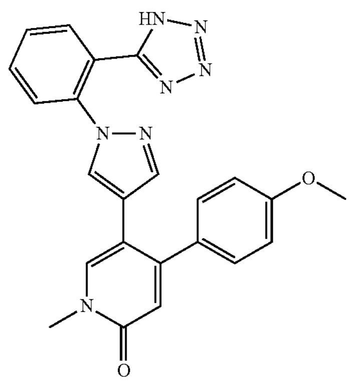 [SMILES: COc1ccc(-c2cc(=O)n(C)cc2-c2cnn(-c3ccccc3-c3nnn[nH]3)c2)cc1] | 4-(4-Methoxy-phenyl)-1-methyl-5-{1-[2-(1H-tetrazol-5-yl)-phenyl]-1H-pyrazol-4-yl}-1H-pyridin-2-one |
| 299 | 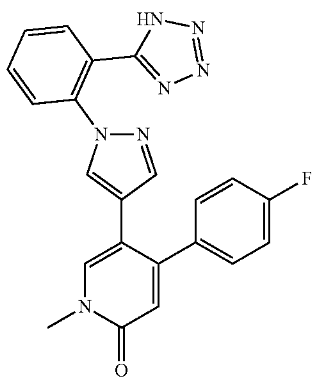 [SMILES: Cn1cc(-c2cnn(-c3ccccc3-c3nnn[nH]3)c2)c(-c2ccc(F)cc2)cc1=O] | 4-(4-Fluoro-phenyl)-1-methyl-5-{1-[2-(1H-tetrazol-5-yl)-phenyl]-1H-pyrazol-4-yl}-1H-pyridin-2-one |
| 300 | 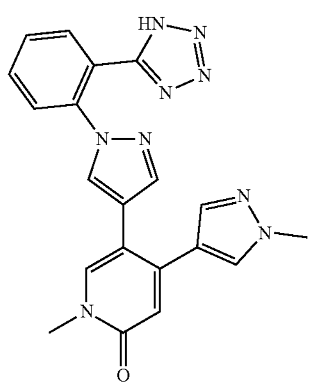 [SMILES: Cn1cc(-c2cc(=O)n(C)cc2-c2cnn(-c3ccccc3-c3nnn[nH]3)c2)cn1] | 1-Methyl-4-(1-methyl-1H-pyrazol-4-yl)-5-{1-[2-(1H-tetrazol-5-yl)-phenyl]-1H-pyrazol-4-yl}-1H-pyridin-2-one |
| 301 | 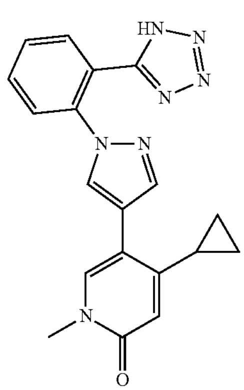 [SMILES: Cn1cc(-c2cnn(-c3ccccc3-c3nnn[nH]3)c2)c(C2CC2)cc1=O] | 4-Cyclopropyl-1-methyl-5-{1-[2-(1H-tetrazol-5-yl)-phenyl]-1H-pyrazol-4-yl}-1H-pyridin-2-one |

TABLE 1-continued

| Example | Structure | Name |
|---|---|---|
| 302 | 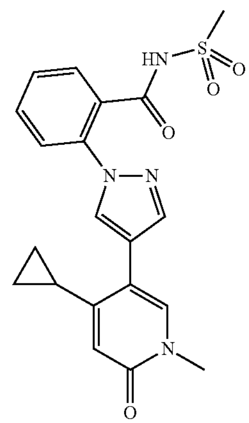 [SMILES: Cn1cc(-c2cnn(-c3ccccc3C(=O)NS(C)(=O)=O)c2)c(C2CC2)cc1=O] | N-{2-[4-(4-Cyclopropyl-1-methyl-6-oxo-1,6-dihydro-pyridin-3-yl)-pyrazol-1-yl]-benzoyl}-methanesulfonamide |
| 303 | 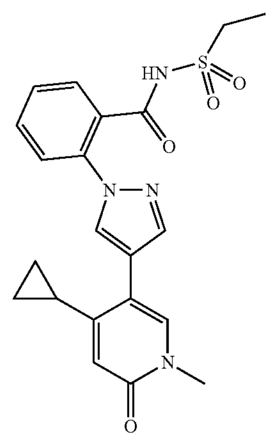 [SMILES: CCS(=O)(=O)NC(=O)c1ccccc1-n1cc(-c2cn(C)c(=O)cc2C2CC2)cn1] | Ethanesulfonic acid 2-[4-(4-cyclopropyl-1-methyl-6-oxo-1,6-dihydro-pyridin-3-yl)-pyrazol-1-yl]-benzoylamide |
| 304 | 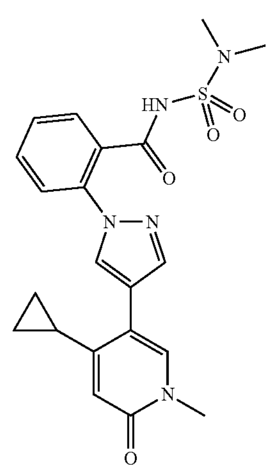 [SMILES: CN(C)S(=O)(=O)NC(=O)c1ccccc1-n1cc(-c2cn(C)c(=O)cc2C2CC2)cn1] | N-[(dimethylamino)sulfonyl]-{2-[4-(4-cyclopropyl-1-methyl-6-oxo(3-hydropyridyl))pyrazolyl]phenyl}carboxamide |

TABLE 1-continued

| Example | Name |
|---|---|
| 305 | 3-(4-(1,1'-dimethyl-2',6-dioxo-1,1',2',6-tetrahydro-[4,4'-bipyridin]-3-yl)-1H-pyrazol-1-yl)-4-methoxybenzonitrile |
| 306 | 4-Methoxy-3-[4-(6-methoxy-1'-methyl-6'-oxo-1',6'-dihydro-[3,4']bipyridinyl-3'-yl)-pyrazol-1-yl]-benzonitrile |
| 307 | 3-{4-[4-(4-Chloro-phenyl)-1-methyl-6-oxo-1,6-dihydro-pyridin-3-yl]-pyrazol-1-yl}-4-methoxy-benzonitrile |
| 308 | 6-methoxy-1'-methyl-5'-(1-(1-phenylethyl)-1H-pyrazol-4-yl)-[3,4'-bipyridin]-2'(1'H)-one. |

TABLE 1-continued

| Example | Structure | Name |
|---|---|---|
| 309 | 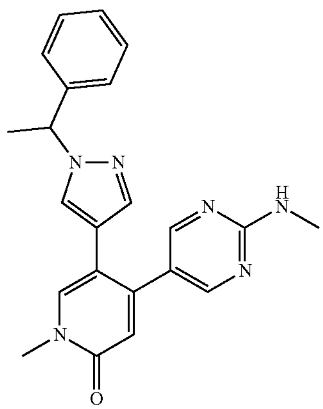 [SMILES: CNc1ncc(-c2cc(=O)n(C)cc2-c2cnn(C(C)c3ccccc3)c2)cn1] | 1-methyl-4-(2-(methylamino)pyrimidin-5-yl)-5-(1-(1-phenylethyl)-1H-pyrazol-4-yl)pyridin-2(1H)-one |
| 310 | 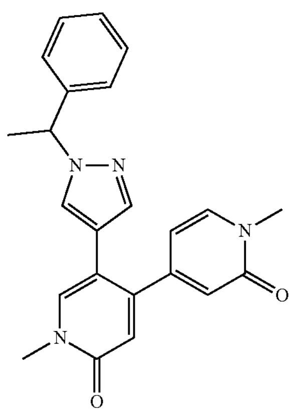 [SMILES: CC(c1ccccc1)n1cc(-c2cn(C)c(=O)cc2-c2ccn(C)c(=O)c2)cn1] | 1,1'-dimethyl-5-(1-(1-phenylethyl)-1H-pyrazol-4-yl)-[4,4'-bipyridine]-2,2'(1H,1'H)-dione |
| 311 | 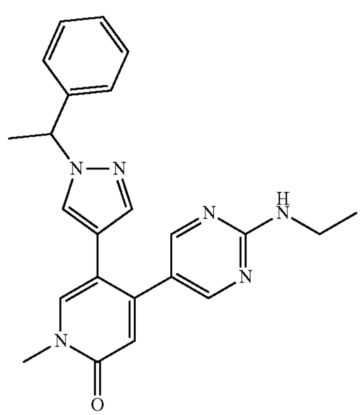 [SMILES: CCNc1ncc(-c2cc(=O)n(C)cc2-c2cnn(C(C)c3ccccc3)c2)cn1] | 4-(2-(ethylamino)pyrimidin-5-yl)-1-methyl-5-(1-(1-phenylethyl)-1H-pyrazol-4-yl)pyridin-2(1H)-one |

TABLE 1-continued

| Example | Structure | Name |
|---|---|---|
| 312 | 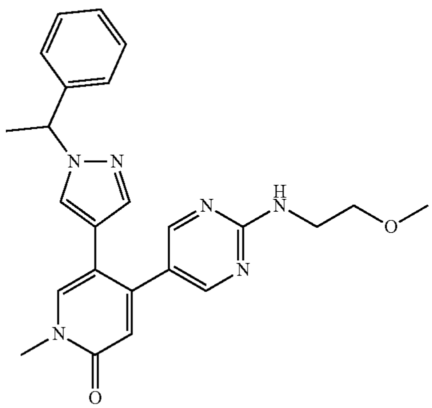 [SMILES: COCCNc1ncc(-c2cc(=O)n(C)cc2-c2cnn(C(C)c3ccccc3)c2)cn1] | 4-(2-((2-methoxyethyl)amino)pyrimidin-5-yl)-1-methyl-5-(1-(1-phenylethyl)-1H-pyrazol-4-yl)pyridin-2(1H)-one |
| 313 | 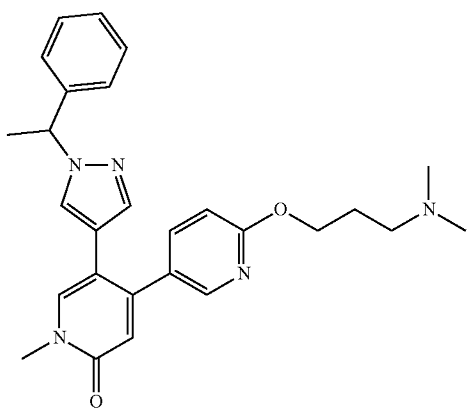 [SMILES: CC(c1ccccc1)n1cc(-c2cn(C)c(=O)cc2-c2ccc(OCCCN(C)C)nc2)cn1] | 6-(3-(dimethylamino)propoxy)-1'-methyl-5'-(1-(1-phenylethyl)-1H-pyrazol-4-yl)-[3,4'-bipyridin]-2'(1'H)-one |
| 314 | 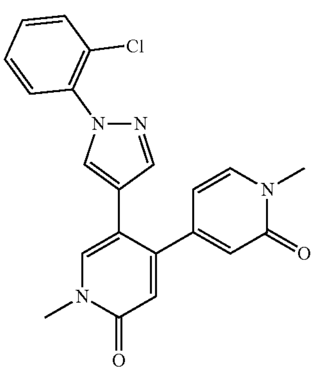 [SMILES: Cn1ccc(-c2cc(=O)n(C)cc2-c2cnn(-c3ccccc3Cl)c2)cc1=O] | 5-(1-(2-chlorophenyl)-1H-pyrazol-4-yl)-1,1'-dimethyl-[4,4'-bipyridine]-2,2'(1H,1'H)-dione |
| 315 | 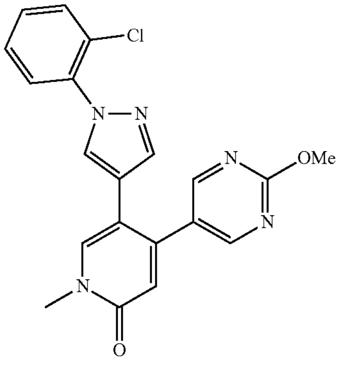 [SMILES: COc1ncc(-c2cc(=O)n(C)cc2-c2cnn(-c3ccccc3Cl)c2)cn1] | 5-(1-(2-chlorophenyl)-1H-pyrazol-4-yl)-4-(2-methoxypyrimidin-5-yl)-1-methylpyridin-2(1H)-one |

TABLE 1-continued

| Example | Structure | Name |
|---|---|---|
| 316 | 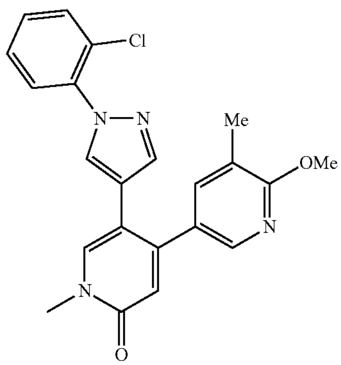 [SMILES: COc1ncc(-c2cc(=O)n(C)cc2-c2cnn(-c3ccccc3Cl)c2)cc1C] | 5'-(1-(2-chlorophenyl)-1H-pyrazol-4-yl)-6-methoxy-1',5-dimethyl-[3,4'-bipyridin]-2'(1'H)-one |
| 317 | 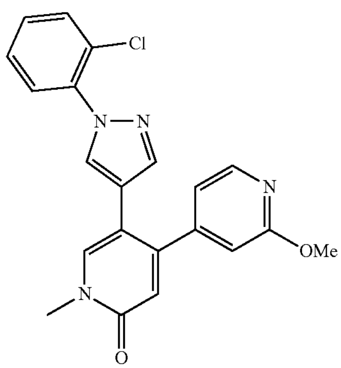 [SMILES: COc1cc(-c2cc(=O)n(C)cc2-c2cnn(-c3ccccc3Cl)c2)ccn1] | 5-(1-(2-chlorophenyl)-1H-pyrazol-4-yl)-2'-methoxy-1-methyl-[4,4'-bipyridin]-2(1H)-one |
| 318 | 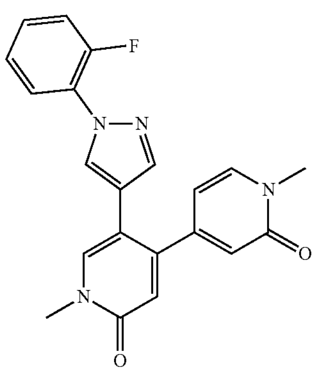 [SMILES: Cn1ccc(-c2cc(=O)n(C)cc2-c2cnn(-c3ccccc3F)c2)cc1=O] | 5-(1-(2-fluorophenyl)-1H-pyrazol-4-yl)-1,1'-dimethyl-[4,4'-bipyridine]-2,2'(1H,1'H)-dione |
| 319 | 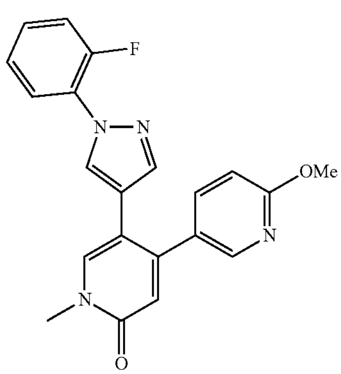 [SMILES: COc1ccc(-c2cc(=O)n(C)cc2-c2cnn(-c3ccccc3F)c2)cn1] | 5'-(1-(2-fluorophenyl)-1H-pyrazol-4-yl)-6-methoxy-1'-methyl-[3,4'-bipyridin]-2'(1'H)-one |

TABLE 1-continued

| Example | Structure | Name |
|---|---|---|
| 320 | 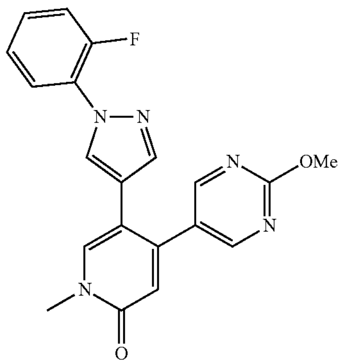 | 5-(1-(2-fluorophenyl)-1H-pyrazol-4-yl)-4-(2-methoxypyrimidin-5-yl)-1-methylpyridin-2(1H)-one |
| 321 | 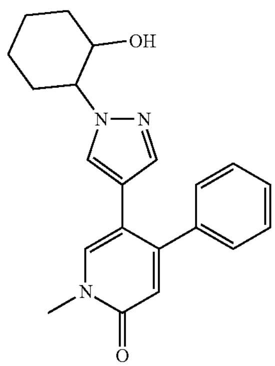 [SMILES: Cn1cc(-c2cnn(C3CCCCC3O)c2)c(-c2ccccc2)cc1=O] | 5-(1-(2-hydroxycyclohexyl)-1H-pyrazol-4-yl)-1-methyl-4-phenylpyridin-2(1H)-one |
| 322 | 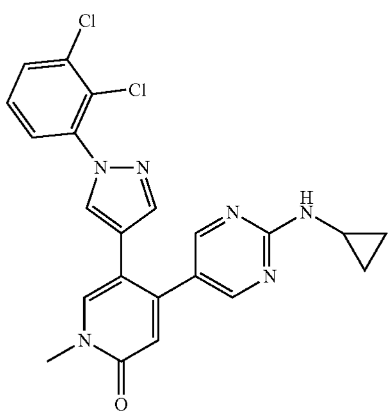 [SMILES: Cn1cc(-c2cnn(-c3cccc(Cl)c3Cl)c2)c(-c2cnc(NC3CC3)nc2)cc1=O] | 2-chloro-6-[4-[4-[2-(cyclopropylamino)pyrimidin-5-yl]-1-methyl-6-oxo-3-pyridyl]pyrazol-1-yl]benzonitrile |
| 323 | 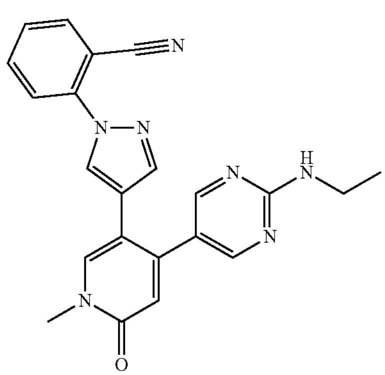 [SMILES: CCNc1ncc(-c2cc(=O)n(C)cc2-c2cnn(-c3ccccc3C#N)c2)cn1] | 2-(4-(4-(2-(ethylamino)pyrimidin-5-yl)-1-methyl-6-oxo-1,6-dihydropyridin-3-yl)-1H-pyrazol-1-yl)benzonitrile |

TABLE 1-continued

| Example | Structure | Name |
|---------|-----------|------|
| 324 | 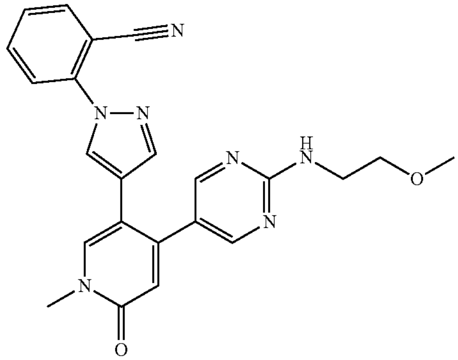 [SMILES: COCCNc1ncc(-c2cc(=O)n(C)cc2-c2cnn(-c3ccccc3C#N)c2)cn1] | 2-(4-(4-(2-((2-methoxyethyl)amino)pyrimidin-5-yl)-1-methyl-6-oxo-1,6-dihydropyridin-3-yl)-1H-pyrazol-1-yl)benzonitrile |
| 325 | 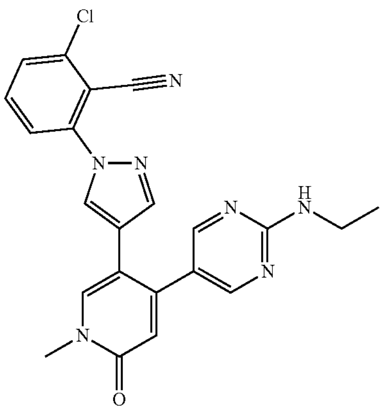 | 2-chloro-6-(4-(4-(2-(ethylamino)pyrimidin-5-yl)-1-methyl-6-oxo-1,6-dihydropyridin-3-yl)-1H-pyrazol-1-yl)benzonitrile |
| 326 | 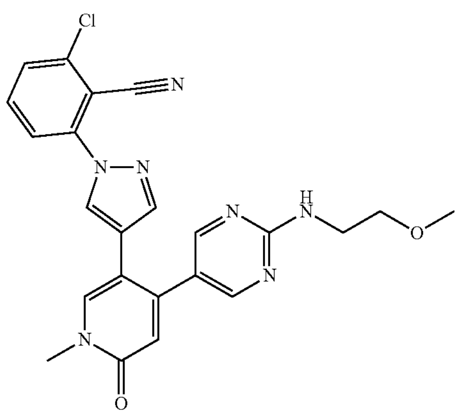 [SMILES: COCCNc1ncc(-c2cc(=O)n(C)cc2-c2cnn(-c3cccc(Cl)c3C#N)c2)cn1] | 2-chloro-6-(4-(4-(2-((2-methoxyethyl)amino)pyrimidin-5-yl)-1-methyl-6-oxo-1,6-dihydropyridin-3-yl)-1H-pyrazol-1-yl)benzonitrile |
| 327 | 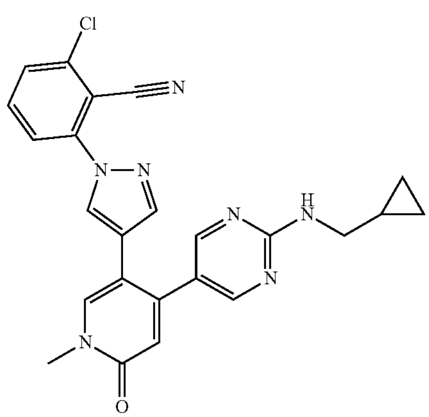 | 2-chloro-6-(4-(4-(2-((cyclopropylmethyl)amino)pyrimidin-5-yl)-1-methyl-6-oxo-1,6-dihydropyridin-3-yl)-1H-pyrazol-1-yl)benzonitrile |

TABLE 1-continued

| Example | Structure | Name |
|---------|-----------|------|
| 328 | 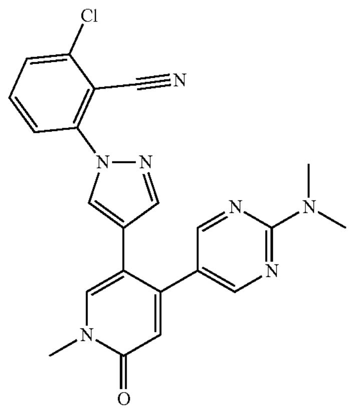 | 2-chloro-6-(4-(4-(2-(dimethylamino)pyrimidin-5-yl)-1-methyl-6-oxo-1,6-dihydropyridin-3-yl)-1H-pyrazol-1-yl)benzonitrile |
| 329 | 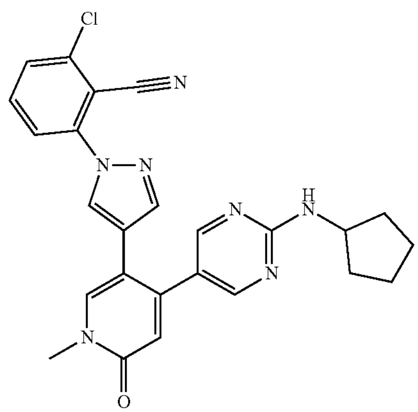 | 2-chloro-6-(4-(4-(2-(cyclopentylamino)pyrimidin-5-yl)-1-methyl-6-oxo-1,6-dihydropyridin-3-yl)-1H-pyrazol-1-yl)benzonitrile |
| 330 | 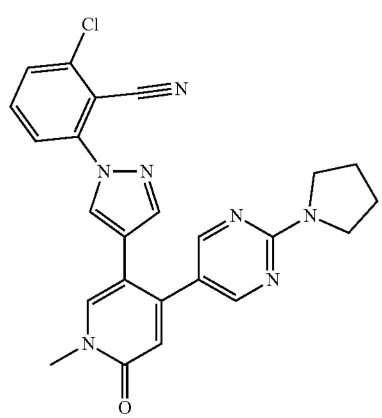 | 2-chloro-6-(4-(1-methyl-6-oxo-4-(2-(pyrrolidin-1-yl)pyrimidin-5-yl)-1,6-dihydropyridin-3-yl)-1H-pyrazol-1-yl)benzonitrile |

TABLE 1-continued

| Example | Structure | Name |
|---|---|---|
| 331 | 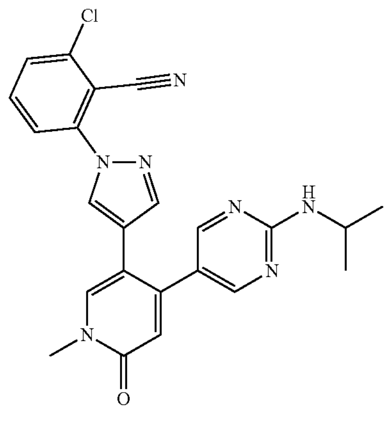 [SMILES: CC(C)Nc1ncc(-c2cc(=O)n(C)cc2-c2cnn(-c3cccc(Cl)c3C#N)c2)cn1] | 2-chloro-6-(4-(4-(2-(isopropylamino)pyrimidin-5-yl)-1-methyl-6-oxo-1,6-dihydropyridin-3-yl)-1H-pyrazol-1-yl)benzonitrile |
| 332 | 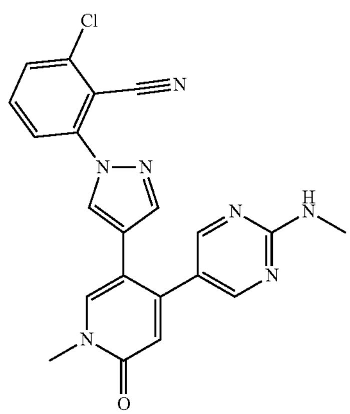 | 2-chloro-6-(4-(1-methyl-4-(2-(methylamino)pyrimidin-5-yl)-6-oxo-1,6-dihydropyridin-3-yl)-1H-pyrazol-1-yl)benzonitrile |
| 333 | 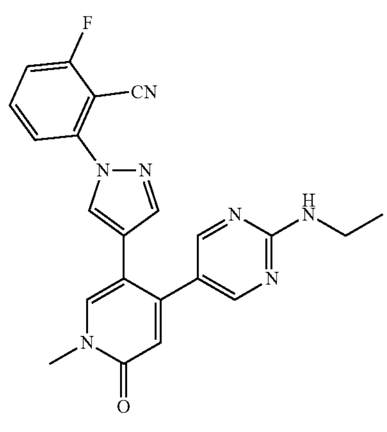 [SMILES: CCNc1ncc(-c2cc(=O)n(C)cc2-c2cnn(-c3cccc(F)c3C#N)c2)cn1] | 2-[4-[4-[2-(ethylamino)pyrimidin-5-yl]-1-methyl-6-oxo-3-pyridyl]pyrazol-1-yl]-6-fluoro-benzonitrile |

TABLE 1-continued

| Example | Structure | Name |
|---|---|---|
| 334 | 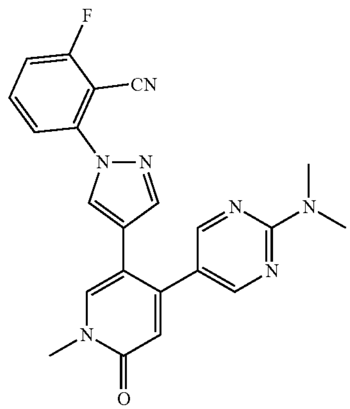 [SMILES: CN(C)c1ncc(-c2cc(=O)n(C)cc2-c2cnn(-c3cccc(F)c3C#N)c2)cn1] | 2-[4-[4-[2-(dimethylamino)pyrimidin-5-yl]-1-methyl-6-oxo-3-pyridyl]pyrazol-1-yl]-6-fluoro-benzonitrile |
| 335 | 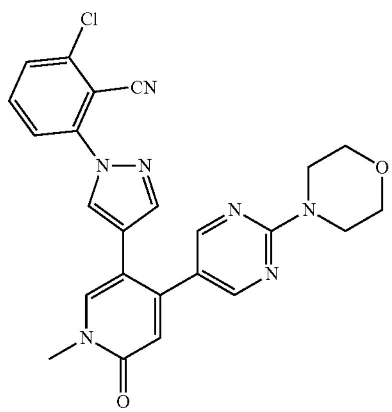 [SMILES: Cn1cc(-c2cnn(-c3cccc(Cl)c3C#N)c2)c(-c2cnc(N3CCOCC3)nc2)cc1=O] | 2-chloro-6-(4-(1-methyl-4-(2-morpholinopyrimidin-5-yl)-6-oxo-1,6-dihydropyridin-3-yl)-1H-pyrazol-1-yl)benzonitrile |
| 336 | 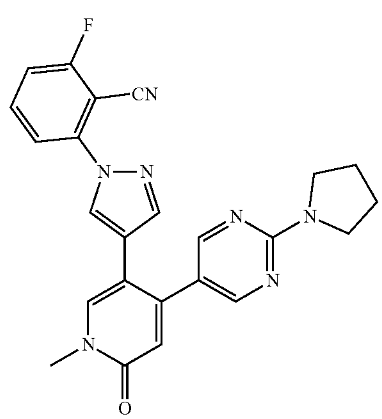 [SMILES: Cn1cc(-c2cnn(-c3cccc(F)c3C#N)c2)c(-c2cnc(N3CCCC3)nc2)cc1=O] | 2-fluoro-6-[4-[1-methyl-6-oxo-4-(2-pyrrolidin-1-ylpyrimidin-5-yl)-3-pyridyl]pyrazol-1-yl]benzonitrile |

TABLE 1-continued

| Example | Structure | Name |
|---|---|---|
| 337 | 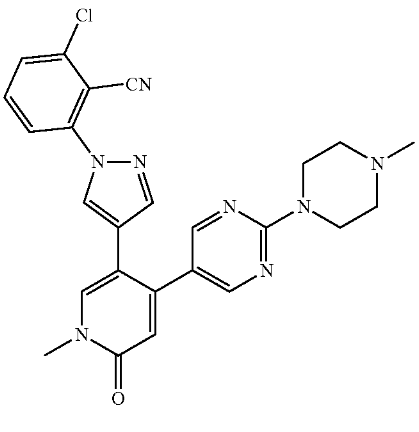 [SMILES: CN1CCN(c2ncc(-c3cc(=O)n(C)cc3-c3cnn(-c4cccc(Cl)c4C#N)c3)cn2)CC1] | 2-chloro-6-(4-(1-methyl-4-(2-(4-methylpiperazin-1-yl)pyrimidin-5-yl)-6-oxo-1,6-dihydropyridin-3-yl)-1H-pyrazol-1-yl)benzonitrile |
| 338 | 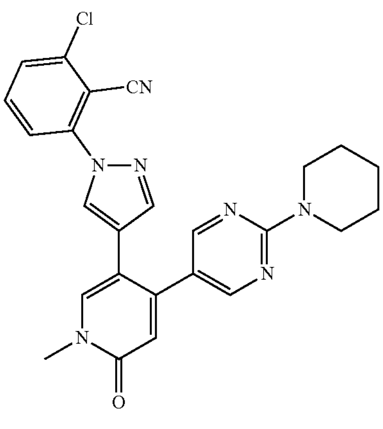 [SMILES: Cn1cc(-c2cnn(-c3cccc(Cl)c3C#N)c2)c(-c2cnc(N3CCCCC3)nc2)cc1=O] | 2-chloro-6-(4-(1-methyl-6-oxo-4-(2-(piperidin-1-yl)pyrimidin-5-yl)-1,6-dihydropyridin-3-yl)-1H-pyrazol-1-yl)benzonitrile |
| 339 | 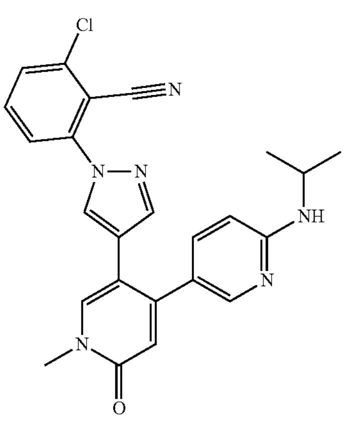 [SMILES: CC(C)Nc1ccc(-c2cc(=O)n(C)cc2-c2cnn(-c3cccc(Cl)c3C#N)c2)cn1] | 2-chloro-6-[4-[4-[6-(isopropylamino)-3-pyridyl]-1-methyl-6-oxo-3-pyridyl]-pyrazol-1-yl]benzonitrile |

TABLE 1-continued

| Example | Structure | Name |
|---|---|---|
| 340 | 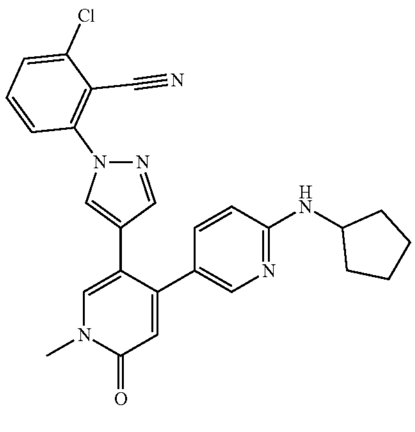 | 2-chloro-6-(4-(6-(cyclopentylamino)-1'-methyl-6'-oxo-1',6'-dihydro-[3,4'-bipyridin]-3'-yl)-1H-pyrazol-1-yl)benzonitrile |
| 341 | 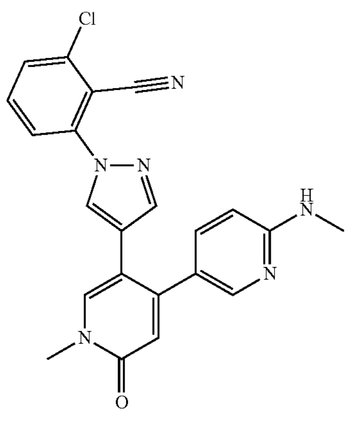 | 2-chloro-6-(4-(1'-methyl-6-(methylamino)-6'-oxo-1',6'-dihydro-[3,4'-bipyridin]-3'-yl)-1H-pyrazol-1-yl)benzonitrile |
| 342 | 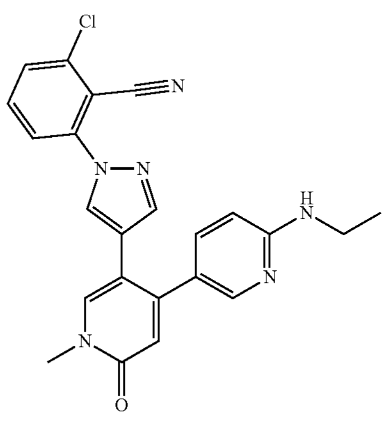 | 2-chloro-6-(4-(6-(ethylamino)-1'-methyl-6'-oxo-1',6'-dihydro-[3,4'-bipyridin]-3'-yl)-1H-pyrazol-1-yl)benzonitrile |

TABLE 1-continued

| Example | Structure | Name |
|---|---|---|
| 343 | 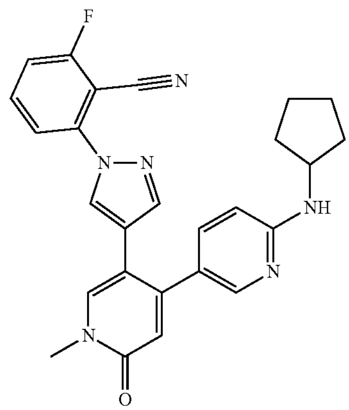 | 2-(4-(6-(cyclopentylamino)-1'-methyl-6'-oxo-1', 6'-dihydro-[3, 4'-bipyridin]-3'-yl)-1H-pyrazol-1-yl)-6-fluorobenzonitrile |
| 344 | 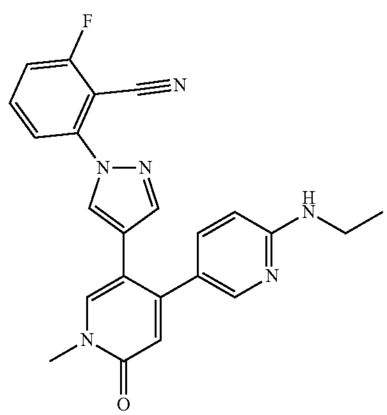 | 2-(4-(6-(ethylamino)-1'-methyl-6'-oxo-11, 6'-dihydro-[3, 4'-bipyridin]-3'-yl)-1H-pyrazol-1-yl)-6-fluorobenzonitrile |
| 345 | 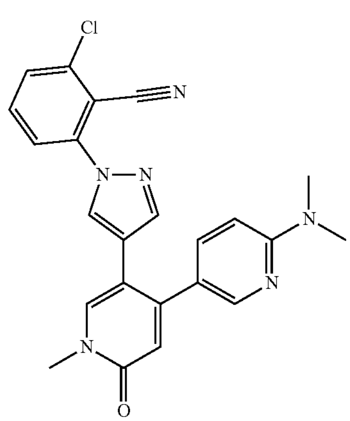 [SMILES: CN(C)c1ccc(-c2cc(=O)n(C)cc2-c2cnn(-c3cccc(Cl)c3C#N)c2)cn1] | 2-chloro-6-{4-[6-(dimethylamino)-1'-methyl-6'-oxo-1', 6'-dihydro-[3,4'-bipyridine]-3'-yl]-1H-pyrazol-1-yl}benzonitrile |

TABLE 1-continued

| Example | Structure | Name |
|---|---|---|
| 346 | 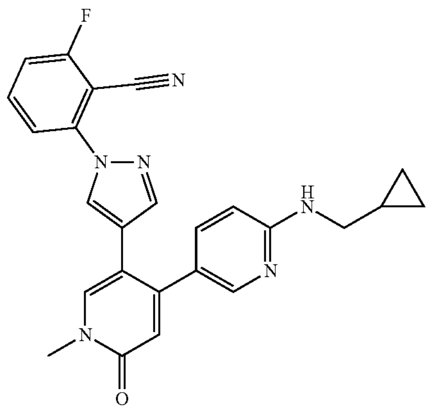 [SMILES: Cn1cc(-c2cnn(-c3cccc(F)c3C#N)c2)c(-c2ccc(NCC3CC3)nc2)cc1=O] | 2-(4-{6-[(cyclopropylmethyl)amino]-1'-methyl-6'-oxo-1',6'-dihydro-[3,4'-bipyridine]-3'-yl}-1H-pyrazol-1-yl)-6-fluorobenzonitrile |
| 347 | 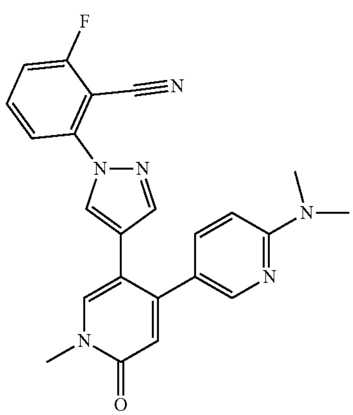 [SMILES: CN(C)c1ccc(-c2cc(=O)n(C)cc2-c2cnn(-c3cccc(F)c3C#N)c2)cn1] | 2-{4-[6-(dimethylamino)-1'-methyl-6'-oxo-1',6'-dihydro-[3,4'-bipyridine]-3'-yl]-1H-pyrazol-1-yl}-6-fluorobenzonitrile |
| 348 | 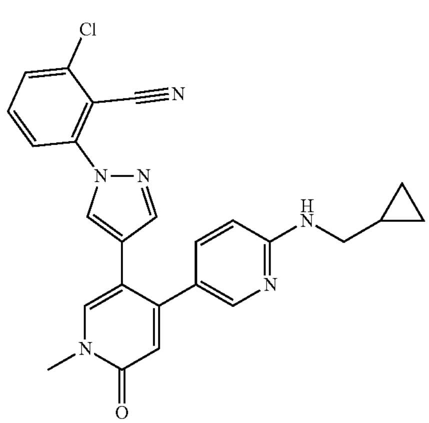 | 2-chloro-6-(4-{6-[(cyclopropylmethyl)amino]-1'-methyl-6'-oxo-1',6'-dihydro-[3,4'-bipyridine]-3'-yl}-1H-pyrazol-1-yl)benzonitrile |

TABLE 1-continued

| Example | Structure | Name |
|---|---|---|
| 349 | 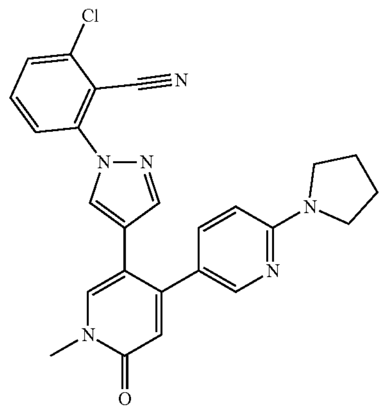 | 2-chloro-6-[4-[1-methyl-6-oxo-4-(6-pyrrolidin-1-yl-3-pyridyl)-3-pyridyl]pyrazol-1-yl]benzonitrile |
| 350 | 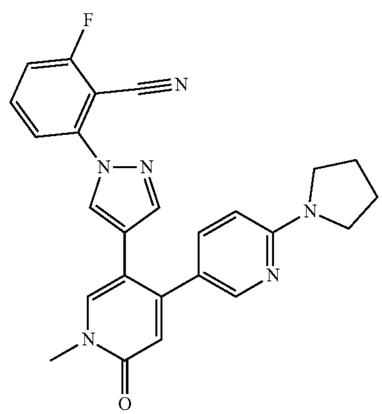 | 2-fluoro-6-[4-[1-methyl-6-oxo-4-(6-pyrrolidin-1-yl-3-pyridyl)-3-pyridyl]pyrazol-1-yl]benzonitrile |
| 351 | 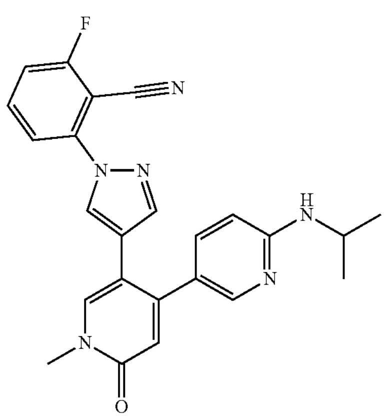 [SMILES: CC(C)Nc1ccc(-c2cc(=O)n(C)cc2-c2cnn(-c3cccc(F)c3C#N)c2)cn1] | 2-fluoro-6-(4-(6-(isopropylamino)-1'-methyl-6'-oxo-1',6'-dihydro-[3,4'-bipyridin]-3'-yl)-1H-pyrazol-1-yl)benzonitrile |

TABLE 1-continued

| Example | Structure | Name |
|---|---|---|
| 352 | 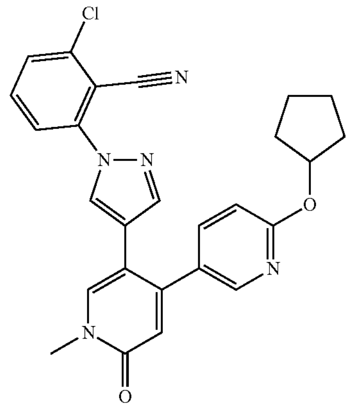 | 2-chloro-6-[4-[4-[6-(cyclopentoxy)-3-pyridyl]-1-methyl-6-oxo-3-pyridyl]pyrazol-1-yl]benzonitrile |
| 353 | 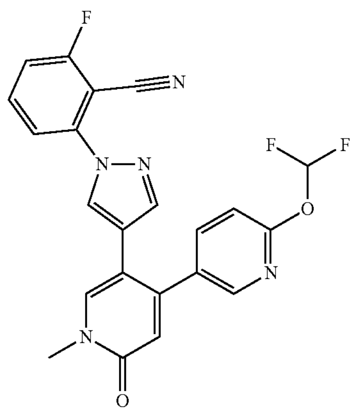 [SMILES: Cn1cc(-c2cnn(-c3cccc(F)c3C#N)c2)c(-c2ccc(OC(F)F)nc2)cc1=O] | 2-(4-(6-(difluoromethoxy)-1'-methyl-6'-oxo-1',6'-dihydro-[3,4'-bipyridin]-3'-yl)-1H-pyrazol-1-yl)-6-fluorobenzonitrile |
| 354 | 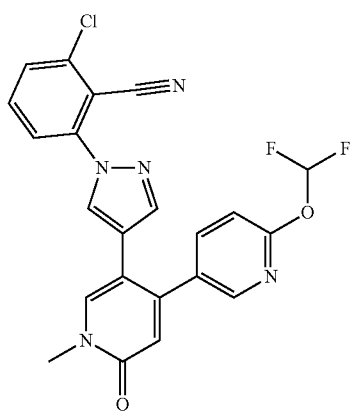 | 2-chloro-6-(4-(6-(difluoromethoxy)-1'-methyl-6'-oxo-1',6'-dihydro-[3,4'-bipyridin]-3'-yl)-1H-pyrazol-1-yl)benzonitrile |
| 355 | 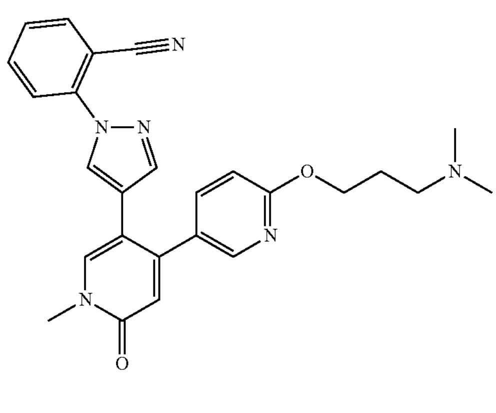 [SMILES: CN(C)CCCOc1ccc(-c2cc(=O)n(C)cc2-c2cnn(-c3ccccc3C#N)c2)cn1] | 2-(4-(6-(3-(dimethylamino)propoxy)-1'-methyl-6'-oxo-1',6'-dihydro-[3,4'-bipyridin]-3'-yl)-1H-pyrazol-1-yl)benzonitrile |

TABLE 1-continued

| Example | Structure | Name |
|---|---|---|
| 356 | 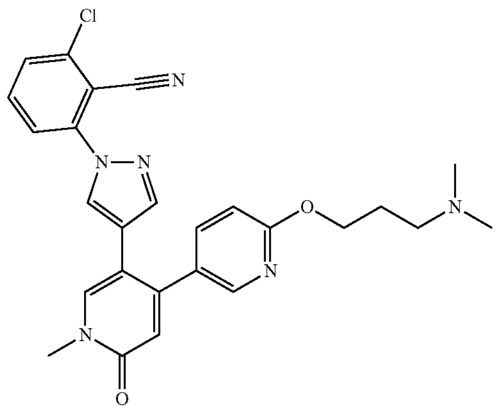 [SMILES: CN(C)CCCOc1ccc(-c2cc(=O)n(C)cc2-c2cnn(-c3cccc(Cl)c3C#N)c2)cn1] | 2-chloro-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile |
| 357 | 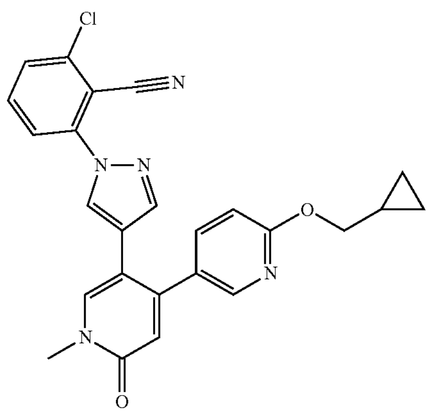 | 2-chloro-6-[4-[4-[6-(cyclopropylmethoxy)-3-pyridyl]-1-methyl-6-oxo-3-pyridyl]pyrazol-1-yl]benzonitrile |
| 358 | 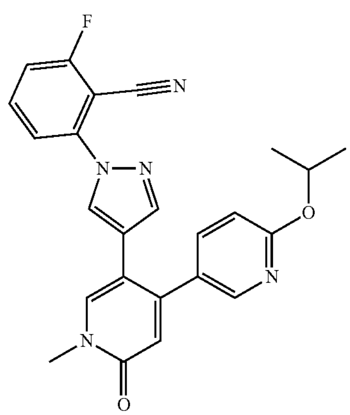 [SMILES: CC(C)Oc1ccc(-c2cc(=O)n(C)cc2-c2cnn(-c3cccc(F)c3C#N)c2)cn1] | 2-fluoro-6-[4-[4-(6-isopropoxy-3-pyridyl)-1-methyl-6-oxo-3-pyridyl]pyrazol-1-yl]benzonitrile |

TABLE 1-continued

| Example | Structure | Name |
|---|---|---|
| 359 | 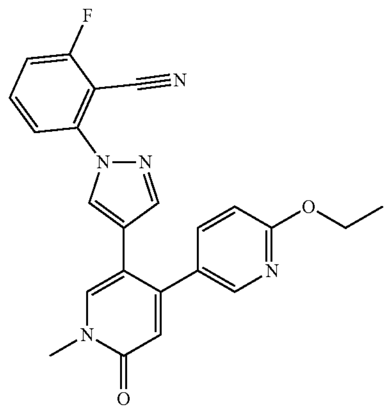 [SMILES: CCOc1ccc(-c2cc(=O)n(C)cc2-c2cnn(-c3cccc(F)c3C#N)c2)cn1] | 2-(4-(6-ethoxy-1'-methyl-6'-oxo-1', 6'-dihydro-[3, 4'-bipyridin]-3'-yl)-1H-pyrazol-1-yl)-6-fluorobenzonitrile |
| 360 | 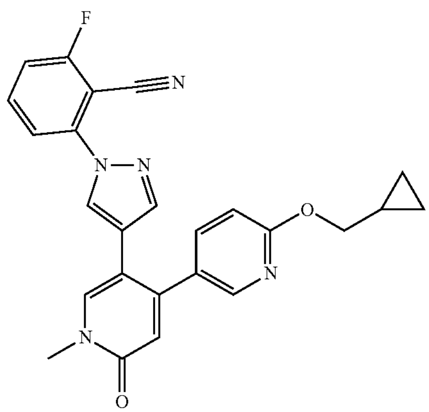 [SMILES: Cn1cc(-c2cnn(-c3cccc(F)c3C#N)c2)c(-c2ccc(OCC3CC3)nc2)cc1=O] | 2-[4-[4-[6-(cyclopropylmethoxy)-3-pyridyl]-1-methyl-6-oxo-3-pyridyl]pyrazol-1-yl]-6-fluoro-benzonitrile |
| 361 | 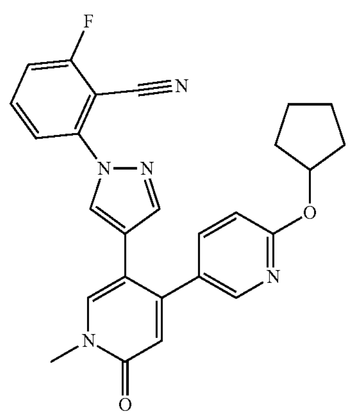 [SMILES: Cn1cc(-c2cnn(-c3cccc(F)c3C#N)c2)c(-c2ccc(OC3CCCC3)nc2)cc1=O] | 2-[4-[4-[6-(cyclopentoxy)-3-pyridyl]-1-methyl-6-oxo-3-pyridyl]pyrazol-1-yl]-6-fluoro-benzonitrile |

TABLE 1-continued

| Example | Structure | Name |
|---|---|---|
| 362 | 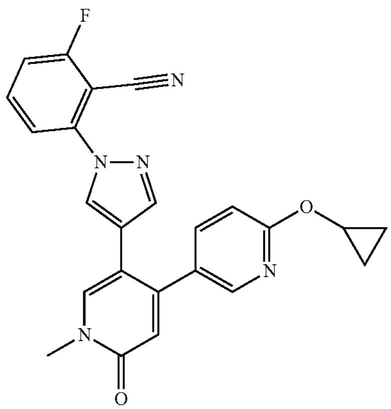 [SMILES: Cn1cc(-c2cnn(-c3cccc(F)c3C#N)c2)c(-c2ccc(OC3CC3)nc2)cc1=O] | 2-[4-[4-[6-(cyclopropoxy)-3-pyridyl]-1-methyl-6-oxo-3-pyridyl]pyrazol-1-yl]-6-fluoro-benzonitrile |
| 363 | 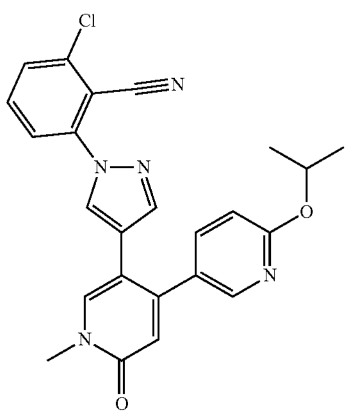 | 2-chloro-6-[4-[4-(6-isopropoxy-3-pyridyl)-1-methyl-6-oxo-3-pyridyl]pyrazol-1-yl]benzonitrile |
| 364 | 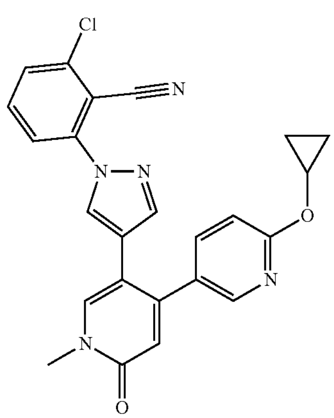 [SMILES: Cn1cc(-c2cnn(-c3cccc(Cl)c3C#N)c2)c(-c2ccc(OC3CC3)nc2)cc1=O] | 2-chloro-6-[4-[4-[6-(cyclopropoxy)-3-pyridyl]-1-methyl-6-oxo-3-pyridyl]pyrazol-1-yl]benzonitrile |

TABLE 1-continued

| Example | Structure | Name |
|---|---|---|
| 365 | 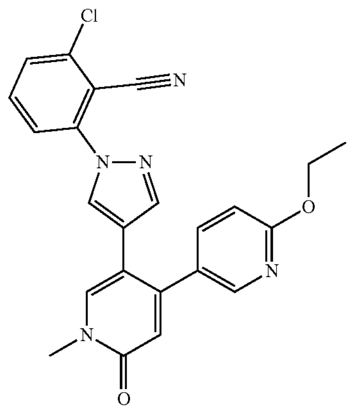 [SMILES: CCOc1ccc(-c2cc(=O)n(C)cc2-c2cnn(-c3cccc(Cl)c3C#N)c2)cn1] | 2-chloro-6-(4-(6-ethoxy-1'-methyl-6'-oxo-1', 6'-dihydro-[3, 4'-bipyridin]-3'-yl)-1H-pyrazol-1-yl)benzonitrile |
| 366 | 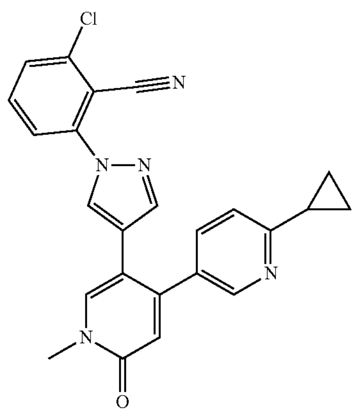 | 2-chloro-6-[4-[4-(6-cyclopropyl-3-pyridyl)-1-methyl-6-oxo-3-pyridyl]pyrazol-1-yl]benzonitrile |
| 367 | 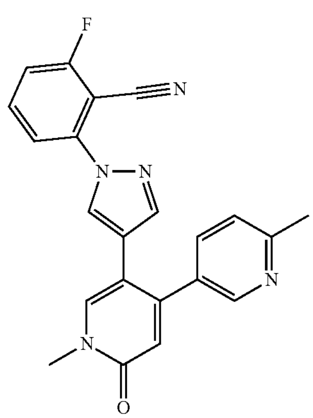 [SMILES: Cc1ccc(-c2cc(=O)n(C)cc2-c2cnn(-c3cccc(F)c3C#N)c2)cn1] | 2-(4-(1',6-dimethyl-6'-oxo-1',6'-dihydro-[3,4'-bipyridin]-3'-yl)-1H-pyrazol-1-yl)-6-fluorobenzonitrile |

TABLE 1-continued

| Example | Structure | Name |
|---|---|---|
| 368 | 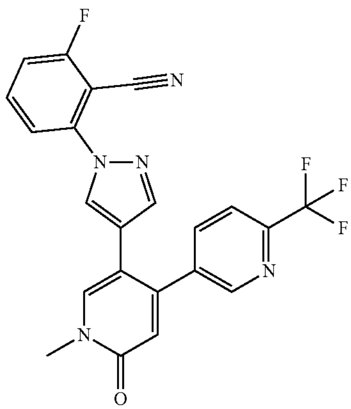 [SMILES: Cn1cc(-c2cnn(-c3cccc(F)c3C#N)c2)c(-c2ccc(C(F)(F)F)nc2)cc1=O] | 2-fluoro-6-(4-(1'-methyl-6'-oxo-6-(trifluoromethyl)-1',6'-dihydro-[3,4'-bipyridin]-3'-yl)-1H-pyrazol-1-yl)benzonitrile |
| 369 | 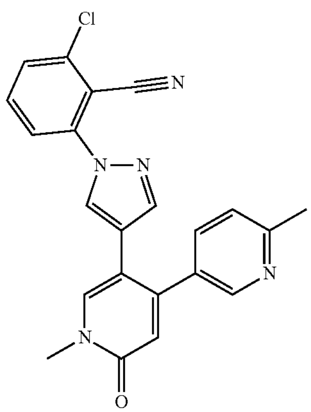 | 2-chloro-6-(4-(1',6-dimethyl-6'-oxo-1',6'-dihydro-[3,4'-bipyridin]-3'-yl)-1H-pyrazol-1-yl)benzonitrile |
| 370 | 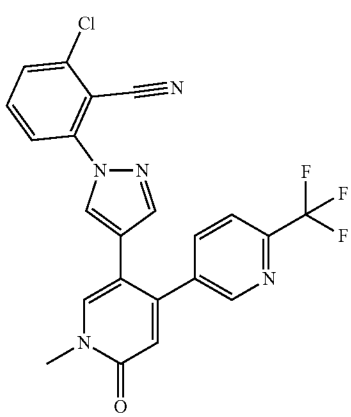 [SMILES: Cn1cc(-c2cnn(-c3cccc(Cl)c3C#N)c2)c(-c2ccc(C(F)(F)F)nc2)cc1=O] | 2-chloro-6-(4-(1'-methyl-6'-oxo-6-(trifluoromethyl)-1',6'-dihydro-[3,4'-bipyridin]-3'-yl)-1H-pyrazol-1-yl)benzonitrile |

TABLE 1-continued

| Example | Structure | Name |
|---|---|---|
| 371 | 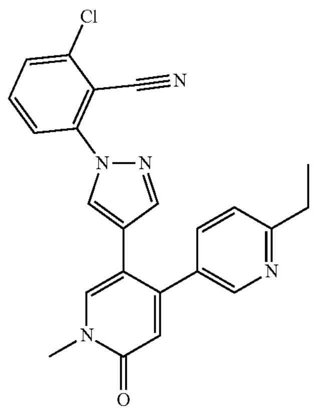 | 2-chloro-6-(4-(6-ethyl-1'-methyl-6'-oxo-1',6'-dihydro-[3,4'-bipyridin]-3'-yl)-1H-pyrazol-1-yl)benzonitrile |
| 372 | 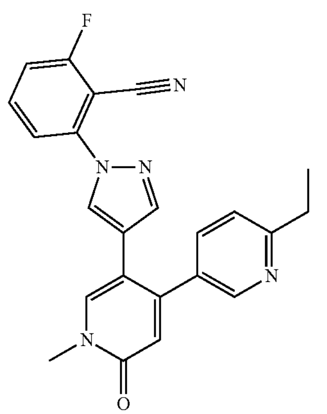 [SMILES: CCc1ccc(-c2cc(=O)n(C)cc2-c2cnn(-c3cccc(F)c3C#N)c2)cn1] | 2-(4-(6-ethyl-1'-methyl-6'-oxo-1',6'-dihydro-[3,4'-bipyridin]-3'-yl)-1H-pyrazol-1-yl)-6-fluorobenzonitrile |
| 373 | 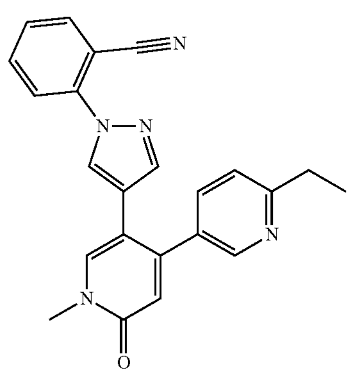 [SMILES: CCc1ccc(-c2cc(=O)n(C)cc2-c2cnn(-c3ccccc3C#N)c2)cn1] | 2-(4-(6-ethyl-1'-methyl-6'-oxo-1',6'-dihydro-[3,4'-bipyridin]-3'-yl)-1H-pyrazol-1-yl)benzonitrile |
| 374 | 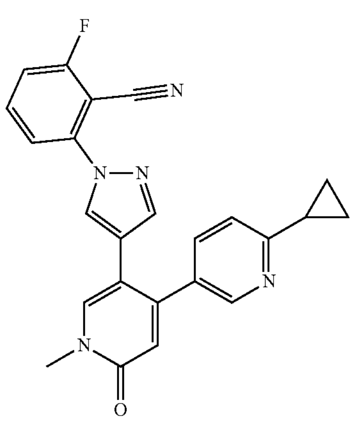 [SMILES: Cn1cc(-c2cnn(-c3cccc(F)c3C#N)c2)c(-c2ccc(C3CC3)nc2)cc1=O] | 2-[4-[4-(6-cyclopropyl-3-pyridyl)-1-methyl-6-oxo-3-pyridyl]pyrazol-1-yl]-6-fluoro-benzonitrile |

TABLE 1-continued

| Example | Structure | Name |
|---|---|---|
| 375 | 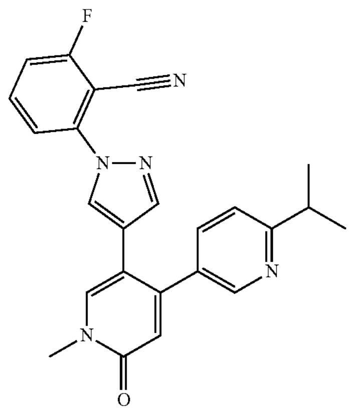 [SMILES: CC(C)c1ccc(-c2cc(=O)n(C)cc2-c2cnn(-c3cccc(F)c3C#N)c2)cn1] | 2-fluoro-6-[4-[4-(6-isopropyl-3-pyridyl)-1-methyl-6-oxo-3-pyridyl]pyrazol-1-yl]benzonitrile |
| 376 | 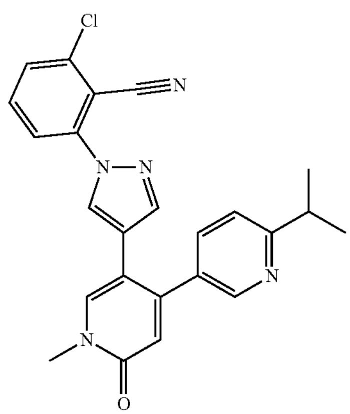 | 2-chloro-6-[4-[4-(6-isopropyl-3-pyridyl)-1-methyl-6-oxo-3-pyridyl]pyrazol-1-yl]benzonitrile |
| 377 | 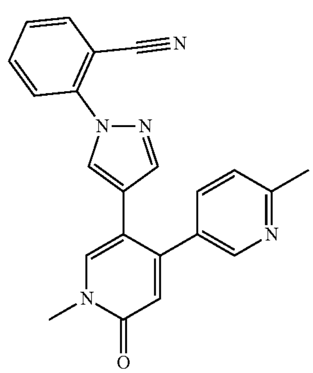 [SMILES: Cc1ccc(-c2cc(=O)n(C)cc2-c2cnn(-c3ccccc3C#N)c2)cn1] | 2-(4-(1',6-dimethyl-6'-oxo-1',6'-dihydro-[3,4'-bipyridin]-3'-yl)-1H-pyrazol-1-yl)benzonitrile |
| 378 | 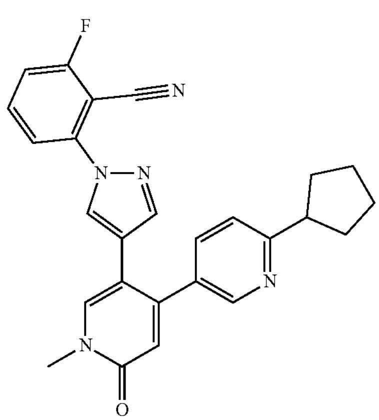 | 2-(4-(6-cyclopentyl-1'-methyl-6'-oxo-1',6'-dihydro-[3,4'-bipyridin]-3'-yl)-1H-pyrazol-1-yl)-6-fluorobenzonitrile |

TABLE 1-continued

| Example | Structure | Name |
| --- | --- | --- |
| 379 | 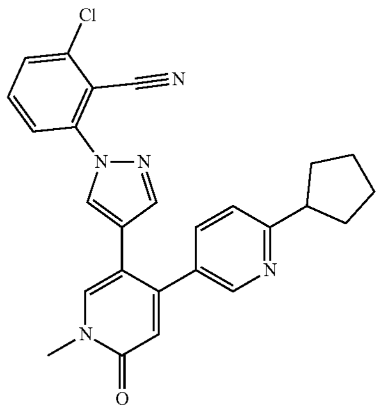 | 2-chloro-6-(4-(6-cyclopentyl-1'-methyl-6'-oxo-1',6'-dihydro-[3,4'-bipyridin]-3'-yl)-1H-pyrazol-1-yl)benzonitrile |
| 380 | 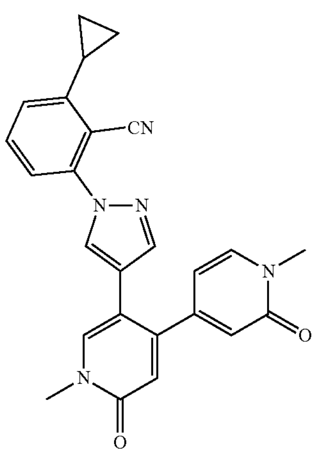 [SMILES: Cn1ccc(-c2cc(=O)n(C)cc2-c2cnn(-c3cccc(C4CC4)c3C#N)c2)cc1=O] | 2-cyclopropyl-6-[4-[1-methyl-4-(1-methyl-2-oxo-4-pyridyl)-6-oxo-3-pyridyl]pyrazol-1-yl]benzonitrile |
| 381 | 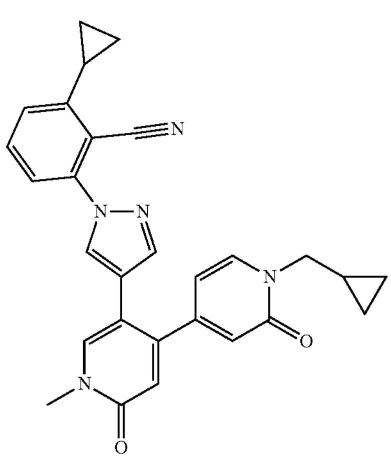 [SMILES: Cn1cc(-c2cnn(-c3cccc(C4CC4)c3C#N)c2)c(-c2ccn(CC3CC3)c(=O)c2)cc1=O] | 2-cyclopropyl-6-[4-[4-[1-(cyclopropylmethyl)-2-oxo-4-pyridyl]-1-methyl-6-oxo-3-pyridyl]pyrazol-1-yl]benzonitrile |

TABLE 1-continued

| Example | Structure | Name |
| --- | --- | --- |
| 382 | 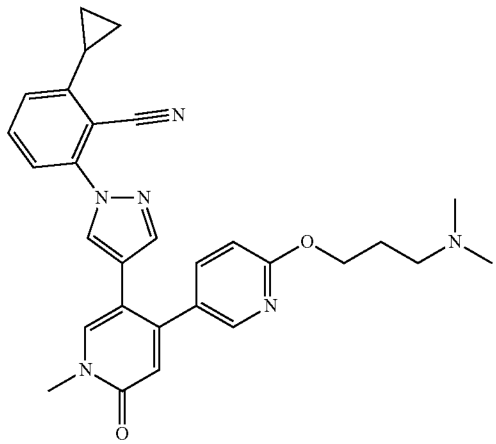 [SMILES: CN(C)CCCOc1ccc(-c2cc(=O)n(C)cc2-c2cnn(-c3cccc(C4CC4)c3C#N)c2)cn1] | 2-cyclopropyl-6-(4-(6-(3-(dimethylamino)propoxy)-1'-methyl-6'-oxo-1', 6'-dihydro-[3, 4'-bipyridin]-3'-yl)-1H-pyrazol-1-yl)benzonitrile |
| 383 | 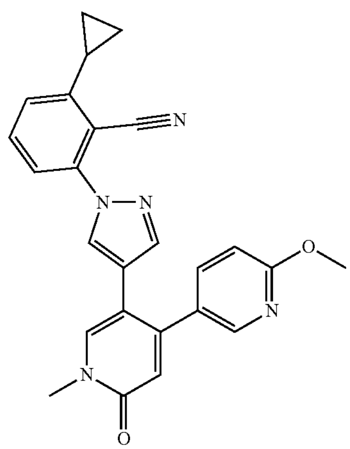 [SMILES: COc1ccc(-c2cc(=O)n(C)cc2-c2cnn(-c3cccc(C4CC4)c3C#N)c2)cn1] | 2-cyclopropyl-6-(4-(6-methoxy-1'-methyl-6'-oxo-1', 6'-dihydro-[3, 4'-bipyridin]-3'-yl)-1H-pyrazol-1-yl)benzonitrile |
| 384 | 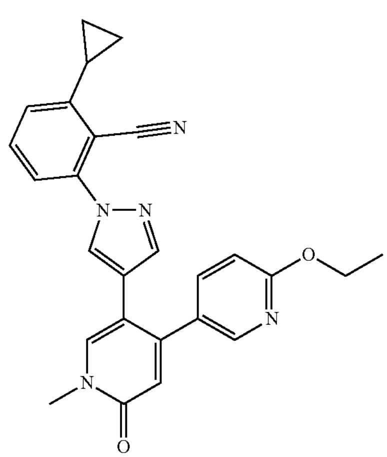 [SMILES: CCOc1ccc(-c2cc(=O)n(C)cc2-c2cnn(-c3cccc(C4CC4)c3C#N)c2)cn1] | 2-cyclopropyl-6-(4-(6-ethoxy-1'-methyl-6'-oxo-1', 6'-dihydro-[3, 4'-bipyridin]-3'-yl)-1H-pyrazol-1-yl)benzonitrile |

TABLE 1-continued

| Example | Structure | Name |
| --- | --- | --- |
| 385 | 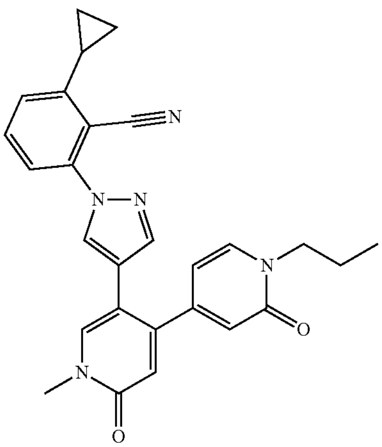 [SMILES: CCCn1ccc(-c2cc(=O)n(C)cc2-c2cnn(-c3cccc(C4CC4)c3C#N)c2)cc1=O] | 2-cyclopropyl-6-[4-[1-methyl-6-oxo-4-(2-oxo-1-propyl-4-pyridyl)-3-pyridyl]pyrazol-1-yl]benzonitrile |
| 386 | 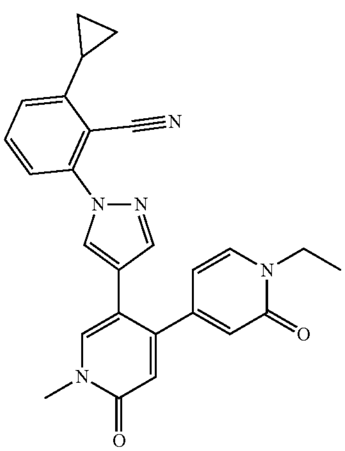 [SMILES: CCn1ccc(-c2cc(=O)n(C)cc2-c2cnn(-c3cccc(C4CC4)c3C#N)c2)cc1=O] | 2-cyclopropyl-6-[4-[4-(1-ethyl-2-oxo-4-pyridyl)-1-methyl-6-oxo-3-pyridyl]pyrazol-1-yl]benzonitrile |
| 387 | 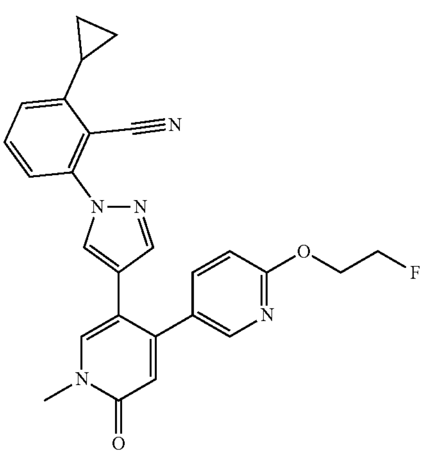 [SMILES: Cn1cc(-c2cnn(-c3cccc(C4CC4)c3C#N)c2)c(-c2ccc(OCCF)nc2)cc1=O] | 2-cyclopropyl-6-[4-[4-[6-(2-fluoroethoxy)-3-pyridyl]-1-methyl-6-oxo-3-pyridyl]pyrazol-1-yl]benzonitrile |

TABLE 1-continued

| Example | Structure | Name |
| --- | --- | --- |
| 388 | 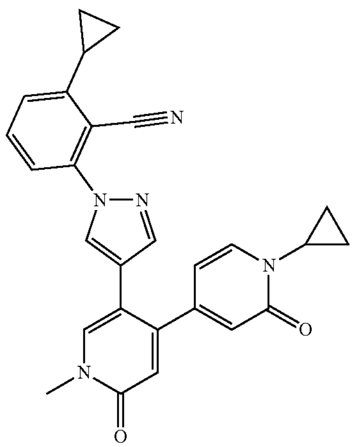 [SMILES: Cn1cc(-c2cnn(-c3cccc(C4CC4)c3C#N)c2)c(-c2ccn(C3CC3)c(=O)c2)cc1=O] | 2-cyclopropyl-6-(4-(1'-cyclopropyl-1-methyl-2',6-dioxo-1,1',2',6-tetrahydro-[4,4'-bipyridin]-3-yl)-1H-pyrazol-1-yl)benzonitrile |
| 389 | 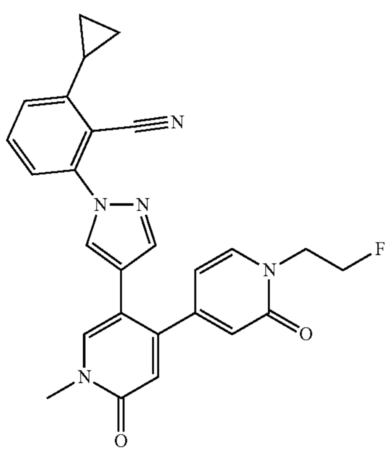 [SMILES: Cn1cc(-c2cnn(-c3cccc(C4CC4)c3C#N)c2)c(-c2ccn(CCF)c(=O)c2)cc1=O] | 2-cyclopropyl-6-[4-[4-[1-(2-fluoroethyl)-2-oxo-4-pyridyl]-1-methyl-6-oxo-3-pyridyl]pyrazol-1-yl]benzonitrile |
| 390 | 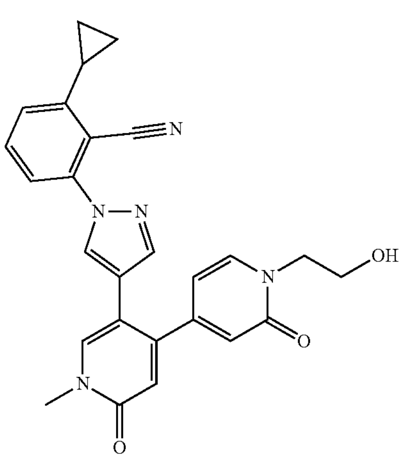 [SMILES: Cn1cc(-c2cnn(-c3cccc(C4CC4)c3C#N)c2)c(-c2ccn(CCO)c(=O)c2)cc1=O] | 2-cyclopropyl-6-[4-[4-[1-(2-hydroxyethyl)-2-oxo-4-pyridyl]-1-methyl-6-oxo-3-pyridyl]pyrazol-1-yl]benzonitrile |

TABLE 1-continued

| Example | Structure | Name |
|---|---|---|
| 391 | 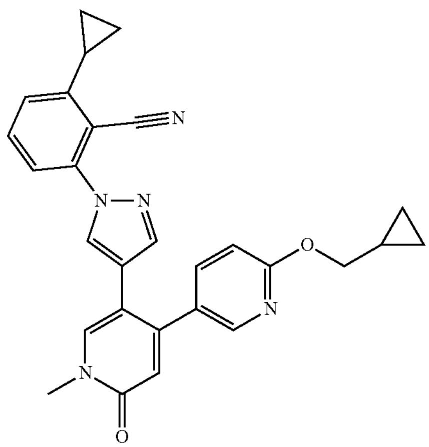 [SMILES: Cn1cc(-c2cnn(-c3cccc(C4CC4)c3C#N)c2)c(-c2ccc(OCC3CC3)nc2)cc1=O] | 2-cyclopropyl-6-(4-(6-(cyclopropylmethoxy)-1'-methyl-6'-oxo-1',6'-dihydro-[3,4'-bipyridin]-3'-yl)-1H-pyrazol-1-yl)benzonitrile |
| 392 | 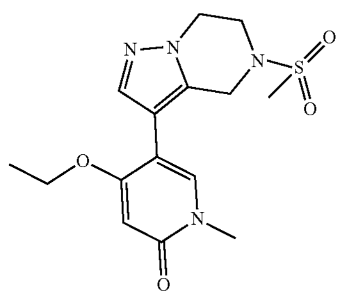 [SMILES: CCOc1cc(=O)n(C)cc1-c1cnn2c1CN(S(C)(=O)=O)CC2] | 4-Ethoxy-5-(5-methanesulfonyl-4,5,6,7-tetrahydro-pyrazolo[1,5-a]pyrazin-3-yl)-1-methyl-1H-pyridin-2-one |
| 393 | 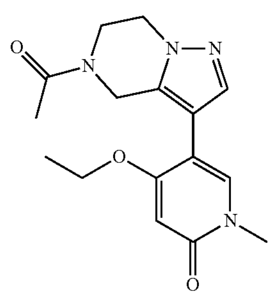 [SMILES: CCOc1cc(=O)n(C)cc1-c1cnn2c1CN(C(C)=O)CC2] | 5-(5-Acetyl-4,5,6,7-tetrahydro-pyrazolo[1,5-a]pyrazin-3-yl)-4-ethoxy-1-methyl-1H-pyridin-2-one |
| 394 | 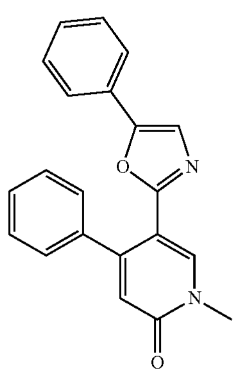 [SMILES: Cn1cc(-c2ncc(-c3ccccc3)o2)c(-c2ccccc2)cc1=O] | 1-methyl-4-phenyl-5-(5-phenyloxazol-2-yl)pyridin-2(1H)-one |

TABLE 1-continued

| Example | Structure | Name |
|---|---|---|
| 395 | 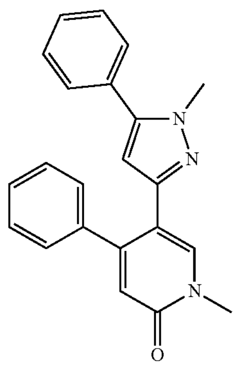 [SMILES: Cn1nc(-c2cn(C)c(=O)cc2-c2ccccc2)cc1-c1ccccc1] | 1-methyl-5-(1-methyl-5-phenyl-1H-pyrazol-3-yl)-4-phenylpyridin-2(1H)-one |
| 396 | 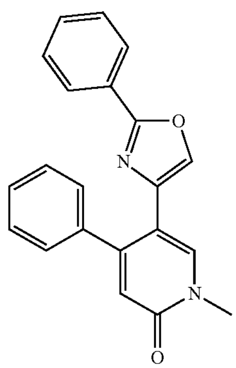 [SMILES: Cn1cc(-c2coc(-c3ccccc3)n2)c(-c2ccccc2)cc1=O] | 1-methyl-4-phenyl-5-(2-phenyloxazol-4-yl)pyridin-2(1H)-one |
| 397 | 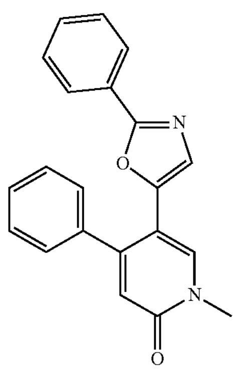 [SMILES: Cn1cc(-c2cnc(-c3ccccc3)o2)c(-c2ccccc2)cc1=O] | 1-methyl-4-phenyl-5-(2-phenyloxazol-5-yl)pyridin-2(1H)-one |

In some embodiments, a compound of Formula I is selected from:
5-(1-benzyl-1H-pyrazol-4-yl)-1-methylpyridin-2(1H)-one;
5-(1-benzyl-1H-pyrazol-4-yl)-1,3-dimethylpyridin-2(1H)-one;
2-((4-(1-methyl-6-oxo-1,6-dihydropyridin-3-yl)-1H-pyrazol-1-yl) methyl)benzonitrile;
3-((4-(1-methyl-6-oxo-1,6-dihydropyridin-3-yl)-1H-pyrazol-1-yl) methyl)benzonitrile;
1-methyl-5-(1-(pyridin-2-ylmethyl)-1H-pyrazol-4-yl)pyridin-2(1H)-one;
5-(1-(4-fluorobenzyl)-1H-pyrazol-4-yl)-1-methylpyridin-2(1H)-one;
5-(1-benzyl-1H-pyrazol-4-yl)-1,4-dimethylpyridin-2(1H)-one;
4-(1-benzyl-1H-pyrazol-4-yl)-2-methylisoquinolin-1(2H)-one;
4-(1-benzyl-1H-pyrazol-4-yl)-2-methyl-2,6-naphthyridin-1(2H)-one;
5-(1-benzyl-1H-pyrazol-4-yl)-1-ethylpyridin-2(1H)-one;
5-(1-(1-(3-(difluoromethyl)phenyl)ethyl)-1H-pyrazol-4-yl)-1,3-dimethylpyridin-2(1H)-one;
1-methyl-5-(1-(1-phenylethyl)-1H-pyrazol-4-yl)pyridin-2(1H)-one;
5-(1-(cyclopropyl(phenyl)methyl)-1H-pyrazol-4-yl)-1-methylpyridin-2(1H)-one;
(S)-1-methyl-5-(1-(1-phenylethyl)-1H-pyrazol-4-yl)pyridin-2(1H)-one;
(R)-1-methyl-5-(1-(1-phenylethyl)-1H-pyrazol-4-yl)pyridin-2(1H)-one;
3-(1-(4-(1-methyl-6-oxo-1,6-dihydropyridin-3-yl)-1H-pyrazol-1-yl) ethyl)benzonitrile;
1,3-dimethyl-5-(1-(1-phenylethyl)-1H-pyrazol-4-yl)pyridin-2(1H)-one;
5-(1-(cyclopropyl(phenyl)methyl)-1H-pyrazol-4-yl)-1,3-dimethylpyridin-2(1H)-one;
5-(1-(1-(2-chlorophenyl)ethyl)-1H-pyrazol-4-yl)-1-methylpyridin-2(1H)-one;

1-methyl-5-(1-(1-(m-tolyl)ethyl)-1H-pyrazol-4-yl)pyridin-2 (1H)-one;
4-fluoro-1-methyl-5-(1-(1-phenylethyl)-1H-pyrazol-4-yl) pyridin-2(1H)-one;
1-methyl-5-(1-(1-(o-tolyl)ethyl)-1H-pyrazol-4-yl)pyridin-2 (1H)-one;
5-(1-(1-(3-chlorophenyl)ethyl)-1H-pyrazol-4-yl)-1-methylpyridin-2(1H)-one;
1-methyl-5-(1-(1-(pyridin-3-yl)ethyl)-1H-pyrazol-4-yl) pyridin-2(1H)-one;
4-(1-(4-(1-methyl-6-oxo-1,6-dihydropyridin-3-yl)-1H-pyrazol-1-yl) ethyl) benzonitrile;
3-fluoro-1-methyl-5-(1-(1-phenylethyl)-1H-pyrazol-4-yl) pyridin-2(1H)-one;
5-(1-(1-(2-methoxyphenyl)ethyl)-1H-pyrazol-4-yl)-1-methylpyridin-2(1H)-one;
5-(1-(1-(3-methoxyphenyl)ethyl)-1H-pyrazol-4-yl)-1-methylpyridin-2(1H)-one;
1-methyl-5-(1-(1-(pyridin-4-yl)ethyl)-1H-pyrazol-4-yl) pyridin-2(1H)-one;
1,3,4-trimethyl-5-(1-(1-phenylethyl)-1H-pyrazol-4-yl)pyridin-2(1H)-one;
3-chloro-1-methyl-5-(1-(1-phenylethyl)-1H-pyrazol-4-yl) pyridin-2(1H)-one;
3-methoxy-1-methyl-5-(1-(1-phenylethyl)-1H-pyrazol-4-yl) pyridin-2(1H)-one;
2-methyl-4-(1-(1-phenylethyl)-1H-pyrazol-4-yl)-2,5,6,7-tetrahydro-1H-cyclopenta[c]pyridin-1-one;
1,3-dimethyl-5-(5-methyl-1-(1-phenylethyl)-1H-pyrazol-4-yl) pyridin-2(1H)-one;
5-(1-benzyl-1H-pyrazol-4-yl)-1-(difluoromethyl)-4-phenylpyridin-2(1H)-one;
4-isopropoxy-1-methyl-5-(1-(1-phenylethyl)-1H-pyrazol-4-yl) pyridin-2(1H)-one;
4-methoxy-1-methyl-5-(1-(1-phenylethyl)-1H-pyrazol-4-yl) pyridin-2(1H)-one;
4-chloro-1-methyl-5-(1-(1-phenylethyl)-1H-pyrazol-4-yl) pyridin-2(1H)-one;
4-ethoxy-1-methyl-5-(1-(1-phenylethyl)-1H-pyrazol-4-yl) pyridin-2(1H)-one;
4-(azetidin-1-yl)-1-methyl-5-(1-(1-phenylethyl)-1H-pyrazol-4-yl) pyridin-2(1H)-one;
1-methyl-5-(1-(1-phenylethyl)-1H-pyrazol-4-yl)-4-(pyrrolidin-1-yl) pyridin-2(1H)-one;
1-methyl-4-(methylamino)-5-(1-(1-phenylethyl)-1H-pyrazol-4-yl) pyridin-2(1H)-one;
1-methyl-4-morpholino-5-(1-(1-phenylethyl)-1H-pyrazol-4-yl) pyridin-2(1H)-one;
1-methyl-4-((1-methyl-1H-pyrazol-3-yl)methoxy)-5-(1-(1-phenylethyl)-1H-pyrazol-4-yl)pyridin-2(1H)-one;
(R)-4-isopropoxy-1-methyl-5-(1-(1-phenylethyl)-1H-pyrazol-4-yl) pyridin-2(1H)-one;
(S)-4-isopropoxy-1-methyl-5-(1-(1-phenylethyl)-1H-pyrazol-4-yl) pyridin-2(1H)-one;
(S)-1-methyl-5-(1-(1-phenylethyl)-1H-pyrazol-4-yl)-4-(pyrrolidin-1-yl) pyridin-2(1H)-one;
4-isobutoxy-1-methyl-5-(1-(1-phenylethyl)-1H-pyrazol-4-yl) pyridin-2(1H)-one;
4-cyclobutoxy-1-methyl-5-(1-(1-phenylethyl)-1H-pyrazol-4-yl) pyridin-2(1H)-one;
4-((1-acetylazetidin-3-yl)oxy)-1-methyl-5-(1-(1-phenylethyl)-1H-pyrazol-4-yl)pyridin-2(1H)-one;
4-(cyclopentyloxy)-1-methyl-5-(1-(1-phenylethyl)-1H-pyrazol-4-yl) pyridin-2(1H)-one;
4-(cyclohexyloxy)-1-methyl-5-(1-(1-phenylethyl)-1H-pyrazol-4-yl) pyridin-2(1H)-one;
1-methyl-5-(1-(1-phenylethyl)-1H-pyrazol-4-yl)-4-(1H-pyrazol-1-yl) pyridin-2(1H)-one;
1-methyl-4-(3-methylazetidin-1-yl)-5-(1-(1-phenylethyl)-1H-pyrazol-4-yl) pyridin-2(1H)-one;
(R)-1-methyl-5-(1-(1-phenylethyl)-1H-pyrazol-4-yl)-4-(pyrrolidin-1-yl) pyridin-2(1H)-one;
4-(benzyloxy)-1-methyl-5-(1-(1-phenylethyl)-1H-pyrazol-4-yl) pyridin-2(1H)-one;
1-methyl-4-phenoxy-5-(1-(1-phenylethyl)-1H-pyrazol-4-yl) pyridin-2(1H)-one;
4-(3-methoxyazetidin-1-yl)-1-methyl-5-(1-(1-phenylethyl)-1H-pyrazol-4-yl) pyridin-2(1H)-one;
4-cyclopropoxy-1-methyl-5-(1-(1-phenylethyl)-1H-pyrazol-4-yl) pyridin-2(1H)-one;
(S)-1-methyl-5-(1-(1-phenylethyl)-1H-pyrazol-4-yl)-4-(1H-pyrazol-1-yl) pyridin-2(1H)-one;
(R)-1-methyl-5-(1-(1-phenylethyl)-1H-pyrazol-4-yl)-4-(1H-pyrazol-1-yl) pyridin-2(1H)-one;
4-ethoxy-1-methyl-5-(1-(1-(p-tolyl)ethyl)-1H-pyrazol-4-yl) pyridin-2(1H)-one;
5-(1-(1-([1,1'-biphenyl]-4-yl)ethyl)-1H-pyrazol-4-yl)-4-ethoxy-1-methylpyridin-2(1H)-one;
5-(1-benzyl-1H-pyrazol-4-yl)-4-ethoxy-1-methylpyridin-2 (1H)-one;
4-ethoxy-1-methyl-5-(1-(4-methylbenzyl)-1H-pyrazol-4-yl) pyridin-2(1H)-one;
5-(1-benzyl-1H-pyrazol-4-yl)-1-methyl-4-(1H-pyrazol-1-yl) pyridin-2(1H)-one;
5-(1-benzyl-1H-pyrazol-4-yl)-1-methyl-4-morpholinopyridin-2(1H)-one;
5-(1-benzyl-1H-pyrazol-4-yl)-1-methyl-4-(1H-pyrrol-1-yl) pyridin-2(1H)-one;
4-ethoxy-1-methyl-5-(1H-pyrazol-4-yl)pyridin-2(1H)-one;
methyl 2-((4-(4-ethoxy-1-methyl-6-oxo-1,6-dihydropyridin-3-yl)-1H-pyrazol-1-yl)methyl)benzoate;
methyl 3-((4-(4-ethoxy-1-methyl-6-oxo-1,6-dihydropyridin-3-yl)-1H-pyrazol-1-yl)methyl)benzoate;
(R)—N-(1-(5-(1-benzyl-1H-pyrazol-4-yl)-1-methyl-2-oxo-1,2-dihydro-pyridin-4-yl)pyrrolidin-3-yl)acetamide;
(S)—N-(1-(5-(1-benzyl-1H-pyrazol-4-yl)-1-methyl-2-oxo-1,2-dihydro-pyridin-4-yl)pyrrolidin-3-yl)acetamide;
(R)-1-(5-(1-benzyl-1H-pyrazol-4-yl)-1-methyl-2-oxo-1,2-dihydro-pyridin-4-yl)pyrrolidine-3-carboxylic acid;
(S)-1-(5-(1-benzyl-1H-pyrazol-4-yl)-1-methyl-2-oxo-1,2-dihydro-pyridin-4-yl)pyrrolidine-3-carboxylic acid;
1-(5-(1-benzyl-1H-pyrazol-4-yl)-1-methyl-2-oxo-1,2-dihydropyridin-4-yl)-1H-pyrrole-3-carboxamide;
methyl 1-(5-(1-benzyl-1H-pyrazol-4-yl)-1-methyl-2-oxo-1,2-dihydro-pyridin-4-yl)-1H-pyrrole-3-carboxylate
1-(5-(1-benzyl-1H-pyrazol-4-yl)-1-methyl-2-oxo-1,2-dihydropyridin-4-yl)-N,N-dimethyl-1H-pyrrole-3-carboxamide;
1-(5-(1-benzyl-1H-pyrazol-4-yl)-1-methyl-2-oxo-1,2-dihydropyridin-4-yl)-1H-pyrrole-3-carboxylic acid;
1-(5-(1-benzyl-1H-pyrazol-4-yl)-1-methyl-2-oxo-1,2-dihydropyridin-4-yl)-1H-pyrrole-3-carbonitrile;
1-(5-(1-benzyl-1H-pyrazol-4-yl)-1-methyl-2-oxo-1,2-dihydropyridin-4-yl)-N-ethyl-1H-pyrrole-3-carboxamide;
1-(5-(1-benzyl-1H-pyrazol-4-yl)-1-methyl-2-oxo-1,2-dihydropyridin-4-yl)-N-isopropyl-1H-pyrrole-3-carboxamide;
1-methyl-5-(1-methyl-1H-pyrazol-4-yl)-4-(1H-pyrrol-1-yl) pyridin-2(1H)-one
1-(1-methyl-5-(1-methyl-1H-pyrazol-4-yl)-2-oxo-1,2-dihydropyridin-4-yl)-1H-pyrrole-3-carboxylic acid;
1-(5-(1-benzyl-1H-pyrazol-4-yl)-1-methyl-2-oxo-1,2-dihydropyridin-4-yl)-1H-pyrrole-3-carboxamide;

1-(5-(1-(cyclopropylmethyl)-1H-pyrazol-4-yl)-1-methyl-2-oxo-1,2-dihydropyridin-4-yl)-1H-pyrrole-3-carboxylic acid;

5-(1-benzyl-1H-pyrazol-4-yl)-1-methyl-4-pyrrolidin-1-yl-1H-pyridin-2-one;

N-{2-[5-(1-benzyl-1H-pyrazol-4-yl)-1-methyl-2-oxo-1,2-dihydro-pyridin-4-yl]-cyclopentyl}-acetamide;

N-{1-[5-(1-benzyl-1H-pyrazol-4-yl)-1-methyl-2-oxo-1,2-dihydro-pyridin 4-yl]-pyrrolidin-3-ylmethyl}-acetamide;

N-{1-[5-(1-benzyl-1H-pyrazol-4-yl)-1-methyl-2-oxo-1,2-dihydro-pyridin-4-yl]-pyrrolidin-3-ylmethyl}-acetamide;

5-(1-benzyl-1H-pyrazol-4-yl)-1-methyl-4-(2,2,2-trifluoro-ethoxy) pyridin-2(1H)-one;

5-(1-benzyl-1H-pyrazol-4-yl)-1-methyl-4-(3,3,3-trifluoro-propoxy) pyridin-2(1H)-one;

1-[5-(1-Benzyl-1H-pyrazol-4-yl)-1-methyl-2-oxo-1,2-dihydro-pyridin-4-yl]-pyrrolidine-3-carboxylic acid methylamide;

5-(1-benzyl-1H-pyrazol-4-yl)-4-(1H-imidazol-1-yl)-1-methyl-pyridin-2(1H)-one;

5-(5,6-dihydro-4H-pyrrolo[1,2-b]pyrazol-3-yl)-4-ethoxy-1-methyl-pyridin-2(1H)-one;

4-ethoxy-1-methyl-5-(1-phenyl-1H-pyrazol-4-yl)pyridin-2(1H)-one;

5-(1-(2-chlorophenyl)-1H-pyrazol-4-yl)-4-ethoxy-1-methyl-pyridin-2(1H)-one;

5-(1-(2,6-dichlorophenyl)-1H-pyrazol-4-yl)-4-ethoxy-1-methyl-pyridin-2(1H)-one;

5-(1-benzyl-1H-pyrazol-4-yl)-1-methyl-4-(2-methylhydrazinyl) pyridin-2(1H)-one;

4-ethoxy-1-methyl-5-(1-{1-[4-(1-methyl-1H-pyrazol-4-yl)-phenyl]-ethyl}-1H-pyrazol-4-yl)-1H-pyridin-2-one;

4-ethoxy-5-[1-(4-isopropyl-benzyl)-1H-pyrazol-4-yl]-1-methyl-1H-pyridin-2-one;

4-ethoxy-1-methyl-5-{1-[4-(1-methyl-1H-pyrazol-4-yl)-benzyl]-1H-pyrazol-4-yl}-1H-pyridin-2-one;

4-ethoxy-1-methyl-5-{1-[4-(1H-pyrazol-4-yl)-benzyl]-1H-pyrazol-4-yl}-1H-pyridin-2-one;

4-ethoxy-1-methyl-5-(1-(1-(3-(1-methyl-1H-pyrazol-4-yl)phenyl)ethyl)-1H-pyrazol-4-yl)pyridin-2(1H)-one;

5-(1-(3-bromobenzyl)-1H-pyrazol-4-yl)-4-ethoxy-1-methyl-pyridin-2(1H)-one;

5-(1-benzyl-1H-pyrazol-4-yl)-1-methyl-4-o-tolyl-1H-pyridin-2-one;

1-methyl-5-(1-methyl-1H-pyrazol-4-yl)-4-phenylpyridin-2(1H)-one;

5-(1-benzyl-1H-pyrazol-4-yl)-1-methyl-4-(1-methyl-1H-pyrazol-4-yl) pyridin-2(1H)-one;

5-(1-benzyl-1H-pyrazol-4-yl)-1-methyl-4-(1-methyl-1H-pyrazol-3-yl) pyridin-2(1H)-one;

5-(1-benzyl-1H-pyrazol-4-yl)-1-methyl-4-(1-methyl-1H-pyrazol-5-yl)pyridin-2(1H)-one;

5-(1-benzyl-1H-pyrazol-4-yl)-1-methyl-4-(m-tolyl)pyridin-2(1H)-one;

5-(1-benzyl-1H-pyrazol-4-yl)-1-methyl-4-(p-tolyl)pyridin-2(1H)-one;

5-(1-benzyl-1H-pyrazol-4-yl)-4-(3-methoxyphenyl)-1-methyl-pyridin-2(1H)-one;

5-(1-benzyl-1H-pyrazol-4-yl)-1-methyl-4-(1H-pyrazol-5-yl) pyridin-2(1H)-one;

5-(1-benzyl-1H-pyrazol-4-yl)-1-methyl-4-(3-methyl-1H-pyrazol-5-yl) pyridin-2(1H)-one;

5-(1-benzyl-1H-pyrazol-4-yl)-1-methyl-4-(thiophen-2-yl) pyridin-2(1H)-one;

5-(1-benzyl-1H-pyrazol-4-yl)-1-methyl-4-(thiophen-3-yl) pyridin-2(1H)-one;

5-(1-benzyl-1H-pyrazol-4-yl)-4-(3-chlorophenyl)-1-methyl-pyridin-2(1H)-one;

5-(1-benzyl-1H-pyrazol-4-yl)-4-(4-chlorophenyl)-1-methyl-pyridin-2(1H)-one;

5-(1-benzyl-1H-pyrazol-4-yl)-4-(4-methoxyphenyl)-1-methyl-pyridin-2(1H)-one;

5-(1-benzyl-1H-pyrazol-4-yl)-4-(isoxazol-3-yl)-1-methylpyridin-2(1H)-one;

5'-(1-benzyl-1H-pyrazol-4-yl)-1'-methyl-[3,4'-bipyridin]-2'(1'H)-one;

5-(1-benzyl-1H-pyrazol-4-yl)-4-(2-chlorophenyl)-1-methyl-pyridin-2(1H)-one;

5-(1-benzyl-1H-pyrazol-4-yl)-1-methyl-[4,4'-bipyridin]-2(1H)-one;

5-(1-cyclohexyl-1H-pyrazol-4-yl)-1-methyl-4-phenylpyridin-2(1H)-one;

1-methyl-4-phenyl-5-(1-(tetrahydro-2H-pyran-4-yl)-1H-pyrazol-4-yl) pyridin-2(1H)-one;

1-methyl-5-(1-(1-(methylsulfonyl)piperidin-4-yl)-1H-pyrazol-4-yl)-4-phenylpyridin-2(1H)-one;

1-methyl-4-phenyl-5-(1-phenyl-1H-pyrazol-4-yl)pyridin-2(1H)-one;

1-methyl-5-(1-((methylsulfonyl)methyl)-1H-pyrazol-4-yl)-4-phenyl-pyridin-2(1H)-one;

1-methyl-5-(1-(2-morpholinoethyl)-1H-pyrazol-4-yl)-4-phenyl-pyridin-2(1H)-one;

5'-(1-benzyl-1H-pyrazol-4-yl)-1'-methyl-[2,4'-bipyridin]-2'(1'H)-one;

5-(1-ethyl-1H-pyrazol-4-yl)-1-methyl-4-phenylpyridin-2(1H)-one;

1-methyl-4-phenyl-5-(1H-pyrazol-4-yl)pyridin-2(1H)-one;

N-methyl-2-(4-(1-methyl-6-oxo-4-phenyl-1,6-dihydropyridin-3-yl)-1H-pyrazol-1-yl)acetamide;

N,N-dimethyl-2-(4-(1-methyl-6-oxo-4-phenyl-1,6-dihydropyridin-3-yl)-1H-pyrazol-1-yl)acetamide;

5-(1,3-dimethyl-1H-pyrazol-4-yl)-1-methyl-4-phenylpyridin-2(1H)-one;

5-(1-isobutyl-1H-pyrazol-4-yl)-1-methyl-4-phenylpyridin-2(1H)-one;

5-(1-isopropyl-1H-pyrazol-4-yl)-1-methyl-4-phenylpyridin-2(1H)-one;

1-methyl-4-phenyl-5-(1-propyl-1H-pyrazol-4-yl)pyridin-2(1H)-one;

methyl 2-(4-(1-methyl-6-oxo-4-phenyl-1,6-dihydropyridin-3-yl)-1H-pyrazol-1-yl)acetate 2-(4-(1-methyl-6-oxo-4-phenyl-1,6-dihydropyridin-3-yl)-1H-pyrazol-1-yl)-N-propylacetamide;

4-cyclopentyl-1-methyl-5-(1-methyl-1H-pyrazol-4-yl)pyridin-2(1H)-one;

4-cyclohexyl-1-methyl-5-(1-methyl-1H-pyrazol-4-yl)pyridin-2(1H)-one;

4-cyclopropyl-1-methyl-5-(1-methyl-1H-pyrazol-4-yl)pyridin-2(1H)-one;

1-methyl-4-phenyl-5-(1,3,5-trimethyl-1H-pyrazol-4-yl) pyridin-2(1H)-one;

5-(1-(cyclopropylmethyl)-1H-pyrazol-4-yl)-1-methyl-4-phenyl-pyridin-2(1H)-one;

5-(1-cyclopropylmethyl-1H-pyrazol-4-yl)-1-methyl-4-(4-trifluoromethyl-phenyl)-1H-pyridin-2-one;

4-[5-(1-cyclopropylmethyl-1H-pyrazol-4-yl)-1-methyl-2-oxo-1,2-dihydro-pyridin-4-yl]-N-methyl-benzamide;

5-(1-benzyl-1H-pyrazol-4-yl)-4-(4-fluorophenyl)-1-methyl-pyridin-2(1H)-one;

4-(5-(1-benzyl-1H-pyrazol-4-yl)-1-methyl-2-oxo-1,2-dihydro-pyridin-4-yl)benzonitrile;

4-(5-(1-benzyl-1H-pyrazol-4-yl)-1-methyl-2-oxo-1,2-dihydro-pyridin-4-yl)benzamide;

5-(1-benzyl-1H-pyrazol-4-yl)-1-methyl-4-(1H-pyrazol-4-yl) pyridin-2(1H)-one;
4-(4-chloro-phenyl)-5-(1-cyclopropylmethyl-1H-pyrazol-4-yl)-1-methyl-1H-pyridin-2-one;
4-[5-(1-cyclopropylmethyl-1H-pyrazol-4-yl)-1-methyl-2-oxo-1,2-dihydro-pyridin-4-yl]-benzoic acid;
4-(5-(1-benzyl-1H-pyrazol-4-yl)-1-methyl-2-oxo-1,2-dihydropyridin-4-yl) benzoic acid;
4-[5-(1-cyclopropylmethyl-1H-pyrazol-4-yl)-1-methyl-2-oxo-1,2-dihydro-pyridin-4-yl]-benzonitrile;
5-(1-(cyclohexylmethyl)-1H-pyrazol-4-yl)-1-methyl-4-phenyl-pyridin-2(1H)-one;
2-(4-(5-(1-benzyl-1H-pyrazol-4-yl)-1-methyl-2-oxo-1,2-dihydro-pyridin-4-yl)-1H-pyrazol-1-yl)acetamide;
2-(4-(5-(1-benzyl-1H-pyrazol-4-yl)-1-methyl-2-oxo-1,2-dihydro-pyridin-4-yl)-1H-pyrazol-1-yl)acetic acid;
5-(1-benzyl-1H-pyrazol-4-yl)-4-(1-(difluoromethyl)-1H-pyrazol-4-yl)-1-methylpyridin-2(1H)-one;
5-(1-benzyl-1H-pyrazol-4-yl)-4-(1-(2-hydroxy-2-methylpropyl)-1H-pyrazol-4-yl)-1-methylpyridin-2(1H)-one;
5-(5,6-dihydro-4H-pyrrolo[1,2-b]pyrazol-3-yl)-1-methyl-4-phenyl-pyridin-2(1H)-one;
2-(4-(5-(1-benzyl-1H-pyrazol-4-yl)-1-methyl-2-oxo-1,2-dihydro-pyridin-4-yl)-1H-pyrazol-1-yl)acetonitrile;
5-(1,5-dimethyl-1H-pyrazol-4-yl)-1-methyl-4-phenylpyridin-2(1H)-one;
5-(1-Benzyl-1H-pyrazol-4-yl)-1-methyl-4-propoxy-1H-pyridin-2-one;
3-[5-(1-Benzyl-1H-pyrazol-4-yl)-1-methyl-2-oxo-1,2-dihydro-pyridin-4-yloxy]-propionic acid;
[5-(1-Benzyl-1H-pyrazol-4-yl)-1-methyl-2-oxo-1,2-dihydro-pyridin-4-yloxy]-acetonitrile;
5-(1-Benzyl-1H-pyrazol-4-yl)-4-ethylsulfanyl-1-methyl-1H-pyridin-2-one;
[5-(1-Benzyl-1H-pyrazol-4-yl)-1-methyl-2-oxo-1,2-dihydro-pyridin-4-ylsulfanyl]-acetic acid;
5-(1-benzyl-1H-pyrazol-4-yl)-1-methyl-4-((methylamino)oxy)pyridin-2(1H)-one;
5-[1-(2,2-Difluoro-cyclopropylmethyl)-1H-pyrazol-4-yl]-4-ethoxy-1-methyl-1H-pyridin-2-one;
1-(5-(1-benzyl-1H-pyrazol-4-yl)-1-methyl-2-oxo-1,2-dihydropyridin-4-yl)-N-methylpyrrolidine-3-sulfonamide;
(R)—N-(1-(5-(1-benzyl-1H-pyrazol-4-yl)-1-methyl-2-oxo-1,2-dihydropyridin-4-yl)pyrrolidin-3-yl)-1,1,1-trifluoromethanesulfonamide;
(R)—N-(1-(5-(1-benzyl-1H-pyrazol-4-yl)-1-methyl-2-oxo-1,2-dihydropyridin-4-yl)pyrrolidin-3-yl)methanesulfonamide;
5-(1-Benzyl-1H-pyrazol-4-yl)-4-(3-methanesulfonyl-pyrrolidin-1-yl)-1-methyl-1H-pyridin-2-one;
2-[4-(4-Ethoxy-1-methyl-6-oxo-1,6-dihydro-pyridin-3-yl)-pyrazol-1-yl]-6-isopropyl-benzonitrile;
2-[4-(4-Ethoxy-1-methyl-6-oxo-1,6-dihydro-pyridin-3-yl)-pyrazol-1-yl]-6-methoxy-benzonitrile;
2-Chloro-6-[4-(4-ethoxy-1-methyl-6-oxo-1,6-dihydro-pyridin-3-yl)-pyrazol-1-yl]-benzonitrile;
2-[4-(4-Ethoxy-1-methyl-6-oxo-1,6-dihydro-pyridin-3-yl)-pyrazol-1-yl]-6-methyl-benzonitrile;
4-Ethoxy-5-[1-(2-methanesulfonyl-phenyl)-1H-pyrazol-4-yl]-1-methyl-1H-pyridin-2-one;
4-ethoxy-1-methyl-5-(1-(1-(methylsulfonyl)piperidin-3-yl)-1H-pyrazol-4-yl)pyridin-2(1H)-one;
2-[4-(4-Ethoxy-1-methyl-6-oxo-1,6-dihydro-pyridin-3-yl)-pyrazol-1-yl]-4-methoxy-benzonitrile;
2-[4-(4-Ethoxy-1-methyl-6-oxo-1,6-dihydro-pyridin-3-yl)-pyrazol-1-yl]-4-phenoxy-benzonitrile;
4-Cyclopropoxy-2-[4-(4-ethoxy-1-methyl-6-oxo-1,6-dihydro-pyridin-3-yl)-pyrazol-1-yl]-benzonitrile;
5-(1-benzyl-3-nitro-1H-pyrazol-4-yl)-4-ethoxy-1-methylpyridin-2(1H)-one;
5-(3-amino-1-benzyl-1H-pyrazol-4-yl)-4-ethoxy-1-methylpyridin-2(1H)-one;
N-[1-Benzyl-4-(4-ethoxy-1-methyl-6-oxo-1,6-dihydro-pyridin-3-yl)-1H-pyrazol-3-yl]-acetamide;
5-(1-Benzyl-1H-pyrazol-4-yl)-4-(2-methoxy-phenyl)-1-methyl-1H-pyridin-2-one;
5-(1-Benzyl-1H-pyrazol-4-yl)-4-(2,6-dimethyl-phenyl)-1-methyl-1H-pyridin-2-one;
5-[1-(2,2-Difluoro-cyclopropylmethyl)-1H-pyrazol-4-yl]-1-methyl-4-phenyl-1H-pyridin-2-one;
5-[1-(2,2-Difluoro-cyclopropylmethyl)-1H-pyrazol-4-yl]-4-(4-methoxy-phenyl)-1-methyl-1H-pyridin-2-one;
5-[1-(2,2-Difluoro-cyclopropylmethyl)-1H-pyrazol-4-yl]-1-methyl-4-(1-methyl-1H-pyrazol-4-yl)-1H-pyridin-2-one;
5-(1-Benzyl-1H-pyrazol-4-yl)-1-methyl-1H,1'H-[4,4']bipyridinyl-2,2'-dione;
5'-(1-Benzyl-1H-pyrazol-4-yl)-1'-methyl-1H,1'H-[3,4']bipyridinyl-6,2'-dione;
5-(1-Benzyl-1H-pyrazol-4-yl)-1,6-dimethyl-1H-pyridin-2-one;
3-Dimethylamino-1-methyl-5-[1-(1-phenyl-ethyl)-1H-pyrazol-4-yl]-1H-pyridin-2-one;
3-Cyclopropyl-1-methyl-5-[1-(1-phenyl-ethyl)-1H-pyrazol-4-yl]-1H-pyridin-2-one;
1-Benzyl-4-(1,5-dimethyl-6-oxo-1,6-dihydro-pyridin-3-yl)-1H-pyrazole-3-carboxylic acid ethyl ester;
2-Benzyl-4-(1,5-dimethyl-6-oxo-1,6-dihydro-pyridin-3-yl)-2H-pyrazole-3-carboxylic acid ethyl ester;
4-amino-5-(1-benzyl-1H-pyrazol-4-yl)-1-methylpyridin-2(1H)-one;
3-((5-(1-benzyl-1H-pyrazol-4-yl)-1-methyl-2-oxo-1,2-dihydropyridin-4-yl)amino)propanoic acid;
2-[4-(4-Isopropoxy-1-methyl-6-oxo-1,6-dihydro-pyridin-3-yl)-pyrazol-1-yl]-benzonitrile;
2-[4-(4-Isopropoxy-1-methyl-6-oxo-1,6-dihydro-pyridin-3-yl)-pyrazol-1-yl]-benzoic acid;
2-{4-[1-Methyl-4-(1-methyl-1H-pyrazol-4-yl)-6-oxo-1,6-dihydro-pyridin-3-yl]-pyrazol-1-yl}-benzonitrile;
2-[4-(1-Methyl-6,2'-dioxo-1,6,1',2'-tetrahydro-[4,4']bipyridinyl-3-yl)-pyrazol-1-yl]-benzonitrile;
2-[4-(1'-Methyl-6,6'-dioxo-1,6,1',6'-tetrahydro-[3,4']bipyridinyl-3'-yl)-pyrazol-1-yl]-benzonitrile;
2-[4-(4-Cyclopropyl-1-methyl-6-oxo-1,6-dihydro-pyridin-3-yl)-pyrazol-1-yl]-benzonitrile;
2-{4-[1-Methyl-4-(1-methyl-1H-pyrazol-4-yl)-6-oxo-1,6-dihydro-pyridin-3-yl]-pyrazol-1-yl}-benzoic acid;
2-[4-(1,1'-Dimethyl-6,6'-dioxo-1,6,1',6'-tetrahydro-[3,4']bipyridinyl-3'-yl)-pyrazol-1-yl]-benzonitrile;
2-[4-(5,1'-Dimethyl-6,6'-dioxo-1,6,1',6'-tetrahydro-[3,4']bipyridinyl-3'-yl)-pyrazol-1-yl]-benzonitrile;
2-[4-(4-Cyclopropyl-1-methyl-6-oxo-1,6-dihydro-pyridin-3-yl)-pyrazol-1-yl]-benzoic acid;
2-[4-(1-Methyl-6-oxo-4-phenyl-1,6-dihydro-pyridin-3-yl)-pyrazol-1-yl]-benzonitrile;
2-[4-(1-Methyl-6-oxo-4-p-tolyl-1,6-dihydro-pyridin-3-yl)-pyrazol-1-yl]-benzonitrile;
2-{4-[4-(4-Chloro-phenyl)-1-methyl-6-oxo-1,6-dihydro-pyridin-3-yl]-pyrazol-1-yl}-benzonitrile;
2-{4-[4-(4-Fluoro-phenyl)-1-methyl-6-oxo-1,6-dihydro-pyridin-3-yl]-pyrazol-1-yl}-benzonitrile;
2-{4-[4-(3-Chloro-phenyl)-1-methyl-6-oxo-1,6-dihydro-pyridin-3-yl]-pyrazol-1-yl}-benzonitrile;

4-{5-[1-(2-Cyano-phenyl)-1H-pyrazol-4-yl]-1-methyl-2-oxo-1,2-dihydro-pyridin-4-yl}-benzoic acid;
4-{5-[1-(2-Cyano-phenyl)-1H-pyrazol-4-yl]-1-methyl-2-oxo-1,2-dihydro-pyridin-4-yl}-benzamide;
4-{5-[1-(2-Cyano-phenyl)-1H-pyrazol-4-yl]-1-methyl-2-oxo-1,2-dihydro-pyridin-4-yl}-N-methyl-benzamide;
2-[4-(2'-Methoxy-1-methyl-6-oxo-1,6-dihydro-[4,4']bipyridinyl-3-yl)-pyrazol-1-yl]-benzonitrile;
2-[4-(1,1'-Dimethyl-6,2'-dioxo-1,6,1',2'-tetrahydro-[4,4']bipyridinyl-3-yl)-pyrazol-1-yl]-benzonitrile;
2-[4-(1'-Cyclopropyl-1-methyl-6,2'-dioxo-1,6,1',2'-tetrahydro-[4,4']bipyridinyl-3-yl)-pyrazol-1-yl]-benzonitrile;
2-[4-(1-Methyl-6-oxo-4-phenyl-1,6-dihydro-pyridin-3-yl)-pyrazol-1-yl]-benzoic acid;
2-[4-(1-Methyl-6-oxo-4-p-tolyl-1,6-dihydro-pyridin-3-yl)-pyrazol-1-yl]-benzoic acid;
2-(4-(4-(4-chlorophenyl)-1-methyl-6-oxo-1,6-dihydropyridin-3-yl)-1H-pyrazol-1-yl)benzoic acid;
2-{4-[4-(4-Fluoro-phenyl)-1-methyl-6-oxo-1,6-dihydro-pyridin-3-yl]-pyrazol-1-yl}-benzoic acid;
2-[4-(1'-Methyl-6'-oxo-1',6'-dihydro-[3,4']bipyridinyl-3'-yl)-pyrazol-1-yl]-benzoic acid;
2-[4-(6-Methoxy-1'-methyl-6'-oxo-1',6'-dihydro-[3,4']bipyridinyl-3'-yl)-pyrazol-1-yl]-benzoic acid;
2-{4-[4-(4-Methoxy-phenyl)-1-methyl-6-oxo-1,6-dihydro-pyridin-3-yl]-pyrazol-1-yl}-benzoic acid;
2-[4-(6-Ethoxy-1'-methyl-6'-oxo-1',6'-dihydro-[3,4']bipyridinyl-3'-yl)-pyrazol-1-yl]-benzoic acid;
2-[4-(6-Isopropoxy-1'-methyl-6'-oxo-1',6'-dihydro-[3,4']bipyridinyl-3'-yl)-pyrazol-1-yl]-benzoic acid;
2-[4-(6-Isobutoxy-1'-methyl-6'-oxo-1',6'-dihydro-[3,4']bipyridinyl-3'-yl)-pyrazol-1-yl]-benzoic acid;
2-{4-[4-(4-Methoxy-phenyl)-1-methyl-6-oxo-1,6-dihydro-pyridin-3-yl]-pyrazol-1-yl}-benzonitrile;
2-[4-(6-Ethoxy-1'-methyl-6'-oxo-1',6'-dihydro-[3,4']bipyridinyl-3'-yl)-pyrazol-1-yl]-benzonitrile;
2-[4-(6-Isopropoxy-1'-methyl-6'-oxo-1',6'-dihydro-[3,4']bipyridinyl-3'-yl)-pyrazol-1-yl]-benzonitrile;
2-[4-(6-Isobutoxy-1'-methyl-6'-oxo-1',6'-dihydro-[3,4']bipyridinyl-3'-yl)-pyrazol-1-yl]-benzonitrile;
2-[4-(1'-Methyl-6'-oxo-1',6'-dihydro-[3,4']bipyridinyl-3'-yl)-pyrazol-1-yl]-benzonitrile;
2-(4-(6-methoxy-1'-methyl-6'-oxo-1',6'-dihydro-[3,4'-bipyridin]-3'-yl)-1H-pyrazol-1-yl)benzonitrile;
2-(4-(1,1',5-trimethyl-6,6'-dioxo-1,1',6,6'-tetrahydro-[3,4'-bipyridin]-3'-yl)-1H-pyrazol-1-yl)benzonitrile;
2-(4-(5-fluoro-1'-methyl-6,6'-dioxo-1,1',6,6'-tetrahydro-[3,4'-bipyridin]-3'-yl)-1H-pyrazol-1-yl)benzonitrile;
2-{4-[4-(3-Methoxy-phenyl)-1-methyl-6-oxo-1,6-dihydro-pyridin-3-yl]-pyrazol-1-yl}-benzonitrile;
2-(4-(5-methoxy-1'-methyl-6'-oxo-1',6'-dihydro-[3,4'-bipyridin]-3'-yl)-1H-pyrazol-1-yl)benzonitrile;
2-(4-(4-(3,4-dimethoxyphenyl)-1-methyl-6-oxo-1,6-dihydropyridin-3-yl)-1H-pyrazol-1-yl)benzonitrile;
2-{4-[4-(2-Methoxy-pyrimidin-5-yl)-1-methyl-6-oxo-1,6-dihydro-pyridin-3-yl]-pyrazol-1-yl}-benzonitrile;
2-(4-(1-methyl-4-(2-(methylamino)pyrimidin-5-yl)-6-oxo-1,6-dihydropyridin-3-yl)-1H-pyrazol-1-yl)benzonitrile;
2-{4-[1-Methyl-6-oxo-4-(3,4,5-trimethoxy-phenyl)-1,6-dihydro-pyridin-3-yl]-pyrazol-1-yl}-benzonitrile;
2-[4-(4-Ethoxy-1-methyl-6-oxo-1,6-dihydro-pyridin-3-yl)-pyrazol-1-yl]-4-methoxy-benzoic acid;
4-Cyclopropoxy-2-[4-(4-ethoxy-1-methyl-6-oxo-1,6-dihydro-pyridin-3-yl)-pyrazol-1-yl]-benzoic acid;
2-(4-(4-ethoxy-1-methyl-6-oxo-1,6-dihydropyridin-3-yl)-1H-pyrazol-1-yl)benzoic acid;
5-(1-(2-chlorophenyl)-1H-pyrazol-4-yl)-1-methyl-4-((1-methyl-1H-pyrazol-4-yl)methoxy)pyridin-2(1H)-one;
3-(4-(4-ethoxy-1-methyl-6-oxo-1,6-dihydropyridin-3-yl)-1H-pyrazol-1-yl)benzonitrile;
4-ethoxy-5-(1-(2-fluorophenyl)-1H-pyrazol-4-yl)-1-methylpyridin-2(1H)-one;
4-ethoxy-1-methyl-5-(1-(pyridin-2-yl)-1H-pyrazol-4-yl)pyridin-2(1H)-one;
2-[4-(1,5-Dimethyl-6-oxo-1,6-dihydro-pyridin-3-yl)-pyrazol-1-yl]-benzonitrile;
2-[4-(1,5-Dimethyl-6-oxo-1,6-dihydro-pyridin-3-yl)-pyrazol-1-yl]-benzoic acid;
2-[4-(5-Ethyl-1-methyl-6-oxo-1,6-dihydro-pyridin-3-yl)-pyrazol-1-yl]-benzonitrile;
2-[4-(5-Ethyl-1-methyl-6-oxo-1,6-dihydro-pyridin-3-yl)-pyrazol-1-yl]-benzoic acid;
2-[4-(1,5-Dimethyl-6-oxo-1,6-dihydro-pyridin-3-yl)-pyrazol-1-yl]-4-phenoxy-benzonitrile;
2-[4-(1,5-Dimethyl-6-oxo-1,6-dihydro-pyridin-3-yl)-pyrazol-1-yl]-4-phenoxy-benzoic acid;
4-Methoxy-2-[4-(1'-methyl-6,6'-dioxo-1,6,1',6'-tetrahydro-[3,4']bipyridinyl-3'-yl)-pyrazol-1-yl]-benzonitrile;
4-Methoxy-2-[4-(1-methyl-6-oxo-4-phenyl-1,6-dihydro-pyridin-3-yl)-pyrazol-1-yl]-benzonitrile;
2-{4-[4-(4-Chloro-phenyl)-1-methyl-6-oxo-1,6-dihydro-pyridin-3-yl]-pyrazol-1-yl}-4-methoxy-benzonitrile;
2-{4-[4-(4-Fluoro-phenyl)-1-methyl-6-oxo-1,6-dihydro-pyridin-3-yl]-pyrazol-1-yl}-4-methoxy-benzonitrile;
4-Methoxy-2-[4-(6-methoxy-1'-methyl-6'-oxo-1',6'-dihydro-[3,4']bipyridinyl-3'-yl)-pyrazol-1-yl]-benzonitrile;
2-[4-(6-Ethoxy-1'-methyl-6'-oxo-1',6'-dihydro-[3,4']bipyridinyl-3'-yl)-pyrazol-1-yl]-4-methoxy-benzonitrile;
4-Methoxy-2-[4-(2'-methoxy-1-methyl-6-oxo-1,6-dihydro-[4,4']bipyridinyl-3-yl)-pyrazol-1-yl]-benzonitrile;
4-Methoxy-2-[4-(1-methyl-6-oxo-4-phenyl-1,6-dihydro-pyridin-3-yl)-pyrazol-1-yl]-benzoic acid;
2-{4-[4-(4-Chloro-phenyl)-1-methyl-6-oxo-1,6-dihydro-pyridin-3-yl]-pyrazol-1-yl}-4-methoxy-benzoic acid;
2-{4-[4-(4-Fluoro-phenyl)-1-methyl-6-oxo-1,6-dihydro-pyridin-3-yl]-pyrazol-1-yl}-4-methoxy-benzoic acid;
4-Methoxy-2-[4-(6-methoxy-1'-methyl-6'-oxo-1',6'-dihydro-[3,4']bipyridinyl-3'-yl)-pyrazol-1-yl]-benzoic acid;
2-[4-(6-Ethoxy-1'-methyl-6'-oxo-1',6'-dihydro-[3,4']bipyridinyl-3'-yl)-pyrazol-1-yl]-4-methoxy-benzoic acid;
4-Methoxy-2-[4-(2'-methoxy-1-methyl-6-oxo-1,6-dihydro-[4,4']bipyridinyl-3-yl)-pyrazol-1-yl]-benzoic acid;
2-[4-(1,1'-Dimethyl-6,2'-dioxo-1,6,1',2'-tetrahydro-[4,4']bipyridinyl-3-yl)-pyrazol-1-yl]-6-fluoro-benzonitrile;
2-Fluoro-6-[4-(6-methoxy-1'-methyl-6'-oxo-1',6'-dihydro-[3,4']bipyridinyl-3'-yl)-pyrazol-1-yl]-benzonitrile;
2-{4-[4-(4-Chloro-phenyl)-1-methyl-6-oxo-1,6-dihydro-pyridin-3-yl]-pyrazol-1-yl}-6-fluoro-benzonitrile;
2-Chloro-6-[4-(1,1'-dimethyl-6,2'-dioxo-1,6,1',2'-tetrahydro-[4,4']bipyridinyl-3-yl)-pyrazol-1-yl]-benzonitrile;
2-Chloro-6-[4-(6-methoxy-1'-methyl-6'-oxo-1',6'-dihydro-[3,4']bipyridinyl-3'-yl)-pyrazol-1-yl]-benzonitrile;
2-fluoro-6-(4-(4-(3-methoxy-4-methylphenyl)-1-methyl-6-oxo-1,6-dihydropyridin-3-yl)-1H-pyrazol-1-yl)benzonitrile;
2-chloro-6-(4-(4-(3-methoxy-4-methylphenyl)-1-methyl-6-oxo-1,6-dihydropyridin-3-yl)-1H-pyrazol-1-yl)benzonitrile;
2-chloro-6-(4-(4-(2-ethylpyrimidin-5-yl)-1-methyl-6-oxo-1,6-dihydropyridin-3-yl)-1H-pyrazol-1-yl)benzonitrile;
2-(4-(4-ethoxy-1-methyl-6-oxo-1,6-dihydropyridin-3-yl)-1H-pyrazol-1-yl)benzonitrile;

2-(4-(4-ethoxy-1-methyl-6-oxo-1,6-dihydropyridin-3-yl)-1H-pyrazol-1-yl)benzamide;
2-(4-(1-methyl-4-(2-morpholinoethoxy)-6-oxo-1,6-dihydropyridin-3-yl)-1H-pyrazol-1-yl)benzonitrile;
5-[1-(2-Methanesulfonyl-phenyl)-1H-pyrazol-4-yl]-1,1'-dimethyl-1H,1'H-[4,4']bipyridinyl-2,2'-dione;
5'-[1-(2-Methanesulfonyl-phenyl)-1H-pyrazol-4-yl]-6-methoxy-1'-methyl-1'H-[3,4']bipyridinyl-2'-one;
4-(4-Chloro-phenyl)-5-[1-(2-methanesulfonyl-phenyl)-1H-pyrazol-4-yl]-1-methyl-1H-pyridin-2-one;
5'-[1-(2-Methanesulfonyl-phenyl)-1H-pyrazol-4-yl]-1,1'-dimethyl-1H,1'H-[3,4']bipyridinyl-6,2'-dione;
N-cyano-2-(4-(4-(4-fluorophenyl)-1-methyl-6-oxo-1,6-dihydropyridin-3-yl)-1H-pyrazol-1-yl)benzamide;
N-cyano-2-(4-(1-methyl-4-(1-methyl-1H-pyrazol-4-yl)-6-oxo-1,6-dihydropyridin-3-yl)-1H-pyrazol-1-yl)benzamide;
N-cyano-2-(4-(4-(4-methoxyphenyl)-1-methyl-6-oxo-1,6-dihydropyridin-3-yl)-1H-pyrazol-1-yl)benzamide;
2-(4-(4-(4-chlorophenyl)-1-methyl-6-oxo-1,6-dihydropyridin-3-yl)-1H-pyrazol-1-yl)-N-cyanobenzamide;
N-cyano-2-(4-(2'-methoxy-1-methyl-6-oxo-1,6-dihydro-[4,4'-bipyridin]-3-yl)-1H-pyrazol-1-yl)benzamide;
N-cyano-2-(4-(1,1'-dimethyl-2',6-dioxo-1,1',2',6-tetrahydro-[4,4'-bipyridin]-3-yl)-1H-pyrazol-1-yl)benzamide;
N-cyano-2-(4-(6-methoxy-1'-methyl-6'-oxo-1',6'-dihydro-[3,4'-bipyridin]-3'-yl)-1H-pyrazol-1-yl)benzamide;
N-cyano-2-(4-(1-methyl-4-(2-(methylamino)pyrimidin-5-yl)-6-oxo-1,6-dihydropyridin-3-yl)-1H-pyrazol-1-yl)benzamide;
N-cyano-2-(4-(6-ethoxy-1'-methyl-6'-oxo-1',6'-dihydro-[3,4'-bipyridin]-3'-yl)-1H-pyrazol-1-yl)benzamide;
5-(1-(2-(1H-tetrazol-5-yl)phenyl)-1H-pyrazol-4-yl)-4-(4-chlorophenyl)-1-methylpyridin-2(1H)-one;
4-(4-Methoxy-phenyl)-1-methyl-5-{1-[2-(1H-tetrazol-5-yl)-phenyl]-1H-pyrazol-4-yl}-1H-pyridin-2-one;
4-(4-Fluoro-phenyl)-1-methyl-5-{1-[2-(1H-tetrazol-5-yl)-phenyl]-1H-pyrazol-4-yl}-1H-pyridin-2-one;
1-Methyl-4-(1-methyl-1H-pyrazol-4-yl)-5-{1-[2-(1H-tetrazol-5-yl)-phenyl]-1H-pyrazol-4-yl}-1H-pyridin-2-one;
4-Cyclopropyl-1-methyl-5-{1-[2-(1H-tetrazol-5-yl)-phenyl]-1H-pyrazol-4-yl}-1H-pyridin-2-one;
N-{2-[4-(4-Cyclopropyl-1-methyl-6-oxo-1,6-dihydro-pyridin-3-yl)-pyrazol-1-yl]-benzoyl}-methanesulfonamide;
Ethanesulfonic acid 2-[4-(4-cyclopropyl-1-methyl-6-oxo-1,6-dihydro-pyridin-3-yl)-pyrazol-1-yl]-benzoylamide;
N-[(dimethylamino)sulfonyl]-{2-[4-(4-cyclopropyl-1-methyl-6-oxo(3-hydropyridyl))pyrazolyl]phenyl}carboxamide;
3-(4-(1,1'-dimethyl-2',6-dioxo-1,1',2',6-tetrahydro-[4,4'-bipyridin]-3-yl)-1H-pyrazol-1-yl)-4-methoxybenzonitrile;
4-Methoxy-3-[4-(6-methoxy-1'-methyl-6'-oxo-1',6'-dihydro-[3,4']bipyridinyl-3'-yl)-pyrazol-1-yl]-benzonitrile;
3-{4-[4-(4-Chloro-phenyl)-1-methyl-6-oxo-1,6-dihydropyridin-3-yl]-pyrazol-1-yl}-4-methoxy-benzonitrile;
6-methoxy-1'-methyl-5'-(1-(1-phenylethyl)-1H-pyrazol-4-yl)-[3,4'-bipyridin]-2'(1'H)-one;
1-methyl-4-(2-(methylamino)pyrimidin-5-yl)-5-(1-(1-phenylethyl)-1H-pyrazol-4-yl)pyridin-2(1H)-one;
1,1'-dimethyl-5-(1-(1-phenylethyl)-1H-pyrazol-4-yl)-[4,4'-bipyridine]-2,2'(1H,1'H)-dione;
4-(2-(ethylamino)pyrimidin-5-yl)-1-methyl-5-(1-(1-phenylethyl)-1H-pyrazol-4-yl)pyridin-2(1H)-one;
4-(2-((2-methoxyethyl)amino)pyrimidin-5-yl)-1-methyl-5-(1-(1-phenylethyl)-1H-pyrazol-4-yl)pyridin-2(1H)-one;
6-(3-(dimethylamino)propoxy)-1'-methyl-5'-(1-(1-phenylethyl)-1H-pyrazol-4-yl)-[3,4'-bipyridin]-2'(1'H)-one;
5-(1-(2-chlorophenyl)-1H-pyrazol-4-yl)-1,1'-dimethyl-[4,4'-bipyridine]-2,2'(1H,1'H)-dione;
5-(1-(2-chlorophenyl)-1H-pyrazol-4-yl)-4-(2-methoxypyrimidin-5-yl)-1-methylpyridin-2(1H)-one;
5'-(1-(2-chlorophenyl)-1H-pyrazol-4-yl)-6-methoxy-1',5-dimethyl-[3,4'-bipyridin]-2'(1'H)-one;
5-(1-(2-chlorophenyl)-1H-pyrazol-4-yl)-2'-methoxy-1-methyl-[4,4'-bipyridin]-2(1H)-one;
5-(1-(2-fluorophenyl)-1H-pyrazol-4-yl)-1,1'-dimethyl-[4,4'-bipyridine]-2,2'(1H,1'H)-dione;
5'-(1-(2-fluorophenyl)-1H-pyrazol-4-yl)-6-methoxy-1'-methyl-[3,4'-bipyridin]-2'(1'H)-one;
5-(1-(2-fluorophenyl)-1H-pyrazol-4-yl)-4-(2-methoxypyrimidin-5-yl)-1-methylpyridin-2(1H)-one;
5-(1-(2-hydroxycyclohexyl)-1H-pyrazol-4-yl)-1-methyl-4-phenylpyridin-2(1H)-one;
2-chloro-6-[4-[4-[2-(cyclopropylamino)pyrimidin-5-yl]-1-methyl-6-oxo-3-pyridyl]pyrazol-1-yl]benzonitrile;
2-(4-(4-(2-(ethylamino)pyrimidin-5-yl)-1-methyl-6-oxo-1,6-dihydropyridin-3-yl)-1H-pyrazol-1-yl)benzonitrile;
2-(4-(4-(2-((2-methoxyethyl)amino)pyrimidin-5-yl)-1-methyl-6-oxo-1,6-dihydropyridin-3-yl)-1H-pyrazol-1-yl)benzonitrile;
2-chloro-6-(4-(4-(2-(ethylamino)pyrimidin-5-yl)-1-methyl-6-oxo-1,6-dihydropyridin-3-yl)-1H-pyrazol-1-yl)benzonitrile;
2-chloro-6-(4-(4-(2-((2-methoxyethyl)amino)pyrimidin-5-yl)-1-methyl-6-oxo-1,6-dihydropyridin-3-yl)-1H-pyrazol-1-yl)benzonitrile;
2-chloro-6-(4-(4-(2-((cyclopropylmethyl)amino)pyrimidin-5-yl)-1-methyl-6-oxo-1,6-dihydropyridin-3-yl)-1H-pyrazol-1-yl)benzonitrile;
2-chloro-6-(4-(4-(2-(dimethylamino)pyrimidin-5-yl)-1-methyl-6-oxo-1,6-dihydropyridin-3-yl)-1H-pyrazol-1-yl)benzonitrile;
2-chloro-6-(4-(4-(2-(cyclopentylamino)pyrimidin-5-yl)-1-methyl-6-oxo-1,6-dihydropyridin-3-yl)-1H-pyrazol-1-yl)benzonitrile;
2-chloro-6-(4-(1-methyl-6-oxo-4-(2-(pyrrolidin-1-yl)pyrimidin-5-yl)-1,6-dihydropyridin-3-yl)-1H-pyrazol-1-yl)benzonitrile;
2-chloro-6-(4-(4-(2-(isopropylamino)pyrimidin-5-yl)-1-methyl-6-oxo-1,6-dihydropyridin-3-yl)-1H-pyrazol-1-yl)benzonitrile;
2-chloro-6-(4-(1-methyl-4-(2-(methylamino)pyrimidin-5-yl)-6-oxo-1,6-dihydropyridin-3-yl)-1H-pyrazol-1-yl)benzonitrile;
2-[4-[4-[2-(ethylamino)pyrimidin-5-yl]-1-methyl-6-oxo-3-pyridyl]pyrazol-1-yl]-6-fluoro-benzonitrile;
2-[4-[4-[2-(dimethylamino)pyrimidin-5-yl]-1-methyl-6-oxo-3-pyridyl]pyrazol-1-yl]-6-fluoro-benzonitrile;
2-chloro-6-(4-(1-methyl-4-(2-morpholinopyrimidin-5-yl)-6-oxo-1,6-dihydropyridin-3-yl)-1H-pyrazol-1-yl)benzonitrile;
2-fluoro-6-[4-[1-methyl-6-oxo-4-(2-pyrrolidin-1-ylpyrimidin-5-yl)-3-pyridyl]pyrazol-1-yl]benzonitrile;
2-chloro-6-(4-(1-methyl-4-(2-(4-methylpiperazin-1-yl)pyrimidin-5-yl)-6-oxo-1,6-dihydropyridin-3-yl)-1H-pyrazol-1-yl)benzonitrile;
2-chloro-6-(4-(1-methyl-6-oxo-4-(2-(piperidin-1-yl)pyrimidin-5-yl)-1,6-dihydropyridin-3-yl)-1H-pyrazol-1-yl)benzonitrile;
2-chloro-6-[4-[4-[6-(isopropylamino)-3-pyridyl]-1-methyl-6-oxo-3-pyridyl]-pyrazol-1-yl]benzonitrile;
2-chloro-6-(4-(6-(cyclopentylamino)-1'-methyl-6'-oxo-1',6'-dihydro-[3,4'-bipyridin]-3'-yl)-1H-pyrazol-1-yl)benzonitrile;

2-chloro-6-(4-(1'-methyl-6-(methylamino)-6'-oxo-1', 6'-dihydro-[3,4'-bipyridin]-3'-yl)-1H-pyrazol-1-yl)benzonitrile 2-chloro-6-(4-(6-(ethylamino)-1'-methyl-6'-oxo-1', 6'-dihydro-[3,4'-bipyridin]-3'-yl)-1H-pyrazol-1-yl)benzonitrile;

2-(4-(6-(cyclopentylamino)-1'-methyl-6'-oxo-1', 6'-dihydro-[3,4'-bipyridin]-3'-yl)-1H-pyrazol-1-yl)-6-fluorobenzonitrile;

2-(4-(6-(ethylamino)-1'-methyl-6'-oxo-1', 6'-dihydro-[3,4'-bipyridin]-3'-yl)-1H-pyrazol-1-yl)-6-fluorobenzonitrile;

2-chloro-6-{4-[6-(dimethylamino)-1'-methyl-6'-oxo-1', 6'-dihydro-[3,4'-bipyridine]-3'-yl]-1H-pyrazol-1-yl}benzonitrile;

2-(4-{6-[(cyclopropylmethyl)amino]-1'-methyl-6'-oxo-1',6'-dihydro-[3,4'-bipyridine]-3'-yl}-1H-pyrazol-1-yl)-6-fluorobenzonitrile;

2-{4-[6-(dimethylamino)-1'-methyl-6'-oxo-1',6'-dihydro-[3, 4'-bipyridine]-3'-yl]-1H-pyrazol-1-yl}-6-fluorobenzonitrile;

2-chloro-6-(4-{6-[(cyclopropylmethyl)amino]-1'-methyl-6'-oxo-1',6'-dihydro-[3,4'-bipyridine]-3'-yl}-1H-pyrazol-1-yl)benzonitrile;

2-chloro-6-[4-[1-methyl-6-oxo-4-(6-pyrrolidin-1-yl-3-pyridyl)-3-pyridyl]pyrazol-1-yl]benzonitrile;

2-fluoro-6-[4-[1-methyl-6-oxo-4-(6-pyrrolidin-1-yl-3-pyridyl)-3-pyridyl]pyrazol-1-yl]benzonitrile;

2-fluoro-6-(4-(6-(isopropylamino)-1'-methyl-6'-oxo-1',6'-dihydro-[3,4'-bipyridin]-3'-yl)-1H-pyrazol-1-yl)benzonitrile;

2-chloro-6-[4-[4-[6-(cyclopentoxy)-3-pyridyl]-1-methyl-6-oxo-3-pyridyl]pyrazol-1-yl]benzonitrile;

2-(4-(6-(difluoromethoxy)-1'-methyl-6'-oxo-1',6'-dihydro-[3,4'-bipyridin]-3'-yl)-1H-pyrazol-1-yl)-6-fluorobenzonitrile;

2-chloro-6-(4-(6-(difluoromethoxy)-1'-methyl-6'-oxo-1',6'-dihydro-[3,4'-bipyridin]-3'-yl)-1H-pyrazol-1-yl)benzonitrile 2-(4-(6-(3-(dimethylamino)propoxy)-1'-methyl-6'-oxo-1',6'-dihydro-[3,4'-bipyridin]-3'-yl)-1H-pyrazol-1-yl)benzonitrile;

2-chloro-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile;

2-chloro-6-[4-[4-[6-(cyclopropylmethoxy)-3-pyridyl]-1-methyl-6-oxo-3-pyridyl]pyrazol-1-yl]benzonitrile;

2-fluoro-6-[4-[4-(6-isopropoxy-3-pyridyl)-1-methyl-6-oxo-3-pyridyl]pyrazol-1-yl]benzonitrile;

2-(4-(6-ethoxy-1'-methyl-6'-oxo-1', 6'-dihydro-[3,4'-bipyridin]-3'-yl)-1H-pyrazol-1-yl)-6-fluorobenzonitrile;

2-[4-[4-[6-(cyclopropylmethoxy)-3-pyridyl]-1-methyl-6-oxo-3-pyridyl]pyrazol-1-yl]-6-fluoro-benzonitrile;

2-[4-[4-[6-(cyclopentoxy)-3-pyridyl]-1-methyl-6-oxo-3-pyridyl]pyrazol-1-yl]-6-fluoro-benzonitrile;

2-[4-[4-[6-(cyclopropoxy)-3-pyridyl]-1-methyl-6-oxo-3-pyridyl]pyrazol-1-yl]-6-fluoro-benzonitrile;

2-chloro-6-[4-[4-(6-isopropoxy-3-pyridyl)-1-methyl-6-oxo-3-pyridyl]pyrazol-1-yl]benzonitrile;

2-chloro-6-[4-[4-[6-(cyclopropoxy)-3-pyridyl]-1-methyl-6-oxo-3-pyridyl]pyrazol-1-yl]benzonitrile;

2-chloro-6-(4-(6-ethoxy-1'-methyl-6'-oxo-1', 6'-dihydro-[3, 4'-bipyridin]-3'-yl)-1H-pyrazol-1-yl)benzonitrile;

2-chloro-6-[4-[4-(6-cyclopropyl-3-pyridyl)-1-methyl-6-oxo-3-pyridyl]pyrazol-1-yl]benzonitrile;

2-(4-(1',6-dimethyl-6'-oxo-1',6'-dihydro-[3,4'-bipyridin]-3'-yl)-1H-pyrazol-1-yl)-6-fluorobenzonitrile;

2-fluoro-6-(4-(1'-methyl-6'-oxo-6-(trifluoromethyl)-1',6'-dihydro-[3,4'-bipyridin]-3'-yl)-1H-pyrazol-1-yl)benzonitrile;

2-chloro-6-(4-(1',6-dimethyl-6'-oxo-1',6'-dihydro-[3,4'-bipyridin]-3'-yl)-1H-pyrazol-1-yl)benzonitrile;

2-chloro-6-(4-(1'-methyl-6'-oxo-6-(trifluoromethyl)-1',6'-dihydro-[3,4'-bipyridin]-3'-yl)-1H-pyrazol-1-yl)benzonitrile;

2-chloro-6-(4-(6-ethyl-1'-methyl-6'-oxo-1',6'-dihydro-[3,4'-bipyridin]-3'-yl)-1H-pyrazol-1-yl)benzonitrile;

2-(4-(6-ethyl-1'-methyl-6'-oxo-1',6'-dihydro-[3,4'-bipyridin]-3'-yl)-1H-pyrazol-1-yl)-6-fluorobenzonitrile;

2-(4-(6-ethyl-1'-methyl-6'-oxo-1',6'-dihydro-[3,4'-bipyridin]-3'-yl)-1H-pyrazol-1-yl)benzonitrile;

2-[4-[4-(6-cyclopropyl-3-pyridyl)-1-methyl-6-oxo-3-pyridyl]pyrazol-1-yl]-6-fluoro-benzonitrile;

2-fluoro-6-[4-[4-(6-isopropyl-3-pyridyl)-1-methyl-6-oxo-3-pyridyl]pyrazol-1-yl]benzonitrile;

2-chloro-6-[4-[4-(6-isopropyl-3-pyridyl)-1-methyl-6-oxo-3-pyridyl]pyrazol-1-yl]benzonitrile;

2-(4-(1',6-dimethyl-6'-oxo-1',6'-dihydro-[3,4'-bipyridin]-3'-yl)-1H-pyrazol-1-yl)benzonitrile;

2-(4-(6-cyclopentyl-1'-methyl-6'-oxo-1',6'-dihydro-[3,4'-bipyridin]-3'-yl)-1H-pyrazol-1-yl)-6-fluorobenzonitrile;

2-chloro-6-(4-(6-cyclopentyl-1'-methyl-6'-oxo-1',6'-dihydro-[3,4'-bipyridin]-3'-yl)-1H-pyrazol-1-yl)benzonitrile;

2-cyclopropyl-6-[4-[1-methyl-4-(1-methyl-2-oxo-4-pyridyl)-6-oxo-3-pyridyl]pyrazol-1-yl]benzonitrile;

2-cyclopropyl-6-[4-[4-[1-(cyclopropylmethyl)-2-oxo-4-pyridyl]-1-methyl-6-oxo-3-pyridyl]pyrazol-1-yl]benzonitrile;

2-cyclopropyl-6-(4-(6-(3-(dimethylamino)propoxy)-1'-methyl-6'-oxo-1', 6'-dihydro-[3,4'-bipyridin]-3'-yl)-1H-pyrazol-1-yl)benzonitrile;

2-cyclopropyl-6-(4-(6-methoxy-1'-methyl-6'-oxo-1', 6'-dihydro-[3,4'-bipyridin]-3'-yl)-1H-pyrazol-1-yl)benzonitrile;

2-cyclopropyl-6-(4-(6-ethoxy-1'-methyl-6'-oxo-1', 6'-dihydro-[3,4'-bipyridin]-3'-yl)-1H-pyrazol-1-yl)benzonitrile;

2-cyclopropyl-6-[4-[1-methyl-6-oxo-4-(2-oxo-1-propyl-4-pyridyl)-3-pyridyl]pyrazol-1-yl]benzonitrile;

2-cyclopropyl-6-[4-[4-(1-ethyl-2-oxo-4-pyridyl)-1-methyl-6-oxo-3-pyridyl]pyrazol-1-yl]benzonitrile;

2-cyclopropyl-6-[4-[4-[6-(2-fluoroethoxy)-3-pyridyl]-1-methyl-6-oxo-3-pyridyl]pyrazol-1-yl]benzonitrile;

2-cyclopropyl-6-(4-(1'-cyclopropyl-1-methyl-2',6-dioxo-1, 1',2',6-tetrahydro-[4,4'-bipyridin]-3-yl)-1H-pyrazol-1-yl)benzonitrile;

2-cyclopropyl-6-[4-[4-[1-(2-fluoroethyl)-2-oxo-4-pyridyl]-1-methyl-6-oxo-3-pyridyl]pyrazol-1-yl]benzonitrile;

2-cyclopropyl-6-[4-[4-[1-(2-hydroxyethyl)-2-oxo-4-pyridyl]-1-methyl-6-oxo-3-pyridyl]pyrazol-1-yl]benzonitrile;

2-cyclopropyl-6-(4-(6-(cyclopropylmethoxy)-1'-methyl-6'-oxo-1',6'-dihydro-[3,4'-bipyridin]-3'-yl)-1H-pyrazol-1-yl)benzonitrile;

4-Ethoxy-5-(5-methanesulfonyl-4,5,6,7-tetrahydro-pyrazolo[1,5-a]pyrazin-3-yl)-1-methyl-1H-pyridin-2-one;

5-(5-Acetyl-4,5,6,7-tetrahydro-pyrazolo[1,5-a]pyrazin-3-yl)-4-ethoxy-1-methyl-1H-pyridin-2-one;

1-methyl-4-phenyl-5-(5-phenyloxazol-2-yl)pyridin-2(1H)-one;

1-methyl-5-(1-methyl-5-phenyl-1H-pyrazol-3-yl)-4-phenylpyridin-2(1H)-one;

1-methyl-4-phenyl-5-(2-phenyloxazol-4-yl)pyridin-2(1H)-one; or
1-methyl-4-phenyl-5-(2-phenyloxazol-5-yl)pyridin-2(1H)-one.
In some embodiments, the substituted heterocyclic derivative compound disclosed herein has the structure provided in Table 2.
TABLE 2
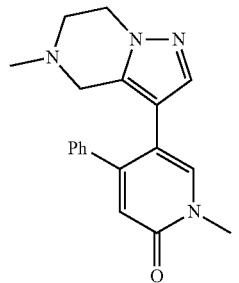
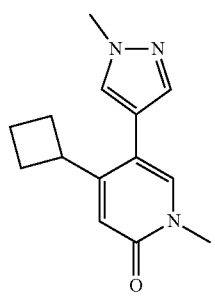 [SMILES: Cn1cc(-c2cn(C)c(=O)cc2C2CCC2)cn1]
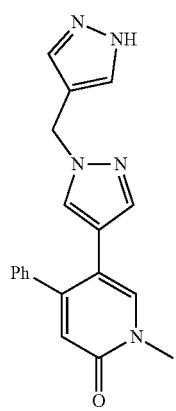 [SMILES: Cn1cc(-c2cnn(Cc3cn[nH]c3)c2)c(-c2ccccc2)cc1=O]
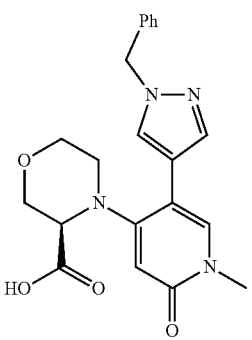 [SMILES: Cn1cc(-c2cnn(Cc3ccccc3)c2)c(N2CCOC[C@@H]2C(=O)O)cc1=O]
TABLE 2-continued
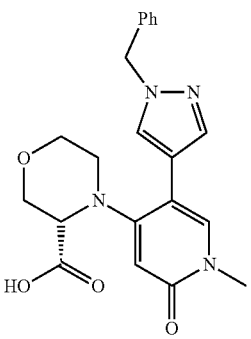
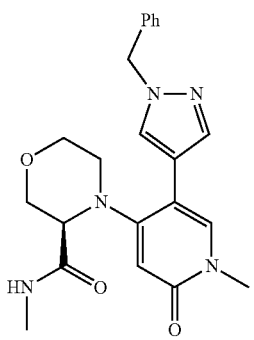 [SMILES: CNC(=O)[C@H]1COCCN1c1cc(=O)n(C)cc1-c1cnn(Cc2ccccc2)c1]
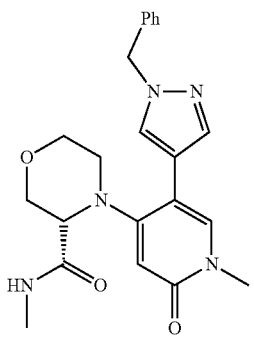
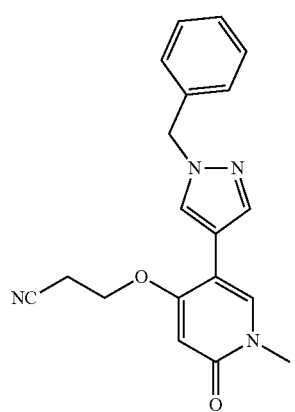 [SMILES: Cn1cc(-c2cnn(Cc3ccccc3)c2)c(OCCC#N)cc1=O]

TABLE 2-continued
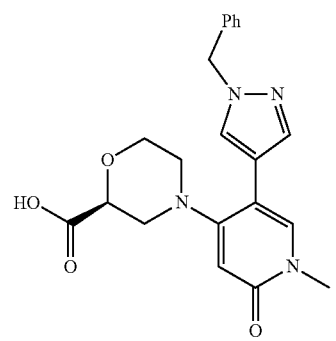 [SMILES: Cn1cc(-c2cnn(Cc3ccccc3)c2)c(N2CCO[C@H](C(=O)O)C2)cc1=O]
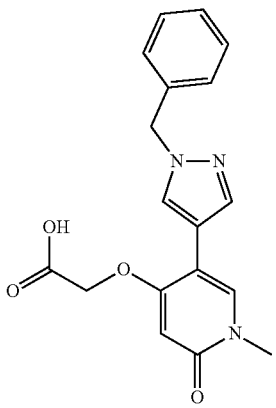
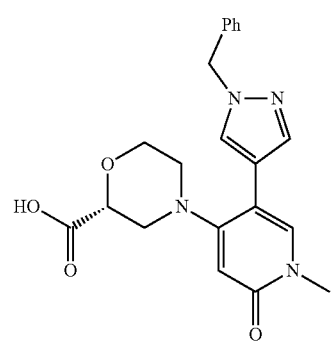 [SMILES: Cn1cc(-c2cnn(Cc3ccccc3)c2)c(N2CCO[C@@H](C(=O)O)C2)cc1=O]
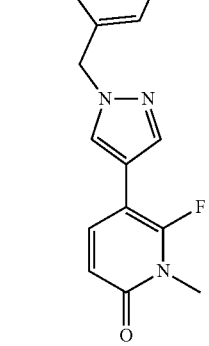
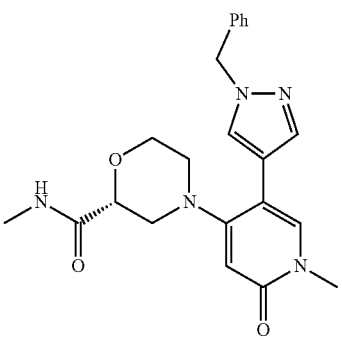
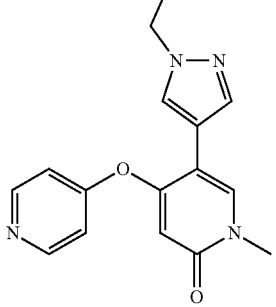
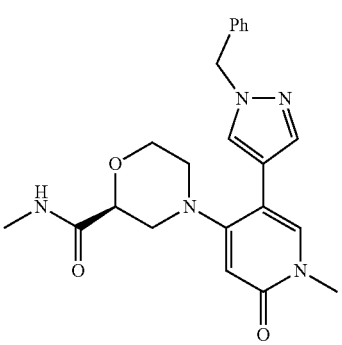
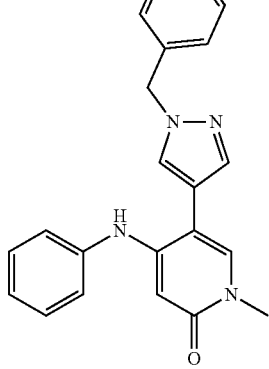

TABLE 2-continued
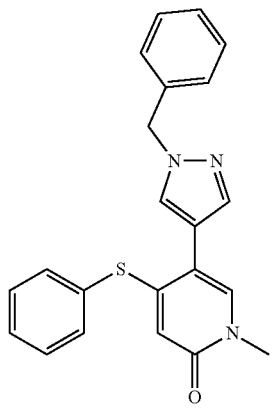 [SMILES: Cn1cc(-c2cnn(Cc3ccccc3)c2)c(Sc2ccccc2)cc1=O]
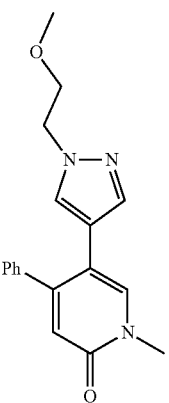 [SMILES: COCCn1cc(-c2cn(C)c(=O)cc2-c2ccccc2)cn1]
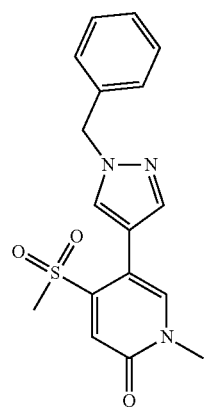 [SMILES: Cn1cc(-c2cnn(Cc3ccccc3)c2)c(S(C)(=O)=O)cc1=O]
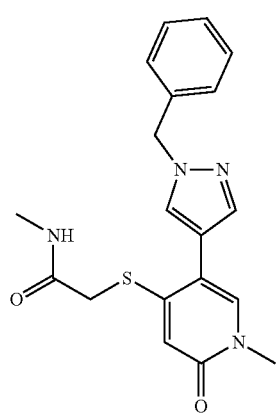 [SMILES: CNC(=O)CSc1cc(=O)n(C)cc1-c1cnn(Cc2ccccc2)c1]
TABLE 2-continued
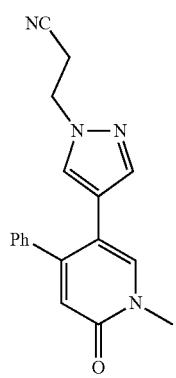
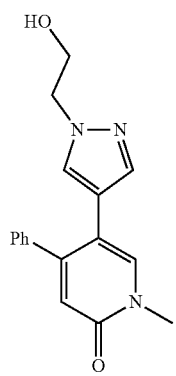
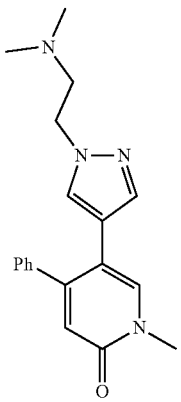
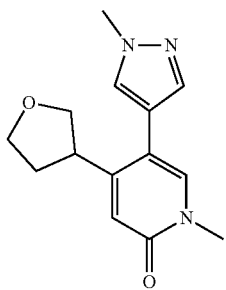

TABLE 2-continued
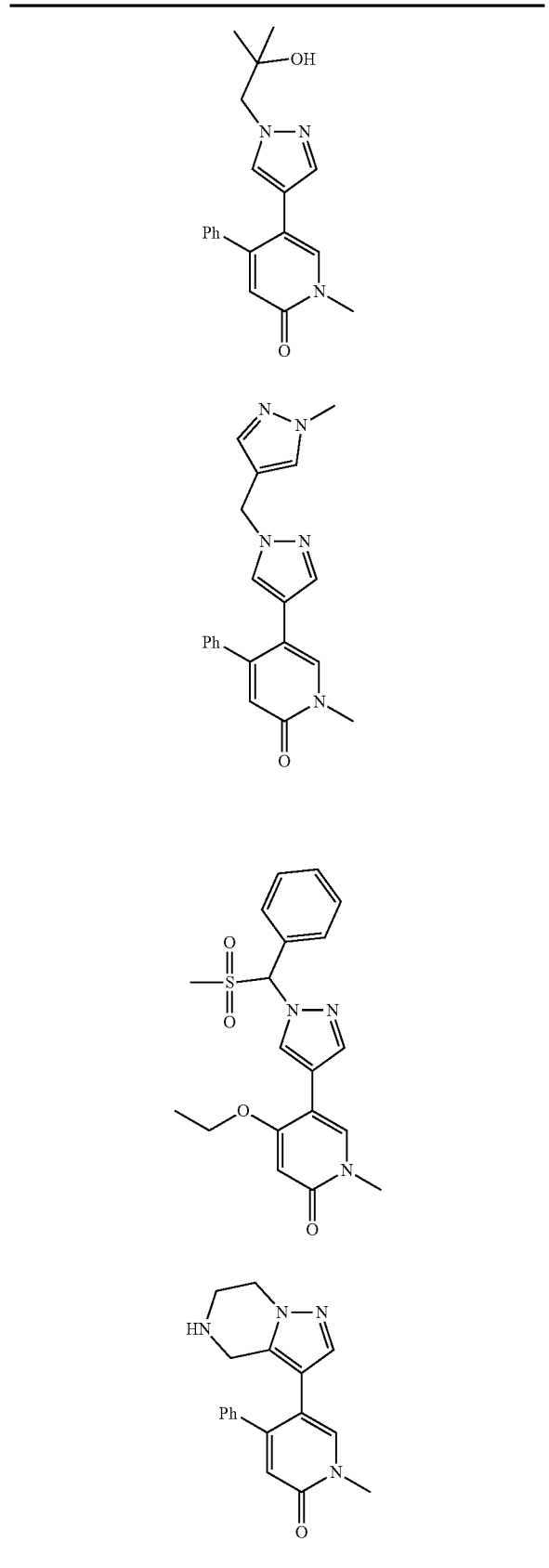
TABLE 2-continued
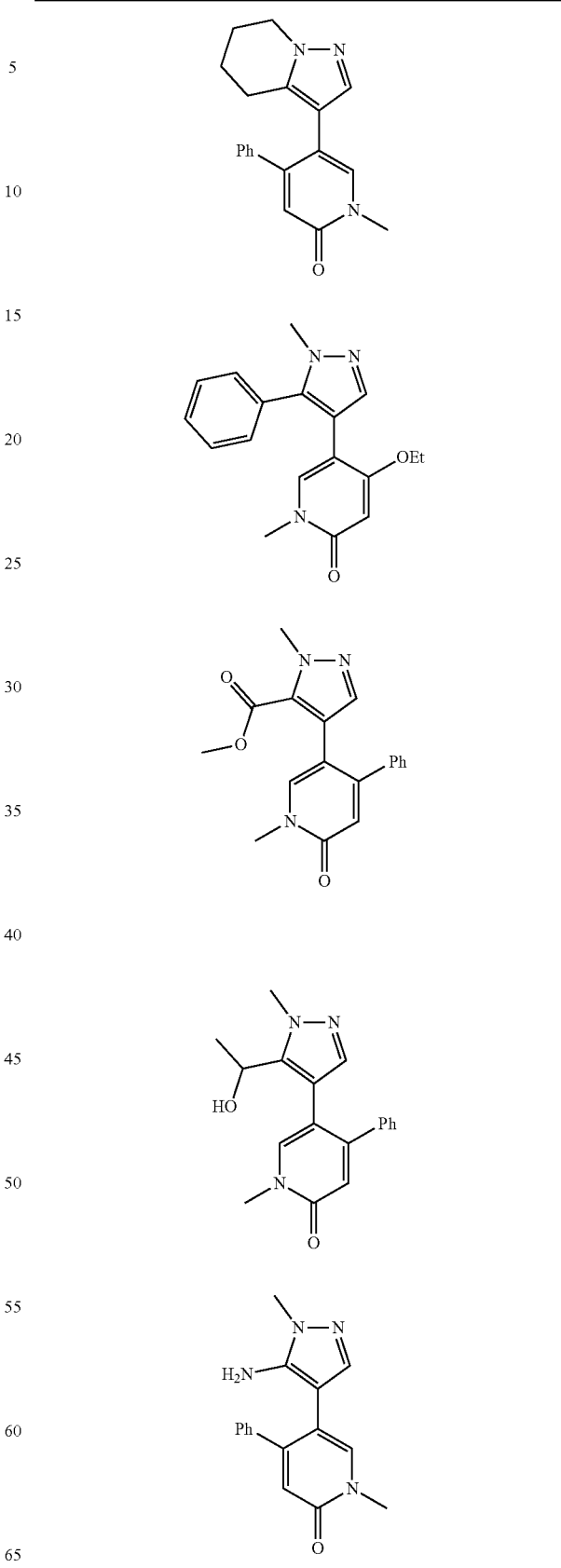

TABLE 2-continued

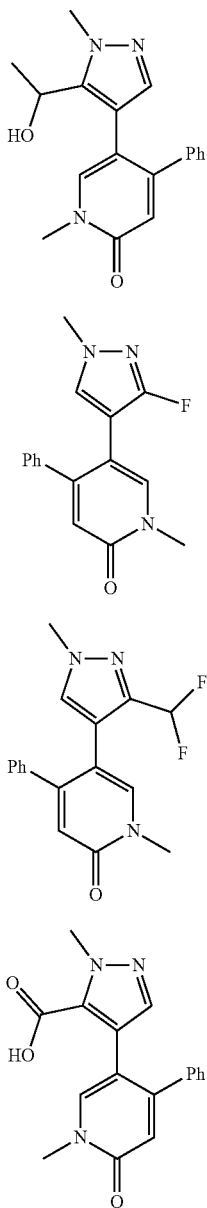

Preparation of the Substituted Heterocyclic Derivative Compounds

The compounds used in the reactions described herein are made according to organic synthesis techniques known to those skilled in this art, starting from commercially available chemicals and/or from compounds described in the chemical literature. "Commercially available chemicals" are obtained from standard commercial sources including Acros Organics (Pittsburgh, Pa., US), Aldrich Chemical (Milwaukee, Wis., US; includes Sigma Chemical and Fluka), Apin Chemicals Ltd. (Milton Park, UK), Avocado Research (Lancashire, UK), BDH Inc. (Toronto, CA), Bionet (Cornwall, UK), Chemservice Inc. (West Chester, Pa., US), Crescent Chemical Co. (Hauppauge, N.Y., US), Eastman Organic Chemicals, Eastman Kodak Company (Rochester, N.Y., US), Fisher Scientific Co. (Pittsburgh, Pa., US), Fisons Chemicals (Leicestershire, UK), Frontier Scientific (Logan, Utah, US), ICN Biomedicals, Inc. (Costa Mesa, Calif., US), Key Organics (Cornwall, UK), Lancaster Synthesis (Windham, N.H., US), Maybridge Chemical Co. Ltd. (Cornwall, UK), Parish Chemical Co. (Orem, Utah, US), Pfaltz & Bauer, Inc. (Waterbury, Conn., US), Polyorganix (Houston, Tex., US), Pierce Chemical Co. (Rockford, Ill., US), Riedel de Haen AG (Hanover, Del.), Spectrum Quality Product, Inc. (New Brunswick, N.J., US), TCI America (Portland, Or., US), Trans World Chemicals, Inc. (Rockville, Md., US), and Wako Chemicals USA, Inc. (Richmond, Va., US).

Methods known to one of ordinary skill in the art are identified through various reference books and databases. Suitable reference books and treatise that detail the synthesis of reactants useful in the preparation of compounds described herein, or provide references to articles that describe the preparation. See, e.g., SYNTHETIC ORGANIC CHEM. (John Wiley & Sons, Inc., N.Y.); Sandler et al., ORGANIC FUNCTIONAL GROUP PREP., 2nd Ed. (Academic Press, N.Y., 1983); House, MODERN SYNTHETIC REACTIONS, 2nd Ed. (W. A. Benjamin, Inc., Menlo Park, Calif., 1972); Gilchrist, HETEROCYCLIC CHEM., 2nd Ed. (John Wiley & Sons, N.Y., 1992); March, ADVANCED ORGANIC CHEM.: REACTIONS, MECHANISMS & STRUCTURE, 4th Ed., (Wiley-Interscience, N.Y., 1992). Additional suitable references that detail the synthesis of reactants useful in the preparation of compounds described herein, or provide references to articles that describe the preparation, are known in the art. See, e.g., Fuhrhop & Penzlin, ORGANIC SYNTH.: CONCEPTS, METHODS, STARTING MAT'LS, 2nd Revised & Enlarged Ed. (John Wiley & Sons, ISBN: 3-527-29074-5, 1994); HOFFMAN, ORGANIC CHEM., INTERMEDIATE TEXT (Oxford Univ. Press, ISBN 0-19-509618-5, 1996); Larock, COMPREHENSIVE ORGANIC TRANSFORMATIONS: GUIDE TO FUNCTIONAL GROUP PREPARATIONS, 2nd Ed. (Wiley-VCH, ISBN: 0-471-19031-4, 1999); March, ADVANCED ORGANIC CHEM.: REACTIONS, MECHANISMS, & STRUCTURE, 4th Ed. (John Wiley & Sons, ISBN: 0-471-60180-2, 1992); MODERN CARBONYL CHEM. (Otera (Ed.), Wiley-VCH, ISBN: 3-527-29871-1, 2000); Patai, PATAI'S 1992 GUIDE TO CHEM. OF FUNCTIONAL GROUPS (Interscience ISBN: 0-471-93022-9, 1992); Solomons, ORGANIC CHEM., 7th Ed. (John Wiley & Sons, ISBN: 0-471-19095-0, 2000); Stowell, INTERMEDIATE ORGANIC CHEM., 2nd Ed. (Wiley-Interscience, ISBN: 0-471-57456-2, 1993); INDUSTRIAL ORGANIC CHEM.: STARTING MATERIALS & INTERMEDIATES: ULLMANN'S ENCYCLOPEDIA (John Wiley & Sons, ISBN: 3-527-29645-X, 1999) in 8 volumes; ORGANIC REACTIONS (1942-2000) (John Wiley & Sons), in over 55 volumes; CHEM. FUNCTIONAL GROUPS (John Wiley & Sons), in 73 volumes.

Specific and analogous reactants may also be identified through the indices of known chemicals prepared by the Chemical Abstract Service of the American Chemical Society, which are available in most public and university libraries, as well as through on-line databases (American Chemical Society, Washington, D.C., US). Chemicals that are known but not commercially available in catalogs may be prepared by custom chemical synthesis houses, where many of the standard chemical supply houses (e.g., those listed above) provide custom synthesis services. A reference for the preparation and selection of pharmaceutical salts of the substituted heterocyclic derivative compounds described herein is Stahl & Wermuth, HANDBOOK OF PHARMACEUTICAL SALTS (Verlag Helvetica Chimica Acta, Zurich, Del., 200)2.

General methods for the synthesis of substituted heterocyclic derivatives are also known. See, e.g., WO 2009158396; WO 200563768; WO 2006112666; Briet et. al., 58 Tetrahedron 5761 (2002); WO 200877550; WO 200877551; WO 200877556; WO 200712421; WO 200712422; US200799911; WO 200877550; Havera et al., 42 J. Med. Chem. 3860 (1999); WO 200429051; US20090054434. Additional examples of the synthesis of substituted heterocyclic derivatives are known. See, e.g., WO 2012/171337; WO 2011/044157; WO 2009/097567; WO 2005/030791; EP 203216; Becknell et al., 21 Bioorg. Med. Chem. Letts. 7076 (2011); Svechkarev et al., Visnik Kharkivs'kogo Natsional'nogo Univ. im. V. N. Karazina, 770:201 (2007); Coskun et al., 35 Synth. Commun. 2435 (2005); Alvarez et al., 15 Sci. Synth. 839 (2005); Kihara et al., 53 Heterocycl. 359 (2000); Couture et al., 7 J. Chem. Soc'y, Perkin Transact. 1: Org. Bio-Org. Chem. 789 (1999); Kihara et al., 48 Heterocycles 2473 (1998); Couture et al., 52 Tetrahed. 4433 (1996); Couturre et al., 37 Tetrahed. Lett. 3697 (1996); Natsugari et al., 38 J. Med. Chem. 3106 (1995); Moehrle et al., 321 Archiv Pharm. 759 (Weinheim, Del.) 321:759 (1988); Gore et al., 3 J. Chem. Soc'y, Perkin Transact. 1: Org. Bio-Org. Chem. 481 (1972-1999) (1988); Narasimhan et al., 3 J. Chem. Soc'y, Chem. Commun. 191 (1987); Henry et al., 40 J. Org. Chem. 1760 (1975); Berti, 90 Gazzetta Chim. Italiana 559 (1960); Berti et al., 49 Annal. Chim. 2110 (Rome, IT; 1959); Berti et al., 49 Annal. Chim. 1253 (Rome, IT; 1959); WO 2012000595; Couture et al., 52 Tetrahed. 4433 (1996); WO 2010069504; WO 2010069504; WO 2006030032; WO 2005095384; US20050222159; WO 2013064984; Mishra et al., 2013 Eur. J. Org. Chem. 693 (2013); Vachhani et al., 69 Tetrahed. 359 (2013); Xie et al., 45 Eur. J. Med. Chem. 210 (2010); Mukaiyama et al., 15 Bioorg. Med. Chem. 868 (2007); JP2005/089352; Wang et al., 9 Molec. 574 (2004); WO 2000023487; US20060287341; CN103183675; Hares et al., 32 Egyptian J. Pharm. Sci. 303 (1991); DE2356005; DE2133898; DE2133998; U.S. Pat. No. 3,816,422; DE2011970; Staehle et al., 8 Justus Liebigs Annalen der Chem. 1275 (1973).

In some embodiments, the substituted heterocyclic derivative compounds disclosed herein are prepared by the general synthetic routes described below in Schemes 1-8. These schemes are intended to exemplary to one of skill in the art and are not limiting. Additional methods for the synthesis of the substituted heterocyclic derivative compounds are disclosed herein or readily available to one of skill in the art.

The pyrazole pyridone compounds of the present embodiments can be prepared according to the general synthetic routes described in the following schemes:

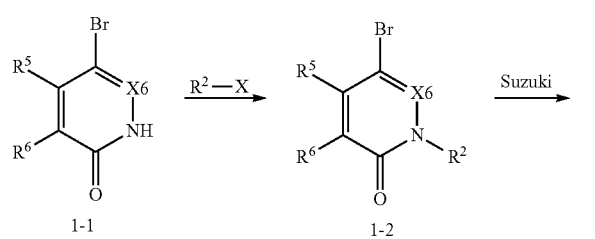

A method for preparing some of the substituted derivative compounds described herein is provided in the preceeding Scheme 1. 5-Bromopyridin-2(1H)-one derivative (1-1) is subjected to alkylation with alkyl halide under basic conditions to provide the related 5-bromo-1-alkylpyridin-2(1H)-one derivative (1-2). Further palladium-catalyzed cross coupling reaction of compound 1-2 with a suitable halide provides compound 1-3.

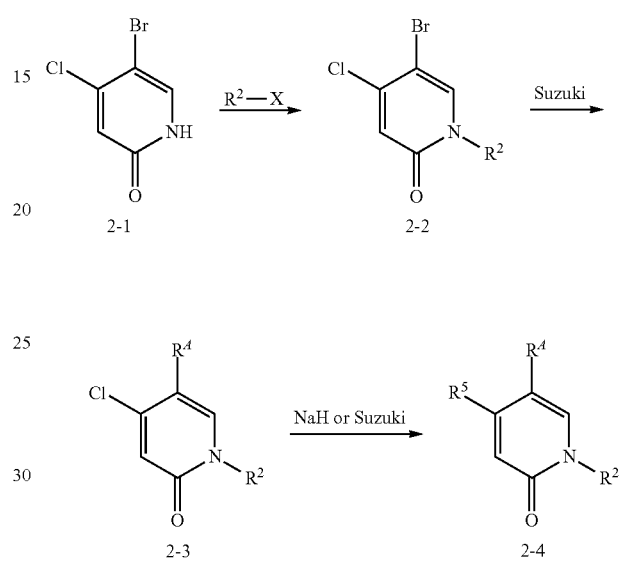

A method for preparing some of the substituted derivative compounds described herein is provided in Scheme 2, above. 5-Bromo-4-chloropyridin-2(1H)-one (2-1) is subjected to alkylation with alkyl halide under basic conditions to provide the related 5-bromo-4-chloro-1-alkylpyridin-2 (1H)-one derivative (2-2). Palladium-catalyzed cross coupling reaction of compound 2-2 with a suitable halide provides compound 2-3. Further palladium-catalyzed cross coupling reaction of compound 2-3 with a suitable halide provides compound 2-4. Alternatively, 2-3 is subjected to substitution with a suitable alcohol or amine or thiol under basic conditions to provide compound 2-4.

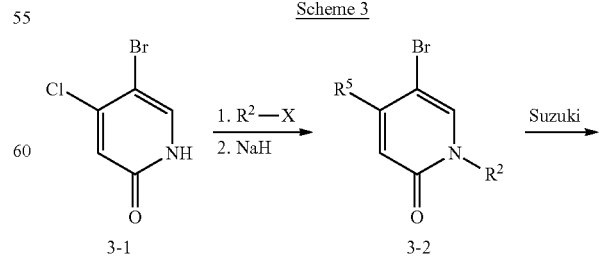

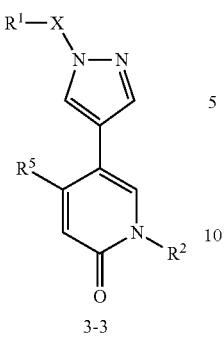

3-3

A method for preparing some of the substituted derivative compounds described herein is provided in Scheme 3, above. 5-Bromo-4-chloropyridin-2(1H)-one (3-1) is converted to the related compound 3-2 following a two-step sequence. More specifically, (1) alkylation with alkyl halide under basic conditions, (2) substitution with a suitable alcohol or amine or thiol under basic conditions provides compound 3-2. Further palladium-catalyzed cross coupling reaction of compound 3-2 with a suitable halide provides compound 3-3.

Scheme 4

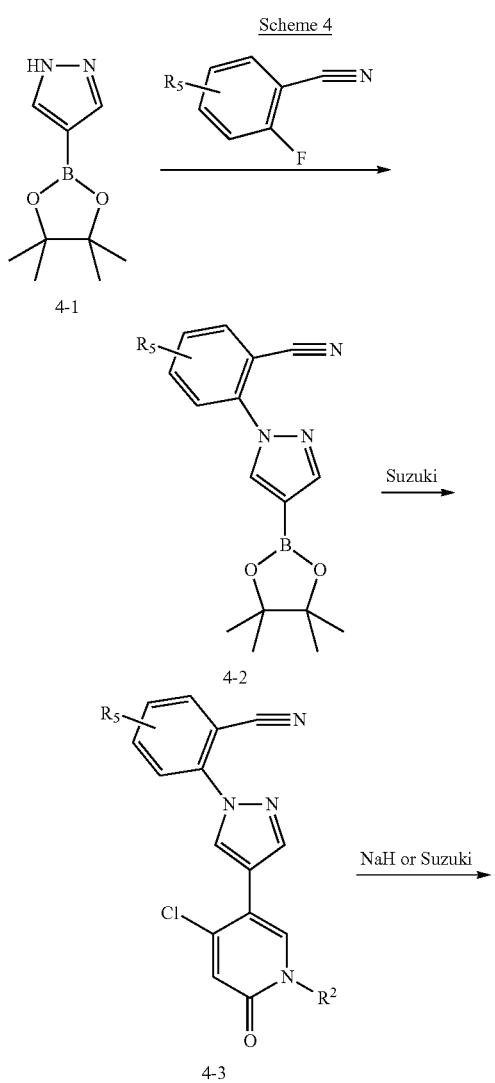

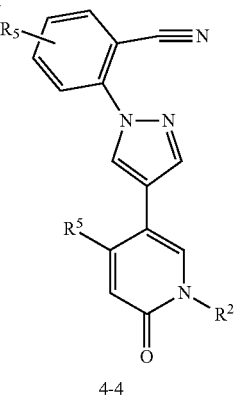

4-4

In each of the above reaction procedures or schemes, the various substituents may be selected from among the various substituents otherwise taught herein.

Pharmaceutical Compositions

In certain embodiments, the substituted heterocyclic derivative compound as described herein is administered as a pure chemical. In other embodiments, the substituted heterocyclic derivative compound described herein is combined with a pharmaceutically suitable or acceptable carrier (also referred to herein as a pharmaceutically suitable (or acceptable) excipient, physiologically suitable (or acceptable) excipient, or physiologically suitable (or acceptable) carrier) selected on the basis of a chosen route of administration and standard pharmaceutical practice as described, for example, in REMINGTON: SCIENCE & PRACTICE OF PHARMACY, 21ST ED. (Gennaro (Ed.) Mack Pub. Co., Easton, Pa. US (2005)).

Accordingly, provided herein is a pharmaceutical composition comprising at least one substituted heterocyclic derivative compound, such as a compound of Formula I, the reference to which includes a stereoisomer, pharmaceutically acceptable salt, hydrate, solvate, or N-oxide thereof, together with one or more pharmaceutically acceptable carriers. The carrier(s) (or excipient(s)) is acceptable or suitable if the carrier is compatible with the other ingredients of the composition and not deleterious to the recipient (i.e., the subject) of the composition.

One embodiment provides a pharmaceutical composition comprising a compound of Formula I and a pharmaceutically acceptable excipient. In certain embodiments, the substituted heterocyclic derivative compound as described herein is substantially pure, in that it contains less than about 5%, or less than about 1%, or less than about 0.1%, of other organic small molecules, such as contaminating intermediates or by-products that are created, for example, in one or more of the steps of a synthesis method.

Suitable oral dosage forms include, for example, tablets, pills, sachets, or capsules of hard or soft gelatin, methylcellulose or of another suitable material easily dissolved in the digestive tract. Suitable nontoxic solid carriers are used which include, for example, pharmaceutical grades of mannitol, lactose, starch, magnesium stearate, sodium saccharin, talcum, cellulose, glucose, sucrose, magnesium carbonate, and the like. See, e.g., REMINGTON, 2005.

The dose of the composition comprising at least one substituted heterocyclic derivative compound as described herein may differ, depending upon the patient's (e.g., human) condition, that is, stage of the disease, general health status, age, and other factors that a person skilled in the medical art will use to determine dose.

Pharmaceutical compositions may be administered in a manner appropriate to the disease to be treated (or prevented) as determined by persons skilled in the medical arts. An appropriate dose and a suitable duration and frequency of administration will be determined by such factors as the condition of the patient, the type and severity of the patient's disease, the particular form of the active ingredient, and the method of administration. In general, an appropriate dose and treatment regimen provides the composition(s) in an amount sufficient to provide therapeutic or prophylactic benefit (e.g., an improved clinical outcome, such as more frequent complete or partial remissions, or longer disease-free and/or overall survival, or a lessening of symptom severity. Optimal doses may generally be determined using experimental models and/or clinical trials. The optimal dose may depend upon the body mass, weight, or blood volume of the patient.

Oral doses typically range from about 1.0 mg to about 1000 mg, one to four times, or more, per day.

Bromodomain Inhibition and cAMP Response Element-Binding Protein

Histone acetylation is generally associated with the activation of gene transcription, as the modification is known to loosen the interaction of the DNA and the histone octamer by changing the electrostatics. In addition to this physical change, specific proteins are known to bind to acetylated lysine residues within histones in order to read the epigenetic code. Bromodomains are small (~110 amino acid) distinct domains within proteins that are known to bind to acetylated lysine resides commonly, but not exclusively, in the context of histones. Some fifty proteins are known to contain bromodomains, and they have a range of functions within the cell, including bromodomain and extra-terminal (BET) family of proteins and cAMP response element-binding protein (CREB)-binding protein (CBP).

CBP and its paralog p300 are highly homologous, ubiquitous, versatile transcriptional coactivator proteins that are essential for development and many other physiological processes. In addition to involvement in transcriptional events, the coactivator proteins are known to contribute to other processes such DNA repair, RNA splicing. Janknecht, 17 Histol. Histopathol. 657 (2002).

The human CBP protein contains 2442 amino acids. Several structural and functional domains have been identified in CBP, including the bromodomain (BRD), three cysteine-histidine rich regions (CH1, CH2 and CH3), and the histone acetyltransferase (HAT) domain. The bromodomain, which is found in many chromatin associated proteins, is thought to function as a histone binding motif. The three cysteine/histidine-rich domains are known to serve as docking modules for numerous transcriptional regulators. The CH2 domain is partly located within the HAT domain. Based on sequence homology data, part of the CH2 region has been classified as a plant homeodomain (PHD) type zinc finger which is found predominantly in proteins that function at the chromatin level. Kalkhoven et al., 22 Molec. Cell. Biol. 1961 (2002).

Bromodomains are made up of about 110 amino acids arranged in a characteristic structure made up of four α-helices (αZ, αA, αB, αC) connected by interhelical loops, termed the BRD fold. Bromodomains are known to bind specifically to acetylated lysine. Hay et al., 136 J. Am. Chem. Soc. 9308 (2014). The human bromodomain family consists of 61 members, of which there are two distinct subgroups representing the histone acetyltransferase transcriptional co-activators, such as CBP/p300 which contains a single bromodomain, and the BET family proteins that usually contain two tandem bromodomains, such as BRD4. The bromodomains of BRD4 and CBP are also known to function differently as a transcriptional co-activator and a chromatin organizer, respectively. Plotnikov et al., 22 Structure 353 (2014).

Recent studies have elucidated the structure of the bromodomain-PHD tandem module of human CBP protein bound lysine-acetylated histone H4 peptides. Two different histone H4 peptides were used in the study, containing the same H4 residues 5-25, but carrying distinct lysine acetylation sites, i.e., lysine residue 20 was acetylated in case of H4K20ac and lysine residues 12 and 16 were acetylated in case of H4K12ac/K16ac. The structural analysis revealed various distinctions between the bromodomains of BRD4 and that of CBP. For example, it was observed that unlike the BRD4 bromodomains, which prefer di-acetylated histone H4 sequences, the CBP bromodomain demonstrated a clear preference of a singly-acetylated H4 sequence motif. The study further provided insights into distinct modes of singly and di-acetylated histone H4 recognition by the bromodomains of CBP and BRD4. Plotnikov et al., 2014. Without being bound by any specific theory, it is hypothesized that the differences between the bromodomains of CBP and BRD4 will facilitate the identification of inhibitors that selectively target the bromodomain of CBP.

The CBP proteins have been associated with various clinical conditions. Haplo-insufficiency of CBP in humans leads to Rubinstein-Taybi syndrome, characterized by mental retardation, craniofacial abnormalities, and broad thumbs and big toes. Heterozygous deletion of CBP in mice has been shown to cause defects in multiple tissues including the hematopoietic system. Altered function of CBP, resulting from chromosomal translocations, also contributes to the formation of leukemias. Blobel, 71 J. Leukocyte Biol. 545 (2002). The CBP protein has also been implicated to play a role in human cancers characterized by p53 mutations. In response to cellular stress, p53 undergoes post-translational modification of the C and N-terminal regions, including acetylation at the C-terminal region (e.g., lysine acetylation at K382 pf p53), which results in recruitment of CBP via its bromodomain. The CBP-p53 acetylated lysine interaction in turn is crucial for p53-induced p21 mediated G1 cell cycle arrest.

Thus, it is hypothesized that inhibition of the CBP bromodomain, and thereby p53-mediated p21 activation, has important clinical applications in cancer and other diseases wherein hyperactive p53 is known to play a role, such as Alzheimer's disease, Parkinson's disease, Huntington's disease spinal cord diseases, multiple sclerosis, ischemic brain injury, infectious and auto-immune diseases, and myocardial ischemia. Hay et al., 2014. Furthermore, studies have suggested that sequestration of CBP is one of the underlying cause of neurodegenerative diseases caused by expanded polyglutamine repeats, such as Huntington's disease, Dentatorubral pallioluysian atrophy, spinal bulbar muscular atrophy and spinocerebellar ataxia type 1, 2, 3, 6, 7 and 12. Janknecht, 2002.

Therapeutic targeting of bromodomains has recently been recognized as an important potential therapeutic modality in human malignant and inflammatory diseases. Muller et al., 13 Expert Rev. Molec. Med. e29 (2011); Filippakoupoulos & Knapp, 13 Nat. Rev. Drug Discov. 337 (2014). Inhibitors of bromodomains exhibit anti-inflammatory activity by inhibiting expression of anti-inflammatory genes. For example, Th17 cells serve an important role in host immune responses by mediating the recruitment of neutrophils and macrophages in infected areas. Aberrant regulation of Th17 cells has been suggested to be a component in the pathogenies of multiple inflammatory and autoimmune disorders. Th17 cells have been understood to play a role in autoimmune and inflammatory processes, but more recently Th17 cells have received new attention for their role in tumor immunology. Zou & Restifo, 10 Nat. Rev. Immunol. 248 (2010); Coffelt et al., 522 Nature 345 (2015). Th17 cells are a subset of T helper cells which produce IL-17A, IL17F, IL-21, IL-22, and GM-CSF. Th17 cells have been implicated as key effectors of autoimmune diseases such as ankylosing spondylitis (AS), psoriasis and psoriatic arthritis (PSA), rheumatoid arthritis, Crohn's disease, and multiple sclerosis (MS). JQ1, a bromo and extraterminal domain (BET) bromodomain inhibitor, was shown to reduce collagen-induced arthritis and experimental autoimmune encephalomyelitis, two other human inflammatory diseases in which Th17 is implicated. Belkina et al., 190 J. Immunol. 3670 (2013). Secukinumab, an anti-IL-17A antibody, was shown to ameliorate ankylosing spondylitis. Baeten et al., 382 Lancet 1705 (2013). In addition to supporting the importance of TH17 cells in such inflammatory diseases, this finding has intensified the search for new drugs capable of targeting TH17 cytokine production.

Additionally, regulatory T-cells (Tregs) are often recruited to and accumulate within tumors, which lead to immune evasion by cancer cells. These intra-tumoral regulatory T-cells decrease the response of effector T-cells, which is a major roadblock to clearance of tumor cells by the immune system. One approach to strengthening the immune response to tumors is to specifically inhibit regulatory T-cell recruitment or accumulation within tumors, an approach referred to as cancer immunotherapy. Dougan & Dranoff, 27 Ann. Rev. Immunol. 83 (2009); Mellman et al., 480 Nature 480 (2011); Curiel, 117 J. Clinical. Invest. 1167 (2007); Nishikawa & Sakaguchi, 27 Curr. Op. Immunol. 1 (2014).

CBP has been shown to be a critical component in regulatory T-cell biology and suggested to be required for differentiation of Tregs from naïve T-cells. Specifically, deletion of CBP in mouse regulatory T-cells led to impaired Treg suppressive function and reduced tumor growth in murine cancer models. Liu et al., 19 Nat. Med. 1173 (2013); Liu et al., 34 Molec. Cel. Biol. 3993 (2014). The CBP bromodomain comprises a hydrophobic pocket well suited to binding inhibitors, while the diversity of the surface and loop residues across the bromodomain allows for selective targeting by pharmacological agents. Muller et al., 13 Exp. Rev. Mol. Med. e29 (2011); Hay et al., 2014. These characteristics make CBP an ideal target for immunotherapy. In support of this approach, Th17 cytokine production is disrupted by CBP bromodomain inhibition. Ghosh et al., 291 J. Biol. Chem. 13014 (2016); Hammitzsch et al., 112 PNAS 10768 (2015).

The activity of CBP inhibitors could result in impaired Treg differentiation and function, thus releasing suppression of effector responses in cancer and possibly reinitiate antitumor immunity. Therefore, these inhibitors, either alone or in conjunction with complementary cancer immunotherapies, could potentiate tumor eradication, such as through the reversal of cytotoxic CD8+ T cell exhaustion by antibody-mediated checkpoint inhibition. Brahmer et al., 366 NEJM 2455 (2012); Topalian et al., 366 NEJM 2443 (2012); Hodi et al., 363 NEJM 711 (2010). Other CBP inhibitors have been studied in the context of leukemia therapy. Picaud et al., 75 Cancer Res. 1 (2015).

Accordingly, in at least one embodiment, a compound of Formula I disclosed herein is capable of inhibiting activity of CBP, or a mutant or homolog thereof, in a biological sample; and this feature is useful for a variety of purposes well-known to one of skill in the art. Examples of such purposes include, but are not limited to, biological assays, blood transfusion, organ-transplantation, biological specimen storage.

In at least one embodiment, a compound of Formula I as disclosed herein is capable of inhibiting activity of CBP protein, or a mutant or homolog thereof, in a patient; specifically, for example, in a method comprising administering to a patient in need thereof a compound of Formula I or a pharmaceutical composition comprising said compound.

At least one embodiment provides a method of inhibiting CBP protein, or a mutant or homolog thereof, in a biological sample, comprising the step of contacting the biological sample with a compound as disclosed herein. Some embodiments provide a method for treating a disorder mediated by a CBP protein, such as a BET protein, in a patient in need thereof, comprising the step of administering to the patient a compound of Formula I of a pharmaceutical composition comprising a compound of Formula I.

Diseases and conditions treatable according to the methods of this include, but are not limited to, cancer and other proliferative disorders, Alzheimer's disease, Parkinson's disease, Huntington's disease spinal cord diseases, multiple sclerosis, ischemic brain injury, infectious and auto-immune diseases, Dentatorubral pallioluysian atrophy, spinal bulbar muscular atrophy and spinocerebellar ataxia type 1, 2, 3, 6, 7 and 12, viral infections, and myocardial ischemia. Thus one aspect is a method of treating a subject having a disease, disorder, or symptom thereof the method including administration of a compound or composition herein to the subject. In one embodiment, a human patient is treated with a compound of the embodiments and a pharmaceutically acceptable carrier, adjuvant, or vehicle, wherein said compound is present in an amount to measurably inhibit CBP protein activity in the patient.

The embodiments further provide a method of treating a subject, such as a human, suffering from one of the conditions, illnesses, disorders or diseases disclosed herein. The method comprises administering a therapeutically effective amount of one or more provided compounds, which function by inhibiting CBP protein and, in general, by modulating gene expression, to induce various cellular effects, in particular induction or repression of gene expression, arresting cell proliferation, inducing cell differentiation and/or inducing apoptosis, to a subject in need of such treatment.

The embodiments further provide a therapeutic method of modulating protein methylation, gene expression, cell proliferation, cell differentiation or apoptosis in vivo in conditions, illnesses, disorders or diseases disclosed herein, in particular cancer, inflammatory disease, or viral disease comprising administering to a subject in need of such therapy a pharmacologically active and therapeutically effective amount of one or more compounds described herein.

In certain embodiments, the compounds disclosed herein treat or ameliorate inflammatory or autoimmune disorders. In some aspects the inflammatory or autoimmune disorders include, but are not limited to, ankylosing spondylitis (AS), psoriasis and psoriatic arthritis (PSA), rheumatoid arthritis, Crohn's disease, and multiple sclerosis (MS).

In some embodiments, the compounds disclosed herein inhibit Th17 cell function. In some aspects, the embodiments provide a compound of Formula I that inhibits cytokine secretion, such as, but not limited to, IL-17A secretion.

In some embodiments, the compounds disclosed herein are used in immune-oncology therapies. In some aspects, the disclosed compounds impair regulatory T cell differentiation and function. In some aspects, use of the disclosed compounds decreased recruitment or accumulation of regulatory T-cells in tumors. In some aspects, use of the disclosed compounds reduces suppression of effector cells in cancer contexts.

The embodiments provided herein further relate to a method for treating or ameliorating cancer or another proliferative disorder by administration of an effective amount of a compound of Formula I to a mammal, in particular a human, in need of such treatment. In some embodiments, the disease to be treated by the methods of the is cancer.

In certain embodiments, the cancer is adult T-cell leukemia/lymphoma, breast cancer, brain cancer, or lung cancer.

In some embodiments, the compounds disclosed herein treat or prevent viral infections such as herpes virus, human papilloma virus, adenovirus, poxvirus and other DNA viruses.

One embodiment provides a method of regulating gene transcription in a cell comprising exposing a bromodomain containing protein to a compound of Formula I. One embodiment provides a method of inhibiting bromodomain-mediated recognition of an acetyl lysine region of a protein comprising exposing the bromodomain to a compound of Formula I.

One embodiment provides a method of regulating gene transcription in a cell comprising exposing a CBP to a compound of Formula I. One embodiment provides a method of inhibiting CBP-mediated recognition of an acetyl lysine region of a protein comprising exposing the CBP to a compound of Formula I.

At least one embodiment provides a compound of Formula I that exhibits a lower $IC_{50}$ for CBP than for BRD4. In a particular embodiment, the compound of Formula I is, for example, 5-(1-benzyl-1H-pyrazol-4-yl)-1-methyl-4-(1H-pyrrol-1-yl)pyridin-2(1H)-one.

Methods of Treatment

An aspect of the present embodiments provides a method of treating cancer in a patient in need thereof, comprising administering to the patient a compound of Formula I as described herein, or a pharmaceutical composition comprising a compound of Formula I.

Other embodiments and uses will be apparent to one skilled in the art in light of the present disclosures. The following examples are provided merely as illustrative of various embodiments and shall not be construed to limit the invention in any way.

EXAMPLES

I. Chemical Synthesis

Unless otherwise noted, reagents and solvents were used as received from commercial suppliers. Anhydrous solvents and oven-dried glassware were used for synthetic transformations sensitive to moisture and/or oxygen. Yields were not optimized. Reaction times are approximate and were not optimized. Column chromatography and thin layer chromatography (TLC) were performed on silica gel unless otherwise noted. Spectra are given in ppm (δ) and coupling constants (J) are reported in Hertz. For $^1$H NMR spectra, the solvent peak was used as the reference peak.

Example 1: 5-(1-benzyl-1H-pyrazol-4-yl)-1-methylpyridin-2(1H)-one

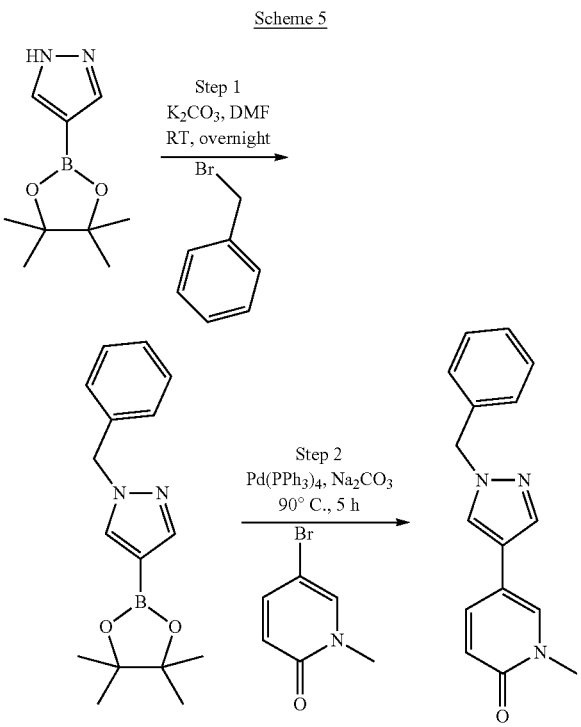

Step 1: 1-benzyl-4-(4,4,5,5-tetramethyl-1,3,2-dioxaborolan-2-yl)-1H-pyrazole

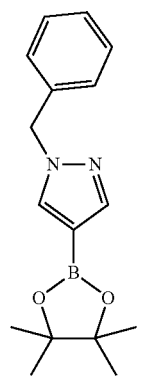

A mixture of 4-(4,4,5,5-tetramethyl-[1,3,2]dioxaborolan-2-yl)-1H-pyrazole (3.0 g, 15.5 mmol), bromomethyl-benzene (3.2 g, 18.7 mmol) and $K_2CO_3$ (4.3 g, 31.2 mmol) in DMF (30 mL) was stirred at room temp overnight. After dilution with EtOAc (50 mL) and $H_2O$ (50 mL), the organic layer was separated and washed with brine (50 mL), dried over $Na_2SO_4$, filtered and concentrated in vacuum. The residue was purified by column chromatography on silica gel eluting with PE/EtOAc (5:1) to give the compound 1-benzyl-4-(4,4,5,5-tetramethyl-[1,3,2]dioxaborolan-2-yl)-1H-pyrazole (3.5 g, 12.3 mmol) as a light yellow solid in 79% yield. $^1$H NMR (400 MHz, $CDCl_3$): δ 7.81 (s, 1H), 7.66

(s, 1H), 7.37-7.29 (m, 3H), 7.24-7.22 (m, 2H), 5.30 (s, 2H), 1.29 (s, 12H). LCMS (M+H)+ 285.

Step 2: 5-(1-benzyl-1H-pyrazol-4-yl)-1-methylpyridin-2(1H)-one

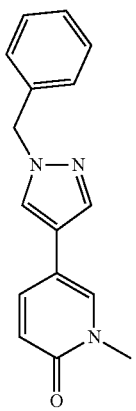 [SMILES: Cn1cc(-c2cnn(Cc3ccccc3)c2)ccc1=O]

A mixture of 1-benzyl-4-(4,4,5,5-tetramethyl-[1,3,2]dioxaborolan-2-yl)-1H-pyrazole (140 mg, 0.495 mmol), 5-bromo-1H-pyridin-2-one (100 mg, 0.495 mmol), Pd(PPh₃)₄ (60 mg, 0.049 mmol), and Na₂CO₃ (104 mg, 0.990 mmol) in dioxane (5 mL) and H₂O (1 mL) was heated to 90° C. for 5 hr under N₂. Then, the mixture was diluted with EtOAc (60 mL) and H₂O (50 mL). The organic phase was washed with brine (60 mL), dried over Na₂SO₄, filtered and concentrated under vacuum. The residue was purified by preparative HPLC to give the compound 5-(1-benzyl-1H-pyrazol-4-yl)-1-methylpyridin-2(1H)-one (60 mg, 0.22 mmol) as a yellow oil in 44% yield. $^1$H NMR (400 MHz, CD₃OD): δ 7.96 (s, 1H), 7.38-7.31 (m, 2H), 7.38-7.28 (m, 6H), 6.58 (d, J=9.3 Hz, 1H), 5.22 (s, 2H), 3.59 (s, 3H). LCMS (M+H)+ 266.

Example 2: 5-(1-(cyclopropyl(phenyl)ethyl)-1H-pyrazol-4-yl)-1-methylpyridin-2(1H)-one Step 1:
4-bromo-1-(cyclopropyl(phenyl)methyl)-1H-pyrazole

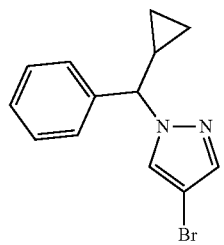 [SMILES: Brc1cnn(C(c2ccccc2)C2CC2)c1]

To a mixture of 4-bromo-1H-pyrazole (200 mg, 1.36 mmol), cyclopropyl(phenyl)methanol (405 mg, 2.72 mmol) and PPh₃ (720 mg, 2.72 mmol) in anhydrous THF (6 ml) cooled to 0° C. was added di-t-butyl azodicarboxylate (0.4 ml, 2.72 mmol) dropwise. The reaction was heated at 150° C. in a microwave reactor for 15 minutes. It was then cooled to room temperature and concentrated under reduced pressure. The residue was purified by silica gel column chromatography (0-30% EtOAc/Hex) to afford the title compound (160 mg, 42%) as a clear oil.

Step 2: 5-(1-(cyclopropyl(phenyl)ethyl)-1H-pyrazol-4-yl)-1-methylpyridin-2(1H)-one

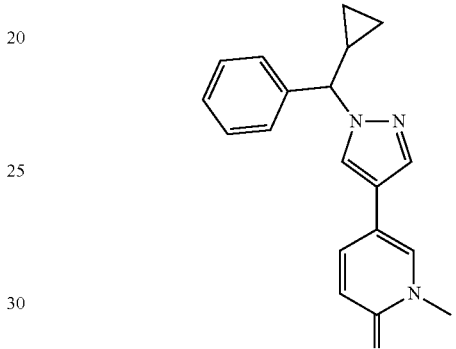

The title compound from Step 1 (60 mg, 0.22 mmol) and 1-methyl-5-(4,4,5,5-tetramethyl-1,3,2-dioxaborolan-2-yl)pyridine-2(1H)-one (61 mg, 0.26 mmol) were dissolved in dioxane (0.5 mL). To this solution was added Pd(PPh₃)₄ (12.5 mg, 0.011 mmol) and Na₂CO₃ (2 M in water, 0.22 mL). The reaction was heated at 120° C. in a microwave for 20 min. The solvent was removed under reduced pressure. The residue was dissolved in MeOH (2 mL), filtered through Celite and purified by preparative-HPLC (10% to 100% MeCN/water, 0.1% FA) to afford the title compound (11 mg, 17% yield). $^1$H NMR (CD₃OD, 400 MHz) δ 8.15 (s, 1H), 7.80 (s, 1H), 7.75 (s, 1H), 7.68 (s, 1H), 7.32-7.26 (m, 5H), 6.55 (d, J=9.3 Hz, 1H), 4.66 (d, J=9.8 Hz, 1H), 3.60 (s, 3H), 1.76-1.70 (m, 1H), 0.83-0.73 (m, 2H), 0.58-0.45 (m, 2H). LCMS (M+H)+ 306.

Examples 3-13, 17 and 19-35 were prepared using the appropriate pyridone and halide in a similar multi-step manner as Example 1. Examples 14-16 and 18 were prepared using the appropriate pyridone and alcohol in a similar multi-step manner as Example 2, and are shown in Table 3:

TABLE 3

| Example | Structure | Name | $^1$H NMR ppm ($\delta$) | MS (M + H) |
|---|---|---|---|---|
| 3 | 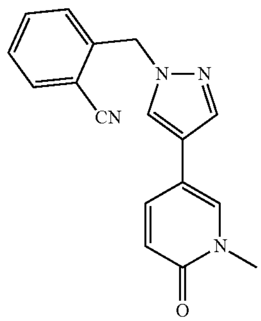 [SMILES: Cn1cc(-c2cnn(Cc3ccccc3C#N)c2)ccc1=O] | 2-((4-(1-methyl-6-oxo-1,6-dihydropyridin-3-yl)-1H-pyrazol-1-yl)methyl)benzonitrile | (DMSO-d$_6$, 400 MHz) $\delta$ 8.25 (s, 1H), 8.07 (d, J = 1.0 Hz, 1H), 7.90 (d, J = 7.8 Hz, 1H), 7.72 (s, 1H), 7.72-7.64 (m, 2H), 7.56-7.53 (m, 2H), 7.30 (d, J = 7.8 Hz, 1H), 6.44 (d, J = 9.3 Hz, 1H), 5.53 (s, 2H), 3.44 (s, 3H) | 291 |
| 4 | 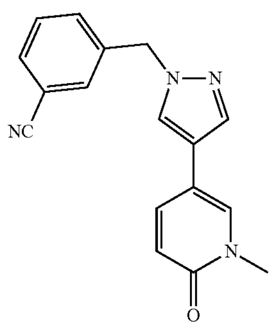 [SMILES: Cn1cc(-c2cnn(Cc3cccc(C#N)c3)c2)ccc1=O] | 3-((4-(1-methyl-6-oxo-1,6-dihydropyridin-3-yl)-1H-pyrazol-1-yl)methyl)benzonitrile | (DMSO-d$_6$, 400 MHz) $\delta$ 8.12 (s, 1H), 8.01 (s, 1H), 7.80-7.68 (m, 2H), 7.68-7.65 (m, 2H), 7.63-7.56 (m, 2H), 6.43 (d, J = 9.3 Hz, 1H), 5.40 (s, 2H), 3.50 (s, 3H) | 291 |
| 5 | 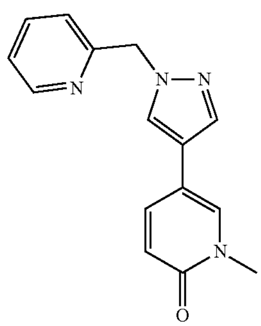 [SMILES: Cn1cc(-c2cnn(Cc3ccccn3)c2)ccc1=O] | 1-methyl-5-(1-(pyridin-2-ylmethyl)-1H-pyrazol-4-yl)pyridin-2(1H)-one | (CD$_3$OD, 400 MHz) $\delta$ 8.53 (m, 1H), 8.03 (s, 1H), 7.95 (s, 1H), 7.83-7.77 (m, 3H), 7.36-7.35 (m, 1H), 7.34 (m, 1H), 6.60 (d, J = 9.3 Hz, 1H), 5.46 (s, 2H), 3.60 (s, 3H) | 267 |
| 6 | 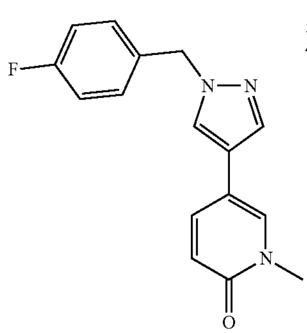 | 5-(1-(4-fluorobenzyl)-1H-pyrazol-4-yl)-1-methylpyridin-2(1H)-one | (CD$_3$OD, 400 MHz) $\delta$ 7.96 (s, 1H), 7.92 (s, 1H), 7.74-7.75 (m, 2H), 7.31-7.28 (m, 2H), 7.09-7.05 (m, 2H), 6.59 (d, J = 9.3 Hz, 1H), 5.32 (s, 2H), 3.59 (s, 3H) | 284 |

TABLE 3-continued

| Example | Structure | Name | ¹H NMR ppm (δ) | MS (M + H) |
|---|---|---|---|---|
| 7 | 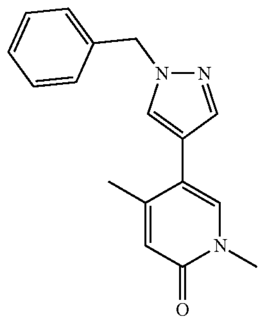 [SMILES: Cc1cc(=O)n(C)cc1-c1cnn(Cc2ccccc2)c1] | 5-(1-benzyl-1H-pyrazol-4-yl)-1,4-dimethyl-pyridin-2(1H)-one | (CDCl$_3$, 400 MHz) δ 7.50 (s, 1H), 7.37-7.33 (m, 4H), 7.26-7.25 (m, 2H), 7.16 (s, 1H), 6.46 (s, 1H), 5.33 (s, 2H), 3.52 (s, 3H), 2.14 (s, 3H) | 280 |
| 8 | 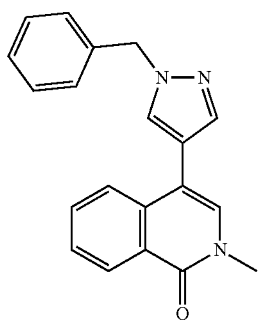 [SMILES: Cn1cc(-c2cnn(Cc3ccccc3)c2)c2ccccc2c1=O] | 4-(1-benzyl-1H-pyrazol-4-yl)-2-methyliso-quinolin-1(2H)-one | (CDCl$_3$, 400 MHz) δ 8.50 (d, J = 7.6 Hz, 1H), 7.66-7.62 (m, 3H), 7.50-7.49 (m, 2H), 7.40-7.26 (m, 5H), 7.04 (s, 1H), 5.38 (s, 2H), 3.62 (s, 3H) | 316 |
| 9 | 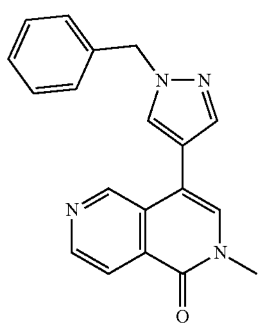 [SMILES: Cn1cc(-c2cnn(Cc3ccccc3)c2)c2cnccc2c1=O] | 4-(1-benzyl-1H-pyrazol-4-yl)-2-methyl-2,6-naphthyridin-1(2H)-one | (CD$_3$OD, 400 MHz) δ 9.06 (s, 1H), 8.66 (d, J = 5.3 Hz, 1H), 8.22 (d, J = 5.3 Hz, 1H), 8.01 (s, 1H), 7.76 (s, 1H), 7.54 (s, 1H), 7.38 (s, 1H), 7.36-7.31 (m, 5 H), 5.44 (s, 2H), 3.65 (s, 3H) | 317 |
| 10 | 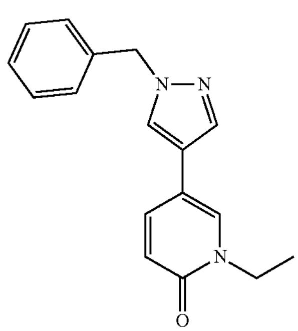 [SMILES: CCn1cc(-c2cnn(Cc3ccccc3)c2)ccc1=O] | 5-(1-benzyl-1H-pyrazol-4-yl)-1-ethylpyridin-2(1H)-one | (CDCl$_3$, 300 MHz) δ 7.64 (s, 1H), 7.45-7.33 (m, 6H), 7.24 (s, 2H), 6.61 (d, J = 9.0 Hz, 1H), 5.33 (s, 2H), 4.01 (q, J = 7.5 Hz, 2H), 1.39 (t, J = 7.2 Hz, 3H) | 280 |

TABLE 3-continued

| Example | Structure | Name | $^1$H NMR ppm (δ) | MS (M + H) |
|---|---|---|---|---|
| 11 | 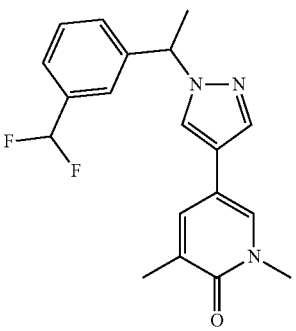 [SMILES: Cc1cc(-c2cnn(C(C)c3cccc(C(F)F)c3)c2)cn(C)c1=O] | 5-(1-(1-(3-(difluoro-methyl) phenyl)ethyl)-1H-pyrazol-4-yl)-1,3-dimethylpyridin-2(1H)-one | (CD$_3$OD, 400 MHz) δ 8.05 (s, 1H), 7.83 (s, 2H), 7.67 (s, 1H), 7.45-7.38 (m, 4H), 6.87 (s, 0.25H), 6.73 (s, 0.5H), 6.59 (s, 0.25H), 5.68-5.64 (m, 1H), 3.59 (s, 3H), 2.15 (s, 3H), 1.92 (d, J = 7.0 Hz, 3H) | 343 |
| 12 | 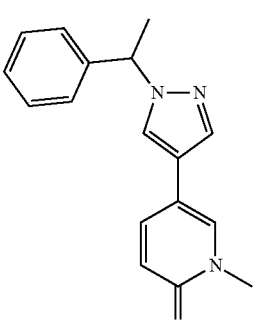 | 1-methyl-5-(1-(1-phenylethyl)-1H-pyrazol-4-yl)pyridin-2(1H)-one | (DMSO-d$_6$, 400 MHz) δ 8.15 (s, 1H), 8.01 (d, J = 2.5 Hz, 1H), 7.76 (s, 1H), 7.70 (d, J = 2.5 Hz, 1H), 7.35-7.22 (m, 5H), 5.59-5.57 (m, 1H), 3.43 (s, 3H), 1.81 (d, J = 7.0 Hz, 3H) | 280 |
| 13 | 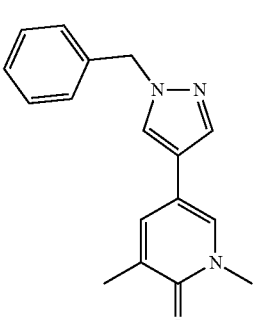 | 5-(1-benzyl-1H-pyrazol-4-yl)-1,3-dimethyl-pyridin-2(1H)-one | (CDCl$_3$, 300 MHz) δ 7.64 (s, 1H), 7.45 (s, 1H), 7.41-7.31 (m, 4H), 7.28-7.26 (m, 3H), 5.33 (s, 2H), 3.58 (s, 3H), 2.19 (s, 3H) | 280 |
| 14 | 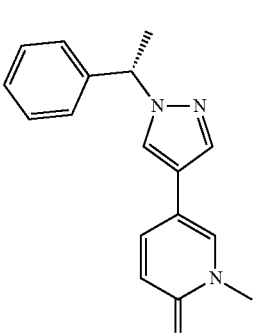 | (S)-1-methyl-5-(1-(1-phenylethyl)-1H-pyrazol-4-yl)pyridin-2(1H)-one | (CD$_3$OD, 400 MHz) δ 8.01 (s, 1H), 7.92 (s, 1H), 7.78-7.76 (m, 2H), 7.34-7.23 (m, 5H), 6.59 (d, J = 9.3 Hz, 1H), 5.59 (m, 1H), 3.59 (s, 3H), 1.90 (d, J = 7.1 Hz, 3H) | 281 |

TABLE 3-continued

| Example | Name | ¹H NMR ppm (δ) | MS (M + H) |
|---|---|---|---|
| 15 | (R)-1-methyl-5-(1-(1-phenylethyl)-1H-pyrazol-4-yl)pyridin-2(1H)-one | (CD$_3$OD, 400 MHz) δ 8.02 (s, 1H), 7.92 (s, 1H), 7.78-7.76 (m, 2H), 7.34-7.23 (m, 5H), 6.59 (d, J = 9.3 Hz, 1H), 5.59 (m, 1H), 3.59 (s, 3H), 1.90 (d, J = 7.1 Hz, 3H) | 281 |
| 16 | 3-(1-(4-(1-methyl-6-oxo-1,6-dihydropyridin-3-yl)-1H-pyrazol-1-yl)ethyl)benzonitrile | (CD$_3$OD, 400 MHz) δ 8.09 (s, 1H), 7.94 (d, J = 2.5 Hz, 1H), 7.81-7.77 (m, 2H), 7.66-7.53 (m, 4H), 6.60 (d, J = 9.3 Hz, 1H), 5.68 (m, 1H), 3.60 (s, 3H), 1.92 (d, J = 7.1 Hz, 3H) | 305 |
| 17 | 1,3-dimethyl-5-(1-(1-phenylethyl)-1H-pyrazol-4-yl)pyridin-2(1H)-one | (CD$_3$OD, 400 MHz) δ 8.00 (s, 1H), 7.77-7.75 (m, 2H), 7.66 (d, J = 0.9 Hz, 1H), 7.34-7.23 (m, 5H), 5.59 (m, 1H), 3.59 (s, 3H), 2.19 (s, 3H), 1.90 (d, J = 7.1 Hz, 3H) | 294 |
| 18 | 5-(1-(cyclopropyl (phenyl)methyl)-1H-pyrazol-4-yl)-1,3-dimethyl-pyridin-2(1H)-one | (CD$_3$OD, 400 MHz) δ 8.15 (s, 1H), 7.80 (s, 1H), 7.75 (s, 1H), 7.68 (s, 1H), 7.32-7.26 (m, 5H), 4.66 (d, J = 9.8 Hz, 1H), 3.60 (s, 3H), 2.16 (s, 3H), 1.76-1.70 (m, 1H), 0.83-0.73 (m, 2H), 0.58-0.45 (m, 2H) | 319 |

TABLE 3-continued

| Example | Structure | Name | ¹H NMR ppm (δ) | MS (M + H) |
|---|---|---|---|---|
| 19 | 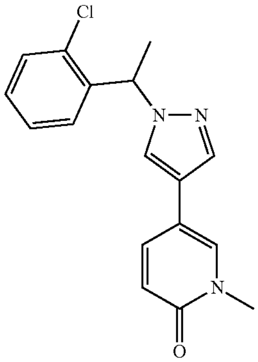 [SMILES: CC(c1ccccc1Cl)n1cc(-c2ccc(=O)n(C)c2)cn1] | 5-(1-(1-(2-chlorophenyl)ethyl)-1H-pyrazol-4-yl)-1-methyl-pyridin-2(1H)-one | (CDCl$_3$, 400 MHz) δ 7.65 (s, 1H), 7.53 (s, 1H), 7.47-7.46 (m, 1H), 7.40-7.38 (m, 2H), 7.24-7.22 (m, 2H), 7.17-7.15 (m, 1H), 6.62 (d, J = 9.2 Hz, 1H), 5.96 (q, J = 6.8 Hz, 1H), 3.76 (s, 3H), 1.93 (d, J = 7.2 Hz, 3H) | 314 |
| 20 | 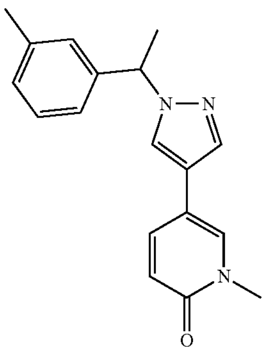 | 1-methyl-5-(1-(1-(m-tolyl)ethyl)-1H-pyrazol-4-yl)pyridin-2(1H)-one | (CDCl$_3$, 400 MHz) δ 7.62 (s, 1H), 7.46-7.43 (m, 2H), 7.38 (d, J = 2.4 Hz, 1H), 7.26-7.24 (d, J = 7.6 Hz, 1H), 7.13-7.11 (m, 1H), 7.06-7.04 (m, 2H), 6.61-6.59 (d, J = 9.2 Hz, 1H), 5.48 (q, J = 6.8 Hz, 1H), 3.57 (s, 3H), 2.34 (s, 3H), 1.91 (d, J = 7.6 Hz, 3H) | 294 |
| 21 | 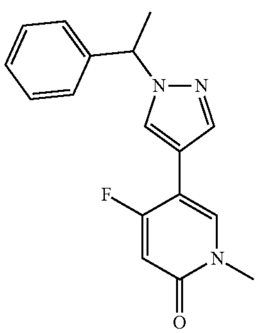 [SMILES: CC(c1ccccc1)n1cc(-c2cn(C)c(=O)cc2F)cn1] | 4-fluoro-1-methyl-5-(1-(1-phenylethyl)-1H-pyrazol-4-yl)pyridin-2(1H)-one | (DMSO-d$_6$, 400 MHz) δ 8.23 (d, J = 9.9 Hz, 1H), 8.08 (d, J = 1.0 Hz, 1H), 7.74 (s, 1H), 7.35-7.25 (m, 5H), 6.31 (d, J = 13 Hz, 1H), 5.75-5.63 (m, 1H), 3.44 (s, 3H), 1.82 (d, J = 7.0 Hz, 1H) | 299 |
| 22 | 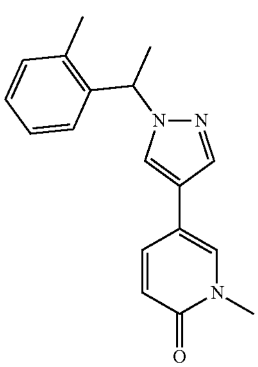 [SMILES: Cc1ccccc1C(C)n1cc(-c2ccc(=O)n(C)c2)cn1] | 1-methyl-5-(1-(1-(o-tolyl)ethyl)-1H-pyrazol-4-yl)pyridin-2(1H)-one | (CDCl$_3$, 400 MHz) δ 7.61 (s, 1H), 7.44-7.29 (m, 3H), 7.24-7.20 (m, 4H), 6.60-6.58 (m, 1H), 5.75 (q, J = 6.8 Hz, 1H), 3.57 (s, 3H), 2.30 (s, 3H), 1.87 (d, J = 6.4 Hz, 3H) | 295 |

TABLE 3-continued

| Example | Structure | Name | ¹H NMR ppm (δ) | MS (M + H) |
|---|---|---|---|---|
| 23 | 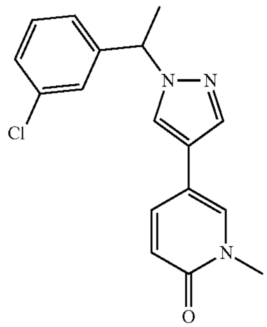 | 5-(1-(1-(3-chlorophenyl)ethyl)-1H-pyrazol-4-yl)-1-methyl-pyridin-2(1H)-one | (CDCl$_3$, 400 MHz) δ 7.63 (s, 1H), 7.48 (s, 1H), 7.5 (dd, J = 9.2 Hz, 2.4 Hz, 1H), 7.40 (d, J = 2.4 Hz, 1H), 7.29-7.27 (m, 2H), 7.21 (s, 1H), 7.12-7.09 (m, 1H), 6.61 (d, J = 9.2 Hz, 1H), 5.49 (q, J = 6.8 Hz, 1H), 3.58 (s, 3H), 1.91 (d, J = 7.2 Hz, 3H) | 314 |
| 24 | 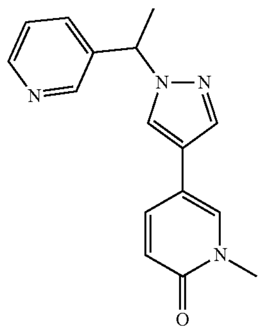 [SMILES: CC(c1cccnc1)n1cc(-c2ccc(=O)n(C)c2)cn1] | 1-methyl-5-(1-(1-(pyridin-3-yl)ethyl)-1H-pyrazol-4-yl)pyridin-2(1H)-one | (CDCl$_3$, 400 MHz) δ 8.61-8.58 (m, 2H), 7.68 (s, 1H), 7.60-7.55 (m, 2H), 7.49-7.43 (m, 2H), 7.32-7.30 (m, 1H), 6.64 (d, J = 9.2 Hz, 1H), 5.60 (q, J = 6.8 Hz, 1H), 3.62 (s, 3H), 2.01 (d, J = 7.6 Hz, 3H) | 281 |
| 25 | 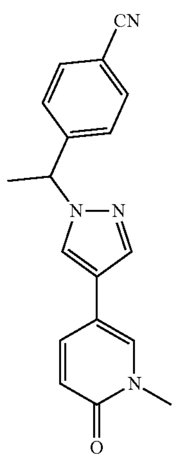 [SMILES: CC(c1ccc(C#N)cc1)n1cc(-c2ccc(=O)n(C)c2)cn1] | 4-(1-(4-(1-methyl-6-oxo-1,6-dihydropyridin-3-yl)-1H-pyrazol-1-yl)ethyl)benzonitrile | (CDCl$_3$, 400 MHz) δ 7.65 (s, 1H), 7.63 (d, J = 8.4 Hz, 2H), 7.52 (s, 1H), 7.46-7.44 (dd, J = 8.8 Hz, 2.0 Hz, 1H), 7.41-7.40 (m, 1H), 7.28 (d, J = 8.8 Hz, 2H), 6.61 (d, J = 9.2 Hz, 1H), 5.57 (q, J = 6.8 Hz, 1H), 3.56 (s, 3H), 1.94 (d, J = 6.8 Hz, 3H) | 305 |
| 26 | 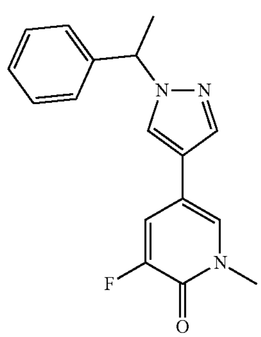 | 3-fluoro-1-methyl-5-(1-(1-phenylethyl)-1H-pyrazol-4-yl)pyridin-2(1H)-one | (CD$_3$OD, 400 MHz) δ 8.03 (s, 1H), 7.78-7.76 (m, 2H), 7.67-7.62 (m, 1H), 7.34-723 (m, 5H), 5.57 (q, J = 7.2 Hz, 1H), 3.64 (s, 3H), 1.89 (d, J = 7.2 Hz, 3H) | 298 |

TABLE 3-continued

| Example | Structure | Name | $^1$H NMR ppm ($\delta$) | MS (M + H) |
|---|---|---|---|---|
| 27 | 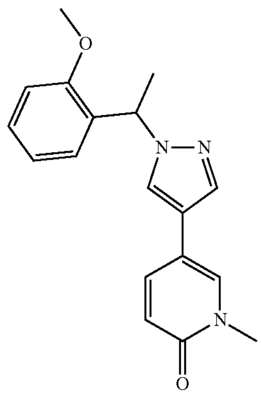 [SMILES: COc1ccccc1C(C)n1cc(-c2ccc(=O)n(C)c2)cn1] | 5-(1-(1-(2-methoxy-phenyl)ethyl)-1H-pyrazol-4-yl)-1-methyl-pyridin-2(1H) one | (CDCl$_3$, 400 MHz) $\delta$ 7.61 (s, 1H), 7.50 (s, 1H), 7.47-7.44 (m, 1H), 7.38 (d, J = 2.4 Hz, 1H), 7.29-7.25 (m, 1H), 7.07-7.05 (m, 1H), 6.95-6.89 (dd, J = 7.5, 6.8 Hz, 2H), 6.60 (d, J = 9.2 Hz, 1H), 5.95 (q, J = 6.8 Hz, 1H), 3.86 (s, 3H), 3.57 (s, 3H), 1.87 (d, J = 7.2 Hz, 3H) | 310 |
| 28 | 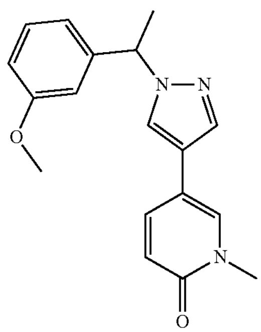 [SMILES: COc1cccc(C(C)n2cc(-c3ccc(=O)n(C)c3)cn2)c1] | 5-(1-(1-(3-methoxy-phenyl)ethyl)-1H-pyrazol-4-yl)-1-methyl-pyridin-2(1H)-one | (CDCl$_3$, 400 MHz) $\delta$ 7.62 (s, 1H), 4.46-7.43 (m, 2H), 7.38-7.37 (d, J = 2.4 Hz, 1H), 7.29-7.26 (m, 1H), 6.85-6.84 (m, 2H), 6.78-6.77 (m, 1H), 6.61-6.59 (d, J = 9.6 Hz, 1H), 5.49 (q, J = 6.8 Hz, 1H), 3.79 (s, 3H), 3.57 (s, 3H), 1.92 (d, J = 6.8 Hz. 3H) | 310 |
| 29 | 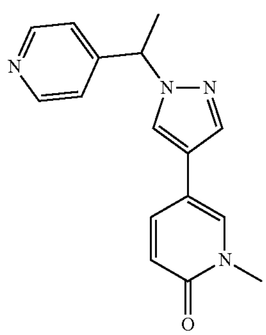 [SMILES: CC(c1ccncc1)n1cc(-c2ccc(=O)n(C)c2)cn1] | 1-methyl-5-(1-(1-(pyridin-4-yl)ethyl)-1H-pyrazol-4-yl)pyridin-2(1H)-one | (CDCl$_3$, 400 MHz) $\delta$ 8.59-8.57 (m, 2H), 7.66 (s, 1H), 7.54 (s, 1H), 7.48-7.45 (dd, J = 9.2 Hz, 2.8 Hz, 1H), 7.42 (d, J = 2.4 Hz, 1H), 7.07-1.06 (d, J = 5.6 Hz, 2H), 6.64-6.61 (d, J = 9.6 Hz, 1H), 5.53 (q, J = 6.8 Hz, 1H), 3.59 (s, 3H), 1.94 (d, J = 6.8 Hz, 3H) | 281 |
| 30 | 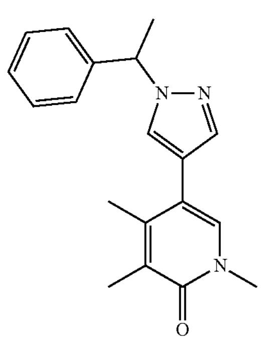 [SMILES: Cc1c(-c2cnn(C(C)c3ccccc3)c2)cn(C)c(=O)c1C] | 1,3,4-trimethyl-5-(1-(1-phenylethyl)-1H-pyrazol-4-yl)pyridin-2(1H)-one | CD$_3$OD, 400 MHz) $\delta$ 7.79 (s, 1H), 7.54 (s, 1H), 7.44 (s, 1H), 7.37-7.31 (m, 2H), 7.30-7.24 (m, 3H), 5.61 (q, J = 7.2 Hz, 1H), 3.56 (s, 3H), 2.18 (s, 3H), 2.15 (s, 3H), 1.90 (d, J = 7.2 Hz, 3H) | 308 |

TABLE 3-continued

| Example | Structure | Name | ¹H NMR ppm (δ) | MS (M + H) |
|---------|-----------|------|----------------|------------|
| 31 | 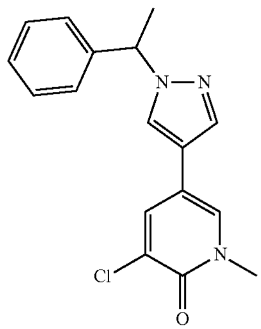 | 3-chloro-1-methyl-5-(1-(1-phenylethyl)-1H-pyrazol-4-yl)pyridin-2(1H)-one | (CD₃OD, 400 MHz) δ 8.06 (s, 1H), 8.03 (d, J = 2.4 Hz, 1H), 7.93 (d, J = 2.4 Hz, 1H), 7.79 (s, 1H), 7.37-7.24 (m, 5H), 5.60 (q, J = 7.2 Hz, 1H), 3.64 (s, 3H), 1.91 (d, J = 7.2 Hz, 3H) | 314 |
| 32 | 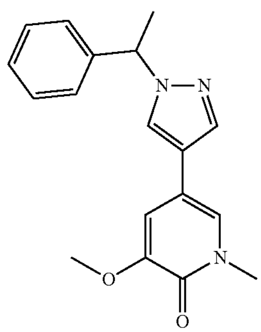 [SMILES: COc1cc(-c2cnn(C(C)c3ccccc3)c2)cn(C)c1=O] | 3-methoxy-1-methyl-5-(1-(1-phenylethyl)-1H-pyrazol-4-yl)pyridin-2(1H)-one | (CD₃OD, 400 MHz) δ 8.07 (s, 1H), 7.80 (s, 1H), 7.49 (d, J = 2.0 Hz, 1H), 7.35-7.23 (m, 5H), 7.13 (d, J = 2.0 Hz, 1H), 5.59 (q, J = 7.2 Hz, 1H), 3.87 (s, 3H), 3.60 (s, 3H) 1.90 (d, J = 6.8 Hz, 3H) | 310 |
| 33 | 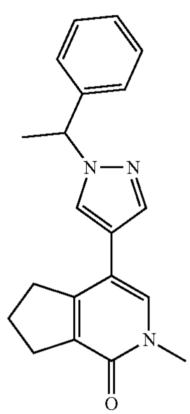 [SMILES: CC(c1ccccc1)n1cc(-c2cn(C)c(=O)c3c2CCC3)cn1] | 2-methyl-4-(1-(1-phenylethyl)-1H-pyrazol-4-yl)-2,5,6,7-tetrahydro-1H-cyclopenta[c]pyridin-1-one | (CD₃OD, 400 MHz) δ 7.90 (s, 1H), 7.69 (s, 2H), 7.35-7.24 (m, 5H), 5.60 (q, J = 6.8 Hz, 1H), 3.59 (s, 3H), 2.99 (t, J = 7.2 Hz, 2H), 2.83 (t, J = 7.2 Hz, 2H), 2.10-2.07 (m, J = 7.6 Hz, 2H), 1.90 (d, J = 7.2 Hz, 3H) | 320 |
| 34 | 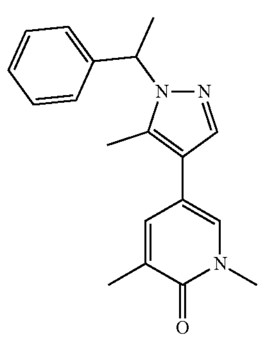 [SMILES: Cc1cc(-c2cnn(C(C)c3ccccc3)c2C)cn(C)c1=O] | 1,3-dimethyl-5-(5-methyl-1-(1-phenylethyl)-1H-pyrazol-4-yl)pyridin-2(1H)-one | (DMSO-d₆, 400 MHz) δ 7.57 (s, 1H), 7.55 (d, J = 2.3 Hz, 1H), 7.39 (s, 1H), 7.33-7.18 (m, 5H), 5.65-5.63 (m, 1H), 3.45 (s, 3H), 2.22 (s, 3H), 2.02 (s, 3H), 1.80 (d, J = 6.9 Hz, 3H) | 308 |

TABLE 3-continued

| Example | Structure | Name | $^1$H NMR ppm (δ) | MS (M + H) |
|---|---|---|---|---|
| 35 | 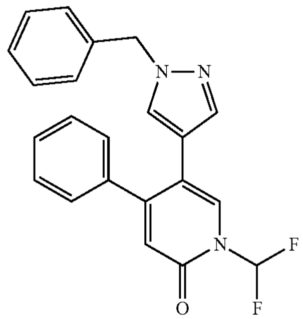 [SMILES: O=c1cc(-c2ccccc2)c(-c2cnn(Cc3ccccc3)c2)cn1C(F)F] | 5-(1-benzyl-1H-pyrazol-4-yl)-1-(difluoromethyl)-4-phenyl-pyridin-2(1H)-one | (CD$_3$OD, 400 MHz) δ 7.97 (s, 0.25H), 7.82 (0.5H), 7.75 (s, 1H), 7.67 (0.25H), 7.37-7.06 (m, 12H), 6.51 (s, 1H), 5.19 (s, 2H) | 378 |

Example 36: 4-isopropoxy-1-methyl-5-(1-(1-phenyl-ethyl)-1H-pyrazol-4-yl)pyridin-2(1H)-one

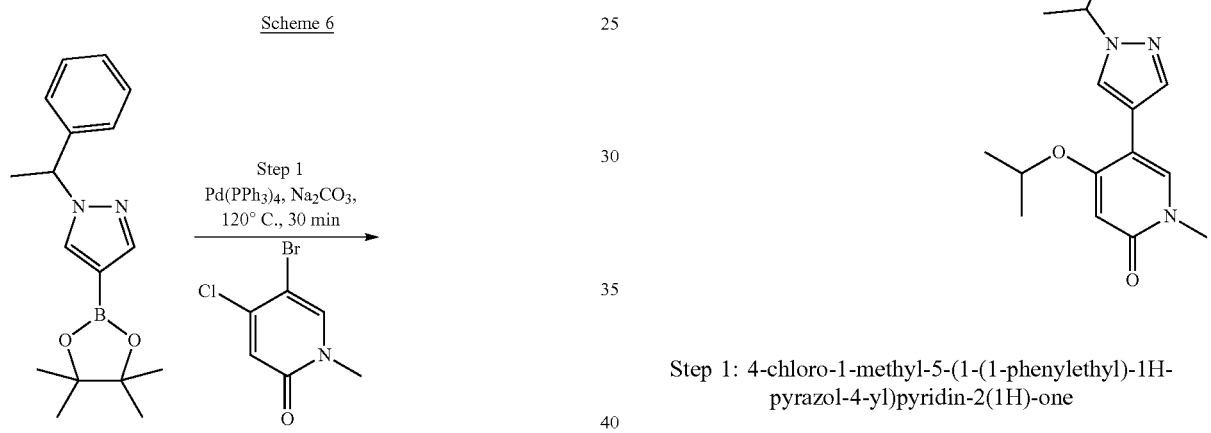

Step 1: 4-chloro-1-methyl-5-(1-(1-phenylethyl)-1H-pyrazol-4-yl)pyridin-2(1H)-one A mixture of 5-bromo-4-chloro-1-methylpyridin-2(1H)-one (100 mg, 0.45 mmol) and 1-(1-phenylethyl)-4-(4,4,5,5-tetramethyl-1,3,2-dioxaborolan-2-yl)-1H-pyrazole (160 mg, 0.54 mmol), Pd(dppf)Cl$_2$—CH$_2$Cl$_2$ (35 mg, 0.04 mmol) and K$_3$PO$_4$ (190 mg, 0.9 mmol) in dioxane (3 ml) and water (3 drops) was purged with nitrogen, capped and heated to 80° C. for 2 hr. The reaction was cooled and filtered through Celite, the solvent removed under reduced pressure, and the resulting residue was purified by pre-HPLC to afford the title compound as a white form (70 mg, 50%). ¹H NMR (400 MHz, CD₃OD): δ 8.08 (s, 1H), 8.00 (s, 1H), 7.67 (s, 1H), 7.33-7.26 (m, 5H), 6.64 (s, 1H), 5.75 (s, 1H), 5.65-5.63 (m, 1H), 3.44 (s, 3H), 1.82 (d, J=7.0 Hz, 3H). LCMS (M+H)⁺ 314.

Step 2: 5-(1-benzyl-1H-pyrazol-4-yl)-1-methylpyridin-2(1H)-one

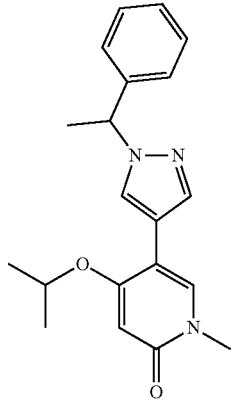 [SMILES: CC(C)Oc1cc(=O)n(C)cc1-c1cnn(C(C)c2ccccc2)c1]

4-chloro-1-methyl-5-(1-(1-phenylethyl)-1H-pyrazol-4-yl)pyridin-2(1H)-one (50 mg, 0.16 mmol) in anhydrous THF (0.5 mL) was added isopropanol (0.5 mL) followed by NaH (16 mg, 0.4 mmol). The reaction was heated at 100° C. for 20 min in a microwave reactor. The solvent was removed and the residue was purified by pre-HPLC to afford 5-(1-benzyl-1H-pyrazol-4-yl)-1-methylpyridin-2(1H)-one (17 mg, 0.05 mmol) as a yellow oil in 31% yield. ¹H NMR (400 MHz, CD₃OD): 7.91 (s, 1H), 7.83 (s, 1H), 7.79 (s, 1H), 7.35-7.25 (m, 5H), 5.99 (s, 1H), 5.58 (q, J=6.8 Hz, 1H), 4.72-4.66 (m, 1H), 3.52 (s, 3H), 1.89 (d, J=7.2 Hz, 3H), 1.36 (d, J=6.0 Hz, 6H). LCMS (M+H)⁺ 338.

Example 37: 5-(1-Benzyl-1H-pyrazol-4-yl)-4-(3-methanesulfonyl-pyrrolidin-1-yl)-1-methyl-1H-pyridin-2-one

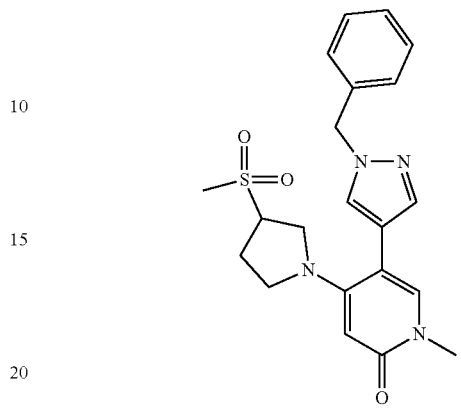

A mixture of 5-(1-benzyl-H-pyrazol-4-yl)-4-chloro-1-methyl-1H-pyridin-2-one (100 mg, 0.334 mmol), 3-methanesulfonyl-pyrrolidine (60 mg, 0.403 mmol), Pd—NHC (22 mg, 0.034 mmol) and Cs₂CO₃ (269 mg, 0.825 mmol) in dioxane/H₂O (5 mL/1 mL) was stirred at 120° C. under N₂ for 12 hours. The reaction was cooled down to room temperature, diluted with aqueous saturated NH₄Cl (50 mL) and extracted with DCM (25 mL×3). The combined organic layers were washed with brine (15 mL×5), dried over Na₂SO₄ and filtered. The residue was purified by preparative-HPLC to afford the title compound as a colorless oil. ¹H NMR (CD₃OD, 400 MHz) δ 7.80 (s, 1H), 7.57 (s, 1H), 7.55 (s, 1H), 7.37-7.28 (m, 6H), 5.36 (s, 2H), 3.87-3.84 (m, 1H), 3.60-3.58 (m, 1H), 3.57 (s, 3H), 3.48-3.36 (m, 2H), 3.22-3.18 (m, 1H), 2.90 (s, 3H), 2.33-2.27 (m, 2H). LCMS (M+H)⁺ 413.

Examples 38-46, 48-53, 56-57, 59-71, 76-86, 91-92 and 94-99 in Table 4 were prepared using the appropriate nucleophile and substituted pyrazole in a similar multi-step manner as Example 36. Examples 47, 54-55, 58, 72-75, 87-90 and 93 were prepared using the appropriate amine and substituted pyrazole in a similar multi-step manner as Example 37.

TABLE 4

| Example | Structure | IUPAC Name | ¹H NMR (ppm) | MS (M + H) |
|---|---|---|---|---|
| 38 | 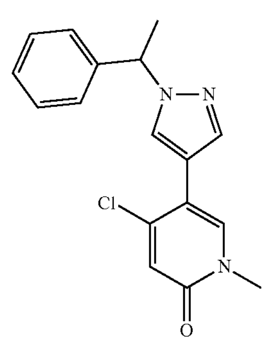 | 4-chloro-1-methyl-5-(1-(1-phenylethyl)-1H-pyrazol-4-yl)pyridin-2(1H)-one | (CD₃OD, 400 MHz) δ 8.08 (s, 1H), 8.00 (s, 1H), 7.67 (s, 1H), 7.33-7.26 (m, 5H), 6.64 (s, 1H), 5.75 (s, 1H), 5.65-5.63 (m, 1H), 3.44 (s, 3H), 1.82 (d, J = 7.0 Hz, 3H) | 314 |

TABLE 4-continued

| Example | Structure | IUPAC Name | ¹H NMR (ppm) | MS (M + H) |
|---|---|---|---|---|
| 39 | 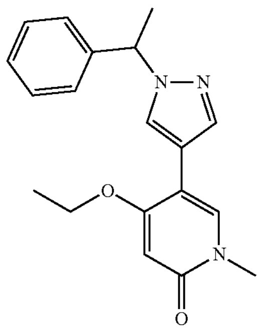 [SMILES: CCOc1cc(=O)n(C)cc1-c1cnn(C(C)c2ccccc2)c1] | 4-ethoxy-1-methyl-5-(1-(1-phenylethyl)-1H-pyrazol-4-yl)pyridin-2(1H)-one | (DMSO-d₆, 400 MHz) δ 7.98 (s, 1H), 7.92 (s, 1H), 7.74 (s, 1H), 7.35-7.25 (m, 5H), 5.61-5.59 (m, 1H), 4.03 (q, J = 6.8 Hz, 2H), 3.37 (s, 3H), 1.81 (d, J = 7.0 Hz, 3H), 1.35 (t, J = 6.9 Hz, 3H) | 324 |
| 40 | 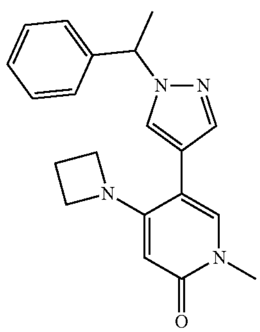 [SMILES: CC(c1ccccc1)n1cc(-c2cn(C)c(=O)cc2N2CCC2)cn1] | 4-(azetidin-1-yl)-1-methyl-5-(1-(1-phenylethyl)-1H-pyrazol-4-yl)pyridin-2(1H)-one | (CD₃OD, 400 MHz) δ 7.74 (s, 1H), 7.49 (s, 1H), 7.32-7.25 (m, 6H), 5.60 (m, 1H), 5.29 (s, 1H), 3.67-3.63 (m, 4H), 3.42 (s, 3H), 2.16-2.13 (m, 2H), 1.90 (d, J = 7.1 Hz, 3H) | 335 |
| 41 | 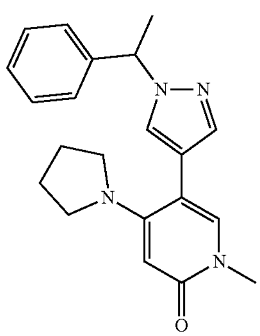 | 1-methyl-5-(1-(1-phenylethyl)-1H-pyrazol-4-yl)-4-(pyrrolidin-1-yl)pyridin-2(1H)-one | (CD₃OD, 400 MHz) δ 7.73 (s, 1H), 7.48 (s, 1H), 7.34-7.25 (m, 6H), 5.62-5.58 (m, 2H), 3.43 (s, 3H), 3.02-2.98 (m, 4H), 1.89 (d, J = 7.2 Hz, 3H), 1.78-1.75 (m, 4H) | 349 |
| 42 | 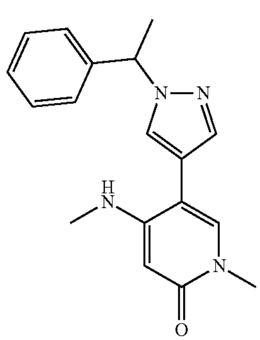 | 1-methyl-4-(methyl-amino)-5-(1-(1-phenylethyl)-1H-pyrazol-4-yl)pyridin-2(1H)-one | (CD₃OD, 400 MHz) δ 7.83 (s, 1H), 7.56 (s, 1H), 7.33-7.28 (m, 6H), 5.60-5.59 (m, 1H), 5.51 (s, 1H), 3.42 (s, 3H), 2.75 (s, 3H), 1.91 (d, J = 7.1 Hz, 3H) | 309 |

TABLE 4-continued

| Example | Structure | IUPAC Name | ¹H NMR (ppm) | MS (M + H) |
|---|---|---|---|---|
| 43 | 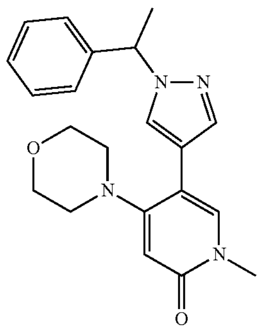 [SMILES: CC(c1ccccc1)n1cc(-c2cn(C)c(=O)cc2N2CCOCC2)cn1] | 1-methyl-4-morpholino-5-(1-(1-phenylethyl)-1H-pyrazol-4-yl)pyridin-2(1H)-one | (CDCl₃, 400 MHz) δ 7.62 (s, 1H), 7.57 (s, 1H), 7.38-7.31 (m, 3H), 7.25-7.24 (m, 2H), 7.23 (s, 1H), 5.98 (s, 1H), 5.53 (q, J = 6.8 Hz, 1H), 3.54-3.50 (m, 4H), 3.48 (s, 3H), 3.83-3.80 (m, 4H), 1.93 (d, J = 6.8 Hz, 3H) | 365 |
| 44 | 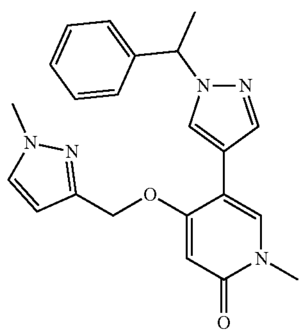 [SMILES: CC(c1ccccc1)n1cc(-c2cn(C)c(=O)cc2OCc2ccn(C)n2)cn1] | 1-methyl-4-((1-methyl-1H-pyrazol-3-yl)methoxy)-5-(1-(1-phenyl-ethyl)-1H-pyrazol-4-yl)pyridin-2(1H)-one | (CD₃OD, 400 MHz) δ 7.95 (s, 1H), 7.86 (s, 1H), 7.76 (s, 1H), 7.58 (s, 1H), 7.31-7.26 (m, 3H), 7.16-7.14 (m, 2H), 6.33 (d, J = 2.4 Hz, 1H), 6.16 (s, 1H), 5.52 (m, 1H), 5.09 (s, 2H), 3.87 (s, 3H), 3.52 (s, 3H), 1.81 (d, J = 7.1 Hz, 3H) | 390 |
| 45 | 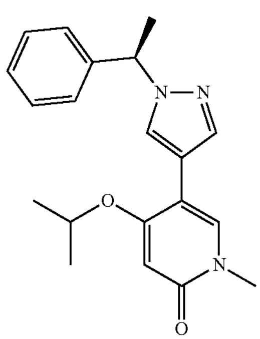 [SMILES: CC(C)Oc1cc(=O)n(C)cc1-c1cnn([C@H](C)c2ccccc2)c1] | (R)-4-isopropoxy-1-methyl-5-(1-(1-phenylethyl)-1H-pyrazol-4-yl)pyridin-2(1H)-one | (CD₃OD, 400 MHz) δ 7.91 (s, 1H), 7.83 (s, 1H), 7.79 (s, 1H), 7.35-7.25 (m, 5H), 5.99 (s, 1H), 5.58 (q, J = 6.8 Hz, 1H), 4.72-4.66 (m, 1H), 3.52 (s, 3H), 1.89 (d, J = 7.2 Hz, 3H), 1.36 (d, J = 6.0 Hz, 6H) | 338 |
| 46 | 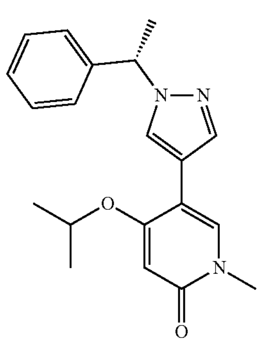 [SMILES: CC(C)Oc1cc(=O)n(C)cc1-c1cnn([C@@H](C)c2ccccc2)c1] | (S)-4-isopropoxy-1-methyl-5-(1-(1-phenylethyl)-1H-pyrazol-4-yl)pyridin-2(1H)-one | (CD₃OD, 400 MHz), δ 7.91 (s, 1H), 7.84 (s, 1H), 7.79 (s, 1H), 7.35-7.33 (m, 2H), 7.27-7.26 (m, 3H), 6.00 (s, 1H), 5.58 (q, J = 6.8 Hz, 1H), 4.70-4.67 (m, 1H), 3.52 (s, 3H), 1.90 (d, J = 7.6 Hz, 3H), 1.36 (d, J = 6.0 Hz, 6H) | 338 |

TABLE 4-continued

| Example | Structure | IUPAC Name | ¹H NMR (ppm) | MS (M + H) |
|---|---|---|---|---|
| 47 | 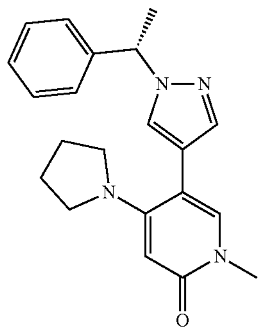 [SMILES: C[C@@H](c1ccccc1)n1cc(-c2cn(C)c(=O)cc2N2CCCC2)cn1] | (S)-1-methyl-5-(1-(1-phenylethyl)-1H-pyrazol-4-yl)-4-(pyrrolidin-1-yl)pyridin-2(1H)-one | (CD₃OD, 400 MHz) δ 7.73 (s, 1H), 7.48 (s, 1H), 7.34-7.25 (m, 6H), 5.62-5.58 (m, 2H), 3.43 (s, 3H), 3.02-2.98 (m, 4H), 1.89 (d, J = 7.2 Hz, 3H), 1.78-1.75 (m, 4H) | 349 |
| 48 | 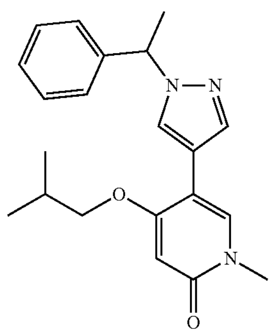 [SMILES: CC(C)COc1cc(=O)n(C)cc1-c1cnn(C(C)c2ccccc2)c1] | 4-isobutoxy-1-methyl-5-(1-(1-phenylethyl)-1H-pyrazol-4-yl)pyridin-2(1H)-one | (CD₃OD, 400 MHz) δ 7.91 (s, 1H), 7.83 (s, 1H), 7.79 (s, 1H), 7.36-7.23 (m, 5H), 5.99 (s, 1H), 5.58 (q, J = 6.8 Hz, 1H), 3.81 (d, J = 6.4 Hz, 2H), 2.08-2.05 (m, 1H), 1.88 (d, J = 7.2 Hz, 3H), 0.97 (d, J = 6.4 Hz, 6H) | 352 |
| 49 | 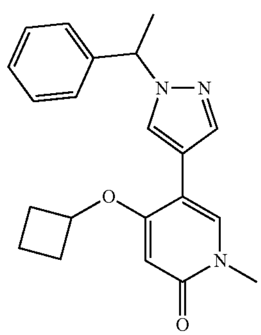 [SMILES: CC(c1ccccc1)n1cc(-c2cn(C)c(=O)cc2OC2CCC2)cn1] | 4-cyclobutoxy-1-methyl-5-(1-(1-phenylethyl)-1H-pyrazol-4-yl)pyridin-2(1H)-one | (CD₃OD, 400 MHz) δ 7.94 (s, 1H), 7.84 (s, 1H), 7.80 (s, 1H), 7.36-7.25 (m, 5H), 5.84 (s, 1H), 5.59 (q, J = 6.8 Hz, 1H), 4.80-4.73 (m, 1H), 3.52 (s, 3H), 2.54-2.46 (m, 2H), 2.17-2.10 (m, 2H), 1.89 (d, J = 7.2 Hz, 3H), 1.85-1.73 (m, 2H) | 350 |
| 50 | 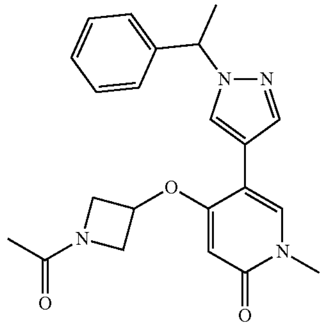 [SMILES: CC(=O)N1CC(Oc2cc(=O)n(C)cc2-c2cnn(C(C)c3ccccc3)c2)C1] | 4-((1-acetylazetidin-3-yl)oxy)-1-methyl-5-(1-(1-phenylethyl)-1H-pyrazol-4-yl)pyridin-2(1H)-one | (CD₃OD, 400 MHz) δ 7.97 (s, 1H), 7.89 (s, 1H), 7.80 (s, 1H), 7.37-7.26 (m, 5H), 5.73 (s, 1H), 5.61 (q, J = 6.8 Hz, 1H), 5.11-5.08 (m, 1H), 4.66-4.61 (m, 1H), 4.43-4.38 (m, 1H), 4.21-4.18 (m, 1H), 3.98-3.95 (m, 1H), 3.51 (s, 3H), 1.90 (d, J = 6.8 Hz, 3H), 1.89 (s, 3H) | 393 |

TABLE 4-continued

| Example | Structure | IUPAC Name | ¹H NMR (ppm) | MS (M + H) |
|---|---|---|---|---|
| 51 | 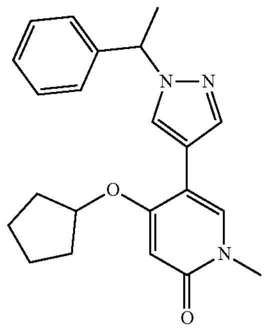 [SMILES: CC(c1ccccc1)n1cc(-c2cn(C)c(=O)cc2OC2CCCC2)cn1] | 4-(cyclopentyloxy)-1-methyl-5-(1-(1-phenylethyl)-1H-pyrazol-4-yl)pyridin-2(1H)-one | (CD₃OD, 400 MHz) δ 7.85 (s, 1H), 7.84 (s, 1H), 7.77 (s, 1H), 7.37-7.25 (m, 5H), 5.98 (s, 1H), 5.58 (q, J = 6.8 Hz, 1H), 4.89-4.86 (m, 1H), 3.52 (s, 3H), 1.98-1.91 (m, 2H), 1.88 (d, J = 7.2 Hz, 3H), 1.83-1.78 (m, 2H), 1.70-1.63 (m, 4H) | 364 |
| 52 | 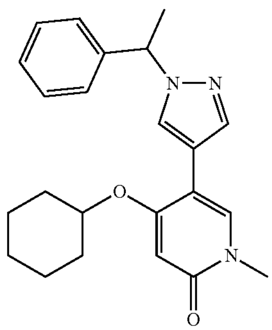 [SMILES: CC(c1ccccc1)n1cc(-c2cn(C)c(=O)cc2OC2CCCCC2)cn1] | 4-(cyclohexyloxy)-1-methyl-5-(1-(1-phenylethyl)-1H-pyrazol-4-yl)pyridin-2(1H)-one | (CD₃OD, 400 MHz) δ 7.90 (s, 1H), 7.83 (s, 1H), 7.79 (s, 1H), 7.37-7.23 (m, 5H), 6.00 (s, 1H), 5.59 (q, J = 7.2 Hz, 1H), 4.49-4.47 (m, 1H), 3.52 (s, 3H) 1.94-1.93 (m, 2H), 1.89 (d, J = 7.2 Hz, 3H), 1.69-1.66 (m, 2H), 1.62-1.53 (m, 3H), 1.48-1.30 (m, 3H) | 378 |
| 53 | 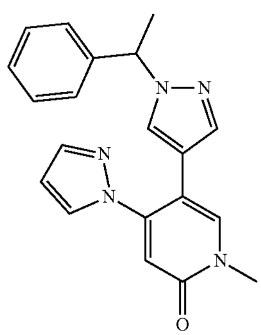 [SMILES: CC(c1ccccc1)n1cc(-c2cn(C)c(=O)cc2-n2cccn2)cn1] | 1-methyl-5-(1-(1-phenylethyl)-1H-pyrazol-4-yl)-4-(1H-pyrazol-1-yl)pyridin-2(1H)-one | (CD₃OD, 400 MHz) δ 7.95 (s, 1H), 7.67 (d, J = 2.0 Hz, 1H), 7.58 (d, J = 2.4 Hz, 1H), 7.34-7.27 (m, 3H), 7.24 (s, 2H), 7.18-7.16 (m, 2H), 6.67 (s, 1H), 6.41-6.40 (m, 1H), 5.50 (q, J = 7.2 Hz, 1H), 3.64 (s, 3H), 1.80 (d, J = 7.2 Hz, 3H) | 346 |
| 54 | 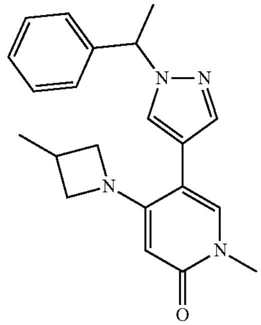 [SMILES: CC1CN(c2cc(=O)n(C)cc2-c2cnn(C(C)c3ccccc3)c2)C1] | 1-methyl-4-(3-methylazetidin-1-yl)-5-(1-(1-phenylethyl)-1H-pyrazol-4-yl)pyridin-2(1H)-one | CD₃OD, 400 MHz), δ 7.72 (s, 1H), 7.47 (s, 1H), 7.34-7.26 (m, 5H), 7.24 (s, 1H), 5.58 (q, J = 6.8 Hz, 1H), 5.28 (s, 1H), 3.75-3.72 (m, 2H), 3.41 (s, 3H), 3.30-3.15 (m, 2H), 2.56-2.54 (m, 1H), 1.90 (d, J = 6.8 Hz, 3H), 1.11 (d, J = 6.8 Hz, 3H) | 349 |

TABLE 4-continued

| Example | Structure | IUPAC Name | ¹H NMR (ppm) | MS (M + H) |
|---|---|---|---|---|
| 55 | 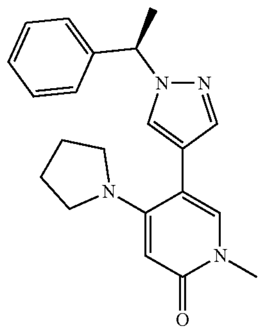 [SMILES: C[C@H](c1ccccc1)n1cc(-c2cn(C)c(=O)cc2N2CCCC2)cn1] | (R)-1-methyl-5-(1-(1-phenylethyl)-1H-pyrazol-4-yl)-4-(pyrrolidin-1-yl)pyridin-2(1H)-one | (CD₃OD, 400 MHz) δ 7.73 (s, 1H), 7.48 (s, 1H), 7.34-7.25 (m, 6H), 5.62-5.58 (m, 2H), 3.43 (s, 3H), 3.02-2.98 (m, 4H), 1.89 (d, J = 7.2 Hz, 3H), 1.78-1.75 (m, 4H) | 349 |
| 56 | 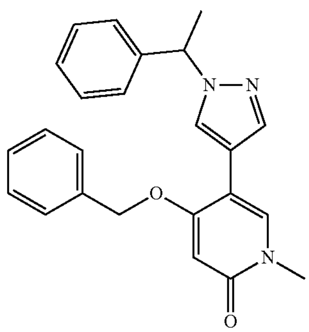 [SMILES: CC(c1ccccc1)n1cc(-c2cn(C)c(=O)cc2OCc2ccccc2)cn1] | 4-(benzyloxy)-1-methyl-5-(1-(1-phenylethyl)-1H-pyrazol-4-yl)pyridin-2(1H)-one | (CD₃OD, 400 MHz) δ 7.89 (s, 1H), 7.88 (s, 1H), 7.76 (s, 1H), 7.46-7.42 (m, 2H), 7.40-7.35 (m, 3H), 7.31-7.24 (m, 3H), 7.14-7.10 (m, 2H), 6.15 (s, 1H), 5.50 (q, J = 7.2 Hz, 1H), 5.15 (s, 2H), 3.54 (s, 3H), 1.77 (d, J = 7.2 Hz, 3H) | 386 |
| 57 | 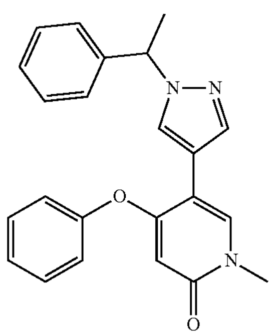 [SMILES: CC(c1ccccc1)n1cc(-c2cn(C)c(=O)cc2Oc2ccccc2)cn1] | 1-methyl-4-phenoxy-5-(1-(1-phenylethyl)-1H-pyrazol-4-yl)pyridin-2(1H)-one | (CD₃OD, 400 MHz) δ 8.05 (s, 1H), 7.97 (s, 1H), 7.87 (s, 1H), 7.50-7.48 (m, 2H), 7.34-7.22 (m, 6H), 7.18-7.14 (m, 2H), 5.65-5.55 (m, 2H), 3.54 (s, 3H), 1.88 (d, J = 7.2 Hz, 3H) | 372 |
| 58 | 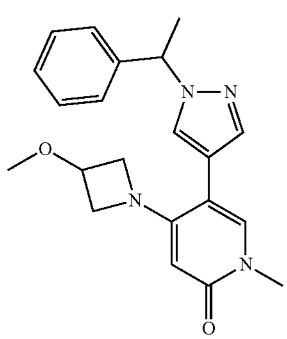 | 4-(3-methoxyazetidin-1-yl)-1-methyl-5-(1-(1-phenylethyl)-1H-pyrazol-4-yl)pyridin-2(1H)-one | (CD₃OD, 400 MHz) δ 7.75 (s, 1H), 7.49 (s, 1H), 7.34-7.25 (m, 6H), 5.60 (q, J = 6.8 Hz, 1H), 5.34 (s, 1H), 4.07-4.04 (m, 1H), 3.80-3.76 (m, 2H), 3.46-3.42 (m, 5H), 3.17 (s, 3H), 1.90 (d, J = 7.2 Hz, 3H) | 365 |

TABLE 4-continued

| Example | Structure | IUPAC Name | ¹H NMR (ppm) | MS (M + H) |
|---|---|---|---|---|
| 59 | 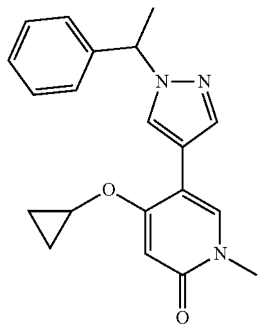 [SMILES: CC(c1ccccc1)n1cc(-c2cn(C)c(=O)cc2OC2CC2)cn1] | 4-cyclopropoxy-1-methyl-5-(1-(1-phenylethyl)-1H-pyrazol-4-yl)pyridin-2(1H)-one | (CDCl₃, 400 MHz) δ 7.64 (s, 1H), 7.53 (s, 1H), 7.37-7.28 (m, 4H), 7.26-7.22 (m, 2H), 6.37 (s, 1H), 5.51 (q, J = 6.8 Hz, 1H), 3.74-3.71 (m, 1H), 3.52 (s, 3H), 1.91 (d, J = 7.2 Hz, 3H), 0.88-0.80 (m, 2H), 0.77-0.74 (m, 2H) | 336 |
| 60 | 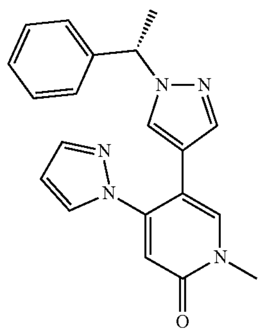 [SMILES: C[C@@H](c1ccccc1)n1cc(-c2cn(C)c(=O)cc2-n2cccn2)cn1] | (S)-1-methyl-5-(1-(1-phenylethyl)-1H-pyrazol-4-yl)-4-(1H-pyrazol-1-yl)pyridin-2(1H)-one | (CD₃OD, 400 MHz) δ 7.94 (s, 1H), 7.67 (d, J = 1.5 Hz, 1H), 7.58 (d, J = 2.3 Hz, 1H), 7.34-7.27 (m, 3H), 7.23 (s, 1H), 7.17 (d, J = 7.5 Hz, 1H), 6.67 (s, 1H), 6.41-6.40 (m, 1H), 5.50-5.48 (m, 1H), 3.64 (s, 3H), 1.80 (d, J = 7.1 Hz, 3H) | 346 |
| 61 | 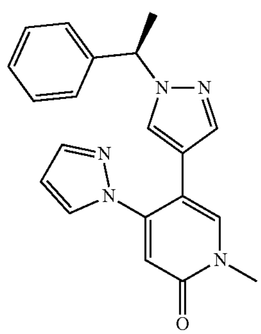 [SMILES: C[C@H](c1ccccc1)n1cc(-c2cn(C)c(=O)cc2-n2cccn2)cn1] | (R)-1-methyl-5-(1-(1-phenylethyl)-1H-pyrazol-4-yl)-4-(1H-pyrazol-1-yl)pyridin-2(1H)-one | (CD₃OD, 400 MHz) δ 7.94 (s, 1H), 7.67 (d, J = 1.5 Hz, 1H), 7.58 (d, J = 2.3 Hz, 1H), 7.34-7.27 (m, 3H), 7.23 (s, 1H), 7.17 (d, J = 7.5 Hz, 1H), 6.67 (s, 1H), 6.41-6.40 (m, 1H), 5.50-5.48 (m, 1H), 3.64 (s, 3H), 1.80 (d, J = 7.1 Hz, 3H) | 346 |
| 62 | 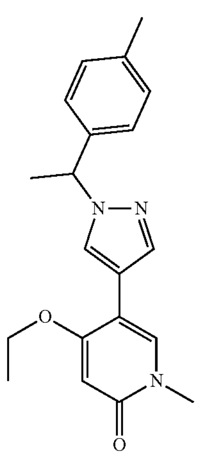 [SMILES: CCOc1cc(=O)n(C)cc1-c1cnn(C(C)c2ccc(C)cc2)c1] | 4-ethoxy-1-methyl-5-(1-(1-(p-tolyl)ethyl)-1H-pyrazol-4-yl)pyridin-2(1H)-one | (CD₃OD, 400 MHz) δ 7.89 (s, 1H), 7.83 (s, 1H), 7.79 (s, 1H), 7.15 (m, 5H), 5.98 (s, 1H), 5.54-5.48 (m, 1H), 4.11 (q, J = 5.0 Hz, 2H), 3.51 (s, 3H), 2.30 (s, 3H), 1.87 (d, J = 7.0 Hz, 3H), 1.42 (t, J = 6.9 Hz, 3H) | 338 |

TABLE 4-continued

| Example | Structure | IUPAC Name | ¹H NMR (ppm) | MS (M + H) |
|---|---|---|---|---|
| 63 | 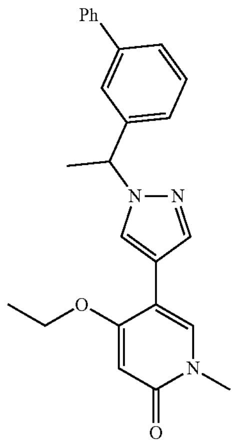 [SMILES: CCOc1cc(=O)n(C)cc1-c1cnn(C(C)c2cccc(-c3ccccc3)c2)c1] | 5-(1-(1-([1,1'-biphenyl]-4-yl)ethyl)-1H-pyrazol-4-yl)-4-ethoxy-1-methylpyridin-2(1H)-one | (DMSO-d₆, 400 MHz) δ 8.04 (s, 1H), 7.92 (s, 1H), 7.76 (s, 1H), 7.63-7.56 (m, 4H), 7.48-7.41 (m, 4H), 7.38-7.37 (m, 1H), 5.83 (s, 1H), 5.69-5.68 (m, 1H), 4.02 (q, J = 7.0 Hz, 2H), 3.36 (s, 3H), 1.87 (d, J = 7.0 Hz, 3H), 1.33 (t, J = 6.9 Hz, 3H) | 400 |
| 64 | 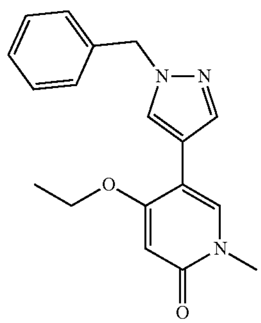 [SMILES: CCOc1cc(=O)n(C)cc1-c1cnn(Cc2ccccc2)c1] | 5-(1-benzyl-1H-pyrazol-4-yl)-4-ethoxy-1-methylpyridin-2(1H)-one | (DMSO-d₆, 400 MHz) δ 7.97 (s, 1H), 7.93 (s, 1H), 7.74 (s, 1H), 7.37-7.24 (m, 5H), 5.84 (s, 1H), 5.33 (s, 2H), 4.05 (q, J = 7.0 Hz, 2H), 3.37 (s, 3H), 1.36 (t, J = 6.9 Hz, 3H) | 310 |
| 65 | 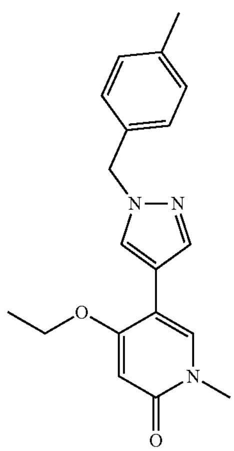 [SMILES: CCOc1cc(=O)n(C)cc1-c1cnn(Cc2ccc(C)cc2)c1] | 4-ethoxy-1-methyl-5-(1-(4-methylbenzyl)-1H-pyrazol-4-yl)pyridin-2(1H)-one | (DMSO-d₆, 400 MHz) δ 7.93 (s, 1H), 7.91 (s, 1H), 7.73 (s, 1H), 7.15 (s, 4H), 5.84 (s, 1H), 5.26 (s, 2H), 4.05 (q, J = 7.0 Hz, 2H), 3.37 (s, 3H), 2.27 (s, 2H), 1.36 (t, J = 6.9 Hz, 3H) | 324 |
| 66 | 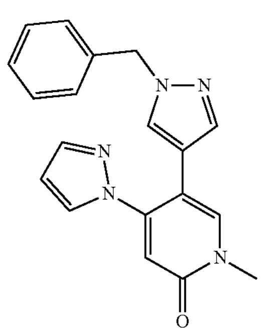 [SMILES: Cn1cc(-c2cnn(Cc3ccccc3)c2)c(-n2cccn2)cc1=O] | 5-(1-benzyl-1H-pyrazol-4-yl)-1-methyl-4-(1H-pyrazol-1-yl)pyridin-2(1H)-one | (CD₃OD, 400 MHz) δ 7.93 (s, 1H), 7.66 (s, 1H), 7.58 (s, 1H), 7.33-7.17 (m, 7H), 6.67 (s, 1H), 6.40-6.39 (m, 1H), 5.25 (s, 2H), 3.63 (s, 3H) | 332 |

TABLE 4-continued

| Example | Structure | IUPAC Name | ¹H NMR (ppm) | MS (M + H) |
|---|---|---|---|---|
| 67 | 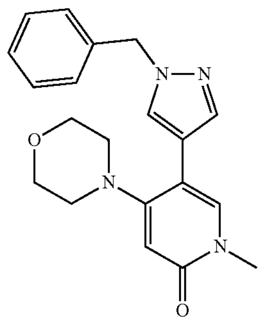 [SMILES: Cn1cc(-c2cnn(Cc3ccccc3)c2)c(N2CCOCC2)cc1=O] | 5-(1-benzyl-1H-pyrazol-4-yl)-1-methyl-4-morpholino-pyridin-2(1H)-one | (CD$_3$OD, 400 MHz) δ 7.92 (s, 1H), 7.72 (s, 1H), 7.52 (s, 1H), 7.35-7.25 (m, 5H), 5.96 (s, 1H), 5.36 (s, 2H), 3.54-3.53 (m, 4H), 3.49 (s, 3H), 2.86-2.84 (m, 4H) | 351 |
| 68 | 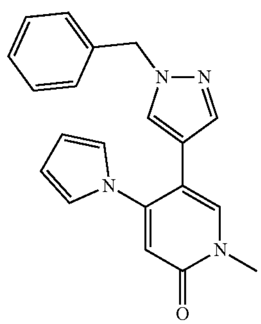 [SMILES: Cn1cc(-c2cnn(Cc3ccccc3)c2)c(-n2cccc2)cc1=O] | 5-(1-benzyl-1H-pyrazol-4-yl)-1-methyl-4-(1H-pyrrol-1-yl)pyridi-2(1H)-one | (CD$_3$OD, 400 MHz) δ 7.89 (s, 1H), 7.32-7.24 (m, 3H), 7.24 (s, 1H), 7.18-7.14 (m, 3H), 6.67 (d, J = 2.2 Hz, 2H), 6.46 (s, 1H), 6.19-6.18 (m, 2H), 5.23 (s, 2H), 3.61 (s, 3H) | 331 |
| 69 | 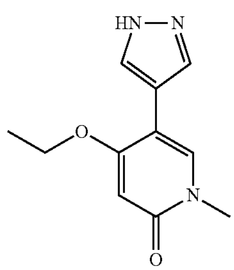 [SMILES: CCOc1cc(=O)n(C)cc1-c1cn[nH]c1] | 4-ethoxy-1-methyl-5-(1H-pyrazol-4-yl)pyridin-2(1H)-one | (DMSO-d$_6$, 400 MHz) δ 7.99 (s, 1H), 7.88 (s, 2H), 5.92 (s, 1H), 4.07 (q, J = 6.8 Hz, 2H), 1.39 (t, J = 6.8 Hz, 3H) | 220 |
| 70 | 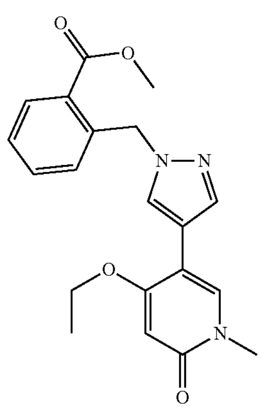 [SMILES: CCOc1cc(=O)n(C)cc1-c1cnn(Cc2ccccc2C(=O)OC)c1] | methyl 2-((4-(4-ethoxy-1-methyl-6-oxo-1,6-dihydropyridin-3-yl)-1H-pyrazol-1-yl)methyl)benzoate | (CD$_3$OD, 400 MHz) δ 8.02 (d, J = 7.7 Hz, 1H), 7.98 (s, 1H), 7.86 (s, 1H), 7.83 (s, 1H), 7.51-7.49 (m, 2H), 7.43-7.39 (m, 1H), 5.99 (s, 1H), 5.76 (s, 2H), 4.05 (q, J = 7.0 Hz, 2H), 3.90 (s, 3H), 3.52 (s, 3H), 1.44 (t, J = 6.9 Hz, 3H) | 368 |

TABLE 4-continued

| Example | Structure | IUPAC Name | ¹H NMR (ppm) | MS (M + H) |
|---|---|---|---|---|
| 71 | 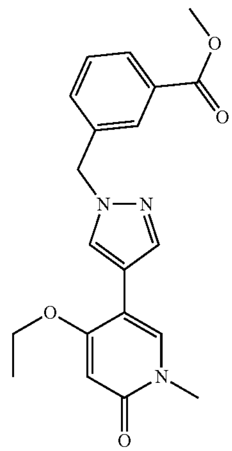 [SMILES: CCOc1cc(=O)n(C)cc1-c1cnn(Cc2cccc(C(=O)OC)c2)c1] | methyl 3-((4-(4-ethoxy-1-methyl-6-oxo-1,6-dihydropyridin-3-yl)-1H-pyrazol-1-yl)methyl)benzoate | (CD$_3$OD, 400 MHz) δ 7.99 (s, 1H), 7.95 (d, J = 7.2 Hz, 1H), 7.92 (s, 1H), 7.49 (d, J = 3.2 Hz, 1H), 7.49-7.47 (m, 3H), 5.99 (s, 1H), 5.42 (s, 2H), 4.12 (q, J = 7.0 Hz, 2H), 3.88 (s, 3H), 3.52 (s, 3H), 1.45 (t, J = 7.0 Hz, 3H) | 368 |
| 72 | 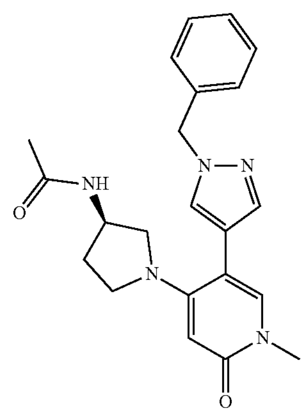 [SMILES: CC(=O)N[C@@H]1CCN(c2cc(=O)n(C)cc2-c2cnn(Cc3ccccc3)c2)C1] | (R)-N-(1-(5-(1-benzyl-1H-pyrazol-4-yl)-1-methyl-2-oxo-1,2-dihydropyridin-4-yl)pyrrolidin-3-yl)acetamide | (CD$_3$OD, 400 MHz) δ 7.77 (s, 1H), 7.54 (d, J = 7.2 Hz, 2H), 7.37-7.25 (m, 6H), 5.37 (s, 2H), 4.26-4.23 (m, 1H), 3.57 (s, 3H), 3.39-3.35 (m, 2H), 3.26-3.20 (m, 1H), 3.00-2.96 (m, 1H), 2.09-2.04 (m, 1H), 1.90 (s, 3H), 1.88-1.81 (m, 1H) | 392 |
| 73 | 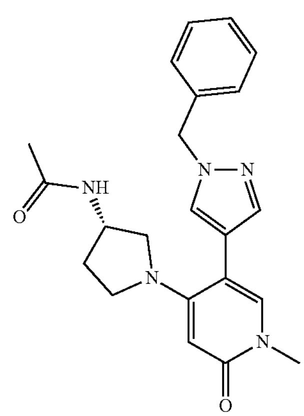 [SMILES: CC(=O)N[C@H]1CCN(c2cc(=O)n(C)cc2-c2cnn(Cc3ccccc3)c2)C1] | (S)-N-(1-(5-(1-benzyl-1H-pyrazol-4-yl)-1-methyl-2-oxo-1,2-dihydropyridin-4-yl)pyrrolidin-3-yl) acetamide | (CD$_3$OD, 400 MHz) δ 7.62 (s, 1H), 7.41 (s, 1H), 7.26-7.14 (m, 6H), 5.53 (s, 1H), 5.26 (s, 2H), 4.13-4.11 (m, 1H), 3.33 (s, 3H), 3.21-3.10 (m, 2H), 3.03-3.02 (m, 1H), 2.81-2.78 (m, 1H), 1.95-1.90 (m, 1H), 1.80 (s, 3H), 1.71-1.67 (m, 1H) | 392 |

TABLE 4-continued

| Example | Structure | IUPAC Name | ¹H NMR (ppm) | MS (M + H) |
|---|---|---|---|---|
| 74 | 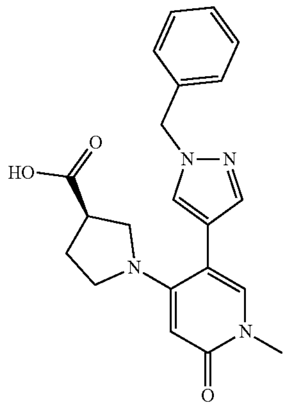 | (R)-1-(5-(1-benzyl-1H-pyrazol-4-yl)-1-methyl-2-oxo-1,2-dihydropyridin-4-yl)pyrrolidine-3-carboxylic acid | (CD$_3$OD, 400 MHz) δ 7.78 (s, 1H), 7.56-7.55 (m, 2H), 7.37-7.25 (m, 6H), 5.38 (s, 2H), 3.59 (s, 3H), 3.38-3.34 (m, 2H), 3.26-3.19 (m, 2H), 3.08-3.04 (m, 1H), 2.13-2.09 (m, 2H) | 379 |
| 75 | 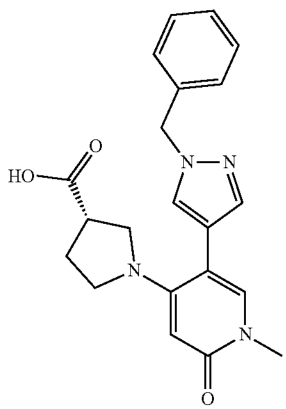 [SMILES: Cn1cc(-c2cnn(Cc3ccccc3)c2)c(N2CC[C@H](C(=O)O)C2)cc1=O] | (S)-1-(5-(1-benzyl-1H-pyrazol-4-yl)-1-methyl-2-oxo-1,2-dihydropyridin-4-yl)pyrrolidine-3-carboxylic acid | (CD$_3$OD, 400 MHz) δ 7.73 (s, 1H), 7.52 (s, 1H), 7.36-7.24 (m, 6H), 5.64 (s, 1H), 5.36 (s, 2H), 3.44 (s, 3H), 3.26-3.24 (m, 2H), 3.15-3.09 (m, 2H), 2.99-2.95 (m, 1H), 2.08-2.02 (m, 2H). | 379 |
| 76 | 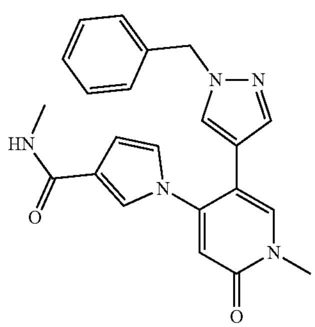 [SMILES: CNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-1H-pyrrole-3-carboxamide | (CD$_3$OD, 400 MHz) δ 7.94 (s, 1H), 7.31-7.14 (m, 8H), 6.73 (d, J = 2.4 Hz, 1H), 6.59 (d, J = 1.6 Hz, 1H), 6.53 (s, 1H), 5.22 (s, 2H), 3.62 (s, 3H), 2.84 (s, 3H) | 388 |
| 77 | 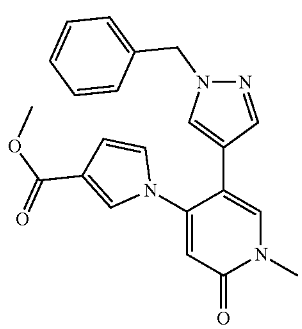 [SMILES: COC(=O)c1ccn(-c2cc(=O)n(C)cc2-c2cnn(Cc3ccccc3)c2)c1] | methyl 1-(5-(1-benzyl-1H-pyrazol-4-yl)-1-methyl-2-oxo-1,2-dihydropyridin-4-yl)-1H-pyrrole-3-carboxylate | (DMSO-d$_6$, 400 MHz) δ 8.05 (s, 1H), 7.38 (d, J = 1.8 Hz, 1H), 7.37-7.28 (m, 4H), 7.25 (s, 1H), 7.14 (s, 1H), 7.11 (d, J = 1.8 Hz, 1H), 6.86-6.84 (m, 1H), 6.53-6.52 (m, 1H), 6.47 (s, 1H), 5.24 (s, 2H), 3.70 (s, 3H), 3.50 (s, 3H) | 389 |

| Example | Structure | IUPAC Name | ¹H NMR (ppm) | MS (M + H) |
|---|---|---|---|---|
| 78 | 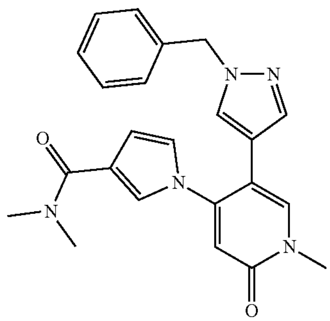 | 1-(5-(1-benzyl-1H-pyrazol-4-yl)-1-methyl-2-oxo-1,2-dihydropyridin-4-yl)-N,N-dimethyl-1H-pyrrole-3carboxamide | (CD$_3$OD, 400 MHz) δ 7.93 (s, 1H), 7.31-7.28 (m, 3H), 7.24 (s, 1H), 7.20-7.15 (m, 3H), 7.06 (d, J = 1.9 Hz, 1H), 6.79-6.78 (m, 1H), 6.55 (s, 1H), 6.49-6.48 (m, 1H), 5.24 (s, 2H), 3.62 (s, 3H), 2.99 (s, 6H) | 402 |
| 79 | 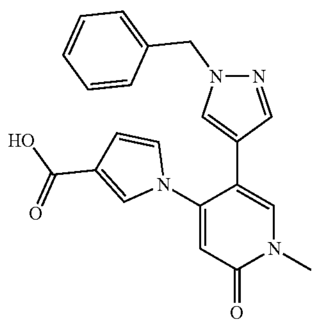 [SMILES: Cn1cc(-c2cnn(Cc3ccccc3)c2)c(-n2ccc(C(=O)O)c2)cc1=O] | 1-(5-(1-benzyl-1H-pyrazol-4-yl)-1-methyl-2-oxo-1,2-dihydropyridin-4-yl)-1H-pyrrole-3-carboxylic acid | (DMSO-d$_6$, 400 MHz) δ 12.0 (br s, 1H), 8.03 (s, 1H), 7.32-7.26 (m, 5H), 7.15 (s, 1H), 7.11 (d, J = 7.0 Hz, 1H), 6.85-6.84 (m, 1H), 6.49-6.46 (m, 2H), 5.76 (s, 1H), 5.25 (s, 2H), 3.49 (s, 3H) | 375 |
| 80 | 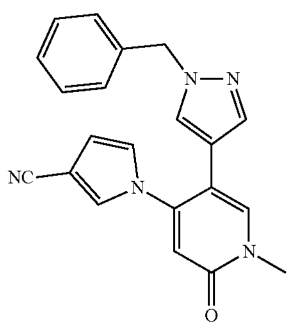 [SMILES: Cn1cc(-c2cnn(Cc3ccccc3)c2)c(-n2ccc(C#N)c2)cc1=O] | 1-(5-(1-benzyl-1H-pyrazol-4-yl)-1-methyl-2-oxo-1,2-dihydropyridin-4-yl)-1H-pyrrole-3-carbonitrile | (CD$_3$OD, 400 MHz) δ 7.93 (s, 1H), 7.39-7.26 (m, 4H), 7.18-7.15 (m, 3H), 6.82-6.81 (m, 1H), 6.55 (s, 1H), 6.48 (d, J = 1.6 Hz, 1H), 6.47 (d, J = 1.6 Hz, 1H), 5.25 (s, 2H), 3.49 (s, 3H) | 356 |
| 81 | 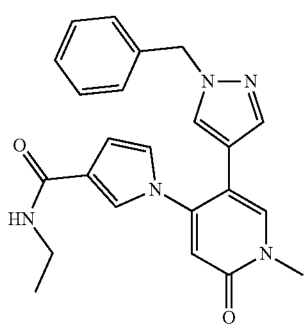 [SMILES: CCNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydro-pyridin-4-yl)-N-ethyl-1H-pyrrole-3-carboxamide | (DMSO-d$_6$, 400 MHz) δ 8.03 (s, 1H), 7.09-7.88 (m, 1H), 7.34-7.27 (m, 4H), 7.26-7.10 (m, 3H), 6.75 (s, 1H), 6.59-6.58 (m, 1H), 6.41 (s, 1H), 5.24 (s, 2H), 3.49 (s, 3H), 3.21 (q, J = 6.8 Hz, 2H), 1.07 (t, J = 1.0 Hz, 3H) | 402 |

TABLE 4-continued

| Example | Structure | IUPAC Name | ¹H NMR (ppm) | MS (M + H) |
|---|---|---|---|---|
| 82 | 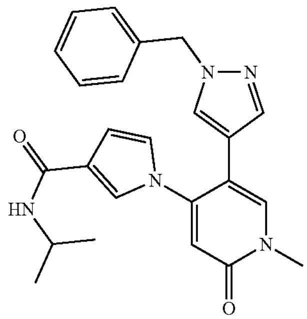 [SMILES: CC(C)NC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-N-isopropyl-1H-pyrrole-3-carboxamide | (DMSO-$d_6$, 400 MHz) δ 8.03 (s, 1H), 7.64 (d, J = 7.8 Hz, 1H), 7.34-7.26 (m, 4H), 7.12-7.10 (m, 3H), 6.72-6.71 (m, 1H), 6.61-6.60 (m, 1H), 6.40 (s, 1H), 5.25 (s, 2H), 4.06-4.01 (m, 1H), 3.49 (s, 3H), 1.12 (d, J = 6.6 Hz, 6H) | 416 |
| 83 | 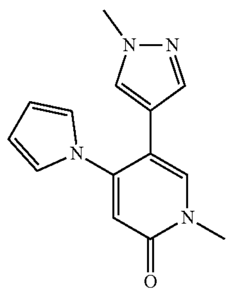 [SMILES: Cn1cc(-c2cn(C)c(=O)cc2-n2cccc2)cn1] | 1-methyl-5-(1-methyl-1H-pyrazol-4-yl)-4-(1H-pyrrol-1-yl)pyridin-2(1H)-one | (DMSO-$d_6$, 400 MHz) δ 7.97 (s, 1H), 7.20 (s, 1H), 6.94 (s, 1H), 6.76-6.74 (m, 2H), 6.35 (s, 1H), 6.18-6.17 (m, 2H), 3.75 (s, 3H), 3.49 (s, 3H) | 255 |
| 84 | 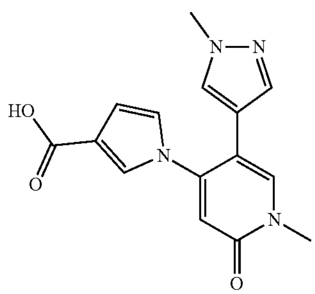 [SMILES: Cn1cc(-c2cn(C)c(=O)cc2-n2ccc(C(=O)O)c2)cn1] | 1-(1-methyl-5-(1-methyl-1H-pyrazol-4-yl)-2-oxo-1,2-dihydropyridin-4-yl)-1H-pyrrole-3-carboxylic acid | (CD$_3$OD, 400 MHz) δ 7.93 (s, 1H), 7.34 (s, 1H), 7.24 (s, 1H), 6.76-6.75 (m, 1H), 6.62 (d, J = 1.5 Hz, 1H), 6.61 (d, J = 1.5 Hz, 1H), 6.55 (s, 1H), 3.82 (s, 3H), 3.64 (s, 3H) | 299 |
| 85 | 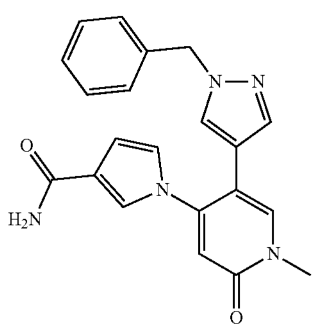 [SMILES: Cn1cc(-c2cnn(Cc3ccccc3)c2)c(-n2ccc(C(N)=O)c2)cc1=O] | 1-(5-(1-benzyl-1H-pyrazol-4-yl)-1-methyl-2-oxo-1,2-dihydropyridin-4-yl)-1H-pyrrole-3-carboxamide | (DMSO-$d_6$, 400 MHz) δ 8.03 (s, 1H), 7.41 (s, 1H), 7.35-7.26 (m, 5H), 7.13-7.11 (m, 3H), 6.90 (s, 1H), 6.77-6.76 (m, 1H), 6.58-6.57 (m, 1H), 6.41 (s, 1H), 5.25 (s, 2H), 3.49 (s, 3H) | 374 |
| 86 | 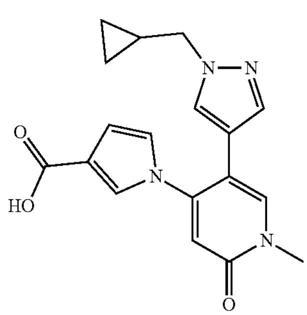 [SMILES: Cn1cc(-c2cnn(CC3CC3)c2)c(-n2ccc(C(=O)O)c2)cc1=O] | 1-(5-(1-(cyclopropylmethyl)-1H-pyrazol-4-yl)-1-methyl-2-oxo-1,2-dihydropyridin-4-yl)-1H-pyrrole-3-carboxylic acid | (DMSO-$d_6$, 400 MHz) δ 8.06 (s, 1H), 7.30-7.29 (m, 1H), 7.12 (d, J = 8.6 Hz, 1H), 6.84-6.83 (m, 2H), 6.53-6.51 (m, 1H), 6.47 (s, 1H), 3.98 (d, J = 7.1 Hz, 2H), 3.51 (s, 3H), 0.49-0.44 (m, 2H), 0.27-0.23 (m, 2H) | 339 |

TABLE 4-continued

| Example | Structure | IUPAC Name | ¹H NMR (ppm) | MS (M + H) |
|---|---|---|---|---|
| 87 | 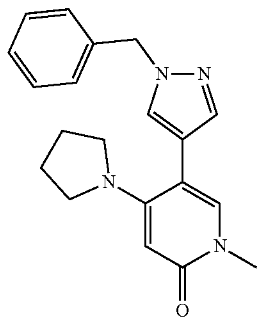 [SMILES: Cn1cc(-c2cnn(Cc3ccccc3)c2)c(N2CCCC2)cc1=O] | 5-(1-benzyl-1H-pyrazol-4-yl)-1-methyl-4-pyrrolidin-1-yl-1H-pyridin-2-one | (CD₃OD, 400 MHz) δ 7.70 (s, 1H), 7.49 (s, 1H), 734-7.25 (m, 6H), 5.61 (s, 1H), 5.34 (s, 2H), 3.42 (s, 3H), 3.03-3.00 (m, 4H), 1.79-1.76 (m, 4H) | 335 |
| 88 | 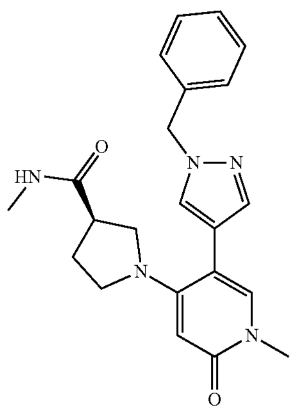 | N-{2-[5-(1-benzyl-1H-pyrazol-4-yl)-1-methyl-2-oxo-1,2-dihydro-pyridin-4-yl]-cyclo-pentyl}-acetamide | (CD₃OD, 400 MHz) δ 7.77 (s, 1H), 7.54 (d, J = 7.2 Hz, 2H), 737-7.25 (m, 6H), 5.37 (s, 2H), 4.26-4.23 (m, 1H), 3.57 (s, 3H), 3.39-3.35 (m, 2H), 3.26-3.20 (m, 1H), 3.00-2.96 (m, 1H), 2.09-2.04 (m, 1H), 1.90 (s, 3H), 1.88-1.81 (m, 1H). | 392 |
| 89 | 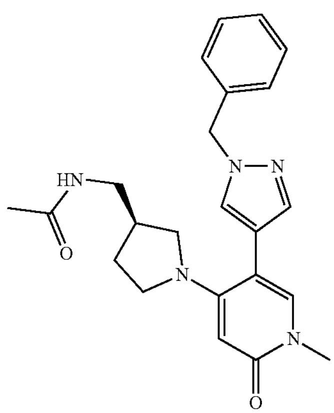 [SMILES: CC(=O)NC[C@@H]1CCN(c2cc(=O)n(C)cc2-c2cnn(Cc3ccccc3)c2)C1] | N-{1-[5-(1-benzyl-1H-pyrazol-4-yl)-1-methyl-2-oxo-1,2-dihydro-pyridin-4-yl]-pyrrolidin-3-ylmethyl}-acetamide | (CD₃OD, 400 MHz) δ 7.71 (s, 1H), 7.51 (s, 1H), 7.38-7.29 (m, 6H), 5.65 (s, 1H), 5.35 (s, 2H), 3.44 (s, 3H), 3.14-3.04 (m, 5H), 2.83-2.79 (m, 1H), 2.31-2.28 (m, 1H), 1.94-1.89 (m, 4H), 1.56-1.51 (m, 1H) | 406 |
| 90 | 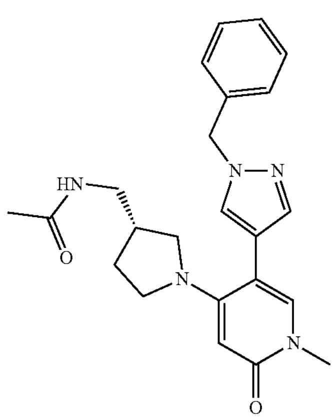 [SMILES: CC(=O)NC[C@H]1CCN(c2cc(=O)n(C)cc2-c2cnn(Cc3ccccc3)c2)C1] | N-{1-[5-(1-benzyl-1H-pyrazol-4-yl)-1-methyl-2-oxo-1,2-dihydro-pyridin-4-yl]-pyrrolidin-3-yl-methyl}-acetamide | (CD₃OD, 400 MHz) δ 7.70 (s, 1H), 7.50 (s, 1H), 7.37-7.26 (m, 6H), 5.61 (s, 1H), 5.35 (s, 2H), 3.42 (s, 3H), 3.15-3.01 (m, 5H), 2.81-2.77 (m, 1H), 2.30-2.26 (m, 1H), 1.93-1.89 (m, 4H), 1.56-1.51 (m, 1H). | 406 |

TABLE 4-continued

| Example | IUPAC Name | ¹H NMR (ppm) | MS (M + H) |
|---|---|---|---|
| 91 | 5-(1-benzyl-1H-pyrazol-4-yl)-1-methyl-4-(2,2,2-trifluoro-ethoxy)pyridin-2(1H)-one | (DMSO-d$_6$, 400 MHz) δ 8.00 (s, 1H), 7.85 (s, 1H), 7.70 (s, 1H), 7.35-7.29 (m, 3H), 7.25-7.23 (m, 2H), 6.03 (s, 1H), 5.32 (s, 2H), 4.84 (q, J = 8.4 Hz, 2H), 3.40 (s, 3H) | 364 |
| 92 | 5-(1-benzyl-1H-pyrazol-4-yl)-1-methyl-4-(3,3,3-trifluoroprop-oxy)pyridin-2(1H)-one | (DMSO-d$_6$, 400 MHz) δ 7.98-7.95 (m, 2H), 7.74 (s, 1H), 7.34-7.22 (m, 5H), 5.95 (s, 1H), 5.31 (s, 2H), 4.24-4.21 (m, 2H), 3.38 (s, 3H), 2.88-2.65 (m, 2H) | 378 |
| 93 | 1-[5-(1-benzyl-1H-pyrazol-4-yl)-1-methyl-2-oxo-1,2-dihydro-pyridin-4-yl]-pyrrolidine-3-methylacetamide | (CD$_3$OD, 400 MHz) δ 7.72 (s, 1H), 7.50 (s, 1H), 7.35-7.23 (m, 6H), 5.62 (s, 1H), 5.34 (s, 2H), 3.43 (s, 3H), 3.22-3.16 (m, 3H), 3.10-3.03 (m, 1H), 2.87-2.83 (m, 1H), 2.70 (s, 3H), 2.02-1.95 (m, 2H) | 392 |
| 94 | 5-(1-benzyl-1H-pyrazol-4-yl)-4-(1H-imidazol-1-yl)-1-methyl-pyridin-2(1H)-one | (DMSO-d$_6$, 400 MHz) δ 8.14 (s, 1H), 8.04 (s, 1H), 7.70 (s, 1H), 7.36 (s, 1H), 7.35-7.30 (m, 3H), 7.28-7.26 (m, 2H), 7.14 (s, 1H), 7.09 (s, 1H), 6.50 (s, 1H), 5.25 (s, 2H), 3.50 (s, 3H) | 332 |

TABLE 4-continued

| Example | Structure | IUPAC Name | $^1$H NMR (ppm) | MS (M + H) |
|---|---|---|---|---|
| 95 | 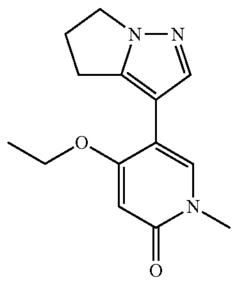 [SMILES: CCOc1cc(=O)n(C)cc1-c1cnn2c1CCC2] | 5-(5,6-dihydro-4H-pyrrolo[1,2-b]-pyrazol-3-yl)-4-ethoxy-1-methylpyridin-2(1H)-one | (DMSO-$d_6$, 400 MHz) δ 7.60 (s, 1H), 7.56 (s, 1H), 5.84 (s, 1H), 4.06-4.02 (m, 4H), 3.52 (s, 3H), 2.93-2.90 (m, 2H), 2.55-2.53 (m, 2H), 1.35 (t, J = 7.0 Hz, 3H) | 260 |
| 96 | 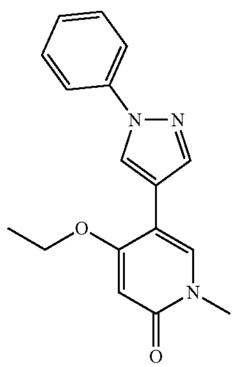 | 4-ethoxy-1-methyl-5-(1-phenyl-1H-pyrazol-4-yl)pyridin-2(1H)-one | (DMSO-$d_6$, 400 MHz) δ 8.61 (s, 1H), 8.06 (s, 1H), 8.02 (s, 1H), 7.82 (d, J = 7.6 Hz, 2H), 7.54-7.50 (m, 2H), 7.33-7.30 (m, 1H), 5.90 (s, 1H), 4.12 (q, J = 6.9 Hz, 2H), 3.41 (s, 3H), 1.44 (t, J = 7.0 Hz, 3H) | 296 |
| 97 | 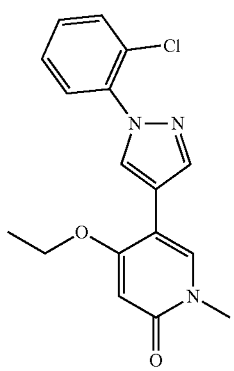 | 5-(1-(2-chloro-phenyl)-1H-pyrazol-4-yl)-4-ethoxy-1-methyl-pyridin-2(1H)-one | (DMSO-$d_6$, 400 MHz) δ 8.33 (s, 1H), 8.08 (s, 1H), 8.07 (s, 1H), 7.71-7.63 (m, 2H), 7.53-7.48 (m, 2H), 5.89 (s, 1H), 4.08 (q, J = 6.9 Hz, 2H), 3.41 (s, 3H), 1.41 (t, J = 7.0 Hz, 3H) | 330 |
| 98 | 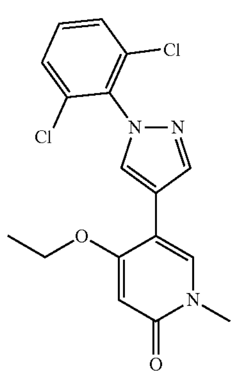 [SMILES: CCOc1cc(=O)n(C)cc1-c1cnn(-c2c(Cl)cccc2Cl)c1] | 5-(1-(2,6-dichlorophenyl)-1H-pyrazol-4-yl)-4-ethoxy-1-methyl-pyridin-2(1H)-one | (DMSO-$d_6$, 400 MHz), δ 8.14 (s, 1H), 8.08 (s, 1H), 8.07 (s, 1H), 7.73-7.71 (m, 2H), 7.62-7.58 (m, 2H), 4.09 (q, J = 6.9 Hz, 2H), 3.41 (s, 3H), 1.38 (t, J = 7.0 Hz, 3H) | 364 |

| Example | Structure | IUPAC Name | ¹H NMR (ppm) | MS (M + H) |
|---|---|---|---|---|
| 99 | 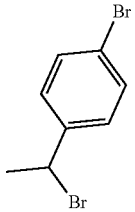 | 5-(1-benzyl-1H-pyrazol-4-yl)-1-methyl-4-(2-methyl-hydrazinyl)-pyridin-2(1H)-one | (DMSO-d$_6$, 400 MHz) δ 7.89 (s, 1H), 7.58 (s, 1H), 7.36 (s, 1H), 7.30 (s, 1H), 7.28-7.22 (m, 5H), 6.08 (s, 1H), 5.33 (s, 2H), 3.32 (s, 3H), 2.63 (s, 3H) | 310 |

Example 100: 4-ethoxy-1-methyl-5-(1-{1-[4-(1-methyl-1H-pyrazol-4-yl)-phenyl]-ethyl}-1H-pyrazol-4-yl)-1H-pyridin-2-one Scheme 7

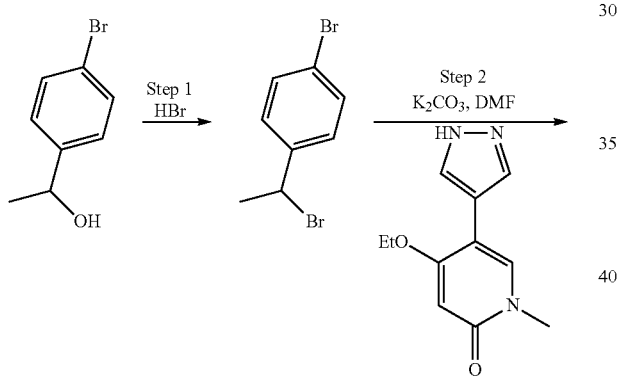

Step 1: 1-bromo-4-(1-bromo-ethyl)-benzene

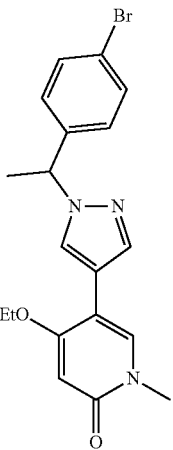 [SMILES: CCOc1cc(=O)n(C)cc1-c1cnn(C(C)c2ccc(Br)cc2)c1]

A mixture of 1-(4-bromo-phenyl)-ethanol (1 g, 5 mmol) in HBr (15 mL) was heated to 90° C. for 5 hr. The mixture was cooled to room temperature, poured into water (5 mL), and extracted with ether (5 mL×3). The organic layer was concentrated under vacuum and the residue was purified with chromatography silica gel, PE:EtOAc (50:1) to give 1-bromo-4-(1-bromo-ethyl)-benzene (900 mg, 3.4 mmol) as colorless oil in 68% yield. ¹H NMR (300 MHz, CDCl$_3$): δ 7.50 (d, J=8.7 Hz, 2H), 7.35 (d, J=8.1 Hz 2H), 5.18 (q, J=7.8 Hz 1H), 2.05 (d, J=6.9 Hz 3H).

Step 2: 5-{1-[1-(4-Bromo-phenyl)-ethyl]-1H-pyrazol-4-yl}-4-ethoxy-1-methyl-1H-pyridin-2-one

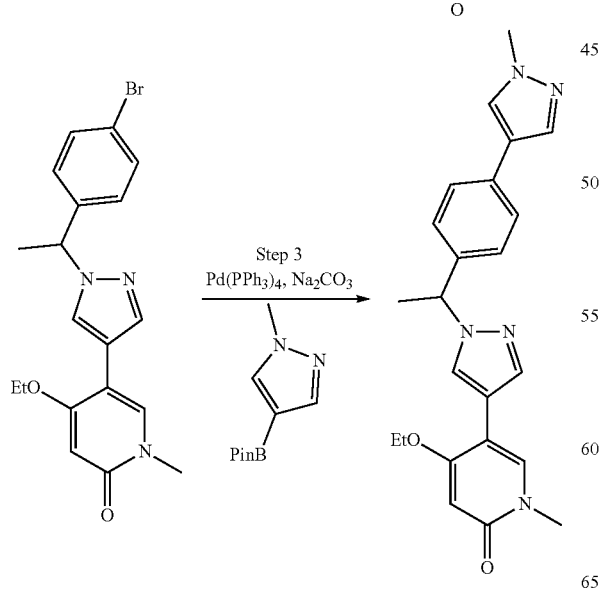

A mixture of 4-ethoxy-1-methyl-5-(1H-pyrazol-4-yl)-1H-pyridin-2-one (50 mg, 0.22 mmol), 1-bromo-4-(1-bromoethyl)-benzene (72 mg, 0.27 mmol) and K$_2$CO$_3$ (63 mg, 0.45 mmol) in DMF (5 mL) was heated to 60° C. overnight. The reaction was cooled to room temp, poured into aqueous NH$_4$Cl (5 mL), and extracted with DCM (5 mL×3). The organic layer was dried over Na$_2$SO$_4$, filtered, and the filtrate was concentrated in vacuum. The residue was purified by preparative-TLC, DCM:MeOH (30:1), to give 5-{1-[1-(4-bromo-phenyl)-ethyl]-1H-pyrazol-4-yl}-4-ethoxy-1-methyl-1H-pyridin-2-one (15 mg, 0.037 mmol) as yellow oil in 16% yield.

Step 3: 4-Ethoxy-1-methyl-5-(1-{1-[4-(1-methyl-1H-pyrazol-4-yl)-phenyl]-ethyl}-1H-pyrazol-4-yl)-1H-pyridin-2-one

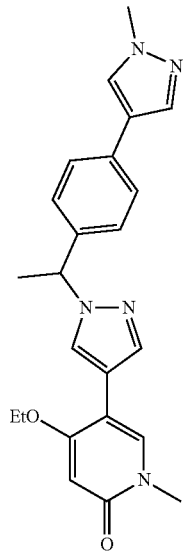 [SMILES: CCOc1cc(=O)n(C)cc1-c1cnn(C(C)c2ccc(-c3cnn(C)c3)cc2)c1]

A mixture of 5-{1-[1-(4-bromo-phenyl)-ethyl]-1H-pyrazol-4-yl}-4-ethoxy-1-methyl-1H-pyridin-2-one (26 mg, 0.06 mmol) 1-methyl-4-(4,4,5,5-tetramethyl-[1,3,2]dioxaborolan-2-yl)-1H-pyrazole (16.2 mg, 0.04 mmol), Na$_2$CO$_3$ (14 mg, 0.12 mmol) and Pd(PPh$_3$)$_4$ in dioxane/water (2 mL/0.2 mL) was stirred at 130° C. for 3 hr in a microwave. The reaction was cooled to room temp, poured into aqueous NH$_4$Cl (5 mL), and extracted with DCM (5 ml×3). The organic layer was dried over Na$_2$SO$_4$, filtered, and the filtrate was concentrated under vacuum. The residue was purified by preparative TLC (DCM:MeOH (20:1), to give 4-ethoxy-1-methyl-5-(1-{1-[4-(1-methyl-1H-pyrazol-4-yl)-phenyl]-ethyl}-1H-pyrazol-4-yl)-1H-pyridin-2-one (8 mg, 0.02 mmol) as colorless oil in 31% yield. $^1$H NMR (400 MHz, MeOD): δ 7.94 (d, J=3.6 Hz, 2H), 7.84 (s, 1H), 7.81 (d, J=8.4 Hz, 2H), 7.54 (d, J=8.0 Hz, 2H), 7.26 (d, J=8.0 Hz, 2H), 5.98 5.98 (s, 1H), 5.58 (q, J=6.8 Hz, 1H), 4.12 (q, J=7.2 Hz, 2H), 3.91 (s, 3H), 3.52 (s, 3H), 1.91 (d, J=7.2 Hz, 3H), 1.42 (t, J=6.4 Hz, 3H). LCMS (M+H)$^+$ 404.

Examples 101-105 in were prepared using the appropriate halide and boronic acid derivative in a similar multi-step manner as Example 100, and are presented in Table 5.

TABLE 5

| Example | Structure | IUPAC Name | $^1$HNMR(ppm) | MS (M + H) |
|---|---|---|---|---|
| 101 | 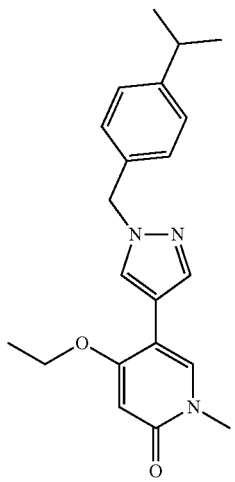 [SMILES: CCOc1cc(=O)n(C)cc1-c1cnn(Cc2ccc(C(C)C)cc2)c1] | 4-ethoxy-5-[1-(4-isopropyl-benzyl)-1H-pyrazol-4-yl]-1-methyl-1H-pyridin-2-one | (CD$_3$OD, 400 MHz) δ 7.89 (s, 1H), 7.86 (s, 1H), 7.80 (s, 1H), 7.24-7.18 (m, 4H), 6.02 (s, 1H), 5.30 (s, 2H), 4.11 (q, J = 6.8 Hz, 2H), 3.54 (s, 3H), 2.92-2.85 (m, 1H), 1.41 (t, J = 6.8 Hz, 3H), 1.22 (d, J = 7.2 Hz, 6H) | 352 |

TABLE 5-continued

| Example | Structure | IUPAC Name | ¹HNMR(ppm) | MS (M + H) |
|---|---|---|---|---|
| 102 | 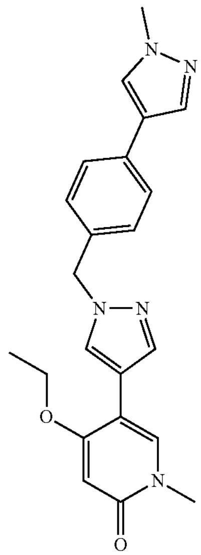 [SMILES: CCOc1cc(=O)n(C)cc1-c1cnn(Cc2ccc(-c3cnn(C)c3)cc2)c1] | 4-ethoxy-1-methyl-5-{1-[4-(1-methyl-1H-pyrazol-4-yl)-benzyl]-1H-pyrazol-4-yl}-1H-pyridin-2-one | (CD$_3$OD, 400 MHz) δ 7.94 (d, J = 4.0 Hz, 2H), 7.84 (s, 1H), 7.80 (d, J = 4.8 Hz, 2H), 7.53 (d, J = 8.0 Hz, 2H), 7.26 (d, J = 8.0 Hz, 2H), 5.99 (s, 1H), 5.30 (s, 2H), 4.10 (q, J = 6.8 Hz, 2H), 3.91 (s, 3H), 3.52 (s, 3H), 1.42 (t, J = 7.0 Hz, 3H) | 390 |
| 103 | 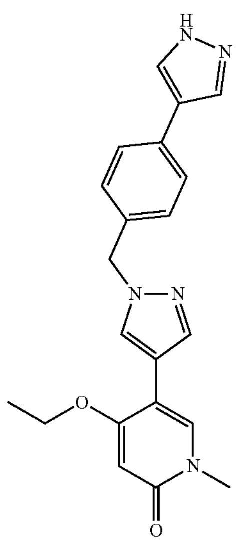 [SMILES: CCOc1cc(=O)n(C)cc1-c1cnn(Cc2ccc(-c3cn[nH]c3)cc2)c1] | 4-ethoxy-1-methyl-5-{1-[4-(1H-pyrazol-4-yl)-benzyl]-1H-pyrazol-4-yl}-1H-pyridin-2-one | (CD$_3$OD, 400 MHz) δ 7.94 (br, 3H), 7.85 (s, 1H), 7.81 (s, 1H), 7.58 (d, J = 8.4 Hz, 2H), 7.27 (d, J = 7.6 Hz, 2H), 5.99 (s, 1H), 5.34 (s, 2H), 4.11 (q, J = 6.8 Hz, 2H), 3.53 (s, 3H), 1.42 (t, J = 7.2 Hz, 3H) | 376 |
| 104 | 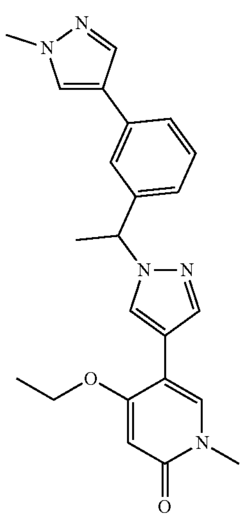 | 4-ethoxy-1-methyl-5-(1-(1-(3-(1-methyl-1H-pyrazol-4-yl)phenyl)ethyl)-1H-pyrazol-4-yl)pyridin-2(1H)-one | (CD$_3$OD, 400 MHz) δ 7.97 (s, 1H), 7.93 (s, 1H), 7.84 (s, 1H), 7.81 (s, 1H), 7.78 (s, 1H), 7.48-7.46 (m, 2H), 7.34-7.31 (m, 1H), 7.11-7.09 (m, 1H), 5.98 (s, 1H), 5.60-5.59 (m, 1H), 4.11 (q, J = 6.8 Hz, 2H), 3.90 (s, 3H), 3.51 (s, 3H), 1.92 (d, J = 7.1 Hz, 3H), 1.40 (t, J = 7.2 Hz, 3H) | 403 |

TABLE 5-continued

| Example | Structure | IUPAC Name | ¹HNMR(ppm) | MS (M + H) |
|---|---|---|---|---|
| 105 | 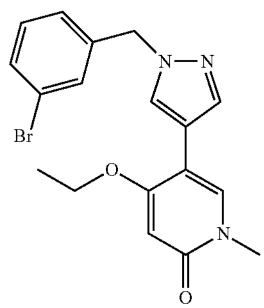 [SMILES: CCOc1cc(=O)n(C)cc1-c1cnn(Cc2cccc(Br)c2)c1] | 5-(1-(3-bromo-benzyl)-1H-pyrazol-4-yl)-4-ethoxy-1-methyl-pyridin-2(1H)-one | (CD$_3$OD, 400 MHz) 7.98 (s, 1H), 7.85 (s, 1H), 7.82 (s, 1H), 7.46 (d, J = 7.6 Hz, 1H), 7.41 (s, 1H), 7.29-7.24 (m, 2H), 6.00 (s, 1H), 5.35 (s, 2H), 4.12 (q, J = 7.2 Hz, 2H), 3.53 (s, 3H), 1.45 (t, J = 7.2 Hz, 3H) | 388 |

Example 106: 5-(1-benzyl-1H-pyrazol-4-yl)-1-methyl-4-o-tolyl-1H-pyridin-2-one

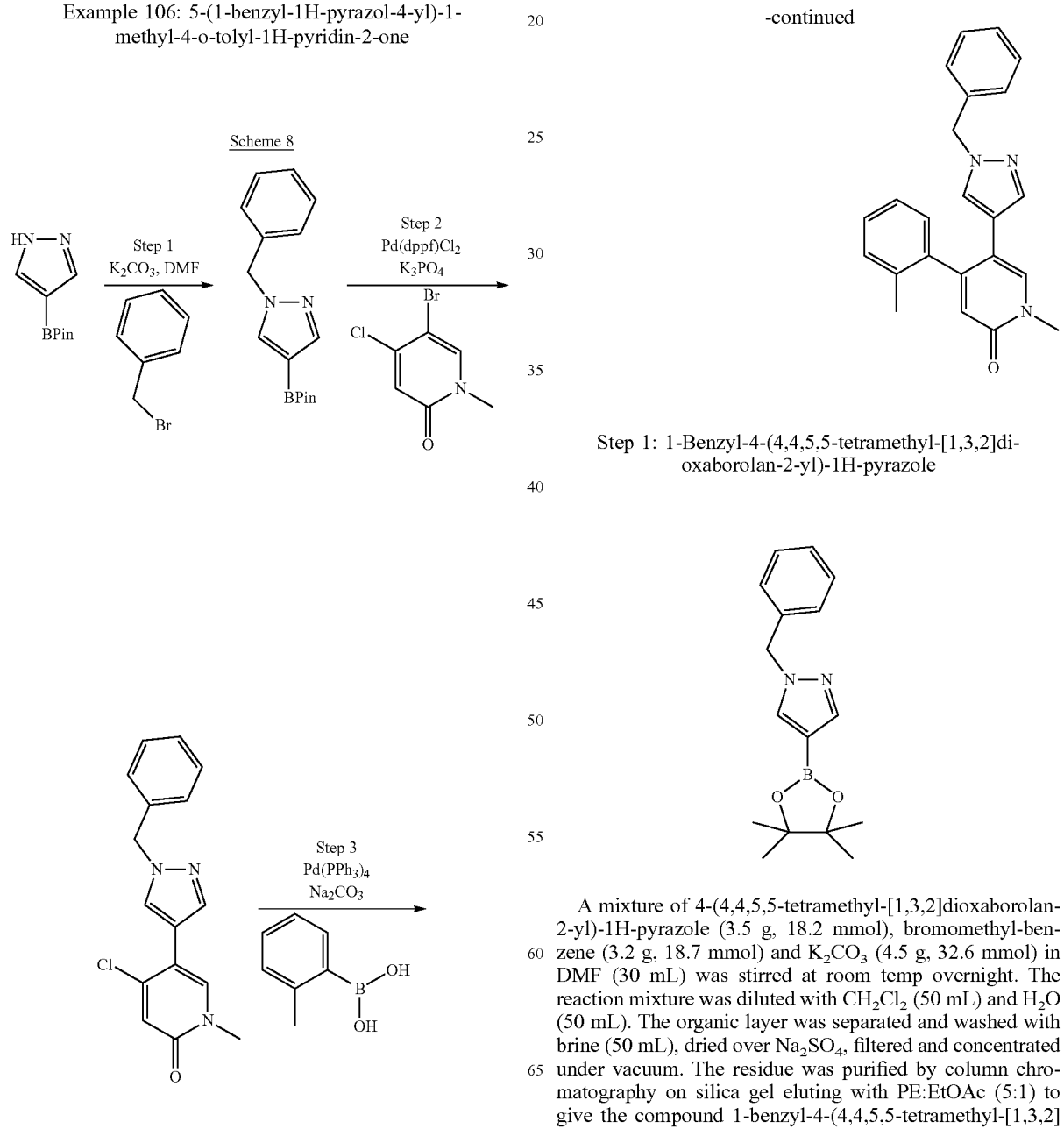

Step 1: 1-Benzyl-4-(4,4,5,5-tetramethyl-[1,3,2]dioxaborolan-2-yl)-1H-pyrazole

A mixture of 4-(4,4,5,5-tetramethyl-[1,3,2]dioxaborolan-2-yl)-1H-pyrazole (3.5 g, 18.2 mmol), bromomethyl-benzene (3.2 g, 18.7 mmol) and K$_2$CO$_3$ (4.5 g, 32.6 mmol) in DMF (30 mL) was stirred at room temp overnight. The reaction mixture was diluted with CH$_2$Cl$_2$ (50 mL) and H$_2$O (50 mL). The organic layer was separated and washed with brine (50 mL), dried over Na$_2$SO$_4$, filtered and concentrated under vacuum. The residue was purified by column chromatography on silica gel eluting with PE:EtOAc (5:1) to give the compound 1-benzyl-4-(4,4,5,5-tetramethyl-[1,3,2]

dioxaborolan-2-yl)-1H-pyrazole (2.8 g, 9.8 mmol) as a light yellow solid in 54% yield. ¹H NMR (400 MHz, CDCl₃): δ 7.81 (s, 1H), 7.66 (s, 1H), 7.37-7.29 (m, 3H), 7.24-7.22 (m, 2H), 5.30 (s, 2H), 1.29 (s, 12H). LCMS (M+H)⁺ 285.

Step 2: 5-(1-Benzyl-1H-pyrazol-4-yl)-4-chloro-1-methyl-1H-pyridin-2-one

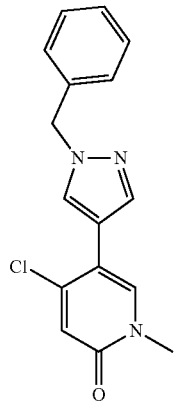 [SMILES: Cn1cc(-c2cnn(Cc3ccccc3)c2)c(Cl)cc1=O]

A mixture of 1-benzyl-4-(4,4,5,5-tetramethyl-[1,3,2]dioxaborolan-2-yl)-1H-pyrazole (2.4 g, 8.5 mmol), 5-bromo-4-chloro-1-methyl-1H-pyridin-2-one (1.9 g, 8.5 mmol) Pd(dppf)Cl₂ (622 mg, 0.85 mmol) and K₃PO₄ (4.7 g, 21.2 mmol) in dioxane/H₂O (20/4 mL) was stirred at 80° C. for 4 hr. Then the reaction mixture was diluted with DCM (50 mL) and H₂O (50 mL); the organic layer was separated and washed with brine (50 mL), dried over Na₂SO₄, filtered and concentrated in vacuum. The residue was purified by column chromatography on silica gel eluting with PE:EtOAc (1:3) to give the compound 5-(1-benzyl-1H-pyrazol-4-yl)-4-chloro-1-methyl-H-pyridin-2-one (1.2 g, 0.4 mmol) as a gray solid in 47% yield. LCMS (M+H)⁺ 300.

Step 3: 5-(1-Benzyl-1H-pyrazol-4-yl)-1-methyl-4-o-tolyl-1H-pyridin-2-one

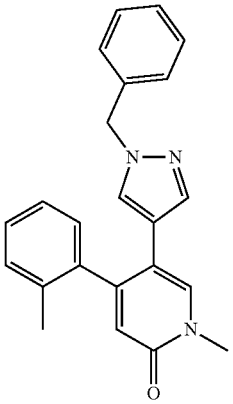 [SMILES: Cc1ccccc1-c1cc(=O)n(C)cc1-c1cnn(Cc2ccccc2)c1]

A mixture of 5-(1-benzyl-1H-pyrazol-4-yl)-4-chloro-1-methyl-H-pyridin-2-one (50 mg, 0.167 mmol), 2-tolylboronic acid (28 mg, 0.206 mmol), Pd(PPh₃)₄ (20 mg, 0.017 mmol), and Na₂CO₃ (44 mg, 0.418 mmol) in dioxane (5 mL) and H₂O (1 mL) was heated to 90° C. for 5 hr under N₂. The mixture was then diluted with CH₂Cl₂ (60 mL) and H₂O (50 mL); the organic phase was washed with brine (60 mL), dried over Na₂SO₄, filtered and concentrated in vacuum. The residue was purified by preparative-TLC to give the compound 5-(1-benzyl-H-pyrazol-4-yl)-1-methyl-4-o-tolyl-1H-pyridin-2-one (57 mg, 0.160 mmol) as a brown oil in 96% yield. ¹H NMR (400 MHz, DMSO-d6): δ 7.95 (s, 1H), 7.30-7.22 (m, 5H), 7.16 (d, J=7.2 Hz, 1H), 7.10 (d, J=7.2 Hz, 1H), 7.01 (d, J=6.0 Hz, 2H), 6.96 (d, J=6.4 Hz, 2H), 6.19 (s, 1H), 5.13 (s, 2H), 3.51 (s, 3H), 1.90 (s, 3H). LCMS (M+H)⁺ 356.

Examples 107-164 were prepared using the appropriate boronic acid derivative and substituted pyrazole in a similar multi-step manner as Example 106, and these compounds are shown in Table 6:

TABLE 6

| Example | Structure | IUPAC Name | ¹HNMR (ppm) | MS (M + H) |
|---|---|---|---|---|
| 107 | 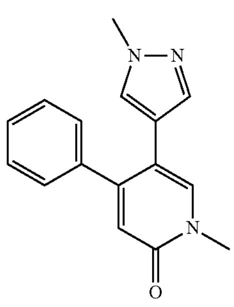 [SMILES: Cn1cc(-c2cn(C)c(=O)cc2-c2ccccc2)cn1] | 1-methyl-5-(1-methyl-1H-pyrazol-4-yl)-4-phenylpyridin-2(1H)-one | (CD₃OD, 400 MHz) δ 7.78 (s, 1H), 7.37-7.35 (m, 3H), 7.21-7.19 (m, 3H), 7.18 (s, 1H), 6.59 (s, 1H), 3.75 (s, 3H), 3.64 (s, 3H) | 266 |

TABLE 6-continued

| Example | Structure | IUPAC Name | ¹HNMR (ppm) | MS (M + H) |
|---|---|---|---|---|
| 108 | 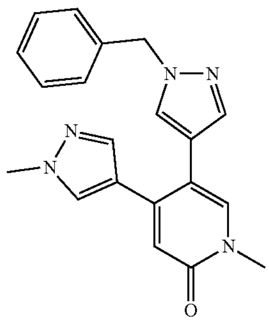 | 5-(1-benzyl-1H-pyrazol-4-yl)-1-methyl-4-(1-methyl-1H-pyrazol-4-yl)pyridin-2(1H)-one | (CD₃OD, 400 MHz) δ 7.63 (s, 1H), 7.58 (s, 1H), 7.42 (s, 1H), 7.39 (s, 1H), 7.36-7.25 (m, 6H), 6.61 (s, 1H), 5.33 (s, 2H), 3.76 (s, 3H), 3.57 (s, 3H) | 346 |
| 109 | 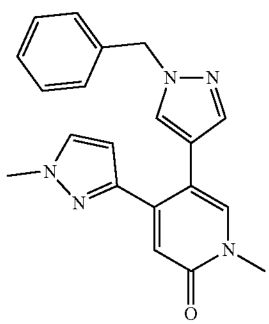 | 5-(1-benzyl-1H-pyrazol-4-yl)-1-methyl-4-(1-methyl-1H-pyrazol-3-yl)pyridin-2(1H)-one | (CD₃OD, 400 MHz) δ 7.94 (s, 1H), 7.50 (s, 1H), 7.34-7.30 (m, 3H), 7.28 (s, 1H), 7.20-7.12 (m, 3H), 6.56 (s, 1H), 6.36 (s, 1H), 5.21 (s, 2H), 3.64 (s, 3H), 3.35 (s, 3H) | 346 |
| 110 | 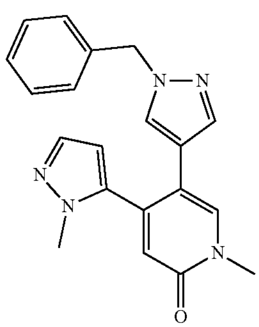 [SMILES: Cn1nccc1-c1cc(=O)n(C)cc1-c1cnn(Cc2ccccc2)c1] | 5-(1-benzyl-1H-pyrazol-4-yl)-1-methyl-4-(1-methyl-1H-pyrazol-5-yl)pyridin-2(1H)-one | (CD₃OD, 400 MHz) δ 7.94 (s, 1H), 7.50 (s, 1H), 7.33-7.31 (m, 3H), 7.21 (s, 1H), 7.15-7.12 (m, 3H), 6.56 (s, 1H), 6.36 (d, J = 1.9 Hz, 1H), 5.22 (s, 2H), 3.65 (s, 3H), 3.35 (s, 3H) | 346 |
| 111 | 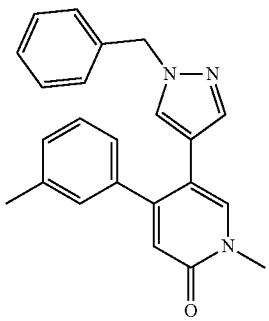 | 5-(1-benzyl-1H-pyrazol-4-yl)-1-methyl-4-(m-tolyl)-pyridin-2(1H)-one | (DMSO-d6, 400 MHz) δ 7.86 (s, 1H), 7.33-7.27 (m, 3H), 7.24-7.16 (m, 3H), 7.18 (d, J = 7.2 Hz, 1H), 7.04 (d, J = 6.4 Hz, 2H), 6.99 (s, 1H) 6.94 (d, J = 7.2 Hz, 1H), 6.28 (s, 1H), 5.19 (s, 2H), 3.49 (s, 3H), 2.32 (s, 3H). | 356 |

TABLE 6-continued

| Example | Structure | IUPAC Name | ¹HNMR (ppm) | MS (M + H) |
|---|---|---|---|---|
| 112 | 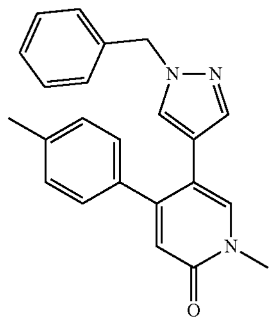 | 5-(1-benzyl-1H-pyrazol-4-yl)-1-methyl-4-(p-tolyl)pyridin-2(1H)-one | (CD₃OD, 400 MHz) δ 7.78 (s, 1H), 7.33-7.27 (m, 3H), 7.22 (s, 1H), 7.12-7.03 (m, 7H), 6.47 (s, 1H), 5.18 (s, 2H), 3.62 (s, 3H), 2.33 (s, 3H) | 356 |
| 113 | 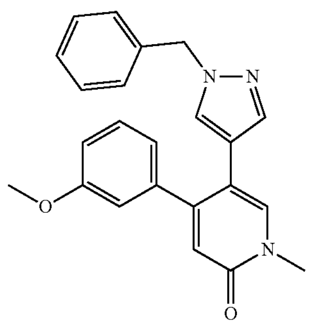 | 5-(1-benzyl-1H-pyrazol-4-yl)-4-(3-methoxyphenyl)-1-methyl-pyridin-2(1H)-one | (CD₃OD, 400 MHz) δ 7.79 (s, 1H), 7.32-7.21 (m, 5H), 7.17 (s, 1H), 7.08-7.06 (m, 2H), 6.90 (dd, J = 8.4 Hz, 2.0 Hz, 1H), 6.76 (d, J = 8.0 Hz, 1H), 6.66 (s, 1H), 6.50 (s, 1H), 5.19 (s, 2H), 3.63 (s, 3H), 3.63 (s, 3H) | 372 |
| 114 | 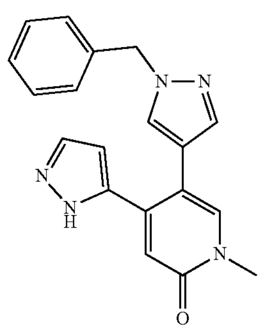 [SMILES: Cn1cc(-c2cnn(Cc3ccccc3)c2)c(-c2ccn[nH]2)cc1=O] | 5-(1-benzyl-1H-pyrazol-4-yl)-1-methyl-4-(1H-pyrazol-5-yl)pyridin-2(1H)-one | (DMSO-d₆, 400 MHz) δ 13.0 (s, 1H), 7.74 (s, 1H), 7.68 (s, 1H), 7.58 (s, 1H), 7.37-7.18 (m, 5H), 6.58 (s, 1H), 5.90 (s, 1H), 5.27 (s, 2H), 3.45 (s, 3H) | 332 |
| 115 | 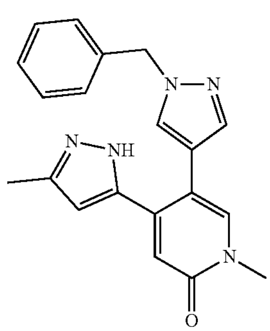 | 5-(1-benzyl-1H-pyrazol-4-yl)-1-methyl-4-(3-methyl-1H-pyrazol-5-yl) pyridin-2(1H)-one | (CD₃OD, 400 MHz) δ 7.73 (s, 1H), 7.42 (s, 1H), 7.34-7.19 (m, 5H), 6.71 (s, 1H), 5.72 (s, 1H), 5.28 (s, 2H), 3.60 (s, 3H), 2.18 (s, 3H) | 346 |

TABLE 6-continued

| Example | Structure | IUPAC Name | ¹HNMR (ppm) | MS (M + H) |
|---|---|---|---|---|
| 116 | 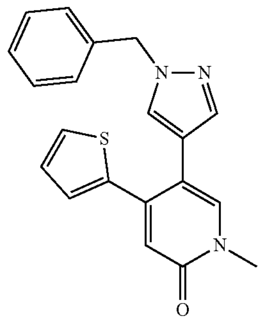 [SMILES: Cn1cc(-c2cnn(Cc3ccccc3)c2)c(-c2cccs2)cc1=O] | 5-(1-benzyl-1H-pyrazol-4-yl)-1-methyl-4-(thiophen-2-yl)pyridi-2(1H)-one | (CD₃OD, 400 MHz) δ 7.69 (s, 1H), 7.47-7.44 (m, 2H), 7.34-7.28 (m, 4H), 7.21-7.19 (m, 2H), 7.00-6.95 (m, 2H), 6.66 (s, 1H), 5.28 (s, 2H), 3.58 (s, 3H) | 348 |
| 117 | 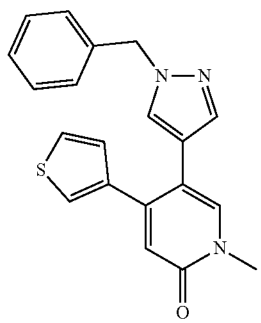 | 5-(1-benzyl-1H-pyrazol-4-yl)-1-methyl-4-(thiophen-3-yl)pyridin-2(1H)-one | (CD₃OD, 400 MHz) δ 7.74 (s, 1H), 7.34-7.28 (m, 7H), 7.16-7.15 (m, 2H), 6.83-6.81 (m, 1H), 6.58 (s, 1H), 5.24 (s, 2H), 3.61 (s, 3H) | 348 |
| 118 | 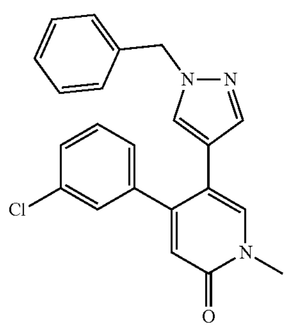 [SMILES: Cn1cc(-c2cnn(Cc3ccccc3)c2)c(-c2cccc(Cl)c2)cc1=O] | 5-(1-benzyl-1H-pyrazol-4-yl)-4-(3-chlorophenyl)-1-methyl-pyridin-2(1H)-one | (CD₃OD, 400 MHz) δ 7.81 (s, 1H), 7.38-7.28 (m, 5H), 7.23 (s, 1H), 7.20 (s, 2H), 7.12 (d, J = 7.2 Hz, 1H), 7.07 (d, J = 7.2 Hz, 2H), 6.50 (s, 1H), 5.21 (s, 2H), 3.63 (s, 3H) | 377 |
| 119 | 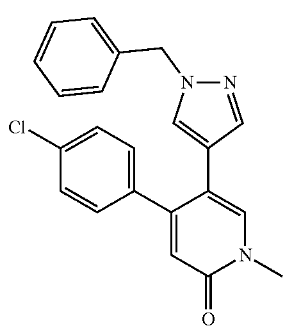 [SMILES: Cn1cc(-c2cnn(Cc3ccccc3)c2)c(-c2ccc(Cl)cc2)cc1=O] | 5-(1-benzyl-1H-pyrazol-4-yl)-4-(4-chlorophenyl)-1-methyl-pyridin-2(1H)-one | (CD₃OD, 400 MHz) δ 7.79 (s, 1H), 7.32-7.26 (m, 6H), 7.15-7.13 (m, 3H), 7.07 (d, J = 7.2 Hz, 2H), 6.49 (s, 1H), 5.19 (s, 2H), 3.62 (s, 3H) | 377 |

TABLE 6-continued

| Example | Structure | IUPAC Name | ¹HNMR (ppm) | MS (M + H) |
|---------|-----------|------------|-------------|------------|
| 120 | 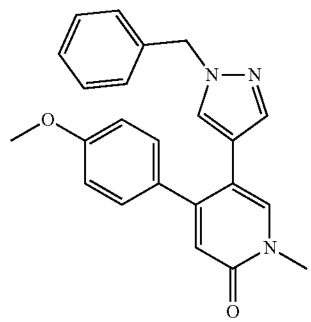 | 5-(1-benzyl-1H-pyrazol-4-yl)-4-(4-methoxyphenyl)-1-methyl-pyridin-2(1H)-one | (CD₃OD, 400 MHz) δ 7.76 (s, 1H), 7.33-7.28 (m, 3H), 7.25 (s, 1H), 7.15 (s, 1H), 7.10-7.08 (m, 4H), 6.84 (d, J = 8.8 Hz, 2H), 6.47 (s, 1H), 5.12 (s, 2H), 3.79 (s, 3H), 3.61 (s, 3H) | 372 |
| 121 | 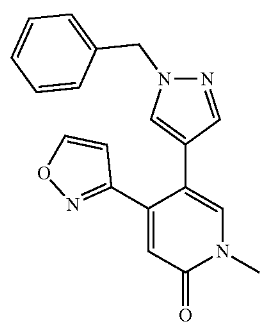 [SMILES: Cn1cc(-c2cnn(Cc3ccccc3)c2)c(-c2ccon2)cc1=O] | 5-(1-benzyl-1H-pyrazol-4-yl)-4-(isoxazol-3-yl)-1-methyl-pyridin-2(1H)-one | (CD₃OD, 400 MHz) δ 8.58 (s, 1H), 8.27 (s, 1H), 7.72 (s, 1H), 7.61 (s, 1H), 7.41 (s, 1H), 7.35-7.30 (m, 3H), 7.23 (d, J = 7.2 Hz, 2H), 6.69 (s, 1H), 5.33 (s, 2H), 3.59 (s, 3H) | 333 |
| 122 | 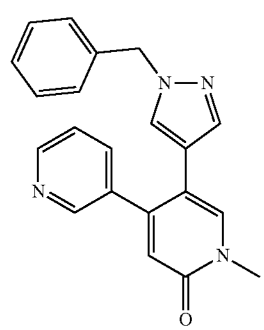 [SMILES: Cn1cc(-c2cnn(Cc3ccccc3)c2)c(-c2cccnc2)cc1=O] | 5'-(1-benzyl-1H-pyrazol-4-yl)-1'-methyl-[3,4'-bipyridin]-2'(1'H)-one | (CD₃OD, 400 MHz) δ 8.72 (d, J = 5.2 Hz, 1H), 8.66 (s, 1H), 8.15-8.12 (m, 1H), 7.89 (s, 1H), 7.76-7.73 (m, 1H), 7.35-7.30 (m, 4H), 7.27 (s, 1H), 7.13-7.11 (m, 2H), 6.66 (s, 1H), 5.22 (s, 2H), 3.65 (s, 3H) | 343 |
| 123 | 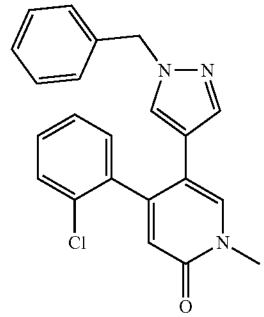 [SMILES: Cn1cc(-c2cnn(Cc3ccccc3)c2)c(-c2ccccc2Cl)cc1=O] | 5-(1-benzyl-1H-pyrazol-4-yl)-4-(2-chlorophenyl)-1-methyl-pyridin-2(1H)-one | (CD₃OD, 400 MHz) δ 7.87 (s, 1H), 7.32-7.22 (m, 7H), 7.20 (s, 1H), 7.04 (s, 1H), 7.00-6.98 (m, 2H), 6.44 (s, 1H), 5.16 (s, 2H), 3.66 (s, 3H) | 377 |

TABLE 6-continued

| Example | Structure | IUPAC Name | ¹HNMR (ppm) | MS (M + H) |
| --- | --- | --- | --- | --- |
| 124 | 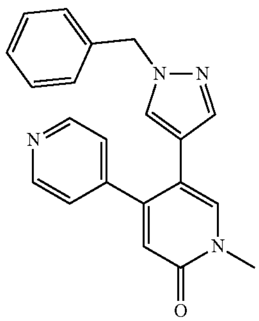 [SMILES: Cn1cc(-c2cnn(Cc3ccccc3)c2)c(-c2ccncc2)cc1=O] | 5-(1-benzyl-1H-pyrazol-4-yl)-1-methyl-[4,4'-bipyridin]-2(1H)-one | (CD₃OD, 400 MHz) δ 8.47 (d, J = 6.0 Hz, 2H), 7.85 (s, 1H), 7.32-7.25 (m, 7H), 7.07 (d, J = 7.6 Hz, 2H), 6.55 (s, 1H), 5.21 (s, 2H), 3.64 (s, 3H) | 343 |
| 125 | 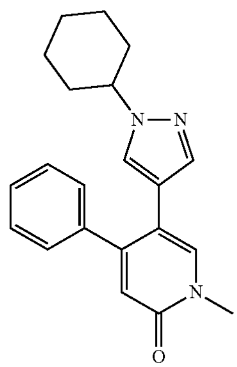 [SMILES: Cn1cc(-c2cnn(C3CCCCC3)c2)c(-c2ccccc2)cc1=O] | 5-(1-cyclohexyl-1H-pyrazol-4-yl)-1-methyl-4-phenylpyridin-2(1H)-one | (CD₃OD, 400 MHz) δ 7.81 (s, 1H), 7.39-7.34 (m, 3H), 7.21-7.18 (m, 2H), 7.14 (s, 1H), 7.10 (s, 1H), 6.51 (s, 1H), 4.00-3.94 (m, 1H), 3.65 (s, 3H), 1.96-1.93 (m, 2H), 1.84-1.81 (m, 2H), 1.71-1.68 (m, 1H), 1.62-1.51 (m, 2H), 1.45-1.35 (m, 2H), 1.27-1.20 (m, 1H) | 334 |
| 126 | 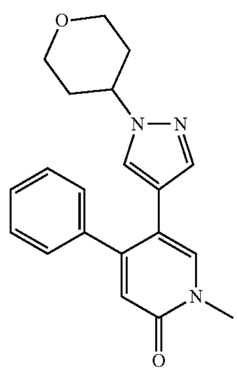 [SMILES: Cn1cc(-c2cnn(C3CCOCC3)c2)c(-c2ccccc2)cc1=O] | 1-methyl-4-phenyl-5-(1-(tetrahydro-2H-pyran-4-yl)-1H-pyrazol-4-yl)pyridin-2(1H)-one | (CD₃OD, 400 MHz) δ 7.82 (s, 1H), 7.39-7.34 (m, 3H), 7.11 (s, 1H), 6.51 (s, 1H), 4.27-4.23 (m, 1H), 4.00-3.96 (m, 2H), 3.69 (s, 3H), 3.52-3.46 (m, 2H), 1.91-1.86 (m, 4H) | 336 |
| 127 | 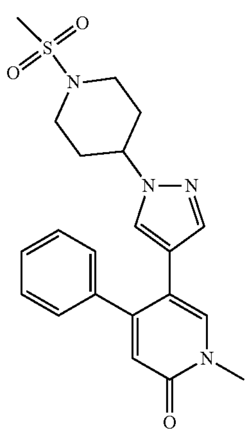 [SMILES: Cn1cc(-c2cnn(C3CCN(S(C)(=O)=O)CC3)c2)c(-c2ccccc2)cc1=O] | 1-methyl-5-(1-(1-(methyl-sulfonyl)-piperidin-4-yl)-1H-pyrazol-4-yl)-4-phenylpyridin-2(1H)-one | (DMSO-d6, 400 MHz) δ 7.88 (s, 1H), 7.39-7.35 (m, 3H), 7.27 (s, 1H), 7.19-7.17 (m, 2H), 6.99 (s, 1H), 6.31 (s, 1H), 4.20-4.13 (m, 1H), 3.59-3.56 (m, 2H), 3.49 (s, 3H), 2.91-2.84 (m, 5H), 2.00-1.96 (m, 2H), 1.84-1.74 (m, 2H) | 413 |

TABLE 6-continued

| Example | Structure | IUPAC Name | $^1$HNMR (ppm) | MS (M + H) |
|---|---|---|---|---|
| 128 | 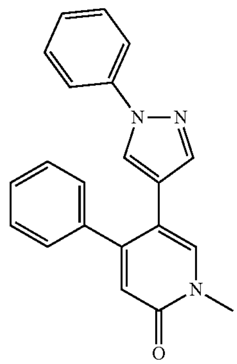 [SMILES: Cn1cc(-c2cnn(-c3ccccc3)c2)c(-c2ccccc2)cc1=O] | 1-methyl-4-phenyl-5-(1-phenyl-1H-pyrazol-4-yl) pyridin-2(1H)-one | (CD$_3$OD, 400 MHz) δ 7.93 (s, 1H), 7.80 (s 1H), 7.57-7.55 (m, 2H), 7.46-7.40 (m, 5H), 7.31-7.26 (m, 3H), 7.22 (s, 1H), 6.54 (s, 1H), 3.67 (s, 3H) | 328 |
| 129 | 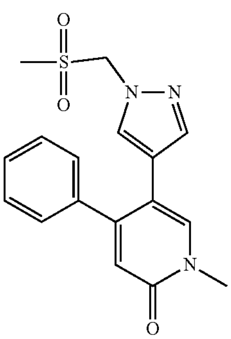 [SMILES: Cn1cc(-c2cnn(CS(C)(=O)=O)c2)c(-c2ccccc2)cc1=O] | 1-methyl-5-(1-((methyl-sulfonyl)-methyl)-1H-pyrazol-4-yl)-4-phenylpyridin-2(1H)-one | (DMSO-d6, 400 MHz) δ 7.92 (s, 1H), 7.39-7.33 (m, 4H), 7.20-7.17 (m, 3H), 6.32 (s, 1H), 5.62 (s, 2H), 3.51 (s, 3H), 2.89 (s, 3H) | 344 |
| 130 | 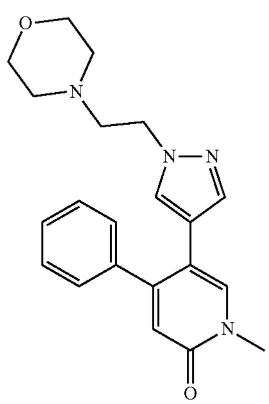 [SMILES: Cn1cc(-c2cnn(CCN3CCOCC3)c2)c(-c2ccccc2)cc1=O] | 1-methyl-5-(1-(2-morpholinoethyl)-1H-pyrazol-4-yl)-4-phenylpyridin-2(1H)-one | (CD$_3$OD, 400 MHz) δ 7.80 (s, 1H), 7.39-7.34 (m, 3H), 7.25 (s, 1H), 7.22-7.20 (m, 2H), 7.11 (s, 1H), 6.50 (s, 1H), 4.15-4.12 (m, 2H), 3.65 (s, 3H), 3.63-3.60 (m, 4H), 2.67 (t, J = 6.4 Hz, 2H), 2.40-2.38 (m, 4H). | 365 |
| 131 | 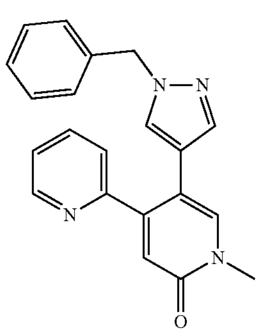 [SMILES: Cn1cc(-c2cnn(Cc3ccccc3)c2)c(-c2ccccn2)cc1=O] | 5'-(1-benzyl-1H-pyrazol-4-yl)-1'-methyl-[2,4'-bipyridin]-2'(1'H)-one | (CD$_3$OD, 400 MHz) δ 8.50 (d, J = 5.2 Hz, 1H), 7.86 (s, 1H), 7.79-7.75 (m, 1H), 7.41-7.37 (m, 1H), 7.33-7.28 (m, 4H), 7.18 (s, 1H), 7.15 (s, 1H), 7.09-7.07 (m, 2H), 6.61 (s, 1H), 5.19 (s, 2H), 3.65 (s, 3H). | |

TABLE 6-continued

| Example | Structure | IUPAC Name | ¹HNMR (ppm) | MS (M + H) |
|---|---|---|---|---|
| 132 | 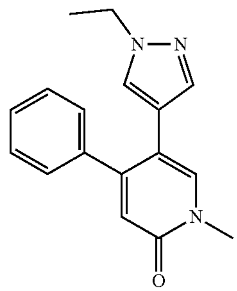 [SMILES: CCn1cc(-c2cn(C)c(=O)cc2-c2ccccc2)cn1] | 5-(1-ethyl-1H-pyrazol-4-yl)-1-methyl-4-phenylpyridin-2(1H)-one | (CD$_3$OD, 400 MHz) δ 7.80 (s, 1H), 7.39-7.34 (m, 3H), 7.21-7.17 (s, 3H), 7.06 (s, 1H), 6.50 (s, 1H), 4.03 (q, J = 7.2 Hz, 2H), 3.64 (s, 3H), 1.32 (t, J = 7.2 Hz, 3H) | 280 |
| 133 | 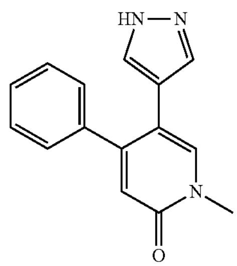 [SMILES: Cn1cc(-c2cn[nH]c2)c(-c2ccccc2)cc1=O] | 1-methyl-4-phenyl-5-(1H-pyrazol-4-yl)pyridin-2(1H)-one | (CD$_3$OD, 400 MHz) δ 7.83 (s, 1H), 7.37-7.35 (m, 3H), 7.22-7.19 (m, 4H), 6.51 (s, 1H), 3.65 (s, 3H) | 252 |
| 134 | 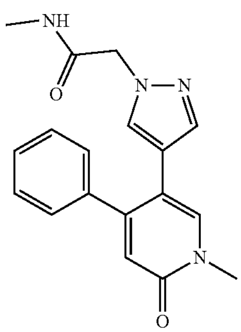 | N-methyl-2-(4-(1-methyl-6-oxo-4-phenyl-1,6-dihydropyridin-3-yl)-1H-pyrazol-1-yl) acetamide | (CD$_3$OD, 400 MHz) δ 7.83 (s, 1H), 7.37-7.35 (m, 3H), 7.28 (s, 1H), 7.24-7.21 (m, 2H), 7.07 (s, 1H), 6.51 (s, 1H), 4.70 (s, 2H), 3.65 (s, 3H), 2.73 (s, 3H) | 333 |
| 135 | 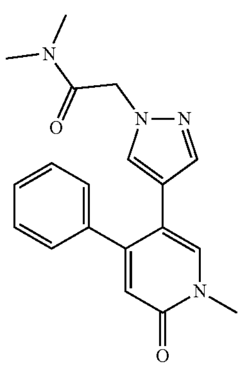 | N,N-dimethyl-2-(4-(1-methyl-6-oxo-4-phenyl-1,6-dihydropyridin-3-yl)-1H-pyrazol-1-yl)acetamide | (CD$_3$OD, 400 MHz) δ 7.83 (s, 1H), 7.37-7.35 (m, 3H), 7.25-7.22 (m, 3H), 7.06 (s, 1H), 6.51 (s, 1H), 4.99 (s, 2H), 3.65 (s, 3H), 3.04 (s, 3H), 2.94 (s, 3H) | 337 |
| 136 | 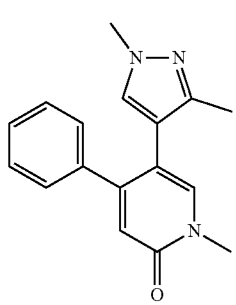 [SMILES: Cc1nn(C)cc1-c1cn(C)c(=O)cc1-c1ccccc1] | 5-(1,3-dimethyl-1H-pyrazol-4-yl)-1-methyl-4-phenylpyridin-2(1H)-one | (CD$_3$OD, 400 MHz) δ 7.64 (s, 1H), 7.33-7.30 (m, 4H), 7.21-7.19 (m, 2H), 6.58 (s, 1H), 3.75 (s, 3H), 3.64 (s, 3H), 1.66 (s, 3H) | 280 |

TABLE 6-continued

| Example | IUPAC Name | ¹HNMR (ppm) | MS (M + H) |
|---|---|---|---|
| 137 | 5-(1-isobutyl-1H-pyrazol-4-yl)-1-methyl-4-phenylpyridin-2(1H)-one | (CD$_3$OD, 400 MHz) δ 7.80 (s, 1H), 7.38-7.33 (m, 3H), 7.21-7.19 (m, 2H), 7.16 (s, 1H), 7.08 (s, 1H), 6.51 (s, 1H), 3.78 (d, J = 6.8 Hz, 2H), 3.65 (s, 3H), 2.04-1.99 (m, 1H), 0.78 (d, J = 6.8 Hz, 6H). | 308 |
| 138 | 5-(1-isopropyl-1H-pyrazol-4-yl)-1-methyl-4-phenylpyridin-2(1H)-one | (CDCl$_3$, 300 MHz) δ 7.38 (s, 1H), 7.35-7.34 (m, 3H), 7.24 (s, 1H), 7.18-7.15 (m, 2H), 6.67 (s, 1H), 6.62 (s, 1H), 4.36-4.31 (m, 1H), 1.35 (d, J = 6.6 Hz, 6H) | 294 |
| 139 | 1-methyl-4-phenyl-5-(1-propyl-1H-pyrazol-4-yl)pyridin-2(1H)-one | (CD$_3$OD, 300 MHz) δ 7.82 (s, 1H), 7.39-7.35 (m, 3H), 7.23-7.20 (m, 2H), 7.14 (s, 2H), 6.52 (s, 1H), 3.97 (t, J = 6.6 Hz, 2H), 3.66 (s, 3H), 1.78-1.70 (m, 2H), 0.79 (t, J = 6.9 Hz, 3H) | 294 |
| 140 | methyl 2-(4-(1-methyl-6-oxo-4-phenyl-1,6-dihydropyridin-3-yl)-1H-pyrazol-1-yl)acetate | (CD$_3$OD, 400 MHz) δ 7.82 (s, 1H), 7.37-7.35 (m, 3H), 7.26 (s, 1H), 7.22-7.20 (m, 2H), 7.11 (s, 1H), 6.51 (s, 1H), 4.91 (s, 2H), 3.72 (s, 3H), 3.64 (s, 3H) | 324 |

TABLE 6-continued

| Example | Structure | IUPAC Name | ¹HNMR (ppm) | MS (M + H) |
|---|---|---|---|---|
| 141 | 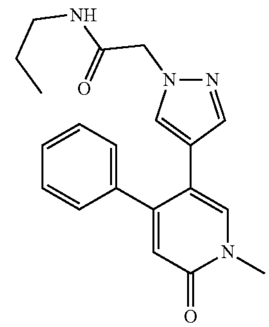 [SMILES: CCCNC(=O)Cn1cc(-c2cn(C)c(=O)cc2-c2ccccc2)cn1] | 2-(4-(1-methyl-6-oxo-4-phenyl-1,6-dihydro-pyridin-3-yl)-1H-pyrazol-1-yl)-N-propylacetamide | (CD$_3$OD, 400 MHz) δ 7.83 (s, 1H), 7.37-7.35 (m, 3H), 7.29 (s, 1H), 7.24-7.21 (m, 2H), 7.06 (s, 1H), 6.51 (s, 1H), 4.70 (s, 2H), 3.65 (s, 3H), 3.14 (t, J = 7.2 Hz, 2H), 1.52-1.48 (m, 2H), 0.92-0.88 (m, 3H) | 351 |
| 142 | 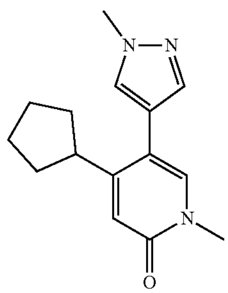 | 4-cyclopentyl-1-methyl-5-(1-methyl-1H-pyrazol-4-yl)pyridin-2(1H)-one | (CD$_3$OD, 400 MHz) δ 7.68 (s, 1H), 7.57 (s, 1H), 7.50 (s, 1H), 6.56 (s, 1H), 3.94 (s, 3H), 3.58 (s, 3H), 3.13-3.04 (m, 1H), 1.93-1.88 (m, 2H), 1.81-1.78 (m, 2H), 1.65-1.59 (m, 2H), 1.57-1.50 (m, 2H) | 258 |
| 143 | 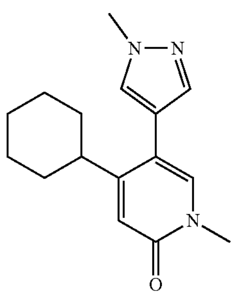 [SMILES: Cn1cc(-c2cn(C)c(=O)cc2C2CCCCC2)cn1] | 4-cyclohexyl-1-methyl-5-(1-methyl-1H-pyrazol-4-yl)pyridin-2 (1H)-one | (CD$_3$OD, 400 MHz) δ 7.66 (s, 1H), 7.52 (s, 1H), 7.47 (s, 1H), 6.47 (s, 1H), 3.93 (s, 3H), 3.54 (s, 3H), 2.61-2.58 (m, 1H), 1.79-1.70 (m, 5H), 1.35-1.23 (m, 5H) | 272 |
| 144 | 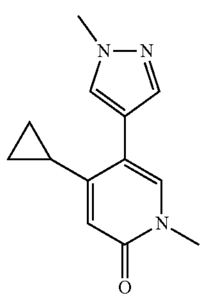 [SMILES: Cn1cc(-c2cn(C)c(=O)cc2C2CC2)cn1] | 4-cyclopropyl-1-methyl-5-(1-methyl-1H-pyrazol-4-yl)pyridin-2(1H)-one | (CD$_3$OD, 400 MHz) δ 7.77 (s, 1H), 7.60 (s, 1H), 7.59 (s, 1H), 6.11 (s, 1H), 3.93 (s, 3H), 3.55 (s, 3H), 1.88-1.84 (m, 1H), 1.05-1.00 (m, 2H), 0.81-0.77 (m, 2H) | 230 |
| 145 | 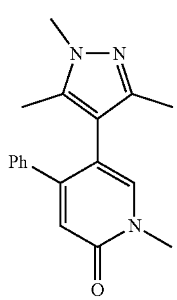 | 1-methyl-4-phenyl-5-(1,3,5-tri-methyl-1H-pyrazol-4-yl)pyridin-2(1H)-one | (CD$_3$OD, 400 MHz) δ 7.60 (s, 1H), 7.31-7.27 (m, 3H), 7.14-7.12 (m, 2H), 6.61 (s, 1H), 3.65 (s, 3H), 3.62 (s, 3H), 1.91 (s, 3H) 1.81 (s, 3H) | 294 |

TABLE 6-continued

| Example | Structure | IUPAC Name | ¹HNMR (ppm) | MS (M + H) |
|---|---|---|---|---|
| 146 | 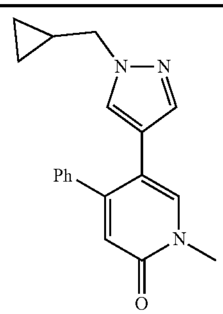 | 5-(1-(cyclopropyl-methyl)-1H-pyrazol-4-yl)-1-methyl-4-phenyl-pyridin-2(1H)-one | (CD₃OD, 400 MHz) δ 7.83 (s, 1H), 7.39-7.34 (m, 3H), 7.22-7.20 (m, 2H), 7.15 (d, J = 1.6 Hz, 2H), 6.51 (s, 1H), 3.84 (d, J = 6.8 Hz, 2H), 3.65 (s, 3H), 1.14-1.10 (m, 1H), 0.54-0.49 (m, 2H), 0.25-0.21 (m, 2H) | 306 |
| 147 | 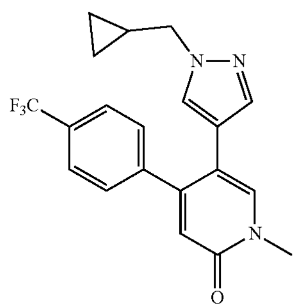 [SMILES: Cn1cc(-c2cnn(CC3CC3)c2)c(-c2ccc(C(F)(F)F)cc2)cc1=O] | 5-(1-cyclopropyl-methyl-1H-pyrazol-4-yl)-1-methyl-4-(4-tri-fluoromethyl-phenyl)-1H-pyridin-2-one | (CD₃OD, 400 MHz) δ 7.85 (s, 1H), 7.68 (d, J = 8.0 Hz, 2H), 7.42 (d, J = 8.0 Hz, 2H), 7.18 (s, 2H), 6.55 (s, 1H), 3.85 (d, J = 6.8 Hz, 2H), 3.66 (s, 3H), 1.14-1.10 (m, 1H), 0.52-0.48 (m, 2H), 0.23-0.19 (m, 2H) | 374 |
| 148 | 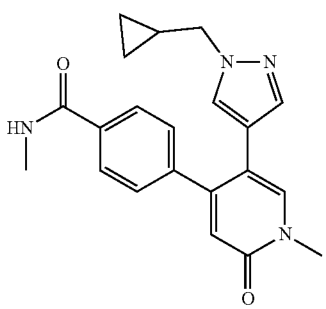 [SMILES: CNC(=O)c1ccc(-c2cc(=O)n(C)cc2-c2cnn(CC3CC3)c2)cc1] | 4-[5-(1-cyclopropyl-methyl-1H-pyrazol-4-yl)-1-methyl-2-oxo-1,2-dihydro-pyridin-4-yl]-N-methyl-benzamide | (CD₃OD, 300 MHz) δ 7.86-7.81 (m, 3H), 7.34 (d, J = 7.8 Hz, 2H), 7.19 (d, J = 6.9 Hz, 2H), 6.55 (s, 1H), 3.87-3.85 (m, 2H), 3.67 (s, 3H), 2.93 (s, 3H), 1.18-1.08 (m, 1H), 0.53-0.50 (m, 2H), 0.25-0.23 (m, 2H) | 363 |
| 149 | 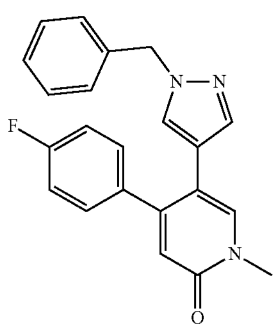 [SMILES: Cn1cc(-c2cnn(Cc3ccccc3)c2)c(-c2ccc(F)cc2)cc1=O] | 5-(1-benzyl-1H-pyrazol-4-yl)-4-(4-fluorophenyl)-1-methyl-pyridin-2(1H)-one | (DMSO-d₆, 400 MHz) δ 7.85 (s, 1H), 7.32-7.29 (m, 3H), 7.22-7.03 (m, 8H), 6.32 (s, 1H), 5.20 (s, 2H), 3.48 (s, 3H) | 360 |
| 150 | 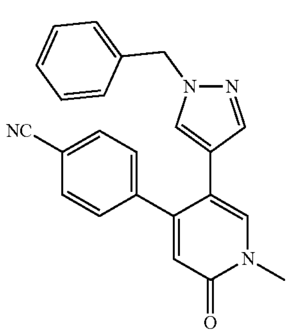 [SMILES: Cn1cc(-c2cnn(Cc3ccccc3)c2)c(-c2ccc(C#N)cc2)cc1=O] | 4-(5-(1-benzyl-1H-pyrazol-4-yl)-1-methyl-2-oxo-1,2-dihydro-pyridin-4-yl)benzonitrile | (DMSO-d₆, 400 MHz) δ 7.90 (s, 1H), 7.79 (s, 1H), 7.77 (s, 1H), 7.36-7.28 (m, 5H), 7.19-7.17 (m, 2H), 7.03-7.01 (m, 1H), 6.36 (s, 1H), 5.19 (s, 2H), 3.49 (s, 3H) | 367 |

TABLE 6-continued

| Example | Structure | IUPAC Name | $^1$HNMR (ppm) | MS (M + H) |
|---|---|---|---|---|
| 151 | 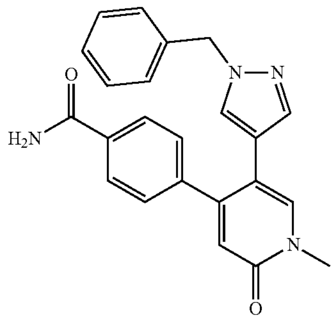 [SMILES: Cn1cc(-c2cnn(Cc3ccccc3)c2)c(-c2ccc(C(N)=O)cc2)cc1=O] | 4-(5-(1-benzyl-1H-pyrazol-4-yl)-1-methyl-2-oxo-1,2-dihydro-pyridin-4-yl)benzamide | (DMSO-d$_6$, 400 MHz) δ 8.03 (s, 1H), 7.87-7.84 (m, 3H), 7.44 (s, 1H), 7.32-7.23 (m, 6H), 7.11 (s, 1H), 7.01-6.99 (m, 1H), 6.34 (s, 1H), 5.18 (s, 2H), 3.49 (s, 3H) | 385 |
| 152 | 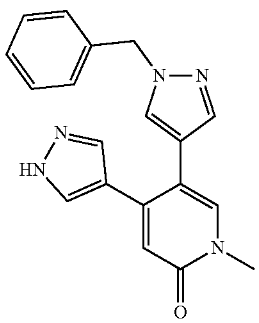 [SMILES: Cn1cc(-c2cnn(Cc3ccccc3)c2)c(-c2cn[nH]c2)cc1=O] | 5-(1-benzyl-1H-pyrazol-4-yl)-1-methyl-4-(1H-pyrazol-4-yl)pyridin-2(1H)-one | (DMSO-d$_6$, 400 MHz) δ 13.0 (s, 1H), 7.71 (s, 1H), 7.65 (s, 1H), 7.47 (s, 1H), 7.37-7.21 (m, 7H), 6.52 (s, 1H), 5.32 (s, 2H), 3.42 (s, 3H) | 332 |
| 153 | 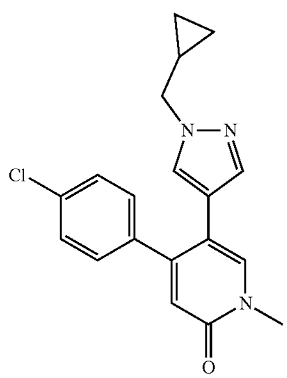 [SMILES: Cn1cc(-c2cnn(CC3CC3)c2)c(-c2ccc(Cl)cc2)cc1=O] | 4-(4-chloro-phenyl)-5-(1-cyclopropylmethyl-1H-pyrazol-4-yl)-1-methyl-1H-pyridin-2-one | (CD$_3$OD, 400 MHz) δ 7.82 (s, 1H), 7.38 (d, J = 8.8 Hz, 2H), 7.22-7.19 (m, 4H), 6.52 (s, 1H), 3.87 (d, J = 7.2 Hz, 2H), 3.65 (s, 3H), 1.16-1.12 (m, 1H), 0.55-0.51 (m, 2H), 0.27-0.23 (m, 2H) | 340 |
| 154 | 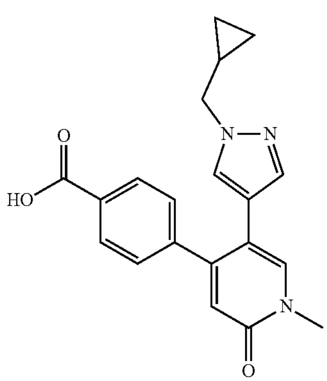 [SMILES: Cn1cc(-c2cnn(CC3CC3)c2)c(-c2ccc(C(=O)O)cc2)cc1=O] | 4-[5-(1-cyclopropyl-methyl-1H-pyrazol-4-yl)-1-methyl-2-oxo-1,2-dihydro-pyridin-4-yl]-benzoic acid | (DMSO-d$_6$, 400 MHz) δ 12.95 (br, 1H), 7.92-7.91 (m, 3H), 7.30 (d, J = 8.0 Hz, 2H), 7.12 (s, 1H), 7.08 (s, 1H), 6.35 (s, 1H), 3.80 (d, J = 7.2 Hz, 2H), 3.51 (s, 3H), 1.07-1.03 (m, 1H), 0.41-0.38 (m, 2H), 0.18-0.16 (m, 2H) | 350 |

TABLE 6-continued

| Example | Structure | IUPAC Name | ¹HNMR (ppm) | MS (M + H) |
| --- | --- | --- | --- | --- |
| 155 | 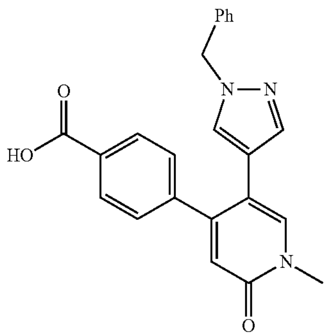 [SMILES: Cn1cc(-c2cnn(Cc3ccccc3)c2)c(-c2ccc(C(=O)O)cc2)cc1=O] | 4-(5-(1-benzyl-1H-pyrazol-4-yl)-1-methyl-2-oxo-1,2-dihydropyridin-4-yl)benzoic acid | (DMSO-$d_6$, 400 MHz) δ 13.0 (s, 1H), 7.89-7.87 (m, 2H), 7.28-7.26 (m, 4H), 7.16 (s, 1H), 7.00 (s, 1H), 6.99 (s, 1H), 6.35 (s, 1H), 5.18 (s, 2H), 3.5 (s, 3H) | 386 |
| 156 | 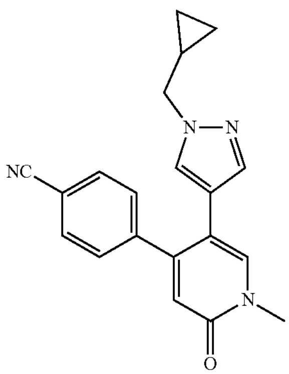 [SMILES: Cn1cc(-c2cnn(CC3CC3)c2)c(-c2ccc(C#N)cc2)cc1=O] | 4-[5-(1-cyclopropyl-methyl-1H-pyrazol-4-yl)-1-methyl-2-oxo-1,2-dihydro-pyridin-4-yl]-benzonitrile | (CD$_3$OD, 400 MHz) δ 7.85 (s, 1H), 7.74 (d, J = 8.0 Hz, 2H), 7.41 (d, J = 8.0 Hz, 2H), 7.22 (s, 1H), 7.17 (s, 1H), 6.54 (s, 1H), 3.87 (d, J = 7.2 Hz, 2H), 3.65 (s, 3H), 1.14-1.12 (m, 1H), 0.55-0.50 (m, 2H), 0.26-0.22 (m 2H) | 331 |
| 157 | 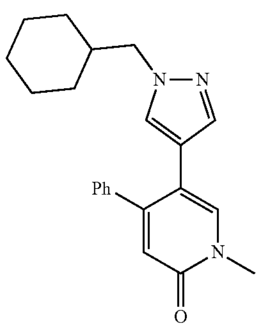 [SMILES: Cn1cc(-c2cnn(CC3CCCCC3)c2)c(-c2ccccc2)cc1=O] | 5-(1-(cyclohexyl-methyl)-1H-pyrazol-4-yl)-1-methyl-4-phenyl-pyridin-2(1H)-one | (DMSO-$d_6$, 400 MHz) δ 7.84 (s, 1H), 7.34-7.32 (m, 4H), 7.17-7.15 (m, 1H), 7.09 (s, 1H), 6.99 (s, 1H), 6.30 (s, 1H), 3.76 (m, 2H), 3.49 (s, 3H), 1.63-1.57 (m, 4H), 1.35-1.32 (m, 2H), 1.15-1.05 (m, 3H), 0.80-0.71 (m, 2H) | 384 |
| 158 | 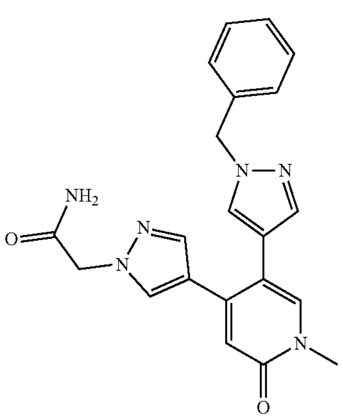 [SMILES: Cn1cc(-c2cnn(Cc3ccccc3)c2)c(-c2cnn(CC(N)=O)c2)cc1=O] | 2-(4-(5-(1-benzyl-1H-pyrazol-4-yl)-1-methyl-2-oxo-1,2-dihydro-pyridin-4-yl)-1H-pyrazol-1-yl)acetamide | (CD$_3$OD, 400 MHz) δ 7.65 (s, 1H), 7.59 (s, 1H), 7.53 (s, 1H), 7.45 (s, 1H), 7.39 (s, 1H), 7.32-7.24 (m, 5H), 6.64 (s, 1H), 5.31 (s, 2H), 4.77 (s, 2H), 3.57 (s, 3H) | 389 |

TABLE 6-continued

| Example | Structure | IUPAC Name | ¹HNMR (ppm) | MS (M + H) |
|---|---|---|---|---|
| 159 | 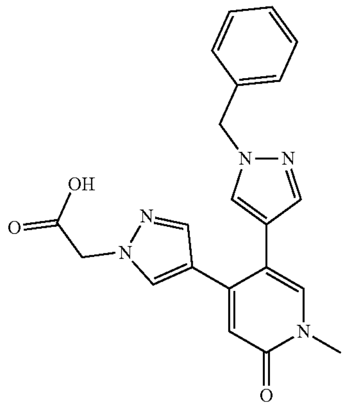 [SMILES: Cn1cc(-c2cnn(Cc3ccccc3)c2)c(-c2cnn(CC(=O)O)c2)cc1=O] | 2-(4-(5-(1-benzyl-1H-pyrazol-4-yl)-1-methyl-2-oxo-1,2-dihydropyridin-4-yl)-1H-pyrazol-1-yl) acetic acid | (CD$_3$OD, 400 MHz) δ 7.67 (s, 1H), 7.57 (s, 1H), 7.44 (s, 1H), 7.34-7.29 (m, 7H), 6.63 (s, 1H), 5.30 (s, 2H), 4.77 (s, 2H), 3.58 (s, 3H) | 388 |
| 160 | 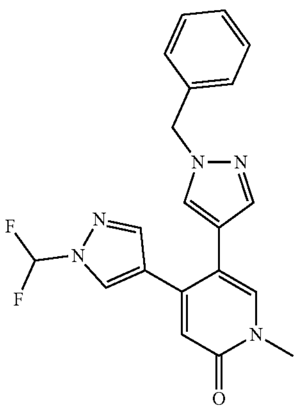 [SMILES: Cn1cc(-c2cnn(Cc3ccccc3)c2)c(-c2cnn(C(F)F)c2)cc1=O] | 5-(1-benzyl-1H-pyrazol-4-yl)-4-(1-(difluoromethyl)-1H-pyrazol-4-yl)-1-methylpyridin-2(1H)-one | (DMSO-d$_6$, 400 MHz) δ 8.08 (s, 1H), 7.76 (s, 1H), 7.74 (s, 1H), 7.71 (s, 1H), 7.66 (s, 1H), 7.34-7.19 (m, 5H), 6.58 (s, 1H), 5.31 (s, 1H), 3.44 (s, 3H) | 382 |
| 161 | 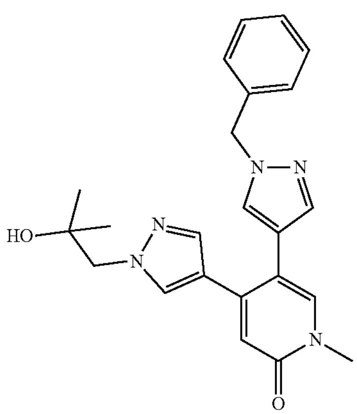 [SMILES: Cn1cc(-c2cnn(Cc3ccccc3)c2)c(-c2cnn(CC(C)(C)O)c2)cc1=O] | 5-(1-benzyl-1H-pyrazol-4-yl)-4-(1-(2-hydroxy-2-methylpropyl)-1H-pyrazol-4-yl)-1-methyl-pyridin-2(1H)-one | (CD$_3$OD, 400 MHz) δ 7.63 (s, 1H), 7.59 (s, 1H), 7.48 (s, 1H), 7.39 (s, 1H), 7.35-7.24 (m, 6H), 6.64 (s, 1H), 5.31 (s, 2H), 3.97 (s, 2H), 3.30 (d, J = 1.4 Hz, 3H), 1.12 (s, 6H) | 404 |
| 162 | 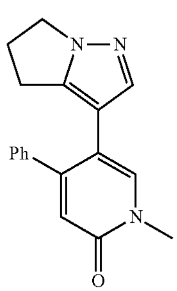 [SMILES: Cn1cc(-c2cnn3c2CCC3)c(-c2ccccc2)cc1=O] | 5-(5,6-dihydro-4H-pyrrolo[1,2-b]pyrazol-3-yl)-1-methyl-4-phenylpyridin-2(1H)-one | (DMSO-d$_6$, 400 MHz) δ 7.74 (s, 1H), 7.37-7.34 (m, 3H), 7.20-7.17 (m, 2H), 7.12 (s, 1H), 6.34 (s, 1H), 3.92 (m, 2H), 3.49 (s, 3H), 2.27-2.23 (m, 2H), 1.98-1.96 (m, 2H) | 292 |

TABLE 6-continued

| Example | Structure | IUPAC Name | ¹HNMR (ppm) | MS (M + H) |
|---|---|---|---|---|
| 163 | 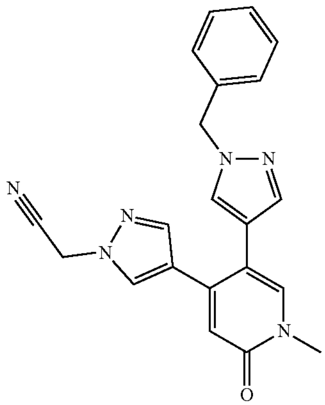 [SMILES: Cn1cc(-c2cnn(Cc3ccccc3)c2)c(-c2cnn(CC#N)c2)cc1=O] | 2-(4-(5-(1-benzyl-1H-pyrazol-4-yl)-1-methyl-2-oxo-1,2-dihydropyridin-4-yl)-1H-pyrazol-1-yl)acetonitrile | (DMSO-$d_6$, 400 MHz) δ 7.73 (s, 1H), 7.69 (s, 1H), 7.69 (s, 1H), 7.49 (s, 1H), 7.36-7.32 (m, 4H), 7.24-7.22 (m, 2H), 6.50 (s, 1H), 5.43 (s, 2H), 5.31 (s, 2H), 3.43 (s, 3H) | 371 |
| 164 | 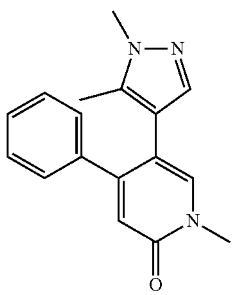 [SMILES: Cc1c(-c2cn(C)c(=O)cc2-c2ccccc2)cnn1C] | 5-(1,5-dimethyl-1H-pyrazol-4-yl)-1-methyl-4-phenylpyridin-2(1H)-one | (DMSO-$d_6$, 400 MHz) δ 7.65 (s, 1H), 7.31-7.28 (m, 2H), 7.17-7.12 (m, 2H), 6.96 (s, 1H), 6.74-6.73 (m, 1H), 6.36 (s, 1H), 3.60 (s, 3H), 3.48 (s, 3H), 1.75 (s, 3H) | 280 |

Examples 165-174 in Table 7 were prepared using the appropriate alkyl or aralkyl bromide and nucleophile in a similar multi-step manner as Example 36.

TABLE 7

| Example | Structure | IUPAC Name | ¹H NMR (ppm) | MS (M + H) |
|---|---|---|---|---|
| 165 | 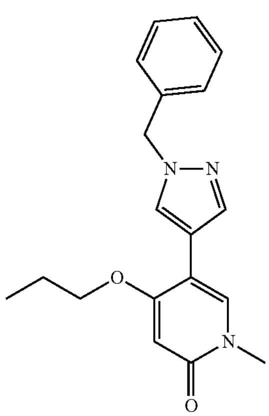 [SMILES: CCCOc1cc(=O)n(C)cc1-c1cnn(Cc2ccccc2)c1] | 5-(1-Benzyl-1H-pyrazol-4-yl)-1-methyl-4-propoxy-1H-pyridin-2-one | (CD$_3$OD, 400 MHz) δ 7.91 (s, 1H), 7.85 (s, 1H) 7.81 (s, 1H), 7.38-7.26 (m, 5H), 6.00 (s, 1H), 5.36 (s, 2H), 4.03 (t, J = 6.0 Hz, 2H), 3.53 (s, 3H), 1.85-1.79 (m, 2H), 0.99 (t, J = 7.6 Hz, 3H). | 324 |

TABLE 7-continued

| Example | Structure | IUPAC Name | ¹H NMR (ppm) | MS (M + H) |
|---|---|---|---|---|
| 166 | 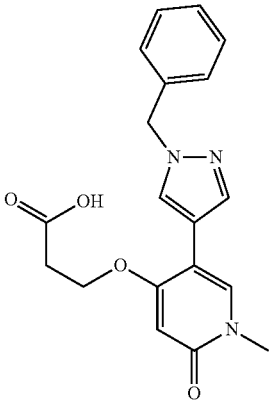 [SMILES: Cn1cc(-c2cnn(Cc3ccccc3)c2)c(OCCC(=O)O)cc1=O] | 3-[5-(1-Benzyl-1H-pyrazol-4-yl)-1-methyl-2-oxo-1,2-dihydro-pyridin-4-yloxy]-propionic acid | (DMSO-$d_6$, 400 MHz) δ 7.98 (s, 1H), 7.94 (s, 1H), 7.72 (s, 1H), 7.34-7.24 (m, 5H), 5.88 (s, 1H), 5.28 (s, 2H), 4.18 (t, J = 5.6 Hz, 2H), 3.38 (s, 3H), 2.75 (t, J = 5.2 Hz, 2H). | 354 |
| 167 | 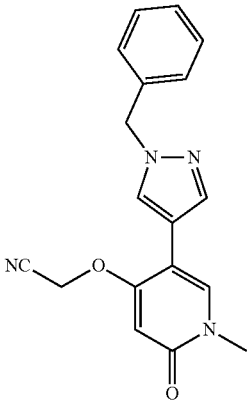 [SMILES: Cn1cc(-c2cnn(Cc3ccccc3)c2)c(OCC#N)cc1=O] | [5-(1-Benzyl-1H-pyrazol-4-yl)-1-methyl-2-oxo-1,2-dihydro-pyridin-4-yloxy]-acetonitrile | (CDCl$_3$, 400 MHz) δ 7.64 (s, 1H), 7.55 (s, 1H), 7.37-7.33 (m, 4H), 7.27-7.26 (m, 2H), 6.01 (s, 1H), 5.33 (s, 2H), 4.75 (s, 2H), 3.54 (s, 3H). | 321 |
| 168 | 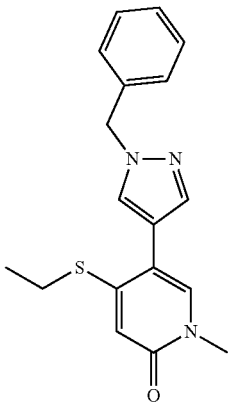 [SMILES: CCSc1cc(=O)n(C)cc1-c1cnn(Cc2ccccc2)c1] | 5-(1-Benzyl-1H-pyrazol-4-yl)-4-ethylsulfanyl-1-methyl-1H-pyridin-2-one | (CDCl$_3$, 400 MHz) δ 7.58 (s, 1H), 7.49 (s, 1H) 7.38-7.33 (m, 3H), 7.26-7.25 (m, 2H), 7.07 (s, 1H), 6.33 (s, 1H), 5.34 (s, 2H), 3.51 (s, 3H), 2.89 (q, J = 7.6 Hz, 2H), 1.38 (t, J = 7.6 Hz, 3H). | 326 |

TABLE 7-continued

| Example | Structure | IUPAC Name | ¹H NMR (ppm) | MS (M + H) |
|---|---|---|---|---|
| 169 | 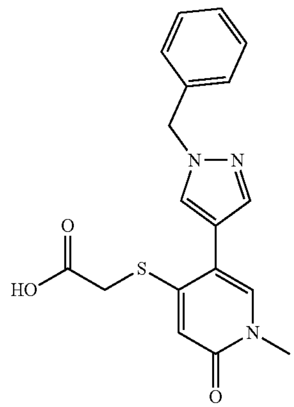 [SMILES: Cn1cc(-c2cnn(Cc3ccccc3)c2)c(SCC(=O)O)cc1=O] | [5-(1-Benzyl-1H-pyrazol-4-yl)-1-methyl-2-oxo-1,2-dihydro-pyridin-4-ylsulfanyl]-acetic acid | (DMSO-d₆, 400 MHz) δ 7.91 (s, 1H), 7.61 (s, 1H), 7.55 (s, 1H), 7.38-7.25 (m, 5H), 6.14 (s, 1H), 5.36 (s, 2H), 3.85 (s, 2H), 3.36 (s, 3H). | 356 |
| 170 | 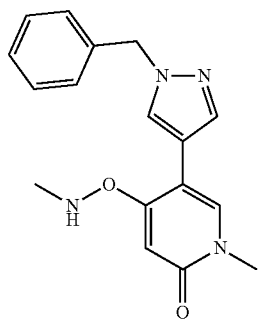 [SMILES: CNOc1cc(=O)n(C)cc1-c1cnn(Cc2ccccc2)c1] | 5-(1-benzyl-1H-pyrazol-4-yl)-1-methyl-4-((methylamino)oxy)pyridin-2(1H)-one | (DMSO-d₆, 400 MHz) δ 8.26 (s, 1H), 7.98 (s, 1H), 7.82 (m, 1H), 7.73 (s, 1H), 7.37-7.23 (m, 5H), 6.18 (s, 1H), 5.34 (s, 2H), 2.76 (d, J = 6.5 Hz) | 311 |
| 171 | 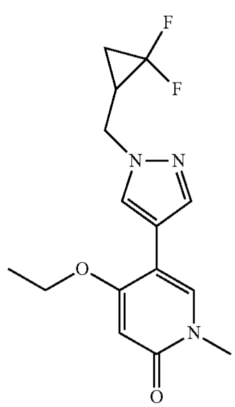 [SMILES: CCOc1cc(=O)n(C)cc1-c1cnn(CC2CC2(F)F)c1] | 5-[1-(2,2-Difluoro-cyclopropylmethyl)-1H-pyrazol-4-yl]-4-ethoxy-1-methyl-1H-pyridin-2-one | (CD₃OD, 400 MHz) δ 7.96 (s, 1H), 7.86 (s, 1H), 7.80 (s, 1H), 6.01 (s, 1H), 4.35-4.21 (m, 2H), 4.13 (q, J = 6.8 Hz, 2H), 3.54 (s, 3H), 2.20-2.14 (m, 1H), 1.65-1.59 (m, 1H). 1.49 (t, J = 6.8 Hz, 3H), 1.44-1.37 (m, 1H). | 310 |
| 172 | 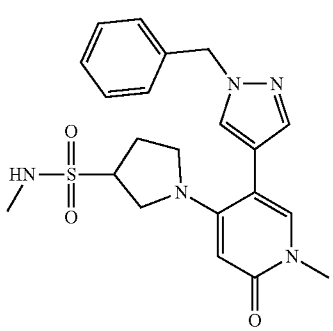 | 1-(5-(1-benzyl-1H-pyrazol-4-yl)-1-methyl-2-oxo-1,2-dihydropyridin-4-yl)-N-methylpyrrolidine-3-sulfonamide | (DMSO-d₆, 400 MHz) δ 7.85 (s, 1H), 7.49 (s, 1H), 7.38-7.22 (m, 6H), 7.11-7.10 (m, 1H), 5.46 (s, 1H), 5.33 (s, 2H), 3.84 (br t, J = 6.2 Hz, 1H), 3.28 (s, 3H), 3.28-3.26 (m, 5H), 3.02-3.02 (m, 1H), 2.55-2.51 (m, 3H), 2.11-2.07 (m, 2H) | 428 |

TABLE 7-continued

| Example | Structure | IUPAC Name | ¹H NMR (ppm) | MS (M + H) |
|---|---|---|---|---|
| 173 | 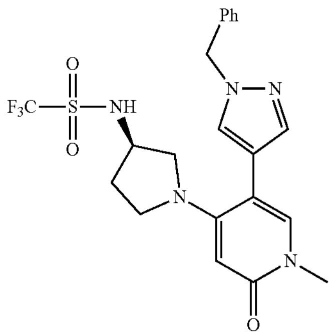 [SMILES: Cn1cc(-c2cnn(Cc3ccccc3)c2)c(N2CC[C@@H](NS(=O)(=O)C(F)(F)F)C2)cc1=O] | (R)-N-(1-(5-(1-benzyl-1H-pyrazol-4-yl)-1-methyl-2-oxo-1,2-dihydropyridin-4-yl)pyrrolidin-3-yl)-1,1,1-trifluoromethanesulfonamide | (DMSO-$d_6$, 400 MHz) δ 9.65 (br s, 1H), 7.77 (s, 1H), 7.39 (s, 1H), 7.28 (s, 1H), 7.27-7.16 (m, 5H), 5.32 (s, 1H), 5.26 (s, 2H), 3.93 (quin, J = 7.0 Hz, 2H), 3.22 (s, 3H), 3.20-3.05 (m, 2H), 2.95 (td, J = 7.0 Hz, 9.9 Hz, 1H), 2.80 (dd, J = 5.0 Hz, 10.7 Hz, 1H), 2.43 (td J = 1.8 Hz, 3.6 Hz, 1H), 2.07-1.92 (m, 1H), 1.70 (qd J = 6.6 Hz, 12.7 Hz, 1H) | |
| 174 | 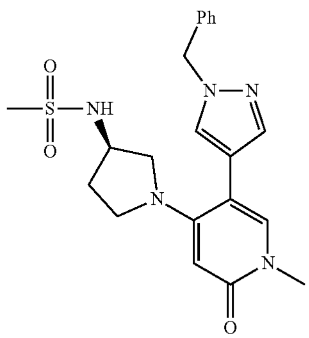 | (R)-N-(1-(5-(1-benzyl-1H-pyrazol-4-yl)-1-methyl-2-oxo-1,2-dihydropyridin-4-yl)pyrrolidin-3-yl)methanesulfonamide | (DMSO-$d_6$, 400 MHz) δ 7.76 (s, 1H), 7.38 (s, 1H), 7.32-7.18 (m, 5H), 7.18-7.11 (m, 2H), 5.30 (s, 1H), 5.26 (s, 2H), 3.74 (sxt, J = 6.2 Hz, 1H), 3.21 (s, 3H), 3.24-3.17 (m, 1H), 3.12 (dd, J = 6.4, 10.5 Hz, 1H), 3.09-2.99 (m, 1H), 2.92 (td J = 7.2, 10.2 Hz, 1H), 2.84-2.72 (m, 4H), 1.95 (qd, J = 6.3, 12.4 Hz, 1H), 1.73-1.59 (m, 1H) | 428 |

Example 175: 4-methoxy-1-methyl-5-(1-(1-phenyl-ethyl)-1H-pyrazol-4-yl)pyridin-2(1H)-one

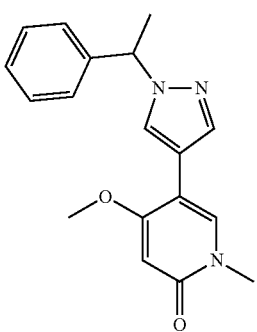 [SMILES: COc1cc(=O)n(C)cc1-c1cnn(C(C)c2ccccc2)c1]

The title compound was prepared in a manner similar to Example 36 by substituting methanol for isopropanol in Step 2. ¹H NMR (DMSO-$d_6$, 400 MHz) δ 8.03 (s, 1H), 7.92 (s, 1H), 7.73 (s, 1H), 7.31-7.23 (m, 5H), 5.87 (s, 1H), 5.61-5.59 (m, 1H), 3.80 (s, 3H), 3.33 (s, 3H), 1.81 (d, J=7.1 Hz, 3H). LCMS (M+H)⁺ 310.

Example 176: 2-[4-(4-Ethoxy-1-methyl-6-oxo-1,6-dihydro-pyridin-3-yl)-pyrazol-1-yl]-6-isopropyl-benzonitrile Step 1: 2-(4-Iodo-pyrazol-1-yl)-6-isopropyl-benzonitrile

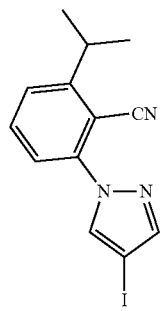 [SMILES: CC(C)c1cccc(-n2cc(I)cn2)c1C#N]

To a solution of 4-iodo-1H-pyrazole (200 mg, 1.0 mmol) in DMF (10 mL) at room temperature under $N_2$ was added NaH (50 mg, 1.2 mmol). The mixture was stirred for 30 min and then 2-fluoro-6-isopropyl-benzonitrile (183 mg, 1.1 mmol) was added. The resulting mixture was stirred at room temperature for 10 hours. The reaction was quenched by addition of water (45 mL) and extracted with DCM (15 mL×2). The combined organic layers were washed with brine, dried over $Na_2SO_4$, filtered and concentrated under reduced pressure. The residue was purified by preparative-HPLC to afford the title compound (140 mg, 0.4 mmol) as a white solid.

Step 2:
5-Bromo-4-ethoxy-1-methyl-1H-pyridin-2-one

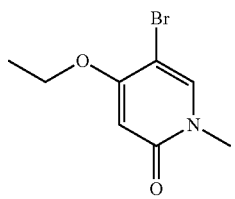

To a solution of 5-bromo-4-chloro-1-methyl-1H-pyridin-2-one (1.0 g, 4.5 mmol) in DMF (30 mL) was added sodium ethoxide (616 mg, 9.0 mmol). The mixture was stirred at 30° C. under $N_2$ overnight. The reaction was quenched by addition of water (50 mL) and extracted with EtOAc (25 mL×2). The combined organic layers were washed with brine, dried over $Na_2SO_4$, filtered and concentrated under reduced pressure. The residue was purified by silica gel column chromatography eluting with PE/EtOAc (1:1) to afford the title compound as a yellow solid in 67% yield. LCMS $(M+H)^+$ 232.

Step 3: 4-Ethoxy-1-methyl-5-(4,4,5,5-tetramethyl-[1,3,2]dioxaborolan-2-yl)-1H-pyridin-2-one

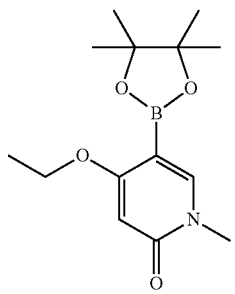 [SMILES: CCOc1cc(=O)n(C)cc1B1OC(C)(C)C(C)(C)O1]

To a solution of 5-bromo-4-ethoxy-1-methyl-1H-pyridin-2-one (700 mg, 3.0 mmol) and bis(pimacolato)diboron (1.5 g, 6.0 mmol) in dioxane (30 mL) was added $Pd_2(dba)_3$ (270 mg, 0.3 mmol), XPhos (214 mg, 0.45 mmol) and KOAc (882 mg, 9.0 mmol). The reaction mixture was stirred at 75° C. under $N_2$ for 10 hours. The reaction was cooled to room temperature, filtered and concentrated under reduced pressure. The residue was purified by silica column chromatography eluting with PE/EtOAc (1:1) to afford the title compound as a yellow solid. $^1H$ NMR (300 MHz, $CDCl_3$): δ 7.53 (s, 1H), 5.75 (s, 1H), 3.91 (q, J=6.8 Hz, 2H), 3.41 (s, 3H), 1.34 (t, J=6.8 Hz, 3H), 1.24 (s, 12H). LCMS $(M+H)^+$ 280.

Step 4: 2-[4-(4-Ethoxy-1-methyl-6-oxo-1,6-dihydro-pyridin-3-yl)-pyrazol-1-yl]-6-isopropyl-benzonitrile

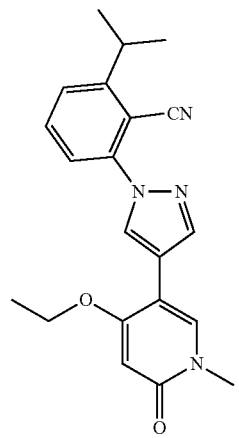 [SMILES: CCOc1cc(=O)n(C)cc1-c1cnn(-c2cccc(C(C)C)c2C#N)c1]

To a solution of the title compound from Step 1 (140 mg, 0.4 mmol) and the title compound from Step 3 (174 mg, 0.6 mmol) in mixture of dioxane (20 mL) and $H_2O$ (4 mL) was added $Pd(dppf)Cl_2$ (30 mg, 0.04 mmol) and $K_3PO_4$ (176 mg, 0.8 mmol). The resulting mixture was stirred at 60° C. under $N_2$ for 3 hours. The reaction was cooled to room temperature, diluted with water (60 mL) and extracted with DCM (15 mL×2). The combined organic layers were washed with brine, dried over $Na_2SO_4$, filtered and concentrated under reduced pressure. The residue was purified by preparative-HPLC to afford the title compound (70 mg, 0.19 mmol) as a white solid. $^1H$ NMR ($CDCl_3$, 400 MHz) δ 8.33 (s, 1H), 7.95 (s, 1H), 7.66 (t, J=8.0 Hz, 1H), 7.58 (t, J=6.4 Hz, 1H), 7.45 (s, 1H), 7.41 (d, J=8.0 Hz, 1H), 6.02 (s, 1H), 4.10 (q, J=6.8 Hz, 2H), 3.57 (s, 3H), 3.55-3.49 (m, 1H), 1.51 (t, J=7.2 Hz, 3H), 1.37 (d, J=6.8 Hz, 6H). LCMS $(M+H)^+$ 363.

Examples 177-180 in Table 8 were prepared using the appropriate substituted pyrazole in a similar multi-step manner as Example 176.

TABLE 8

| Example | Structure | IUPAC Name | $^1H$ NMR (ppm) | MS (M + H) |
|---|---|---|---|---|
| 177 | 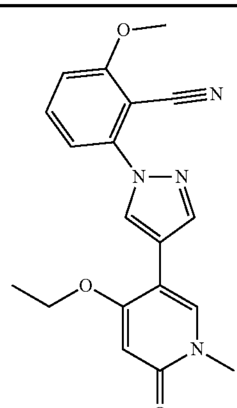 | 2-[4-(4-Ethoxy-1-methyl-6-oxo-1,6-dihydro-pyridin-3-yl)-pyrazol-1-yl]-6-methoxy-benzonitrile | ($CDCl_3$, 400 MHz) δ 8.45 (s, 1H), 7.94 (s, 1H), 7.63 (t, J = 8.4 Hz, 1H), 7.45 (s, 1H), 7.41 (d, J = 8.0 Hz, 1H), 6.95 (d, J = 8.8 Hz, 1H), 6.01 (s, 1H), 4.10 (q, J = 7.1 Hz, 2H), 4.02 (s, 3H), 3.57 (s, 3H), 1.52 (t, J = 7.2 Hz, 3H). | 351 |

TABLE 8-continued

| Example | Structure | IUPAC Name | ¹H NMR (ppm) | MS (M + H) |
|---|---|---|---|---|
| 178 | 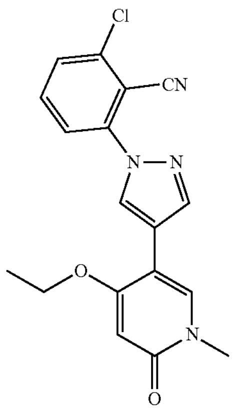 [SMILES: CCOc1cc(=O)n(C)cc1-c1cnn(-c2cccc(Cl)c2C#N)c1] | 2-Chloro-6-[4-(4-ethoxy-1-methyl-6-oxo-1,6-dihydro-pyridin-3-yl)-pyrazol-1-yl]-benzonitrile | (CD$_3$OD, 400 MHz) δ 8.57 (s, 1H), 8.16 (s, 1H), 8.01 (s, 1H), 7.80-7.75 (m, 2H), 7.70-7.68 (m, 1H), 6.05 (s, 1H), 4.18 (q, J = 6.8 Hz 2H), 3.57 (s, 3H), 1.53 (t, J = 7.2 Hz, 3H). | 355 |
| 179 | 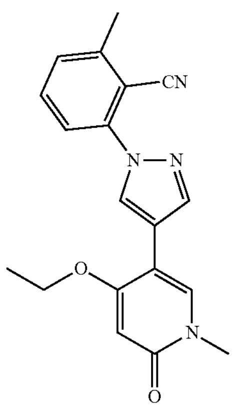 [SMILES: CCOc1cc(=O)n(C)cc1-c1cnn(-c2cccc(C)c2C#N)c1] | 2-[4-(4-Ethoxy-1-methyl-6-oxo-1,6-dihydro-pyridin-3-yl)-pyrazol-1-yl]-6-methyl-benzonitrile | (CDCl$_3$, 400 MHz) δ 8.38 (s, 1H), 7.96 (s, 1H), 7.60-7.58 (m, 2H), 7.48 (s, 1H), 7.34-7.32 (m, 1H), 6.13 (s, 1H), 4.13 (q, J = 7.2 Hz, 2H), 3.59 (s, 3H), 2.66 (s, 3H), 1.52 (t, J = 6.8 Hz, 3H). | 335 |
| 180 | 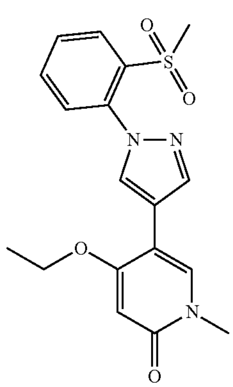 [SMILES: CCOc1cc(=O)n(C)cc1-c1cnn(-c2ccccc2S(C)(=O)=O)c1] | 4-Ethoxy-5-[1-(2-methanesulfonyl-phenyl)-1H-pyrazol-4-yl]-1-methyl-1H-pyridin-2-one | (CDCl$_3$, 400 MHz) δ 8.25 (dd, J = 7.6, 1.2 Hz, 1H), 8.11 (s, 1H), 7.94 (s, 1H), 7.79-7.75 (m, 1H), 7.69-7.65 (m, 1H), 7.53 (dd, J = 8.0, 1.2 Hz, 1H), 7.45 (s, 1H), 6.01 (s, 1H), 4.09 (q, J = 7.1 Hz, 2H), 3.55 (s, 3H), 3.07 (s, 3H), 1.48 (t, J = 7.2 Hz, 3H). | 374 |

Example 181: 4-ethoxy-1-methyl-5-(1-(1-(methyl-sulfonyl)piperidin-3-yl)-1H-pyrazol-4-yl)pyridin-2(1H)-one Step 1: 3-(4-bromo-1H-pyrazol-1-yl)-1-(methyl-sulfonyl)piperidine

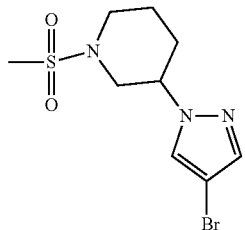 [SMILES: CS(=O)(=O)N1CCCC(n2cc(Br)cn2)C1]

3-(4-bromo-1H-pyrazol-1-yl)piperidine hydrochloride (300 mg, 1.13 mmol) was dissolved in anhydrous pyridine (5 mL). DMAP (catalytic) and methanesulfonyl chloride (0.15 mL, 1.7 mmol) were added to the solution at 0° C. The reaction was warmed up to room temperature and stirred for 30 minutes. Solvents were removed under reduced pressure. The residue was dissolved in EtOAc (100 mL), washed with 1N HCl (30 mL×2), water (30 mL×2) and brine (30 mL). The organic solvent was removed under reduced pressure and the residue purified by silica gel column chromatography (EtOAc/Hex 0 to 100%) to afford the title compound as a clear solid (300 mg, 87%).

Step 2: 4-ethoxy-1-methyl-5-(1-(1-(methylsulfonyl) piperidin-3-yl)-1H-pyrazol-4-yl)pyridin-2(1H)-one

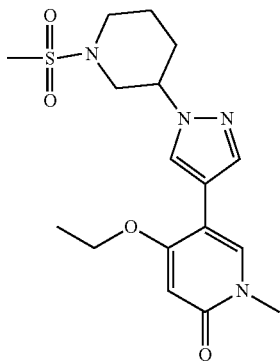

A mixture of 4-ethoxy-1-methyl-5-(4,4,5,5-tetramethyl-1,3,2-dioxaborolan-2-yl)pyridin-2(1H)-one (50 mg, 0.18 mmol) and 3-(4-bromo-1H-pyrazol-1-yl)-1-(methylsulfonyl)piperidine (45 mg, 0.22 mmol), Pd(dppf)Cl$_2$-DCM (15 mg, 0.02 mmol) and K$_3$PO$_4$ (76 mg, 0.36 mmol) in 1,4-dioxane (1 mL) and water (3 drops) was purged with nitrogen, capped and heated to 100° C. for 1 h. The reaction was cooled to room temperature, filtered through Celite and purified by preparative-HPLC (MeCN/water/0.1% formic acid) to afford the title compound as a white solid (18 mg, 26%). $^1$H NMR (DMSO-d$_6$, 400 MHz) δ 8.04 (s, 1H), 7.93 (s, 1H), 7.78 (s, 1H), 5.86 (s, 1H), 4.48-4.31 (m, 1H), 4.06 (q, J=7.0 Hz, 2H), 3.76 (dd, J=4.2, 11.5 Hz, 1H), 3.50 (br d J=11.6 Hz, 1H), 3.39 (s, 3H), 3.09 (dd, J=9.9, 11.3 Hz, 1H), 2.92 (s, 3H), 2.89-2.70 (m, 1H), 2.20-1.79 (m, 3H), 1.75-1.59 (m, 1H), 1.40 (t, J=7.0 Hz, 3H). LCMS (M+H)$^+$ 381.

Example 182: 2-[4-(4-Ethoxy-1-methyl-6-oxo-1,6-dihydro-pyridin-3-yl)-pyrazol-1-yl]-4-methoxy-benzonitrile Step 1: 4-Methoxy-2-[4-(4,4,5,5-tetramethyl-[1,3,2] dioxaborolan-2-yl)-pyrazol-1-yl]-benzonitrile

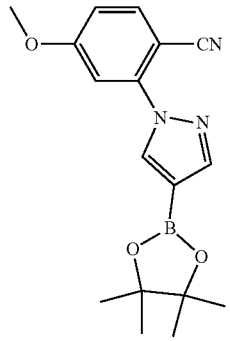

To a mixture of 4-(4,4,5,5-tetramethyl-[1,3,2]dioxaborolan-2-yl)-1H-pyrazole (505 mg, 2.6 mmol) in DMF (5 mL) cooled to 0° C. under N$_2$ was added NaH (258 mg, 6.5 mmol). The reaction mixture was stirred for 15 minutes followed by addition of 2-fluoro-4-methoxy-benzonitrile (470 mg, 3.1 mmol). The reaction mixture was warmed to 45° C. and stir for 5 hours. The contents were cooled to room temperature, diluted with an ice water mixture and extracted with DCM (25 mL×3). The combined organic layers were dried over Na$_2$SO$_4$, filtered and concentrated under reduced pressure to afford the title compound as a brown solid that was used in the following step without further purification.

Step 2: 2-[4-(4-Ethoxy-1-methyl-6-oxo-1,6-dihydro-pyridin-3-yl)-pyrazol-1-yl]-4-methoxy-benzonitrile

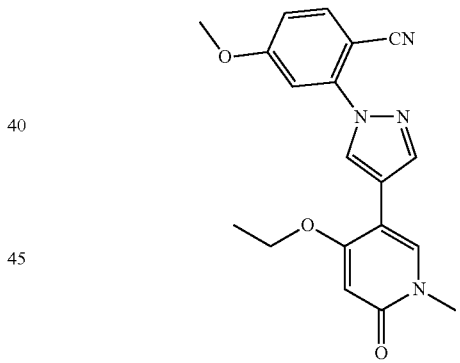

A mixture of the title compound from Step 1 (100 mg, 0.3 mmol), 5-bromo-4-ethoxy-1-methyl-1H-pyridin-2-one (56 mg, 0.24 mmol), K$_3$PO$_4$ (127 mg, 0.60 mmol) and Pd(dppf) Cl$_2$ (22 mg, 0.02 mmol) in a 1,4-dioxane (5 mL) and water (1 mL) mixture was stirred at 80° C. overnight. It was then cooled to room temperature, diluted with an ice water mixture and extracted with DCM (25 mL×3). The combined organic layers were dried over Na$_2$SO$_4$, filtered and concentrated under reduced pressure. The residue was purified by preparative-TLC DCM/MeOH (15:1) to afford the title compound (14 mg, 0.04 mmol) as a white solid. $^1$H NMR (400 MHz, CDCl$_3$) □□□8.50 (s, 1H), 7.95 (s, 1H) 7.69-7.62 (d, J=8.8 Hz, 1H), 7.45 (s, 1H), 7.38 (d, J=2.4 Hz, 1H), 6.95 (dd, J=2.4, 8.8 Hz, 1H), 6.02 (s, 1H), 4.15-4.13 (m, 2H), 3.94 (s, 3H), 3.57 (s, 3H), 1.54 (t, J=7.2 Hz, 3H). LCMS (M+H)$^+$ 351.

Examples 183-184 in Table 9 were prepared using the appropriate substituted pyrazole in a similar multi-step manner as Example 182.

TABLE 9

| Example | Structure | IUPAC Name | ¹H NMR (ppm) | MS (M + H) |
|---|---|---|---|---|
| 183 | 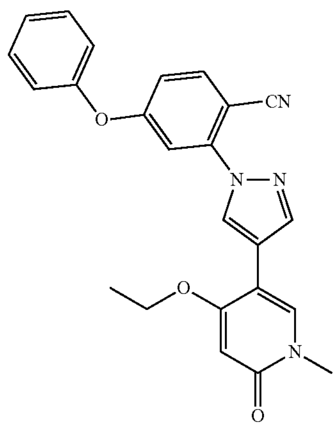 [SMILES: CCOc1cc(=O)n(C)cc1-c1cnn(-c2cc(Oc3ccccc3)ccc2C#N)c1] | 2-[4-(4-Ethoxy-1-methyl-6-oxo-1,6-dihydro-pyridin-3-yl)-pyrazol-1-yl]-4-phenoxy-benzonitrile | (CD₃OD, 400 MHz) δ 8.56 (s, 1H), 8.10 (s, 1H), 8.00 (s, 1H), 7.86 (d, J = 8.8 Hz, 1H), 7.51 (t, J = 8.0 Hz, 2H), 7.32 (m, 2H), 7.19 (d, J = 8.0 Hz, 2H), 7.07 (dd, J = 2.0, 8.4 Hz, 1H), 6.04 (s, 1H), 4.18-4.13 (m, 2H), 3.56 (s, 3H), 1.51 (t, J = 7.2 Hz, 3H). | 413 |
| 184 | 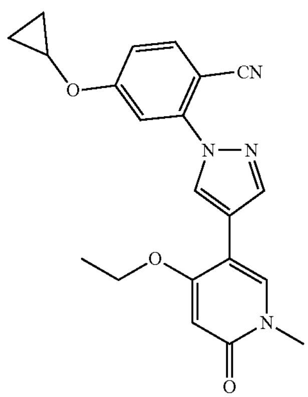 [SMILES: CCOc1cc(=O)n(C)cc1-c1cnn(-c2cc(OC3CC3)ccc2C#N)c1] | 4-Cyclopropoxy-2-[4-(4-ethoxy-1-methyl-6-oxo-1,6-dihydro-pyridin-3-yl)-pyrazol-1-yl]-benzonitrile | (DMSO-d₆, 400 MHz) δ Hz, 1H), 5.92 (s, 1H), 8.59 (s, 1H), 8.18 (s, 1H), 8.12 (s, 1H), 7.94 (d, J = 8.4 Hz, 1H), 7.48 (s, 1H), 7.22 (dd, J = 8.4 Hz, 2.4 4.11-4.07 (m, 3H), 3.42 (s, 3H), 1.43 (t, J = 7.2 Hz, 3H), 0.88-0.86 (m, 2H), 0.76-0.75 (m, 2H). | 377 |

Example 185: 5-(1-benzyl-3-nitro-1H-pyrazol-4-yl)-4-ethoxy-1-methylpyridin-2(1H)-one

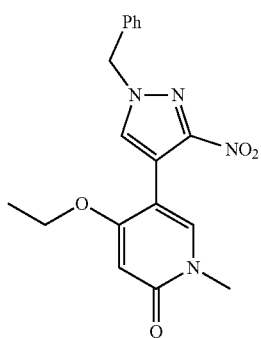 [SMILES: CCOc1cc(=O)n(C)cc1-c1cn(Cc2ccccc2)nc1N]

A mixture of 4-ethoxy-1-methyl-5-(4,4,5,5-tetramethyl-1,3,2-dioxaborolan-2-yl)pyridin-2(1H)-one (60 mg, 0.2 mmol), 1-benzyl-4-bromo-3-nitro-1H-pyrazole (75 mg, 0.26 mmol), Pd(dppf)Cl₂—CH₂Cl₂ (20 mg, 0.025 mmol) and K₃PO₄ (90 mg, 0.43 mmol) in a dioxane (1 mL) and water (3 drops) mixture was purged with nitrogen, capped and heated to 100° C. for one hour. The reaction was cooled to room temperature, filtered through Celite and purified by preparative-HPLC (MeCN/water/0.1% formic acid) to afford the title compound as white solid (12 mg, 16%). ¹H NMR (DMSO-d₆, 400 MHz) δ 8.06 (s, 1H), 7.72 (s, 1H), 7.36-7.22 (m, 5H), 5.79 (s, 1H), 5.39 (s, 2H), 3.83 (q, J=6.9 Hz, 2H), 3.31 (s, 3H), 1.04 (t, J=7.0 Hz, 3H). LCMS (M+H)⁺ 355.

Example 186: 5-(3-amino-1-benzyl-1H-pyrazol-4-yl)-4-ethoxy-1-methylpyridin-2(1H)-one

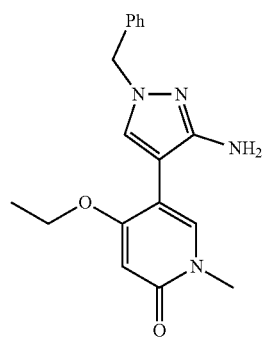

To a mixture of the title compound from Example 185 (0.5 g, 1.4 mmol) in MeOH (5 mL) at 0° C. was added AcOH (0.5 mL) followed by Zn powder (137 mg, 2.1 mmol). The reaction mixture was stirred at room temperature for 4 hours and filtered through Celite. The pH of the filtrate was adjusted to 8 by addition of a saturated aqueous NaHCO₃ solution. The mixture was concentrated under reduced pressure and purified by silica gel column chromatography eluting with DCM/MeOH (20:1) to afford the title com pound as a red oil. ¹H NMR (CD₃OD, 400 MHz) δ 7.61 (s, 1H), 7.53 (s, 1H), 7.35-7.23 (m, 5H), 5.99 (s, 1H), 5.12 (s, 2H), 4.08 (q, J=7.2 Hz, 2H), 3.51 (s, 3H), 1.38 (t, J=6.8 Hz, 3H). LCMS (M+H)⁺ 325.

Example 187: N-[1-Benzyl-4-(4-ethoxy-1-methyl-6-oxo-1,6-dihydro-pyridin-3-yl)-1H-pyrazol-3-yl]-acetamide

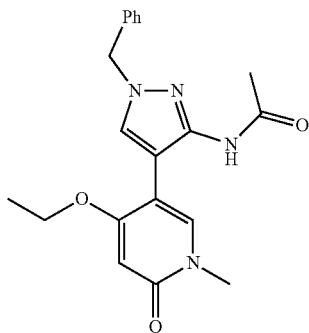 [SMILES: CCOc1cc(=O)n(C)cc1-c1cn(Cc2ccccc2)nc1NC(C)=O]

To a solution of the title compound from Example 186 (100 mg, 0.31 mmol) in DCM (3 mL) at room temperature was added TEA (157 mg, 1.5 mmol) and acetyl chloride (30 mg, 0.37 mmol). The reaction mixture was stirred at room temperature overnight. It was then poured over an ice water mixture and extracted with DCM (15 mL). The organic layer was dried over Na₂SO₄, filtered and concentrated under reduced pressure. The residue was purified by preparative-HPLC to afford the title compound (41 mg) as a white solid. ¹H NMR (400 MHz, CDCl₃): δ 7.71 (s, 1H), 7.49 (s, 1H), 7.34-7.29 (m, 5H), 5.95 (s, 1H), 5.28 (s, 2H), 4.03 (q, J=6.8 Hz, 2H), 3.48 (s, 3H), 2.07 (s, 3H), 1.33 (t, J=7.2 Hz, 3H). LCMS (M+H)⁺ 367.

Examples 188-194 in Table 10 were prepared using the appropriate alkyl or aralkyl halide and boronic acid derivative in a similar multi-step manner as Example 106.

TABLE 10

| Example | Structure | IUPAC Name | ¹H NMR (ppm) | MS (M + H) |
|---|---|---|---|---|
| 188 | 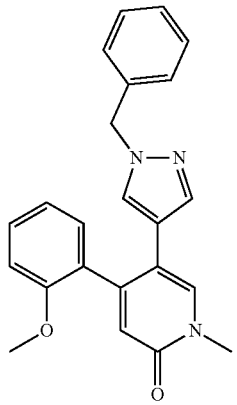 [SMILES: COc1ccccc1-c1cc(=O)n(C)cc1-c1cnn(Cc2ccccc2)c1] | 5-(1-Benzyl-1H-pyrazol-4-yl)-4-(2-methoxy-phenyl)-1-methyl-1H-pyridin-2-one | (CD₃OD, 400 MHz) δ 7.76 (s, 1H), 7.35-7.30 (m, 4H), 7.19 (s, 1H), 7.13 (d, J = 7.2 Hz, 1H), 7.05 (d, J = 7.2 Hz, 2H), 7.01-6.97 (m, 2H), 6.81 (d, J = 8.4 Hz, 1H), 6.42 (s, 1H), 5.13 (s, 2H), 3.63 (s, 3H), 3.35 (s, 3H). | 373 |
| 189 | 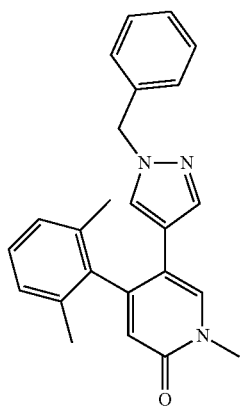 [SMILES: Cc1cccc(C)c1-c1cc(=O)n(C)cc1-c1cnn(Cc2ccccc2)c1] | 5-(1-Benzyl-1H-pyrazol-4-yl)-4-(2,6-dimethyl-phenyl)-1-methyl-1H-pyridin-2-one | (CD₃OD, 400 MHz) δ 8.01 (s, 1H), 7.29-7.27 (m, 3H), 7.21 (s, 1H), 7.16 (t, J = 8.0 Hz, 1H), 7.04 (d, J = 8.0 Hz, 2H), 6.98-6.95 (m, 2H), 6.83 (s, 1H), 6.35 (s, 1H), 5.11 (s, 2H), 3.68 (s, 3H), 1.97 (s, 6H) | 370 |

TABLE 10-continued

| Example | IUPAC Name | ¹H NMR (ppm) | MS (M + H) |
|---|---|---|---|
| 190 | 5-[1-(2,2-Difluoro-cyclopropylmethyl)-1H-pyrazol-4-yl]-1-methyl-4-phenyl-1H-pyridin-2-one | (CD₃OD, 400 MHz) δ 7.82 (s, 1H), 7.39-7.33 (m, 3H), 7.22-7.19 (m, 2H), 7.17 (s, 1H), 7.16 (s, 1H), 6.51 (s, 1H), 4.12 (d, J = 7.6 Hz, 2H), 3.65 (s, 3H), 2.07-1.99 (m, 1H), 1.55-1.47 (m, 1H). 1.27-1.20 (m, 1H). | 342 |
| 191 | 5-[1-(2,2-Difluoro-cyclopropylmethyl)-1H-pyrazol-4-yl]-4-(4-methoxy-phenyl)-1-methyl-1H-pyridin-2-one | (CD₃OD, 400 MHz) δ 7.78 (s, 1H), 7.21 (s, 1H), 7.18 (s, 1H), 7.13 (d, J = 8.8 Hz, 2H), 6.90 (d, J = 8.8 Hz, 2H), 6.49 (s, 1H), 4.16-4.13 (m, 2H), 3.80 (s, 3H), 3.64 (s, 3H), 2.11-2.00 (m, 1H), 1.58-1.49 (m, 1H), 1.30-1.22 (m, 1H). | 372 |
| 192 | 5-[1-(2,2-Difluoro-cyclopropylmethyl)-1H-pyrazol-4-yl]-1-methyl-4-(1-methyl-1H-pyrazol-4-yl)-1H-pyridin-2-one | (CD₃OD, 400 MHz) δ 7.64 (s, 1H), 7.55 (s, 1H), 7.51 (s, 1H), 7.39 (s, 1H), 7.30 (s, 1H), 6.62 (s, 1H), 4.30-4.26 (m, 2H), 3.83 (s, 3H), 3.59 (s, 3H), 2.24-2.16 (m, 1H), 1.65-1.57 (m, 1H), 1.42-1.35 (m, 1H). | 346 |
| 193 | 5-(1-Benzyl-1H-pyrazol-4-yl)-1-methyl-1H,1'H-[4,4']bipyridinyl-2,2'-dione | (CD₃OD, 400 MHz) δ 7.81 (s, 1H), 7.42 (s, 1H), 7.40 (s, 1H), 7.34-7.27 (m, 4H), 7.14-7.12 (m, 2H), 6.51(s, 1H), 6.41(s, 1H), 6.07 (d, J = 9.6 Hz, 1H), 5.26 (s, 2H), 3.63 (s, 3H). | 359 |

TABLE 10-continued

| Example | Structure | IUPAC Name | ¹H NMR (ppm) | MS (M + H) |
|---|---|---|---|---|
| 194 | (structure shown) | 5'-(1-Benzyl-1H-pyrazol-4-yl)-1'-methyl-1H,1'H-[3,4']bipyridinyl-6,2'-dione | (CD$_3$OD, 400 MHz) δ 7.76 (s, 1H), 7.45 (s, 1H), 7.42 (d, J = 2.8 Hz, 1H), 7.41 (s, 1H), 7.34-7.23 (m, 4H), 7.18-7.16 (m, 2H), 6.53(s, 1H), 6.34 (d, J = 9.6 Hz, 1H), 5.28 (s, 2H), 3.61 (s, 3H). | 359 |

Example 195: 5-(1-Benzyl-1H-pyrazol-4-yl)-1,6-dimethyl-1H-pyridin-2-one

Step 1: 5-Bromo-1,6-dimethyl-1H-pyridin-2-one

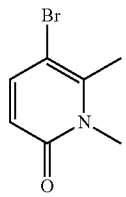

A mixture of 5-bromo-6-methyl-1H-pyridin-2-one (500 mg, 2.66 mmol), iodomethane (415 mg, 2.92 mmol) and K$_2$CO$_3$ (551 mg, 3.99 mmol) in DMF (8 mL) was stirred at room temperature overnight. The reaction mixture was diluted with DCM (50 mL) and H$_2$O (50 mL). The organic layer was separated and washed with brine (50 mL), dried over Na$_2$SO$_4$, filtered and concentrated under reduced pressure. The residue was purified by silica gel column chromatography eluting with PE/EtOAc (5:1) to afford the title compound (240 mg, 1.19 mmol) as a gray solid. ¹H NMR (300 MHz, CDCl$_3$): δ 7.39 (d, J=9.6 Hz, 1H), 6.40 (d, J=9.6 Hz, 1H), 3.60 (s, 3H), 2.53 (s, 3H). LCMS (M+H)$^+$ 202.

Step 2: 5-(1-Benzyl-1H-pyrazol-4-yl)-1,6-dimethyl-1H-pyridin-2-one

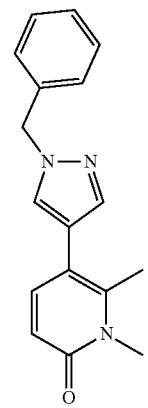 [SMILES: Cc1c(-c2cnn(Cc3ccccc3)c2)ccc(=O)n1C]

A mixture of 1-benzyl-4-(4,4,5,5-tetramethyl-[1,3,2]dioxaborolan-2-yl)-1H-pyrazole (140 mg, 0.495 mmol), the title compound from Step 1 (100 mg, 0.495 mmol), Pd(PPh$_3$)$_4$ (60 mg, 0.049 mmol) and Na$_2$CO$_3$ (104 mg, 0.990 mmol) in dioxane (5 mL) and H$_2$O (1 mL) under N$_2$ was heated to 90° C. for 5 hours. The mixture was cooled to room temperature and diluted with EtOAc (60 mL) and H$_2$O (50 mL). The organic phase was washed with brine (60 mL), dried over Na$_2$SO$_4$, filtered and concentrated under reduced pressure. The residue was purified by preparative-HPLC to afford the title compound (60 mg, 0.22 mmol) as a yellow oil. ¹H NMR (400 MHz, CDCl$_3$): δ 7.48 (s, 1H), 7.39-7.32 (m, 4H), 7.30 (s, 1H), 7.27-7.26 (m, 1H), 7.22 (d, J=8.8 Hz, 1H), 6.48 (d, J=9.2 Hz, 1H), 5.33 (s, 2H), 3.59 (s, 3H), 2.36 (s, 3H). LCMS (M+H)$^+$ 280.

Examples 196-199 in Table 11 were prepared using the appropriate pyrazole and pyridone in a similar multi-step manner as Example 195.

TABLE 11

| Example | Structure | IUPAC Name | ¹H NMR (ppm) | MS (M + H) |
|---|---|---|---|---|
| 196 | 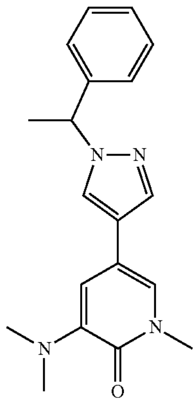 | 3-Dimethylamino-1-methyl-5-[1-(1-phenyl-ethyl)-1H-pyrazol-4-yl]-1H-pyridin-2-one | (CD$_3$OD, 400 MHz) δ 7.50 (d, J = 2.4 Hz, 1H), 8.02 (s, 1H), 7.76 (s, 1H), 7.34-7.23 (m, 5H), 7.01 (d, J = 2.0 Hz, 1H), 5.58 (q, J = 7.2 Hz, 1H), 3.56 (s, 3H), 2.84 (s, 6H), 1.90 (d, J = 6.8 Hz, 3H). | 323 |
| 197 | 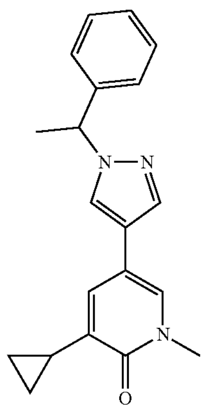 [SMILES: CC(c1ccccc1)n1cc(-c2cc(C3CC3)c(=O)n(C)c2)cn1] | 3-Cyclopropyl-1-methyl-5-[1-(1-phenyl-ethyl)-1H-pyrazol-4-yl]-1H-pyridin-2-one | (CD$_3$OD, 400 MHz) δ 8.01 (s, 1H), 7.74 (s, 1H), 7.72 (d, J = 2.4 Hz, 1H), 7.34-7.22 (m, 6H), 5.57 (q, J = 6.8 Hz, 1H), 3.59 (s, 3H), 2.07-2.03 (m, 1H), 1.89 (d, J = 7.2 Hz, 3H), 0.95-0.91 (m, 2H), 0.72-0.68 (m, 2H). | 320 |
| 198 | 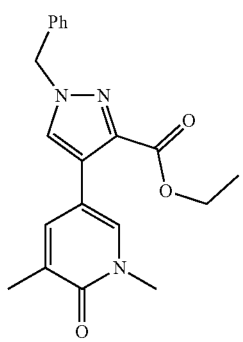 [SMILES: CCOC(=O)c1nn(Cc2ccccc2)cc1-c1cc(C)c(=O)n(C)c1] | 1-Benzyl-4-(1,5-dimethyl-6-oxo-1,6-dihydro-pyridin-3-yl)-1H-pyrazole-3-carboxylic acid ethyl ester | (CD$_3$OD, 400 MHz) δ 7.85 (s, 1H), 7.71 (s, 1H), 7.53 (s, 1H), 7.37-7.31 (m, 5H), 5.39 (s, 2H), 4.29 (q, J = 6.8 Hz, 2H), 3.58 (s, 3H), 2.13 (s, 3H), 1.29 (t, J = 6.8 Hz, 3H). | 352 |
| 199 | 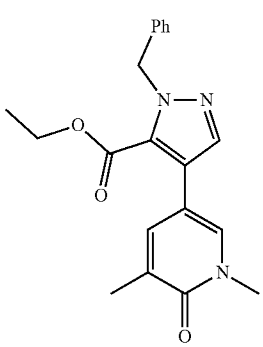 [SMILES: CCOC(=O)c1c(-c2cc(C)c(=O)n(C)c2)cnn1Cc1ccccc1] | 2-Benzyl-4-(1,5-dimethyl-6-oxo-1,6-dihydro-pyridin-3-yl)-2H-pyrazole-3-carboxylic acid ethyl ester | (CD$_3$OD, 400 MHz) δ 7.66-7.63 (m, 2H), 7.50 (s, 1H), 7.29-7.24 (m, 3H), 7.19-7.17 (m, 2H), 5.76 (s, 2H), 4.22 (q, J = 7.2 Hz, 2H), 3.59 (s, 3H), 2.13 (s, 3H), 1.15 (t, J = 7.2 Hz, 3H). | 352 |

Example 200: 4-amino-5-(1-benzyl-1H-pyrazol-4-yl)-1-methylpyridin-2(1H)-one

Step 1: tert-butyl (5-(1-benzyl-1H-pyrazol-4-yl)-1-methyl-2-oxo-1,2-dihydropyridin-4-yl)carbamate

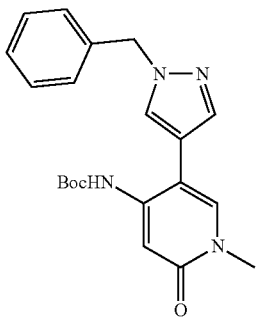 [SMILES: Cn1cc(-c2cnn(Cc3ccccc3)c2)c(NC(=O)OC(C)(C)C)cc1=O]

A solution of 5-(1-benzyl-1H-pyrazol-4-yl)-4-chloro-1-methylpyridin-2(1H)-one (300 mg, 1 mmol), tert-butyl carbamate (229 mg, 2 mmol), $Pd_2(dba)_3$ (46 mg, 0.05 mmol), XPhos (72 mg, 0.05 mmol) and $Cs_2CO_3$ (456 mg, 1.4 mmol) in 1,4-dioxane (20 mL) was stirred at 95° C. under nitrogen overnight. Upon cooling to room temperature, solvents were removed under reduced pressure. The residue was diluted with dichloromethane and washed with brine. The organic phase was dried over $Na_2SO_4$, filtered and concentrated under reduced pressure. The residue was purified by silica gel column chromatography (EtOAc) to afford the title compound (340 mg) as yellow solid.

Step 2: 4-amino-5-(1-benzyl-1H-pyrazol-4-yl)-1-methylpyridin-2(1H)-one

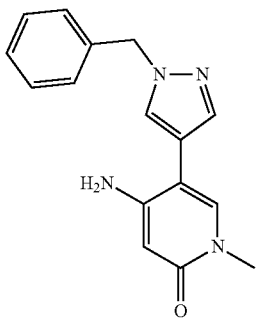 [SMILES: Cn1cc(-c2cnn(Cc3ccccc3)c2)c(N)cc1=O]

A solution of the title compound from Step 1 (340 mg, 0.89 mmol) in 1N HCl in 1,4-dioxane (20 mL) was stirred at room temperature for 12 hours. Solvents were removed under reduced pressure to afford the title compound as a yellow solid. $^1$H NMR (DMSO-d6, 400 MHz) 8.13 (s, 1H), 7.96 (s, 1H), 7.67 (s, 1H), 7.38-7.30 (m, 5H), 6.45 (s, 1H), 5.37 (s, 2H), 3.58 (s, 3H). LCMS (M+H)$^+$ 281.

Example 201: 3-((5-(1-benzyl-1H-pyrazol-4-yl)-1-methyl-2-oxo-1,2-dihydropyridin-4-yl)amino)propanoic Acid

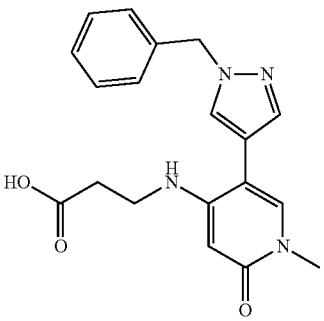

To a solution of the title compound from Example 200 (100 mg, 0.36 mmol) in DMF (20 mL) under nitrogen was added NaH (28 mg, 0.71 mmol, 60%). The reaction was stirred 1 h. methyl 3-bromopropanoate (89 mg, 0.53 mmol) was added and the resulting mixture was stirred for 2 days. Reaction contents were concentrated under reduced pressure to yield a residue that was purified by preparative-HPLC to afford the title compound (25 mg, 0.07 mmol) as a white solid. $^1$H NMR (CD$_3$OD, 400 MHz) 7.83 (s, 1H), 7.58 (s, 1H), 7.35-7.28 (m, 6H), 5.60 (s, 1H), 5.37 (s, 2H), 3.43 (s, 3H), 3.37 (t, J=6.0 Hz, 2H), 2.52 (t, J=6.0 Hz, 2H). LCMS (M+H)$^+$ 353.

Example 202: 2-[4-(4-Isopropoxy-1-methyl-6-oxo-1,6-dihydro-pyridin-3-yl)-pyrazol-1-yl]-benzonitrile Step 1: 2-[4-(4,4,5,5-Tetramethyl-[1,3,2]dioxaborolan-2-yl)-pyrazol-1-yl]-benzonitrile

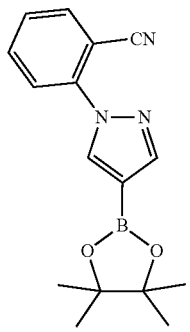 [SMILES: CC1(C)OB(c2cnn(-c3ccccc3C#N)c2)OC1(C)C]

NaH (464 mg, 11.6 mmol, 60% in oil) was added to a solution of 4-(4,4,5,5-tetramethyl-[1,3,2]dioxaborolan-2-yl)-1H-pyrazole (1.1 g, 5.8 mmol) in DMF (14 mL) at 0° C. The resulting mixture was stirred at the same temperature for 0.5 hour. 2-Fluoro-benzonitrile (0.9 g, 7.0 mmol) was added dropwise to the mixture that was stirred at 40° C. for 7 hours. It was then quenched with saturated NH$_4$Cl (40 mL) and extracted with DCM (30 mL×3). The combined organic layers were dried over Na$_2$SO$_4$, filtered and concentrated. The crude title compound (1.6 g, 5.4 mmol) was used directly in the next step.

Step 2: 2-[4-(4-Chloro-1-methyl-6-oxo-1,6-dihydro-pyridin-3-yl)-pyrazol-1-yl]-benzonitrile

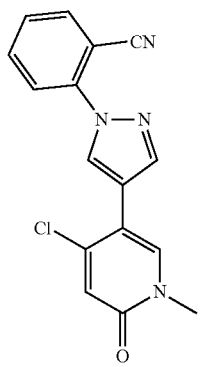 [SMILES: Cn1cc(-c2cnn(-c3ccccc3C#N)c2)c(Cl)cc1=O]

A mixture of the title compound from Step 1 (5.0 g, 17.0 mmol), 5-bromo-4-chloro-1-methyl-1H-pyridin-2-one (3.8 g, 17.0 mmol), Pd(dppf)Cl$_2$ (1.2 g, 1.7 mmol) and K$_3$PO$_4$ (9.0 g, 42.5 mmol) in a 1,4-dioxane/water mixture (90 mL/18 mL) was purged with N$_2$ and stirred at 80° C. for 5 hours. The mixture was quenched with water (50 mL) and extracted with DCM (50 mL×3). The combined organic layers were dried over Na$_2$SO$_4$, filtered and concentrated. The residue was purified by silica gel column chromatography eluting with DCM/MeOH (50:1) to give the title compound (1.8 g, 5.8 mmol) as a yellow solid in 34% yield. $^1$H NMR (300 MHz, CDCl$_3$) δ 8.31 (s, 1H), 7.91 (s, 1H), 7.85-7.76 (m, 3H), 7.50-7.46 (m, 2H), 6.81 (s, 1H), 3.61 (s, 3H). LCMS (M+H)$^+$ 311.

Step 3: 2-[4-(4-Isopropoxy-1-methyl-6-oxo-1,6-dihydro-pyridin-3-yl)-pyrazol-1-yl]-benzonitrile

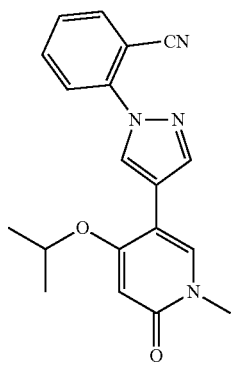 [SMILES: CC(C)Oc1cc(=O)n(C)cc1-c1cnn(-c2ccccc2C#N)c1]

NaH (68 mg, 1.2 mmol, 60% in oil) was added to a solution of propan-2-ol (1.1 g, 5.8 mmol) in DMF (8 mL) at 0° C. The resulting mixture was stirred at the same temperature for 0.5 hour. The title compound from Step 2 (124 mg, 0.4 mmol) was added to the mixture which was stirred at 0° C. for 0.5 hours. It was then warmed up to room temperature and stirred overnight. The reaction was quenched with water (10 mL) and extracted with DCM (15 mL*3). The combined organic layers were dried over Na$_2$SO$_4$, filtered and concentrated to give a brown residue. The residue was purified by reverse phase column chromatography to give the title compound (51 mg, 0.2 mmol) as a yellow solid. 1H NMR (CD$_3$OD, 400 MHz) δ 8.54 (s, 1H), 8.13 (s, 1H), 8.00 (s, 1H), 7.93-7.91 (m, 1H), 7.84-7.80 (m, 2H), 7.59-7.55 (m, 1H), 6.06 (s, 1H), 4.80-4.74 (m, 1H), 3.57 (s, 3H), 1.44 (d, J=6.0 Hz, 6H). LCMS (M+H)$^+$ 335.

Example 203: 2-[4-(4-Isopropoxy-1-methyl-6-oxo-1,6-dihydro-pyridin-3-yl)-pyrazol-1-yl]-benzoic Acid

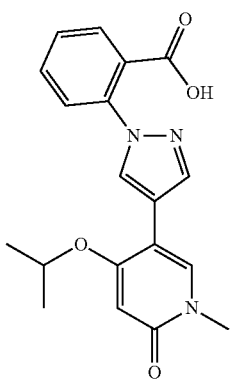 [SMILES: CC(C)Oc1cc(=O)n(C)cc1-c1cnn(-c2ccccc2C(=O)O)c1]

A solution of 2-[4-(4-isopropoxy-1-methyl-6-oxo-1,6-dihydro-pyridin-3-yl)-pyrazol-1-yl]-benzonitrile (30 mg, 0.09 mmol) and KOH (50 mg, 0.9 mmol) in water (7 mL) was stirred at 110° C. for 3 days. The pH was adjusted to 46 followed by extraction with DCM (10 mL×3). The combined organic layers were dried over Na$_2$SO$_4$, filtered and concentrated to give the title compound (16 mg, 0.05 mmol) as a yellow solid. $^1$H NMR (CD$_3$OD, 400 MHz) δ 8.16 (s, 1H), 8.00 (s, 1H), 7.96 (s, 1H), 7.89 (d, J=7.6 Hz, 1H), 7.68 (t, J=6.8 Hz, 1H), 7.58-7.55 (m, 2H), 6.04 (s, 1H), 4.78-4.72 (m, 1H), 3.56 (s, 3H), 1.42 (d, J=6.0 Hz, 6H). LCMS (M+H)$^+$ 354.

Example 204: 2-{4-[1-Methyl-4-(1-methyl-H-pyrazol-4-yl)-6-oxo-1,6-dihydro-pyridin-3-yl]-pyrazol-1-yl}-benzonitrile

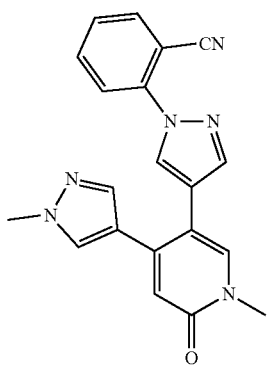

A mixture of the title compound from Example 202, Step 2 (200 mg, 0.65 mmol), 1-methyl-4-(4,4,5,5-tetramethyl-1,3,2-dioxaborolan-2-yl)-1H-pyrazole (201 mg, 0.97 mmol), Pd(dppf)Cl$_2$ (48 mg, 0.07 mmol) and K$_3$PO$_4$ (342 mg, 1.6 mmol) in a 1,4-dioxane/water mixture (10 mL/2 mL) was purged with N$_2$ and stirred at 100° C. for 4 hours. The mixture was quenched with water (10 mL) and extracted with DCM (7 mL×3). The combined organic layers were dried over Na₂SO₄, filtered and concentrated. The residue was purified by preparative TLC eluting with DCM/MeOH (30:1) to give the title compound (70 mg, 0.2 mmol) as a white solid. ¹H NMR (300 MHz, CD3OD) δ 8.15 (s, 1H), 7.92 (dd, J=7.6 Hz, J=1.2 Hz, 1H), 7.84-7.82 (m, 1H), 7.76 (d, J=7.6 Hz, 1H), 7.75 (s, 2H), 7.62-7.60 (m, 1H), 7.53 (s, 1H), 7.47 (s, 1H), 6.67 (s, 1H), 3.84 (s, 3H), 3.61 (s, 3H). LCMS (M+H)⁺ 357.

Examples 205-246 in Table 12 were prepared using the appropriate boronic acid or ester in a manner similar to Example 204. Carboxylic acids were prepared from the corresponding nitriles in a manner similar to Example 203.

TABLE 12

| Example | Structure | IUPAC Name | ¹H NMR (ppm) | MS (M + H) |
|---|---|---|---|---|
| 205 | 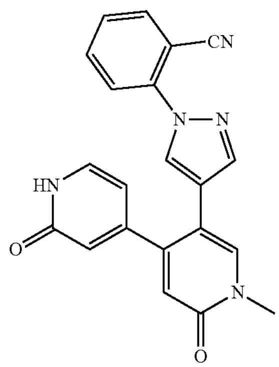 [SMILES: Cn1cc(-c2cnn(-c3ccccc3C#N)c2)c(-c2cc[nH]c(=O)c2)cc1=O] | 2-[4-(1-Methyl-6,2'-dioxo-1,6,1',2'-tetrahydro-[4,4']bipyridinyl-3-yl)-pyrazol-1-yl]-benzonitrile | (CD₃OD, 400 MHz) δ 8.10 (s, 1H), 7.93 (s, 1H), 7.87 (d, J = 6.4 Hz, 1H), 7.78 (t, J = 6.8 Hz, 1H), 7.71 (d, J = 8.4 Hz, 1H), 7.65 (s, 1H), 7.56 (t, J = 7.2 Hz, 1H), 7.39 (d, J = 6.4 Hz, 1H), 6.58 (s, 1H), 6.51 (s, 1H), 6.21 (d, J = 6.4 Hz, 1H), 3.66 (s, 3H). | 370 |
| 206 | 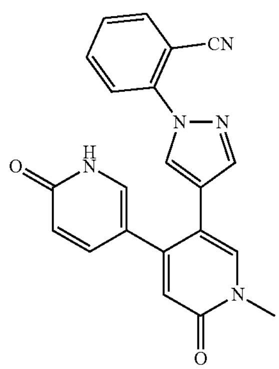 [SMILES: Cn1cc(-c2cnn(-c3ccccc3C#N)c2)c(-c2ccc(=O)[nH]c2)cc1=O] | 2-[4-(1'-Methyl-6,6'-dioxo-1,6,1',6'-tetrahydro-[3,4']bipyridinyl-3'-yl)-pyrazol-1-yl]-benzonitrile | (CD₃OD, 400 MHz) δ 8.12 (s, 1H), 7.90-7.87 (m, 2H), 7.80 (t, J = 6.8 Hz, 1H), 7.71 (d, J = 8.4 Hz, 1H), 7.65 (s, 1H), 7.58 (t, J = 7.2 Hz, 1H), 7.50 (s, 1H), 7.37 (d, J = 6.4 Hz, 1H), 6.58 (s, 1H), 6.46 (d, J = 6.4 Hz, 1H), 3.65 (s, 3H). | 370 |
| 207 | 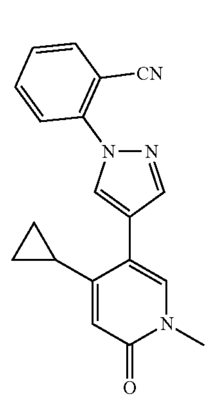 [SMILES: Cn1cc(-c2cnn(-c3ccccc3C#N)c2)c(C2CC2)cc1=O] | 2-[4-(4-Cyclopropyl-1-methyl-6-oxo-1,6-dihydro-pyridin-3-yl)-pyrazol-1-yl]-benzonitrile | (CD₃OD, 400 MHz) δ 8.47 (s, 1H), 8.01 (s, 1H), 7.95-7.93 (m, 1H), 7.87-7.86 (m, 2H), 7.76 (s, 1H), 7.63-7.59 (m, 1H), 6.19 (s, 1H), 3.60 (s, 3H), 1.99-1.96 (m, 1H), 1.14-1.09 (m, 2H), 0.87-0.83 (m, 2H). | 317 |

TABLE 12-continued

| Example | Structure | IUPAC Name | ¹H NMR (ppm) | MS (M + H) |
|---|---|---|---|---|
| 208 | 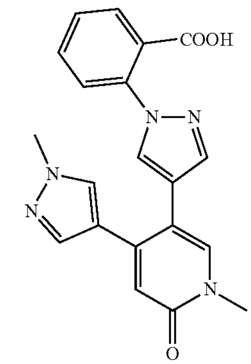 [SMILES: Cn1cc(-c2cc(=O)n(C)cc2-c2cnn(-c3ccccc3C(=O)O)c2)cn1] | 2-{4-[1-Methyl-4-(1-methyl-1H-pyrazol-4-yl)-6-oxo-1,6-dihydro-pyridin-3-yl]-pyrazol-1-yl}-benzoic acid | (DMSO-d6, 400 MHz) δ 6.4 Hz, J = 1.2 Hz, 1H), 8.07 (s, 1H), 7.78 (dd, J = 6.8 Hz, 1.2 Hz, 1H), 7.73 (s, 1H), 7.66 (td, J = 7.55-7.52 (m, 4H), 7.48 (s, 1H), 6.57 (s, 1H), 3.75 (s, 3H), 3.45 (s, 3H). | 376 |
| 209 | 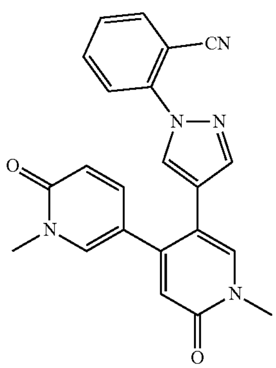 | 2-[4-(1,1'-Dimethyl-6,6'-dioxo-1,6,1',6'-tetrahydro-[3,4']bipyridinyl-3'-yl)-pyrazol-1-yl]-benzonitrile | (CD₃OD, 400 MHz) δ 8.12 (s, 1H), 7.92-7.90 (m, 2H), 7.85-7.80 (m, 2H), 7.74 (d, J = 8.0 Hz, 1H), 7.70 (s, 1H), 7.59 (t, J = 6.8 Hz, 1H), 7.31 (dd, J = 9.2 Hz, 2.0 Hz, 1H), 6.61 (s, 1H), 6.48 (d, J = 9.6 Hz, 1H), 3.67 (s, 3H), 3.58 (s, 3H). | 384 |
| 210 | 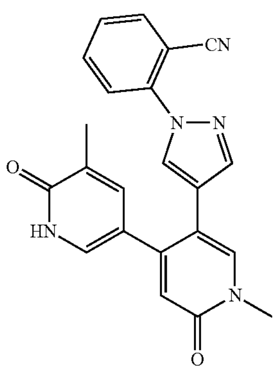 [SMILES: Cc1cc(-c2cc(=O)n(C)cc2-c2cnn(-c3ccccc3C#N)c2)c[nH]c1=O] | 2-[4-(5,1'-Dimethyl-6,6'-dioxo-1,6,1',6'-tetrahydro-[3,4']bipyridinyl-3'-yl)-pyrazol-1-yl]-benzonitrile | (CD₃OD, 400 MHz) δ 8.10 (s, 1H), 7.89 (d, J = 8.4 Hz, 1H), 7.86 (s, 1H), 7.81 (t, J = 8.4 Hz, 1H), 7.69 (d, J = 7.6 Hz, 1H), 7.63 (s, 1H), 7.57 (t, J = 7.6 Hz, 1H), 7.35-7.34 (m, 1H), 7.25 (s, 1H), 6.57 (s, 1H), 3.64(s, 3H), 2.02 (s, 3H). | 384 |
| 211 | 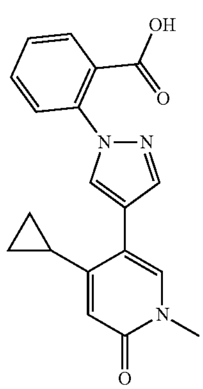 [SMILES: Cn1cc(-c2cnn(-c3ccccc3C(=O)O)c2)c(C2CC2)cc1=O] | 2-[4-(4-Cyclopropyl-1-methyl-6-oxo-1,6-dihydro-pyridin-3-yl)-pyrazol-1-yl]-benzoic acid | (CD₃OD, 400 MHz) δ 8.06 (s, 1H), 7.93-7.90 (m, 1H), 7.83 (s, 1H), 7.71-7.67 (m, 2H), 7.61-7.54 (m, 2H), 6.15 (s, 1H), 3.57 (s, 3H), 1.97-1.93 (m, 1H), 1.09-1.04 (m, 2H), 0.83-0.79 (m, 2H). | 336 |

TABLE 12-continued

| Example | Structure | IUPAC Name | ¹H NMR (ppm) | MS (M + H) |
|---|---|---|---|---|
| 212 | 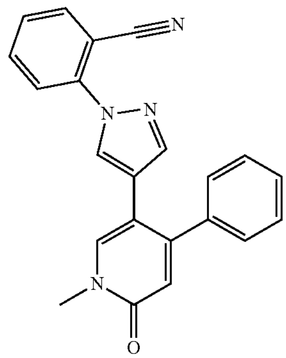 [SMILES: Cn1cc(-c2cnn(-c3ccccc3C#N)c2)c(-c2ccccc2)cc1=O] | 2-[4-(1-Methyl-6-oxo-4-phenyl-1,6-dihydro-pyridin-3-yl)-pyrazol-1-yl]-benzonitrile | (DMSO-$d_6$, 400 MHz,) δ 8.03 (s, 1H), 7.99-7.97 (m, 2H), 7.85-7.81 (m, 1H), 7.61 (d, J = 8.4 Hz, 1H), 7.55 (t, J = 7.6 Hz, 1H), 7.41-7.39 (m, 3H), 7.32 (s, 1H), 7.27-7.25 (m, 2H), 6.37 (s, 1H), 3.53 (s, 3H). | 353 |
| 213 | 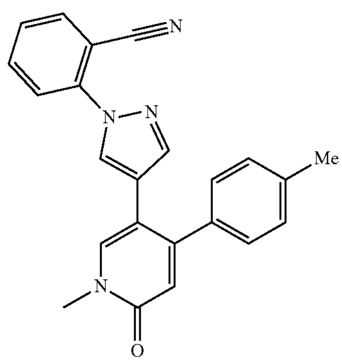 [SMILES: Cc1ccc(-c2cc(=O)n(C)cc2-c2cnn(-c3ccccc3C#N)c2)cc1] | 2-[4-(1-Methyl-6-oxo-4-p-tolyl-1,6-dihydro-pyridin-3-yl)-pyrazol-1-yl]-benzonitrile | (CDCl$_3$, 400 MHz) δ 7.77-7.75 (m, 2H), 7.68-7.65 (m, 2H), 7.43-7.42 (m, 2H), 7.30 (s, 1H), 7.16-7.10 (m, 4H), 6.62 (s, 1H), 3.65 (s, 3H), 2.36 (s, 3H). | 367 |
| 214 | 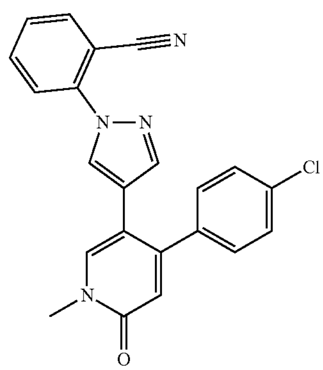 [SMILES: Cn1cc(-c2cnn(-c3ccccc3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-benzonitrile | (CDCl$_3$, 400 MHz) δ 7.78-7.76 (m, 2H), 7.72-7.66 (m, 2H), 7.46-7.42 (m, 2H), 7.34-7.32 (m, 3H), 7.18-7.15 (m, 2H), 6.61 (s, 1H), 3.65 (s, 3H). | 387 |
| 215 | 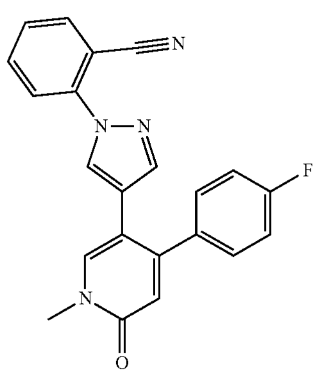 [SMILES: Cn1cc(-c2cnn(-c3ccccc3C#N)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzonitrile | (CD$_3$OD, 400 MHz) δ 7.91 (d, J = 1.6 Hz, 2H), 7.88 (dd, J = 7.6, 1.6 Hz, 1H), 7.79 (td, J = 7.6, 0.8 Hz, 1H), 7.63 (d, J = 7.6 Hz, 1H), 7.56 (td, J = 7.6, 0.8 Hz, 1H), 7.37 (s, 1H), 7.32-7.29 (m, 2H), 7.14-7.10 (m, 2H), 6.56 (s, 1H), 3.67 (s, 3H). | 371 |

TABLE 12-continued

| Example | IUPAC Name | ¹H NMR (ppm) | MS (M + H) |
|---|---|---|---|
| 216 | 2-{4-[4-(3-Chloro-phenyl)-1-methyl-6-oxo-1,6-dihydro-pyridin-3-yl]-pyrazol-1-yl}-benzonitrile | (CD$_3$OD, 400 MHz) δ 7.93-7.86 (m, 3H), 7.79 (t, J = 8.0 Hz, 1H), 7.61 (d, J = 7.6 Hz, 1H), 7.58 (t, J = 7.6 Hz, 1H), 7.40-7.35 (m, 3H), 7.32 (s, 1H), 7.21 (d, J = 7.2 Hz, 1H), 6.59 (s, 1H), 3.67 (s, 3H). | 387 |
| 217 | 4-{5-[1-(2-Cyano-phenyl)-1H-pyrazol-4-yl]-1-methyl-2-oxo-1,2-dihydro-pyridin-4-yl}-benzoic acid | (DMSO-d$_6$, 400 MHz) δ 13.04 (br, 1H), 8.09 (s, 1H), 8.05 (s, 1H), 7.98 (dd, J = 7.6, 1.2 Hz, 1H), 7.93 (d, J = 8.4 Hz, 2H), 7.85-7.81 (m, 1H), 7.66 (d, J = 8.0 Hz, 1H), 7.56 (td, J = 7.6, 0.8 Hz, 1H), 7.38 (d, J = 8.4 Hz, 2H), 7.34 (s, 1H), 6.43 (s, 1H), 3.35 (s, 3H). | 397 |
| 218 | 4-{5-[1-(2-Cyano-phenyl)-1H-pyrazol-4-yl]-1-methyl-2-oxo-1,2-dihydro-pyridin-4-yl}-benzamide | (DMSO-d$_6$, 400 MHz) δ 8.08 (s, 1H), 8.03-7.97 (m, 3H), 7.88-7.80 (m, 3H), 7.64 (d, J = 7.6 Hz, 1H), 7.55 (t, J = 7.6 Hz, 1H), 7.41 (s, 1H), 7.35-7.33 (m, 3H), 6.41 (s, 1H), 3.54 (s, 3H). | 396 |
| 219 | 4-{5-[1-(2-Cyano-phenyl)-1H-pyrazol-4-yl]-1-methyl-2-oxo-1,2-dihydro-pyridin-4-yl}-N-methyl-benzamide | (DMSO-d$_6$, 400 MHz) δ 8.49 (q, J = 4.8, 1H), 8.08 (s, 1H), 8.03 (s, 1H), 7.98 (dd, J = 8.0, 1.2 Hz, 1H), 7.85-7.80 (m, 3H), 7.65 (m, d, J = 8.0 Hz, 1H), 7.55 (td, J = 7.6, 0.8 Hz, 1H), 7.35 (d, J = 8.0 Hz, 2H), 7.32 (s, 1H), 6.41 (s, 1H), 3.54 (s, 3H), 2.78 (d, J = 4.4 Hz, 3H). | 410 |

TABLE 12-continued

| Example | Structure | IUPAC Name | ¹H NMR (ppm) | MS (M + H) |
|---|---|---|---|---|
| 220 | 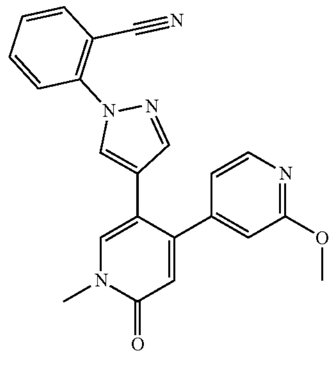 [SMILES: COc1cc(-c2cc(=O)n(C)cc2-c2cnn(-c3ccccc3C#N)c2)ccn1] | 2-[4-(2'-Methoxy-1-methyl-6-oxo-1,6-dihydro-[4,4']bipyridinyl-3-yl)-pyrazol-1-yl]-benzonitrile | (CD$_3$OD, 300 MHz) δ 8.12 (d, J = 5.1 Hz, 1H), 7.99 (s, 1H), 7.95 (s, 1H), 7.90-7.78 (m, 2H), 7.67-7.57 (m, 2H), 7.48 (s, 1H), 6.8 (dd, J = 5.4 Hz, 1.2 Hz, 1H), 6.75 (s, 1H), 6.58 (s, 1H), 3.91 (s, 3H), 3.68 (s, 3H). | 384 |
| 221 | 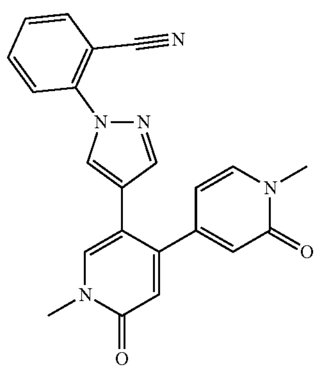 [SMILES: Cn1ccc(-c2cc(=O)n(C)cc2-c2cnn(-c3ccccc3C#N)c2)cc1=O] | 2-[4-(1,1'-Dimethyl-6,2'-dioxo-1,6,1',2'-tetrahydro-[4,4']bipyridinyl-3-yl)-pyrazol-1-yl]-benzonitrile | (CD$_3$OD, 400 MHz) δ 8.05 (s, 1H), 7.93 (s, 1H), 7.86 (dd, J = 7.6, 1.2 Hz, 1H), 7.80 (td, J = 8.0, 1.6 Hz, 1H), 7.75-7.71 (m, 2H), 7.59 (d, J = 7.2 Hz, 1H), 7.55 (td, J = 7.6, 1.2 Hz, 1H), 6.56 (s, 1H), 6.51 (d, J = 1.6 Hz, 1H), 6.19 (dd, J = 7.2 , 1.6 Hz, 1H), 3.66 (s, 3H), 3.54 (s, 3H). | 384 |
| 222 | 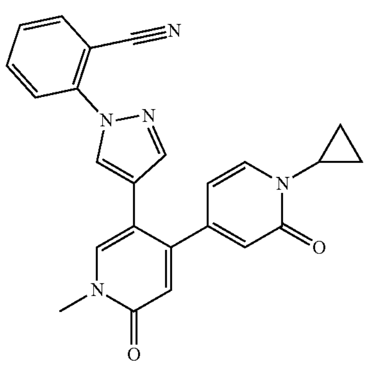 [SMILES: Cn1cc(-c2cnn(-c3ccccc3C#N)c2)c(-c2ccn(C3CC3)c(=O)c2)cc1=O] | 2-[4-(1'-Cyclopropyl-1-methyl-6,2'-dioxo-1,6,1',2'-tetrahydro-[4,4']bipyridinyl-3-yl)-pyrazol-1-yl]-benzonitrile | (CD$_3$OD, 400 MHz) δ 8.04 (s, 1H), 7.93 (s, 1H), 7.87-7.85 (m, 1H), 7.82-7.78 (m, 1H), 7.75-7.72 (m, 2H), 7.57-7.53 (m, 2H), 6.55 (s, 1H), 6.49 (d, J = 2.0 Hz, 1H), 6.15 (dd, J = 7.2, 2.4 Hz, 1H), 3.66 (s. 3H), 3.32-3.30 (m, 1H), 1.11-1.06 (m, 2H), 0.95-0.91 (m, 2H). | 410 |
| 223 | 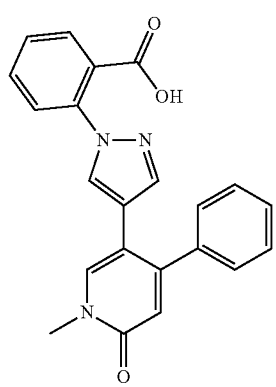 [SMILES: Cn1cc(-c2cnn(-c3ccccc3C(=O)O)c2)c(-c2ccccc2)cc1=O] | 2-[4-(1-Methyl-6-oxo-4-phenyl-1,6-dihydro-pyridin-3-yl)-pyrazol-1-yl]-benzoic acid | (DMSO-d$_6$, 400 MHz) δ 7.99 (s, 1H), 7.67 (d, J = 7.2 Hz, 1H), 7.62 (s, 1H), 7.58 (d, J = 7.2 Hz, 1H), 7.45 (t, J = 7.6 Hz, 1H), 7.39-7.38 (m, 4H), 7.26-7.23 (m, 2H), 7.14 (s, 1H), 6.35 (s, 1H), 3.52 (s, 3H). | 372 |

TABLE 12-continued

| Example | Structure | IUPAC Name | ¹H NMR (ppm) | MS (M + H) |
|---|---|---|---|---|
| 224 | 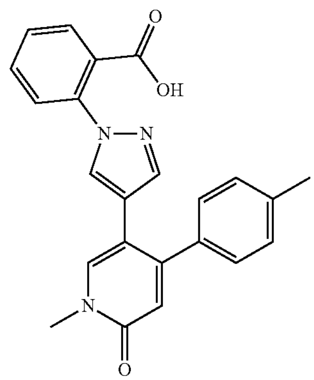 [SMILES: Cc1ccc(-c2cc(=O)n(C)cc2-c2cnn(-c3ccccc3C(=O)O)c2)cc1] | 2-[4-(1-Methyl-6-oxo-4-p-tolyl-1,6-dihydro-pyridin-3-yl)-pyrazol-1-yl]-benzoic acid | (DMSO-d$_6$, 400 MHz) δ 12.87 (br, 1H), 7.96 (s, 1H), 7.70-7.68 (m, 2H), 7.64-7.60 (m, 1H), 7.49-7.40 (m, 2H), 7.20-7.12 (m, 5H), 6.33 (s, 1H), 3.51 (s, 3H), 2.32 (s, 3H). | 386 |
| 225 | 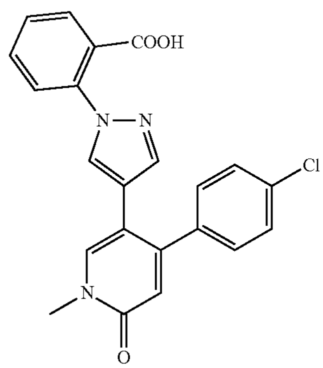 [SMILES: Cn1cc(-c2cnn(-c3ccccc3C(=O)O)c2)c(-c2ccc(Cl)cc2)cc1=O] | 2-(4-(4-(4-chlorophenyl)-1-methyl-6-oxo-1,6-dihydropyridin-3-yl)-1H-pyrazol-1-yl)benzoic acid | (CD$_3$OD, 400 MHz) δ 7.89 (s, 1H), 7.81 (dd, J = 7.6, J = 1.2, 1H), 7.64 (s, 1H), 7.61 7.57 (m, 1H), 7.52-7.48 (m, 1H), 7.43-7.38 (m, 3H), 7.29-7.26 (m, 2H), 7.17 (s, 1H), 6.55 (s, 1H), 3.66 (s, 3H). | 405 |
| 226 | 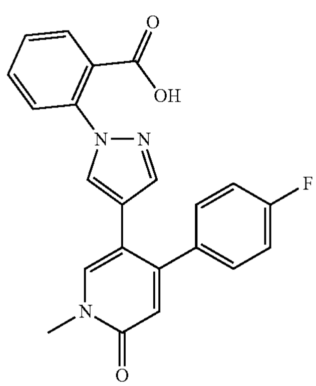 [SMILES: Cn1cc(-c2cnn(-c3ccccc3C(=O)O)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzoic acid | (CD$_3$OD, 300 MHz) δ 7.92-7.89 (m, 2H), 7.66-7.63 (m, 1H), 7.57-7.52 (m, 2H), 7.42 (d, J = 7.5 Hz, 1H), 7.34-7.30 (m, 2H), 7.23 (s, 1H), 7.16-7.10 (m, 2H), 6.56 (s, 1H), 3.67 (s, 3H). | 390 |
| 227 | 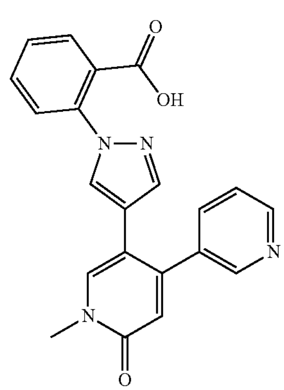 [SMILES: Cn1cc(-c2cnn(-c3ccccc3C(=O)O)c2)c(-c2cccnc2)cc1=O] | 2-[4-(1'-Methyl-6'-oxo-1',6'-dihydro-[3,4']bipyridinyl-3'-yl)-pyrazol-1-yl]-benzoic acid | (DMSO-d$_6$, 400 MHz) δ 8.58 (d, J = 4.8 Hz, 1H), 8.50 (s, 1H), 7.80 (s, 1H), 7.76 (s, 1H), 7.71-7.60 (m, 3H), 7.50-7.37 (m, 3H), 7.20 (s, 1H), 6.47 (s, 1H), 3.53 (s, 3H). | 373 |

TABLE 12-continued

| Example | Structure | IUPAC Name | ¹H NMR (ppm) | MS (M + H) |
|---------|-----------|------------|--------------|------------|
| 228 | 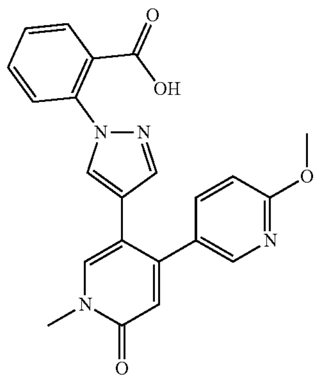 [SMILES: COc1ccc(-c2cc(=O)n(C)cc2-c2cnn(-c3ccccc3C(=O)O)c2)cn1] | 2-[4-(6-Methoxy-1'-methyl-6'-oxo-1',6'-dihydro-[3,4']bipyridinyl-3'-yl)-pyrazol-1-yl]-benzoic acid | (CD$_3$OD, 400 MHz) δ 7.81 (s, 1H), 7.70 (d, J = 8.12 (s, 1H), 7.91 (s, 1H), 8.7 Hz, 1H), 7.57-7.44 (m, 4H), 7.18 (s, 1H), 6.79 (d, J = 8.8 Hz, 1H), 6.58 (s, 1H), 3.93 (s, 3H), 3.67 (s, 3H). | 403 |
| 229 | 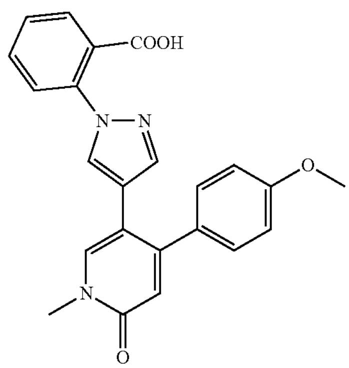 [SMILES: COc1ccc(-c2cc(=O)n(C)cc2-c2cnn(-c3ccccc3C(=O)O)c2)cc1] | 2-{4-[4-(4-Methoxy-phenyl)-1-methyl-6-oxo-1,6-dihydro-pyridin-3-yl]-pyrazol-1-yl}-benzoic acid | (DMSO-d$_6$, 400 MHz) δ 7.94 (s, 1H), 7.71-7.65 (m, 2H), 7.64-7.60 (m, 1H), 7.50-7.42 (m, 2H), 7.19-7.16 (m, 3H), 6.92 (d, J = 8.8 Hz, 2H), 6.33 (s, 1H), 3.77 (s, 3H), 3.51 (s, 3H). | 401 |
| 230 | 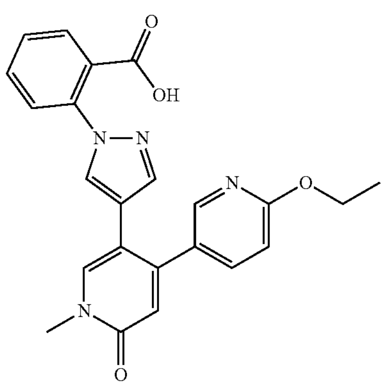 [SMILES: CCOc1ccc(-c2cc(=O)n(C)cc2-c2cnn(-c3ccccc3C(=O)O)c2)cn1] | 2-[4-(6-Ethoxy-1'-methyl-6'-oxo-1',6'-dihydro-[3,4']bipyridinyl-3'-yl)-pyrazol-1-yl]-benzoic acid | (CD$_3$OD, 400 MHz) δ 8.08 (d, J = 2.0 Hz, 1H), 7.89 (s, 1H), 7.78 (s, 1H), 7.70 (d, J = 8.0 Hz, 1H), 7.55-7.44 (m, 4H), 7.18 (s, 1H), 6.75 (d, J = 8.8 Hz, 1H), 6.57 (s, 1H), 4.33 (q, J = 7.2 Hz, 2H), 3.66 (s, 3H), 3.66 (t, J = 7.2 Hz, 3H). | 417 |
| 231 | 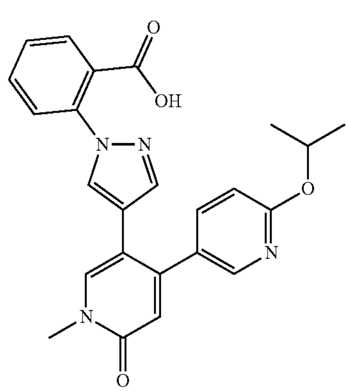 [SMILES: CC(C)Oc1ccc(-c2cc(=O)n(C)cc2-c2cnn(-c3ccccc3C(=O)O)c2)cn1] | 2-[4-(6-Isopropoxy-1'-methyl-6'-oxo-1',6'-dihydro-[3,4']bipyridinyl-3'-yl)-pyrazol-1-yl]-benzoic acid | (DMSO-d$_6$, 400 MHz) δ 7.72-7.70 (m, 1H), 7.64-8.10 (d, J = 2.4 Hz, 1H), 7.94 (s, 1H), 7.83 (s, 1H), 7.60 (m, 1H), 7.50-7.42 (m, 3H), 7.24 (s, 1H), 6.68 (d, J = 8.4 Hz, 1H), 6.43 (s, 1H), 5.27-5.22 (m, 1H), 3.51 (s, 3H), 1.28 (d, J = 6.0 Hz, 6H). | 431 |

TABLE 12-continued

| Example | Structure | IUPAC Name | ¹H NMR (ppm) | MS (M + H) |
|---|---|---|---|---|
| 232 | 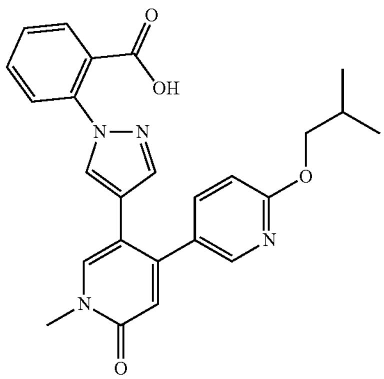 [SMILES: CC(C)COc1ccc(-c2cc(=O)n(C)cc2-c2cnn(-c3ccccc3C(=O)O)c2)cn1] | 2-[4-(6-Isobutoxy-1'-methyl-6'-oxo-1',6'-dihydro-[3,4']bipyridinyl-3'-yl)-pyrazol-1-yl]-benzoic acid | (CD₃OD, 400 MHz) δ 8.07 (d, J = 2.4 Hz, 1H), 7.90 (dd, J = 8.0, 1.6 Hz, 1H), 7.86 (s, 1H), 7.67-7.63 (m, 2H), 7.56-7.53 (m, 2H), 7.43 (d, J = 7.6 Hz, 1H), 7.27 (s, 1H), 6.77 (d, J = 8.4 Hz, 1H), 6.58 (s, 1H), 4.05 (d, J = 6.8 Hz, 2H), 3.65 (s, 3H), 2.11-2.01 (m, 1H), 1.00 (d, J = 6.4 Hz, 6H). | 445 |
| 233 | 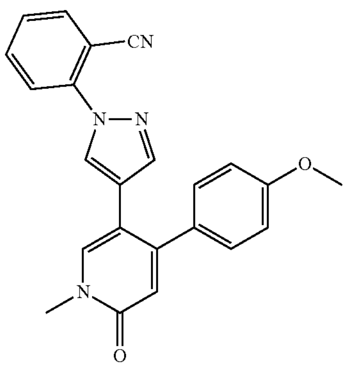 [SMILES: COc1ccc(-c2cc(=O)n(C)cc2-c2cnn(-c3ccccc3C#N)c2)cc1] | 2-{4-[4-(4-Methoxy-phenyl)-1-methyl-6-oxo-1,6-dihydro-pyridin-3-yl]-pyrazol-1-yl}-benzonitrile | (CD₃OD, 400 MHz) δ 7.89-7.87 (m, 3H), 7.81-7.76 (m, 1H), 7.62 (d, J = 8.0 Hz, 1H), 7.55 (t, J = 7.6 Hz, 1H), 7.35 (s, 1H), 7.20 (d, J = 8.4 Hz, 2H), 6.93 (d, J = 8.8 Hz, 2H), 6.53 (s, 1H), 3.80 (s, 3H), 3.66 (s, 3H). | 382 |
| 234 | 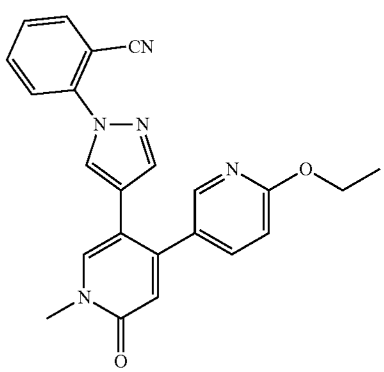 [SMILES: CCOc1ccc(-c2cc(=O)n(C)cc2-c2cnn(-c3ccccc3C#N)c2)cn1] | 2-[4-(6-Ethoxy-1'-methyl-6'-oxo-1',6'-dihydro-[3,4']bipyridinyl-3'-yl)-pyrazol-1-yl]-benzonitrile | (DMSO-d₆, 400 MHz) δ 8.16 (s, 1H), 8.09 (s, 1H), 8.00-7.99 (m, 2H), 7.84-7.82 (m, 1H), 7.70-7.68 (m, 1H), 7.58-7.50 (m, 2H), 7.45 (s, 1H), 6.75 (d, J = 8.4 Hz, 1H), 6.44 (s, 1H), 4.32 (q, J = 7.2 Hz, 2H), 3.52 (s, 3H), 1.30 (t, J = 7.2 Hz, 3H). | 398 |
| 235 | 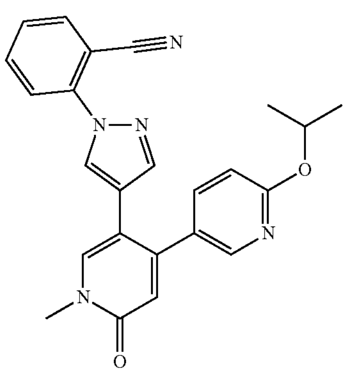 [SMILES: CC(C)Oc1ccc(-c2cc(=O)n(C)cc2-c2cnn(-c3ccccc3C#N)c2)cn1] | 2-[4-(6-Isopropoxy-1'-methyl-6'-oxo-1',6'-dihydro-[3,4']bipyridinyl-3'-yl)-pyrazol-1-yl]-benzonitrile | (CD₃OD, 400 MHz) δ 8.05 (d, J = 2.8 Hz, 1H), 7.99 (s, 1H), 7.89-7.87 (m, 2H), 7.81-7.77 (m, 1H), 7.67-7.65 (m, 1H), 7.58-7.50 (m, 2H), 7.45 (s, 1H), 6.69 (d, J = 8.8 Hz, 1H), 6.58 (s, 1H), 5.28-5.22 (m, 1H), 3.66 (s, 3H), 1.31 (d, J = 6.4 Hz, 6H). | 412 |

TABLE 12-continued

| Example | Structure | IUPAC Name | ¹H NMR (ppm) | MS (M + H) |
|---|---|---|---|---|
| 236 | 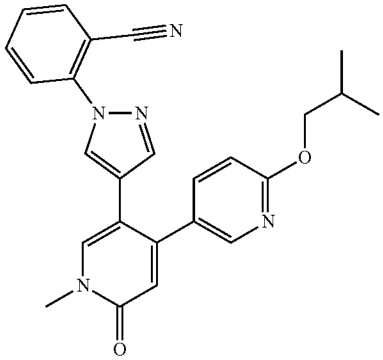 [SMILES: CC(C)COc1ccc(-c2cc(=O)n(C)cc2-c2cnn(-c3ccccc3C#N)c2)cn1] | 2-[4-(6-Isobutoxy-1'-methyl-6'-oxo-1',6'-dihydro-[3,4']bipyridinyl-3'-yl)-pyrazol-1-yl]-benzonitrile | (CD₃OD, 400 MHz) δ 8.05 (d, J = 2.4 Hz, 1H), 7.99 (s, 1H), 7.89-7.86 (m, 2H), 7.81-7.77 (m, 1H), 7.68-7.65 (m, 1H), 7.57-7.52 (m, 2H), 7.45 (s, 1H), 6.77 (d, J = 8.4 Hz, 1H), 6.58 (s, 1H), 4.04 (d, J = 6.8 Hz, 2H), 3.66 (s, 3H), 2.09-2.02 (m, 1H), 1.00 (d, J = 6.8 Hz, 6H). | 426 |
| 237 | 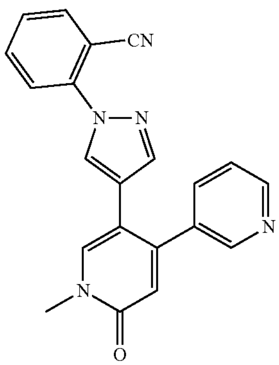 [SMILES: Cn1cc(-c2cnn(-c3ccccc3C#N)c2)c(-c2cccnc2)cc1=O] | 2-[4-(1'-Methyl-6'-oxo-1',6'-dihydro-[3,4']bipyridinyl-3'-yl)-pyrazol-1-yl]-benzonitrile | (CD₃OD, 400 MHz) δ 8.56 (d, J = 4.0 Hz, 1H), 8.47 (s, 1H), 7.97-7.94 (m, 2H), 7.88-7.77 (m, 3H), 7.64-7.42 (m, 3H), 7.42 (s, 1H), 6.63 (s, 1H), 3.68 (s, 3H). | 354 |
| 238 | 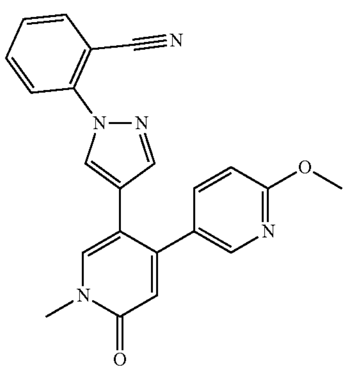 [SMILES: COc1ccc(-c2cc(=O)n(C)cc2-c2cnn(-c3ccccc3C#N)c2)cn1] | 2-(4-(6-methoxy-1'-methyl-6'-oxo-1',6'-dihydro-[3,4'-bipyridin]-3'-yl)-1H-pyrazol-1-yl)benzonitrile | (CDCl₃, 300 MHz) □ 8.11 (d, J = 2.1 Hz, 1H), 7.85 (s, 1H), 7.79-7.71 (m, 3H), 7.47-7.37 (m, 4H), 6.72 (d, J = 8.4 Hz, 1H), 6.64 (s, 1H), 3.96 (s, 3H), 3.66 (s, 3H). | 384 |
| 239 | 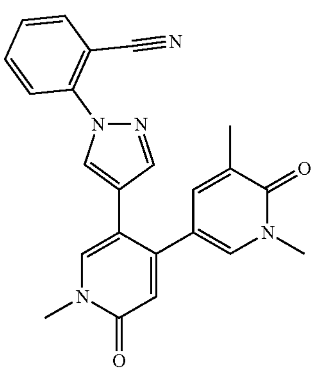 [SMILES: Cc1cc(-c2cc(=O)n(C)cc2-c2cnn(-c3ccccc3C#N)c2)cn(C)c1=O] | 2-(4-(1,1',5-trimethyl-6,6'-dioxo-1,1',6,6'-tetrahydro-[3,4'-bipyridin]-3'-yl)-1H-pyrazol-1-yl)benzonitrile | (CD₃OD, 400 MHz) δ 8.09 (s, 1H), 7.90-7.87 (m, 2H), 7.81 (dd, J = 7.6, 7.6 Hz, 1H), 7.70 (d, J = 8.0 Hz, 1H), 7.66-7.62 (m, 2H), 7.57 (dd, J = 7.6, 7.6 Hz, 1H), 7.16 (s, 1H), 6.58 (s, 1H), 3.65 (s, 3H), 3.56 (s, 3H), 2.01 (s, 3H). | 398 |

TABLE 12-continued

| Example | Structure | IUPAC Name | ¹H NMR (ppm) | MS (M + H) |
|---|---|---|---|---|
| 240 | 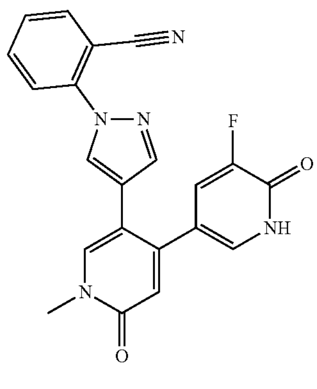 [SMILES: Cn1cc(-c2cnn(-c3ccccc3C#N)c2)c(-c2c[nH]c(=O)c(F)c2)cc1=O] | 2-(4-(5-fluoro-1'-methyl-6,6'-dioxo-1,1',6,6'-tetrahydro-[3,4'-bipyridin]-3'-yl)-1H-pyrazol-1-yl)benzonitrile | (DMSO-d$_6$, 400 MHz) δ 8.27 (s, 1H), 8.00 (dd, J = 7.6, 1.2 Hz, 1H), 7.94 (s, 1H), 7.89-7.85 (m, 1H), 7.75-7.71 (m, 2H), 7.59-7.56 (m, 1H), 7.25 (d, J = 1.6 Hz, 1H), 7.16 (dd, J = 11.4, 2.2 Hz, 1H), 6.47 (s, 1H), 3.49 (s, 3H). | 388 |
| 241 | 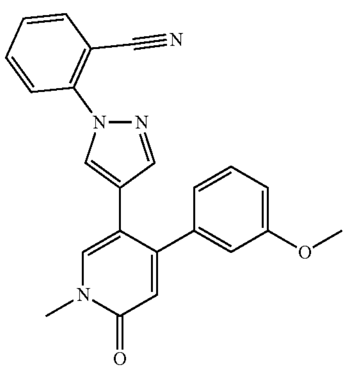 [SMILES: COc1cccc(-c2cc(=O)n(C)cc2-c2cnn(-c3ccccc3C#N)c2)c1] | 2-{4-[4-(3-Methoxy-phenyl)-1-methyl-6-oxo-1,6-dihydro-pyridin-3-yl]-pyrazol-1-y1}-benzonitrile | (CD$_3$OD, 400 MHz) δ 7.92 (s, 1H), 7.88 (s, 1H), 7.86 (s, 1H), 7.77-7.75 (m, 1H), 7.59-7.75 (m, 2H), 7.36 (s, 1H), 7.30 (t, J = 8.0 Hz, 1H), 6.94 (dd, J = 2.8, 8.8 Hz, 1H), 6.84 (d, J = 8.0 Hz, 1H), 6.79 (s, 1H), 6.55 (s, 1H), 3.72 (s, 3H), 3.67 (s, 3H). | 383 |
| 242 | 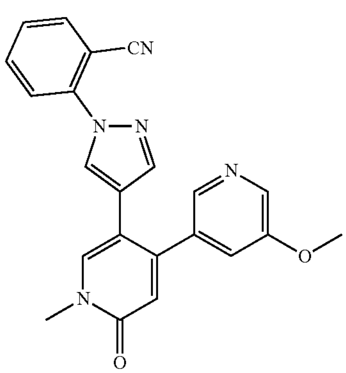 [SMILES: COc1cncc(-c2cc(=O)n(C)cc2-c2cnn(-c3ccccc3C#N)c2)c1] | 2-(4-(5-methoxy-1'-methyl-6'-oxo-1',6'-dihydro-[3,4'-bipyridin]-3'-yl)-1H-pyrazol-1-yl)benzonitrile | (CD$_3$OD, 400 MHz) δ 8.25 (d, J = 2.8 Hz, 1H), 8.06 (d, J = 1.6 Hz, 1H), 7.94 (s, 1H), 7.90 (s, 1H), 7.87-7.76 (m, 2H), 7.67 (s, 1H), 7.57-7.53 (m, 1H), 7.44 (s, 1H), 7.24-7.23 (m, 1H), 6.65 (s, 1H), 3.82 (s, 3H), 3.70 (s, 3H). | 384 |
| 243 | 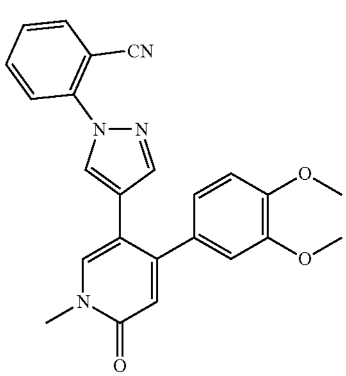 [SMILES: COc1ccc(-c2cc(=O)n(C)cc2-c2cnn(-c3ccccc3C#N)c2)cc1OC] | 2-(4-(4-(3,4-dimethoxyphenyl)-1-methyl-6-oxo-1,6-dihydropyridin-3-yl)-1H-pyrazol-1-yl)benzonitrile | (CD$_3$OD, 400 MHz) δ 7.30 (s, 1H), 7.88-7.87 (m, 2H), 7.81-7.77 (m, 1H), 7.62 (d, J = 7.6 Hz, 1H), 7.57-7.53 (m, 1H), 7.38 (s, 1H), 6.98 (d, J = 8.8 Hz, 1H), 6.91-6.88 (m, 1H), 6.77 (s, 1H), 6.57 (s, 1H), 3.84 (s, 3H), 3.67 (s, 3H), 3.66 (s, 3H). | 413 |

TABLE 12-continued

| Example | Structure | IUPAC Name | ¹H NMR (ppm) | MS (M + H) |
|---|---|---|---|---|
| 244 | 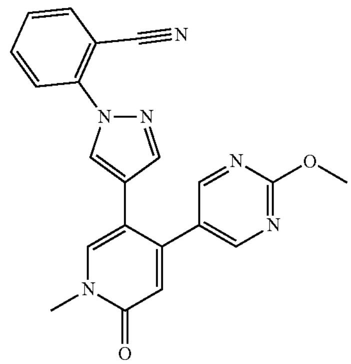 [SMILES: COc1ncc(-c2cc(=O)n(C)cc2-c2cnn(-c3ccccc3C#N)c2)cn1] | 2-{4-[4-(2-Methoxy-pyrimidin-5-yl)-1-methyl-6-oxo-1,6-dihydro-pyridin-3-yl]-pyrazol-1-yl}-benzonitrile | (CD$_3$OD + CDCl$_3$, 400 MHz) δ 8.47 (s, 2H), 8.03 (s, 1H), 7.88 (s, 1H), 7.84 (dd, J = 8.0 Hz, J = 1.2 Hz, 1H), 7.79 (td, J = 8.0 Hz, J = 1.2 Hz, 1H), 7.73 (dd, J = 8.0 Hz, J = 0.8 Hz, 1H), 7.56 (s, 1H), 7.54 (dd, J = 7.6 Hz, J = 0.8 Hz, 1H), 6.66 (s, 1H), 4.03 (s, 3H), 3.68 (s, 3H). | 385 |
| 245 | 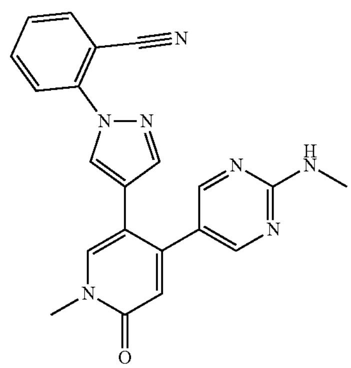 [SMILES: CNc1ncc(-c2cc(=O)n(C)cc2-c2cnn(-c3ccccc3C#N)c2)cn1] | 2-(4-(1-methyl-4-(2-(methylamino)pyrimidin-5-yl)-6-oxo-1,6-dihydropyridin-3-yl)-1H-pyrazol-1-yl)benzonitrile | (CD$_3$OD, 400 MHz,) δ 8.18 (br, 2H), 8.10 (s, 1H), 7.88-7.80 (m, 2H), 7.78 (s, 1H), 7.73 (d, J = 7.6 Hz, 1H), 7.57 (s, 1H), 7.54 (dd, J = 7.6 Hz, 1.2 Hz, 1H), 6.59 (s, 1H), 3.66 (s, 3H), 2.93 (s, 3H). | 384 |
| 246 | 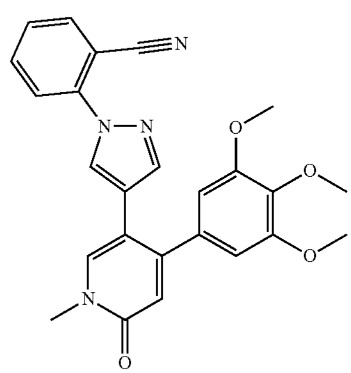 [SMILES: COc1cc(-c2cc(=O)n(C)cc2-c2cnn(-c3ccccc3C#N)c2)cc(OC)c1OC] | 2-{4-[1-Methyl-6-oxo-4-(3,4,5-trimethoxy-phenyl)-1,6-dihydro-pyridin-3-yl]-pyrazol-1-yl}-benzonitrile | (CD$_3$OD, 400 MHz) δ 7.76 (d, J = 4.4 Hz, 2H), 7.76 (d, J =7.6 Hz, 1H), 7.79 (t, J =2.8 Hz, 1H), 7.62 (t, J =7.6 Hz, 1H), 7.56 (t, J =6.8 Hz, 1H), 7.44 (s, 1H), 6.61 (s, 1H), 6.55 (s, 2H) 3.77 (s, 3H), 3.73 (s, 6H), 3.67 (s, 3H). | 443 |

Examples 247-249 in Table 13 were prepared from the corresponding nitriles in a manner similar to Example 203.

TABLE 13

| Example | Structure | IUPAC Name | ¹H NMR (ppm) | MS (M + H) |
|---|---|---|---|---|
| 247 | 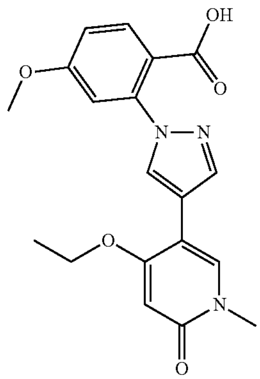 | 2-[4-(4-Ethoxy-1-methyl-6-oxo-1,6-dihydro-pyridin-3-yl)-pyrazol-1-yl]-4-methoxy-benzoic acid | (DMSO-d$_6$, 400 MHz) δ 8.23 (s, 1H), 8.07 (s, 1H), 7.99 (s, 1H), 7.73 (d, J = 8.8 Hz, 1H), 7.11 (d, J = 2.4 Hz, 1H), 7.05 (dd, J = 8.8 Hz, 2.8 Hz, 1H), 5.89 (s, 1H), 4.08 (q, J = 7.2 Hz, 2H), 3.87 (s, 3H), 3.41 (s, 3H), 1.40 (t, J = 6.8 Hz, 3H). | 370 |
| 248 | 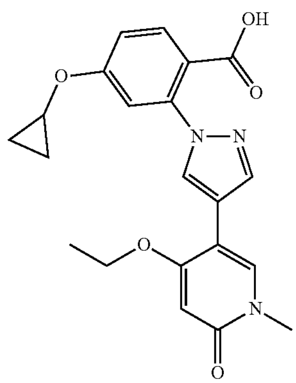 [SMILES: CCOc1cc(=O)n(C)cc1-c1cnn(-c2cc(OC3CC3)ccc2C(=O)O)c1] | 4-Cyclopropoxy-2-[4-(4-ethoxy-1-methyl-6-oxo-1,6-dihydro-pyridin-3-yl)-pyrazol-1-yl]-benzoic acid | (CD$_3$OD+CDCl$_3$, 400 MHz) δ 8.07 (s, 1H), 7.97-7.95 (m, 2H), 7.82 (s, 1H), 7.20-7.18 (m, 2H), 6.03 (s, 1H), 4.15 (q, J = 7.2 Hz, 2H), 3.90-3.87 (m, 1H), 3.58 (s, 3H), 1.51 (t, J = 7.2 Hz, 3H), 0.88-0.85 (m, 2H), 0.82-0.80 (m, 2H). | 396 |
| 249 | 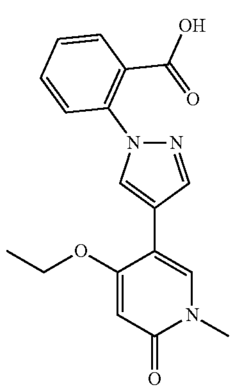 [SMILES: CCOc1cc(=O)n(C)cc1-c1cnn(-c2ccccc2C(=O)O)c1] | 2-(4-(4-ethoxy-1-methyl-6-oxo-1,6-dihydropyridin-3-yl)-1H-pyrazol-1-yl)benzoic acid | (DMSO-d$_6$, 400 MHz) δ 12.96 (br s, 1H), 8.28 (s, 1H), 8.07 (s, 1H), 8.01 (s, 1H), 7.69 (d, J = 7.3 Hz, 1H), 7.67-7.54 (m, 2H), 7.54-7.32 (m, 1H), 5.90 (s, 1H), 4.09 (q, J = 7.0 Hz, 2H), 3.41 (s, 3H), 1.41 (t, J =7.0 Hz, 3H) | 340 |

Example 250: 5-(1-(2-chlorophenyl)-1H-pyrazol-4-yl)-1-methyl-4-((1-methyl-1H-pyrazol-4-yl)methoxy)pyridin-2(1H)-one Step 1: 5-bromo-1-methyl-4-((1-methyl-1H-pyrazol-4-yl)methoxy)pyridin-2(1H)-one

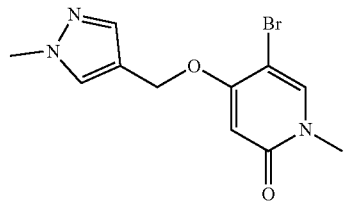

To a solution of 5-bromo-4-chloro-1-methylpyridin-2(1H)-one (100 mg, 0.45 mmol) and (1-methyl-1H-pyrazol-4-yl)methanol (150 mg, 1.35 mmol) in THF (2 mL) was added NaH (90 mg, 2.25 mmol). The reaction was heated at 70° C. for 2 h. It was then cooled to room temperature, diluted with EtOAc (10 mL) and sequentially washed with aqueous HCl (1N), water and brine. The organic phase was dried over Na$_2$SO$_4$, filtered and concentrated under reduced pressure. The residue was purified by silica gel column chromatography (DCM to 5% MeOH/DCM) to afford the title compound as a white solid (80 mg, 60%).

Step 2: 5-(1-(2-chlorophenyl)-1H-pyrazol-4-yl)-1-methyl-4-((1-methyl-1H-pyrazol-4-yl)methoxy)pyridin-2(1H)-one

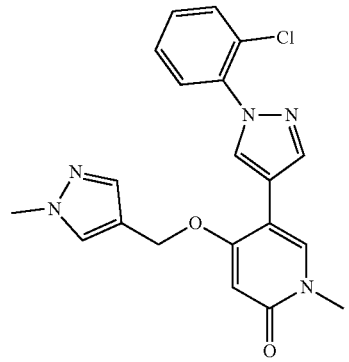

A mixture of (1-(2-chlorophenyl)-1H-pyrazol-4-yl)boronic acid (50 mg, 0.23 mmol) and 5-bromo-1-methyl-4-((1-methyl-1H-pyrazol-4-yl)methoxy)pyridin-2(1H)-one (80 mg, 0.27 mmol), Pd(PPh$_3$)$_4$ (30 mg, 0.03 mmol) and Na$_2$CO$_3$ (2M, 0.25 ml) in dioxane (1 mL) was heated to 120° C. for 10 min in a microwave reactor. The reaction was cooled, filtered through Celite and purified by preparative-HPLC (10-100% ACN/water) to afford the title compound as a white solid (24 mg, 27%). $^1$H NMR (DMSO-d$_6$, 400 MHz) δ 8.24 (s, 1H), 8.08 (s, 1H), 8.01 (s, 1H), 7.87 (s, 1H), 7.67-7.65 (m, 1H), 7.61-7.59 (m, 1H), 7.50 (d, J=1.0 Hz, 1H), 7.48-7.45 (m, 2H), 6.06 (s, 1H), 5.02 (s, 2H), 3.82 (s, 3H), 3.42 (s, 3H). LCMS (M+H)$^+$ 397.

Examples 251-253 in Table 14 were prepared using the appropriate substituted pyrazole and alcohol in a similar multi-step manner as Example 250.

TABLE 14

| Example | Structure | IUPAC Name | $^1$H NMR (ppm) | MS (M + H) |
|---|---|---|---|---|
| 251 | 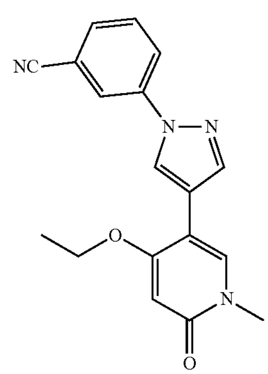 [SMILES: CCOc1cc(=O)n(C)cc1-c1cnn(-c2cccc(C#N)c2)c1] | 3-(4-(4-ethoxy-1-methyl-6-oxo-1,6-dihydropyridin-3-yl)-1H-pyrazol-1-yl)benzonitrile | (DMSO-d$_6$, 400 MHz) δ 8.67 (s, 1H), 8.30 (s, 1H), 8.18-8.07 (m, 1H), 8.02 (s, 1H), 7.98 (s, 1H), 7.80-7.55 (m, 2H), 5.85 (s, 1H), 4.04 (q, J = 7.0 Hz, 2H), 3.35 (s, 3H), 1.35 (t, J = 7.0 Hz, 3H) | 321 |

TABLE 14-continued

| Example | Structure | IUPAC Name | ¹H NMR (ppm) | MS (M + H) |
|---|---|---|---|---|
| 252 | 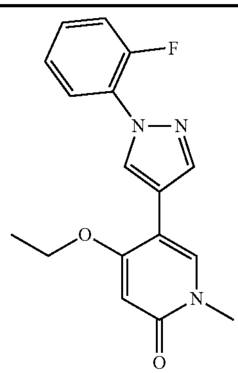 | 4-ethoxy-5-(1-(2-fluorophenyl)-1H-pyrazol-4-yl)-1-methylpyridin-2(1H)-one | (CD$_3$OD, 400 MHz) δ 8.39 (d, J = 2.7 Hz, 1H), 8.07 (s, 1H), 7.97 (s, 1H), 7.83-7.78 (m, 1H), 7.52-7.28 (m, 3H), 6.04 (s, 1H), 4.16 (q, J = 7.0 Hz, 2H), 3.57 (s, 3H), 1.51 (t, J = 7.0 Hz, 3H) | 314 |
| 253 | 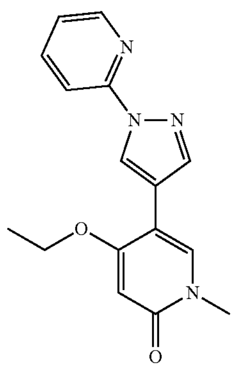 [SMILES: CCOc1cc(=O)n(C)cc1-c1cnn(-c2ccccn2)c1] | 4-ethoxy-1-methyl-5-(1-(pyridin-2-yl)-1H-pyrazol-4-yl)pyridin-2(1H)-one | (DMSO-d$_6$, 400 MHz) δ 8.86 (s, 1H), 8.50 (m, 1H), 8.19 (s, 1H), 8.14 (s, 1H), 8.03-7.92 (m, 2H), 7.36 (ddd, J = 1.2, 4.9, 7.2 Hz), 5.92 (s,1H), 4.12 (q, J = 7.0 Hz, 2H), 3.43 (s, 3H), 1.43 (t, J = 7.0 Hz) | 297 |

Examples 254-259 in Table 15 were prepared in a manner similar to Example 202, Step 2, by using the appropriate 2-fluorobenzonitrile derivative and substituting the corresponding 3-alkyl-5-bromopyridone for 5-bromo-4-chloro-1-methyl-1H-pyridin-2-one. Carboxylic acids were prepared from the corresponding nitriles in a manner similar to Example 203.

TABLE 15

| Example | Structure | IUPAC Name | ¹H NMR (ppm) | MS (M + H) |
|---|---|---|---|---|
| 254 | 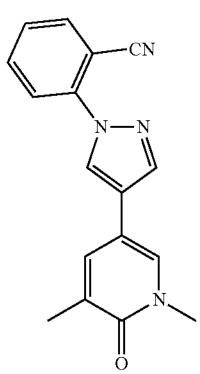 [SMILES: Cc1cc(-c2cnn(-c3ccccc3C#N)c2)cn(C)c1=O] | 2-[4-(1,5-Dimethyl-6-oxo-1,6-dihydro-pyridin-3-yl)-pyrazol-1-yl]-benzonitrile | (DMSO-d$_6$, 400 MHz) δ 8.70 (s, 1H), 8.19 (s, 1H), 8.04-8.01 (m, 2H), 7.89-7.81 (m, 3H), 7.58 (t, J = 7.6 Hz, 1H), 3.50 (s, 3H), 2.07 (s, 3H). | 291 |

TABLE 15-continued

| Example | IUPAC Name | ¹H NMR (ppm) | MS (M + H) |
|---|---|---|---|
| 255 | 2-[4-(1,5-Dimethyl-6-oxo-1,6-dihydro-pyridin-3-yl)-pyrazol-1-yl]-benzoic acid | (DMSO-d₆, 400 MHz) δ 8.18 (s, 1H), 7.94-7.86 (m, 3H), 7.73-7.66 (m, 2H), 7.57-7.54 (m, 2H), 3.62 (s, 3H), 2.18 (s, 3H). | 310 |
| 256 | 2-[4-(5-Ethyl-1-methyl-6-oxo-1,6-dihydro-pyridin-3-yl)-pyrazol-1-yl]-benzonitrile | (CDCl₃, 400 MHz) δ 7.74 (t, J = 7.8Hz, 1H), 8.22 (s, 1H), 7.91 (s, 1H), 7.82 (t, J = 8.4Hz, 2H), 7.46 (t, J = 7.6Hz, 1H), 7.41 (s, 1H), 7.37 (s, 1H), 3.62 (s, 3H), 2.63 (q, J = 7.5 Hz, 2H), 1.24 (t, J = 7.4 Hz, 3H). | 305 |
| 257 | 2-[4-(5-Ethyl-1-methyl-6-oxo-1,6-dihydro-pyridin-3-yl)-pyrazol-1-yl]-benzoic acid | (DMSO-d₆, 400 MHz) δ 12.90 (s, 1H), 8.47 (s, 1H), 8.01 (s, 1H), 7.99 (d, J = 2.4Hz, 1H), 7.73 (dd, J = 7.6Hz, 0.8 Hz, 1H), 7.69-7.60 (m, 3H), 7.50 (td, J = 7.6Hz, 0.8 Hz, 1H), 3.49 (s, 3H), 2.47 (q, J = 7.5 Hz, 2H), 1.15 (t, J = 7.4 Hz, 3H). | 324 |
| 258 | 2-[4-(1,5-Dimethyl-6-oxo-1,6-dihydro-pyridin-3-yl)-pyrazol-1-yl]-4-phenoxy-benzonitrile | (DMSO-d₆, 400 MHz) δ 8.03-7.97 (m, 2H), 7.70 (s, 1H), 7.51-7.49 (m, 3H), 7.42-7.24 (m, 3H), 7.21 (s, 1H), 3.49 (s, 3H), 2.07 (s, 3H). 8.72 (s, 1H), 8.17 (s, 1H), | 383 |

TABLE 15-continued

| Example | Structure | IUPAC Name | ¹H NMR (ppm) | MS (M + H) |
|---|---|---|---|---|
| 259 | 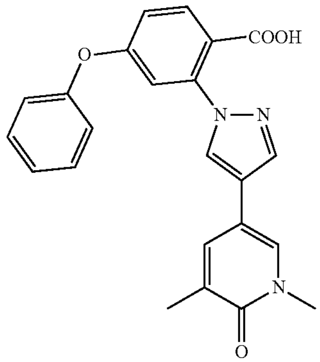 [SMILES: Cc1cc(-c2cnn(-c3cc(Oc4ccccc4)ccc3C(=O)O)c2)cn(C)c1=O] | 2-[4-(1,5-Dimethyl-6-oxo-1,6-dihydro-pyridin-3-yl)-pyrazol-1-yl]-4-phenoxy-benzoic acid | (CD₃OD, 400 MHz) δ 8.12 (s, 1H), 7.96-7.92 (m, 2H), 7.26-7.22 (m, 7.70 (s, 1H), 7.47-7.43 (m, 2H), 7.84 (s, 1H), 1H), 7.15-7.13 (m, 2H), 7.09-7.07 (m, 2H), 3.61 (s, 3H), 2.16 (s, 3H). | 402 |

Examples 260-280 in Table 16 were prepared using the appropriate substituted 2-fluorobenzonitrile and boronic acid derivative in a manner similar to Example 204. Carboxylic acids were prepared from the corresponding nitriles in a manner similar to Example 203.

TABLE 16

| Example | Structure | IUPAC Name | ¹H NMR (ppm) | MS (M + H) |
|---|---|---|---|---|
| 260 | 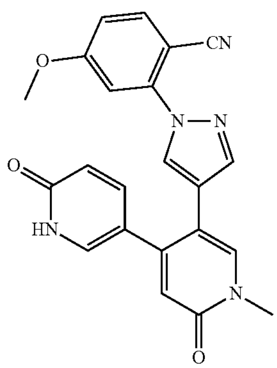 [SMILES: COc1ccc(C#N)c(-n2cc(-c3cn(C)c(=O)cc3-c3ccc(=O)[nH]c3)cn2)c1] | 4-Methoxy-2-[4-(1'-methyl-6,6'-dioxo-1,6,1',6'-tetrahydro-[3,4']bipyridinyl-3'-yl)-pyrazol-1-yl]-benzonitrile | (CD₃OD, 400 MHz) δ 8.12 (s, 1H), 7.87 (s, 1H), 7.78 (d, J = 8.8 Hz, 1H), 7.63 (s, 1H), 7.50 (d, J = 2.4 Hz, 1H), 7.38 (dd, J = 9.6 Hz, 2.8 Hz, 1H), 7.24 (d, J = 2.0 Hz, 1H), 7.11 (dd, J = 9.6 Hz, 2.8 Hz, 1H), 6.58 (s, 1H), 6.47 (d, J = 9.6 Hz, 1H), 3.93 (s, 3H), 3.64 (s, 3H). | 400 |
| 261 | 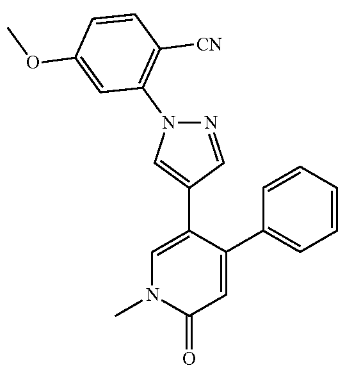 [SMILES: COc1ccc(C#N)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzonitrile | (CD₃OD, 400 MHz) δ 7.94 (s, 1H), 7.83 (s, 1H), 7.78-7.76 (m, 1H), 7.45-7.39 (m, 3H), 7.35 (s, 1H), 7.33-7.27 (m, 2H), 7.11-7.07 (m, 2H), 7.03-6.54 (m, 1H), 3.93 (s, 3H), 3.70 (s, 3H). | 383 |

TABLE 16-continued

| Example | Structure | IUPAC Name | ¹H NMR (ppm) | MS (M + H) |
|---|---|---|---|---|
| 262 | 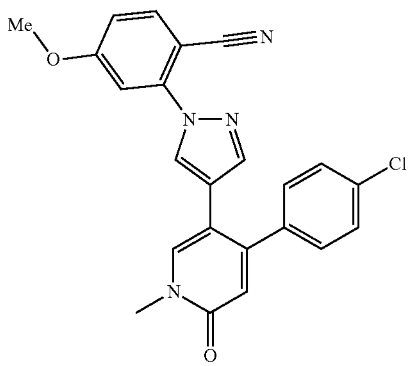 [SMILES: COc1ccc(C#N)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzonitrile | (CD₃OD, 400 MHz) δ 7.92 (s, 2H), 7.77 (d, J = 9.2 Hz, 1H), 7.42-7.37 (m, 3H), 7.28-7.26 (m, 2H), 7.14-7.08 (m, 2H), 6.56 (s, 1H), 3.92 (s, 3H), 3.67 (s, 3H). | 416 |
| 263 | 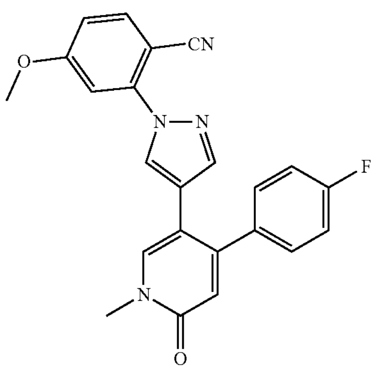 [SMILES: COc1ccc(C#N)c(-n2cc(-c3cn(C)c(=O)cc3-c3ccc(F)cc3)cn2)c1] | 2-{4-[4-(4-Fluoro-phenyl)-1-methyl-6-oxo-1,6-dihydro-pyridin-3-yl]-pyrazol-1-yl}-4-methoxy-benzonitrile | (CD₃OD, 400 MHz) δ 7.91 (d, J = 3.6 Hz, 2H), 7.77 (d, J = 8.8 Hz, 1H), 7.36 (s, 1H), 7.33-7.29 (m, 2H), 7.15-7.08 (m, 4H), 6.56 (s, 1H), 3.92 (s, 3H), 3.67 (s, 3H). | 401 |
| 264 | 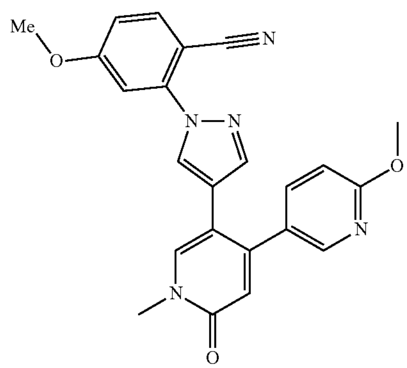 [SMILES: COc1ccc(C#N)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzonitrile | (CD₃OD, 400 MHz) δ 8.07 (d, J = 2.4 Hz, 1H), 8.00 (s, 1H), 7.89 (s, 1H), 7.77 (d, J = 8.8 Hz, 1H), 7.54 (dd, J = 8.4, 2.4 Hz, 1H), 7.44 (s, 1H), 7.18 (d, J = 2.4 Hz, 1H), 7.09 (dd, J = 9.2, 2.8 Hz, 1H), 6.78 (d, J = 8.4 Hz, 1H), 6.58 (s, 1H), 3.92 (s, 3H), 3.91 (s, 3H), 3.66 (s, 3H). | 414 |
| 265 | 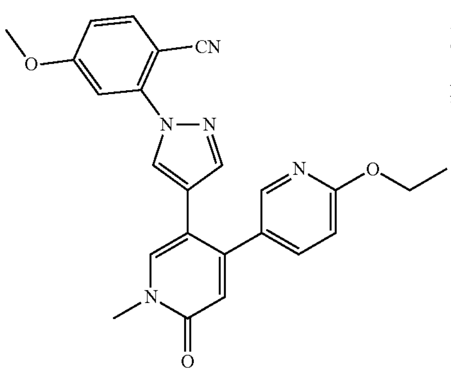 | 2-[4-(6-Ethoxy-1'-methyl-6'-oxo-1',6'-dihydro-[3,4']bipyridinyl-3'-yl)-pyrazol-1-yl]-4-methoxy-benzonitrile | (CD₃OD, 400 MHz) δ 8.05 (s, 1H), 7.99 (s, 1H), 7.89 (s, 1H), 7.77 (d, J = 8.4 Hz, 1H), 7.53 (d, J = 8.4 Hz, 1H), 7.44 (s, 1H), 7.17 (s, 1H), 7.09 (d, J = 8.4 Hz, 1H), 6.76 (d, J = 8.8 Hz, 1H), 6.58 (s, 1H), 4.33 (q, J = 7.2 Hz, 2H), 3.92 (s, 3H), 3.64 (s, 3H), 1.36 (t, J = 7.2 Hz, 3H). | 428 |

TABLE 16-continued

| Example | Structure | IUPAC Name | ¹H NMR (ppm) | MS (M + H) |
|---|---|---|---|---|
| 266 | 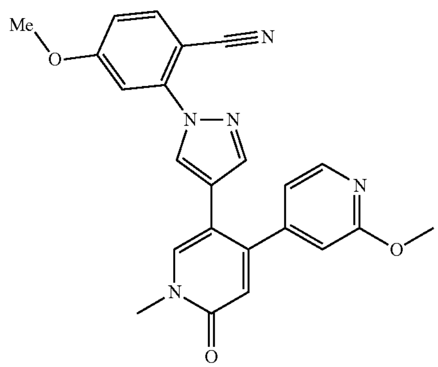 [SMILES: COc1ccc(C#N)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzonitrile | (CD₃OD, 400 MHz) δ 8.13 (d, J = 5.2 Hz, 1H), 7.97 (s, 1H), 7.94 (s, 1H), 7.76 (d, J = 8.8 Hz, 1H), 7.49 (s, 1H), 7.17 (d, J = 2.8 Hz, 1H), 7.08 (dd, J = 8.8 Hz, J = 2.8 Hz, 1H), 6.87 (dd, J = 5.2 Hz, J = 1.2 Hz, 1H), 6.83 (s, 1H), 6.58 (s, 1H), 3.93 (s, 3H), 3.92 (s, 3H), 3.67 (s, 3H). | 414 |
| 267 | 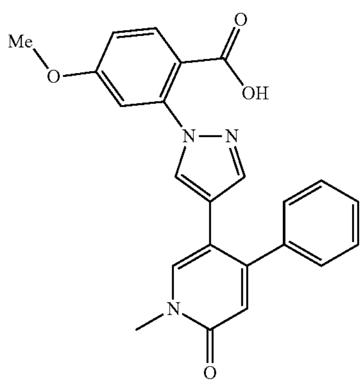 [SMILES: COc1ccc(C(=O)O)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzoic acid | (DMSO-d₆, 400 MHz) δ 12.63 (br, 1H), 7.98 (s, 1H), 7.69 (d, J = 8.8 Hz, 1H), 7.52 (s, 1H), 7.40-7.38 (m, 3H), 7.26-7.23 (m, 2H), 7.15 (s, 1H), 7.02 (dd, J = 9.2, 2.8 Hz, 1H), 6.85 (d, J = 2.4 Hz, 1H), 6.35 (s, 1H), 3.83 (s, 3H), 3.52 (s, 3H). | 402 |
| 268 | 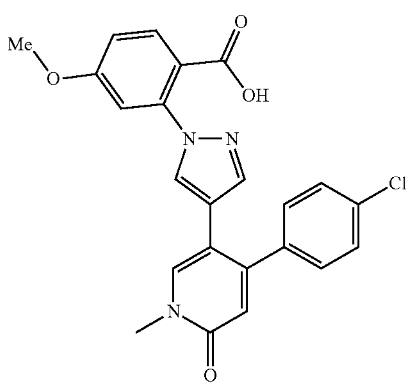 [SMILES: COc1ccc(C(=O)O)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzoic acid | (DMSO-d₆, 400 MHz) δ 7.96 (s, 1H), 7.71 (d, J = 8.4 Hz, 1H), 7.67 (s, 1H), 7.44 (d, J = 8.4 Hz, 2H), 7.27-7.25 (m, 2H), 7.17 (s, 1H), 7.04 (dd, J = 8.4 Hz, J = 6.0 Hz, 1H), 6.89 (d, J = 2.8 Hz, 1H), 6.39 (s, 1H), 3.85 (s, 3H), 3.58 (s, 3H). | 435 |
| 269 | 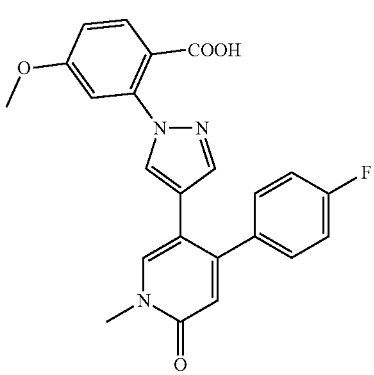 | 2-{4-[4-(4-Fluoro-phenyl)-1-methyl-6-oxo-1,6-dihydro-pyridin-3-yl]-pyrazol-1-yl}-4-methoxy-benzoic acid | (CD₃OD, 400 MHz) δ 7.89 (s, 1H), 7.79 (d, J = 8.8 Hz, 1H), 7.59 (s, 1H), 7.33-7.29 (m, 2H), 7.14-7.01 (m, 4H), 6.93 (d, J = 2.4 Hz, 1H), 6.54 (s, 1H), 3.86 (s, 3H), 3.66 (s, 3H). | 420 |

TABLE 16-continued

| Example | Structure | IUPAC Name | ¹H NMR (ppm) | MS (M + H) |
|---|---|---|---|---|
| 270 | 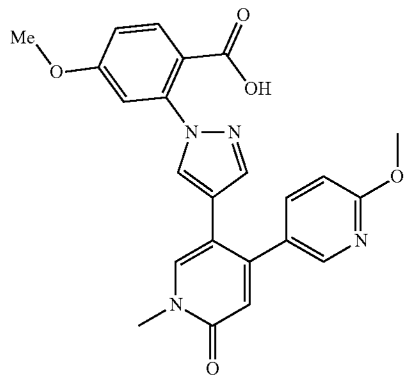 [SMILES: COc1ccc(C(=O)O)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzoic acid | (DMSO-d₆, 400 MHz) δ 8.14 (d, J = 2.0 Hz, 1H), 7.93 (s, 1H), 7.76 (s, 1H), 7.72 (d, J = 8.8 Hz, 1H), 7.46 (dd, J = 8.4, 2.4 Hz, 1H), 7.23 (s, 1H), 7.05 (dd, J = 8.8, 2.8 Hz, 1H), 6.92 (d, J = 2.4 Hz, 1H), 6.77 (d, J = 8.8 Hz, 1H), 6.43 (s, 1H), 3.86 (s, 3H), 3.84 (s, 3H), 3.51 (s, 3H). | 433 |
| 271 | 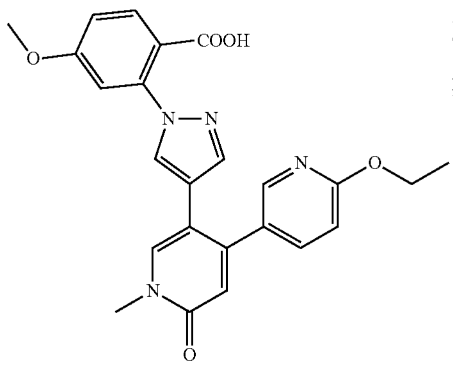 | 2-[4-(6-Ethoxy-1'-methyl-6'-oxo-1',6'-dihydro-[3,4']bipyridinyl-3'-yl)-pyrazol-1-yl]-4-methoxy-benzoic acid | (CD₃OD, 400 MHz) δ 8.08 (s, 1H), 7.90-7.87 (m, 2H), 7.62 (s, 1H), 7.53 (dd, J = 8.8, 6.4 Hz, 1H), 7.25 (s, 1H), 7.07 (dd, J = 8.8, 2.8 Hz, 1H), 6.94 (s, 1H), 6.76 (d, J = 8.8 Hz, 1H), 6.57 (s, 1H), 4.36 (q, J = 7.2 Hz, 2H), 3.88 (s, 3H), 3.66 (s, 3H), 1.36 (t, J = 7.2 Hz, 3H). | 447 |
| 272 | 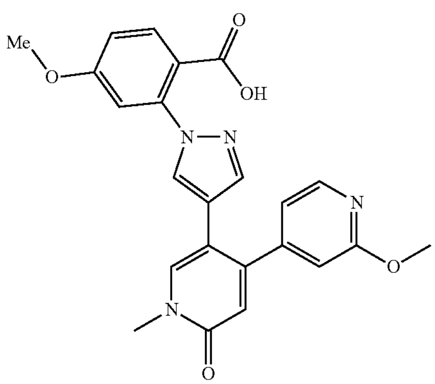 [SMILES: COc1ccc(C(=O)O)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzoic acid | (DMSO-d₆, 400 MHz) δ 8.12 (d, J = 6.4 Hz, 1H), 7.98 (s, 1H), 7.77 (s, 1H), 7.71 (d, J = 8.4 Hz, 1H), 7.24 (s, 1H), 7.04 (dd, J = 8.8, 1.8 Hz, 1H), 6.89 (d, J = 2.4 Hz, 1H), 6.77-6.76 (m, 2H), 6.42 (s, 1H), 3.85 (s, 6H), 3.53 (s, 3H). | 433 |
| 273 | 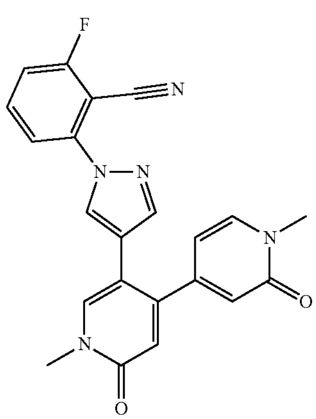 [SMILES: Cn1ccc(-c2cc(=O)n(C)cc2-c2cnn(-c3cccc(F)c3C#N)c2)cc1=O] | 2-[4-(1,1'-Dimethyl-6,2'-dioxo-1,6,1',2'-tetrahydro-[4,4']bipyridinyl-3-yl)-pyrazol-1-yl]-6-fluoro-benzonitrile | (CD₃OD, 400 MHz) δ 6.63 (s, 1H), 6.46 (s, 1H), 6.38-6.32 (m, 1H), 6.26 (s, 1H), 6.14 (d, J = 7.6 Hz, 2H), 5.91 (t, J = 8.8 Hz, 1H), 5.10 (s, 1H), 5.03 (d, J = 2.0 Hz, 1H), 4.73 (dd, J = 6.8, 4.8 Hz, 1H), 2.20 (s, 3H), 2.07 (s, 3H). | 401 |

TABLE 16-continued

| Example | Structure | IUPAC Name | ¹H NMR (ppm) | MS (M + H) |
|---------|-----------|------------|--------------|------------|
| 274 | 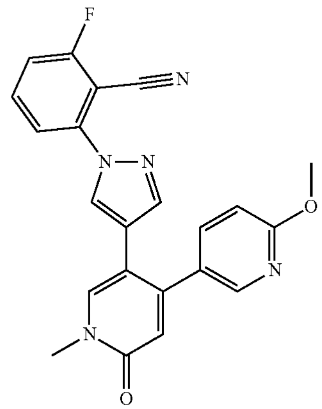 [SMILES: COc1ccc(-c2cc(=O)n(C)cc2-c2cnn(-c3cccc(F)c3C#N)c2)cn1] | 2-Fluoro-6-[4-(6-methoxy-1'-methyl-6'-oxo-1',6'-dihydro-[3,4']bipyridinyl-3'-yl)-pyrazol-1-yl]-benzonitrile | (CD$_3$OD, 400 MHz) δ 8.08-8.06 (m, 2H), 7.90 (s, 1H), 7.83-7.80 (m, 1H), 7.56-7.52 (m, 2H), 7.46 (s, 1H), 7.39 (t, J = 8.0 Hz, 1H), 6.78 (d, J = 8.8 Hz, 1H), 6.58 (s, 1H), 3.92 (s, 3H), 3.67 (s, 3H). | 402 |
| 275 | 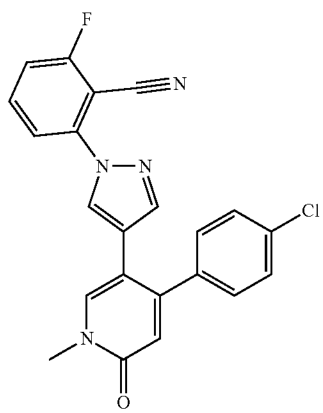 [SMILES: Cn1cc(-c2cnn(-c3cccc(F)c3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-6-fluoro-benzonitrile | (CD$_3$OD, 400 MHz) δ 8.00 (s, 1H), 7.93 (s, 1H), 7.86-7.80 (m, 1H), 7.50 (d, J = 6.3 Hz, 1H), 7.44-7.40 (m, 4H), 7.30-7.26 (m, 2H), 6.57 (s, 1H), 3.68 (s, 3H). | 405 |
| 276 | 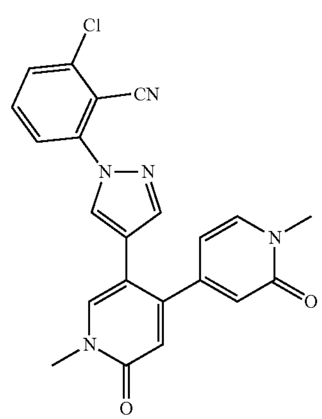 [SMILES: Cn1ccc(-c2cc(=O)n(C)cc2-c2cnn(-c3cccc(Cl)c3C#N)c2)cc1=O] | 2-Chloro-6-[4-(1,1'-dimethyl-6,2'-dioxo-1,6,1',2'-tetrahydro-[4,4']bipyridinyl-3-yl)-pyrazol-1-yl]-benzonitrile | (CD$_3$OD, 400 MHz) δ 6.59 (s, 1H), 6.44 (s, 1H), 6.30-6.17 (m, 4H), 6.11 (d, J = 6.8 Hz, 1H), 5.08 (s, 1H), 5.02 (s, 1H), 4.70 (d, J = 6.8 Hz, 1H), 2.18 (s, 3H), 2.06 (s, 3H). | 418 |

TABLE 16-continued

| Example | Structure | IUPAC Name | ¹H NMR (ppm) | MS (M + H) |
|---|---|---|---|---|
| 277 | 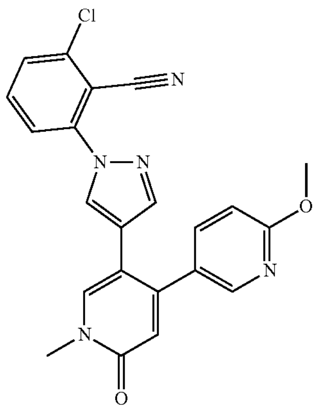 | 2-Chloro-6-[4-(6-methoxy-1'-methyl-6'-oxo-1',6'-dihydro-[3,4']bipyridinyl-3'-yl)-pyrazol-1-yl]-benzonitrile | (CD$_3$OD, 400 MHz) δ 8.09 (d, J = 2.0 Hz, 1H), 8.05 (s, 1H), 7.90 (s, 1H), 7.77 (t, J = 8.4 Hz, 1H), 7.68 (d, J = 7.2 Hz, 1H), 7.63 (d, J = 8.0 Hz, 1H), 7.54 (dd, J = 8.4, 2.4 Hz, 1H), 7.47 (s, 1H), 6.78 (d, J = 8.8 Hz, 1H), 6.59 (s, 1H), 3.93 (s, 3H), 3.68 (s, 3H). | 418 |
| 278 | 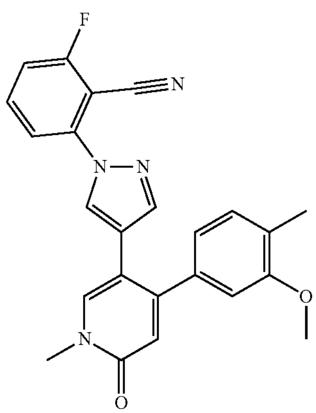 | 2-fluoro-6-(4-(4-(3-methoxy-4-methylphenyl)-1-methyl-6-oxo-1,6-dihydropyridin-3-yl)-1H-pyrazol-1-yl)benzonitrile | (DMSO, 300 MHz) δ 8.21 (s, 1H), 8.02 (s, 1H), 7.99-7.84 (m, 1H), 7.61-7.48 (m, 2H), 7.37 (s, 1H), 7.15 (d, J = 7.4 Hz, 1H), 6.76 (d, J = 7.4 Hz, 2H), 6.44 (s, 1H), 3.68 (s, 3H), 3.54 (s, 3H), 2.16 (s, 3H). | 415 |
| 279 | 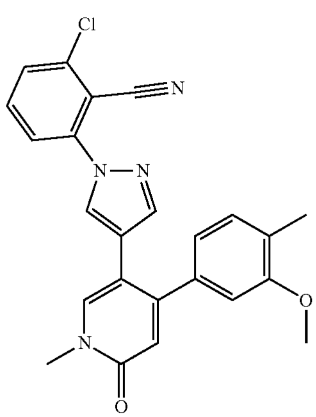 [SMILES: COc1cc(-c2cc(=O)n(C)cc2-c2cnn(-c3cccc(F)c3C#N)c2)ccc1C] | 2-chloro-6-(4-(4-(3-methoxy-4-methylphenyl)-1-methyl-6-oxo-1,6-dihydropyridin-3-yl)-1H-pyrazol-1-yl)benzonitrile | (DMSO-d$_6$, 400 MHz) δ 8.16 (s, 1H), 8.00 (s, 1H), 7.86 (t, J = 8.2 Hz, 1H), 7.78 (dd, J = 8.2, 1.0 Hz, 1H), 7.65 (dd, J = 8.2, 1.1 Hz, 1H), 7.37 (s, 1H), 7.15 (d, J = 7.9 Hz, 1H), 6.82-6.73 (m, 2H), 6.43 (s, 1H), 3.67 (s, 3H), 3.53 (s, 3H), 2.16 (s, 3H). | 431 |

TABLE 16-continued

| Example | Structure | IUPAC Name | ¹H NMR (ppm) | MS (M + H) |
|---|---|---|---|---|
| 280 | 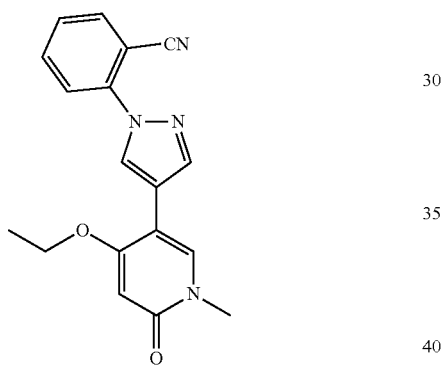 | 2-chloro-6-(4-(4-(2-ethylpyrimidin-5-yl)-1-methyl-6-oxo-1,6-dihydropyridin-3-yl)-1H-pyrazol-1-yl)benzonitrile | (CD$_3$OD, 400 MHz) δ 8.67 (s, 2H), 8.10 (s, 1H), 7.98 (s, 1H), 7.79 (t, J = 8.2 Hz, 1H), 7.74-7.66 (m, 2H), 7.63 (s, 1H), 6.71 (s, 1H), 3.71 (s, 3H), 3.00 (q, J = 7.6 Hz, 2H), 1.37 (t, J = 7.6 Hz, 3H). | 417 |

Example 281: 2-(4-(4-ethoxy-1-methyl-6-oxo-1,6-dihydropyridin-3-yl)-1H-pyrazol-1-yl)benzonitrile Example 282: 2-(4-(4-ethoxy-1-methyl-6-oxo-1,6-dihydropyridin-3-yl)-1H-pyrazol-1-yl)benzamide

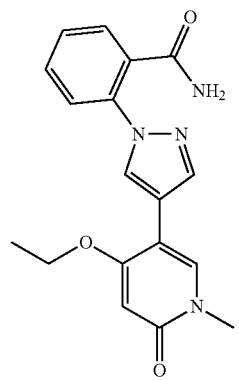 [SMILES: CCOc1cc(=O)n(C)cc1-c1cnn(-c2ccccc2C(N)=O)c1]

5-bromo-4-ethoxy-1-methylpyridin-2(1H)-one (30 mg, 0.13 mmol) and (2-(4-(4,4,5,5-tetramethyl-1,3,2-dioxaborolan-2-yl)-1H-pyrazol-1-yl)benzonitrile (50 mg, 0.16 mmol) were dissolved in anhydrous dioxane (1 mL). To this solution was added Pd(PPh$_3$)$_4$ (15 mg, 0.013 mmol) and Na$_2$CO$_3$ (2M, 0.15 mL). The reaction was heated in a microwave reactor at 120° C. for 20 min. Upon completion, the solvent was removed under reduced pressure. The residue was re-dissolved in MeOH (3 mL), filtered through Celite and purified by preparative-HPLC (10 to 100% MeCN/water/ 0.1% formic acid) to afford the title compound as a white solid (8 mg, 19%). ¹H NMR (CD$_3$OD, 400 MHz) δ 8.55 (s, 1H), 8.14 (s, 1H), 8.01 (s, 1H), 7.92-7.90 (m, 1H), 7.83-7.80 (m, 2H), 7.59-7.55 (m, 1H), 6.05 (s, 1H), 4.21 (q, J=6.9 Hz, 2H), 1.54 (t, J=6.9 Hz, 3H). LCMS (M+H)⁺ 321.

To the title compound from Example 281 (30 mg, 0.009 mmol) was added TFA (1 mL). The reaction was heated to reflux for 1 h and then cooled to room temperature. The solvent was removed. The residue was dissolved in DMF (3 mL), filtered through Celite and purified by preparative-HPLC (10 to 100% MeCN/water/0.1% formic acid) to afford the title compound as a white solid (10 mg, 32%). ¹H NMR (DMSO-d$_6$, 400 MHz) δ 8.27 (s, 1H), 8.09 (s, 1H), 8.03 (s, 1H), 7.86 (s, 1H), 7.66-7.39 (m, 4H), 5.90 (s, 1H), 4.09 (q, J=7.0 Hz, 2H), 3.42 (s, 3H), 1.44 (t, J=7.0 Hz, 3H). LCMS (M+H)⁺ 339.

Example 283: 2-(4-(1-methyl-4-(2-morpholinoethoxy)-6-oxo-1,6-dihydropyridin-3-yl)-1H-pyrazol-1-yl)benzonitrile

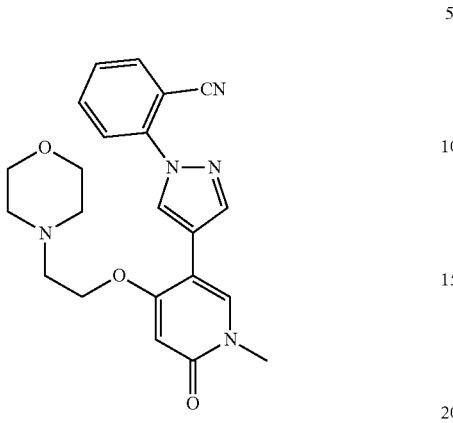

The title compound was prepared in a manner similar to Example 281 by replacing 5-bromo-1-methyl-4-(2-morpholinoethoxy)pyridin-2(1H)-one for 5-bromo-4-ethoxy-1-methylpyridin-2(1H)-one. $^1$H NMR (DMSO-d$_6$, 400 MHz) δ 8.71 (s, 1H), 8.26 (s, 1H), 8.20 (s, 1H), 8.17 (s, 1H), 8.05 (dd, J=1.3, 7.8 Hz, 1H), 7.93-7.82 (m, 1H), 7.83-7.71 (m, 1H), 7.61 (td, J=1.2, 7.6 Hz, 1H), 5.96 (s, 1H), 4.16 (t, J=5.4 Hz, 2H), 3.37-3.54 (m, 2H), 3.44 (s, 3H), 2.78 (t, J=5.4 Hz, 2H), 2.48-2.41 (m, 1H), 2.46-2.32 (m, 3H). LCMS (M+H)$^+$ 406.

Example 284: 5-[1-(2-Methanesulfonyl-phenyl)-1H-pyrazol-4-yl]-1,1'-dimethyl-1H,1'H-[4,4']bipyridinyl-2,2'-dione

Step 1: 4-(4,4,5,5-Tetramethyl-[1,3,2]dioxaborolan-2-yl)-pyrazole-1-carboxylic Acid Tert-Butyl Ester

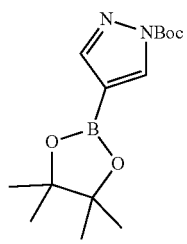 [SMILES: CC(C)(C)OC(=O)n1cc(B2OC(C)(C)C(C)(C)O2)cn1]

To a solution of 4-(4,4,5,5-tetramethyl-[1,3,2]dioxaborolan-2-yl)-1H-pyrazole (5.0 g, 25.8 mmol) and DMAP (3.8 g, 31.1 mmol) in DMF (30 mL) was added (Boc)$_2$O (8.4 g, 38.5 mmol) at 0° C. The mixture was stirred at room temperature overnight. The reaction was diluted with NH$_4$Cl (150 mL) and extracted with DCM (200 mL). The organic layer was washed with aqueous 1N HCl, dried over Na$_2$SO$_4$, filtered and concentrated under reduced pressure to afford the title compound (7.4 g, 25.2 mmol, 99%) as a white solid. $^1$H NMR (CD$_3$OD, 400 MHz) δ 8.36 (s, 1H), 7.87 (s, 1H), 1.58 (s, 9H), 1.27 (s, 12H).

Step 2: 4-Chloro-1-methyl-5-(1H-pyrazol-4-yl)-1H-pyridin-2-one

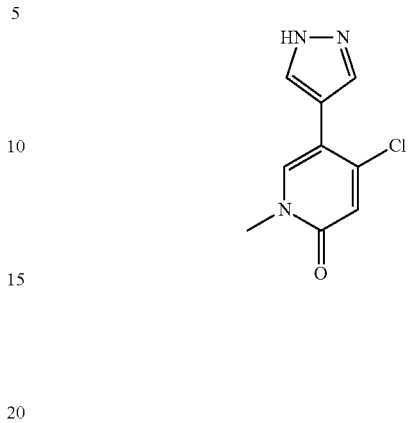

A mixture of the title compound from Step 1 (2.0 g, 6.8 mmol), 5-bromo-4-chloro-1-methyl-1H-pyridin-2-one (1.3 g, 5.9 mmol), Pd(dppf)Cl$_2$ (500 mg, 0.68 mmol) and K$_2$CO$_3$ (2.3 g, 16.7 mmol) in a dioxane/water mixture (30 mL/6 mL) was stirred at 85° C. under N$_2$ overnight. The reaction was concentrated under reduced pressure and purified by silica gel column chromatography (DCM/MeOH=20:1) to afford the title compound (540 mg, 2.6 mmol) as a yellow solid.

Step 3: 4-Chloro-5-[1-(2-methanesulfonyl-phenyl)-1H-pyrazol-4-yl]-1-methyl-1H-pyridin-2-one

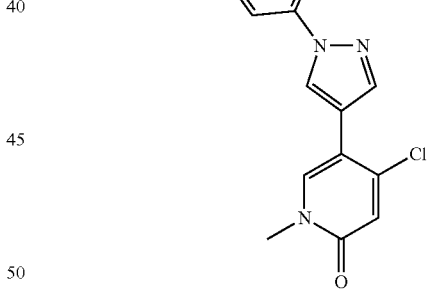

To a solution of the title compound form Step 2 (540 mg, 2.58 mmol) in DMF (25 mL) at 0° C. was added NaH (60%, 207 mg, 5.18 mmol) under N$_2$. After 30 min, a solution of 1-fluoro-2-methanesulfonyl-benzene (674 mg, 3.87 mmol) in DMF (5 mL) was added and the mixture was stirred at room temperature overnight. The reaction mixture was quenched with NH$_4$Cl (80 mL) and extracted with DCM (120 mL). The organic phase was dried over Na$_2$SO$_4$, filtered and concentrated. The residue was purified by silica gel column chromatography (100% EtOAc) to afford the title compound (280 mg, 0.77 mmol) as a yellow solid. $^1$H NMR (CDCl$_3$, 400 MHz) δ 8.24 (dd, J=7.6 Hz, J=1.2 Hz, 1H), 7.99 (s, 1H), 7.86 (s, 1H), 7.79 (t, J=8.0 Hz, 1H), 7.69 (t, J=8.0 Hz, 1H), 7.56 (dd, J=7.6 Hz, J=1.2 Hz, 1H), 7.46 (s, 1H), 6.78 (s, 1H), 3.58 (s, 3H), 3.10 (s, 3H).

Step 4: 5-[1-(2-Methanesulfonyl-phenyl)-1H-pyrazol-4-yl]-1,1'-dimethyl-1H,1'H-[4,4']bipyridinyl-2,2'-dione

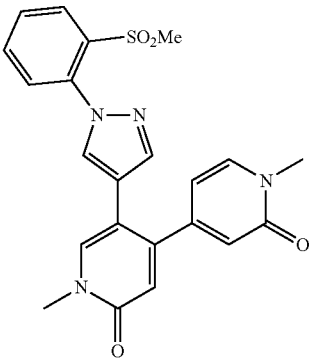 [SMILES: Cn1ccc(-c2cc(=O)n(C)cc2-c2cnn(-c3ccccc3S(C)(=O)=O)c2)cc1=O]

A mixture of the title compound from Step 3 (30 mg, 0.08 mmol), (1-methyl-2-oxo-1,2-dihydropyridin-4-yl)boronic acid (20 mg, 0.13 mmol), Pd(PPh$_3$)$_4$ (10 mg, 0.009 mmol) and Na$_2$CO$_3$ (22 mg, 0.21 mmol) in a dioxane/water mixture (10 mL/2 mL) was stirred at 90° C. under N$_2$ overnight. The mixture was cooled to room temperature and extracted with DCM (60 mL). The organic layer was dried over Na$_2$SO$_4$, filtered and concentrated. The residue was purified by preparative-HPLC to afford the title compound (9 mg, 0.02 mmol) as a white solid. $^1$H NMR (CD$_3$OD, 400 MHz) δ 8.17 (dd, J=7.6 Hz, J=1.2 Hz, 1H), 7.90 (s, 1H), 7.84 (t, J=7.6 Hz, 1H), 7.77-7.73 (m, 2H), 7.63-7.61 (m, 2H), 7.51 (dd, J=8.0 Hz, J=0.8 Hz, 1H), 6.56 (s, 1H), 6.46 (d, J=2.0 Hz, 1H), 6.22 (dd, J=7.6 Hz, J=1.6 Hz, 1H), 3.66 (s, 3H), 3.56 (s, 3H), 3.05 (s, 3H). LCMS (M+H)$^+$ 437.

Examples 285-287 in Table 17 were prepared using the appropriate boronic acid or ester in Step 4 in a similar multi-step manner as Example 284.

TABLE 17

| Example | Structure | IUPAC Name | $^1$H NMR (ppm) | MS (M + H) |
|---|---|---|---|---|
| 285 | 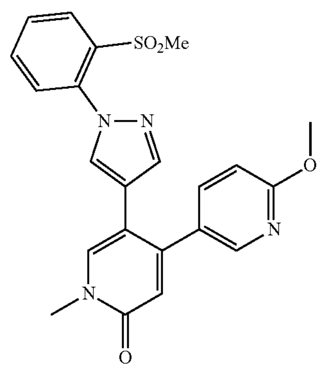 [SMILES: COc1ccc(-c2cc(=O)n(C)cc2-c2cnn(-c3ccccc3S(C)(=O)=O)c2)cn1] | 5'-[1-(2-Methanesulfonyl-phenyl)-1H-pyrazol-4-yl]-6-methoxy-1'-methyl-1'H-[3,4']bipyridinyl-2'-one | (CD$_3$OD, 400 MHz) δ 8.09 (dd, J = 8.0 Hz, J = 1.6 Hz, 1H), 8.01 (d, J = 2.8 Hz, 1H), 7.77 (s, 1H), 7.74 (t, J = 7.6 Hz, 1H), 7.66 (t, J = 7.2 Hz, 1H), 7.63 (s, 1H), 7.45 (dd, J = 8.8 Hz, J = 2.8 Hz, 1H), 7.40 (d, J = 7.6 Hz, 1H), 7.25 (s, 1H), 6.87 (d, J = 8.4 Hz, 1H), 6.49 (s, 1H), 3.83 (s, 3H), 3.56 (s, 3H), 3.05 (s, 3H). | 437 |
| 286 | 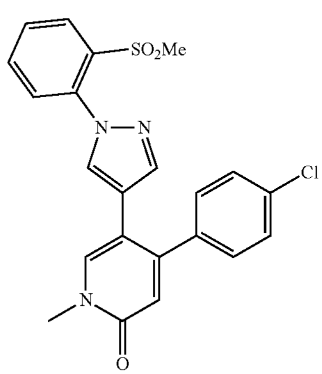 [SMILES: Cn1cc(-c2cnn(-c3ccccc3S(C)(=O)=O)c2)c(-c2ccc(Cl)cc2)cc1=O] | 4-(4-Chloro-phenyl)-5-[1-(2-methanesulfonyl-phenyl)-1H-pyrazol-4-yl]-1-methyl-1H-pyridin-2-one | (CD$_3$OD, 400 MHz) δ 8.18 (d, J = 8.0 Hz, 1H), 7.87 (s, 1H), 7.84 (t, J = 7.6 Hz, 1H), 7.75 (t, J = 8.0 Hz, 1H), 7.66 (s, 1H), 7.46 (d, J = 7.6 Hz, 1H), 7.40-7.38 (m, 2H), 7.29-7.27 (m, 3H), 6.56 (s, 1H), 3.66 (s, 3H), 3.15 (s, 3H). | 440 |

TABLE 17-continued

| Example | Structure | IUPAC Name | ¹H NMR (ppm) | MS (M + H) |
|---|---|---|---|---|
| 287 | 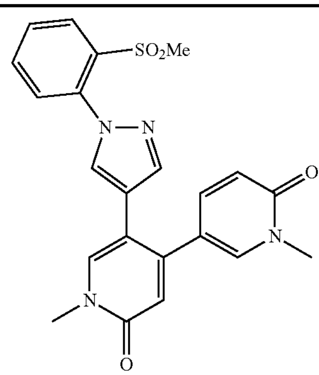 | 5'-[1-(2-Methanesulfonyl-phenyl)-1H-pyrazol-4-yl]-1,1'-dimethyl-1H,1'H-[3,4']bipyridinyl-6,2'-dione | (CD$_3$OD, 400 MHz) δ 8.18 (dd, J = 7.6 Hz, J = 1.2 Hz, 1H), 7.87-7.83 (m, 2H), 7.80 (s, 1H), 7.77-7.73 (m, 2H), 7.54-7.52 (m, 2H), 7.36 (dd, J = 9.6 Hz, J = 2.8 Hz, 1H), 6.58 (s, 1H), 6.48 (d, J = 9.2 Hz, 1H), 3.64 (s, 3H), 3.57 (s, 3H), 3.25 (s, 3H). | 437 |

Example 288: N-cyano-2-(4-(4-(4-fluorophenyl)-1-methyl-6-oxo-1,6-dihydropyridin-3-yl)-1H-pyrazol-1-yl)benzamide

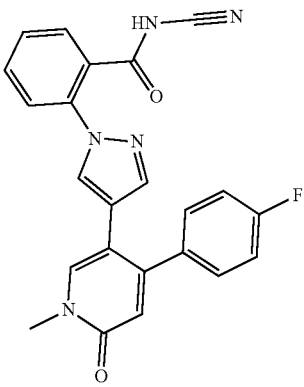 [SMILES: Cn1cc(-c2cnn(-c3ccccc3C(=O)NC#N)c2)c(-c2ccc(F)cc2)cc1=O]

A mixture of 2-(4-(4-(4-fluorophenyl)-1-methyl-6-oxo-1,6-dihydropyridin-3-yl)-1H-pyrazol-1-yl)benzoic acid (53 mg, 0.14 mmol), cyanamide (12 mg, 2 eq), HATU (62 mg, 1.2 eq) and TEA (34 mg, 2.5 eq) in DMF (10 mL) was stirred at room temperature for six hours. The mixture was concentrated under reduced pressure and purified by preparative HPLC to afford the title compound (26 mg, 46% yield) as a white solid. ¹H NMR (DMSO-d$_6$, 400 MHz) δ7.97 (s, 1H), 7.87 (s, 1H), 7.63-7.60 (m, 2H), 7.49-7.44 (m, 2H), 7.31-7.28 (m, 2H), 7.22-7.18 (m, 3H), 6.38 (s, 1H), 3.52 (s, 3H). LCMS (M+H)$^+$ 414.

Examples 289-296 in Table 18 were prepared using the appropriate carboxylic acid in a similar multi-step manner as Example 288.

TABLE 18

| Example | Structure | IUPAC Name | ¹H NMR (ppm) | MS (M + H) |
|---|---|---|---|---|
| 289 | 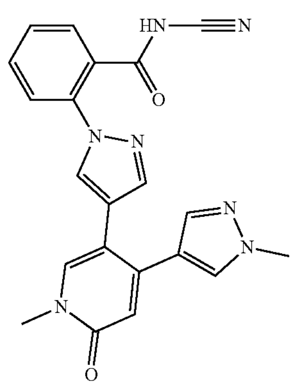 [SMILES: Cn1cc(-c2cc(=O)n(C)cc2-c2cnn(-c3ccccc3C(=O)NC#N)c2)cn1] | N-cyano-2-(4-(1-methyl-4-(1-methyl-1H-pyrazol-4-yl)-6-oxo-1,6-dihydropyridin-3-yl)-1H-pyrazol-1-yl)benzamide | (CD$_3$OD, 400 MHz) δ 7.86 (s, 1H), 7.68-7.66 (m, 3H), 7.53-7.51 (m, 3H), 7.46-7.44 (m, 1H), 7.43 (s, 1H), 6.70 (s, 1H), 3.89 (s, 3H), 3.60 (s, 3H). | 400 |

TABLE 18-continued

| Example | Structure | IUPAC Name | ¹H NMR (ppm) | MS (M + H) |
|---|---|---|---|---|
| 290 | 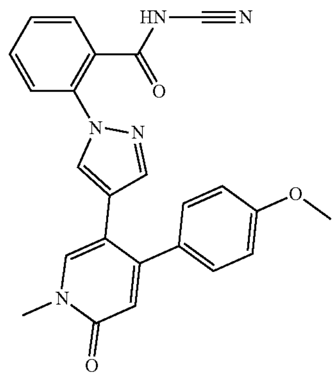 [SMILES: COc1ccc(-c2cc(=O)n(C)cc2-c2cnn(-c3ccccc3C(=O)NC#N)c2)cc1] | N-cyano-2-(4-(4-(4-methoxyphenyl)-1-methyl-6-oxo-1,6-dihydropyridin-3-yl)-1H-pyrazol-1-yl)benzamide | (DMSO-$d_6$, 400 MHz) δ 7.93 (s, 1H), 7.84 (s, 1H), 7.65 (t, J = 8.0 Hz, 1H), 7.60 (d, J = 7.6 Hz, 1H), 7.51 (t, J = 7.6 Hz, 2H), 7.23 (d, J = 8.4 Hz, 2H), 7.12 (s, 1H), 6.99 (d, J = 8.4 Hz, 2H), 6.49 (s, 1H), 3.79 (s, 3H), 3.58 (s, 3H). | 426 |
| 291 | 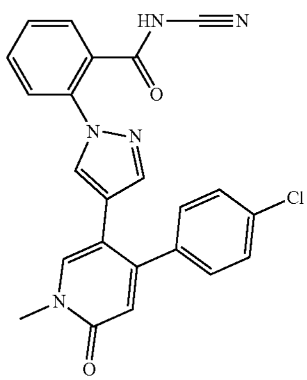 [SMILES: Cn1cc(-c2cnn(-c3ccccc3C(=O)NC#N)c2)c(-c2ccc(Cl)cc2)cc1=O] | 2-(4-(4-(4-chlorophenyl)-1-methyl-6-oxo-1,6-dihydropyridin-3-yl)-1H-pyrazol-1-yl)-N-cyanobenzamide | (DMSO-$d_6$, 400 MHz) δ 7.99-7.98 (m, 2H), 7.68-7.63 (m, 2H), 7.53-7.47 (m, 2H), 7.44-7.42 (m, 2H), 7.28 (s, 1H), 7.27 (s, 1H), 7.18 (s, 1H), 6.40 (s, 1H), 3.52 (s, 3H). | 430 |
| 292 | 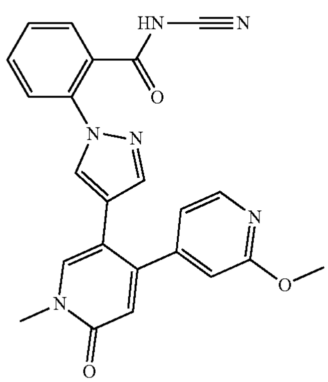 [SMILES: COc1cc(-c2cc(=O)n(C)cc2-c2cnn(-c3ccccc3C(=O)NC#N)c2)ccn1] | N-cyano-2-(4-(2'-methoxy-1-methyl-6-oxo-1,6-dihydro-[4,4'-bipyridin]-3-yl)-1H-pyrazol-1-yl)benzamide | (CD$_3$OD, 400 MHz) δ 7.92 (d, J = 5.2 Hz, 1H), 7.71 (s, 1H), 7.50 (s, 1H), 7.39 (d, J = 7.6 Hz, 1H), 7.31-7.27 (m, 1H), 7.23-7.19 (m, 2H), 7.00 (s, 1H), 6.62 (dd, J = 5.2 Hz, J = 4.0 Hz, 1H), 6.56 (s, 1H), 6.34 (s, 1H), 3.70 (s, 3H), 3.01 (s, 3H). | 426 |
| 293 | 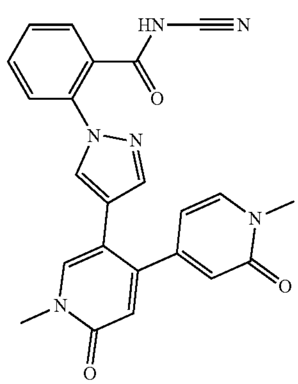 [SMILES: Cn1ccc(-c2cc(=O)n(C)cc2-c2cnn(-c3ccccc3C(=O)NC#N)c2)cc1=O] | N-cyano-2-(4-(1,1'-dimethyl-2',6-dioxo-1,1',2',6-tetrahydro-[4,4'-bipyridin]-3-yl)-1H-pyrazol-1-yl)benzamide | (CD$_3$OD, 400 MHz) δ 7.91 (s, 1H), 7.76 (s, 1H), 7.67-7.60 (m, 2H), 7.52-7.41 (m, 4H), 6.56 (s, 2H), 6.19 (dd, J = 6.8, 1.2 Hz, 1H), 3.66 (s, 3H), 3.58 (s, 3H). | 427 |

TABLE 18-continued

| Example | Structure | IUPAC Name | $^1$H NMR (ppm) | MS (M + H) |
|---|---|---|---|---|
| 294 | 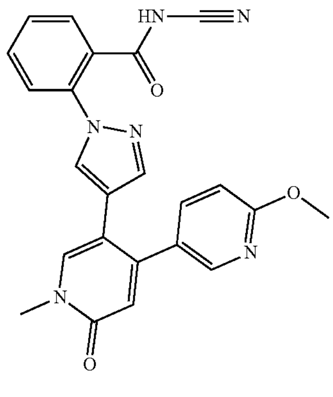 [SMILES: COc1ccc(-c2cc(=O)n(C)cc2-c2cnn(-c3ccccc3C(=O)NC#N)c2)cn1] | N-cyano-2-(4-(6-methoxy-1'-methyl-6'-oxo-1',6'-dihydro-[3,4'-bipyridin]-3'-yl)-1H-pyrazol-1-yl)benzamide | (CD$_3$OD, 400 MHz) δ 8.12 (d, J = 2.4 Hz, 1H), 7.88 (s, 1H), 7.72 (s, 1H), 7.63-7.61 (m, 1H), 7.57-7.54 (m, 2H), 7.51-7.40 (m, 2H), 7.17 (s, 1H), 6.83 (d, J = 8.4 Hz, 1H), 6.57 (s, 1H), 3.92 (s, 3H), 3.66 (s, 3H). | 426 |
| 295 | 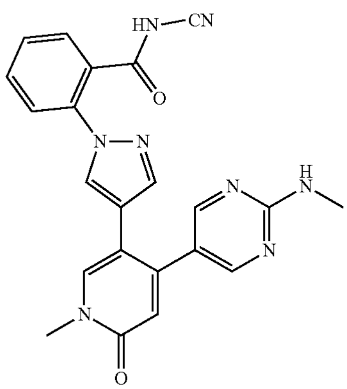 [SMILES: CNc1ncc(-c2cc(=O)n(C)cc2-c2cnn(-c3ccccc3C(=O)NC#N)c2)cn1] | N-cyano-2-(4-(1-methyl-4-(2-(methylamino)pyrimidin-5-yl)-6-oxo-1,6-dihydropyridin-3-yl)-1H-pyrazol-1-yl)benzamide | (CD$_3$OD, 400 MHz) δ 8.21 (s, 2H), 7.86 (s, 1H), 7.82 (s, 1H), 7.62 (dd, J = 7.6 Hz, J = 0.8 Hz, 1H), 7.53-7.41 (m, 3H), 7.35 (s, 1H), 6.57 (s, 1H), 3.63 (d, J = 10.8 Hz, 3H), 2.92 (s, 3H). | 427 |
| 296 | 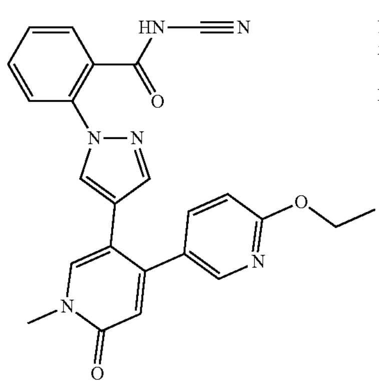 [SMILES: CCOc1ccc(-c2cc(=O)n(C)cc2-c2cnn(-c3ccccc3C(=O)NC#N)c2)cn1] | N-cyano-2-(4-(6-ethoxy-1'-methyl-6'-oxo-1',6'-dihydro-[3,4'-bipyridin]-3'-yl)-1H-pyrazol-1-yl)benzamide | (CD$_3$OD, 400 MHz) δ 8.10 (d, J = 2.4 Hz, 1H), 7.88 (s, 1H), 7.73 (s, 1H), 7.63-7.61 (m, 1H), 7.56-7.55 (m, 2H), 7.46-7.43 (m, 2H), 7.19 (s, 1H), 6.80 (d, J = 8.8 Hz, 1H), 6.57 (s, 1H), 4.33 (q, J = 7.2 Hz, 2H), 3.66 (s, 3H), 1.37 (t, J = 7.2 Hz, 3H). | 441 |

Example 297: 5-(1-(2-(1H-tetrazol-5-yl)phenyl)-H-pyrazol-4-yl)-4-(4-chlorophenyl)-1-methylpyridin-2(1H)-one

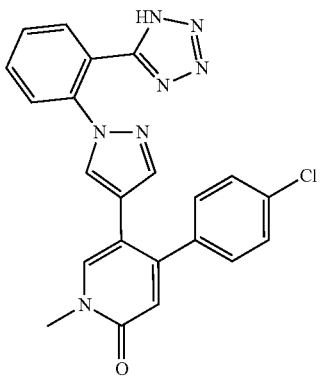 [SMILES: Cn1cc(-c2cnn(-c3ccccc3-c3nnn[nH]3)c2)c(-c2ccc(Cl)cc2)cc1=O]

A mixture of 2-(4-(4-(4-chlorophenyl)-1-methyl-6-oxo-1,6-dihydropyridin-3-yl)-1H-pyrazol-1-yl)benzonitrile (80 mg, 0.21 mmol), sodium azide (140 mg, 2.1 mmol) and CuSO$_4$.5H$_2$O (10 mg, 0.04 mmol) in DMF (15 mL) was stirred at 130° C. overnight. A second portion of sodium azide (140 mg, 2.1 mmol) and CuSO$_4$.5H$_2$O (10 mg, 0.04 mmol) was added followed by additional stirring at 130° C. overnight. The reaction was quenched with NH$_4$Cl and its pH adjusted to 9 with aqueous NH$_4$OH. It was then washed twice with DCM. The aqueous phase was acidified with HCl (6N, aq.) and extracted with DCM. The organic layer was dried over Na$_2$SO$_4$, filtered and concentrated under reduced pressure. The residue was purified by preparative HPLC to afford the title compound (5 mg, 6% yield) as a yellow solid.
$^1$H NMR (CD$_3$OD, 400 MHz) δ 7.82 (s, 1H), 7.80 (d, J=8.8 Hz, 1H), 7.73 (t, J=7.6 Hz, 1H), 7.65 (t, J=7.6 Hz, 1H), 7.56-7.53 (m, 2H), 7.41 (d, J=8.4 Hz, 2H), 7.24 (d, J=8.8 Hz, 2H), 7.03 (s, 1H), 6.54 (s, 1H), 3.65 (s, 3H). LCMS (M+H)$^+$ 430.

Examples 298-301 in Table 19 were prepared using the appropriate benzonitrile in a similar multi-step manner as Example 297.

TABLE 19

| Example | Structure | IUPAC Name | $^1$H NMR (ppm) | MS (M + H) |
|---|---|---|---|---|
| 298 | 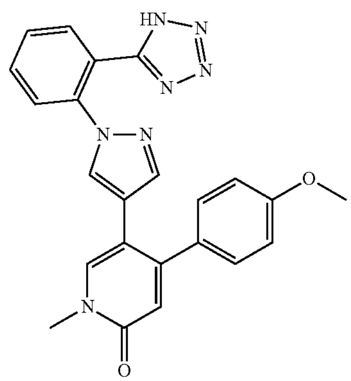 [SMILES: COc1ccc(-c2cc(=O)n(C)cc2-c2cnn(-c3ccccc3-c3nnn[nH]3)c2)cc1] | 4-(4-Methoxy-phenyl)-1-methyl-5-{1-[2-(1H-tetrazol-5-yl)-phenyl]-1H-pyrazol-4-yl}-1H-pyridin-2-one | (CD$_3$OD, 400 MHz) δ 7.79-7.76 (m, 2H), 7.71-7.67 (m, 1H), 7.64-7.60 (m, 1H), 7.55 (d, J = 7.6 Hz, 1H), 7.41 (s, 1H), 7.15 (d, J = 8.4 Hz, 2H), 7.04 (s, 1H), 6.93 (d, J = 8.8 Hz, 2H), 6.51 (s, 1H), 3.83 (s, 3H), 3.64 (s, 3H). | 426 |
| 299 | 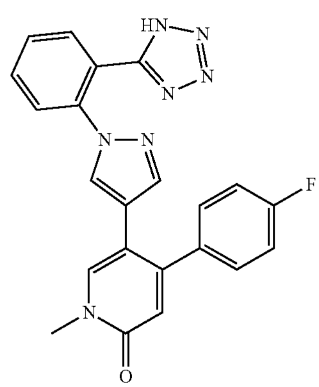 [SMILES: Cn1cc(-c2cnn(-c3ccccc3-c3nnn[nH]3)c2)c(-c2ccc(F)cc2)cc1=O] | 4-(4-Fluoro-phenyl)-1-methyl-5-{1-[2-(1H-tetrazol-5-yl)-phenyl]-1H-pyrazol-4-yl}-1H-pyridin-2-one | (CD$_3$OD, 400 MHz) δ 7.64-7.63 (m, 2H), 7.63-7.44 (m, 3H), 7.15-7.12 (m, 3H), 7.01 (t, J = 8.8 Hz, 2H), 6.89 (s, 1H), 6.41 (s, 1H), 3.54 (s, 3H). | 413 |

TABLE 19-continued

| Example | Structure | IUPAC Name | ¹H NMR (ppm) | MS (M + H) |
|---|---|---|---|---|
| 300 | 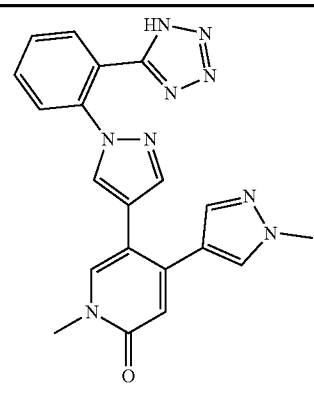 | 1-Methyl-4-(1-methyl-1H-pyrazol-4-yl)-5-{1-[2-(1H-tetrazol-5-yl)-phenyl]-1H-pyrazol-4-yl}-1H-pyridin-2-one | (CD₃OD, 400 MHz) δ 7.77-7.75 (m, 2H), 7.67-7.65 (m, 1H), 7.61-7.56 (m, 3H), 7.51 (d, J = 4.4 Hz, 2H), 7.25 (s, 1H), 6.58 (s, 1H), 3.82 (s, 3H), 3.49 (s, 3H). | 400 |
| 301 | 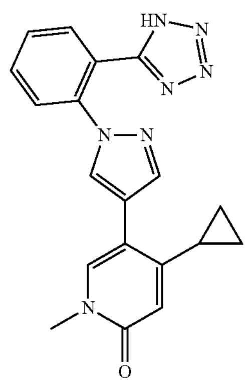 [SMILES: Cn1cc(-c2cnn(-c3ccccc3-c3nnn[nH]3)c2)c(C2CC2)cc1=O] | 4-Cyclopropyl-1-methyl-5-{1-[2-(1H-tetrazol-5-yl)-phenyl]-1H-pyrazol-4-yl}-1H-pyridin-2-one | (CD₃OD, 400 MHz) δ 7.76-7.64 (m, 3H), 7.62-7.42 (m, 3H), 7.41 (s, 1H), 6.07 (s, 1H), 3.55 (s, 3H), 1.59-1.00 (m, 1H), 0.99-0.96 (m, 2H), 0.72-0.70 (m, 2H). | 360 |

Example 302: N-{2-[4-(4-Cyclopropyl-1-methyl-6-oxo-1,6-dihydro-pyridin-3-yl)-pyrazol-1-yl]-benzoyl}-methanesulfonamide

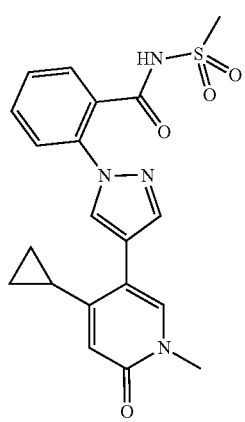 [SMILES: Cn1cc(-c2cnn(-c3ccccc3C(=O)NS(C)(=O)=O)c2)c(C2CC2)cc1=O]

To a mixture of 2-[4-(4-cyclopropyl-1-methyl-6-oxo-1,6-dihydro-pyridin-3-yl)-pyrazol-1-yl]-benzoic acid (50 mg, 0.15 mmol), methanesulfonamide (18 mg, 0.18 mmol) and DMAP (27 mg, 0.22 mmol) in DCM (8 mL) cooled with an ice/water bath was added EDCI (43 mg, 0.22 mmol). The reaction mixture was allowed to slowly warm upto room temperature and stirred overnight. It was then treated with aqueous HCl (3.0 N) and extracted with DCM (25 mL×3). The combined organic layers were washed with brine (35 mL×5), dried over Na₂SO₄ and filtered. The filtrate was concentrated under reduced pressure. The residue was purified by preparative-HPLC to afford the title compound (6 mg, 0.01 mmol) as a white solid. 1H NMR (CD₃OD+CDCl₃, 400 MHz) δ 8.06 (s, 1H), 7.83 (s, 1H), 7.71 (s, 1H), 7.63-7.59 (m, 2H), 7.58-7.56 (m, 1H), 7.50-7.48 (m, 1H), 6.15 (s, 1H), 3.56 (s, 3H), 3.19 (s, 3H), 1.96-1.93 (m, 1H), 1.11-1.07 (m, 2H), 0.86-0.83 (m, 2H). LCMS (M+H)⁺ 413.

Examples 303-304 in Table 20 were prepared using the appropriate sulfonamide in a similar multi-step manner as Example 302.

TABLE 20

| Example | Structure | IUPAC Name | ¹H NMR (ppm) | MS (M + H) |
|---|---|---|---|---|
| 303 | 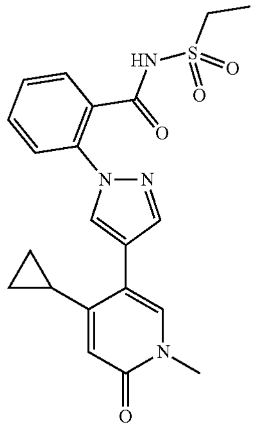 [SMILES: CCS(=O)(=O)NC(=O)c1ccccc1-n1cc(-c2cn(C)c(=O)cc2C2CC2)cn1] | Ethanesulfonic acid 2-[4-(4-cyclopropyl-1-methyl-6-oxo-1,6-dihydro-pyridin-3-yl)-pyrazol-1-yl]-benzoylamide | (DMSO-$d_6$, 400 MHz) δ 12.1 (br, 1H), 8.37 (s, 1H), 7.87 (s, 1H), 7.82 (s, 1H), 7.70-7.68 (m, 1H), 7.59-7.42 (m, 3H), 6.00 (s, 1H), 3.42 (s, 3H), 3.31-3.17 (m, 2H), 1.92-1.88 (m, 1H), 1.28-1.24 (m, 3H), 1.01-0.96 (m, 2H), 0.77-0.73 (m, 2H). | 427 |
| 304 | 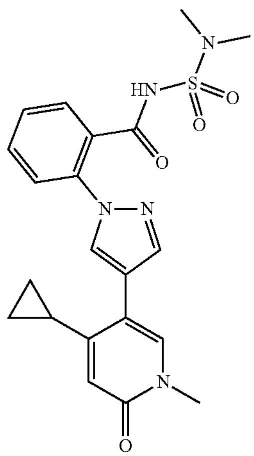 [SMILES: CN(C)S(=O)(=O)NC(=O)c1ccccc1-n1cc(-c2cn(C)c(=O)cc2C2CC2)cn1] | N-[(dimethylamino)sulfonyl]-{2-[4-(4-cyclopropyl-1-methyl-6-oxo(3-hydropyridyl))pyrazolyl]phenyl}carboxamide | (DMSO-$d_6$, 400 MHz) δ 11.8 (s, 1H), 8.32 (s, 1H), 7.90 (s, 1H), 7.79 (s, 1H), 7.69-7.65 (m, 2H), 7.57-7.54 (m, 1H), 7.50-7.47 (m, 1H), 6.01 (s, 1H), 3.43 (s, 3H), 2.85 (s, 6H), 1.93-1.85 (m, 1H), 0.99-0.95 (m, 2H), 0.78-0.71 (m, 2H). | 442 |

Example 305: 3-(4-(1,1'-dimethyl-2',6-dioxo-1,1',2',6-tetrahydro-[4,4'-bipyridin]-3-yl)-1H-pyrazol-1-yl)-4-methoxybenzonitrile Step 1: 3-(4-(4-chloro-1-methyl-6-oxo-1,6-dihydropyridin-3-yl)-1H-pyrazol-1-yl)-4-methoxybenzonitrile

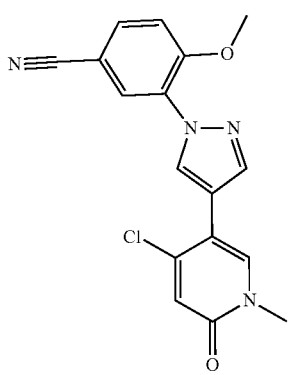 [SMILES: COc1ccc(C#N)cc1-n1cc(-c2cn(C)c(=O)cc2Cl)cn1]

To a solution of 4-chloro-1-methyl-5-(1H-pyrazol-4-yl)pyridin-2(1H)-one (400 mg, 1.9 mmol) and (5-cyano-2-methoxyphenyl)boronic acid (677 mg, 3.8 mmol) in DCM (20 mL) was added Cu(OAc)$_2$ (760 mg, 3.8 mmol) and pyridine (10 mL). The mixture was stirred at room temperature overnight under an oxygen atmosphere. The reaction was diluted with DCM and washed with ammonium hydroxide. The organic phase was dried over Na$_2$SO$_4$, filtered and concentrated under reduced pressure. The residue was purified by silica gel column chromatography to afford the title compound (100 mg, 15% yield) as a white solid.

Step 2: 3-(4-(1,1'-dimethyl-2',6-dioxo-1,1',2',6-tetrahydro-[4,4'-bipyridin]-3-yl)-1H-pyrazol-1-yl)-4-methoxybenzonitrile

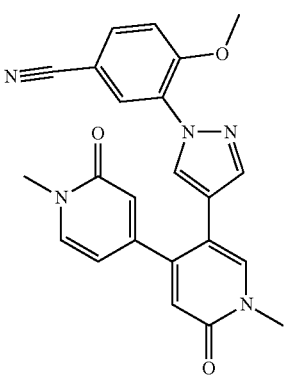

To a solution of the title compound from Step 1 (30 mg, 0.09 mmol) and (1-methyl-2-oxo-1,2-dihydropyridin-4-yl) boronic acid (20 mg, 0.132 mmol) in dioxane/water mixture (10 mL/2 mL) was added Pd(PPh₃)₄ (10 mg, 0.1 eq) and Na₂CO₃ (18 mg, 0.18 mmol). The mixture was stirred at 90° C. for three hours. It was then cooled down to room temperature, diluted with DCM and washed with a saturated NH4Cl aqueous solution. The organic phase was dried over Na₂SO₄, filtered and concentrated under reduced pressure. The residue was purified by preparative TLC to afford the title compound (22 mg, 60% yield) as a yellow solid. ¹H NMR (CDCl₃, 400 MHz) δ8.12 (d, J=2.0 Hz, 1H), 7.87 (s, 1H), 7.59 (dd, J=8 Hz, 1H), 7.49 (s, 1H), 7.41 (s, 1H), 7.19 (d, J=6.8 Hz, 1H), 7.09 (d, J=8.8 Hz, 1H), 6.59 (s, 1H), 6.55 (d, J=1.6 Hz, 1H), 5.88 (dd, J=7.2, 2.0 Hz, 1H), 3.95 (s, 3H), 3.64 (s, 3H), 3.53 (s, 3H). LCMS (M+H)⁺ 414.

Examples 306-307 in Table 21 were prepared using the appropriate boronic acid in Step 2 in a similar multi-step manner as Example 305.

Example 308: 6-methoxy-1'-methyl-5'-(1-(1-phenyl-ethyl)-1H-pyrazol-4-yl)-[3,4'-bipyridin]-2'(1'H)-one

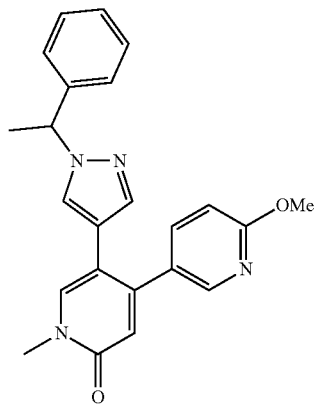

A mixture of 6-methoxy-3-pyridinylboronic acid (38.02 mg, 0.25 mmol), 4-chloro-1-methyl-5-[1-(1-phenylethyl) pyrazol-4-yl]pyridin-2-one (60 mg, 0.19 mmol) and Pd[(Ph)

TABLE 21

| Example | Structure | IUPAC Name | ¹H NMR (ppm) | MS (M + H) |
|---|---|---|---|---|
| 306 | 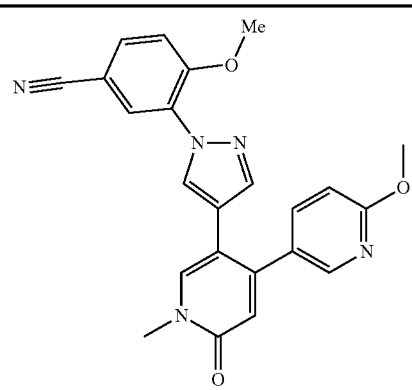 | 4-Methoxy-3-[4-(6-methoxy-1'-methyl-6'-oxo-1',6'-dihydro-[3,4']bipyridinyl-3'-yl)-pyrazol-1-yl]-benzonitrile | (CDCl₃, 400 MHz) δ 8.10-8.09 (m, 2H), 7.62 (s, 1H), 7.57 (dd, J = 8.8, 2.0 Hz, 1H), 7.44 (d, J = 5.6 Hz, 2H), 7.37 (dd, J = 8.8, 2.4 Hz, 1H), 7.06 (d, J = 8.8 Hz, 1H), 6.69 (d, J = 8.8 Hz, 1H), 6.62 (s, 1H), 3.95 (s, 3H), 3.87 (s, 3H), 3.65 (s, 3H). | 414 |
| 307 | 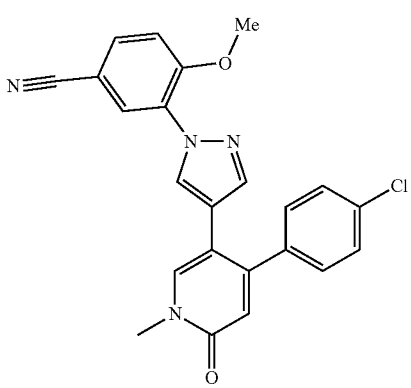 [SMILES: COc1ccc(C#N)cc1-n1cc(-c2cn(C)c(=O)cc2-c2ccc(Cl)cc2)cn1] | 3-{4-[4-(4-Chloro-phenyl)-1-methyl-6-oxo-1,6-dihydro-pyridin-3-yl]-pyrazol-1-yl}-4-methoxy-benzonitrile | (CDCl₃, 400 MHz) δ 8.09 (d, J = 2.0 Hz, 1H), 7.56 (dd, J = 8.4, 2.0 Hz, 1H), 7.49 (s, 1H), 7.45 (d, J = 5.6 Hz, 2H), 7.35-7.33 (m, 2H), 7.18-7.16 (m, 2H), 7.05 (d, J = 8.8 Hz, 1H), 6.60 (s, 1H), 3.85 (s, 3H), 3.65 (s, 3H). | 417 |

₃P]₄ (22.1 mg, 0.02 mmol) in 1,4-dioxane (1.2748 mL) and 2M (aq) sodium carbonate (0.29 mL, 0.57 mmol) was purged with nitrogen. The vial was sealed and heated to 80° C. for 14 h. The mixture was cooled to room temperature, diluted with MeOH (1 mL) and filtered through a 2 A syringe filter. The filtrate was purified by preparative HPLC (10-100% ACN/0.01% formic acid) to afford the title compound (47 mg, 0.11 mmol) as a tan solid. 1H NMR (400 MHz, DMSO-d6) δ 7.98-8.09 (m, 1H), 7.78-7.90 (m, 1H), 7.36-7.45 (m, 2H), 7.22-7.35 (m, 3H), 7.14-7.21 (m, 1H), 7.03-7.13 (m, 2H), 6.67-6.76 (m, 1H), 6.35-6.41 (m, 1H), 5.45-5.55 (m, 1H), 3.83-3.89 (m, 3H), 3.45-3.52 (m, 3H), 1.65-1.74 (m, 3H). LCMS (M+H)⁺ 387.

Examples 309-313 in Table 22 were prepared using the appropriate pyrimidine or pyridine boronic acid derivative in a similar manner as Example 308.

TABLE 22

| Example | Structure | IUPAC Name | $^1$H NMR (ppm) | MS (M + H) |
|---|---|---|---|---|
| 309 | 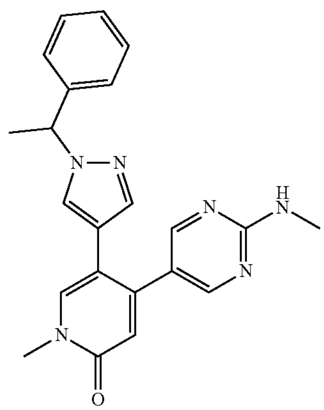 [SMILES: CNc1ncc(-c2cc(=O)n(C)cc2-c2cnn(C(C)c3ccccc3)c2)cn1] | 1-methyl-4-(2-(methylamino)pyrimidin-5-yl)-5-(1-(1-phenylethyl)-1H-pyrazol-4-yl)pyridin-2(1H)-one | 1H NMR (400 MHz, DMSO-d6) δ 7.98-8.15 (m, 2 H), 7.76-7.83 (m, 1 H), 7.57-7.64 (m, 1 H), 7.21-7.39 (m, 5 H), 7.09-7.16 (m, 2 H), 6.35-6.44 (m, 1 H), 5.50-5.61 (m, 1 H), 3.43-3.49 (m, 3 H), 2.78-2.85 (m, 3 H), 1.70-1.77 (m, 3 H) | 387 |
| 310 | 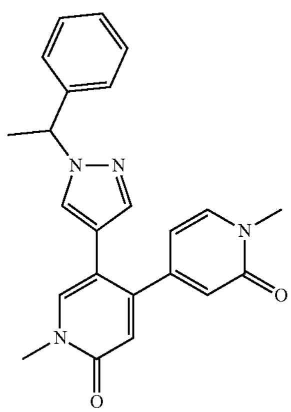 [SMILES: CC(c1ccccc1)n1cc(-c2cn(C)c(=O)cc2-c2ccn(C)c(=O)c2)cn1] | 1,1'-dimethyl-5-(1-(1-phenylethyl)-1H-pyrazol-4-yl)-[4,4'-bipyridine]-2,2'(1H,1'H)-dione | 1H NMR (400 MHz, DMSO-d6) δ 7.84-7.89 (m, 1 H), 7.52-7.59 (m, 2 H), 7.23-7.36 (m, 4 H), 7.05-7.13 (m, 2 H), 6.30-6.34 (m, 1 H), 6.23-6.27 (m, 1 H), 5.82-5.89 (m, 1 H), 5.48-5.59 (m, 1 H), 3.45-3.50 (m, 3 H), 3.38-3.42 (m, 3 H), 1.69-1.77 (m, 3 H) | 387 |
| 311 | 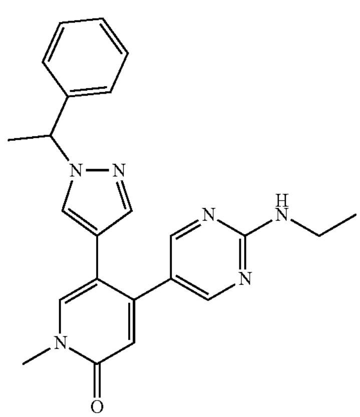 [SMILES: CCNc1ncc(-c2cc(=O)n(C)cc2-c2cnn(C(C)c3ccccc3)c2)cn1] | 4-(2-(ethylamino)pyrimidin-5-yl)-1-methyl-5-(1-(1-phenylethyl)-1H-pyrazol-4-yl)pyridin-2(1H)-one | 1H NMR (400 MHz, DMSO-d6) δ 7.99-8.15 (m, 2 H), 7.76-7.81 (m, 1 H), 7.58-7.64 (m, 1 H), 7.38-7.44 (m, 1 H), 7.29-7.36 (m, 2 H), 7.22-7.29 (m, 2 H), 7.09-7.17 (m, 2 H), 6.36-6.43 (m, 1 H), 5.49-5.61 (m, 1 H), 3.41-3.52 (m, 3 H), 3.25-3.31 (m, 2 H), 1.68-1.79 (m, 3 H), 1.06-1.19 (m, 3 H) | 401 |

TABLE 22-continued

| Example | Structure | IUPAC Name | ¹H NMR (ppm) | MS (M + H) |
|---|---|---|---|---|
| 312 | 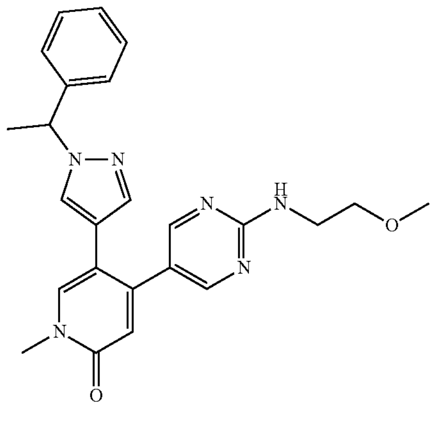 [SMILES: COCCNc1ncc(-c2cc(=O)n(C)cc2-c2cnn(C(C)c3ccccc3)c2)cn1] | 4-(2-((2-methoxyethyl)amino)pyrimidin-5-yl)-1-methyl-5-(1-(1-phenylethyl)-1H-pyrazol-4-yl)pyridin-2(1H)-one | 1H NMR (400 MHz, DMSO-d6) δ 8.08 (br s, 2 H), 7.80 (s, 1 H), 7.60 (s, 1 H), 7.23-7.42 (m, 5 H), 7.13 (m, 2 H), 6.40 (s, 1 H), 5.55 (m, 1 H), 3.42-3.49 (m, 7 H), 3.21-3.29 (m, 3 H), 1.73 (m, 3 H) | 431 |
| 313 | 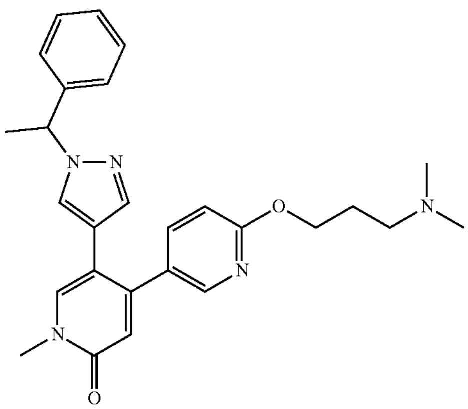 [SMILES: CC(c1ccccc1)n1cc(-c2cn(C)c(=O)cc2-c2ccc(OCCCN(C)C)nc2)cn1] | 6-(3-(dimethylamino)propoxy)-1'-methyl-5'-(1-(1-phenylethyl)-1H-pyrazol-4-yl)-[3,4'-bipyridin]-2'(1'H)-one | 1H NMR (400 MHz, DMSO-d6) δ 7.97-8.04 (m, 1 H), 7.82-7.88 (m, 1 H), 7.36-7.45 (m, 2 H), 7.22-7.34 (m, 3 H), 7.14-7.20 (m, 1 H), 7.04-7.11 (m, 2 H), 6.66-6.73 (m, 1 H), 6.34-6.41 (m, 1 H), 5.44-5.56 (m, 1 H), 4.23-4.32 (m, 2 H), 3.49 (s, 3 H), 2.39-2.47 (m, 2 H), 2.21 (s, 6 H), 1.82-1.94 (m, 2 H), 1.65-1.74 (m, 3 H) | 458 |

Example 314: 5-(1-(2-chlorophenyl)-1H-pyrazol-4-yl)-1,1'-dimethyl-[4,4'-bipyridine]-2,2'(1H,1'H)-dione Step 1: 4-chloro-5-[1-(2-chlorophenyl)pyrazol-4-yl]-1-methyl-pyridin-2-one

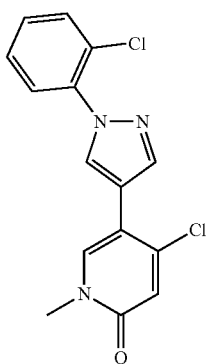 [SMILES: Cn1cc(-c2cnn(-c3ccccc3Cl)c2)c(Cl)cc1=O]

A mixture of 5-bromo-4-chloro-1-methyl-pyridin-2-one (100 mg, 0.45 mmol), [1-(2-chlorophenyl)pyrazol-4-yl]boronic acid (110 mg, 0.49 mmol), and 1,1'-bis(diphenylphosphino)ferrocenedichloro palladium(II) dichloromethane complex (26.3 mg, 0.04 mmol) in 1,4-dioxane (2.7 mL) and 3.5 M K₃PO₄ (0.3 mL, 1.05 mmol) was bubbled with nitrogen for 5 min. The sealed vial was heated to 75° C. for 8 h. After the mixture was cooled to room temperature and diluted with EtOAC and water, it was filtered through a short celite plug. The aqueous layer was separated and extracted with EtOAc (3×15 ml). The combined organic layers were washed with brine, dried over sodium sulfate and filtered. The resulting residue was purified by silica gel column chromatography using a gradient of MeOH (0 to 2% for 17 min, 2-10% for 7 min) in DCM. Appropriate fractions were combined and concentrated under reduced pressure to afford the title (60 mg, 0.19 mmol) as a tan solid. ¹H NMR (400 MHz, DMSO-d₆) δ ppm 8.34-8.39 (s, 1H), 8.10-8.13 (s, 1H), 7.95-7.99 (s, 1H), 7.68-7.73 (m, 1H), 7.61-7.67 (m, 1H), 7.48-7.58 (m, 2H), 6.67-6.72 (s, 1H), 3.46-3.50 (s, 3H). LCMS (M+H)⁺ 320.

Step 2: 5-(1-(2-chlorophenyl)-1H-pyrazol-4-yl)-1,1'-dimethyl-[4,4'-bipyridine]-2,2'(1H,1'H)-dione

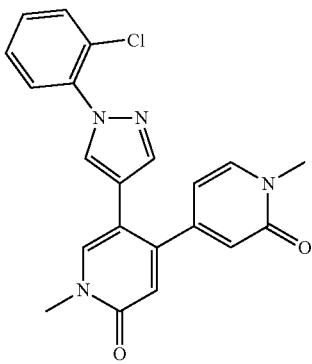 [SMILES: Cn1ccc(-c2cc(=O)n(C)cc2-c2cnn(-c3ccccc3Cl)c2)cc1=O]

The title compound was prepared in a manner similar to Example 305, Step 2, by substituting the title compound from Step 1 for 3-(4-(4-chloro-1-methyl-6-oxo-1,6-dihydro-pyridin-3-yl)-1H-pyrazol-1-yl)-4-methoxybenzonitrile and running the reaction at 78° C. 1H NMR (400 MHz, DMSO-d6) δ ppm 8.00 (s, 1H), 7.83 (s, 1H), 7.62-7.70 (m, 3H), 7.43-7.58 (m, 3H), 6.37 (s, 1H), 6.27-6.32 (m, 1H), 5.95-6.01 (m, 1H), 3.51 (s, 3H), 3.41 (s, 3H). LCMS (M+H)+ 393.

Examples 315-320 in Table 23 were prepared using the appropriate pyrimidine or pyridine boronic acid derivative and substituted pyrazole in a similar multi-step manner as Example 314.

TABLE 23

| Example | Structure | IUPAC Name | $^1$H NMR (ppm) | MS (M + H) |
|---|---|---|---|---|
| 315 | 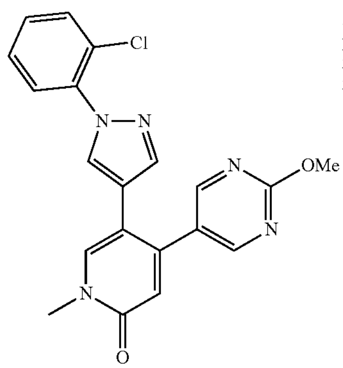 | 5-(1-(2-chlorophenyl)-1H-pyrazol-4-yl)-4-(2-methoxypyrimidin-5-yl)-1-methylpyridin-2(1H)-one | 1H NMR (400 MHz, DMSO-d6) δ 8.48 (s, 2 H), 7.99 (s, 1 H), 7.79 (s, 1 H), 7.62-7.67 (m, 1 H), 7.58-7.60 (m, 1 H), 7.44-7.55 (m, 3 H), 6.54 (s, 1 H), 3.92 (s, 3 H), 3.52 (s, 3 H) | 394 |
| 316 | 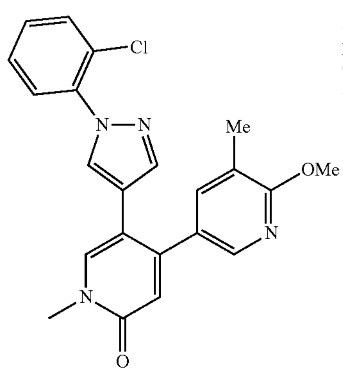 | 5'-(1-(2-chlorophenyl)-1H-pyrazol-4-yl)-6-methoxy-1',5-dimethyl-[3,4'-bipyridin]-2'(1'H)-one | 1H NMR (400 MHz, DMSO-d6) δ 7.97 (s, 1 H), 7.89-7.93 (m, 1 H), 7.61-7.67 (m, 2 H), 7.42-7.55 (m, 4 H), 7.34-7.38 (m, 1 H), 6.40 (s, 1 H), 3.88 (s, 3 H), 3.51 (s, 3 H), 2.08 (s, 3 H) | 407 |

TABLE 23-continued

| Example | IUPAC Name | ¹H NMR (ppm) | MS (M + H) |
|---|---|---|---|
| 317 | 5-(1-(2-chlorophenyl)-1H-pyrazol-4-yl)-2'-methoxy-1-methyl-[4,4'-bipyridin]-2(1H)-one | 1H NMR (400 MHz, DMSO-d6) δ 8.09 (m, 1 H), 7.98 (s, 1 H), 7.67 (s, 1 H), 7.64 ( m, 1 H), 7.44-7.55 (m, 5 H), 6.81 (m, 1 H), 6.43 (s, 1 H), 3.86 (s, 3 H), 3.52 (s, 3 H) | 393 |
| 318 | 5-(1-(2-fluorophenyl)-1H-pyrazol-4-yl)-1,1'-dimethyl-[4,4'-bipyridine]-2,2'(1H,1'H)-dione | 1H NMR (400 MHz, DMSO-d6) δ 7.96 (s, 1 H), 7.91 (s, 1 H), 7.71 (m, 1 H), 7.60 (m, 1 H), 7.52 (s, 1 H), 7.25-7.41 (m, 3 H), 6.30 (s, 1 H), 6.24 (m, 1 H), 5.92 (m, 1 H), 3.44 (s, 3 H), 3.36 (s, 3 H) | 377 |
| 319 | 5'-(1-(2-fluorophenyl)-1H-pyrazol-4-yl)-6-methoxy-1'-methyl-[3,4'-bipyridin]-2'(1'H)-one | 1H NMR (400 MHz, DMSO-d6) δ 7.24-7.31 (m, 1 H), 7.15-7.21 (m, 1 H), 6.98-7.03 (m, 1 H), 6.89-6.97 (m, 1 H), 6.68-6.75 (m, 1 H), 6.48-6.67 (m, 4 H), 5.95-6.02 (m, 1 H), 5.56-5.63 (m, 1 H), 3.02-3.08 (m, 3 H), 2.66-2.73 (m, 3 H) | 377 |
| 320 | 5-(1-(2-fluorophenyl)-1H-pyrazol-4-yl)-4-(2-methoxypyrimidin-5-yl)-1-methylpyridin-2(1H)-one | 1H NMR (400 MHz, DMSO-d6) δ 8.42 (s, 2 H), 7.94 (s, 1 H), 7.87 (m, 1 H), 7.69 (m, 1 H), 7.25-7.46 (m, 4 H), 6.48 (s, 1 H), 3.86 (s, 3 H), 3.45 (s, 3 H) | 378 |

Example 321: 5-(1-(2-hydroxycyclohexyl)-1H-pyrazol-4-yl)-1-methyl-4-phenylpyridin-2(1H)-one Step 1: 4-chloro-5-(1-(2-hydroxycyclohexyl)-1H-pyrazol-4-yl)-1-methylpyridin-2(1H)-one

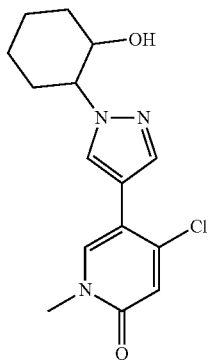 [SMILES: Cn1cc(-c2cnn(C3CCCCC3O)c2)c(Cl)cc1=O]

A mixture of 4-chloro-1-methyl-5-(1H-pyrazol-4-yl)pyridin-2-one (209 mg, 1 mmol), 7-oxabicyclo[4.1.0]heptane (0.2 mL, 2 mmol) and ytterbium(III) trifluoromethanesulfonate (62 mg, 0.10 mmol) was stirred at rt for 15 min before being heated to 40° C. for 2 h. The mixture was diluted with DCM (2 mL), capped and stirred at 45° C. for 12 h. LCMS analysis shows evidence of the desired product as a major peak. The mixture was diluted with DCM and water, and filtered. The organic layer was separated, dried over sodium sulfate, filtered and concentrated in vacuo. The resulting residue was purified by silica gel column chromatography (2.5% MeOH followed by 2.5-10% MeOH in DCM. Appropriate fractions were combined and concentrated under reduced pressure to afford the title compound (250 mg, 0.80 mmol) as a colourless solid. LCMS (M+H)$^+$ 308.

Step 2: 5-(1-(2-hydroxycyclohexyl)-1H-pyrazol-4-yl)-1-methyl-4-phenylpyridin-2(1H)-one

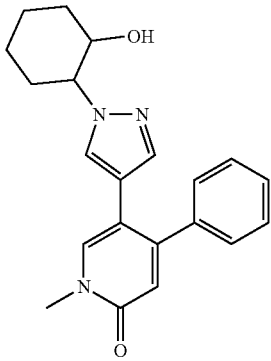 [SMILES: Cn1cc(-c2cnn(C3CCCCC3O)c2)c(-c2ccccc2)cc1=O]

A mixture of the title compound from Step 1 (65 mg, 0.21 mmol), phenylboronic acid (34 mg, 0.28 mmol) and Pd(PPh$_3$)$_4$ (25 mg, 0.02 mmol) was combined in an 8 ml vial with stir bar; the dry mixture was diluted with 1,4-dioxane (1.4 mL) and 2M (aq) sodium carbonate (0.32 mL, 0.64 mmol). After bubbling the stirred suspension for 5 min, the vial was sealed and heated to 80° C. for 14 h. The mixture was diluted with MeOH (1 mL) and filtered through a 2 A syringe filter. The filtrate was purified by silica gel column chromatography (10-60% for 12 min followed by 60-100% for 3 min of ACN/0.1% formic acid). Appropriate fractions were collected and concentrated in vacuo to afford the titled compound (14 mg, 0.04 mmol) as a light pink solid. $^1$H NMR (400 MHz, DMSO-d6) δ ppm 6.99-7.06 (m, 1H), 6.49-6.58 (m, 3H), 6.34-6.40 (m, 2H), 6.27-6.32 (m, 1H), 6.10-6.17 (m, 1H), 5.44-5.50 (m, 1H), 3.75-3.83 (m, 1H), 2.79-2.91 (m, 1H), 2.65-2.70 (m, 3H), 0.71-1.12 (m, 5H), 0.34-0.49 (m, 3H). LCMS (M+H)$^+$ 350.

Example 322: 2-chloro-6-[4-[4-[2-(cyclopropylamino)pyrimidin-5-yl]-1-methyl-6-oxo-3-pyridyl]pyrazol-1-yl]benzonitrile Step 1: 2-chloro-6-(4-(4,4,5,5-tetramethyl-1,3,2-dioxaborolan-2-yl)-1H-pyrazol-1-yl)benzonitrile

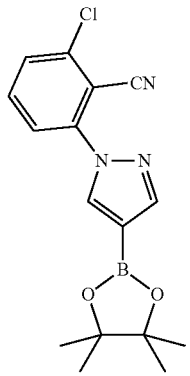 [SMILES: CC1(C)OB(c2cnn(-c3cccc(Cl)c3C#N)c2)OC1(C)C]

To a stirred solution of 4-(4,4,5,5-tetramethyl-1,3,2-dioxaborolan-2-yl)-1H-pyrazole (5 g, 25.8 mmol) in DMF (10 mL) at 0° C. under a nitrogen atmosphere was added NaH (2.58 g, 107.5 mmol) portion wise. The resulting mixture was stirred for 20 min followed by addition of 2-chloro-6-fluoro-benzonitrile (4.8 g, 30.9 mmol). The mixture was stirred at room temperature for 3 h. The reaction mixture was quenched by addition of water (300 mL) at 0° C. It was then extracted with EtOAc (5×500 mL). The combined organic layers were washed with brine, dried over Na$_2$SO$_4$ and concentrated under reduced pressure to afford a 3 grams of the crude) of the crude title compound. LCMS (M+H)$^+$ 330.

Step 2: 2-chloro-6-[4-(4-chloro-1-methyl-6-oxo-3-pyridyl)pyrazol-1-yl]benzonitrile

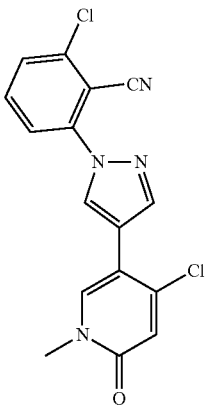 [SMILES: Cn1cc(-c2cnn(-c3cccc(Cl)c3C#N)c2)c(Cl)cc1=O]

To a solution of the title compound from Step 1 (1.3 g, 3.9 mmol), 5-bromo-4-chloro-1-methyl-pyridin-2-one (1.17 g, 5.3 mmol), K₃PO₄ (2.79 g, 13.1 mmol) in water (18 mL) and 1,4-dioxane (90 mL) was added Pd(dppf)Cl₂ (769 mg, 1.1 mmol) under a nitrogen atmosphere. The resulting mixture was stirred at 80° C. for 2.5 h. It was then cooled down to room temperature, diluted with water and extracted with EtOAc. The combined organic layers were concentrated under vacuum. The residue was purified by silica gel column chromatography with a DCM/MeOH mixture (40/1) to afford 500 mg of the title compound (500 mg, 37%) as a yellow solid. LCMS (M+H)⁺ 345.

Step 3: 5-bromo-N-cyclopropyl-pyrimidin-2-amine

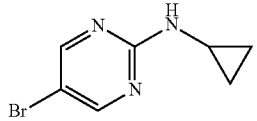 [SMILES: Brc1cnc(NC2CC2)nc1]

To a solution of 5-bromo-2-chloro-pyrimidine (2 g, 10.3 mmol) in ethanol (20 mL) at room temperature was added cyclopropylamine (1.18 g, 20.7 mmol). The resulting mixture was stirred at 80° C. overnight. The reaction mixture was diluted with EtOAc and washed with a saturated NaHCO₃ aqueous solution. The organic layer was dried over sodium sulfate and concentrated under reduced pressure. The residue was purified by silica gel column chromatography to afford the title compound (1.9 g, 86% yield) as a white solid. LCMS (M+H)⁺ 214.

Step 4: N-cyclopropyl-5-(4,4,5,5-tetramethyl-1,3,2-dioxaborolan-2-yl)pyrimidin-2-amine

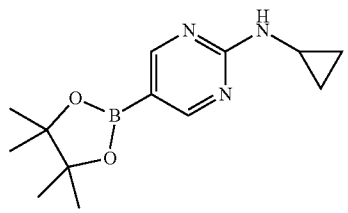 [SMILES: CC1(C)OB(c2cnc(NC3CC3)nc2)OC1(C)C]

A mixture of 5-bromo-N-cyclopropyl-pyrimidin-2-amine (600 mg, 2.8 mmol), 4,4,5,5-tetramethyl-2-(4,4,5,5-tetramethyl-1,3,2-dioxaborolan-2-yl)-1,3,2-dioxaborolane (1.1 g, 4.2 mmol), potassium acetate (550 mg, 5.6 mmol) and PdCl₂(PPh₃)₂ (393 mg, 0.56 mmol) in 1,4-dioxane (20 mL) under a nitrogen atmosphere was stirred overnight at 80° C. in a sealed tube. The solvent was removed under reduced pressure and the residue was purified by silica gel column chromatography to afford the title compound as a yellow solid. LCMS (M+H)⁺ 180 (M-pinacol).

Step 5: 2-chloro-6-[4-[4-[2-(cyclopropylamino)pyrimidin-5-yl]-1-methyl-6-oxo-3-pyridyl]pyrazol-1-yl]benzonitrile

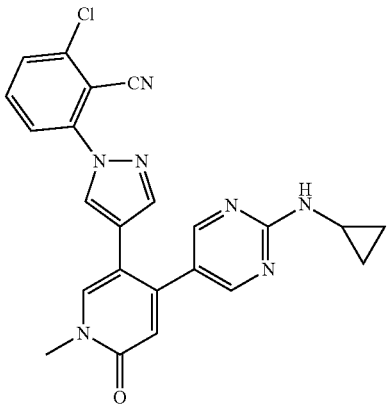 [SMILES: Cn1cc(-c2cnn(-c3cccc(Cl)c3C#N)c2)c(-c2cnc(NC3CC3)nc2)cc1=O]

A mixture of the title compound from Step 2 (100 mg, 0.29 mmol), the title compound from Step 4 (227 mg, 0.87 mmol), Na₂CO₃ (92 mg, 0.87 mmol), Pd(PPh₃)₄ (67 mg, 0.06 mmol) in 1,4-dioxane (15 mL) and water (3 mL) in a sealed tube was degassed and stirred under nitrogen at 80° C. for 2.5 h. The reaction mixture was diluted with water, extracted with ethyl acetate and washed with brine. The organic layer was dried over sodium sulfate and concentrated under reduced pressure. The residue was purified by preparative-HPLC to afford the title compound as a white solid (29.4 mg, 22%). 1H NMR (CD3OD, 400 MHz) δ δ 8.32 (d, 2H), 8.15 (s, 1H), 7.91 (s, 1H), 7.80-7.67 (m, 4H), 6.65 (S, 1H), 3.66-3.48 (m, 3H), 2.71 (s, 1H), 0.89-0.84 (d, 2H), 0.67-0.63 (d, 2H). LCMS (M+H)⁺ 444.

Examples 323-338 in Table 24 were prepared using the appropriate pyrimidine boronic acid pinacol ester and substituted benzonitrile in a similar multi-step manner as Example 322.

TABLE 24

| Example | Structure | IUPAC Name | ¹H NMR (ppm) | MS (M + H) |
| --- | --- | --- | --- | --- |
| 323 | 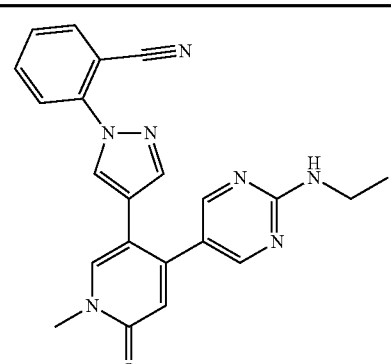 | 2-(4-(4-(2-(ethylamino)pyrimidin-5-yl)-1-methyl-6-oxo-1,6-dihydropyridin-3-yl)-1H-pyrazol-1-yl)benzonitrile | 1H NMR (400 MHz, DMSO-d6) δ 8.27-8.31 (m, 1 H), 8.09-8.21 (m, 2 H), 7.99-8.03 (m, 1 H), 7.92-7.96 (m, 1 H), 7.82-7.89 (m, 1 H), 7.71-7.76 (m, 1 H), 7.54-7.62 (m, 2 H), 7.39-7.47 (m, 1 H), 6.43-6.50 (m, 1 H), 3.47-3.53 (m, 3 H), 3.25-3.31 (m, 2 H), 1.06-1.14 (m, 3 H) | 398 |

TABLE 24-continued

| Example | Structure | IUPAC Name | ¹H NMR (ppm) | MS (M + H) |
|---|---|---|---|---|
| 324 | 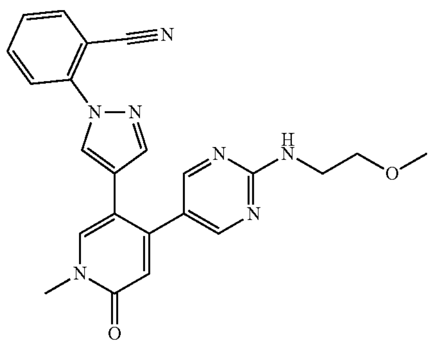 [SMILES: COCCNc1ncc(-c2cc(=O)n(C)cc2-c2cnn(-c3ccccc3C#N)c2)cn1] | 2-(4-(4-(2-((2-methoxyethyl)amino)pyrimidin-5-yl)-1-methyl-6-oxo-1,6-dihydropyridin-3-yl)-1H-pyrazol-1-yl)benzonitrile | 1H NMR (400 MHz, DMSO-d6) δ 7.44-7.47 (m, 1 H), 7.27-7.37 (m, 2 H), 7.15-7.20 (m, 1 H), 7.09-7.13 (m, 1 H), 6.99-7.06 (m, 1 H), 6.88-6.93 (m, 1 H), 6.72-6.78 (m, 2 H), 6.56-6.62 (m, 1 H), 5.62-5.66 (m, 1 H), 2.66-2.70 (m, 3 H), 2.58-2.63 (m, 4 H), 2.38-2.42 (m, 3 H) | 428 |
| 325 | 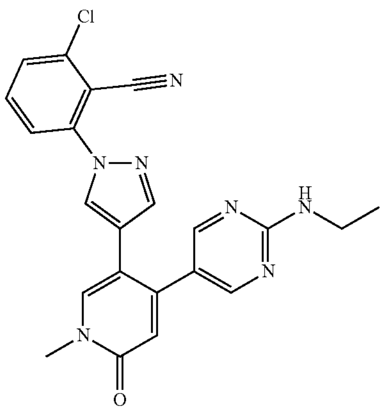 [SMILES: CCNc1ncc(-c2cc(=O)n(C)cc2-c2cnn(-c3cccc(Cl)c3C#N)c2)cn1] | 2-chloro-6-(4-(4-(2-(ethylamino)pyrimidin-5-yl)-1-methyl-6-oxo-1,6-dihydropyridin-3-yl)-1H-pyrazol-1-yl)benzonitrile | (CD₃OD, 300 MHz) δ 8.31 (s, 2H), 8.18 (s, 1H), 7.92 (s, 1H), 7.87-7.75 (m, 1H), 7.77-7.66 (m, 3H), 6.66 (s, 1H), 3.68 (s, 3H), 3.53-3.39 (m, 2H), 1.26 (t, J = 7.2 Hz, 3H). | 432 |
| 326 | 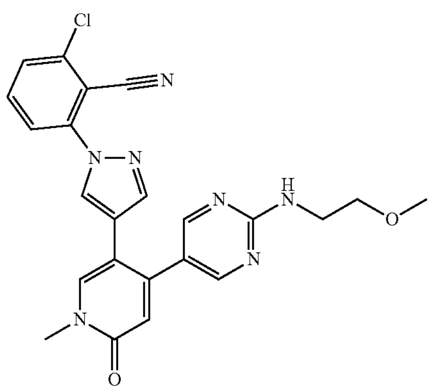 [SMILES: COCCNc1ncc(-c2cc(=O)n(C)cc2-c2cnn(-c3cccc(Cl)c3C#N)c2)cn1] | 2-chloro-6-(4-(4-(2-((2-methoxyethyl)amino)pyrimidin-5-yl)-1-methyl-6-oxo-1,6-dihydropyridin-3-yl)-1H-pyrazol-1-yl)benzonitrile | (CD₃OD, 300 MHz) δ 8.30 (s, 2H), 8.17 (d, J = 0.7 Hz, 1H), 7.92 (s, 1H), 7.84-7.76 (m, 1H), 7.74-7.66 (m, 3H), 6.65 (s, 1H), 3.68 (s, 3H), 3.65-3.55 (m, 4H), 3.38 (s, 3H). | 462 |
| 327 | 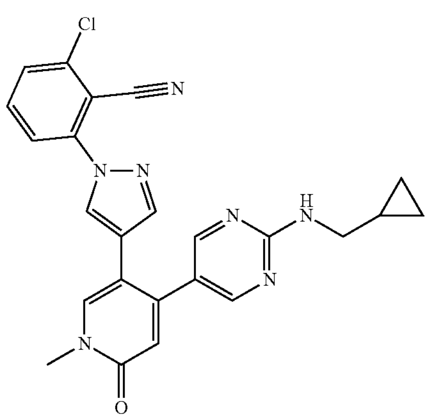 [SMILES: Cn1cc(-c2cnn(-c3cccc(Cl)c3C#N)c2)c(-c2cnc(NCC3CC3)nc2)cc1=O] | 2-chloro-6-(4-(4-(2-((cyclopropylmethyl)amino)pyrimidin-5-yl)-1-methyl-6-oxo-1,6-dihydropyridin-3-yl)-1H-pyrazol-1-yl)benzonitrile | (DMSO, 300 MHz) δ 8.31 (s, 1H), 8.15 (s, 2H) 7.93 (s, 1H), 7.85 (t, J = 8.1 Hz, 1H), 7.79 (d, J = 8.2 Hz, 1H), 7.72 (d, J = 8.1 Hz, 1H), 7.64-7.61(m, 2H) 6.47 (s, 1H), 3.50 (s, 3H), 3.16 (d, J = 6.7 Hz, 2H), 1.09-1.03 (m, 1H), 0.41-0.33 (m, 2H), 0.21-0.17 (m, 2H) | 458 |

TABLE 24-continued

| Example | Structure | IUPAC Name | ¹H NMR (ppm) | MS (M + H) |
|---------|-----------|------------|--------------|------------|
| 328 | 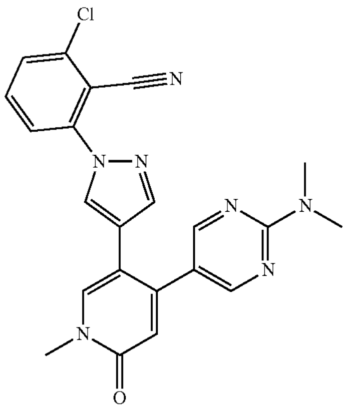 [SMILES: CN(C)c1ncc(-c2cc(=O)n(C)cc2-c2cnn(-c3cccc(Cl)c3C#N)c2)cn1] | 2-chloro-6-(4-(4-(2-(dimethylamino)pyrimidin-5-yl)-1-methyl-6-oxo-1,6-dihydropyridin-3-yl)-1H-pyrazol-1-yl)benzonitrile | (CD$_3$OD, 300 MHz) δ 8.33 (s, 2H), 8.16 (d, J = 0.7 Hz, 1H), 7.91 (s, 1H), 7.84-7.76 (m, 1H), 7.75-7.68 (m, 3H), 6.65 (s, 1H), 3.68 (s, 3H), 3.25 (s, 6H). | 432 |
| 329 | 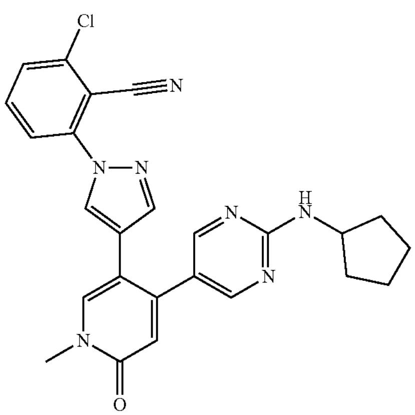 | 2-chloro-6-(4-(4-(2-(cyclopentylamino)pyrimidin-5-yl)-1-methyl-6-oxo-1,6-dihydropyridin-3-yl)-1H-pyrazol-1-yl)benzonitrile | (CD$_3$OD, 300 MHz) δ 8.32 (s, 2H), 8.18 (s, 1H) 7.93 (s, 1H), 7.83-7.69 (m, 4H), 6.67 (s, 1H), 4.28-4.20 (m, 1H), 3.68 (s, 3H), 2.09-1.97 (m, 2H), 1.82-1.73 (m, 2H), 1.68-1.59 (m, 4H) | 472 |
| 330 | 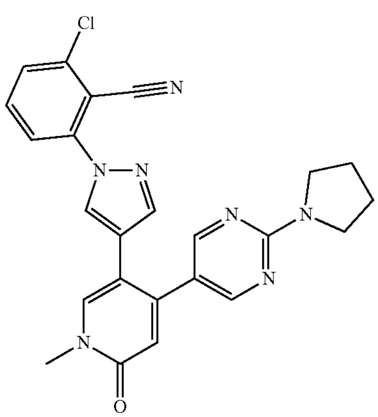 | 2-chloro-6-(4-(1-methyl-6-oxo-4-(2-(pyrrolidin-1-yl)pyrimidin-5-yl)-1,6-dihydropyridin-3-yl)-1H-pyrazol-1-yl)benzonitrile | (CD$_3$OD, 400 MHz) δ 8.35 (s, 2H), 8.17 (s, 1H), 7.92 (s, 1H), 7.85-7.76 (m, 1H), 7.78-7.67 (m, 3H), 6.67 (s, 1H), 3.68 (s, 3H), 3.67-3.59 (m, 4H), 2.13-2.04 (m, 4H) | 458 |

TABLE 24-continued

| Example | Structure | IUPAC Name | ¹H NMR (ppm) | MS (M + H) |
|---|---|---|---|---|
| 331 | 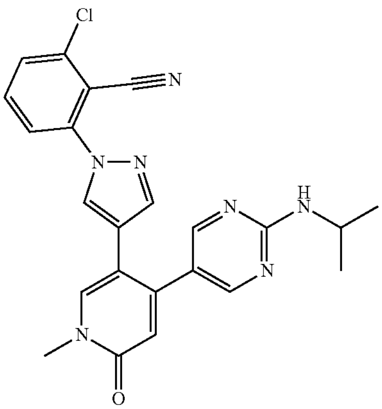 [SMILES: CC(C)Nc1ncc(-c2cc(=O)n(C)cc2-c2cnn(-c3cccc(Cl)c3C#N)c2)cn1] | 2-chloro-6-(4-(4-(2-(isopropylamino)pyrimidin-5-yl)-1-methyl-6-oxo-1,6-dihydropyridin-3-yl)-1H-pyrazol-1-yl)benzonitrile | (CD₃OD, 300 MHz) δ 8.31 (s, 2H), 8.18 (s, 1H) 7.92 (s, 1H), 7.83-7.66 (m, 4H), 7.61-7.35 (m, 1H), 6.66 (s, 1H), 4.20-4.11 (m, 1H), 3.67 (s, 3H), 1.20-1.14 (m, 6H) | 446 |
| 332 | 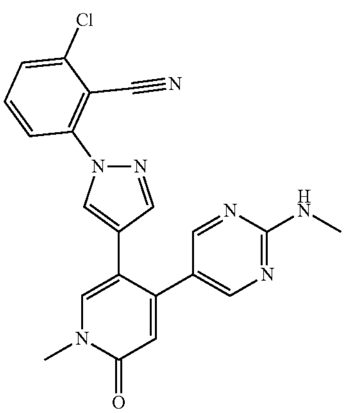 [SMILES: CNc1ncc(-c2cc(=O)n(C)cc2-c2cnn(-c3cccc(Cl)c3C#N)c2)cn1] | 2-chloro-6-(4-(1-methyl-4-(2-(methylamino)pyrimidin-5-yl)-6-oxo-1,6-dihydropyridin-3-yl)-1H-pyrazol-1-yl)benzonitrile | (CD₃OD, 300 MHz) δ 8.38 (s, 2H), 8.18 (d, J = 0.8 Hz, 1H), 7.94 (s, 1H), 7.92-7.61 (m, 5H), 6.68 (s, 1H), 3.68 (s, 3H), 3.03 (s, 3H). | 418 |
| 333 | 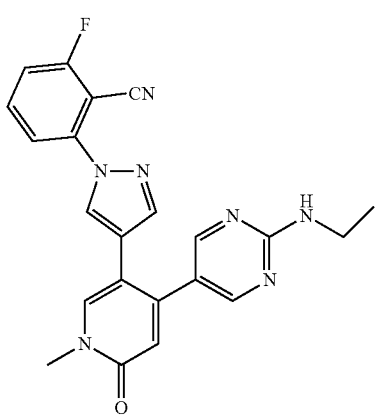 [SMILES: CCNc1ncc(-c2cc(=O)n(C)cc2-c2cnn(-c3cccc(F)c3C#N)c2)cn1] | 2-[4-[4-[2-(ethylamino)pyrimidin-5-yl]-1-methyl-6-oxo-3-pyridyl]pyrazol-1-yl]-6-fluoro-benzonitrile | (CD₃OD, 400 MHz) δ 8.33 (s, 2H), 8.19 (d, J = 0.7 Hz, 1H), 7.92 (s, 1H), 7.91-7.80 (m, 1H), 7.75 (s, 1H), 7.68-7.60 (m, 1H), 7.47-7.37 (m, 1H), 6.66 (s, 1H), 3.68 (s, 3H), 3.52-3.42 (m, 2H), 1.31-1.22 (m, 3H). | 416 |

TABLE 24-continued

| Example | Structure | IUPAC Name | ¹H NMR (ppm) | MS (M + H) |
|---------|-----------|------------|--------------|------------|
| 334 | 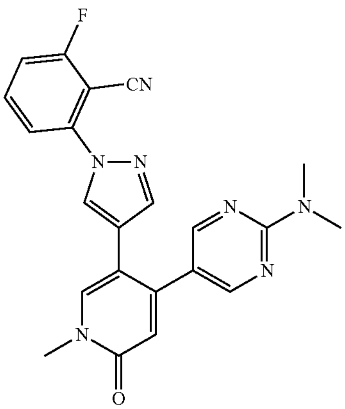 [SMILES: CN(C)c1ncc(-c2cc(=O)n(C)cc2-c2cnn(-c3cccc(F)c3C#N)c2)cn1] | 2-[4-[4-[2-(dimethylamino)pyrimidin-5-yl]-1-methyl-6-oxo-3-pyridyl]pyrazol-1-yl]-6-fluoro-benzonitrile | (CD₃OD, 400 MHz) δ 8.23 (s, 2H), 8.18 (s, 1H), 7.90-7.79 (m, 2H), 7.61 (d, J = 9.3 Hz, 2H), 7.45-7.36 (m, 1H), 6.60 (s, 1H), 3.67 (s, 3H), 3.19 (s, 6H), 2.05 (s, 0H). | 416 |
| 335 | 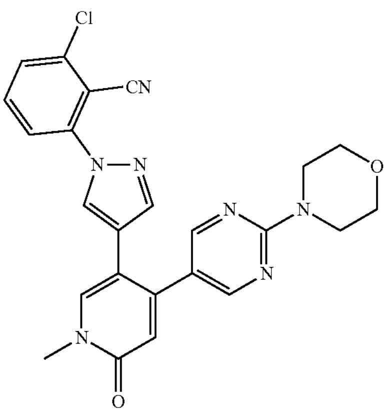 [SMILES: Cn1cc(-c2cnn(-c3cccc(Cl)c3C#N)c2)c(-c2cnc(N3CCOCC3)nc2)cc1=O] | 2-chloro-6-(4-(1-methyl-4-(2-morpholinopyrimidin-5-yl)-6-oxo-1,6-dihydropyridin-3-yl)-1H-pyrazol-1-yl)benzonitrile | (CD₃OD, 400 MHz) δ 8.27 (s, 2H), 8.15 (s, 1H), 7.87 (s, 1H), 7.79 (dd, J = 9.1, 7.2 Hz, 1H), 7.74-7.66 (m, 2H), 7.63 (s, 1H), 6.62 (s, 1H), 3.82 (dd, J = 5.5, 3.7 Hz, 4H), 3.74 (t, J = 4.7 Hz, 4H), 3.67 (s, 3H). | 474 |
| 336 | 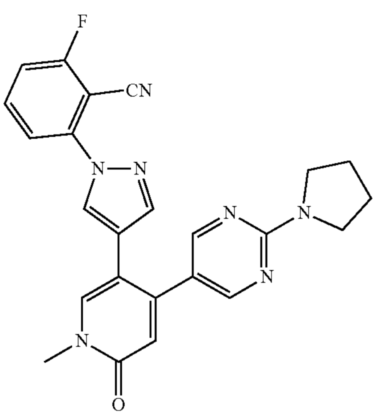 [SMILES: Cn1cc(-c2cnn(-c3cccc(F)c3C#N)c2)c(-c2cnc(N3CCCC3)nc2)cc1=O] | 2-fluoro-6-[4-[1-methyl-6-oxo-4-(2-pyrrolidin-1-ylpyrimidin-5-yl)-3-pyridyl]pyrazol-1-yl]benzonitrile | (CD₃OD, 400 MHz) δ 8.21 (d, J = 17.9 Hz, 3H), 7.86 (d, J = 8.6 Hz, 1H), 7.83 (dd, J = 8.4, 6.1 Hz, 1H), 7.63 (d, J = 4.5 Hz, 1H), 7.61 (d, J = 1.0 Hz, 0H), 7.45-7.36 (m, 1H), 6.61 (s, 1H), 3.67 (s, 3H), 3.61-3.53 (m, 4H), 2.07-1.98 (m, 4H). | 442 |

TABLE 24-continued

| Example | Structure | IUPAC Name | $^1$H NMR (ppm) | MS (M + H) |
|---|---|---|---|---|
| 337 | 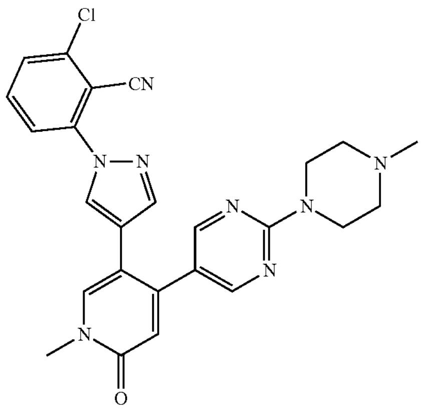 [SMILES: CN1CCN(c2ncc(-c3cc(=O)n(C)cc3-c3cnn(-c4cccc(Cl)c4C#N)c3)cn2)CC1] | 2-chloro-6-(4-(1-methyl-4-(2-(4-methylpiperazin-1-yl)pyrimidin-5-yl)-6-oxo-1,6-dihydropyridin-3-yl)-1H-pyrazol-1-yl)benzonitrile | (DMSO-d6, 400 MHz) δ 9.97 (s, 1H), 8.34 (s, 3H), 7.97 (s, 1H), 7.88 (t, J = 8.2 Hz, 1H), 7.83-7.71 (m, 2H), 7.61 (s, 1H), 6.50 (s, 1H), 4.72 (d, J = 14.4 Hz, 2H), 3.52 (s, 5H), 3.34 (s, 2H), 3.26 (s, 2H), 3.06 (s, 2H), 2.84 (s, 3H). | 487 |
| 338 | 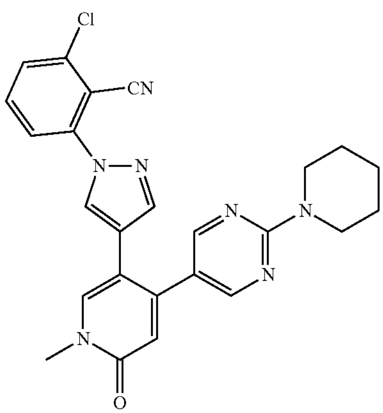 [SMILES: Cn1cc(-c2cnn(-c3cccc(Cl)c3C#N)c2)c(-c2cnc(N3CCCCC3)nc2)cc1=O] | 2-chloro-6-(4-(1-methyl-6-oxo-4-(2-(piperidin-1-yl)pyrimidin-5-yl)-1,6-dihydropyridin-3-yl)-1H-pyrazol-1-yl)benzonitrile | (CD$_3$OD, 400 MHz) δ 8.26 (s, 2H), 8.16 (d, J = 0.7 Hz, 1H), 7.88 (s, 1H), 7.84-7.75 (m, 1H), 7.76-7.59 (m, 3H), 6.63 (s, 1H), 3.87-3.79 (m, 4H), 3.67 (s, 3H), 1.74 (d, J = 5.1 Hz, 2H), 1.74-1.59 (m, 4H). | 472 |

Example 339: 2-chloro-6-[4-[4-[6-(isopropylamino)-3-pyridyl]-1-methyl-6-oxo-3-pyridyl]-pyrazol-1-yl]benzonitrile Step 1: 5-bromo-N-isopropyl-pyridin-2-amine

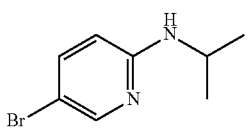

To a stirred solution of 5-bromo-2-fluoro-pyridine (1 g, 5.7 mmol) in DMSO (10 mL) were added propan-2-amine (2 g, 33.8 mmol) and DIEA (2.7 mL, 15.5 mmol) at room temperature. The reaction was stirred at 120° C. for 2 h. The resulting solution was cooled to room temperature and purified by reverse-phase column chromatography to afford the title compound (900 mg, 74% yield) as a yellow solid. LCMS (M+H)$^+$ 215.

Step 2: N-isopropyl-5-(4,4,5,5-tetramethyl-1,3,2-dioxaborolan-2-yl)pyridin-2-amine

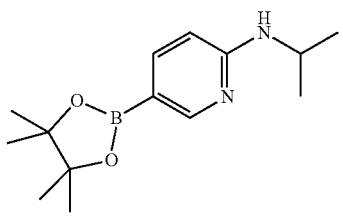 [SMILES: CC(C)Nc1ccc(B2OC(C)(C)C(C)(C)O2)cn1]

To a solution of the title compound from Step 1 (500 mg, 2.3 mmol) in 1,4-dioxane (10 mL) under N$_2$ was added bis(pinacolato)diboron (1.18 g, 4.7 mmol), Pd(dppf)Cl$_2$ (50 mg, 0.07 mmol) and potassium acetate (684 mg, 6.9 mmol). The reaction was stirred at 80° C. for 2 h. The reaction mixture was cooled to room temperature and concentrated under reduced pressure. The residue was purified by reverse-phase column chromatography to obtain the title compound as a white solid. LCMS (M+H)$^+$ 263.

Step 3: 2-chloro-6-[4-[4-[6-(isopropylamino)-3-pyridyl]-1-methyl-6-oxo-3-pyridyl]-pyrazol-1-yl]benzonitrile

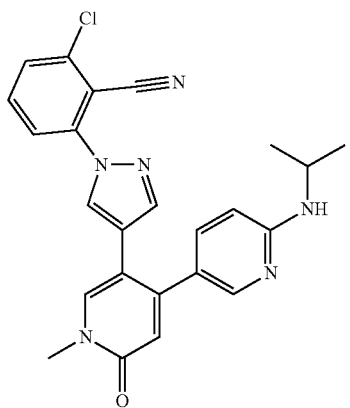 [SMILES: CC(C)Nc1ccc(-c2cc(=O)n(C)cc2-c2cnn(-c3cccc(Cl)c3C#N)c2)cn1]

To a solution of 2-chloro-6-[4-(4-chloro-1-methyl-6-oxo-3-pyridyl)pyrazol-1-yl]benzonitrile (120 mg, 0.35 mmol) in 1,4-dioxane (5 mL) and water (1 mL) under $N_2$ was added the title compound from Step 2 (365 mg, 1.39 mmol), Pd(PPh$_3$)$_4$ (40 mg, 0.03 mmol) and Na$_2$CO$_3$ (111 mg, 1.04 mmol). The mixture was stirred at 80° C. for 2 h. The reaction was cooled to room temperature and concentrated under reduced pressure. The residue was treated with water and extracted with EtOAc. The combined organic layers were dried over sodium sulfate, filtered, concentrated and purified by preparative-TLC to afford the title compound (6.6 mg, 4.2% yield) as a white solid. 1H NMR (CD$_3$OD, 400 MHz) δ 8.11 (s, 1H), 7.93 (s, 1H), 7.83-7.73 (m, 5H), 7.64 (m, 1H), 6.92 (m, 1H), 6.65 (s, 1H), 3.95-3.88 (m, 1H), 3.69 (s, 3H), 1.34 (d, 6H). LCMS (M+H)$^+$ 445.

Examples 340-351 in Table 25 were prepared using the appropriate pyridine boronic acid derivative and substituted benzonitrile in a similar multi-step manner as Example 339.

TABLE 25

| Example | Structure | IUPAC Name | $^1$H NMR (ppm) | MS (M + H) |
|---|---|---|---|---|
| 340 | 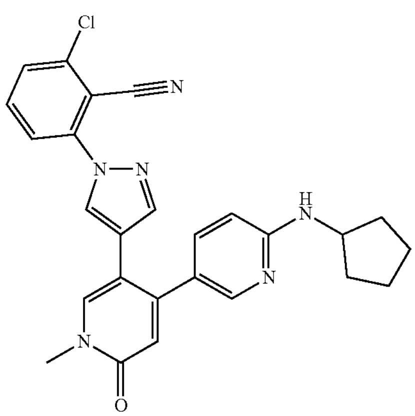 [SMILES: Cn1cc(-c2cnn(-c3cccc(Cl)c3C#N)c2)c(-c2ccc(NC3CCCC3)nc2)cc1=O] | 2-chloro-6-(4-(6-(cyclopentylamino)-1'-methyl-6'-oxo-1',6'-dihydro-[3,4'-bipyridin]-3'-yl)-1H-pyrazol-1-yl)benzonitrile | $^1$H-NMR (DMSO, 300 MHz) δ 8.18 (s, 1H), 7.92-7.72 (m, 4H), 7.65 (d, J = 8.2 Hz, 1H), 7.47 (s, 1H), 7.13 (d, J = 8.8 Hz, 1H), 6.73 (d, J = 6.8 Hz, 1H), 6.34 (d, J = 10.1 Hz, 2H), 4.06 (d, J = 8.8 Hz, 1H), 3.46 (s, 3H), 2.04 (s, 1H), 1.73 (d, J = 67.8 Hz, 4H), 1.43 (d, J = 33.1 Hz, 4H). | 471 |
| 341 | 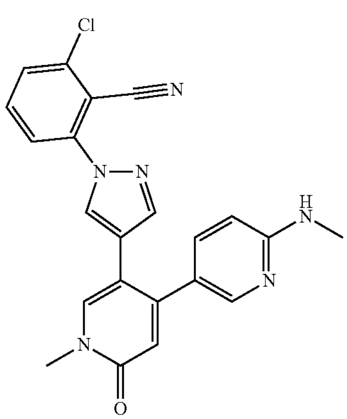 [SMILES: CNc1ccc(-c2cc(=O)n(C)cc2-c2cnn(-c3cccc(Cl)c3C#N)c2)cn1] | 2-chloro-6-(4-(1'-methyl-6-(methylamino)-6'-oxo-1',6'-dihydro-[3,4'-bipyridin]-3'-yl)-1H-pyrazol-1-yl)benzonitrile | $^1$H-NMR (CD$_3$OD, 300 MHz) 8.10 (d, J = 0.7 Hz, 1H), 7.96 (s, 1H), 7.86-7.65 (m, 6H), 6.99 (d, J = 9.3 Hz, 1H), 6.66 (s, 1H), 3.69 (s, 3H), 3.05 (s, 3H). | 417 |

TABLE 25-continued

| Example | Structure | IUPAC Name | ¹H NMR (ppm) | MS (M + H) |
|---|---|---|---|---|
| 342 | 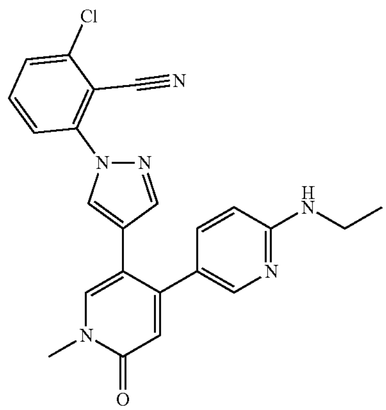 | 2-chloro-6-(4-(6-(ethylamino)-1'-methyl-6'-oxo-1',6'-dihydro-[3,4'-bipyridin]-3'-yl)-1H-pyrazol-1-yl)benzonitrile | ¹H-NMR (CD₃OD, 400 MHz) 8.09 (s, 1H), 7.93 (s, 1H), 7.93-7.76 (m, J = 8.0, 3.7 Hz, 3H), 7.76-7.62 (m, 3H), 6.96 (d, J = 9.3 Hz, 1H), 6.64 (s, 1H), 3.67 (s, 3H), 3.43-3.34 (q, J = 7.3 Hz, 2H), 1.34 (t, J = 7.2 Hz, 3H). | 431 |
| 343 | 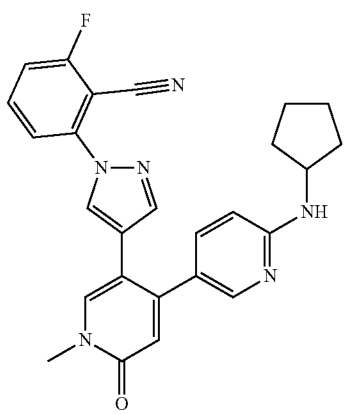 [SMILES: Cn1cc(-c2cnn(-c3cccc(F)c3C#N)c2)c(-c2ccc(NC3CCCC3)nc2)cc1=O] | 2-(4-(6-(cyclopentylamino)-1'-methyl-6'-oxo-1',6'-dihydro-[3,4'-bipyridin]-3'-yl)-1H-pyrazol-1-yl)-6-fluorobenzonitrile | (CD₃OD, 400 MHz) δ 8.15 (s, 1H), 7.96 (s, 1H), 7.94-7.79 (m, 3H), 7.75-7.62 (m, 2H), 7.48-7.38 (m, 1H), 6.99 (d, J = 9.4 Hz, 1H), 6.66 (s, 1H), 4.09-3.99 (m, 1H), 3.69 (s, 3H), 2.17-2.06 (m, 2H), 1.91-1.81 (m, 2H), 1.81-1.64 (m, 4H). | 455 |
| 344 | 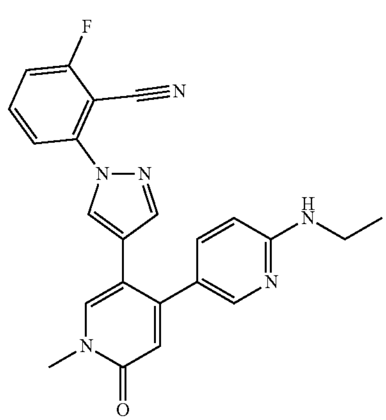 [SMILES: CCNc1ccc(-c2cc(=O)n(C)cc2-c2cnn(-c3cccc(F)c3C#N)c2)cn1] | 2-(4-(6-(ethylamino)-1'-methyl-6'-oxo-1',6'-dihydro-[3,4'-bipyridin]-3'-yl)-1H-pyrazol-1-yl)-6-fluorobenzonitrile | (DMSO, 400 MHz) δ 8.74 (s, 1H), 8.32 (s, 1H), 8.03 (s, 1H), 7.97-7.86 (m, 2H), 7.72 (s, 1H), 7.65 (d, J = 8.3 Hz, 1H), 7.60-7.50 (m, 2H), 6.90 (d, J = 9.3 Hz, 1H), 6.52 (s, 1H), 3.53 (s, 3H), 3.35 (q, J = 7.2 Hz, 2H), 1.22 (t, J = 7.2 Hz, 3H). | 415 |

TABLE 25-continued

| Example | Structure | IUPAC Name | ¹H NMR (ppm) | MS (M + H) |
|---|---|---|---|---|
| 345 | 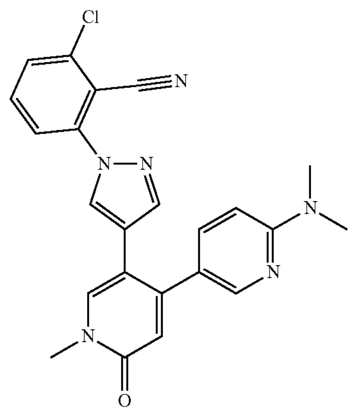 [SMILES: CN(C)c1ccc(-c2cc(=O)n(C)cc2-c2cnn(-c3cccc(Cl)c3C#N)c2)cn1] | 2-chloro-6-{4-[6-(dimethylamino)-1'-methyl-6'-oxo-1',6'-dihydro-[3,4'-bipyridine]-3'-yl]-1H-pyrazol-1-yl}benzonitrile | (CD₃OD, 400 MHz) δ 8.06 (s, 1H), 7.97 (s, 1H), 7.88 (m, 1H), 7.87-7.78 (m, 3H), 7.76 (m, 2H), 7.21 (d, 1H), 6.66 (s, 1H), 3.69 (s, 3H), 3.33 (s, 6H) | 431 |
| 346 | 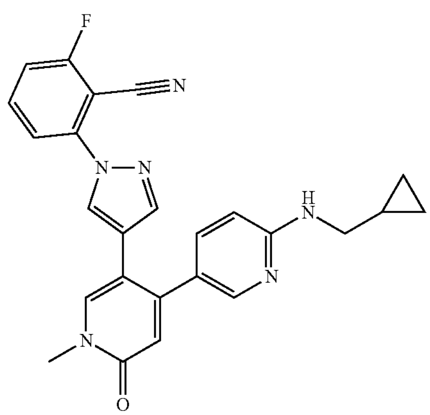 | 2-4-{6-[(cyclopropylmethyl)amino]-1'-methyl-6'-oxo-1',6'-dihydro-[3,4'-bipyridine]-3'-yl}-1H-pyrazol-1-yl)-6-fluorobenzonitrile | (CD₃OD, 400 MHz) δ 8.12 (s, 1H), 7.95 (s, 1H), 7.89-7.78 (m, 3H), 7.70-7.65 (m, 2H), 7.43 (t, 1H), 7.00 (d, 1H), 6.65 (s, 1H), 3.69 (s, 3H), 3.23 (d, 2H), 1.22-1.14 (m, 1H), 0.71-0.66 (m, 2H), 0.39-0.35 (m, 2H). | 441 |
| 347 | 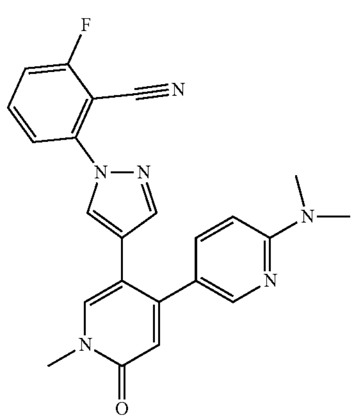 [SMILES: CN(C)c1ccc(-c2cc(=O)n(C)cc2-c2cnn(-c3cccc(F)c3C#N)c2)cn1] | 2-{4-[6-(dimethylamino)-1'-methyl-6'-oxo-1',6'-dihydro-[3,4'-bipyridine]-3'-yl]-1H-pyrazol-1-yl}-6-fluorobenzonitrile | (CD₃OD, 400 MHz) δ 8.06 (s, 1H), 7.93 (s, 1H), 7.87-7.74 (m, 4H), 7.65 (m, 1H), 7.42 (m, 1H), 7.18 (d, 1H), 6.64 (s, 1H), 3.67 (s, 3H), 3.30 (s, 6H) | 415 |

TABLE 25-continued

| Example | Structure | IUPAC Name | ¹H NMR (ppm) | MS (M + H) |
|---|---|---|---|---|
| 348 | 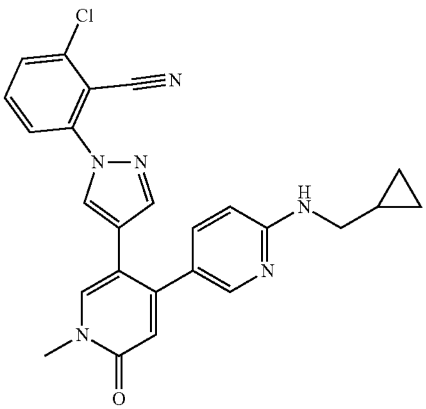 | 2-chloro-6-(4-{6-[(cyclopropylmethyl)amino]-1'-methyl-6'-oxo-1',6'-dihydro-[3,4'-bipyridine]-3'-yl}-1H-pyrazol-1-yl)benzonitrile | (CD$_3$OD, 400 MHz) δ 8.10 (s, 1H), 7.94 (s, 1H), 7.85-7.64 (m, 6H), 7.02 (d, 1H), 6.65 (s, 1H), 3.69 (s, 3H), 3.23 (d, 2H), 1.21 (m, 1H), 0.74-0.64 (m, 2H), 0.38-0.37 (m, 2H) | 457 |
| 349 | 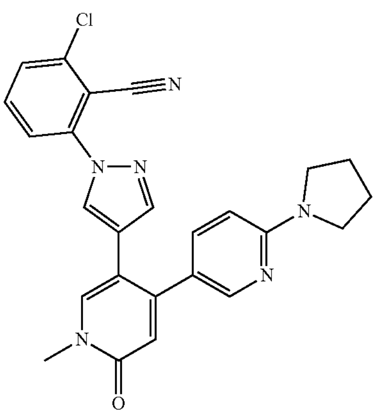 [SMILES: Cn1cc(-c2cnn(-c3cccc(Cl)c3C#N)c2)c(-c2ccc(N3CCCC3)nc2)cc1=O] | 2-chloro-6-[4-[1-methyl-6-oxo-4-(6-pyrrolidin-1-yl-3-pyridyl)-3-pyridyl]pyrazol-1-yl]benzonitrile | (CD$_3$OD, 400 MHz) δ 8.08 (d, J = 0.7 Hz, 1H), 7.96 (s, 1H), 7.86 (dd, J = 2.2, 0.7 Hz, 1H), 7.86-7.71 (m, 4H), 7.72 (dd, J = 7.9, 1.3 Hz, 1H), 7.07 (dd, J = 9.4, 0.8 Hz, 1H), 6.67 (s, 1H), 3.69 (s, 3H), 3.62 (s, 5H), 2.19 (s, 4H), 2.19 (d, J = 13.5 Hz, 1H). | 457 |
| 350 | 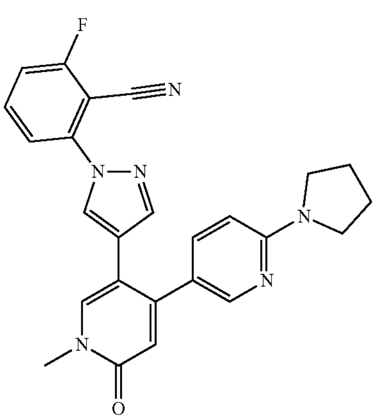 [SMILES: Cn1cc(-c2cnn(-c3cccc(F)c3C#N)c2)c(-c2ccc(N3CCCC3)nc2)cc1=O] | 2-fluoro-6-[4-[1-methyl-6-oxo-4-(6-pyrrolidin-1-yl-3-pyridyl)-3-pyridyl]pyrazol-1-yl]benzonitrile | (CD$_3$OD, 400 MHz) δ 8.10 (d, J = 0.7 Hz, 1H), 7.97 (s, 1H), 7.92-7.79 (m, 3H), 7.77 (dd, J = 9.5, 2.2 Hz, 1H), 7.67 (dd, J = 8.3, 1.0 Hz, 1H), 7.48-7.38 (m, 1H), 7.07 (d, J = 9.5 Hz, 1H), 6.67 (s, 1H), 3.70 (s, 3H), 3.62 (s, 1H), 2.19 (d, J = 6.6 Hz, 1H). | 441 |

TABLE 25-continued

| Example | Structure | IUPAC Name | ¹H NMR (ppm) | MS (M + H) |
|---|---|---|---|---|
| 351 | 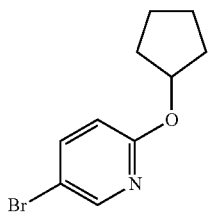 [SMILES: Brc1ccc(OC2CCCC2)nc1] | 2-fluoro-6-(4-(6-(isopropylamino)-1'-methyl-6'-oxo-1',6'-dihydro-[3,4'-bipyridin]-3'-yl)-1H-pyrazol-1-yl)benzonitrile | (CD3OD, 400 MHz) δ 8.14 (s, 1H), 7.95 (s, 1H), 7.93-7.76 (m, 3H), 7.75-7.62 (m, 2H), 7.48-7.38 (m, 1H), 6.96 (d, J = 9.4 Hz, 1H), 6.66 (s, 1H), 3.90 (t, J = 6.4 Hz, 1H), 3.69 (s, 3H), 1.35 (d, J = 6.4 Hz, 6H). | 429 |

Example 352: 2-chloro-6-[4-[4-[6-(cyclopentoxy)-3-pyridyl]-1-methyl-6-oxo-3-pyridyl]pyrazol-1-yl]benzonitrile Step 1: 5-bromo-2-(cyclopentoxy) pyridine

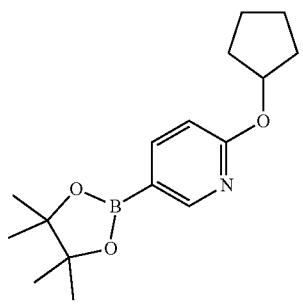 [SMILES: CC1(C)OB(c2ccc(OC3CCCC3)nc2)OC1(C)C]

To a solution of cyclopentanol (587.3 mg, 6.8 mmol) in THF (20 mL) was added NaH (205 mg, 8.5 mmol) at 0° C. in a 100 mL round-bottom flask. The resulting mixture was stirred for 20 min 5-bromo-2-fluoro-pyridine (1 g, 5.7 mmol) was then added. The resulting mixture was stirred at 50° C. for 2 h. The reaction mixture was diluted with water and extracted with ethyl acetate. The organic layer was washed with water, dried over sodium sulfate and concentrated under reduced pressure. The residue was purified by silica gel column chromatography to afford 1.3 g of the title compound as a yellow solid. LCMS (M+H)⁺ 242.

Step 2: 2-(cyclopentoxy)-5-(4,4,5,5-tetramethyl-1,3,2-dioxaborolan-2-yl)pyridine A mixture of the title compound from Step 1 (1.3 g, 5.4 mmol), 4,4,5,5-tetramethyl-2-(4,4,5,5-tetramethyl-1,3,2-dioxaborolan-2-yl)-1,3,2-dioxaborolane (2.7 g, 10.7 mmol), potassium acetate (1.05 g, 10.7 mmol), Pd(dppf)Cl₂ (785.8 mg, 1.07 mmol), and 1,4-dioxane (15 mL) under a nitrogen atmosphere was stirred at 80° C. for 2 h. The solvent was removed under reduced pressure and the residue purified by silica gel column chromatography to afford 2 g of the title compound as a white solid. LCMS (M+H)⁺ 290.

Step 3: 2-chloro-6-[4-[4-[6-(cyclopentoxy)-3-pyridyl]-1-methyl-6-oxo-3-pyridyl]pyrazol-1-yl]benzonitrile

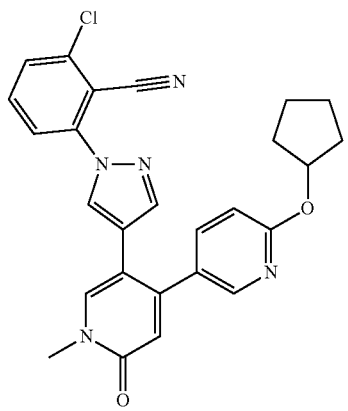

A mixture of 2-chloro-6-[4-(4-chloro-1-methyl-6-oxo-3-pyridyl)pyrazol-1-yl]benzonitrile (120 mg, 0.35 mmol), the title compound from Step 2 (302 mg, 1.04 mmol), Na₂CO₃ (110.6 mg, 1.04 mmol), Pd(PPh₃)₄ (80.3 mg, 0.07 mmol), water (3 mL) and 1,4-dioxane (15 mL) under N₂ atmosphere was stirred at 80° C. for 2 h. The reaction mixture was diluted with water and extracted with ethyl acetate. The organic layer was washed with brine, dried over sodium sulfate and concentrated under reduced pressure. The crude product was purified by preparative-HPLC to afford the title compound as a white solid (30 mg, 18%). 1H NMR (CD3OD, 300 MHz) δ 9.14 (s, 1H), 8.05 (s, 1H), 7.75 (s, 1H), 7.68 (s, 1H), 7.62 (s, 1H), 7.60 (s, 1H), 7.51 (s, 1H), 7.48 (s, 1H), 6.73 (s, 1H), 6.58 (s, 1H), 5.36 (s, 1H), 3.70-3.66 (m, 3H), 2.02-1.96 (d, 2H), 1.79-1.78 (m, 3H), 1.64-1.28 (d, 2H). LCMS (M+H)+ 472.

Examples 353-365 in Table 26 were prepared using the appropriate pyridine boronic acid pinacol ester and substituted benzonitrile in a similar multi-step manner as Example 352.

TABLE 26

| Example | Structure | IUPAC Name | ¹H NMR (ppm) | MS (M + H) |
|---|---|---|---|---|
| 353 | 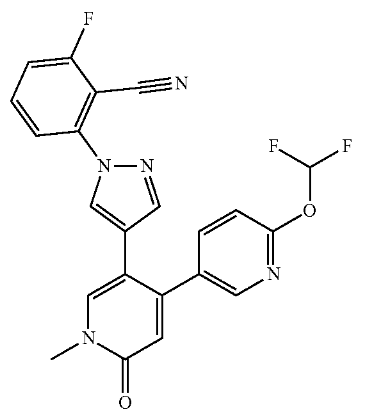 [SMILES: Cn1cc(-c2cnn(-c3cccc(F)c3C#N)c2)c(-c2ccc(OC(F)F)nc2)cc1=O] | 2-(4-(6-(difluoromethoxy)-1'-methyl-6'-oxo-1',6'-dihydro-[3,4'-bipyridin]-3'-yl)-1H-pyrazol-1-yl)-6-fluorobenzonitrile | (CD₃OD, 300 MHz) δ 8.23-8.15 (m, 1H), 8.05 (d, J = 0.7 Hz, 1H), 7.95 (s, 1H), 7.88-7.52 (m, 5H), 7.49-7.35 (m, 1H), 7.04-6.94 (m, 1H), 6.63 (s, 1H), 3.70 (s, 3H) | 438 |
| 354 | 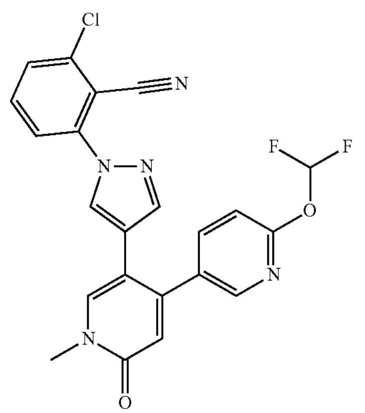 | 2-chloro-6-(4-(6-(difluoromethoxy)-1'-methyl-6'-oxo-1',6'-dihydro-[3,4'-bipyridin]-3'-yl)-1H-pyrazol-1-yl)benzonitrile | (DMSO-d6, 400 MHz) 8.24-8.15 (m, 2H), 8.04 (s, 1H), 7.90-7.83 (m, 1H), 7.82-7.73 (m, 2H), 7.72-7.52 (m, 3H), 7.08 (d, J = 8.5 Hz, 1H), 6.51 (s, 1H), 3.54 (s, 3H). | 454 |
| 355 | 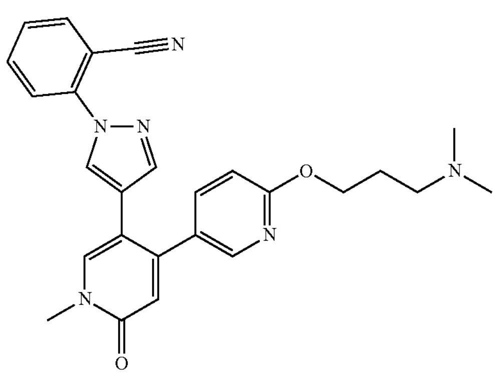 [SMILES: CN(C)CCCOc1ccc(-c2cc(=O)n(C)cc2-c2cnn(-c3ccccc3C#N)c2)cn1] | 2-(4-(6-(3-(dimethylamino)propoxy)-1'-methyl-6'-oxo-1',6'-dihydro-[3,4'-bipyridin]-3'-yl)-1H-pyrazol-1-yl)benzonitrile | 1H NMR (400 MHz, DMSO-d6) δ 8.16 (s, 2 H), 8.07-8.10 (m, 1 H), 7.96-8.01 (m, 1 H), 7.67-7.88 (m, 2 H), 7.53-7.60 (m, 1 H), 7.48-7.54 (m, 1 H), 7.42-7.46 (m, 1 H), 6.73-6.80 (m, 1 H), 6.42-6.45 (m, 1 H), 4.25-4.30 (m, 2 H), 3.49-3.54 (m, 3 H), 2.39-2,45 (m, 2 H), 2.19 (s, 6 H), 1.81-1.90 (m, 2 H) | 455 |

TABLE 26-continued

| Example | Structure | IUPAC Name | ¹H NMR (ppm) | MS (M + H) |
|---|---|---|---|---|
| 356 | 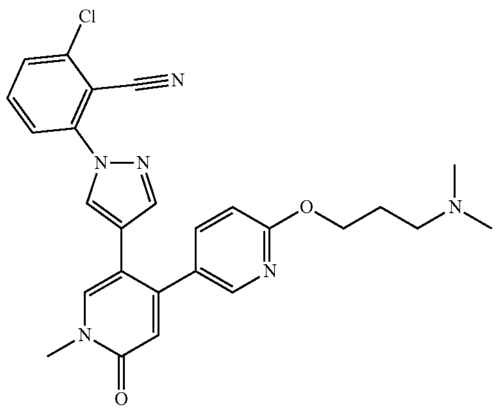 [SMILES: CN(C)CCCOc1ccc(-c2cc(=O)n(C)cc2-c2cnn(-c3cccc(Cl)c3C#N)c2)cn1] | 2-chloro-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile | ¹H NMR (DMSO, 400 MHz) 8.18 (s, 1H), 8.08 (d, J = 2.5 Hz, 1H), 7.98 (s, 1H), 7.85 (t, J = 8.1 Hz, 1H), 7.77 (d, J = 8.1 Hz, 1H), 7.66 (d, J = 8.2 Hz, 1H), 7.51 (d, J = 8.3 Hz, 2H), 6.75 (d, J = 8.6 Hz, 1H), 6.44 (s, 1H), 4.27 (t, J = 6.6 Hz, 2H), 3.51 (s, 3H), 2.31 (t, J = 7.1 Hz, 2H), 2.11 (s, 6H), 1.87-1.76 (m, J = 6.9 Hz, 2H). | 489 |
| 357 | 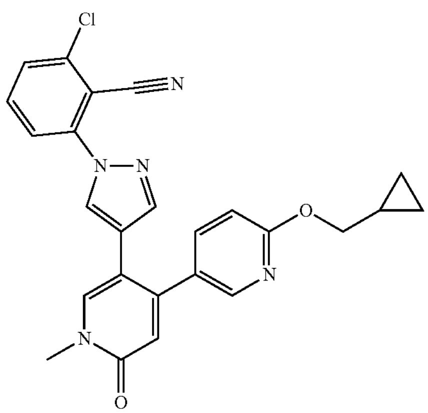 | 2-chloro-6-[4-[4-[6-(cyclopropylmethoxy)-3-pyridyl]-1-methyl-6-oxo-3-pyridyl]pyrazol-1-yl]benzonitrile | (CD₃OD, 400 MHz) δ 8.10-8.02 (m, 2H), 7.91 (s, 1H), 7.78 (t, J = 8.2 Hz, 1H), 7.67 (ddd, J = 23.2, 8.2, 1.1 Hz, 2H), 7.56 (dd, J = 8.6, 2.5 Hz, 1H), 7.49 (d, J = 0.7 Hz, 1H), 6.79 (dd, J = 8.6, 0.8 Hz, 1H), 6.61 (s, 1H), 4.14 (d, J = 7.1 Hz, 2H), 3.69 (s, 3H), 1.29 (t, J = 7.6 Hz, 0H), 0.65-0.55 (m, 2H), 0.35 (q, J = 4.7 Hz, 2H). | 458 |
| 358 | 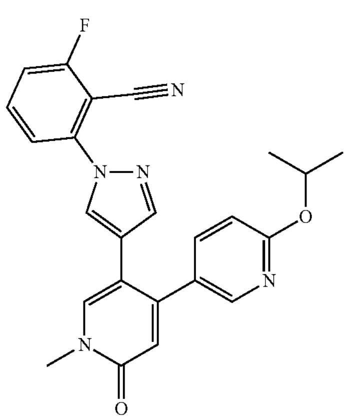 | 2-fluoro-6-[4-[4-[6-isopropoxy-3-pyridyl]-1-methyl-6-oxo-3-pyridyl]pyrazol-1-yl]benzonitrile | (CD₃OD, 400 MHz) δ 8.14-8.04 (m, 2H), 7.94 (s, 1H), 7.83 (d, 1H), 7.64 (d, 1H), 7.60-7.51 (m, 2H), 7.40 (d, 1H), 6.85 (d, 1H), 6.62 (s, 1H), 5.25 (m, 1H), 3.69 (s, 3H), 1.36 (d, 6H). | 430 |

TABLE 26-continued

| Example | Structure | IUPAC Name | ¹H NMR (ppm) | MS (M + H) |
|---|---|---|---|---|
| 359 | 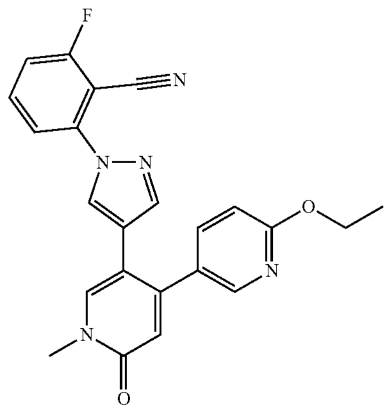 [SMILES: CCOc1ccc(-c2cc(=O)n(C)cc2-c2cnn(-c3cccc(F)c3C#N)c2)cn1] | 2-(4-(6-ethoxy-1'-methyl-6'-oxo-1',6'-dihydro-[3,4'-bipyridin]-3'-yl)-1H-pyrazol-1-yl)-6-fluorobenzonitrile | (CD₃OD, 400 MHz) δ 8.11 (d, J = 2.5 Hz, 1H), 8.05 (s, 1H), 7.92 (s, 1H), 7.85-7.78 (m, 1H), 7.69-7.63 (m, 1H), 7.58-7.50 (m, 2H), 7.42-7.34 (m, 1H), 6.89 (d, J = 8.7 Hz, 1H), 6.61 (s, 1H), 4.41-4.33 (m, 2H), 3.67 (s, 3H), 1.40 (t, J = 7.0 Hz, 3H). | 416 |
| 360 | 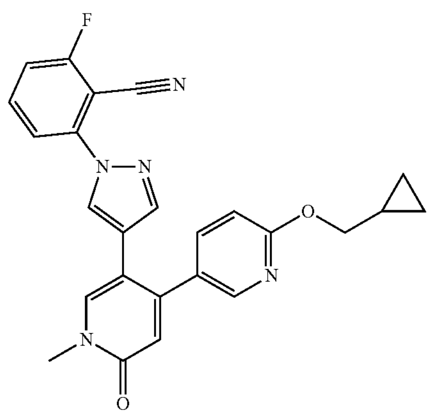 [SMILES: Cn1cc(-c2cnn(-c3cccc(F)c3C#N)c2)c(-c2ccc(OCC3CC3)nc2)cc1=O] | 2-[4-[4-[6-(cyclopropylmethoxy)-3-pyridyl]-1-methyl-6-oxo-3-pyridyl]pyrazol-1-yl]-6-fluoro-benzonitrile | (CD₃OD, 400 MHz) δ 8.12-8.03 (m, 2H), 7.92 (s, 1H), 7.88-7.73 (m, 1H), 7.62 (dd, J = 8.7, 2.5 Hz, 1H), 7.61-7.50 (m, 2H), 7.41 (t, J = 8.6 Hz, 1H), 6.89-6.79 (m, 1H), 6.62 (s, 1H), 4.16 (d, J = 7.1 Hz, 2H), 3.69 (s, 3H), 1.34-1.24 (m, 0H), 0.66-0.56 (m, 2H), 0.41-0.32 (m, 2H). | 442 |
| 361 | 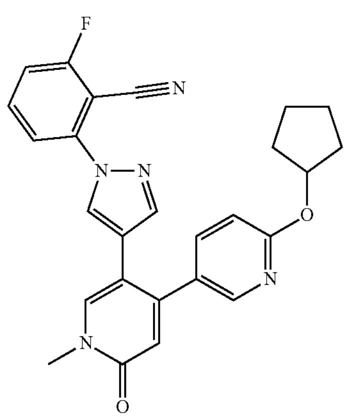 | 2-[4-[4-[6-(cyclopentoxy)-3-pyridyl]-1-methyl-6-oxo-3-pyridyl]pyrazol-1-yl]-6-fluoro-benzonitrile | (CD₃OD, 400 MHz) δ 8.08 (dd, J = 18.3, 1.5 Hz, 2H), 7.94 (s, 1H), 7.83 (td, J = 8.4, 6.1 Hz, 1H), 7.63 (dd, J = 8.7, 2.5 Hz, 1H), 7.60-7.52 (m, 2H), 7.41 (td, J = 8.7, 0.9 Hz, 1H), 6.84 (d, J = 8.7 Hz, 1H), 6.62 (s, 1H), 5.41-5.32 (m, 1H), 3.69 (s, 3H), 2.03-1.95 (m, 3H), 1.84 (d, J = 11.0 Hz, 5H), 1.68 (s, 3H). | 456 |

TABLE 26-continued

| Example | Structure | IUPAC Name | ¹H NMR (ppm) | MS (M + H) |
|---|---|---|---|---|
| 362 | 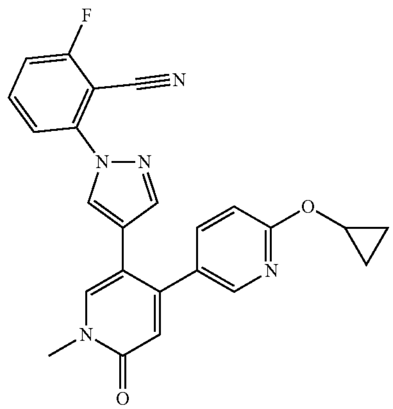 [SMILES: Cn1cc(-c2cnn(-c3cccc(F)c3C#N)c2)c(-c2ccc(OC3CC3)nc2)cc1=O] | 2-[4-[4-[6-(cyclopropoxy)-3-pyridyl]-1-methyl-6-oxo-3-pyridyl]pyrazol-1-yl]-6-fluoro-benzonitrile | (CD₃OD, 400 MHz) δ 8.15-8.05 (m, 2H), 7.93 (s, 1H), 7.84 (td, J = 8.5, 6.2 Hz, 1H), 7.65 (dd, J = 8.6, 2.5 Hz, 1H), 7.60-7.50 (m, 2H), 7.46-7.37 (m, 1H), 6.96 (dd, J = 8.7, 0.7 Hz, 1H), 6.62 (s, 1H), 4.22-4.12 (m, 1H), 3.69 (s, 3H), 0.86-0.73 (m, 4H). | 428 |
| 363 | 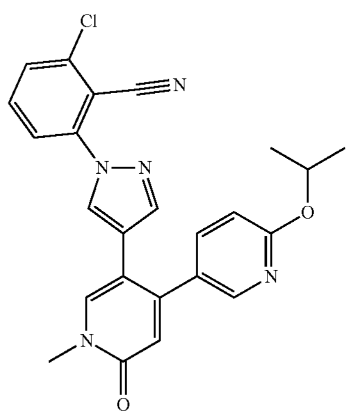 | 2-chloro-6-[4-[4-(6-isopropoxy-3-pyridyl)-1-methyl-6-oxo-3-pyridyl]pyrazol-1-yl]benzonitrile | (CD₃OD, 300 MHz) δ 8.13 (d, 1H), 8.04 (s, 1H), 7.93 (s, 1H), 7.78 (t, 1H), 7.74-7.60 (m, 3H), 7.55 (s, 1H), 6.90 (d, 1H), 6.63 (s, 1H), 5.24 (p, 1H), 3.69 (s, 3H), 1.38 (d, 6H) | 446 |
| 364 | 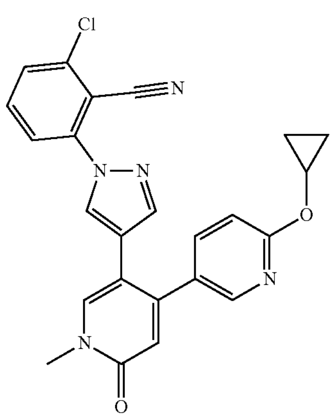 [SMILES: Cn1cc(-c2cnn(-c3cccc(Cl)c3C#N)c2)c(-c2ccc(OC3CC3)nc2)cc1=O] | 2-chloro-6-[4-[4-[6-(cyclopropoxy)-3-pyridyl]-1-methyl-6-oxo-3-pyridyl]pyrazol-1-yl]benzonitrile | (CD₃OD, 400 MHz) δ 8.13 (dd, J = 2.5, 0.7 Hz, 1H), 8.05 (d, J = 0.8 Hz, 1H), 7.93 (s, 1H), 7.79 (t, J = 8.2 Hz, 1H), 7.74-7.62 (m, 3H), 7.53 (d, J = 0.6 Hz, 1H), 6.99 (dd, J = 8.7, 0.8 Hz, 1H), 6.63 (s, 1H), 4.23-4.13 (m, 1H), 3.69 (s, 3H), 2.05 (s, 0H), 0.89-0.72 (m, 4H). | 444 |

TABLE 26-continued

| Example | Structure | IUPAC Name | ¹H NMR (ppm) | MS (M + H) |
|---|---|---|---|---|
| 365 | 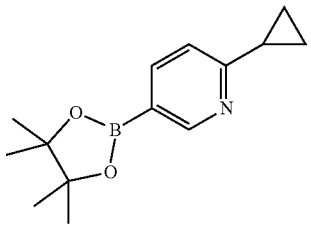 [SMILES: CC1(C)OB(c2ccc(C3CC3)nc2)OC1(C)C] | 2-chloro-6-(4-(6-ethoxy-1'-methyl-6'-oxo-1',6'-dihydro-[3,4'-bipyridin]-3'-yl)-1H-pyrazol-1-yl)benzonitrile | (DMSO, 400 MHz) δ 8.19 (s, 1H), 8.09 (d, J = 2.5 Hz, 1H), 7.98 (s, 1H), 7.85 (t, J = 8.2 Hz, 1H), 7.77 (d, J = 8.2, 1H), 7.67 (d, J = 8.2, 1H), 7.55-7.47 (m, 2H), 6.75 (d, J = 8.6 Hz, 1H), 6.45 (s, 1H), 4.31 (q, J = 7.0 Hz, 2H), 3.53 (s, 3H), 1.31 (t, J = 7.0 Hz, 3H). | 432 |

Example 366: 2-chloro-6-[4-[4-(6-cyclopropyl-3-pyridyl)-1-ethyl-6-oxo-3-pyridyl]pyrazol-1-yl]benzonitrile Step 1: 2-Cyclopropyl-5-(4,4,5,5-tetramethyl-1,3,2-dioxaborolan-2-yl)pyridine To a stirred solution of 5-bromo-2-cyclopropyl-pyridine (1 g) in 1,4-dioxane (20 mL) was added 4,4,5,5-tetramethyl-2-(4,4,5,5-tetramethyl-1,3,2-dioxaborolan-2-yl)-1,3,2-dioxaborolane (2.5 g), Pd(dppf)Cl₂ (27 mg) and potassium acetate (1.3 g) under nitrogen. The resulting mixture was subsequently degassed three times and stirred at 80° C. for 2 hours. The solvent was evaporated under reduced pressure. The crude title compound (800 mg, 65%) was used in the next step without further purification. LCMS (M+H)⁺ 246.

Step 2: 2-chloro-6-[4-[4-(6-cyclopropyl-3-pyridyl)-1-methyl-6-oxo-3-pyridyl]pyrazol-1-yl]benzonitrile

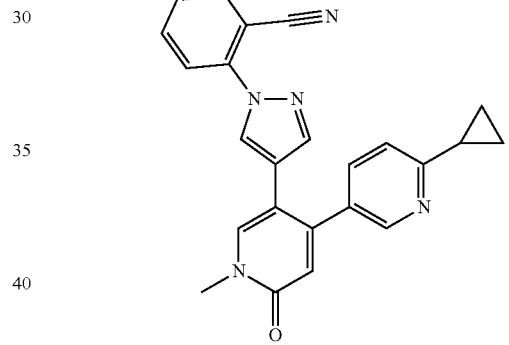

To a stirred solution of 2-chloro-6-[4-(4-chloro-1-methyl-6-oxo-3-pyridyl)pyrazol-1-yl]benzonitrile (120 mg, 0.35 mmol) in 1,4-dioxane (10 mL) was added the title compound from Step 1 (128 mg, 0.52 mmol) and saturated Na₂CO₃ aqueous solution (2 mL) under nitrogen. Pd(PPh₃)₄ (80 mg, 0.07 mmol) was then added to the above mixture. The resulting mixture was subsequently degassed three times and stirred at 80° C. for 2 hours. The reaction mixture was diluted with water and extracted with ethyl acetate. The combined organic layers were washed with brine, dried over sodium sulfate and concentrated under reduced pressure. The crude product was purified by preparative-HPLC to afford the title compound (24 mg, 16% yield) as a yellow solid. ¹H NMR (300 MHz, DMSO-D6) δ 8.37 (s, 1H), 8.16 (s, 1H) 8.01 (s, 1H), 7.88-7.76 (m, 2H), 7.63 (t, J=9.0 Hz, 2H), 7.49 (s, 1H), 7.33 (d, J=4.2 Hz, 1H), 6.48 (s, 1H), 3.53 (s, 3H), 2.20-2.12 (m, 1H), 1.07-0.94 (m, 4H). LCMS (M+H)⁺ 428.

Examples 367-379 in Table 27 were prepared using the appropriate pyridine boronic acid pinacol ester and substituted benzonitrile in a similar multi-step manner as Example 366.

TABLE 27

| Example | Structure | IUPAC Name | ¹H NMR (ppm) | MS (M + H) |
|---|---|---|---|---|
| 367 | 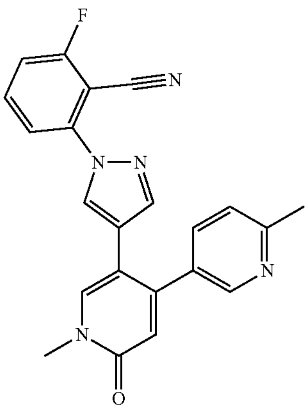 [SMILES: Cc1ccc(-c2cc(=O)n(C)cc2-c2cnn(-c3cccc(F)c3C#N)c2)cn1] | 2-(4-(1',6-dimethyl-6'-oxo-1',6'-dihydro-[3,4'-bipyridin]-3'-yl)-1H-pyrazol-1-yl)-6-fluorobenzonitrile | (DMSO, 300 MHz) δ 8.40 (s, 1H), 8.25 (s, 1H), 8.05 (s, 1H), 7.99-7.84 (m, 1H), 7.73-7.38 (m, 5H), 7.32 (d, J = 7.8 Hz, 1H), 6.48 (s, 1H), 3.53 (d, J = 6.9 Hz, 4H) | 386 |
| 368 | 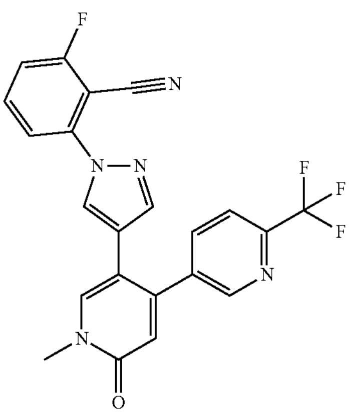 [SMILES: Cn1cc(-c2cnn(-c3cccc(F)c3C#N)c2)c(-c2ccc(C(F)(F)F)nc2)cc1=O] | 2-fluoro-6-(4-(1'-methyl-6'-oxo-6-(trifluoromethyl)-1',6'-dihydro-[3,4'-bipyridin]-3'-yl)-1H-pyrazol-1-yl)benzonitrile | (CD₃OD, 300 MHz) δ 8.69-8.61 (m, 1H), 8.26-8.04 (m, 1H), 8.04-7.88 (m, 2H), 7.88-7.75 (m, 2H), 7.73-7.57 (m, 1H), 7.58-7.46 (m, 2H), 7.46-7.35 (m, 1H), 6.76 (d, J = 38.0 Hz, 1H), 3.70 (d, J = 7.4 Hz, 3H) | 440 |
| 369 | 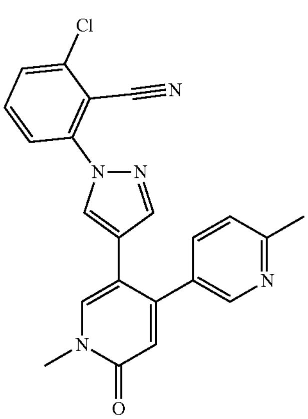 | 2-chloro-6-(4-(1',6-dimethyl-6'-oxo-1',6'-dihydro-[3,4'-bipyridin]-3'-yl)-1H-pyrazol-1-yl)benzonitrile | (DMSO-d6, 300 MHz) 8.36 (d, J = 2.4 Hz, 1H), 8.19 (s, 1H), 8.03 (s, 1H), 7.87 (t, J = 8.1 Hz, 1H), 7.79 (dd, J = 8.2, 1.2 Hz, 1H), 7.67 (dd, J = 8.1, 1.2 Hz, 1H), 7.56 (dd, J = 8.0, 2.4 Hz, 1H), 7.46 (s, 1H), 7.27 (d, J = 8.0 Hz, 1H), 6.47 (s, 1H), 3.54 (s, 3H), 2.49 (s, 4H). | 402 |

TABLE 27-continued

| Example | Structure | IUPAC Name | ¹H NMR (ppm) | MS (M + H) |
|---|---|---|---|---|
| 370 | 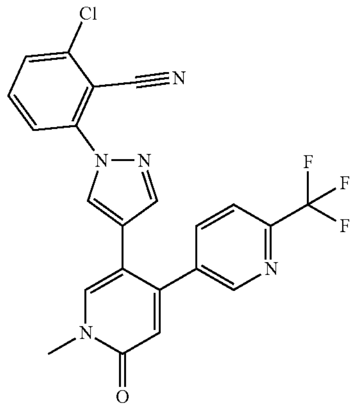 [SMILES: Cn1cc(-c2cnn(-c3cccc(Cl)c3C#N)c2)c(-c2ccc(C(F)(F)F)nc2)cc1=O] | 2-chloro-6-(4-(1'-methyl-6'-oxo-6-(trifluoromethyl)-1',6'-dihydro-[3,4'-bipyridin]-3'-yl)-1H-pyrazol-1-yl)benzonitrile | (DMSO-$d_6$, 400 MHz) 8.68 (d, J = 2.0 Hz, 1H), 8.18 (s, 1H), 8.08 (s, 1H), 7.96 (dd, J = 8.1, 2.1 Hz, 1H), 7.92-7.82 (m, 2H), 7.78 (dd, J = 8.2, 1.1 Hz, 1H), 7.65 (dd, J = 8.1, 1.1 Hz, 1H), 7.58 (s, 1H), 6.60 (s, 1H), 3.56 (s, 3H). | 456 |
| 371 | 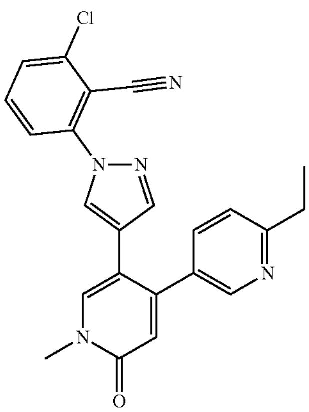 [SMILES: CCc1ccc(-c2cc(=O)n(C)cc2-c2cnn(-c3cccc(Cl)c3C#N)c2)cn1] | 2-chloro-6-(4-(6-ethyl-1'-methyl-6'-oxo-1',6'-dihydro-[3,4'-bipyridin]-3'-yl)-1H-pyrazol-1-yl)benzonitrile | (DMSO-d6, 400 MHz) 8.59 (d, J = 2.1 Hz, 1H), 8.15 (s, 1H), 8.08 (s, 1H), 7.92-7.82 (m, 2H), 7.82-7.75 (m, 1H), 7.66 (d, J = 8.2 Hz, 1H), 7.62-7.52 (m, 2H), 6.56 (s, 1H), 3.56 (s, 3H), 2.94-2.83 (m, 2H), 1.27 (t, J = 7.5 Hz, 3H). | 416 |
| 372 | 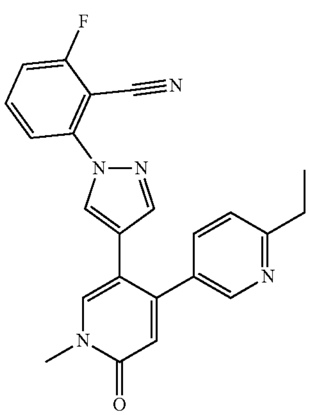 [SMILES: CCc1ccc(-c2cc(=O)n(C)cc2-c2cnn(-c3cccc(F)c3C#N)c2)cn1] | 2-(4-(6-ethyl-1'-methyl-6'-oxo-1',6'-dihydro-[3,4'-bipyridin]-3'-yl)-1H-pyrazol-1-yl)-6-fluorobenzonitrile | (DMSO, 400 MHz) δ 8.64 (d, J = 2.1 Hz, 1H), 8.22 (s, 1H), 8.10 (s, 1H), 8.00-7.86 (m, 2H), 7.66-7.50 (m, 4H), 6.58 (s, 1H), 3.56 (s, 3H), 2.97-2.86 (m, 2H), 1.28 (t, J = 7.6 Hz, 3H) | 400 |
| 373 | 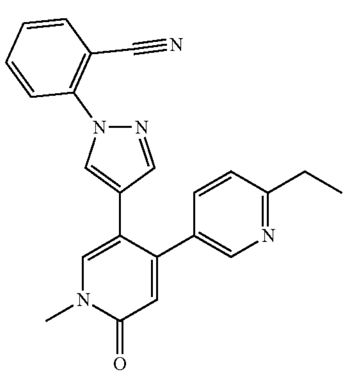 [SMILES: CCc1ccc(-c2cc(=O)n(C)cc2-c2cnn(-c3ccccc3C#N)c2)cn1] | 2-(4-(6-ethyl-1'-methyl-6'-oxo-1',6'-dihydro-[3,4'-bipyridin]-3'-yl)-1H-pyrazol-1-yl)benzonitrile | (DMSO-d6, 400 MHz) δ 8.61 (s, 1H), 8.10 (d, J = 15.4 Hz, 2H), 7.99 (dd, J = 7.8, 1.4 Hz, 1H), 7.96-7.80 (m, 2H), 7.68 (d, J = 8.2 Hz, 1H), 7.62-7.54 (m, 3H), 6.57 (s, 1H), 2.90 (q, J = 7.6 Hz, 2H), 1.28 (t, J = 7.6 Hz, 3H). | 382 |

TABLE 27-continued

| Example | Structure | IUPAC Name | ¹H NMR (ppm) | MS (M + H) |
|---|---|---|---|---|
| 374 | 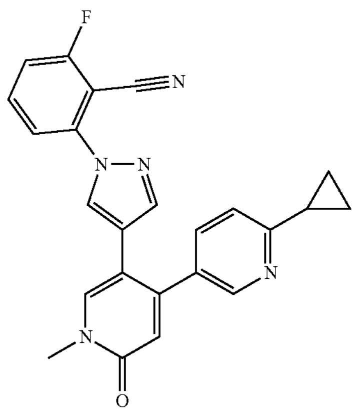 [SMILES: Cn1cc(-c2cnn(-c3cccc(F)c3C#N)c2)c(-c2ccc(C3CC3)nc2)cc1=O] | 2-[4-[4-(6-cyclopropyl-3-pyridyl)-1-methyl-6-oxo-3-pyridyl]pyrazol-1-yl]-6-fluoro-benzonitrile | (DMSO, 300 MHz) δ 8.40 (d, J = 1.8 Hz, 1H), 8.22 (s, 1H), 8.03 (s, 1H), 7.94-7.86 (m, 1H), 7.67-7.63 (m, 1H), 7.58-7.49 (m, 3H), 7.35 (d, J = 8.1 Hz, 1H), 6.49 (s, 1H), 3.53 (s, 3H), 2.22-2.13 (m, 1H), 1.08-1.00 (m, 4H). | 412 |
| 375 | 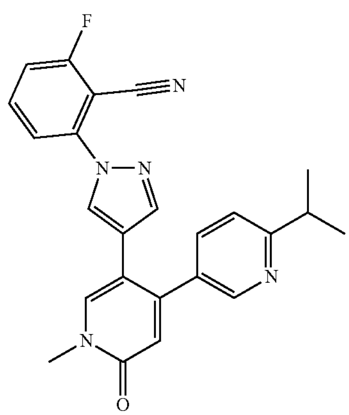 [SMILES: CC(C)c1ccc(-c2cc(=O)n(C)cc2-c2cnn(-c3cccc(F)c3C#N)c2)cn1] | 2-fluoro-6-[4-[4-(6-isopropyl-3-pyridyl)-1-methyl-6-oxo-3-pyridyl]pyrazol-1-yl]benzonitrile | (DMSO, 300 MHz) δ 8.70 (s, 1H), 8.50 (d, J = 1.8 Hz, 2H), 8.45 (s, 1H), 7.92-7.85 (m, 1H), 7.77 (d, J = 3.2 Hz, 1H), 7.56-7.45 (m, 4H), 6.53 (s, 1H), 3.54 (s, 3H), 1.26 (d, J = 6.9 Hz, 6H) | 414 |
| 376 | 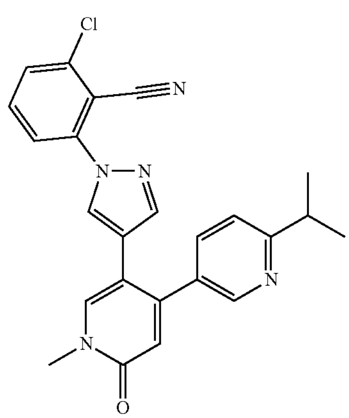 [SMILES: CC(C)c1ccc(-c2cc(=O)n(C)cc2-c2cnn(-c3cccc(Cl)c3C#N)c2)cn1] | 2-chloro-6-[4-[4-(6-isopropyl-3-pyridyl)-1-methyl-6-oxo-3-pyridyl]pyrazol-1-yl]benzonitrile | (DMSO, 300 MHz) δ 8.50 (d, J = 1.8 Hz, 1H), 8.06 (d, J = 8.1 Hz, 2H), 7.86-7.75 (m, 3H), 7.62-7.55 (m, 2H), 7.46 (d, J = 8.4 Hz, 1H), 6.55 (s, 1H), 3.54 (s, 3H), 3.16-3.06 (m, 1H), 1.26 (d, J = 6.9 Hz, 6H). | 430 |

TABLE 27-continued

| Example | Structure | IUPAC Name | ¹H NMR (ppm) | MS (M + H) |
|---|---|---|---|---|
| 377 | 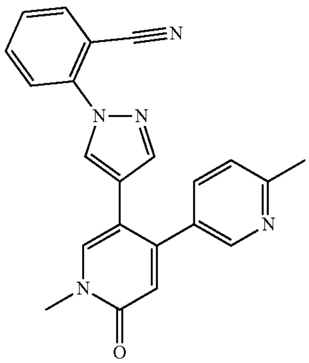 [SMILES: Cc1ccc(-c2cc(=O)n(C)cc2-c2cnn(-c3ccccc3C#N)c2)cn1] | 2-(4-(1',6-dimethyl-6'-oxo-1',6'-dihydro-[3,4'-bipyridin]-3'-yl)-1H-pyrazol-1-yl)benzonitrile | (DMSO-d6, 400 MHz) δ 8.66 (d, J = 2.2 Hz, 1H), 8.15 (s, 1H), 8.09 (s, 1H), 7.99 (ddd, J = 8.0, 6.0, 1.9 Hz, 2H), 7.86 (td, J = 8.0, 7.6, 1.5 Hz, 1H), 7.71 (dd, J = 8.4, 1.1 Hz, 1H), 7.67-7.54 (m, 3H), 6.58 (s, 1H), 2.67 (d, J = 12.4 Hz, 0H), 2.63 (s, 3H). | 368 |
| 378 | 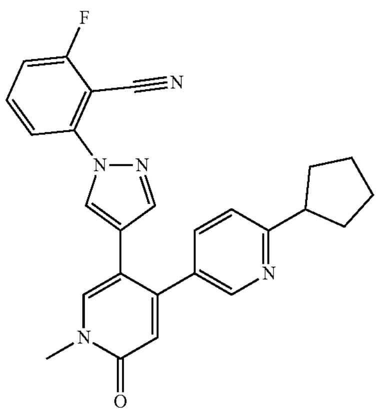 | 2-(4-(6-cyclopentyl-1'-methyl-6'-oxo-1',6'-dihydro-[3,4'-bipyridin]-3'-yl)-1H-pyrazol-1-yl)-6-fluorobenzonitrile | (DMSO-d$_6$, 300 MHz,) δ 8.35 (d, J = 2.3 Hz, 1H), 8.11 (s, 1H), 8.00 (s, 1H), 7.86 (td, J = 8.4, 6.4 Hz, 1H), 7.58-7.41 (m, 4H), 7.25 (d, J = 8.1 Hz, 1H), 6.44 (s, 1H), 3.51 (s, 3H), 3.16 (t, J = 7.8 Hz, 1H), 2.05 (s, 0H), 1.97 (d, J = 7.7 Hz, 2H), 1.80-1.55 (m, 6H). | 440 |
| 379 | 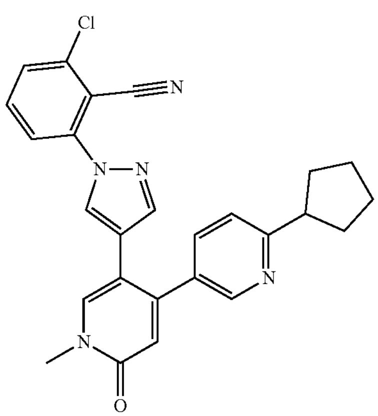 [SMILES: Cn1cc(-c2cnn(-c3cccc(F)c3C#N)c2)c(-c2ccc(C3CCCC3)nc2)cc1=O] | 2-chloro-6-(4-(6-cyclopentyl-1'-methyl-6'-oxo-1',6'-dihydro-[3,4'-bipyridin]-3'-yl)-1H-pyrazol-1-yl)benzonitrile | (DMSO-d$_6$, 400 MHz) δ 8.51 (d, J = 2.2 Hz, 1H), 8.07 (d, J = 15.8 Hz, 2H), 7.84 (t, J = 8.1 Hz, 1H), 7.80-7.73 (m, 2H), 7.62 (dd, J = 8.2, 1.2 Hz, 1H), 7.56 (s, 1H), 7.48 (d, J = 8.2 Hz, 1H), 6.53 (s, 1H), 3.55 (s, 3H), 3.26 (p, J = 8.1 Hz, 1H), 2.04 (t, J = 9.4 Hz, 2H), 1.84-1.48 (m, 6H). | 456 |

Example 380: 2-cyclopropyl-6-[4-[1-methyl-4-(1-methyl-2-oxo-4-pyridyl)-6-oxo-3-pyridyl]pyrazol-1-yl]benzonitrile Step 1: 2-cyclopropyl-6-fluorobenzonitrile

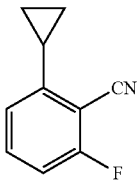 [SMILES: N#Cc1c(F)cccc1C1CC1]

To a stirred solution of 2-bromo-6-fluoro-benzonitrile (5 g, 25 mmol) in 1,4-dioxane (150 mL) under N₂ was sequentially added 2-cyclopropyl-4,4,5,5-tetramethyl-1,3,2-dioxaborolane (6.3 g, 37.5 mmol), Na₂CO₃ (7.95 g, 75 mmol) as a solution in water (40 mL) and Pd(dppf)Cl₂·DCM (2.04 g, 2.5 mmol). The reaction was stirred at 80° C. overnight. 1,4-Dioxane was removed under reduced pressure. The resulting mixture was diluted with water and extracted with EtOAc. The combined organic layers were washed with brine, concentrated and purified by silica gel column chromatography (PE/EA=20/1) to afford the title compound as an off-white solid (3.06 g, 76%).

Step 2: 2-cyclopropyl-6-(4-(4,4,5,5-tetramethyl-1,3,2-dioxaborolan-2-yl)-1H-pyrazol-1-yl)benzonitrile

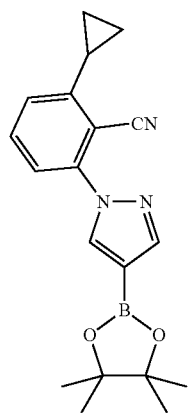 [SMILES: CC1(C)OB(c2cnn(-c3cccc(C4CC4)c3C#N)c2)OC1(C)C]

To a stirred solution of 4-(4,4,5,5-tetramethyl-1,3,2-dioxaborolan-2-yl)-1H-pyrazole (1 g, 5.15 mmol) in DMF (10 mL) at 0° C. was added NaH (310 mg, 12.9 mmol) in portions under N₂. The resulting mixture was stirred for 20 min. A solution of the title compound from Step 1 (1 g, 6.2 mmol) in DMF was added. The resulting mixture was stirred at 0° C. for 30 min and at 30° C. for 3 h. The reaction was quenched by addition of water and extracted with EtOAc. The combined organic layers were washed with brine, dried over sodium sulfate, filtered and concentrated under reduced pressure to afford the title compound (1.3 g) as a yellow oil which was used in the following step without further purification. LCMS (M+H)⁺ 336.

Step 3: 2-(4-(4-chloro-1-methyl-6-oxo-1,6-dihydropyridin-3-yl)-1H-pyrazol-1-yl)-6-cyclopropylbenzonitrile

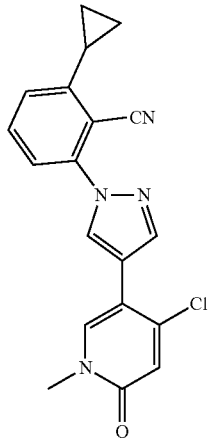 [SMILES: Cn1cc(-c2cnn(-c3cccc(C4CC4)c3C#N)c2)c(Cl)cc1=O]

To a stirred solution of the title compound from Step 2 (3 g, 8.95 mmol) in 1,4-dioxane (60 mL) under N₂ was added 5-bromo-4-chloro-1-methyl-pyridin-2-one (1.99 g, 8.95 mmol), a solution of K₃PO₄ (4.74 g, 22.37 mmol) in water (12 mL) and Pd(dppf)Cl₂ (1.3 g, 1.79 mmol). The reaction was warmed to 80° C. for 3 h. The mixture was cooled to room temperature, quenched with water and extracted with EtOAc. The combined organic layers were washed with brine, concentrated and purified by silica gel column chromatography (EtOAc) to afford the title compound as a yellow solid (1.5 g). LCMS (M+H)⁺ 351.

Step 4: 2-cyclopropyl-6-[4-[1-methyl-4-(1-methyl-2-oxo-4-pyridyl)-6-oxo-3-pyridyl]pyrazol-1-yl]benzonitrile

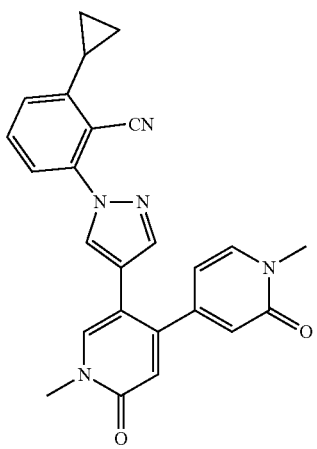 [SMILES: Cn1ccc(-c2cc(=O)n(C)cc2-c2cnn(-c3cccc(C4CC4)c3C#N)c2)cc1=O]

The title compound was prepared in a manner similar to Example 305, Step 2, by substituting the title compound from Step 3 for 3-(4-(4-chloro-1-methyl-6-oxo-1,6-dihydropyridin-3-yl)-1H-pyrazol-1-yl)-4-methoxybenzonitrile. ¹H NMR (CD₃OD, 400 MHz) δ 8.02 (d, J=0.7 Hz, 1H), 7.94 (s, 1H), 7.74-7.59 (m, 2H), 7.47 (dd, J=8.1, 1.1 Hz, 1H), 7.18-7.11 (m, 1H), 6.62-6.52 (m, 2H), 6.22 (dd, J=6.9, 1.9 Hz, 1H), 3.69 (s, 3H), 3.57 (s, 3H), 2.39-2.27 (m, 1H), 1.27-1.17 (m, 2H), 0.95-0.86 (m, 2H). LCMS (M+H)+ 424.

Examples 381-391 in Table 28 were prepared using the appropriate boronic acid derivative in Step 4 in a similar multi-step manner as Example 380.

TABLE 28

| Example | Structure | IUPAC Name | ¹H NMR (ppm) | MS (M + H) |
|---|---|---|---|---|
| 381 | 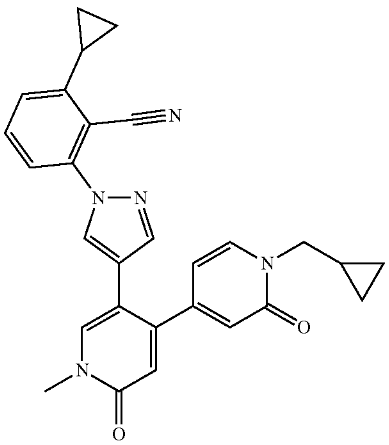 [SMILES: Cn1cc(-c2cnn(-c3cccc(C4CC4)c3C#N)c2)c(-c2ccn(CC3CC3)c(=O)c2)cc1=O] | 2-cyclopropyl-6-[4-[4-[1-(cyclopropylmethyl)-2-oxo-4-pyridyl]-1-methyl-6-oxo-3-pyridyl]pyrazol-1-yl]benzonitrile | (CD₃OD, 400 MHz) δ 8.00 (d, J = 0.7 Hz, 1H), 7.94 (s, 1H), 7.72-7.62 (m, 3H), 7.44 (dd, J = 8.1, 1.0 Hz, 1H), 7.14 (d, J = 8.0 Hz, 1H), 6.63-6.53 (m, 2H), 6.21 (dd, J = 6.9, 2.0 Hz, 1H), 3.85 (d, J = 7.2 Hz, 2H), 3.69 (s, 3H), 2.39-2.27 (m, 1H), 1.22-0.89 (m, 3H), 0.61-0.50 (m, 2H), 0.50-0.37 (m, 2H). | 464 |
| 382 | 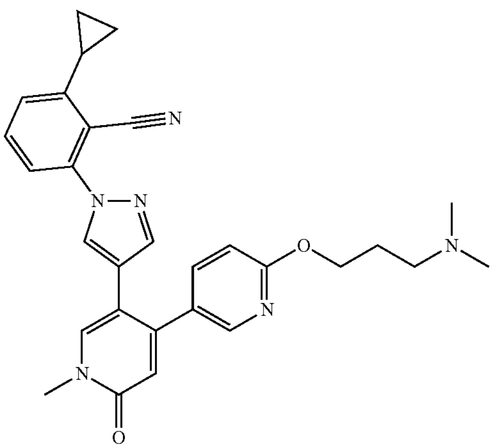 [SMILES: CN(C)CCCOc1ccc(-c2cc(=O)n(C)cc2-c2cnn(-c3cccc(C4CC4)c3C#N)c2)cn1] | 2-cyclopropyl-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile | (DMSO, 400 MHz) δ 8.05-7.99 (m, 2H), 7.90 (s, 1H), 7.66 (t, J = 8.0 Hz, 1H), 7.57-7.50 (m, 1H), 7.36 (t, J = 11.5 Hz, 2H), 7.09 (d, J = 8.0 Hz, 1H), 6.78 (d, J = 8.6 Hz, 1H), 6.46 (s, 1H), 4.29 (t, J = 6.1 Hz, 2H), 3.52 (s, 3H), 3.22-3.13 (m, 2H), 2.77 (s, 6H), 2.24-2.14 (m, 1H), 2.13-2.02 (m, 2H), 1.19-1.07 (m, 2H), 0.87-0.80 (m, 2H) | 495 |
| 383 | 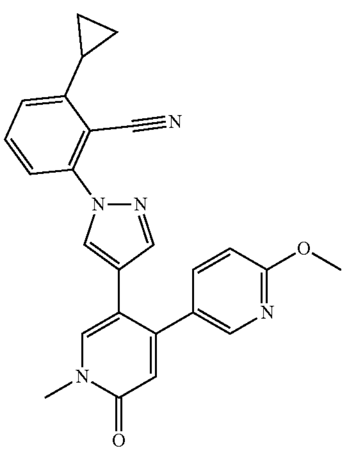 [SMILES: COc1ccc(-c2cc(=O)n(C)cc2-c2cnn(-c3cccc(C4CC4)c3C#N)c2)cn1] | 2-cyclopropyl-6-(4-(6-methoxy-1'-methyl-6'-oxo-1',6'-dihydro-[3,4'-bipyridin]-3'-yl)-1H-pyrazol-1-yl)benzonitrile | (DMSO, 400 MHz) δ 8.13 (s, J = 2.6, 1H), 8.07 (d, J = 0.7 Hz, 1H), 7.99 (s, 1H), 7.70 (t, J = 8.0 Hz, 1H), 7.55-7.49 (m, 1H), 7.46 (d, J = 0.7 Hz, 1H), 7.41 (d, J = 8.1, 1H), 7.14 (d, J = 8.0 Hz, 1H), 6.79 (d, J = 8.6 Hz, 1H), 6.45 (s, 1H), 3.87 (s, 3H), 3.53 (s, 3H), 2.32-2.20 (m, 1H), 1.27-1.13 (m, 2H), 0.94-0.85 (m, 2H). | 424 |

TABLE 28-continued

| Example | Structure | IUPAC Name | ¹H NMR (ppm) | MS (M + H) |
|---|---|---|---|---|
| 384 | 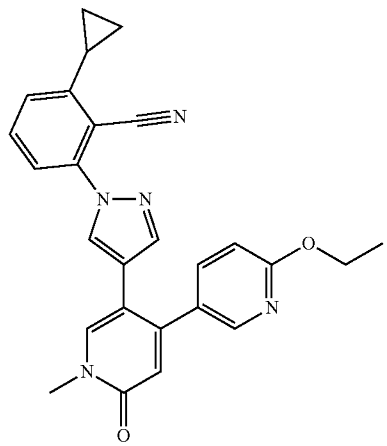 [SMILES: CCOc1ccc(-c2cc(=O)n(C)cc2-c2cnn(-c3cccc(C4CC4)c3C#N)c2)cn1] | 2-cyclopropyl-6-(4-(6-ethoxy-1'-methyl-6'-oxo-1',6'-dihydro-[3,4'-bipyridin]-3'-yl)-1H-pyrazol-1-yl)benzonitrile | (CD₃OD, 400 MHz) δ 8.10 (d, J = 2.5 Hz, 1H), 7.94 (d, 2H), 7.68-7.58 (m, 2H), 7.46 (d, J = 0.7 Hz, 1H), 7.40-7.36 (m, 1H), 7.14-7.10 (m, 1H), 6.87-6.81 (m, 1H), 6.59 (s, 1H), 4.38-4.31 (m, 2H), 3.66 (s, 3H), 2.35-2.26 (m, 1H), 1.38 (t, J = 7.0 Hz, 3H), 1.23-1.16 (m, 2H), 0.91-0.85 (m, 2H). | 438 |
| 385 | 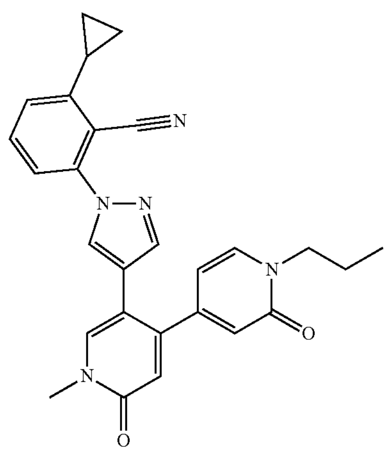 [SMILES: CCCn1ccc(-c2cc(=O)n(C)cc2-c2cnn(-c3cccc(C4CC4)c3C#N)c2)cc1=O] | 2-cyclopropyl-6-[4-[1-methyl-6-oxo-4-(2-oxo-1-propyl-4-pyridyl)-3-pyridyl]pyrazol-1-yl]benzonitrile | (CD₃OD, 400 MHz) δ 8.00 (s, 1H), 7.94 (s, 1H), 7.71-7.62 (m, 2H), 7.60 (d, J = 7.0 Hz, 1H), 7.47-7.40 (m, 1H), 7.15 (d, J = 8.0 Hz, 1H), 6.60 (s, 1H), 6.55 (d, J = 1.9 Hz, 1H), 6.25-6.18 (m, 1H), 4.01-3.92 (m, 2H), 3.69 (s, 3H), 2.39-2.27 (m, 1H), 1.85-1.71 (m, 2H), 1.27-1.17 (m, 2H), 0.99-0.86 (m, 5H). | 452 |
| 386 | 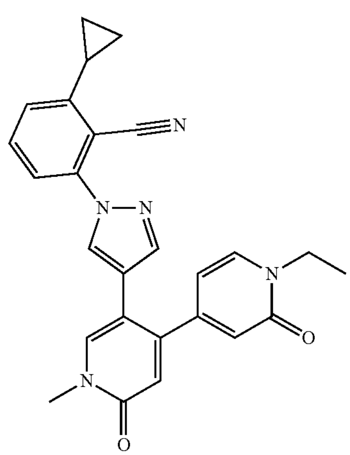 [SMILES: CCn1ccc(-c2cc(=O)n(C)cc2-c2cnn(-c3cccc(C4CC4)c3C#N)c2)cc1=O] | 2-cyclopropyl-6-[4-[4-(1-ethyl-2-oxo-4-pyridyl)-1-methyl-6-oxo-3-pyridyl]pyrazol-1-yl]benzonitrile | (CD₃OD, 400 MHz) δ 8.02 (s, 1H), 7.93 (s, 1H), 7.71-7.60 (m, 3H), 7.52-7.41 (m, 1H), 7.15 (d, J = 8.0 Hz, 1H), 6.62-6.52 (m, 2H), 6.27-6.19 (m, 1H), 4.09-3.99 (m, 2H), 3.69 (s, 3H), 2.39-2.27 (m, 1H), 1.40-1.31 (m, 3H), 1.27-1.17 (m, 2H), 0.98-0.86 (m, 2H). | 438 |

TABLE 28-continued

| Example | Structure | IUPAC Name | ¹H NMR (ppm) | MS (M + H) |
|---|---|---|---|---|
| 387 | 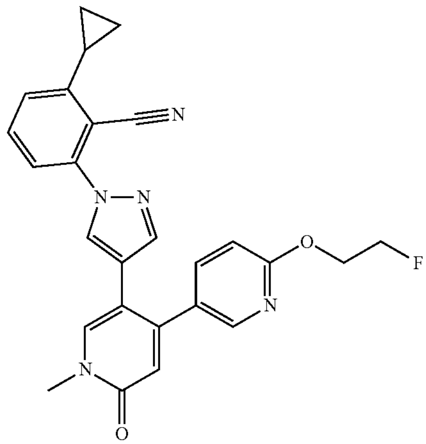 [SMILES: Cn1cc(-c2cnn(-c3cccc(C4CC4)c3C#N)c2)c(-c2ccc(OCCF)nc2)cc1=O] | 2-cyclopropyl-6-[4-[6-(2-fluoroethoxy)-3-pyridyl]-1-methyl-6-oxo-3-pyridyl]pyrazol-1-yl]benzonitrile | (CD₃OD, 400 MHz) δ 8.12 (d, J = 2.5 Hz, 1H), 7.98-7.90 (m, 2H), 7.67 (t, J = 8.1 Hz, 1H), 7.59 (dd, J = 8.6, 2.5 Hz, 1H), 7.47 (d, J = 0.7 Hz, 1H), 7.40 (dd, J = 8.0, 1.0 Hz, 1H), 7.16 (d, J = 7.8 Hz, 1H), 6.85 (d, J = 8.6 Hz, 1H), 6.62 (s, 1H), 4.83-4.76 (m, 1H), 4.71-4.64 (m, 1H), 4.64-4.57 (m, 1H), 4.57-4.50 (m, 1H), 3.69 (s, 3H), 2.41-2.29 (m, 1H), 1.28-1.18 (m, 2H), 0.92 (dt, J = 6.8, 4.7 Hz, 2H). | 456 |
| 388 | 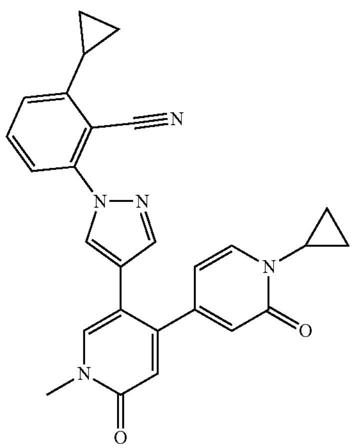 [SMILES: Cn1cc(-c2cnn(-c3cccc(C4CC4)c3C#N)c2)c(-c2ccn(C3CC3)c(=O)c2)cc1=O] | 2-cyclopropyl-6-(4-(1'-cyclopropyl-1-methyl-2',6-dioxo-1,1',2',6-tetrahydro-[4,4'-bipyridin]-3-yl)-1H-pyrazol-1-yl)benzonitrile | (CD₃OD, 400 MHz) δ 8.00 (s, 1H), 7.93 (s, 1H), 7.74-7.62 (m, 2H), 7.58 (d, J = 7.1 Hz, 1H), 7.46 (dd, J = 8.1, 1.0 Hz, 1H), 7.14 (d, J = 8.0 Hz, 1H), 6.58 (s, 1H), 6.53 (d, J = 1.9 Hz, 1H), 6.18 (dd, J = 7.1, 2.0 Hz, 1H), 3.68 (s, 3H), 3.40-3.29 (m, 1H), 2.38-2.26 (m, 1H), 1.28-1.17 (m, 2H), 1.20-1.05 (m, 2H), 1.01-0.86 (m, 4H). | 450 |
| 389 | 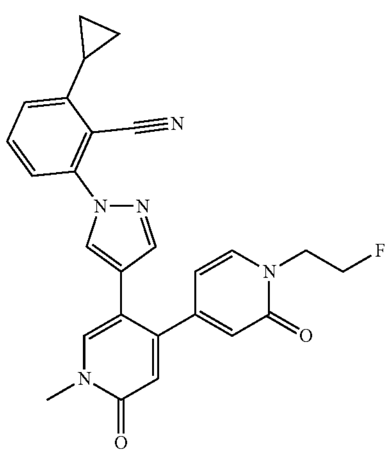 [SMILES: Cn1cc(-c2cnn(-c3cccc(C4CC4)c3C#N)c2)c(-c2ccn(CCF)c(=O)c2)cc1=O] | 2-cyclopropyl-6-[4-[4-[1-(2-fluoroethyl)-2-oxo-4-pyridyl]-1-methyl-6-oxo-3-pyridyl]pyrazol-1-yl]benzonitrile | (CD₃OD, 400 MHz) δ 7.99 (d, J = 0.7 Hz, 1H), 7.95 (s, 1H), 7.72 (d, J = 0.7 Hz, 1H), 7.70-7.61 (m, 1H), 7.59 (d, J = 7.0 Hz, 1H), 7.46-7.39 (m, 1H), 7.15 (d, J = 7.9 Hz, 1H), 6.61 (s, 1H), 6.57 (d, J = 1.9 Hz, 1H), 6.24-6.17 (m, 1H), 4.77 (s, 0H), 4.70-4.63 (m, 1H), 4.38-4.30 (m, 1H), 4.28 (t, J = 4.8 Hz, 1H), 3.69 (s, 3H), 2.39-2.27 (m, 1H), 1.27-1.17 (m, 2H), 0.95-0.86 (m, 2H). | 456 |

TABLE 28-continued

| Example | Structure | IUPAC Name | ¹H NMR (ppm) | MS (M + H) |
|---|---|---|---|---|
| 390 | 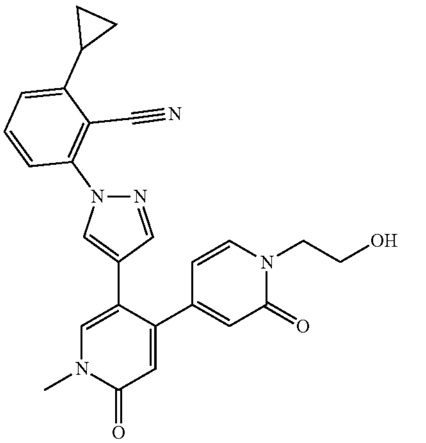 [SMILES: Cn1cc(-c2cnn(-c3cccc(C4CC4)c3C#N)c2)c(-c2ccn(CCO)c(=O)c2)cc1=O] | 2-cyclopropyl-6-[4-[4-[1-(2-hydroxyethyl)-2-oxo-4-pyridyl]-1-methyl-6-oxo-3-pyridyl]pyrazol-1-yl]benzonitrile | (DMSO-$d_6$, 300 MHz) δ 8.07 (s, 1H), 8.00 (s, 1H), 7.66 (s, 2H), 7.66 (d, J = 16.2 Hz, 1H), 7.52 (d, J = 6.9 Hz, 1H), 7.37 (d, J = 7.9 Hz, 1H), 7.11 (d, J = 8.0 Hz, 1H), 6.40-6.27 (m, 2H), 5.98-5.89 (m, 1H), 3.90 (t, J = 5.5 Hz, 2H), 3.61 (d, J = 5.6 Hz, 2H), 3.50 (s, 3H), 2.24 (s, 0H), 1.15 (d, J = 7.7 Hz, 2H), 0.86 (d, J = 5.6 Hz, 2H). | 454 |
| 391 | 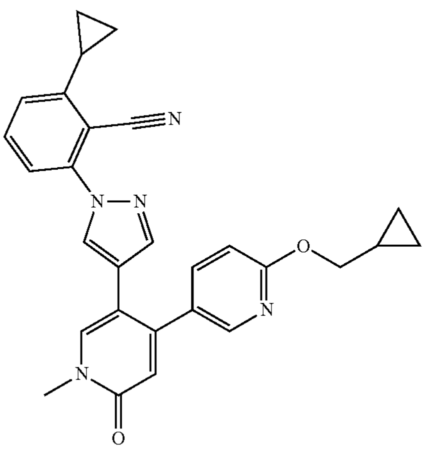 [SMILES: Cn1cc(-c2cnn(-c3cccc(C4CC4)c3C#N)c2)c(-c2ccc(OCC3CC3)nc2)cc1=O] | 2-cyclopropyl-6-(4-(6-(cyclopropylmethoxy)-1'-methyl-6'-oxo-1',6'-dihydro-[3,4'-bipyridin]-3'-yl)-1H-pyrazol-1-yl)benzonitrile | (400 MHz, $CD_3OD$) δ 8.06 (d, J = 2.5 Hz, 1H), 7.93 (s, 1H), 7.89 (s, 1H), 7.67 (t, J = 8.0 Hz, 1H), 7.57 (dd, J = 8.6, 2.5 Hz, 1H), 7.47 (s, 1H), 7.44-7.37 (m, 1H), 7.15 (d, J = 8.0 Hz, 1H), 6.80 (d, J = 8.7 Hz, 1H), 6.61 (s, 1H), 4.15 (d, J = 7.1 Hz, 2H), 3.69 (s, 3H), 2.40-2.29 (m, 1H), 1.34-1.18 (m, 3H), 0.96-0.87 (m, 2H), 0.64-0.55 (m, 2H), 0.40-0.31 (m, 2H). | 464 |

Example 392: 4-Ethoxy-5-(5-methanesulfonyl-4,5,6,7-tetrahydro-pyrazolo[1,5-a]pyrazin-3-yl)-1-methyl-1H-pyridin-2-one Step 1: 2-[Benzyl-(2H-pyrazol-3-ylmethyl)-amino]-ethanol

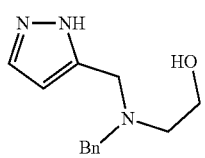

A solution of 2H-pyrazole-3-carbaldehyde (1.6 g, 10.6 mmol) and 2-benzylamino-ethanol (1.0 g, 10.4) in MeOH (40 mL) was stirred room temperature for 1 hour. NaBH(OAc)₃ (6.6 g, 31.1 mmol) and AcOH (1 mL) were added and the mixture was stirred for 4 hours. The mixture was quenched with NaHCO₃ (50 mL) and extracted with DCM (40 mL×3). The combined organic layers were dried over Na₂SO₄, filtered and concentrated under reduced pressure. The title compound (2.4 g, 10.4 mmol) was used in the following step without further purification. LCMS (M+H)⁺ 232.

Step 2: 5-Benzyl-4,5,6,7-tetrahydro-pyrazolo[1,5-a]pyrazine

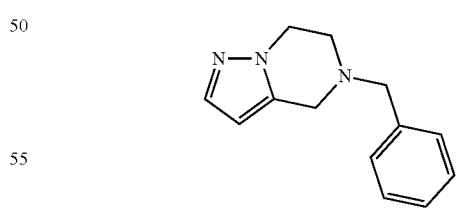

To a solution of the title compound from Step 1 (2.4 g, 10.4 mmol) in DCM (40 mL) at 0° C. was added SOCl₂ (10 mL). The mixture was warmed to room temperature and stirred overnight. The solvent was removed under reduced pressure. The residue was dissolved in DMF (30 mL) followed by addition of NaH (2.2 g, 55 mmol) and stirring for 3 hours. The mixture was quenched with H₂O (30 mL) and extracted with DCM (40 mL×3). The combined organic layers were dried over Na₂SO₄, filtered and concentrated under reduced pressure. The residue was purified by silica gel column chromatography eluting with PE/EtOAc (1:1) to afford the title compound (460 mg, 2.2 mmol). $^1$H NMR (300 MHz, CDCl$_3$) δ 7.46 (s, 1H), 7.38-7.31 (m, 5H), 5.96 (s, 1H), 4.21 (t, J=5.4 Hz, 2H), 3.73 (s, 2H), 3.70 (s, 2H), 2.96 (t, J=5.4 Hz, 2H). LCMS (M+H)$^+$ 214.

Step 3: 6,7-Dihydro-4H-pyrazolo[1,5-a]pyrazine-5-carboxylic Acid Tert-Butyl Ester

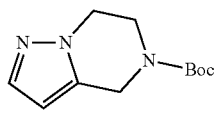 [SMILES: CC(C)(C)OC(=O)N1CCn2nccc2C1]

To a solution of the title compound from Step 2 (460 mg, 2.2 mmol) in MeOH (20 mL) at room temperature was added Pd(OH)$_2$/C (60 mg) and (Boc)$_2$O (1.2 g, 5.4 mmol). The reaction was stirred under a H$_2$ atmosphere overnight. The mixture was filtered and the filtrate was concentrated under reduced pressure. The residue was purified by silica gel column chromatography eluting with PE/EtOAc (1:1) to afford the title compound (400 mg, 1.8 mmol) as a colorless oil. LCMS (M+H)$^+$ 224.

Step 4: 3-Bromo-6,7-dihydro-4H-pyrazolo[1,5-a]pyrazine-5-carboxylic Acid Tert-Butyl Ester

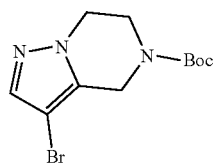 [SMILES: CC(C)(C)OC(=O)N1CCn2ncc(Br)c2C1]

A solution of the title compound from Step 3 (400 mg, 1.8 mmol) and NBS (318 mg, 1.8 mmol) in DCM (200 mL) at room temperature was stirred overnight at room. The mixture was diluted with saturated NH$_4$Cl aqueous solution (50 mL) and extracted with DCM (30 mL×3). The combined organic layers were dried over Na$_2$SO$_4$, filtered and concentrated under reduced pressure to afford the title compound (450 mg, 1.5 mmol) which was used without further purification in the next step. LCMS (M+H)$^+$ 302.

Step 5: 3-(4-Ethoxy-1-methyl-6-oxo-1,6-dihydro-pyridin-3-yl)-6,7-dihydro-4H-pyrazolo[1,5-a]pyrazine-5-carboxylic Acid Tert-Butyl Ester

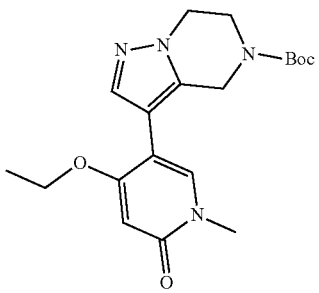 [SMILES: CCOc1cc(=O)n(C)cc1-c1cnn2c1CN(C(=O)OC(C)(C)C)CC2]

A mixture of the title compound from Step 4 (210 mg, 0.70 mmol), 4-ethoxy-1-methyl-5-(4,4,5,5-tetramethyl-[1,3,2]dioxaborolan-2-yl)-1H-pyridin-2-one (190 mg, 0.69 mmol), Pd(dppf)Cl$_2$ (50 mg, 0.07 mmol) and Na$_2$CO$_3$ (288 mg, 2.7 mmol) in a dioxane/H$_2$O mixture (15 mL/3 mL) under N$_2$ was stirred at 110° C. for 4 hours. The mixture was cooled down to room temperature and extracted with DCM (30 mL×3). The combined organic layers were dried over Na$_2$SO$_4$, filtered and concentrated under reduced pressure. The residue was purified by preparative-TLC eluting with DCM/MeOH (30:1) to afford the title compound (103 mg, 0.28 mmol). LCMS (M+H)$^+$ 375.

Step 6: 4-Ethoxy-1-methyl-5-(4,5,6,7-tetrahydro-pyrazolo[1,5-a]pyrazin-3-yl)-1H-pyridin-2-one

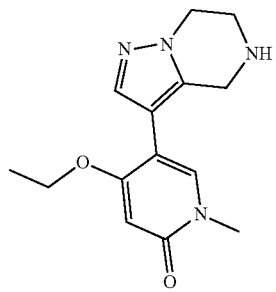 [SMILES: CCOc1cc(=O)n(C)cc1-c1cnn2c1CNCC2]

A solution of the title compound from Step 5 (100 mg, 0.27 mmol) in a DCM/TFA (5 mL/5 mL) mixture was stirred at room temperature for 4 hours. Solvents were removed under reduced pressure. The residue was dissolved in DCM (20 mL) and washed with H$_2$O (40 mL). The organic layer was dried over Na$_2$SO$_4$, filtered and concentrated under reduced pressure to afford the title compound (40 mg, 0.15 mmol) as a yellow oil which was used without further purification in the following step. LCMS (M+H)$^+$ 275.

Step 7: 4-Ethoxy-5-(5-methanesulfonyl-4,5,6,7-tetrahydro-pyrazolo[1,5-a]pyrazin-3-yl)-1-methyl-1H-pyridin-2-one

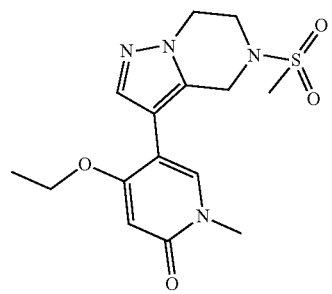 [SMILES: CCOc1cc(=O)n(C)cc1-c1cnn2c1CN(S(C)(=O)=O)CC2]

A mixture of the title compound from Step 6 (30 mg, 0.11 mmol), MsCl (25 mg, 0.22 mmol) and Et$_3$N (33 mg, 0.33 mmol) in DCM (10 mL) was stirred at room temperature for 2 hours. It was then diluted with H$_2$O (50 mL) and extracted with DCM (20 mL×3). The combined organic layers were dried over Na$_2$SO$_4$, filtered and concentrated under reduced pressure. The residue was purified by preparative-TLC eluting with DCM/MeOH (25:1) to afford the title compound (17 mg, 0.05 mmol) as a white solid. $^1$H NMR (400 MHz, CD$_3$OD) δ 7.57 (s, 1H), 7.55 (s, 1H), 6.01 (s, 1H), 4.52 (s, 2H), 4.27 (t, J=5.2 Hz, 2H), 4.11 (q, J=7.2 Hz, 2H), 3.81 (t, J=5.4 Hz, 2H), 3.52 (s, 3H), 2.98 (s, 3H), 1.41 (t, J=7.2 Hz, 3H). LCMS (M+H)$^+$ 353.

Example 393: 5-(5-Acetyl-4,5,6,7-tetrahydro-pyrazolo[1,5-a]pyrazin-3-yl)-4-ethoxy-1-methyl-1H-pyridin-2-one

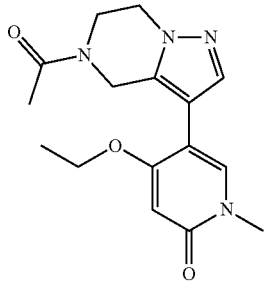 [SMILES: CCOc1cc(=O)n(C)cc1-c1cnn2c1CN(C(C)=O)CC2]

The title compound was prepared in a manner similar to Example 392 by substituting acetyl chloride for methanesulfonyl chloride in Step 7. $^1$H NMR (CD$_3$OD, 400 MHz) 7.56-7.54 (m, 2H), 6.02 (s, 1H), 4.77 (d, J=6.0 Hz, 2H), 4.29-4.01 (m, 6H), 3.52 (s, 3H), 2.23 (s, 3H), 1.40 (t, J=7.2 Hz, 3H). LCMS (M+H)$^+$ 317.

Example 394: 1-methyl-4-phenyl-5-(5-phenyloxazol-2-yl)pyridin-2(1H)-one

Step 1: 5-bromo-2-methoxy-4-phenylpyridine

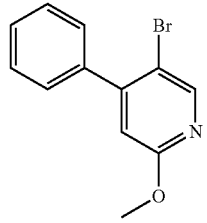

A solution of bromobenzene (4.1 g, 25.9 mmol), (5-bromo-2-methoxy-4-pyridyl)boronic acid (3 g, 12.9 mmol), Pd(PPh$_3$)$_4$ (2.99 g, 2.6 mmol), Na$_2$CO$_3$ (4.11 g, 38.8 mmol), in 1,4-dioxane (20 mL) and water (3 mL) was stirred at 60° C. for 3 hours under a nitrogen atmosphere. The reaction mixture was quenched with water (100 mL) and extracted with EtOAc (2×100 mL). The organic layers were dried over Na$_2$SO$_4$, filtered and concentrated. The crude product was purified by silica gel column chromatography (0 to 25% EtOAc in petroleum ether) to afford the title compound (1.2 g, 35%) as a white solid. (M+H)$^+$ 263/265.

Step 2: 2-methoxy-4-phenyl-5-(4,4,5,5-tetramethyl-1,3,2-dioxaborolan-2-yl)pyridine

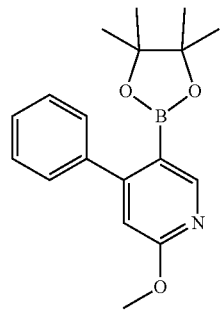 [SMILES: COc1cc(-c2ccccc2)c(B2OC(C)(C)C(C)(C)O2)cn1]

A mixture of 5-bromo-2-methoxy-4-phenyl-pyridine (500 mg, 1.9 mmol), 4,4,5,5-tetramethyl-2-(4,4,5,5-tetramethyl-1,3,2-dioxaborolan-2-yl)-1,3,2-dioxaborolane (961 mg, 3.79 mmol), Pd(dppf)Cl$_2$ (277 mg, 0.38 mmol), KOAc (557 mg, 5.68 mmol) and DMSO (5 mL) under a nitrogen atmosphere was stirred at 80° C. overnight. The reaction mixture was diluted with water and extracted with EtOAc. The organic layer was dried over sodium sulfate, concentrated under reduced pressure and purified by silica gel column chromatography (PE/EA=50/1) to afford the title compound (300 mg) as a white solid. LCMS (M+H)$^+$ 312.

Step 3: 2-(6-methoxy-4-phenylpyridin-3-yl)-5-phenyloxazole

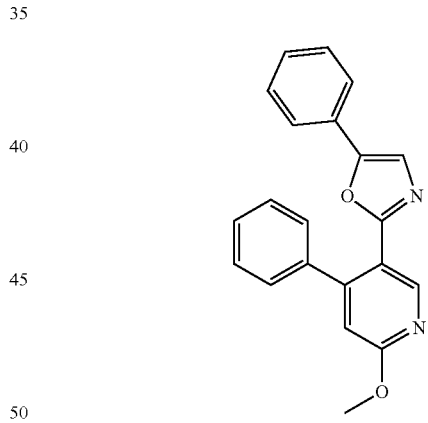

To a mixture of 2-bromo-5-phenyl-oxazole (200 mg, 0.89 mmol), 2-methoxy-4-phenyl-5-(4,4,5,5-tetramethyl-1,3,2-dioxaborolan-2-yl)pyridine (305 mg, 0.98 mmol), Xphos Pd G3 (151 mg, 0.18 mmol) in 1,4-dioxane (5 mL) was added a solution of Cs$_2$CO$_3$ (872 mg, 2.68 mmol) in water (0.5 mL) under a nitrogen atmosphere. The reaction was stirred at 60° C. overnight. It was then cooled to room temperature, diluted with water and extracted with EtOAc. The organic layer was dried over sodium sulfate and concentrated under reduced pressure. The residue was purified by silica gel column chromatography (EA/PE=1/50) to afford the title compound (100 mg, 34%). LCMS (M+H)$^+$ 329.

Step 4: 4-phenyl-5-(5-phenyloxazol-2-yl)pyridin-2-ol

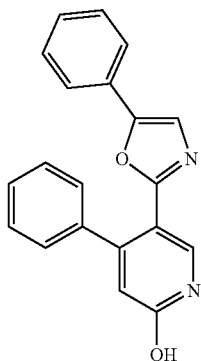 [SMILES: Oc1cc(-c2ccccc2)c(-c2ncc(-c3ccccc3)o2)cn1]

A mixture of 2-(6-methoxy-4-phenyl-3-pyridyl)-5-phenyl-oxazole (100 mg, 0.3 mmol) and HBr (aq) (10 mL, 40 mmol) in ethanol (10 mL) was stirred overnight at 80° C. The mixture was cooled to room temperature, diluted with water, extracted with EtOAc. The organic layer was washed with brine, concentrated under reduced pressure and purified by column chromatography (DCM/MeOH=30/1) to afford (80 mg, 84%) of desired product as a yellow solid. LCMS (M+H)$^+$ 315.

Step 5: 1-methyl-4-phenyl-5-(5-phenyloxazol-2-yl)pyridin-2(1H)-one

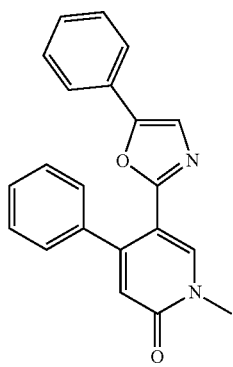 [SMILES: Cn1cc(-c2ncc(-c3ccccc3)o2)c(-c2ccccc2)cc1=O]

To a stirred solution of 4-phenyl-5-(5-phenyloxazol-2-yl)pyridin-2-ol (80 mg, 0.32 mmol) in DMF (2 mL) was added NaH (31.8 mg, 0.80 mmol) portion wise at 0° C. The resulting mixture was stirred at 0° C. for 30 min. CH$_3$I (54.2 mg, 0.38 mmol) was added. The resulting mixture was stirred for 2 h at room temperature. The reaction mixture was diluted with water and extracted with EtOAc. The organic layer was dried over sodium sulfate, filtered, concentrated and purified by preparative-HPLC to afford the title compound as a white solid (37.4 mg, 45%). $^1$H NMR (DMSO-d6, 300 MHz) δ 8.56 (s, 1H), 7.64 (s, 1H), 7.49-7.39 (m, 3H), 7.39-7.21 (m, 7H), 6.41 (s, 1H), 3.61 (s, 3H). LCMS (M+H)$^+$ 329.

Example 395: 1-methyl-5-(1-methyl-5-phenyl-1H-pyrazol-3-yl)-4-phenylpyridin-2(1H)-one

Step 1: 4-bromo-5-chloropyridin-2-ol

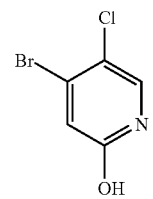

To a stirred solution of 4-bromo-5-chloro-pyridin-2-amine (1 g, 4.8 mmol) in water (2 mL) was added dropwise H$_2$SO$_4$ (2.5 mL). The mixture was then treated dropwise with a solution of NaNO$_2$ (399 mg, 5.8 mmol) in water (2 mL). After stirring the reaction under N$_2$ at 20° C. for 30 min, the mixture was filtered. The filter cake was dried under vacuum to afford the title compound (950 mg, 95%) as a yellow solid that was used directly in the following step.

Step 2: 4-bromo-5-chloro-1-methylpyridin-2(1H)-one

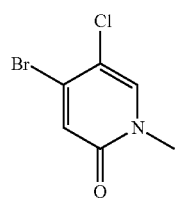

To a stirred solution of 4-bromo-5-chloro-pyridin-2-ol (950 mg, 4.56 mmol) in DMF (10 mL) under nitrogen at 0° C. was added K$_2$CO$_3$ (966 mg, 9.12 mmol) and iodomethane (970 mg, 6.84 mmol). The resulting solution was stirred at 0° C. for one hour. The reaction mixture was quenched with water (10 mL) and extracted with EtOAc (2×50 mL). The organic layer was dried over Na$_2$SO$_4$, filtered and concentrated. The residue was purified by silica gel column chromatography (0 to 25% EtOAc in petroleum ether) to afford the title compound (950 mg, 94%) as a yellow solid. LCMS (M+H)$^+$ 222.

Step 3: 5-chloro-1-methyl-4-phenylpyridin-2(1H)-one

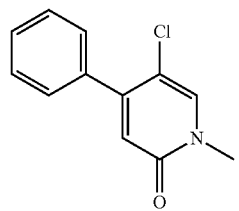

To a stirred solution of 4-bromo-5-chloro-1-methyl-pyridine-2-one (500 mg, 2.25 mmol) in 1,4-dioxane (5 mL) and water (1 mL) was added phenylboronic acid (329 mg, 2.7 mmol), Na$_2$CO$_3$ (715 mg, 6.74 mmol) and Pd(PPh$_3$)$_4$ (519 mg, 0.45 mmol). The mixture was stirred under N$_2$ at 80° C. for 12 hours. The reaction mixture was cooled to room temperature, quenched with water (10 mL) and extracted with EtOAc (2×50 mL). The organic layer was dried over Na$_2$SO$_4$, filtered and concentrated. The residue was purified by silica gel column chromatography (0 to 25% EtOAc in petroleum ether) to afford the title compound (250 mg, 51%) as a yellow solid.

Step 4: 1-methyl-4-phenyl-5-(4,4,5,5-tetramethyl-1,3,2-dioxaborolan-2-yl)pyridin-2(1H)-one

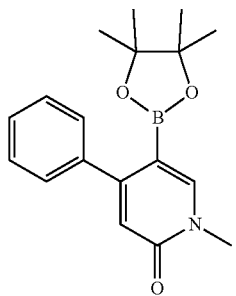 [SMILES: Cn1cc(B2OC(C)(C)C(C)(C)O2)c(-c2ccccc2)cc1=O]

To a stirred solution of 4,4,5,5-tetramethyl-2-5-chloro-1-methyl-4-phenyl-pyridin-2-one (1 g, 4.55 mmol) in 1,4-dioxane (20 mL) at room temperature was added (4,4,5,5-tetramethyl-1, 3, 2-dioxaborolan-2-yl)-1,3,2-dioxaborolane (2.3 g, 9.1 mmol), K$_3$PO$_4$ (2.9 g, 13.66 mmol), SPhos (374 mg, 0.91 mmol) and Pd(OAc)$_2$ (102 mg, 0.46 mmol) under nitrogen. The resulting solution was stirred at 25° C. for 12 hours. The reaction mixture was cooled to room temperature, quenched with water (10 mL) and extracted with EtOAc (2×50 mL). The organic layer was dried over Na$_2$SO$_4$, filtered and evaporated. The residue was purified by silica gel column chromatography (0 to 25% EtOAc in petroleum ether) to afford the title compound (500 mg, 35%) as a yellow oil. LCMS (M+H)$^+$ 312.

Step 5: 1-methyl-5-(1-methyl-5-phenyl-1H-pyrazol-3-yl)-4-phenylpyridin-2(1H)-one

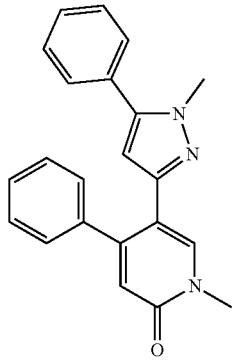 [SMILES: Cn1nc(-c2cn(C)c(=O)cc2-c2ccccc2)cc1-c1ccccc1]

To a stirred solution of 1-methyl-4-phenyl-5-(4,4,5,5-tetramethyl-1,3,2-dioxaborolan-2-yl)pyridin-2-one (394 mg, 1.27 mmol) in 1,4-dioxane (10 mL) and water (1 mL) was added 3-bromo-1-methyl-5-phenyl-pyrazole (200 mg, 0.84 mmol), Na$_2$CO$_3$ (268 mg, 2.53 mmol) and Pd(PPh$_3$)$_4$ (195 mg, 0.17 mmol) at 25° C. under nitrogen. The resulting solution was stirred at 60° C. for 12 hours. The reaction mixture was cooled to room temperature, quenched with water (10 mL) and extracted with EtOAc (2×50 mL). The organic layer was dried over Na$_2$SO$_4$, filtered and evaporated. The crude product was purified by preparative-HPLC (45 to 75% ACN/water/0.05% TFA) to afford the title compound (26.6 mg) as a white solid. $^1$H NMR (DMSO, 400 MHz) δ 8.05 (s, 1H), 7.47-7.37 (m, 6H) 7.33-7.30 (m, 2H), 7.28-7.24 (m, 2H), 6.35 (s, 1H), 5.42 (s, 1H), 3.81 (s, 3H), 3.53 (s, 3H). LCMS (M+H)$^+$ 342.

Example 396: 1-methyl-4-phenyl-5-(2-phenyloxazol-4-yl)pyridin-2(1H)-one

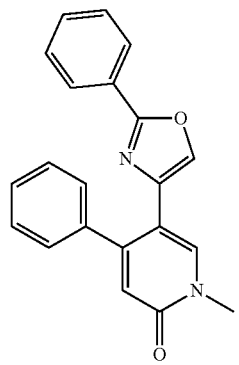 [SMILES: Cn1cc(-c2coc(-c3ccccc3)n2)c(-c2ccccc2)cc1=O]

The title compound was prepared in a manner similar to Example 395 by substituting 4-bromo-2-phenyl-oxazole for 3-bromo-1-methyl-5-phenyl-pyrazole in Step 5. $^1$H NMR (DMSO, 400 MHz) δ=8.26 (s, 1H), 7.93-7.91 (m, 2H), 7.91-7.51 (m, 3H), 7.47-7.43 (m, 3H), 7.34-7.30 (m, 2H), 6.85 (s, 1H), 6.34 (s, 1H), 3.59 (s, 3H). LCMS (M+H)$^+$ 329.

Example 397: 1-methyl-4-phenyl-5-(2-phenyloxazol-5-yl)pyridin-2(1H)-one

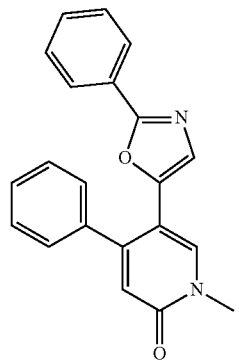 [SMILES: Cn1cc(-c2cnc(-c3ccccc3)o2)c(-c2ccccc2)cc1=O]

The title compound was prepared in a manner similar to Example 395 by substituting 5-bromo-2-phenyl-oxazole for 3-bromo-1-methyl-5-phenyl-pyrazole in Step 5. $^1$H NMR (DMSO, 400 MHz) δ=8.36 (s, 1H), 7.78-7.75 (m, 2H), 7.48-7.44 (m, 6H), 7.33-7.31 (m, 2H), 6.47 (s, 1H), 6.39 (s, 1H), 3.58 (s, 3H). LCMS (M+H)$^+$ 329.

II. Biological Evaluation

Example 1: In Vitro CBP Inhibition

The CBP-inhibitory activity of the compounds described herein was determined by calculating the $IC_{50}$. More specificatlly, CBPinhibitor activity was assayed as follows: CBP was cloned and expressed in *E. coli* as His-tag protein and purified by Nickel affinity and gel-filtration chromatography. The protein was further characterized as a single band with the correct molecular weight by SDS-PAGE. CBP binding and inhibition is assessed by monitoring the interaction of biotinylated H4-tetraacetyl peptide (AnaSpec, H4K5/8/12/16(Ac), biotin-labeled) with the target using the AlphaScreen technology (Perkin Elmer). In a 384-well ProxiPlate CBP (50 nM final) was combined with peptide (20 nM final) in 50 mM HEPES (pH 7.3), 10 mM NaCl, 0.25 mM TCEP, 0.1% (w/v) BSA, and 0.005% (w/v) Brij-35 either in the presence of DMSO (final 0.4% DMSO) or compound dilution series in DMSO. After 20 min incubation at room temp, Alpha-streptavidin donor beads and Nickel Chelate acceptor beads were added to a final concentration of 5 µg/mL. After 2 hr of equilibration, plates were read on an Envision instrument and the $IC_{50}$ calculated using a four parameter non-linear curve fit.

The ability of the compounds disclosed herein to inhibit CBP activity was quantified and the respective $IC_{50}$ value determined. The CBP $IC_{50}$ values of various compounds is shown in Table 29, in which $IC_{50}$ data are designated within the following ranges: A: ≤0.5 µM; B: >0.5 µM to ≤5.0 µM; C: >5.0 µM.

TABLE 29

| Example | Structure | Name | CBP $IC_{50}$ (µM) |
|---|---|---|---|
| 1 | 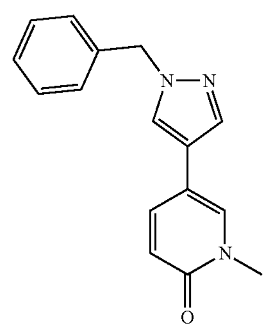 | 5-(1-benzyl-1H-pyrazol-4-yl)-1-methylpyridin-2(1H)-one | B |
| 2 | 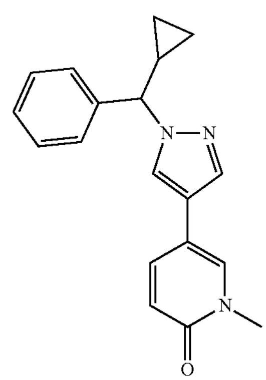 | 5-(1-(cyclopropyl(phenyl)methyl)-1H-pyrazol-4-yl)-1-methylpyridin-2(1H)-one | B |
| 3 | 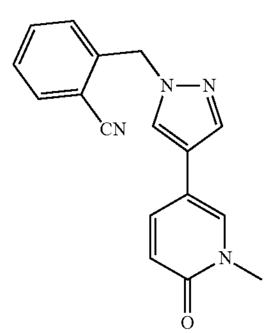 [SMILES: Cn1cc(-c2cnn(Cc3ccccc3C#N)c2)ccc1=O] | 2-((4-(1-methyl-6-oxo-1,6-dihydropyridin-3-yl)-1H-pyrazol-1-yl)methyl)benzonitrile | B |

TABLE 29-continued

| Example | Structure | Name | CBP IC$_{50}$ (μM) |
|---|---|---|---|
| 4 | 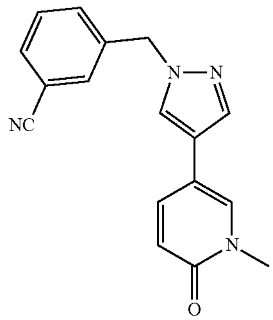 [SMILES: Cn1cc(-c2cnn(Cc3cccc(C#N)c3)c2)ccc1=O] | 3-((4-(1-methyl-6-oxo-1,6-dihydropyridin-3-yl)-1H-pyrazol-1-yl)methyl)benzonitrile | B |
| 5 | 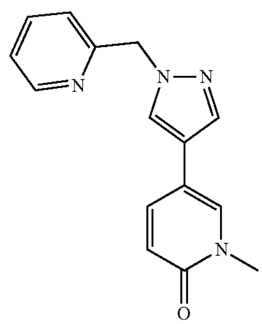 [SMILES: Cn1cc(-c2cnn(Cc3ccccn3)c2)ccc1=O] | 1-methyl-5-(1-(pyridin-2-ylmethyl)-1H-pyrazol-4-yl)pyridin-2(1H)-one | B |
| 6 | 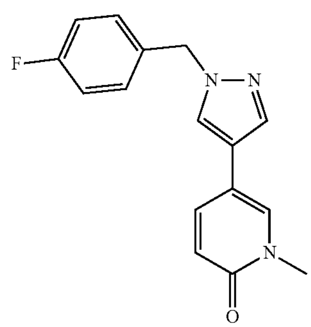 [SMILES: Cn1cc(-c2cnn(Cc3ccc(F)cc3)c2)ccc1=O] | 5-(1-(4-fluorobenzyl)-1H-pyrazol-4-yl)-1-methylpyridin-2(1H)-one | B |
| 7 | 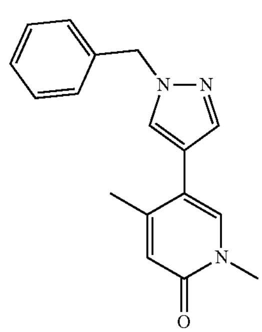 [SMILES: Cc1cc(=O)n(C)cc1-c1cnn(Cc2ccccc2)c1] | 5-(1-benzyl-1H-pyrazol-4-yl)-1,4-dimethylpyridin-2(1H)-one | A |

TABLE 29-continued

| Example | Structure | Name | CBP IC$_{50}$ (μM) |
|---|---|---|---|
| 8 | 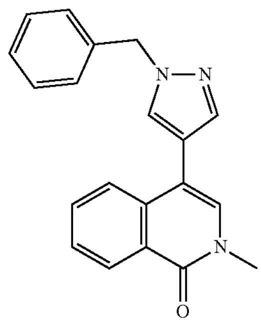 | 4-(1-benzyl-1H-pyrazol-4-yl)-2-methylisoquinolin-1(2H)-one | A |
| 9 | 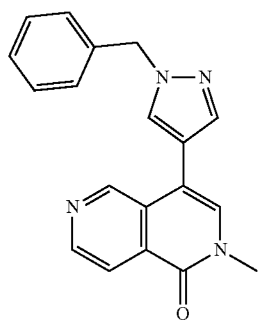 | 4-(1-benzyl-1H-pyrazol-4-yl)-2-methyl-2,6-naphthyridin-1(2H)-one | A |
| 10 | 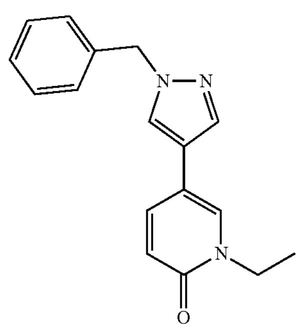 [SMILES: CCn1cc(-c2cnn(Cc3ccccc3)c2)ccc1=O] | 5-(1-benzyl-1H-pyrazol-4-yl)-1-ethylpyridin-2(1H)-one | B |
| 11 | 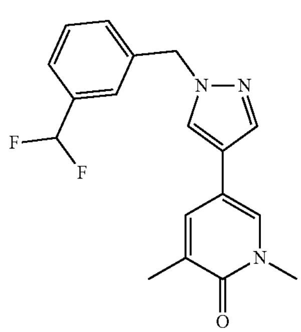 [SMILES: Cc1cc(-c2cnn(Cc3cccc(C(F)F)c3)c2)cn(C)c1=O] | 5-(1-(1-(3-(difluoromethyl)phenyl)ethyl)-1H-pyrazol-4-yl)-1,3-dimethylpyridin-2(1H)-one | A |

TABLE 29-continued
| Example | Structure | Name | CBP IC$_{50}$ (μM) |
|---|---|---|---|
| 12 | 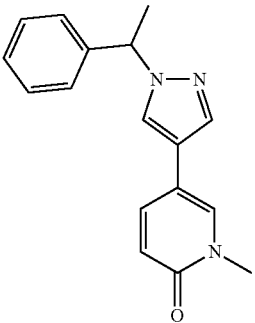 | 1-methyl-5-(1-(1-phenylethyl)-1H-pyrazol-4-yl)pyridin-2(1H)-one | B |
| 13 | 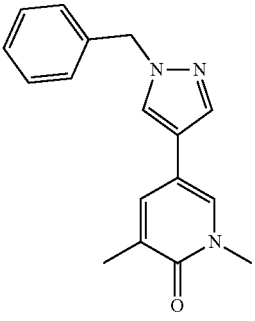 [SMILES: Cc1cc(-c2cnn(Cc3ccccc3)c2)cn(C)c1=O] | 5-(1-benzyl-1H-pyrazol-4-yl)-1,3-dimethylpyridin-2(1H)-one | A |
| 14 | 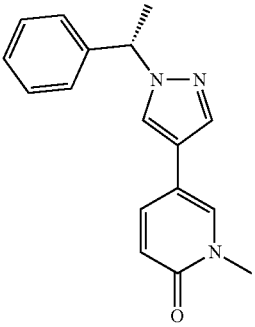 [SMILES: C[C@@H](c1ccccc1)n1cc(-c2ccc(=O)n(C)c2)cn1] | (S)-1-methyl-5-(1-(1-phenylethyl)-1H-pyrazol-4-yl)pyridin-2(1H)-one | A |
| 15 | 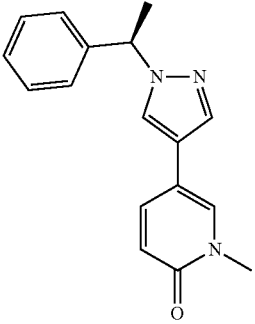 [SMILES: C[C@H](c1ccccc1)n1cc(-c2ccc(=O)n(C)c2)cn1] | (R)-1-methyl-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 16 | 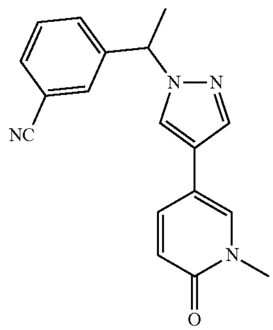 [SMILES: CC(c1cccc(C#N)c1)n1cc(-c2ccc(=O)n(C)c2)cn1] | 3-(1-(4-(1-methyl-6-oxo-1,6-dihydropyridin-3-yl)-1H-pyrazol-1-yl)ethyl)benzonitrile | B |
| 17 | 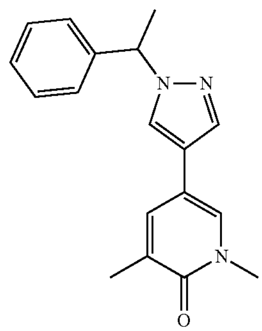 | 1,3-dimethyl-5-(1-(1-phenylethyl)-1H-pyrazol-4-yl)pyridin-2(1H)-one | A |
| 18 | 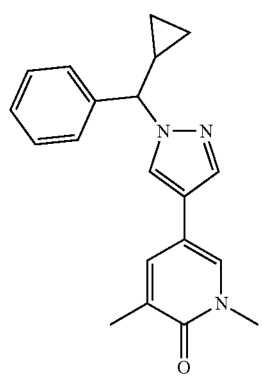 [SMILES: Cc1cc(-c2cnn(C(c3ccccc3)C3CC3)c2)cn(C)c1=O] | 5-(1-(cyclopropyl(phenyl)methyl)-1H-pyrazol-4-yl)-1,3-dimethylpyridin-2(1H)-one | A |
| 19 | 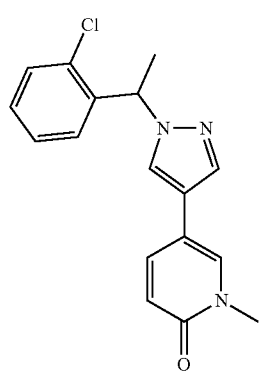 [SMILES: CC(c1ccccc1Cl)n1cc(-c2ccc(=O)n(C)c2)cn1] | 5-(1-(1-(2-chlorophenyl)ethyl)-1H-pyrazol-4-yl)-1-methylpyridin-2(1H)-one | A |

TABLE 29-continued

| Example | Structure | Name | CBP IC$_{50}$ (μM) |
|---|---|---|---|
| 20 | 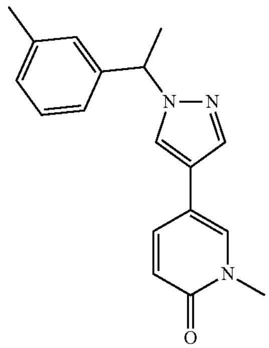 | 1-methyl-5-(1-(1-(m-tolyl)ethyl)-1H-pyrazol-4-yl)pyridin-2(1H)-one | A |
| 21 | 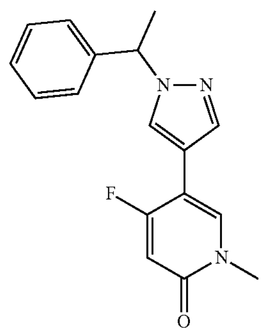 | 4-fluoro-1-methyl-5-(1-(1-phenylethyl)-1H-pyrazol-4-yl)pyridin-2(1H)-one | B |
| 22 | 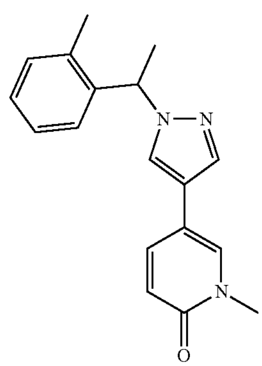 [SMILES: Cc1ccccc1C(C)n1cc(-c2ccc(=O)n(C)c2)cn1] | 1-methyl-5-(1-(1-(o-tolyl)ethyl)-1H-pyrazol-4-yl)pyridin-2(1H)-one | A |
| 23 | 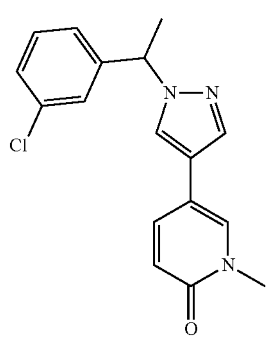 [SMILES: CC(c1cccc(Cl)c1)n1cc(-c2ccc(=O)n(C)c2)cn1] | 5-(1-(1-(3-chlorophenyl)ethyl)-1H-pyrazol-4-yl)-1-methylpyridin-2(1H)-one | A |

TABLE 29-continued

| Example | Structure | Name | CBP IC$_{50}$ (μM) |
|---|---|---|---|
| 24 | 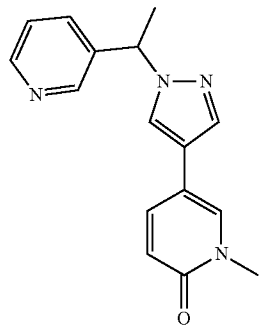 [SMILES: CC(c1cccnc1)n1cc(-c2ccc(=O)n(C)c2)cn1] | 1-methyl-5-(1-(1-(pyridin-3-yl)ethyl)-1H-pyrazol-4-yl)pyridin-2(1H)-one | B |
| 25 | 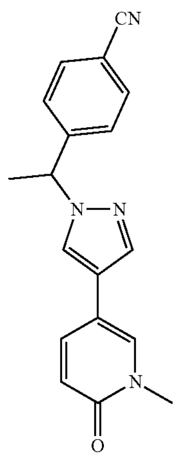 [SMILES: CC(c1ccc(C#N)cc1)n1cc(-c2ccc(=O)n(C)c2)cn1] | 4-(1-(4-(1-methyl-6-oxo-1,6-dihydropyridin-3-yl)-1H-pyrazol-1-yl)ethyl)benzonitrile | B |
| 26 | 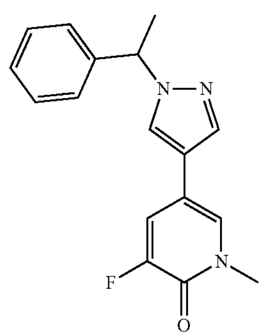 [SMILES: CC(c1ccccc1)n1cc(-c2cc(F)c(=O)n(C)c2)cn1] | 3-fluoro-1-methyl-5-(1-(1-phenylethyl)-1H-pyrazol-4-yl)pyridin-2(1H)-one | B |
| 27 | 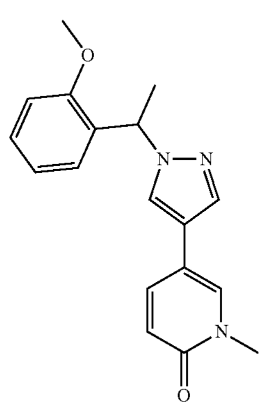 [SMILES: COc1ccccc1C(C)n1cc(-c2ccc(=O)n(C)c2)cn1] | 5-(1-(1-(2-methoxyphenyl)ethyl)-1H-pyrazol-4-yl)-1-methylpyridin-2(1H)-one | A |

TABLE 29-continued

| Example | Structure | Name | CBP IC$_{50}$ (μM) |
|---|---|---|---|
| 28 | 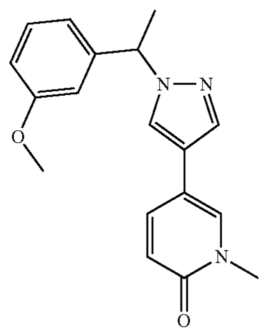 [SMILES: COc1cccc(C(C)n2cc(-c3ccc(=O)n(C)c3)cn2)c1] | 5-(1-(1-(3-methoxyphenyl)ethyl)-1H-pyrazol-4-yl)-1-methylpyridin-2(1H)-one | A |
| 29 | 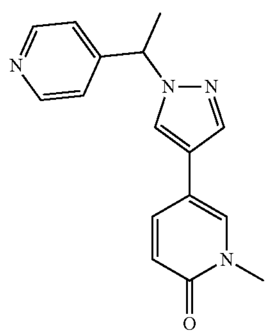 [SMILES: CC(c1ccncc1)n1cc(-c2ccc(=O)n(C)c2)cn1] | 1-methyl-5-(1-(1-(pyridin-4-yl)ethyl)-1H-pyrazol-4-yl)pyridin-2(1H)-one | B |
| 30 | 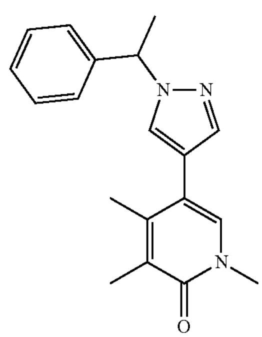 [SMILES: Cc1c(-c2cnn(C(C)c3ccccc3)c2)cn(C)c(=O)c1C] | 1,3,4-trimethyl-5-(1-(1-phenylethyl)-1H-pyrazol-4-yl)pyridin-2(1H)-one | A |
| 31 | 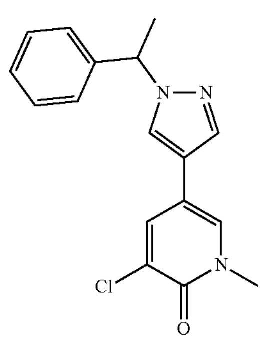 | 3-chloro-1-methyl-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 32 | 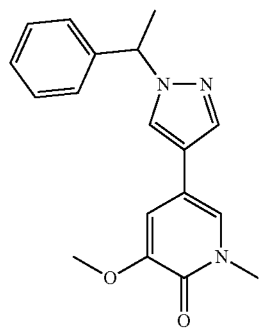 [SMILES: COc1cc(-c2cnn(C(C)c3ccccc3)c2)cn(C)c1=O] | 3-methoxy-1-methyl-5-(1-(1-phenylethyl)-1H-pyrazol-4-yl)pyridin-2(1H)-one | B |
| 33 | 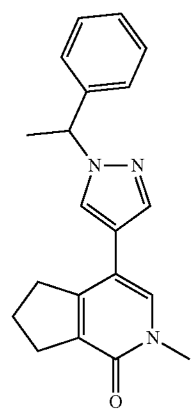 [SMILES: CC(c1ccccc1)n1cc(-c2cn(C)c(=O)c3c2CCC3)cn1] | 2-methyl-4-(1-(1-phenylethyl)-1H-pyrazol-4-yl)-2,5,6,7-tetrahydro-1H-cyclopenta[c]pyridin-1-one | A |
| 34 | 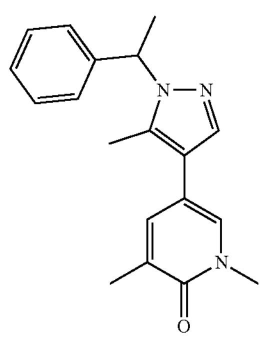 [SMILES: Cc1cc(-c2cnn(C(C)c3ccccc3)c2C)cn(C)c1=O] | 1,3-dimethyl-5-(5-methyl-1-(1-phenylethyl)-1H-pyrazol-4-yl)pyridin-2(1H)-one | A |
| 35 | 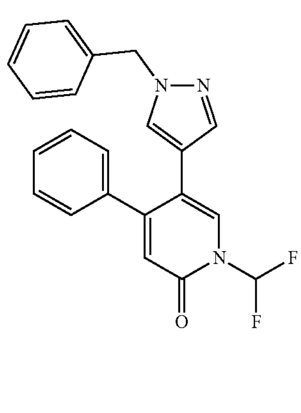 [SMILES: O=c1cc(-c2ccccc2)c(-c2cnn(Cc3ccccc3)c2)cn1C(F)F] | 5-(1-benzyl-1H-pyrazol-4-yl)-1-(difluoromethyl)-4-phenylpyridin-2(1H)-one | B |

TABLE 29-continued

| Example | Structure | Name | CBP IC$_{50}$ (μM) |
|---|---|---|---|
| 36 | 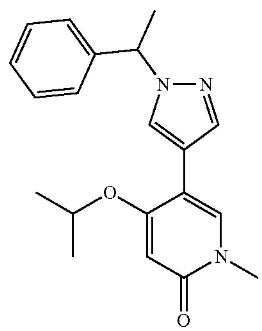 | 4-isopropoxy-1-methyl-5-(1-(1-phenylethyl)-1H-pyrazol-4-y)pyridin-2(1H)-one | A |
| 37 | 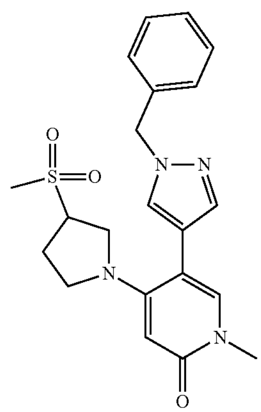 | 5-(1-Benzyl-1H-pyrazol-4-yl)-4-(3-methanesulfonyl-pyrrolidin-1-yl)-1-methyl-1H-pyridin-2-one | A |
| 38 | 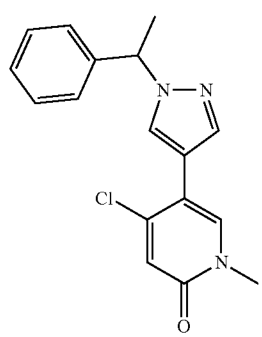 [SMILES: CC(c1ccccc1)n1cc(-c2cn(C)c(=O)cc2Cl)cn1] | 4-chloro-1-methyl-5-(1-(1-phenylethyl)-1H-pyrazol-4-yl)pyridin-2(1H)-one | A |
| 39 | 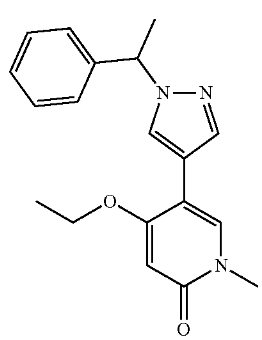 [SMILES: CCOc1cc(=O)n(C)cc1-c1cnn(C(C)c2ccccc2)c1] | 4-ethoxy-1-methyl-5-(1-(1-phenylethyl)-1H-pyrazol-4-yl)pyridin-2(1H)-one | A |

TABLE 29-continued

| Example | Structure | Name | CBP IC$_{50}$ (μM) |
|---------|-----------|------|-------------------|
| 40 | 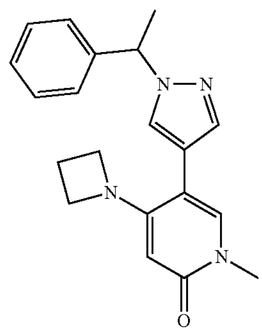 [SMILES: CC(c1ccccc1)n1cc(-c2cn(C)c(=O)cc2N2CCC2)cn1] | 4-(azetidin-1-yl)-1-methyl-5-(1-(1-phenylethyl)-1H-pyrazol-4-yl)pyridin-2(1H)-one | A |
| 41 | 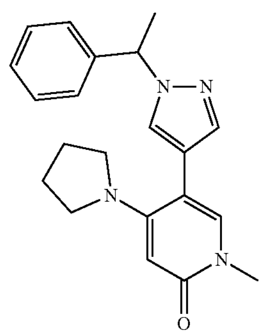 [SMILES: CC(c1ccccc1)n1cc(-c2cn(C)c(=O)cc2N2CCCC2)cn1] | 1-methyl-5-(1-(1-phenylethyl)-1H-pyrazol-4-yl)-4-(pyrrolidin-1-yl)pyridin-2(1H)-one | A |
| 42 | 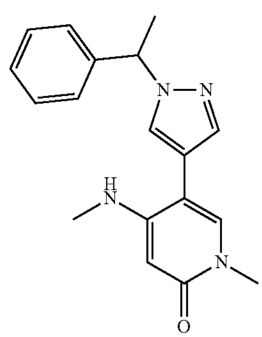 [SMILES: CNc1cc(=O)n(C)cc1-c1cnn(C(C)c2ccccc2)c1] | 1-methyl-4-(methylamino)-5-(1-(1-phenylethyl)-1H-pyrazol-4-yl)pyridin-2(1H)-one | A |
| 43 | 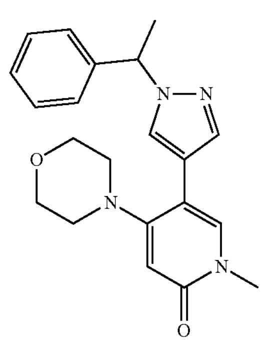 [SMILES: CC(c1ccccc1)n1cc(-c2cn(C)c(=O)cc2N2CCOCC2)cn1] | 1-methyl-4-morpholino-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 44 | 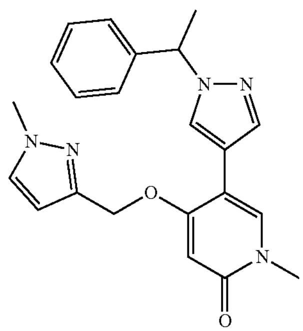 [SMILES: CC(c1ccccc1)n1cc(-c2cn(C)c(=O)cc2OCc2ccn(C)n2)cn1] | 1-methyl-4-((1-methyl-1H-pyrazol-3-yl)methoxy)-5-(1-(1-phenylethyl)-1H-pyrazol-4-yl)pyridin-2(1H)-one | A |
| 45 | 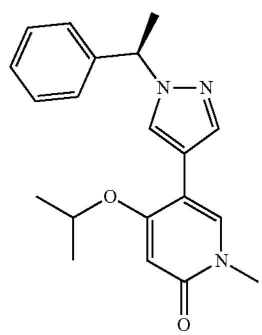 [SMILES: CC(C)Oc1cc(=O)n(C)cc1-c1cnn([C@H](C)c2ccccc2)c1] | (R)-4-isopropoxy-1-methyl-5-(1-(1-phenylethyl)-1H-pyrazol-4-yl)pyridin-2(1H)-one | A |
| 46 | 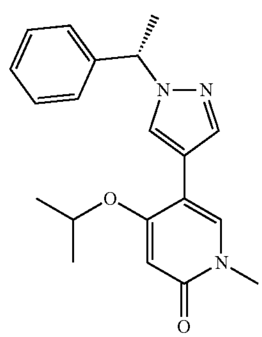 [SMILES: CC(C)Oc1cc(=O)n(C)cc1-c1cnn([C@@H](C)c2ccccc2)c1] | (S)-4-isopropoxy-1-methyl-5-(1-(1-phenylethyl)-1H-pyrazol-4-yl)pyridin-2(1H)-one | A |
| 47 | 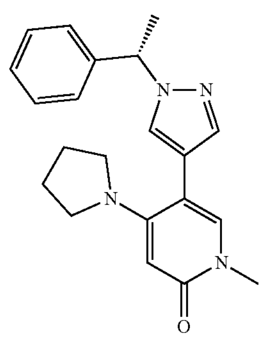 [SMILES: C[C@@H](c1ccccc1)n1cc(-c2cn(C)c(=O)cc2N2CCCC2)cn1] | (S)-1-methyl-5-(1-(1-phenylethyl)-1H-pyrazol-4-yl)-4-(pyrrolidin-1-yl)pyridin-2(1H)-one | A |

TABLE 29-continued

| Example | Structure | Name | CBP IC$_{50}$ (μM) |
|---|---|---|---|
| 48 | 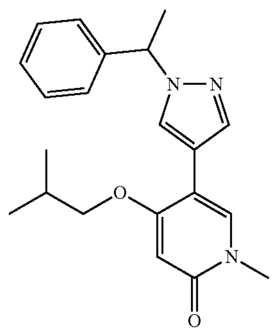 [SMILES: CC(C)COc1cc(=O)n(C)cc1-c1cnn(C(C)c2ccccc2)c1] | 4-isobutoxy-1-methyl-5-(1-(1-phenylethyl)-1H-pyrazol-4-yl)pyridin-2(1H)-one | A |
| 49 | 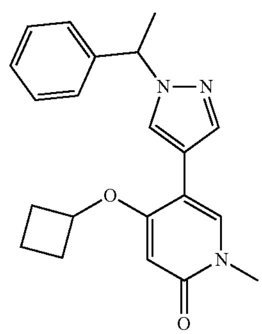 [SMILES: CC(c1ccccc1)n1cc(-c2cn(C)c(=O)cc2OC2CCC2)cn1] | 4-cyclobutoxy-1-methyl-5-(1-(1-phenylethyl)-1H-pyrazol-4-yl)pyridin-2(1H)-one | A |
| 50 | 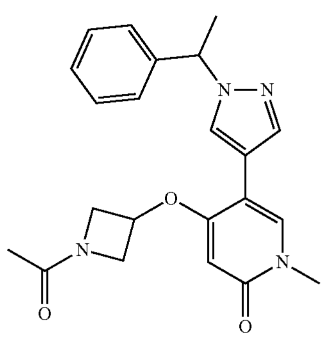 [SMILES: CC(=O)N1CC(Oc2cc(=O)n(C)cc2-c2cnn(C(C)c3ccccc3)c2)C1] | 4-((1-acetylazetidin-3-yl)oxy)-1-methyl-5-(1-(1-phenylethyl)-1H-pyrazol-4-yl)pyridin-2(1H)-one | A |
| 51 | 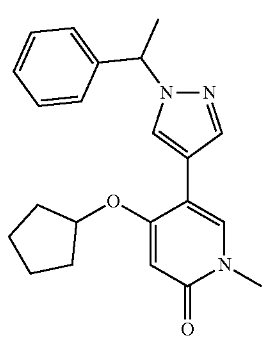 [SMILES: CC(c1ccccc1)n1cc(-c2cn(C)c(=O)cc2OC2CCCC2)cn1] | 4-(cyclopentyloxy)-1-methyl-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 52 | 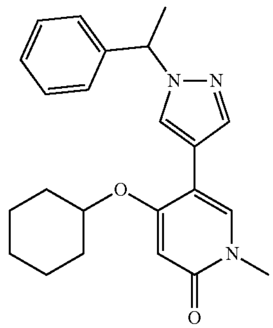 [SMILES: CC(c1ccccc1)n1cc(-c2cn(C)c(=O)cc2OC2CCCCC2)cn1] | 4-(cyclohexyloxy)-1-methyl-5-(1-(1-phenylethyl)-1H-pyrazol-4-yl)pyridin-2(1H)-one | A |
| 53 | 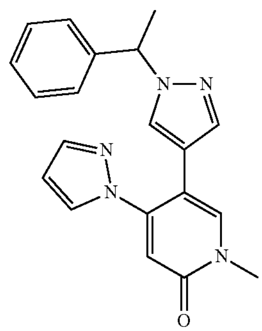 [SMILES: CC(c1ccccc1)n1cc(-c2cn(C)c(=O)cc2-n2cccn2)cn1] | 1-methyl-5-(1-(1-phenylethyl)-1H-pyrazol-4-yl)-4-(1H-pyrazol-1-yl)pyridin-2(1H)-one | A |
| 54 | 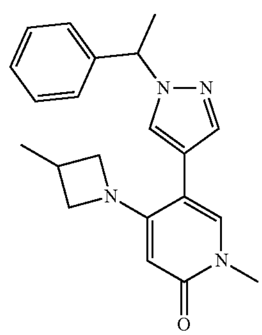 [SMILES: CC1CN(c2cc(=O)n(C)cc2-c2cnn(C(C)c3ccccc3)c2)C1] | 1-methyl-4-(3-methylazetidin-1-yl)-5-(1-(1-phenylethyl)-1H-pyrazol-4-yl)pyridin-2(1H)-one | A |
| 55 | 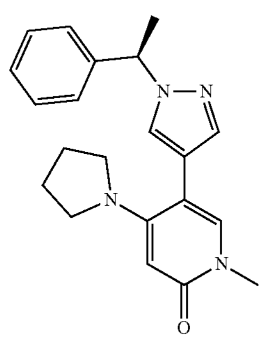 [SMILES: C[C@H](c1ccccc1)n1cc(-c2cn(C)c(=O)cc2N2CCCC2)cn1] | (R)-1-methyl-5-(1-(1-phenylethyl)-1H-pyrazol-4-yl)-4-(pyrrolidin-1-yl)pyridin-2(1H)-one | A |

TABLE 29-continued

| Example | Structure | Name | CBP IC$_{50}$ (μM) |
|---|---|---|---|
| 56 | 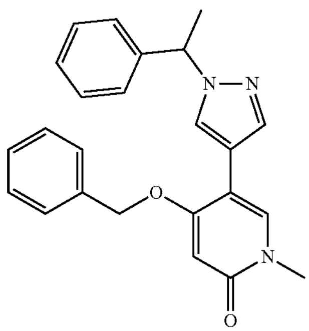 [SMILES: CC(c1ccccc1)n1cc(-c2cn(C)c(=O)cc2OCc2ccccc2)cn1] | 4-(benzyloxy)-1-methyl-5-(1-(1-phenylethyl)-1H-pyrazol-4-yl)pyridin-2(1H)-one | A |
| 57 | 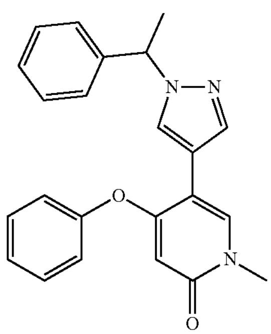 [SMILES: CC(c1ccccc1)n1cc(-c2cn(C)c(=O)cc2Oc2ccccc2)cn1] | 1-methyl-4-phenoxy-5-(1-(1-phenylethyl)-1H-pyrazol-4-yl)pyridin-2(1H)-one | B |
| 58 | 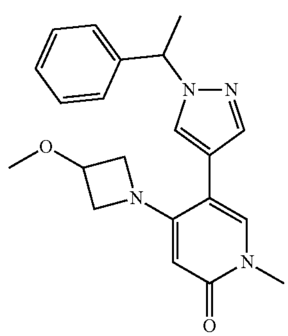 | 4-(3-methoxyazetidin-1-yl)-1-methyl-5-(1-(1-phenylethyl)-1H-pyrazol-4-yl)pyridin-2(1H)-one | B |
| 59 | 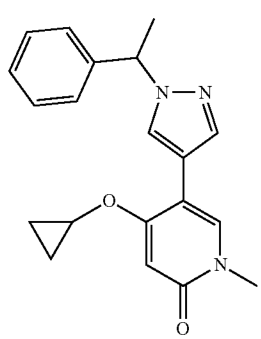 [SMILES: CC(c1ccccc1)n1cc(-c2cn(C)c(=O)cc2OC2CC2)cn1] | 4-cyclopropoxy-1-methyl-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 60 | 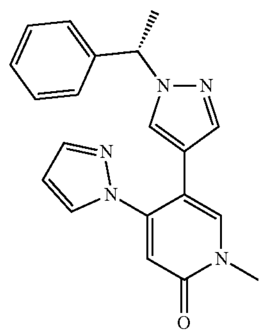 [SMILES: C[C@@H](c1ccccc1)n1cc(-c2cn(C)c(=O)cc2-n2cccn2)cn1] | (S)-1-methyl-5-(1-(1-phenylethyl)-1H-pyrazol-4-yl)-4-(1H-pyrazol-1-yl)pyridin-2(1H)-one | A |
| 61 | 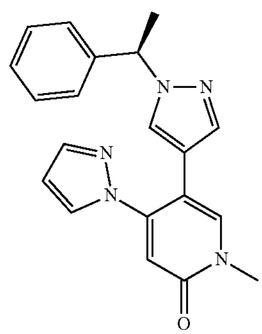 [SMILES: C[C@H](c1ccccc1)n1cc(-c2cn(C)c(=O)cc2-n2cccn2)cn1] | (R)-1-methyl-5-(1-(1-phenylethyl)-1H-pyrazol-4-yl)-4-(1H-pyrazol-1-yl)pyridin-2(1H)-one | A |
| 62 | 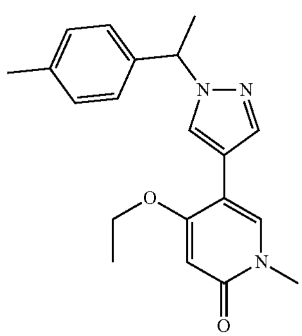 | 4-ethoxy-1-methyl-5-(1-(1-(p-tolyl)ethyl)-1H-pyrazol-4-yl)pyridin-2(1H)-one | A |
| 63 | 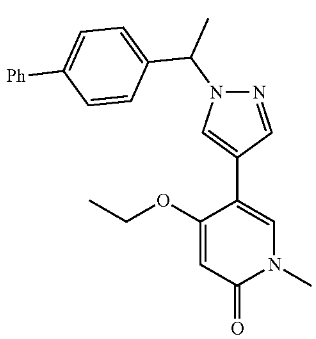 [SMILES: CCOc1cc(=O)n(C)cc1-c1cnn(C(C)c2ccc(-c3ccccc3)cc2)c1] | 5-(1-(1-([1,1'-biphenyl]-4-yl)ethyl)-1H-pyrazol-4-yl)-4-ethoxy-1-methylpyridin-2(1H)-one | A |

TABLE 29-continued

| Example | Structure | Name | CBP IC$_{50}$ (μM) |
|---|---|---|---|
| 64 | 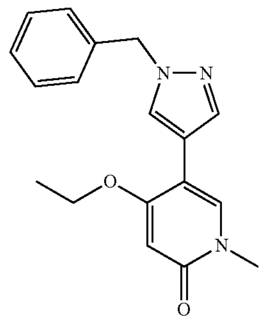 [SMILES: CCOc1cc(=O)n(C)cc1-c1cnn(Cc2ccccc2)c1] | 5-(1-benzyl-1H-pyrazol-4-yl)-4-ethoxy-1-methylpyridin-2(1H)-one | A |
| 65 | 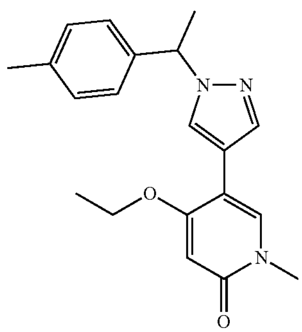 | 4-ethoxy-1-methyl-5-(1-(4-methylbenzyl)-1H-pyrazol-4-yl)pyridin-2(1H)-one | A |
| 66 | 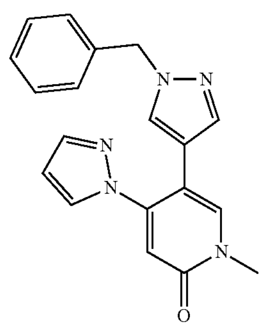 [SMILES: Cn1cc(-c2cnn(Cc3ccccc3)c2)c(-n2cccn2)cc1=O] | 5-(1-benzyl-1H-pyrazol-4-yl)-1-methyl-4-(1H-pyrazol-1-yl)pyridin-2(1H)-one | B |
| 67 | 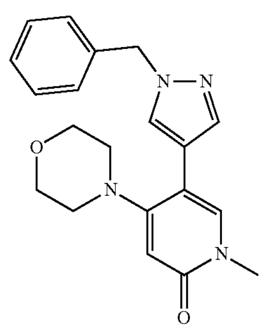 [SMILES: Cn1cc(-c2cnn(Cc3ccccc3)c2)c(N2CCOCC2)cc1=O] | 5-(1-benzyl-1H-pyrazol-4-yl)-1-methyl-4-morpholinopyridin-2(1H)-one | A |

TABLE 29-continued

| Example | Structure | Name | CBP IC$_{50}$ (μM) |
|---|---|---|---|
| 68 | 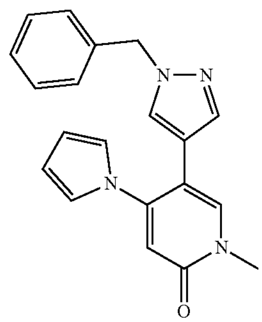 [SMILES: Cn1cc(-c2cnn(Cc3ccccc3)c2)c(-n2cccc2)cc1=O] | 5-(1-benzyl-1H-pyrazol-4-yl)-1-methyl-4-(1H-pyrrol-1-yl)pyridin-2(1H)-one | A |
| 69 | 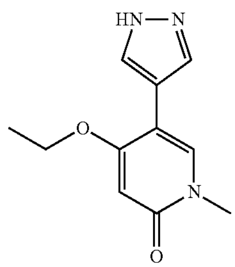 [SMILES: CCOc1cc(=O)n(C)cc1-c1cn[nH]c1] | 4-ethoxy-1-methyl-5-(1H-pyrazol-4-yl)pyridin-2(1H)-one | A |
| 70 | 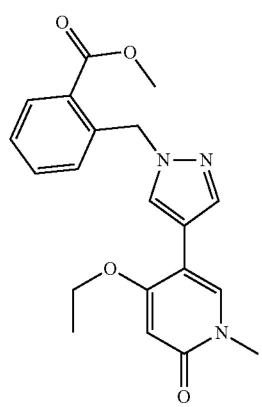 [SMILES: CCOc1cc(=O)n(C)cc1-c1cnn(Cc2ccccc2C(=O)OC)c1] | methyl 2-((4-(4-ethoxy-1-methyl-6-oxo-1,6-dihydropyridin-3-yl)-1H-pyrazol-1-yl)methyl)benzoate | A |
| 71 | 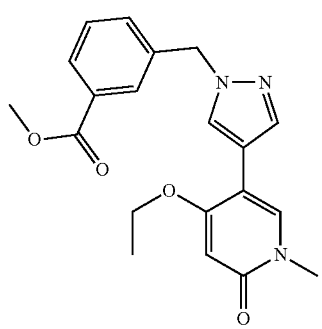 | methyl 3-((4-(4-ethoxy-1-methyl-6-oxo-1,6-dihydropyridin-3-yl)-1H-pyrazol-1-yl)methyl)benzoate | A |

TABLE 29-continued

| Example | Structure | Name | CBP IC$_{50}$ (μM) |
|---|---|---|---|
| 72 | 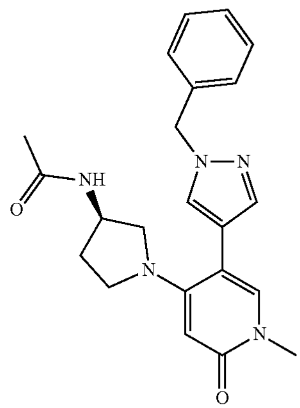 [SMILES: CC(=O)N[C@@H]1CCN(c2cc(=O)n(C)cc2-c2cnn(Cc3ccccc3)c2)C1] | (R)-N-(1-(5-(1-benzyl-1H-pyrazol-4-yl)-1-methyl-2-oxo-1,2-dihydro-pyridin-4-yl)pyrrolidin-3-yl)acetamide | B |
| 73 | 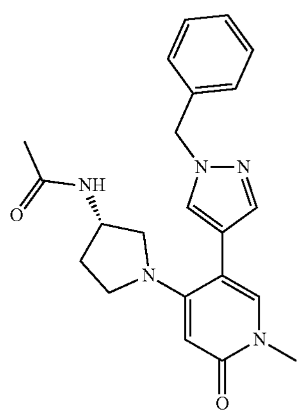 [SMILES: CC(=O)N[C@H]1CCN(c2cc(=O)n(C)cc2-c2cnn(Cc3ccccc3)c2)C1] | (S)-N-(1-(5-(1-benzyl-1H-pyrazol-4-yl)-1-methyl-2-oxo-1,2-dihydro-pyridin-4-yl)pyrrolidin-3-yl)acetamide | B |
| 74 | 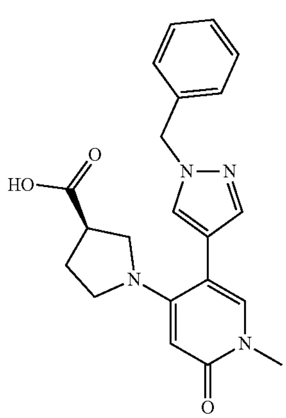 [SMILES: Cn1cc(-c2cnn(Cc3ccccc3)c2)c(N2CC[C@@H](C(=O)O)C2)cc1=O] | (R)-1-(5-(1-benzyl-1H-pyrazol-4-yl)-1-methyl-2-oxo-1,2-dihydropyridin-4-yl)pyrrolidine-3-carboxylic acid | A |

TABLE 29-continued

| Example | Structure | Name | CBP IC$_{50}$ (μM) |
|---|---|---|---|
| 75 | 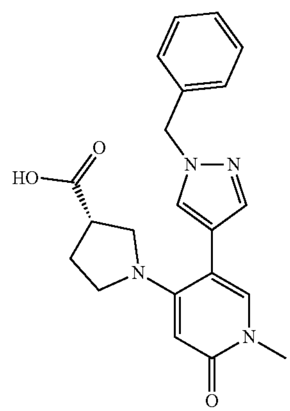 [SMILES: Cn1cc(-c2cnn(Cc3ccccc3)c2)c(N2CC[C@H](C(=O)O)C2)cc1=O] | (S)-1-(5-(1-benzyl-1H-pyrazol-4-yl)-1-methyl-2-oxo-1,2-dihydropyridin-4-yl)pyrrolidine-3-carboxylic acid | A |
| 76 | 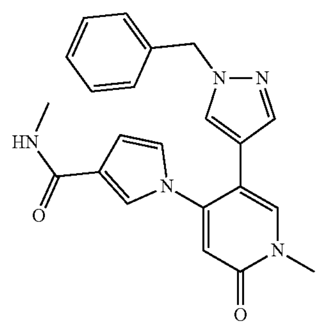 [SMILES: CNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-1H-pyrrole-3-carboxamide | A |
| 77 | 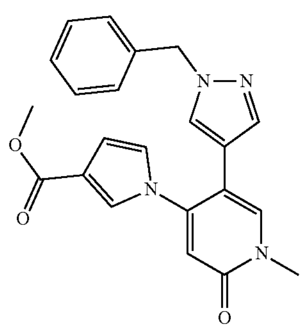 [SMILES: COC(=O)c1ccn(-c2cc(=O)n(C)cc2-c2cnn(Cc3ccccc3)c2)c1] | methyl 1-(5-(1-benzyl-1H-pyrazol-4-yl)-1-methyl-2-oxo-1,2-dihydropyridin-4-yl)-1H-pyrrole-3-carboxylate | A |
| 78 | 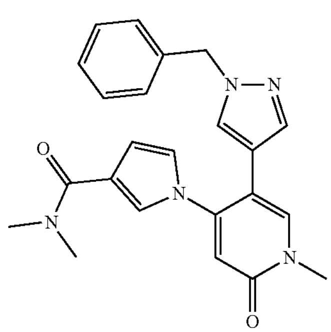 | 1-(5-(1-benzyl-1H-pyrazol-4-yl)-1-methyl-2-oxo-1,2-dihydropyridin-4-yl)-N,N-dimethyl-1H-pyrrole-3-carboxamide | A |

TABLE 29-continued

| Example | Structure | Name | CBP IC$_{50}$ (μM) |
|---|---|---|---|
| 79 | 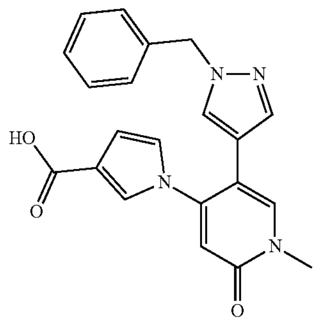 [SMILES: Cn1cc(-c2cnn(Cc3ccccc3)c2)c(-n2ccc(C(=O)O)c2)cc1=O] | 1-(5-(1-benzyl-1H-pyrazol-4-yl)-1-methyl-2-oxo-1,2-dihydropyridin-4-yl)-1H-pyrrole-3-carboxylic acid | A |
| 80 | 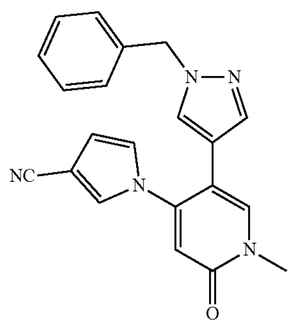 [SMILES: Cn1cc(-c2cnn(Cc3ccccc3)c2)c(-n2ccc(C#N)c2)cc1=O] | 1-(5-(1-benzyl-1H-pyrazol-4-yl)-1-methyl-2-oxo-1,2-dihydropyridin-4-yl)-1H-pyrrole-3-carbonitrile | A |
| 81 | 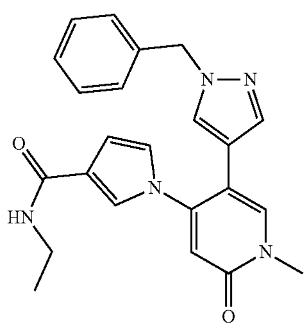 [SMILES: CCNC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-N-ethyl-1H-pyrrole-3-carboxamide | A |
| 82 | 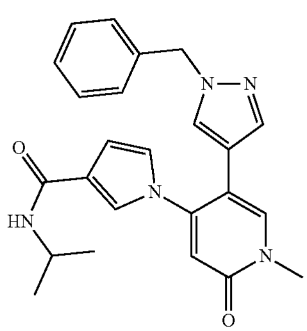 [SMILES: CC(C)NC(=O)c1ccn(-c2cc(=O)n(C)cc2-c2cnn(Cc3ccccc3)c2)c1] | 1-(5-(1-benzyl-1H-pyrazol-4-yl)-1-methyl-2-oxo-1,2-dihydropyridin-4-yl)-N-isopropyl-1H-pyrrole-3-carboxamide | A |

TABLE 29-continued

| Example | Structure | Name | CBP IC$_{50}$ (µM) |
|---|---|---|---|
| 83 | 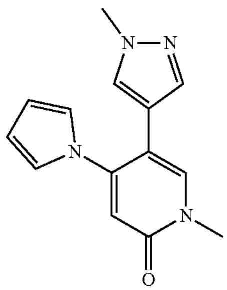 [SMILES: Cn1cc(-c2cn(C)c(=O)cc2-n2cccc2)cn1] | 1-methyl-5-(1-methyl-1H-pyrazol-4-yl)-4-(1H-pyrrol-1-yl)pyridin-2(1H)-one | A |
| 84 | 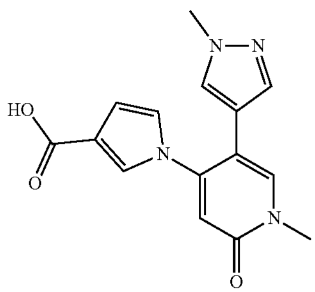 [SMILES: Cn1cc(-c2cn(C)c(=O)cc2-n2ccc(C(=O)O)c2)cn1] | 1-(1-methyl-5-(1-methyl-1H-pyrazol-4-yl)-2-oxo-1,2-dihydropyridin-4-yl)-1H-pyrrole-3-carboxylic acid | A |
| 85 | 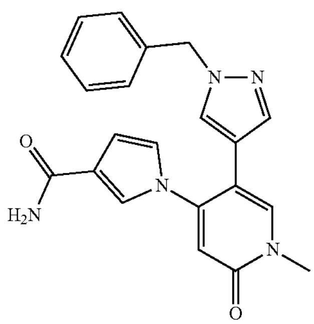 [SMILES: Cn1cc(-c2cnn(Cc3ccccc3)c2)c(-n2ccc(C(N)=O)c2)cc1=O] | 1-(5-(1-benzyl-1H-pyrazol-4-yl)-1-methyl-2-oxo-1,2-dihydropyridin-4-yl)-1H-pyrrole-3-carboxamide | A |
| 86 | 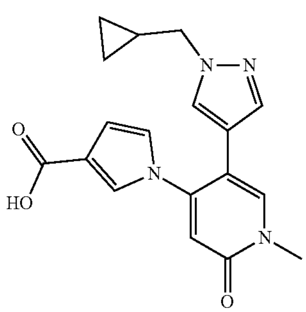 [SMILES: Cn1cc(-c2cnn(CC3CC3)c2)c(-n2ccc(C(=O)O)c2)cc1=O] | 1-(5-(1-(cyclopropylmethyl)-1H-pyrazol-4-yl)-1-methyl-2-oxo-1,2-dihydropyridin-4-yl)-1H-pyrrole-3-carboxylic acid | A |
| 87 | 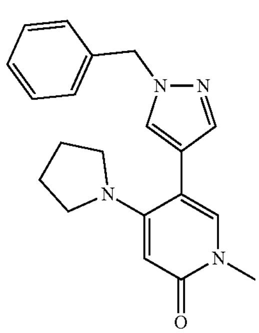 [SMILES: Cn1cc(-c2cnn(Cc3ccccc3)c2)c(N2CCCC2)cc1=O] | 5-(1-Benzyl-1H-pyrazol-4-yl)-1-methyl-4-pyrrolidin-1-yl-1H-pyridin-2-one | A |

TABLE 29-continued

| Example | Structure | Name | CBP IC$_{50}$ (μM) |
|---|---|---|---|
| 88 | 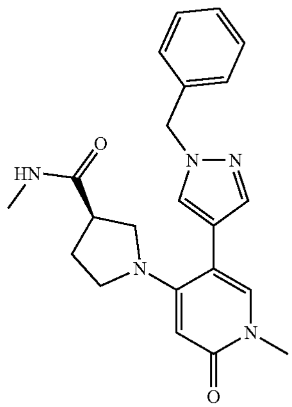 | (R)-1-(5-(1-benzyl-1H-pyrazol-4-yl)-1-methyl-2-oxo-1,2-dihydropyridin-4-yl)-N-methylpyrrolidine-3-carboxamide | A |
| 89 | 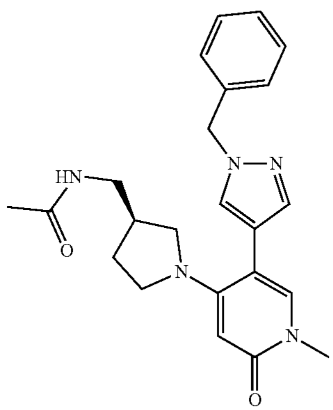 [SMILES: CC(=O)NC[C@@H]1CCN(c2cc(=O)n(C)cc2-c2cnn(Cc3ccccc3)c2)C1] | (S)-N-{1-[5-(1-Benzyl-1H-pyrazol-4-yl)-1-methyl-2-oxo-1,2-dihydro-pyridin-4-yl]-pyrrolidin-3-ylmethyl}-acetamide | A |
| 90 | 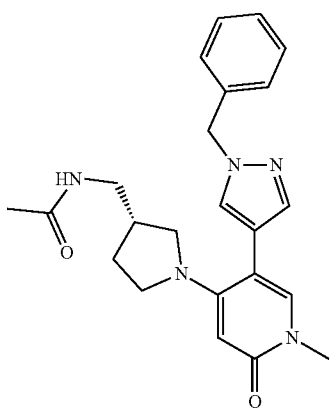 [SMILES: CC(=O)NC[C@H]1CCN(c2cc(=O)n(C)cc2-c2cnn(Cc3ccccc3)c2)C1] | (R)-N-{1-[5-(1-Benzyl-1H-pyrazol-4-yl)-1-methyl-2-oxo-1,2-dihydro-pyridin-4-yl]-pyrrolidin-3-ylmethyl}-acetamide | B |
| 91 | 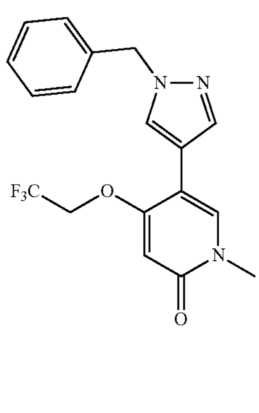 [SMILES: Cn1cc(-c2cnn(Cc3ccccc3)c2)c(OCC(F)(F)F)cc1=O] | 5-(1-benzyl-1H-pyrazol-4-yl)-1-methyl-4-(2,2,2-trifluoro-ethoxy)pyridin-2(1H)-one | A |

TABLE 29-continued

| Example | Structure | Name | CBP IC$_{50}$ (μM) |
|---|---|---|---|
| 92 | 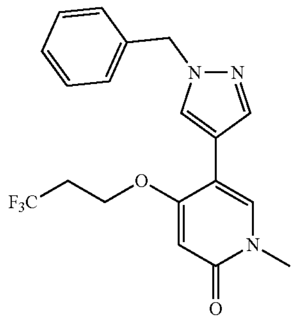 [SMILES: Cn1cc(-c2cnn(Cc3ccccc3)c2)c(OCCC(F)(F)F)cc1=O] | 5-(1-benzyl-1H-pyrazol-4-yl)-1-methyl-4-(3,3,3-trifluoro-propoxy)pyridin-2(1H)-one | A |
| 93 | 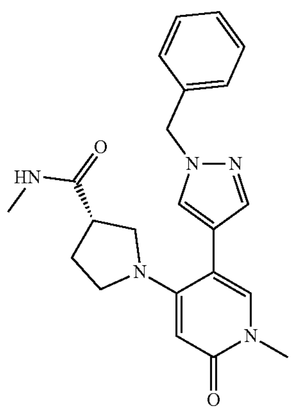 | (S)-1-[5-(1-Benzyl-1H-pyrazol-4-yl)-1-methyl-2-oxo-1,2-dihydro-pyridin-4-yl]-pyrrolidine-3-carboxylic acid methylacetamide | A |
| 94 | 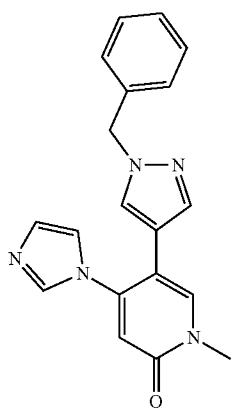 [SMILES: Cn1cc(-c2cnn(Cc3ccccc3)c2)c(-n2ccnc2)cc1=O] | 5-(1-benzyl-1H-pyrazol-4-yl)-4-(1H-imidazol-1-yl)-1-methylpyridin-2(1H)-one | A |
| 95 | 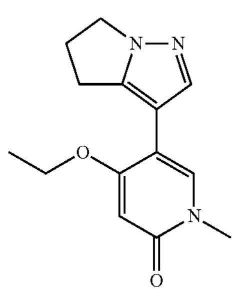 [SMILES: CCOc1cc(=O)n(C)cc1-c1cnn2c1CCC2] | 5-(5,6-dihydro-4H-pyrrolo[1,2-b]pyrazol-3-yl)-4-ethoxy-1-methylpyridin-2(1H)-one | A |

TABLE 29-continued

| Example | Structure | Name | CBP IC$_{50}$ (μM) |
|---|---|---|---|
| 96 | 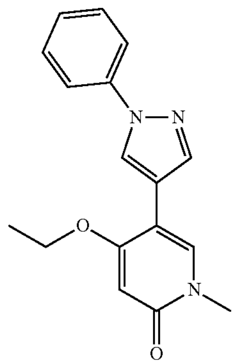 | 4-ethoxy-1-methyl-5-(1-phenyl-1H-pyrazol-4-yl)pyridin-2(1H)-one | A |
| 97 | 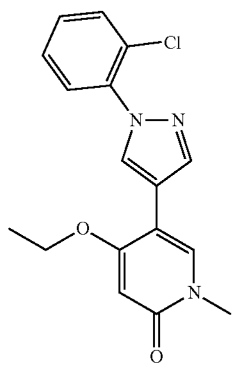 | 5-(1-(2-chlorophenyl)-1H-pyrazol-4-yl)-4-ethoxy-1-methylpyridin-2(1H)-one | A |
| 98 | 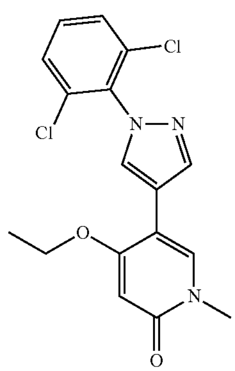 [SMILES: CCOc1cc(=O)n(C)cc1-c1cnn(-c2c(Cl)cccc2Cl)c1] | 5-(1-(2,6-dichlorophenyl)-1H-pyrazol-4-yl)-4-ethoxy-1-methylpyridin-2(1H)-one | A |
| 99 | 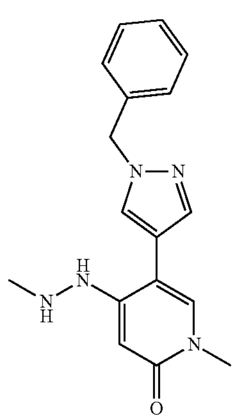 | 5-(1-benzyl-1H-pyrazol-4-yl)-1-methyl-4-(2-methylhydrazinyl)pyridin-2(1H)-one | B |

TABLE 29-continued

| Example | Structure | Name | CBP IC$_{50}$ (μM) |
|---|---|---|---|
| 100 | 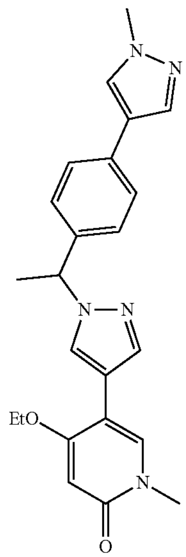 [SMILES: CCOc1cc(=O)n(C)cc1-c1cnn(C(C)c2ccc(-c3cnn(C)c3)cc2)c1] | 4-ethoxy-1-methyl-5-(1-{1-[4-(1-methyl-1H-pyrazol-4-yl)-phenyl]-ethyl}-1H-pyrazol-4-yl)-1H-pyridin-2-one | A |
| 101 | 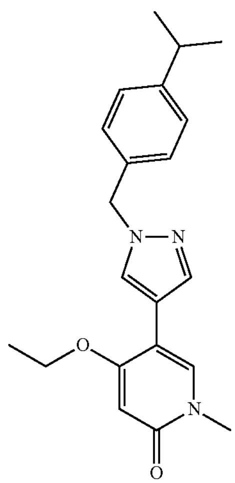 [SMILES: CCOc1cc(=O)n(C)cc1-c1cnn(Cc2ccc(C(C)C)cc2)c1] | 4-Ethoxy-5-[1-(4-isopropyl-benzyl)-1H-pyrazol-4-yl]-1-methyl-1H-pyridin-2-one | A |
| 102 | 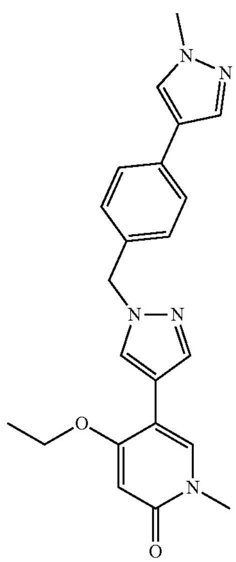 [SMILES: CCOc1cc(=O)n(C)cc1-c1cnn(Cc2ccc(-c3cnn(C)c3)cc2)c1] | 4-ethoxy-1-methyl-5-(1-(4-(1-methyl-1H-pyrazol-4-yl)benzyl)-1H-pyrazol-4-yl)pyridin-2(1H)-one | A |

TABLE 29-continued
| Example | Structure | Name | CBP IC$_{50}$ (μM) |
|---|---|---|---|
| 103 | 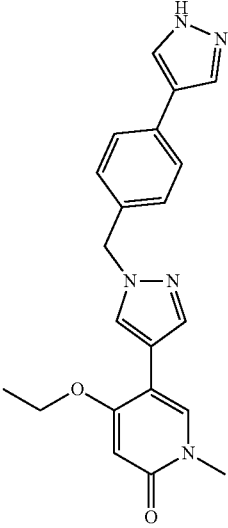 [SMILES: CCOc1cc(=O)n(C)cc1-c1cnn(Cc2ccc(-c3cn[nH]c3)cc2)c1] | 5-(1-(4-(1H-pyrazol-4-yl)benzyl)-1H-pyrazol-4-yl)-4-ethoxy-1-methylpyridin-2(1H)-one | A |
| 104 | 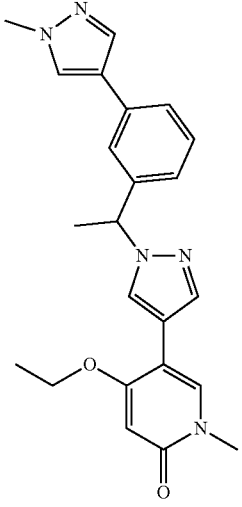 | 4-ethoxy-1-methyl-5-(1-(1-(3-(1-methyl-1H-pyrazol-4-yl)phenyl)ethyl)-1H-pyrazol-4-yl)pyridin-2(1H)-one | A |
| 105 | 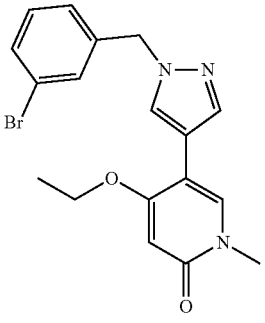 [SMILES: CCOc1cc(=O)n(C)cc1-c1cnn(Cc2cccc(Br)c2)c1] | 5-(1-(3-bromobenzyl)-1H-pyrazol-4-yl)-4-ethoxy-1-methylpyridin-2(1H)-one | A |

TABLE 29-continued

| Example | Structure | Name | CBP IC$_{50}$ (μM) |
|---|---|---|---|
| 106 | 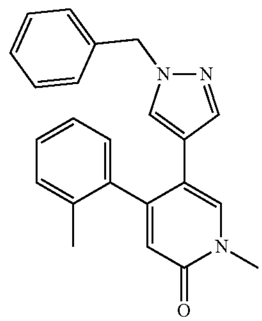 [SMILES: Cc1ccccc1-c1cc(=O)n(C)cc1-c1cnn(Cc2ccccc2)c1] | 5-(1-benzyl-1H-pyrazol-4-yl)-1-methyl-4-(o-tolyl)pyridin-2(1H)-one | B |
| 107 | 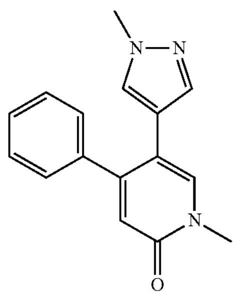 [SMILES: Cn1cc(-c2cn(C)c(=O)cc2-c2ccccc2)cn1] | 1-methyl-5-(1-methyl-1H-pyrazol-4-yl)-4-phenylpyridin-2(1H)-one | A |
| 108 | 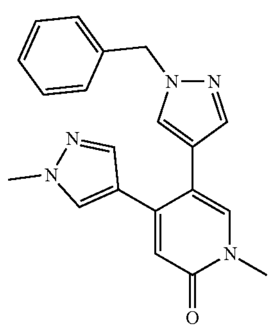 | 5-(1-benzyl-1H-pyrazol-4-yl)-1-methyl-4-(1-methyl-1H-pyrazol-4-yl)pyridin-2(1H)-one | A |
| 109 | 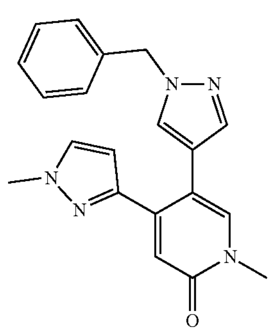 | 5-(1-benzyl-1H-pyrazol-4-yl)-1-methyl-4-(1-methyl-1H-pyrazol-3-yl)pyridin-2(1H)-one | B |

TABLE 29-continued

| Example | Name | CBP IC$_{50}$ (μM) |
|---|---|---|
| 110 | 5-(1-benzyl-1H-pyrazol-4-yl)-1-methyl-4-(1-methyl-1H-pyrazol-5-yl)pyridin-2(1H)-one | B |
| 111 | 5-(1-benzyl-1H-pyrazol-4-yl)-1-methyl-4-(m-tolyl)pyridin-2(1H)-one | A |
| 112 | 5-(1-benzyl-1H-pyrazol-4-yl)-1-methyl-4-(p-tolyl)pyridin-2(1H)-one | A |
| 113 | 5-(1-benzyl-1H-pyrazol-4-yl)-4-(3-methoxyphenyl)-1-methylpyridin-2(1H)-one | A |

TABLE 29-continued

| Example | Structure | Name | CBP IC$_{50}$ (μM) |
|---|---|---|---|
| 114 | 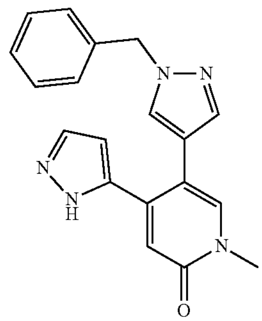 [SMILES: Cn1cc(-c2cnn(Cc3ccccc3)c2)c(-c2ccn[nH]2)cc1=O] | 5-(1-benzyl-1H-pyrazol-4-yl)-1-methyl-4-(1H-pyrazol-5-yl)pyridin-2(1H)-one | A |
| 115 | 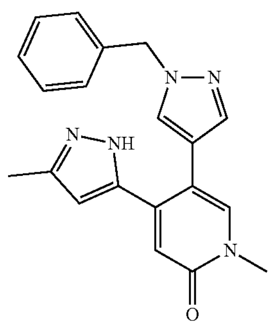 | 5-(1-benzyl-1H-pyrazol-4-yl)-1-methyl-4-(3-methyl-1H-pyrazol-5-yl)pyridin-2(1H)-one | A |
| 116 | 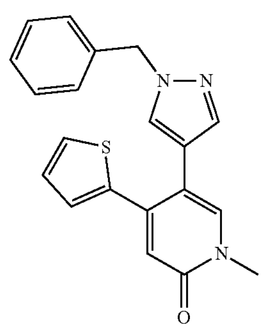 [SMILES: Cn1cc(-c2cnn(Cc3ccccc3)c2)c(-c2cccs2)cc1=O] | 5-(1-benzyl-1H-pyrazol-4-yl)-1-methyl-4-(thiophen-2-yl)pyridin-2(1H)-one | A |
| 117 | 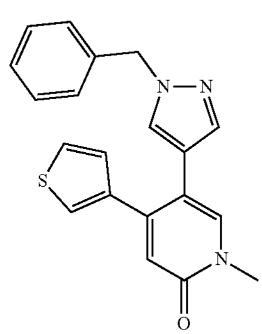 | 5-(1-benzyl-1H-pyrazol-4-yl)-1-methyl-4-(thiophen-3-yl)pyridin-2(1H)-one | A |

TABLE 29-continued

| Example | Structure | Name | CBP IC$_{50}$ (μM) |
|---|---|---|---|
| 118 | 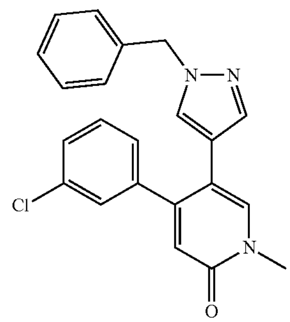 [SMILES: Cn1cc(-c2cnn(Cc3ccccc3)c2)c(-c2cccc(Cl)c2)cc1=O] | 5-(1-benzyl-1H-pyrazol-4-yl)-4-(3-chlorophenyl)-1-methylpyridin-2(1H)-one | A |
| 119 | 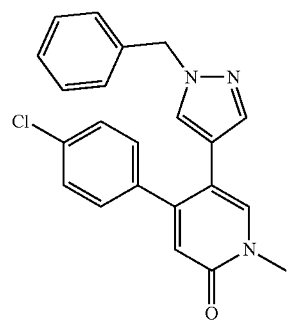 [SMILES: Cn1cc(-c2cnn(Cc3ccccc3)c2)c(-c2ccc(Cl)cc2)cc1=O] | 5-(1-benzyl-1H-pyrazol-4-yl)-4-(4-chlorophenyl)-1-methylpyridin-2(1H)-one | A |
| 120 | 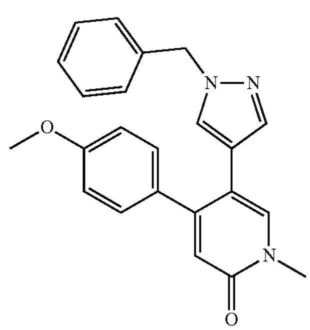 | 5-(1-benzyl-1H-pyrazol-4-yl)-4-(4-methoxyphenyl)-1-methylpyridin-2(1H)-one | A |
| 121 | 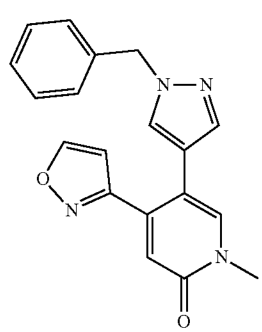 [SMILES: Cn1cc(-c2cnn(Cc3ccccc3)c2)c(-c2ccon2)cc1=O] | 5-(1-benzyl-1H-pyrazol-4-yl)-4-(isoxazol-3-yl)-1-methylpyridin-2(1H)-one | A |

TABLE 29-continued

| Example | Structure | Name | CBP IC$_{50}$ (μM) |
|---|---|---|---|
| 122 | 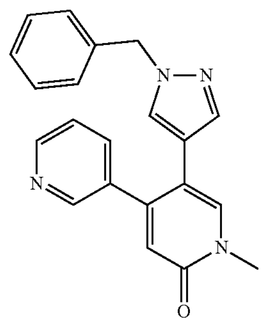 [SMILES: Cn1cc(-c2cnn(Cc3ccccc3)c2)c(-c2cccnc2)cc1=O] | 5'-(1-benzyl-1H-pyrazol-4-yl)-1'-methyl-[3,4'-bipyridin]-2'(1'H)-one | A |
| 123 | 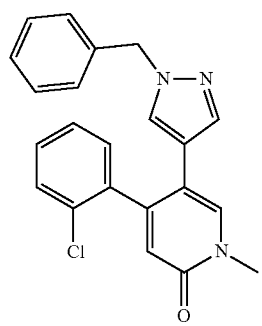 [SMILES: Cn1cc(-c2cnn(Cc3ccccc3)c2)c(-c2ccccc2Cl)cc1=O] | 5-(1-bnezyl-1H-pyrazol-4-yl)-4-(2-chlorophenyl)-1-methylpyridin-2(1H)-one | B |
| 124 | 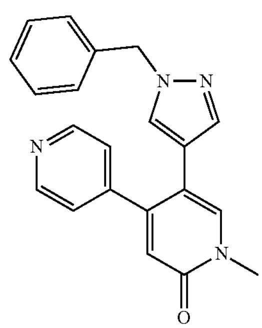 [SMILES: Cn1cc(-c2cnn(Cc3ccccc3)c2)c(-c2ccncc2)cc1=O] | 5-(1-benzyl-1H-pyrazol-4-yl)-1-methyl-[4,4'-bipyridin]-2(1H)-one | A |
| 125 | 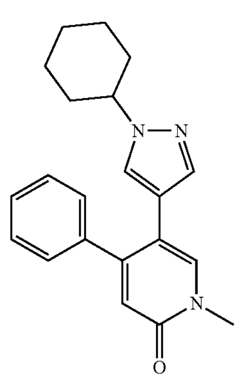 [SMILES: Cn1cc(-c2cnn(C3CCCCC3)c2)c(-c2ccccc2)cc1=O] | 5-(1-cyclohexyl-1H-pyrazol-4-yl)-1-methyl-4-phenylpyridin-2(1H)-one | A |

TABLE 29-continued

| Example | Structure | Name | CBP IC$_{50}$ (μM) |
|---|---|---|---|
| 126 | 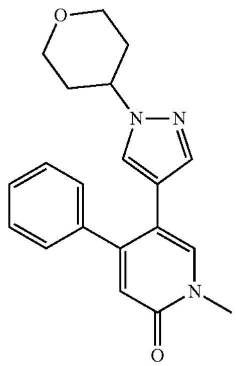 | 1-methyl-4-phenyl-5-(1-(tetrahydro-2H-pyran-4-yl)-1H-pyrazol-4-yl)pyridin-2(1H)-one | A |
| 127 | 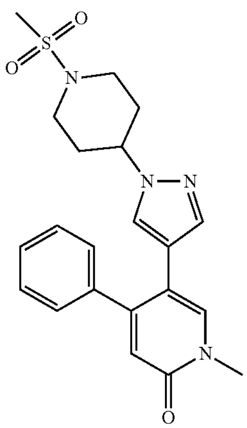 [SMILES: Cn1cc(-c2cnn(C3CCN(S(C)(=O)=O)CC3)c2)c(-c2ccccc2)cc1=O] | 1-methyl-5-(1-(1-(methylsulfonyl)piperidin-4-yl)-1H-pyrazol-4-yl)-4-phenyl-pyridin-2(1H)-one | A |
| 128 | 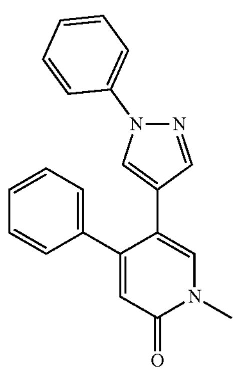 [SMILES: Cn1cc(-c2cnn(-c3ccccc3)c2)c(-c2ccccc2)cc1=O] | 1-methyl-4-phenyl-5-(1-phenyl-1H-pyrazol-4-yl)pyridin-2(1H)-one | A |
| 129 | 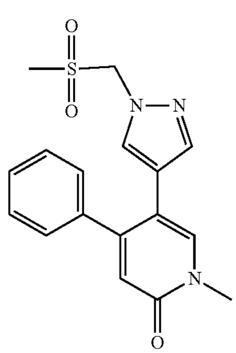 [SMILES: Cn1cc(-c2cnn(CS(C)(=O)=O)c2)c(-c2ccccc2)cc1=O] | 1-methyl-5-(1-((methylsulfonyl)methyl)-1H-pyrazol-4-yl)-4-phenylpyridin-2(1H)-one | A |

TABLE 29-continued

| Example | Structure | Name | CBP IC$_{50}$ (μM) |
|---|---|---|---|
| 130 | 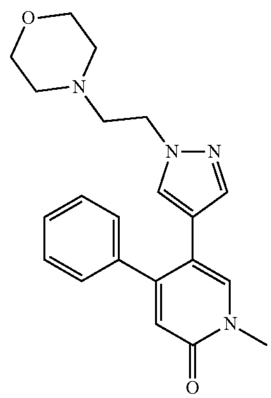 [SMILES: Cn1cc(-c2cnn(CCN3CCOCC3)c2)c(-c2ccccc2)cc1=O] | 1-methyl-5-(1-(2-morpholinoethyl)-1H-pyrazol-4-yl)-4-phenylpyridin-2(1H)-one | A |
| 131 | 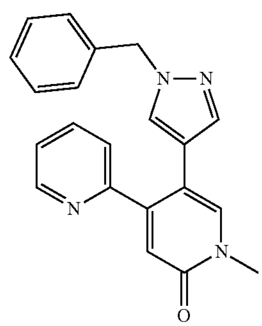 [SMILES: Cn1cc(-c2cnn(Cc3ccccc3)c2)c(-c2ccccn2)cc1=O] | 5'-(1-benzyl-1H-pyrazol-4-yl)-1'-methyl-[2,4'-bipyridin]-2'(1'H)-one | B |
| 132 | 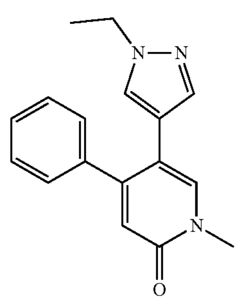 [SMILES: CCn1cc(-c2cn(C)c(=O)cc2-c2ccccc2)cn1] | 5-(1-ethyl-1H-pyrazol-4-yl)-1-methyl-4-phenylpyridin-2(1H)-one | A |
| 133 | 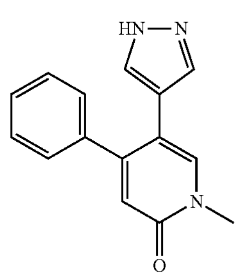 [SMILES: Cn1cc(-c2cn[nH]c2)c(-c2ccccc2)cc1=O] | 1-methyl-4-phenyl-5-(1H-pyrazol-4-yl)pyridin-2(1H)-one | A |

TABLE 29-continued

| Example | Structure | Name | CBP IC$_{50}$ (μM) |
|---|---|---|---|
| 134 | 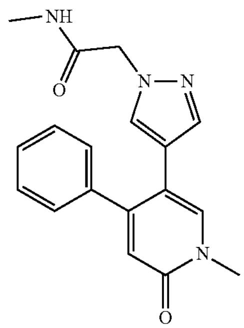 | N-methyl-2-(4-(1-methyl-6-oxo-4-phenyl-1,6-dihydropyridin-3-yl)-1H-pyrazol-1-yl)acetamide | A |
| 135 | 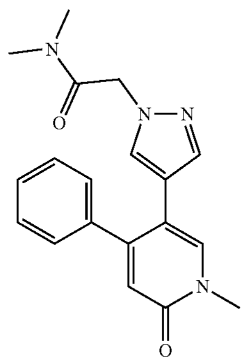 | N,N-dimethyl-2-(4-(1-methyl-6-oxo-4-phenyl-1,6-dihydropyridin-3-yl)-1H-pyrazol-1-yl)acetamide | A |
| 136 | 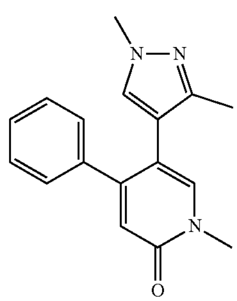 [SMILES: Cc1nn(C)cc1-c1cn(C)c(=O)cc1-c1ccccc1] | 5-(1,3-dimethyl-1H-pyrazol-4-yl)-1-methyl-4-phenylpyridin-2(1H)-one | A |
| 137 | 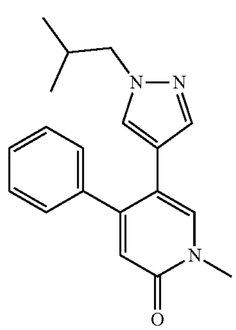 [SMILES: CC(C)Cn1cc(-c2cn(C)c(=O)cc2-c2ccccc2)cn1] | 5-(1-isobutyl-1H-pyrazol-4-yl)-1-methyl-4-phenylpyridin-2(1H)-one | A |

TABLE 29-continued

| Example | Structure | Name | CBP IC$_{50}$ (μM) |
|---|---|---|---|
| 138 | 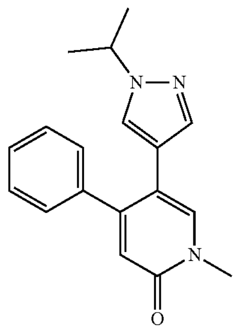 [SMILES: CC(C)n1cc(-c2cn(C)c(=O)cc2-c2ccccc2)cn1] | 5-(1-isopropyl-1H-pyrazol-4-yl)-1-methyl-4-phenylpyridin-2(1H)-one | A |
| 139 | 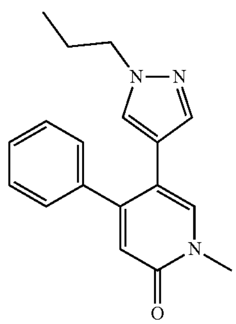 [SMILES: CCCn1cc(-c2cn(C)c(=O)cc2-c2ccccc2)cn1] | 1-methyl-4-phenyl-5-(1-propyl-1H-pyrazol-4-yl)pyridin-2(1H)-one | A |
| 140 | 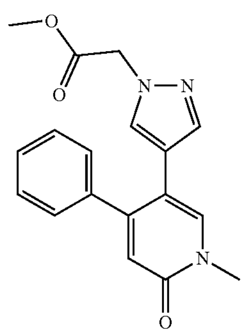 | methyl 2-(4-(1-methyl-6-oxo-4-phenyl-1,6-dihydropyridin-3-yl)-1H-pyrazol-1-yl)acetate | A |
| 141 | 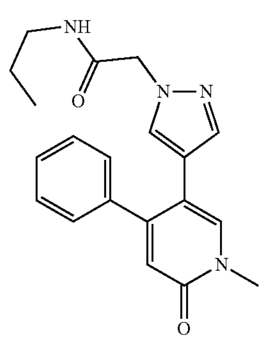 [SMILES: CCCNC(=O)Cn1cc(-c2cn(C)c(=O)cc2-c2ccccc2)cn1] | 2-(4-(1-methyl-6-oxo-4-phenyl-1,6-dihydropyridin-3-yl)-1H-pyrazol-1-yl)-N-propylacetamide | A |

TABLE 29-continued

| Example | Structure | Name | CBP IC$_{50}$ (μM) |
|---|---|---|---|
| 142 | 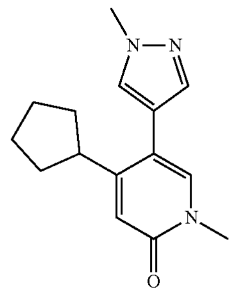 [SMILES: Cn1cc(-c2cn(C)c(=O)cc2C2CCCC2)cn1] | 4-cyclopentyl-1-methyl-5-(1-methyl-1H-pyrazol-4-yl)pyridin-2(1H)-one | B |
| 143 | 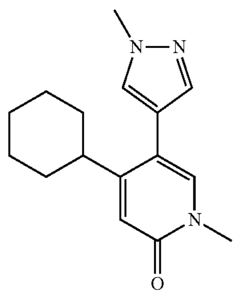 [SMILES: Cn1cc(-c2cn(C)c(=O)cc2C2CCCCC2)cn1] | 4-cyclohexyl-1-methyl-5-(1-methyl-1H-pyrazol-4-yl)pyridin-2(1H)-one | B |
| 144 | 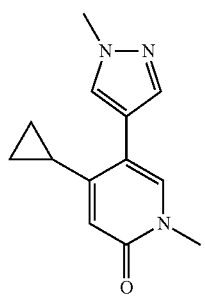 [SMILES: Cn1cc(-c2cn(C)c(=O)cc2C2CC2)cn1] | 4-cyclopropyl-1-methyl-5-(1-methyl-1H-pyrazol-4-yl)pyridin-2(1H)-one | A |
| 145 | 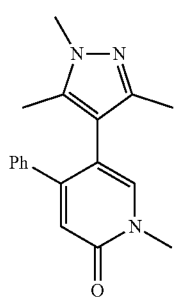 | 1-methyl-4-phenyl-5-(1,3,5-trimethyl-1H-pyrazol-4-yl)pyridin-2(1H)-one | B |
| 146 | 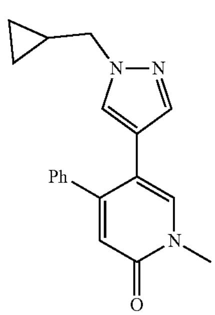 [SMILES: Cn1cc(-c2cnn(CC3CC3)c2)c(-c2ccccc2)cc1=O] | 5-(1-(cyclopropylmethyl)-1H-pyrazol-4-yl)-1-methyl-4-phenylpyridin-2(1H)-one | A |

TABLE 29-continued

| Example | Structure | Name | CBP IC$_{50}$ (μM) |
|---|---|---|---|
| 147 | 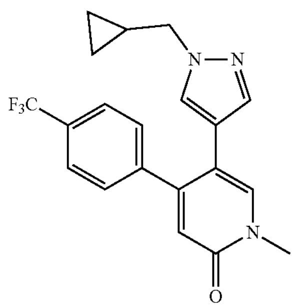 [SMILES: Cn1cc(-c2cnn(CC3CC3)c2)c(-c2ccc(C(F)(F)F)cc2)cc1=O] | 5-(1-Cyclopropylmethyl-1H-pyrazol-4-yl)-1-methyl-4-(4-trifluoromethyl-phenyl)-1H-pyridin-2-one | A |
| 148 | 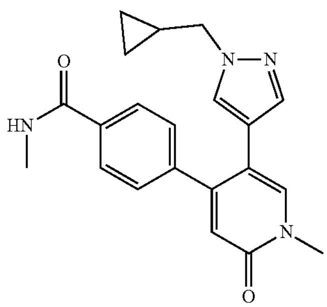 [SMILES: CNC(=O)c1ccc(-c2cc(=O)n(C)cc2-c2cnn(CC3CC3)c2)cc1] | 4-[5-(1-Cyclopropylmethyl-1H-pyrazol-4-yl)-1-methyl-2-oxo-1,2-dihydro-pyridin-4-yl]-N-methylbenzamide | A |
| 149 | 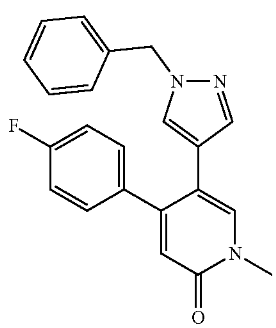 [SMILES: Cn1cc(-c2cnn(Cc3ccccc3)c2)c(-c2ccc(F)cc2)cc1=O] | 5-(1-benzyl-1H-pyrazol-4-yl)-4-(4-fluorophenyl)-1-methylpyridin-2(1H)-one | A |
| 150 | 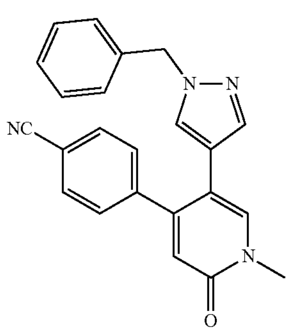 [SMILES: Cn1cc(-c2cnn(Cc3ccccc3)c2)c(-c2ccc(C#N)cc2)cc1=O] | 4-(5-(1-benzyl-1H-pyrazol-4-yl)-1-methyl-2-oxo-1,2-dihydropyridin-4-yl)benzonitrile | A |

TABLE 29-continued

| Example | Structure | Name | CBP IC$_{50}$ (μM) |
|---|---|---|---|
| 151 | 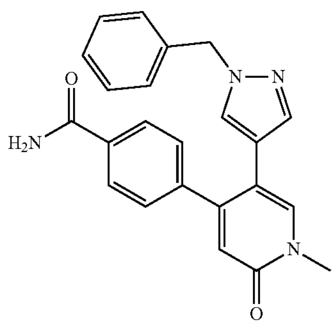 [SMILES: Cn1cc(-c2cnn(Cc3ccccc3)c2)c(-c2ccc(C(N)=O)cc2)cc1=O] | 4-(5-(1-benzyl-1H-pyrazol-4-yl)-1-methyl-2-oxo-1,2-dihydropyridin-4-yl)benzamide | A |
| 152 | 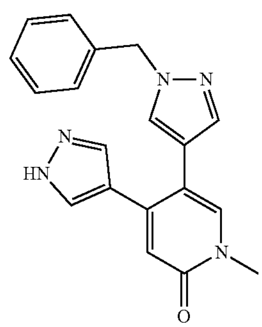 [SMILES: Cn1cc(-c2cnn(Cc3ccccc3)c2)c(-c2cn[nH]c2)cc1=O] | 5-(1-benzyl-1H-pyrazol-4-yl)-1-methyl-4-(1H-pyrazol-4-yl)pyridin-2(1H)-one | A |
| 153 | 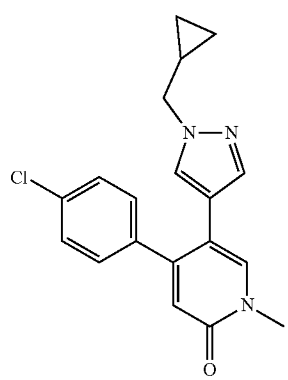 [SMILES: Cn1cc(-c2cnn(CC3CC3)c2)c(-c2ccc(Cl)cc2)cc1=O] | 4-(4-Chloro-phenyl)-5-(1-cyclopropylmethyl-1H-pyrazol-4-yl)-1-methyl-1H-pyridin-2-one | A |
| 154 | 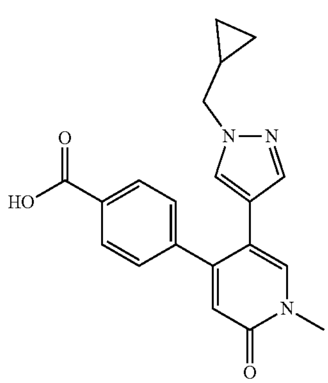 [SMILES: Cn1cc(-c2cnn(CC3CC3)c2)c(-c2ccc(C(=O)O)cc2)cc1=O] | 4-[5-(1-Cyclopropylmethyl-1H-pyrazol-4-yl)-1-methyl-2-oxo-1,2-dihydro-pyridin-4-yl]-benzoic acid | A |

TABLE 29-continued

| Example | Name | CBP IC$_{50}$ (μM) |
|---|---|---|
| 155 | 4-(5-(1-benzyl-1H-pyrazol-4-yl)-1-methyl-2-oxo-1,2-dihydropyridin-4-yl)benzoic acid | A |
| 156 | 4-[5-(1-Cyclopropylmethyl-1H-pyrazol-4-yl)-1-methyl-2-oxo-1,2-dihydro-pyridin-4-yl]-benzonitrile | B |
| 157 | 5-(1-(cyclohexylmethyl)-1H-pyrazol-4-yl)-1-methyl-4-phenylpyridin-2(1H)-one | A |
| 158 | 2-(4-(5-(1-benzyl-1H-pyrazol-4-yl)-1-methyl-2-oxo-1,2-dihydropyridin-4-yl)-1H-pyrazol-1-yl)acetamide | A |

TABLE 29-continued

| Example | Name | CBP IC$_{50}$ (μM) |
|---|---|---|
| 159 | 2-(4-(5-(1-benzyl-1H-pyrazol-4-yl)-1-methyl-2-oxo-1,2-dihydropyridin-4-yl)-1H-pyrazol-1-yl)acetic acid | A |
| 160 | 5-(1-benzyl-1H-pyrazol-4-yl)-4-(1-(difluoromethyl)-1H-pyrazol-4-yl)-1-methylpyridin-2(1H)-one | A |
| 161 | 5-(1-benzyl-1H-pyrazol-4-yl)-4-(1-(2-hydroxy-2-methylpropyl)-1H-pyrazol-4-yl)-1-methylpyridin-2(1H)-one | A |
| 162 | 5-(5,6-dihydro-4H-pyrrolo[1,2-b]pyrazol-3-yl)-1-methyl-4-phenylpyridin-2(1H)-one | A |

TABLE 29-continued

| Example | Name | CBP IC$_{50}$ (μM) |
|---|---|---|
| 163 | 2-(4-(5-(1-benzyl-1H-pyrazol-4-yl)-1-methyl-2-oxo-1,2-dihydropyridin-4-yl)-1H-pyrazol-1-yl)acetonitrile | A |
| 164 | 5-(1,5-dimethyl-1H-pyrazol-4-yl)-1-methyl-4-phenylpyridin-2(1H)-one | B |
| 165 | 5-(1-Benzyl-1H-pyrazol-4-yl)-y1-methyl-4-propoxy-1H-pyridin-2-one | A |
| 166 | 3-[5-(1-Benzyl-1H-pyrazol-4-yl)-1-methyl-2-oxo-1,2-dihydro-pyridin-4-yloxy]-propionic acid | A |

TABLE 29-continued

| Example | Structure | Name | CBP IC$_{50}$ (µM) |
|---|---|---|---|
| 167 | 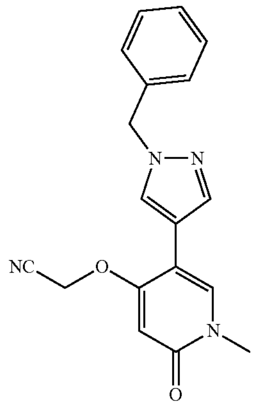 [SMILES: Cn1cc(-c2cnn(Cc3ccccc3)c2)c(OCC#N)cc1=O] | [5-(1-Benzyl-1H-pyrazol-4-yl)-1-methyl-2-oxo-1,2-dihydro-pyridin-4-yloxy]-acetonitrile | A |
| 168 | 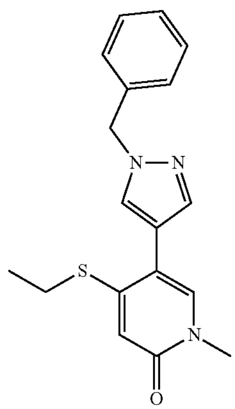 [SMILES: CCSc1cc(=O)n(C)cc1-c1cnn(Cc2ccccc2)c1] | 5-(1-Benzyl-1H-pyrazol-4-yl)-4-ethylsulfanyl-1-methyl-1H-pyridin-2-one | A |
| 169 | 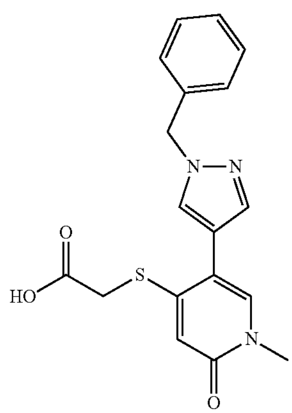 [SMILES: Cn1cc(-c2cnn(Cc3ccccc3)c2)c(SCC(=O)O)cc1=O] | [5-(1-Benzyl-1H-pyrazol-4-yl)-1-methyl-2-oxo-1,2-dihydro-pyridin-4-ylsulfanyl]-acetic acid | A |
| 170 | 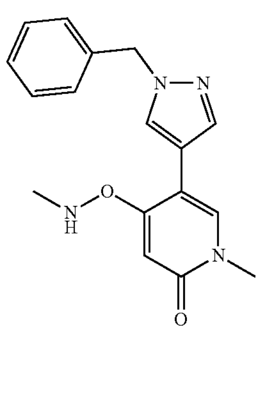 [SMILES: CNOc1cc(=O)n(C)cc1-c1cnn(Cc2ccccc2)c1] | 5-(1-benzyl-1H-pyrazol-4-yl)-1-methyl-4-((methylamino)oxy)pyridin-2(1H)-one | A |

TABLE 29-continued

| Example | Structure | Name | CBP IC$_{50}$ (μM) |
|---|---|---|---|
| 171 | 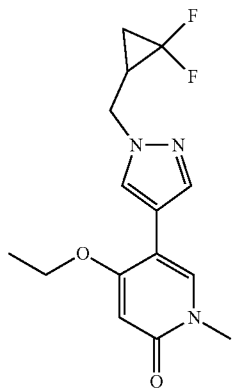 [SMILES: CCOc1cc(=O)n(C)cc1-c1cnn(CC2CC2(F)F)c1] | 5-[1-(2,2-Difluoro-cyclopropylmethyl)-1H-pyrazol-4-yl]-4-ethoxy-1-methyl-1H-pyridin-2-one | A |
| 172 | 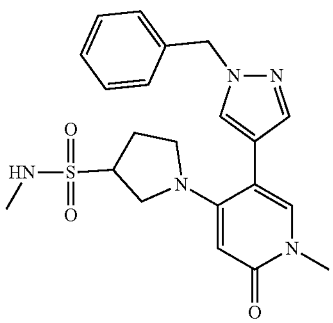 | 1-(5-(1-benzyl-1H-pyrazol-4-yl)-1-methyl-2-oxo-1,2-dihydropyridin-4-yl)-N-methylpyrrolidine-3-sulfonamide | A |
| 173 | 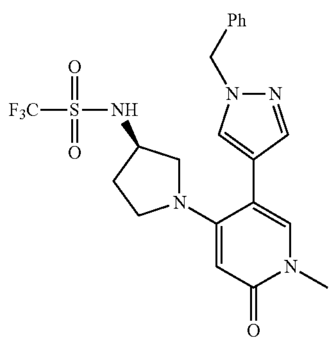 [SMILES: Cn1cc(-c2cnn(Cc3ccccc3)c2)c(N2CC[C@@H](NS(=O)(=O)C(F)(F)F)C2)cc1=O] | (R)-N-(1-(5-(1-benzyl-1H-pyrazol-4-yl)-1-methyl-2-oxo-1,2-dihydropyridin-4-yl)pyrrolidin-3-yl)-1,1,1-trifluoromethanesulfonamide | B |
| 174 | 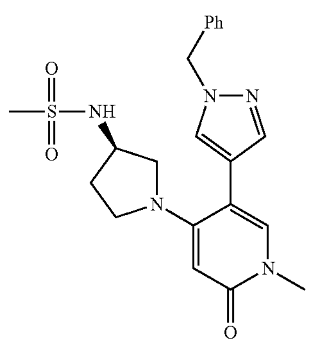 | (R)-N-(1-(5-(1-benzyl-1H-pyrazol-4-yl)-1-methyl-2-oxo-1,2-dihydropyridin-4-yl)pyrrolidin-3-yl)methanesulfonamide | B |

TABLE 29-continued

| Example | Structure | Name | CBP IC$_{50}$ (μM) |
|---|---|---|---|
| 175 | 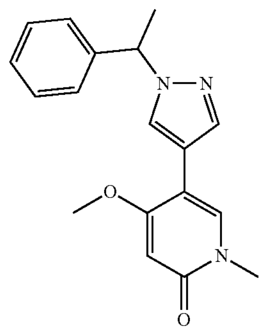 [SMILES: COc1cc(=O)n(C)cc1-c1cnn(C(C)c2ccccc2)c1] | 4-methoxy-1-methyl-5-(1-(1-phenylethyl)-1H-pyrazol-4-yl)pyridin-2(1H)-one | A |
| 176 | 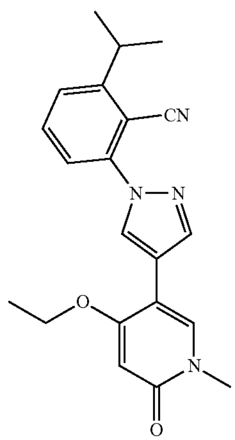 [SMILES: CCOc1cc(=O)n(C)cc1-c1cnn(-c2cccc(C(C)C)c2C#N)c1] | 2-[4-(4-Ethoxy-1-methyl-6-oxo-1,6-dihydro-pyridin-3-yl)-pyrazol-1-yl]-6-isopropyl-benzonitrile | A |
| 177 | 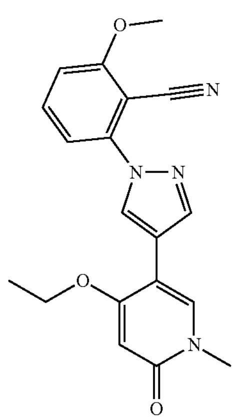 [SMILES: CCOc1cc(=O)n(C)cc1-c1cnn(-c2cccc(OC)c2C#N)c1] | 2-[4-(4-Ethoxy-1-methyl-6-oxo-1,6-dihydro-pyridin-3-yl)-pyrazol-1-yl]-6-methoxy-benzonitrile | A |

TABLE 29-continued

| Example | Name | CBP IC$_{50}$ (μM) |
|---|---|---|
| 178 | 2-Chloro-6-[4-(4-ethoxy-1-methyl-6-oxo-1,6-dihydro-pyridin-3-yl)-pyrazol-1-yl]-benzonitrile | A |
| 179 | 2-[4-(4-Ethoxy-1-methyl-6-oxo-1,6-dihydro-pyridin-3-yl)-pyrazol-1-yl]-6-methyl-benzonitrile | A |
| 180 | 4-Ethoxy-5-[1-(2-methanesulfonyl-phenyl)-1H-pyrazol-4-yl]-1-methyl-1H-pyridin-2-one | A |
| 181 | 4-ethoxy-1-methyl-5-(1-(1-(methylsulfonyl)piperidin-3-yl)-1H-pyrazol-4-yl)pyridin-2(1H)-one | A |

TABLE 29-continued

| Example | Structure | Name | CBP IC$_{50}$ (μM) |
|---|---|---|---|
| 182 | 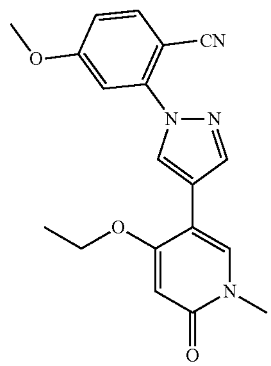 | 2-[4-(4-Ethoxy-1-methyl-6-oxo-1,6-dihydro-pyridin-3-yl)-pyrazol-1-yl]-4-methoxy-benzonitrile | A |
| 183 | 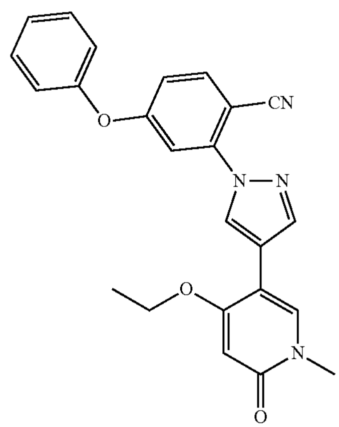 [SMILES: CCOc1cc(=O)n(C)cc1-c1cnn(-c2cc(Oc3ccccc3)ccc2C#N)c1] | 2-[4-(4-Ethoxy-1-methyl-6-oxo-1,6-dihydro-pyridin-3-yl)-pyrazol-1-yl]-4-phenoxy-benzonitrile | A |
| 184 | 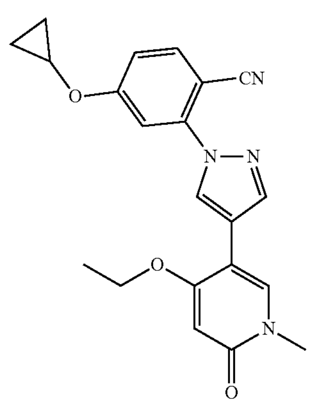 [SMILES: CCOc1cc(=O)n(C)cc1-c1cnn(-c2cc(OC3CC3)ccc2C#N)c1] | 4-Cyclopropoxy-2-[4-(4-ethoxy-1-methyl-6-oxo-1,6-dihydro-pyridin-3-yl)-pyrazol-1-yl]-benzonitrile | A |
| 185 | 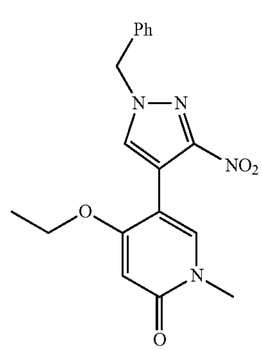 [SMILES: CCOc1cc(=O)n(C)cc1-c1cn(Cc2ccccc2)nc1[N+](=O)[O-]] | 5-(1-benzyl-3-nitro-1H-pyrazol-4-yl)-4-ethoxy-1-methylpyridin-2(1H)-one | A |

TABLE 29-continued

| Example | Structure | Name | CBP IC$_{50}$ (μM) |
|---|---|---|---|
| 186 | 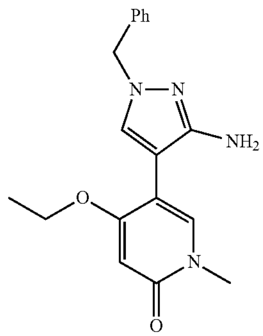 [SMILES: CCOc1cc(=O)n(C)cc1-c1cn(Cc2ccccc2)nc1N] | 5-(3-amino-1-benzyl-1H-pyrazol-4-yl)-4-ethoxy-1-methylpyridin-2(1H)-one | A |
| 187 | 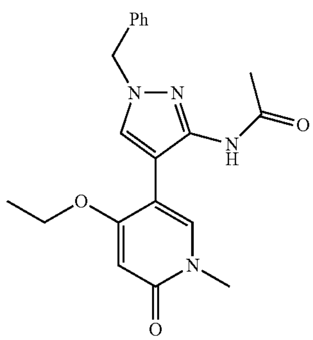 [SMILES: CCOc1cc(=O)n(C)cc1-c1cn(Cc2ccccc2)nc1NC(C)=O] | N-[1-Benzyl-4-(4-ethoxy-1-methyl-6-oxo-1,6-dihydro-pyridin-3-yl)-1H-pyrazol-3-yl]-acetamide | B |
| 188 | 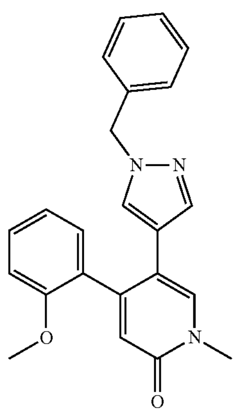 [SMILES: COc1ccccc1-c1cc(=O)n(C)cc1-c1cnn(Cc2ccccc2)c1] | 5-(1-Benzyl-1H-pyrazol-4-yl)-4-(2-methoxy-phenyl)-1-methyl-1H-pyridin-2-one | C |
| 189 | 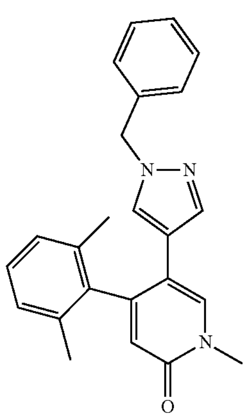 [SMILES: Cc1cccc(C)c1-c1cc(=O)n(C)cc1-c1cnn(Cc2ccccc2)c1] | 5-(1-Benzyl-1H-pyrazol-4-yl)-4-(2,6-dimethyl-phenyl)-1-methyl-1H-pyridin-2-one | C |

TABLE 29-continued

| Example | Structure | Name | CBP IC$_{50}$ (μM) |
|---|---|---|---|
| 190 | 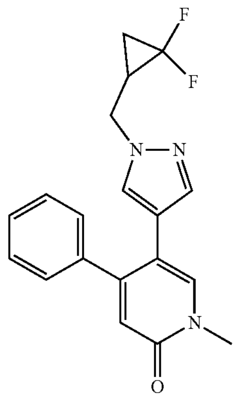 [SMILES: Cn1cc(-c2cnn(CC3CC3(F)F)c2)c(-c2ccccc2)cc1=O] | 5-[1-(2,2-Difluoro-cyclopropylmethyl)-1H-pyrazol-4-yl]-1-methyl-4-phenyl-1H-pyridin-2-one | A |
| 191 | 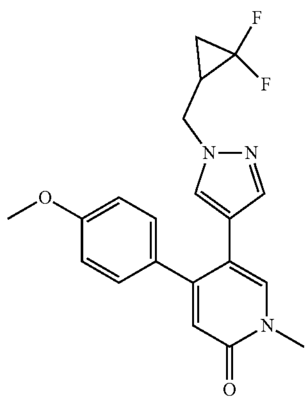 | 5-[1-(2,2-Difluoro-cyclopropymethyl)-1H-pyrazol-4-yl]-4-(4-methoxy-phenyl)-1-methyl-1H-pyridin-2-one | A |
| 192 | 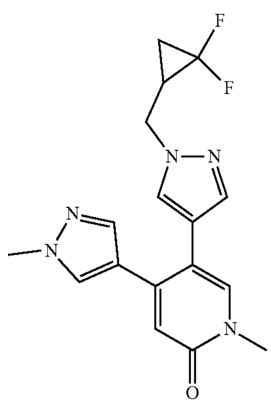 | 5-[1-(2,2-Difluoro-cyclopropylmethyl)-1H-pyrazol-4-yl]-1-methyl-4-(1-methyl-1H-pyrazol-4-yl)-1H-pyridin-2-one | A |
| 193 | 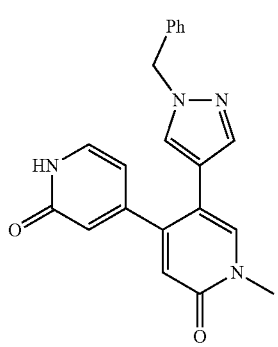 [SMILES: Cn1cc(-c2cnn(Cc3ccccc3)c2)c(-c2cc[nH]c(=O)c2)cc1=O] | 5-(1-Benzyl-1H-pyrazol-4-yl)-1-methyl-1H,1'H-[4,4']bipyridinyl-2,2'-dione | A |

TABLE 29-continued

| Example | Structure | Name | CBP IC$_{50}$ (μM) |
|---|---|---|---|
| 194 | 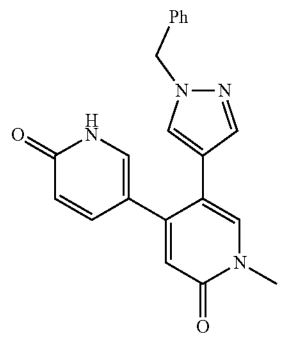 [SMILES: Cn1cc(-c2cnn(Cc3ccccc3)c2)c(-c2ccc(=O)[nH]c2)cc1=O] | 5'-(1-Benzyl-1H-pyrazol-4-yl)-1'-methyl-1H,1'H-[3,4']bipyridinyl-6,2'-dione | A |
| 195 | 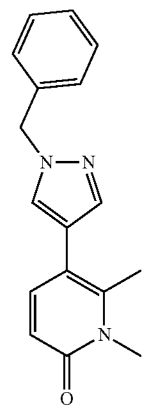 [SMILES: Cc1c(-c2cnn(Cc3ccccc3)c2)ccc(=O)n1C] | 5-(1-Benzyl-1H-pyrazol-4-yl)-1,6-dimethyl-1H-pyridin-2-one | C |
| 196 | 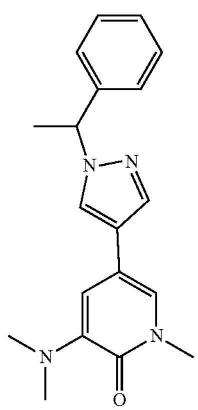 | 3-Dimethylamino-1-methyl-5-[1-(1-phenyl-ethyl)-1H-pyrazol-4-yl]-1H-pyridin-2-one | B |
| 197 | 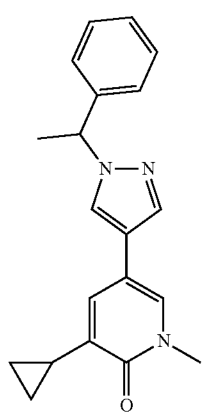 [SMILES: CC(c1ccccc1)n1cc(-c2cc(C3CC3)c(=O)n(C)c2)cn1] | 3-Cyclopropyl-1-methyl-5-[1-(1-phenyl-ethyl)-1H-pyrazol-4-yl]-1H-pyridin-2-one | C |

TABLE 29-continued

| Example | Structure | Name | CBP IC$_{50}$ (μM) |
|---|---|---|---|
| 198 | 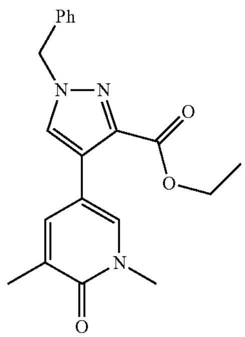 [SMILES: CCOC(=O)c1nn(Cc2ccccc2)cc1-c1cc(C)c(=O)n(C)c1] | 1-Benzyl-4-(1,5-dimethyl-6-oxo-1,6-dihydro-pyridin-3-yl)-1H-pyrazole-3-carboxylic acid ethyl ester | A |
| 199 | 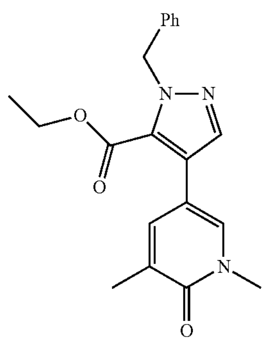 [SMILES: CCOC(=O)c1c(-c2cc(C)c(=O)n(C)c2)cnn1Cc1ccccc1] | 2-Benzyl-4-(1,5-dimethyl-6-oxo-1,6-dihydro-pyridin-3-yl)-2H-pyrazole-3-carboxylic acid ethyl estere | A |
| 200 | 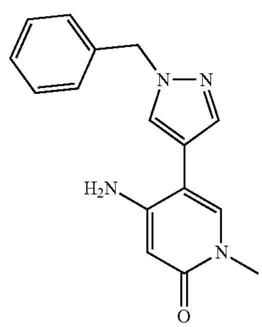 [SMILES: Cn1cc(-c2cnn(Cc3ccccc3)c2)c(N)cc1=O] | 4-amino-5-(1-benzyl-1H-pyrazol-4-yl)-1-methylpyridin-2(1H)-one | B |
| 201 | 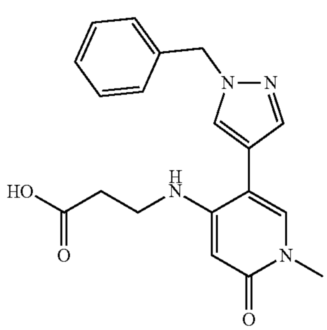 [SMILES: Cn1cc(-c2cnn(Cc3ccccc3)c2)c(NCCC(=O)O)cc1=O] | 3-((5-(1-benzyl-1H-pyrazol-4-yl)-1-methyl-2-oxo-1,2-dihydropyridin-4-yl)amino)propanoic acid | A |

TABLE 29-continued

| Example | Structure | Name | CBP IC$_{50}$ (μM) |
|---|---|---|---|
| 202 | 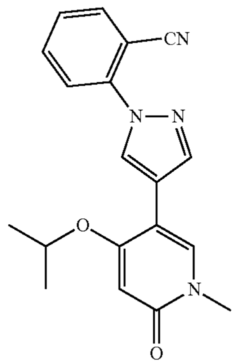 [SMILES: CC(C)Oc1cc(=O)n(C)cc1-c1cnn(-c2ccccc2C#N)c1] | 2-[4-(4-Isopropoxy-1-methyl-6-oxo-1,6-dihydro-pyridin-3-yl)-pyrazol-1-yl]-benzonitrile | A |
| 203 | 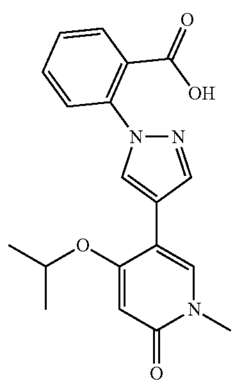 [SMILES: CC(C)Oc1cc(=O)n(C)cc1-c1cnn(-c2ccccc2C(=O)O)c1] | 2-[4-(4-Isopropoxy-1-methyl-6-oxo-1,6-dihydro-pyridin-3-yl)-pyrazol-1-yl]-benzoic acid | A |
| 204 | 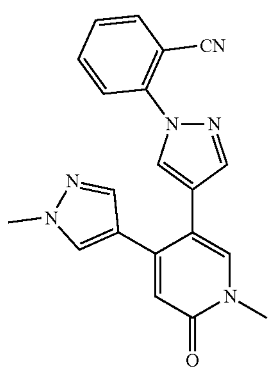 | 2-{4-[1-Methyl-4-(1-methyl-1H-pyrazol-4-yl)-6-oxo-1,6-dihydro-pyridin-3-yl]-pyrazol-1-yl}-benzonitrile | A |
| 205 | 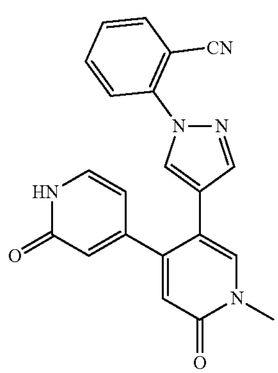 [SMILES: Cn1cc(-c2cnn(-c3ccccc3C#N)c2)c(-c2cc[nH]c(=O)c2)cc1=O] | 2-[4-(1-Methyl-6,2'-dioxo-1,6,1',2'-tetrahydro-[4,4']bipyridinyl-3-yl)-pyrazol-1-yl]-benzonitrile | A |

TABLE 29-continued

| Example | Structure | Name | CBP IC$_{50}$ (μM) |
|---|---|---|---|
| 206 | 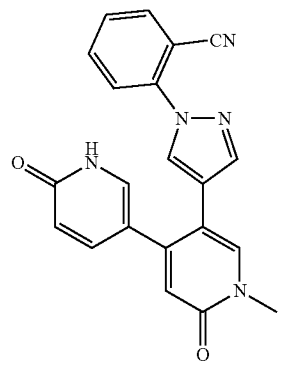 [SMILES: Cn1cc(-c2cnn(-c3ccccc3C#N)c2)c(-c2ccc(=O)[nH]c2)cc1=O] | 2-[4-(1'-Methyl-6,6'-dioxo-1,6,1',6'-tetrahydro-[3,4']bipyridinyl-3'-yl)-pyrazol-1-yl]-benzonitrile | A |
| 207 | 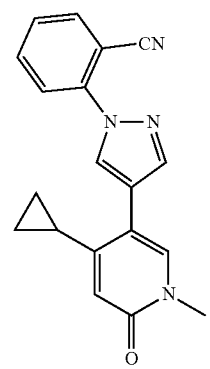 [SMILES: Cn1cc(-c2cnn(-c3ccccc3C#N)c2)c(C2CC2)cc1=O] | 2-[4-(4-Cyclopropyl-1-methyl-6-oxo-1,6-dihydro-pyridin-3-yl)-pyrazol-1-yl]-benzonitrile | A |
| 208 | 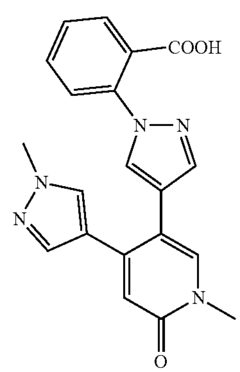 [SMILES: Cn1cc(-c2cc(=O)n(C)cc2-c2cnn(-c3ccccc3C(=O)O)c2)cn1] | 2-{4-[1-Methyl-4-(1-methyl-1H-pyrazol-4-yl)-6-oxo-1,6-dihydro-pyridin-3-yl]-pyrazol-1-yl}-benzoic acid | A |
| 209 | 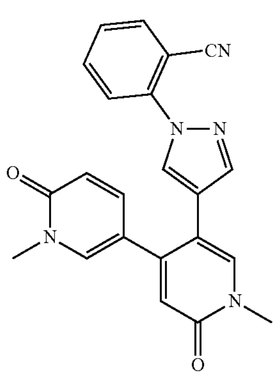 | 2-[4-(1,1'-Dimethyl-6,6'-dioxo-1,6,1',6'-tetrahydro-[3,4']bipyridinyl-3'-yl)-pyrazol-1-yl]-benzonitrile | A |

TABLE 29-continued

| Example | Structure | Name | CBP IC$_{50}$ (μM) |
|---|---|---|---|
| 210 | 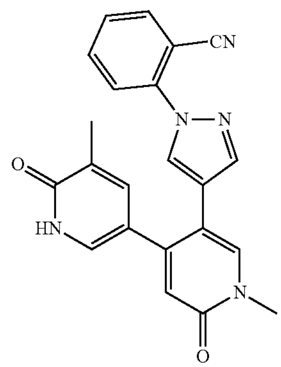 [SMILES: Cc1cc(-c2cc(=O)n(C)cc2-c2cnn(-c3ccccc3C#N)c2)c[nH]c1=O] | 2-{4-(5,1'-Dimethyl-6,6'-dioxo-1,6,1',6'-tetrahydro-[3,4']bipyridinyl-3'-yl)-pyrazol-1-yl]-benzonitrile | A |
| 211 | 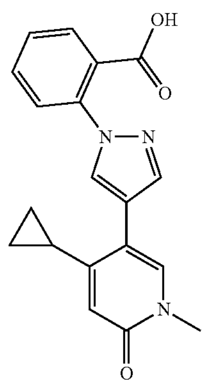 [SMILES: Cn1cc(-c2cnn(-c3ccccc3C(=O)O)c2)c(C2CC2)cc1=O] | 2-[4-(4-Cyclopropyl-1-methyl-6-oxo-1,6-dihydro-pyridin-3-yl)-pyrazol-1-yl]-benzoic acid | A |
| 212 | 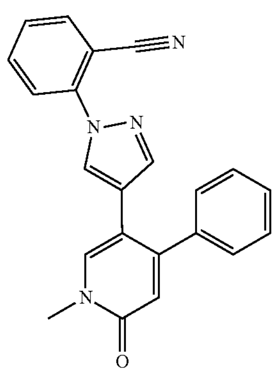 [SMILES: Cn1cc(-c2cnn(-c3ccccc3C#N)c2)c(-c2ccccc2)cc1=O] | 2-[4-(1-Methyl-6-oxo-4-phenyl-1,6-dihydro-pyridin-3-yl)-pyrazol-1-yl]-benzonitrile | A |
| 213 | 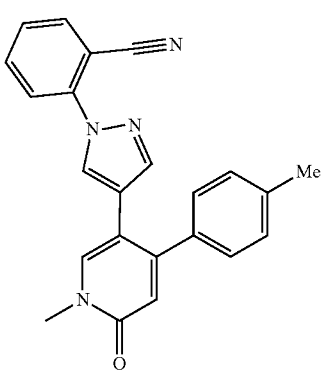 [SMILES: Cc1ccc(-c2cc(=O)n(C)cc2-c2cnn(-c3ccccc3C#N)c2)cc1] | 2-[4-(1-Methyl-6-oxo-4-p-tolyl-1,6-dihydro-pyridin-3-yl)-pyrazol-1-yl]-benzonitrile | A |

TABLE 29-continued

| Example | Structure | Name | CBP IC$_{50}$ (μM) |
|---|---|---|---|
| 214 | 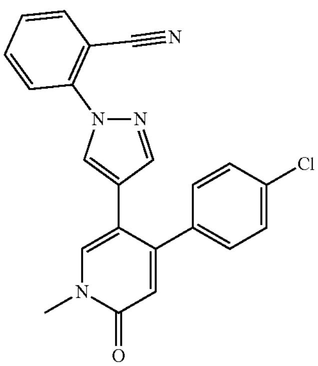 [SMILES: Cn1cc(-c2cnn(-c3ccccc3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-benzonitrile | A |
| 215 | 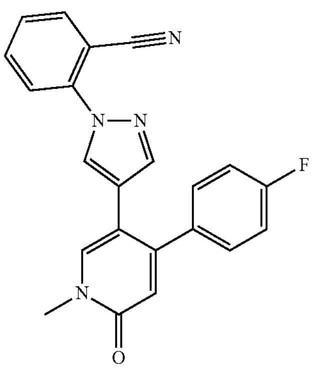 [SMILES: Cn1cc(-c2cnn(-c3ccccc3C#N)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzonitrile | A |
| 216 | 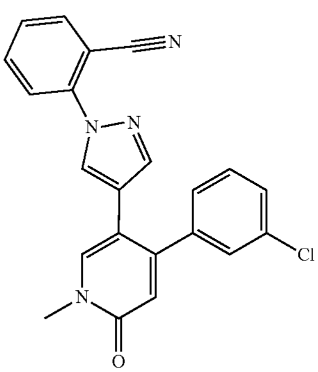 [SMILES: Cn1cc(-c2cnn(-c3ccccc3C#N)c2)c(-c2cccc(Cl)c2)cc1=O] | 2-{4-[4-(3-Chloro-phenyl)-1-methyl-6-oxo-1,6-dihydro-pyridin-3-yl]-pyrazol-1-yl}-benzonitrile | A |
| 217 | 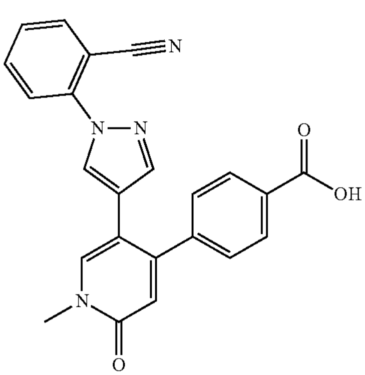 [SMILES: Cn1cc(-c2cnn(-c3ccccc3C#N)c2)c(-c2ccc(C(=O)O)cc2)cc1=O] | 4-{5-[1-(2-Cyano-phenyl)-1H-pyrazol-4-yl]-1-methyl-2-oxo-1,2-dihydro-pyridin-4-yl}-benzoic acid | A |

TABLE 29-continued

| Example | Name | CBP IC$_{50}$ (μM) |
|---|---|---|
| 218 | 4-{5-[1-(2-Cyano-phenyl)-1H-pyrazol-4-yl]-1-methyl-2-oxo-1,2-dihydro-pyridin-4-yl}-benzamide | A |
| 219 | 4-{5-[1-(2-Cyano-phenyl)-1H-pyrazol-4-yl]-1-methyl-2-oxo-1,2-dihydro-pyridin-4-yl}-N-methyl-benzamide | A |
| 220 | 2-[4-(2'-Methoxy-1-methyl-6-oxo-1,6-dihydro-[4,4']bipyridinyl-3-yl)-pyrazol-1-yl]-benzonitrile | A |
| 221 | 2-[4-(1,1'-Dimethyl-6,2'-dioxo-1,6,1',2'-tetrahydro-[4,4']bipyridinyl-3-yl)-pyrazol-1-yl]-benzonitrile | A |

TABLE 29-continued

| Example | Name | CBP IC$_{50}$ (μM) |
|---|---|---|
| 222 | 2-[4-(1'-Cyclopropyl-1-methyl-6,2'-dioxo-1,6,1',2'-tetrahydro-[4,4']bipyridinyl-3-yl)-pyrazol-1-yl]-benzonitrile | A |
| 223 | 2-[4-(1-Methyl-6-oxo-4-phenyl-1,6-dihydro-pyridin-3-yl)-pyrazol-1-yl]-benzoic acid | A |
| 224 | 2-[4-(1-Methyl-6-oxo-4-p-tolyl-1,6-dihydro-pyridin-3-yl)-pyrazol-1-yl]-benzoic acid | A |
| 225 | 2-(4-(4-(4-chlorophenyl)-1-methyl-6-oxo-1,6-dihydropyridin-3-yl)-1H-pyrazol-1-yl)benzoic acid | A |

TABLE 29-continued

| Example | Structure | Name | CBP IC$_{50}$ (μM) |
|---|---|---|---|
| 226 | 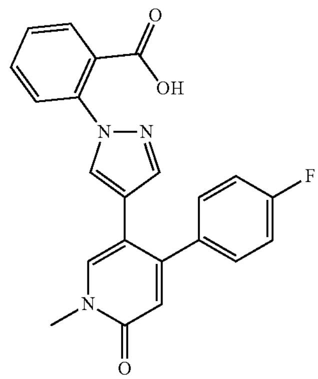 [SMILES: Cn1cc(-c2cnn(-c3ccccc3C(=O)O)c2)c(-c2ccc(F)cc2)cc1=O] | 2-{4-[4-(4-Fluoro-phenyl)-1-methyl-6-oxo-1,6-dihydro-pyridin-3-yl]-pyrazol-1-yl}-benzoic acid | A |
| 227 | 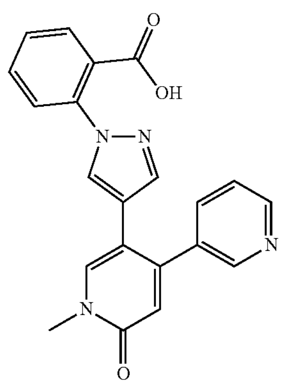 [SMILES: Cn1cc(-c2cnn(-c3ccccc3C(=O)O)c2)c(-c2cccnc2)cc1=O] | 2-[4-(1'-Methyl-6'-oxo-1',6'-dihydro-[3,4']bipyridinyl-3'-yl)-pyrazol-1-yl]-benzoic acid | A |
| 228 | 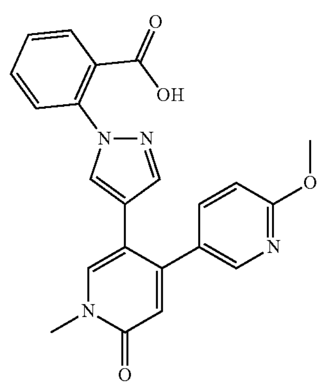 [SMILES: COc1ccc(-c2cc(=O)n(C)cc2-c2cnn(-c3ccccc3C(=O)O)c2)cn1] | 2-[4-(6-Methoxy-1'-methyl-6'-oxo-1',6'-dihydro-[3,4']bipyridinyl-3'-yl)-pyrazol-1-yl]-benzoic acid | A |
| 229 | 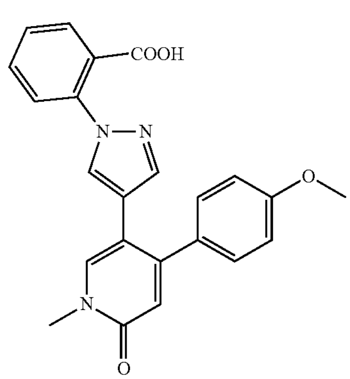 [SMILES: COc1ccc(-c2cc(=O)n(C)cc2-c2cnn(-c3ccccc3C(=O)O)c2)cc1] | 2-{4-(4-Methoxy-phenyl)-1-methyl-6-oxo-1,6-dihydro-pyridin-3-yl]-pyrazol-1-yl}-benzoic acid | A |

TABLE 29-continued

| Example | Structure | Name | CBP IC$_{50}$ (μM) |
|---|---|---|---|
| 230 | 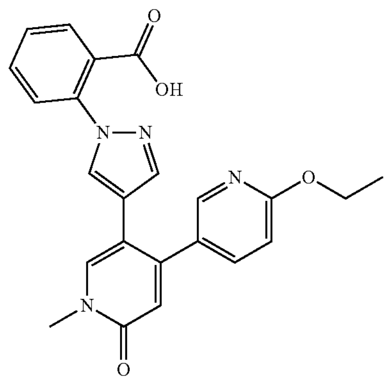 [SMILES: CCOc1ccc(-c2cc(=O)n(C)cc2-c2cnn(-c3ccccc3C(=O)O)c2)cn1] | 2-[4-(6-Ethoxy-1'-methyl-6'-oxo-1',6'-dihydro-[3,4']bipyridinyl-3'-yl)-pyrazol-1-yl]-benzoic acid | A |
| 231 | 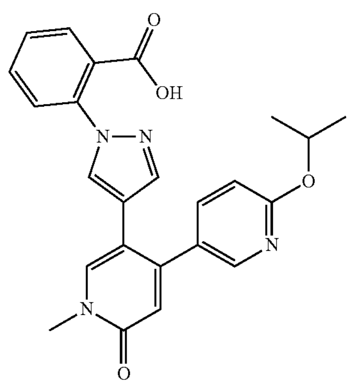 [SMILES: CC(C)Oc1ccc(-c2cc(=O)n(C)cc2-c2cnn(-c3ccccc3C(=O)O)c2)cn1] | 2-[4-(6-Isopropoxy-1'-methyl-6'-oxo-1',6'-dihydro-[3,4']bipyridinyl-3'-yl)-pyrazol-1-yl]-benzoic acid | A |
| 232 | 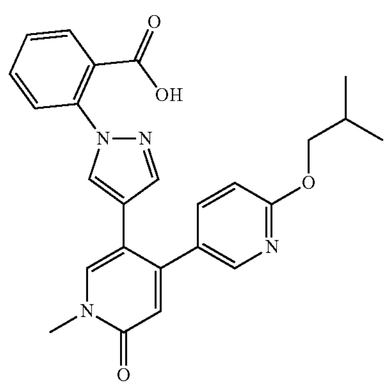 [SMILES: CC(C)COc1ccc(-c2cc(=O)n(C)cc2-c2cnn(-c3ccccc3C(=O)O)c2)cn1] | 2-[4-(6-Isobutoxy-1'-methyl-6'-oxo-1',6'-dihydro-[3,4']bipyridinyl-3'-yl)-pyrazol-1-yl]-benzoic acid | A |
| 233 | 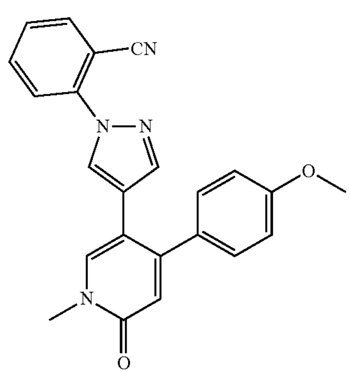 [SMILES: COc1ccc(-c2cc(=O)n(C)cc2-c2cnn(-c3ccccc3C#N)c2)cc1] | 2-{4-[4-(4-Methoxy-phenyl)-1-methyl-6-oxo-1,6-dihydro-pyridin-3-yl]-pyrazol-1-yl}-benzonitrile | A |

TABLE 29-continued

| Example | Structure | Name | CBP IC$_{50}$ (μM) |
|---|---|---|---|
| 234 | 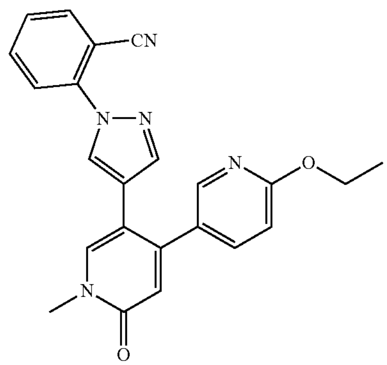 [SMILES: CCOc1ccc(-c2cc(=O)n(C)cc2-c2cnn(-c3ccccc3C#N)c2)cn1] | 2-[4-(6-Ethoxy-1'-methyl-6'-oxo-1',6'-dihydro-[3,4']bipyridinyl-3'-yl)-pyrazol-1-yl]-benzonitrile | A |
| 235 | 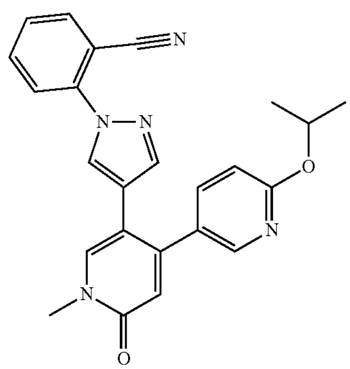 [SMILES: CC(C)Oc1ccc(-c2cc(=O)n(C)cc2-c2cnn(-c3ccccc3C#N)c2)cn1] | 2-[4-(6-Isopropoxy-1'-methyl-6'-oxo-1',6'-dihydro-[3,4']bipyridinyl-3'-yl)-pyrazol-1-yl]-benzonitrile | A |
| 236 | 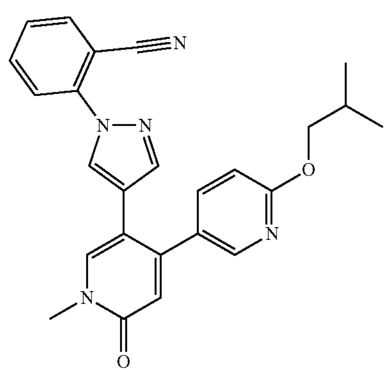 [SMILES: CC(C)COc1ccc(-c2cc(=O)n(C)cc2-c2cnn(-c3ccccc3C#N)c2)cn1] | 2-[4-(6-Isobutoxy-1'-methyl-6'-oxo-1',6'-dihydro-[3,4']bipyridinyl-3'-yl)-pyrazol-1-yl]-benzonitrile | A |
| 237 | 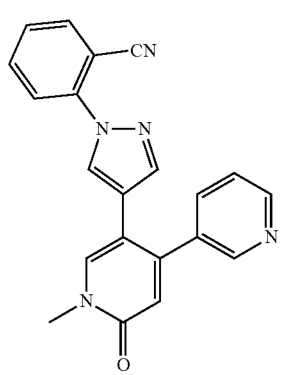 [SMILES: Cn1cc(-c2cnn(-c3ccccc3C#N)c2)c(-c2cccnc2)cc1=O] | 2-[4-(1'-Methyl-6'-oxo-1',6'-dihydro-[3,4']bipyridinyl-3'-yl)-pyrazol-1-yl]-benzonitrile | A |

TABLE 29-continued

| Example | Structure | Name | CBP IC$_{50}$ (μM) |
|---|---|---|---|
| 238 | 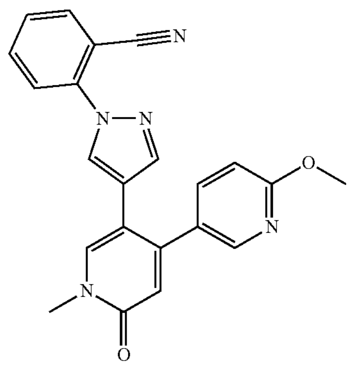 | 2-(4-(6-methoxy-1'-methyl-6'-oxo-1',6'-dihydro-[3,4'-bipyridin]-3'-yl)-1H-pyrazol-1-yl)benzonitrile | A |
| 239 | 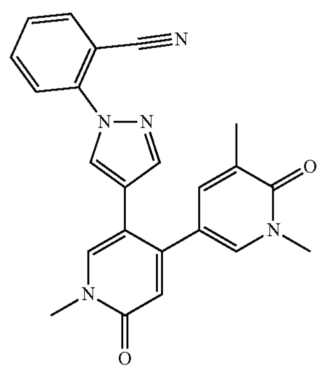 [SMILES: Cc1cc(-c2cc(=O)n(C)cc2-c2cnn(-c3ccccc3C#N)c2)cn(C)c1=O] | 2-(4-(1,1',5-trimethyl-6,6'-dioxo-1,1',6,6'-tetrahydro-[3,4'-bipyridin]-3'-yl)-1H-pyrazol-1-yl)benzonitrile | A |
| 240 | 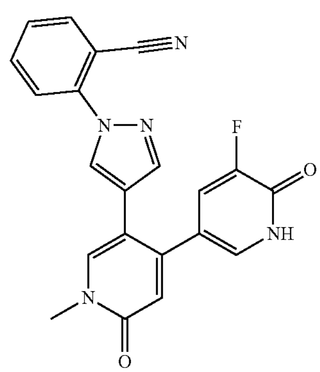 [SMILES: Cn1cc(-c2cnn(-c3ccccc3C#N)c2)c(-c2c[nH]c(=O)c(F)c2)cc1=O] | 2-(4-(5-fluoro-1'-methyl-6,6'-dioxo-1,1',6,6'-tetrahydro-[3,4'-bipyridin]-3'-yl)-1H-pyrazol-1-yl)benzonitrile | A |
| 241 | 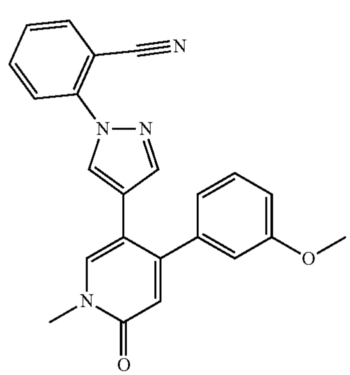 [SMILES: COc1cccc(-c2cc(=O)n(C)cc2-c2cnn(-c3ccccc3C#N)c2)c1] | 2-{4-[4-(3-Methoxy-phenyl)-1-methyl-6-oxo-1,6-dihydro-pyridin-3-yl]-pyrazol-1-yl}-benzonitrile | A |

TABLE 29-continued

| Example | Structure | Name | CBP IC$_{50}$ (μM) |
|---|---|---|---|
| 242 | 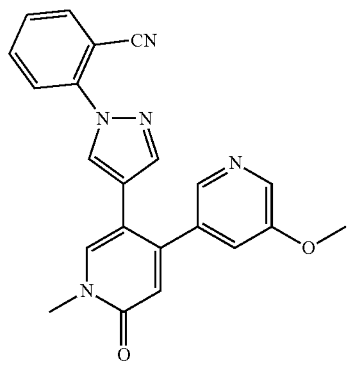 [SMILES: COc1cncc(-c2cc(=O)n(C)cc2-c2cnn(-c3ccccc3C#N)c2)c1] | 2-(4-(5-methoxy-1'-methyl-6'-oxo-1',6'-dihydro-[3,4'-bipyridin]-3'-yl)-1H-pyrazol-1-yl)benzonitrile | A |
| 243 | 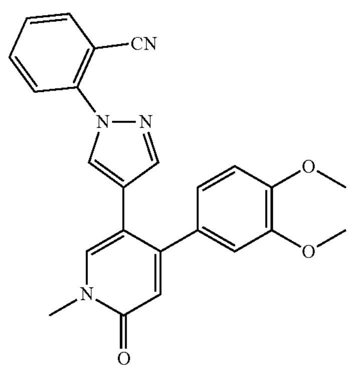 [SMILES: COc1ccc(-c2cc(=O)n(C)cc2-c2cnn(-c3ccccc3C#N)c2)cc1OC] | 2-(4-(4-(3,4-dimethoxyphenyl)-1-methyl-6-oxo-1,6-dihydropyridin-3-yl)-1H-pyrazol-1-yl)benzonitrile | A |
| 244 | 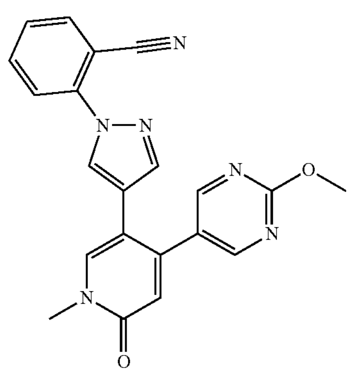 [SMILES: COc1ncc(-c2cc(=O)n(C)cc2-c2cnn(-c3ccccc3C#N)c2)cn1] | 2-{4-[4-(2-Methoxy-pyrimidin-5-yl)-1-methyl-6-oxo-1,6-dihydro-pyridin-3-yl]-pyrazol-1-yl}-benzonitrile | A |
| 245 | 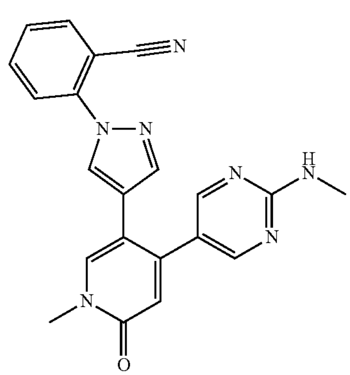 [SMILES: CNc1ncc(-c2cc(=O)n(C)cc2-c2cnn(-c3ccccc3C#N)c2)cn1] | 2-(4-(1-methyl-4-(2-(methylamino)pyrimidin-5-yl)-6-oxo-1,6-dihydropyridin-3-yl)-1H-pyrazol-1-yl)benzonitrile | A |

TABLE 29-continued

| Example | Structure | Name | CBP IC$_{50}$ (μM) |
|---|---|---|---|
| 246 | 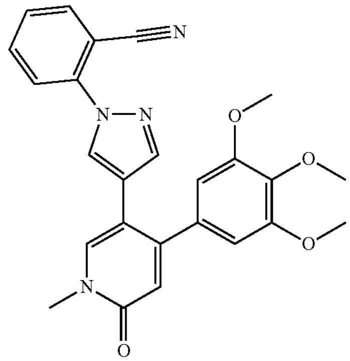 [SMILES: COc1cc(-c2cc(=O)n(C)cc2-c2cnn(-c3ccccc3C#N)c2)cc(OC)c1OC] | 2-{4-[1-Methyl-6-oxo-4-(3,4,5-trimethoxy-phenyl)-1,6-dihydro-pyridin-3-yl]-pyrazol-1-yl}-benzonitrile | B |
| 247 | 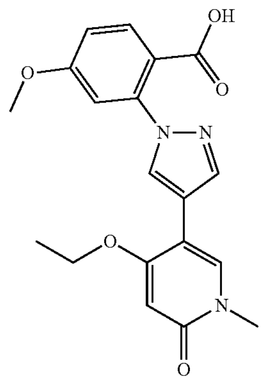 | 2-[4-(4-Ethoxy-1-methyl-6-oxo-1,6-dihydro-pyridin-3-yl)-pyrazol-1-yl]-4-methoxy-benzoic acid | A |
| 248 | 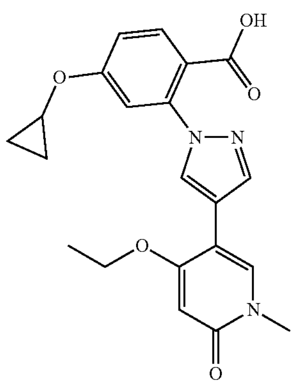 [SMILES: CCOc1cc(=O)n(C)cc1-c1cnn(-c2cc(OC3CC3)ccc2C(=O)O)c1] | 4-Cyclopropoxy-2-[4-(4-ethoxy-1-methyl-6-oxo-1,6-dihydro-pyridin-3-yl)-pyrazol-1-yl]-benzoic acid | A |
| 249 | 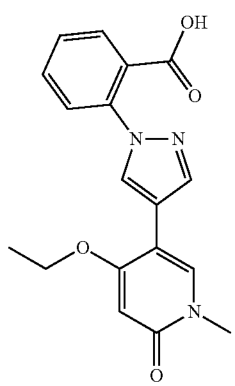 [SMILES: CCOc1cc(=O)n(C)cc1-c1cnn(-c2ccccc2C(=O)O)c1] | 2-(4-(4-ethoxy-1-methyl-6-oxo-1,6-dihydropyridin-3-yl)-1H-pyrazol-1-yl)benzoic acid | A |

TABLE 29-continued

| Example | Structure | Name | CBP IC$_{50}$ (μM) |
|---|---|---|---|
| 250 | 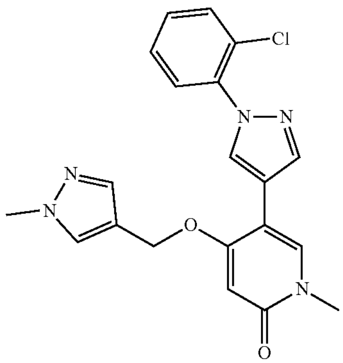 | 5-(1-(2-chlorophenyl)-1H-pyrazol-4-yl)-1-methyl-4-((1-methyl-1H-pyrazol-4-yl)methoxy)pyridin-2(1H)-one | A |
| 251 | 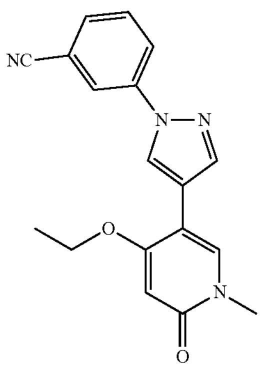 [SMILES: CCOc1cc(=O)n(C)cc1-c1cnn(-c2cccc(C#N)c2)c1] | 3-(4-(4-ethoxy-1-methyl-6-oxo-1,6-dihydropyridin-3-yl)-1H-pyrazol-1-yl)benzonitrile | A |
| 252 | 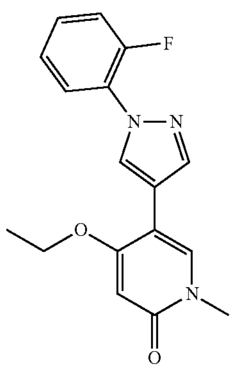 [SMILES: CCOc1cc(=O)n(C)cc1-c1cnn(-c2ccccc2F)c1] | 4-ethoxy-5-(1-(2-fluorophenyl)-1H-pyrazol-4-yl)-1-methylpyridin-2(1H)-one | A |
| 253 | 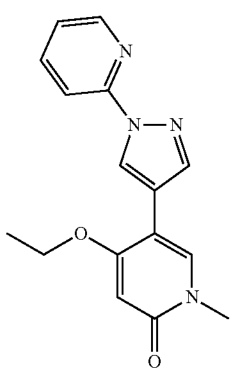 [SMILES: CCOc1cc(=O)n(C)cc1-c1cnn(-c2ccccn2)c1] | 4-ethoxy-1-methyl-5-(1-(pyridin-2-yl)-1H-pyrazol-4-yl)pyridin-2(1H)-one | A |

TABLE 29-continued

| Example | Structure | Name | CBP IC$_{50}$ (μM) |
|---|---|---|---|
| 254 | 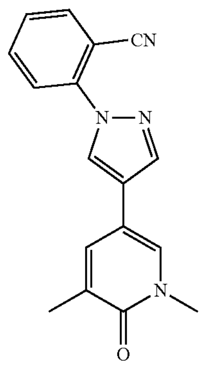 [SMILES: Cc1cc(-c2cnn(-c3ccccc3C#N)c2)cn(C)c1=O] | 2-[4-(1,5-Dimethyl-6-oxo-1,6-dihydro-pyridin-3-yl)-pyrazol-1-yl]-benzonitrile | A |
| 255 | 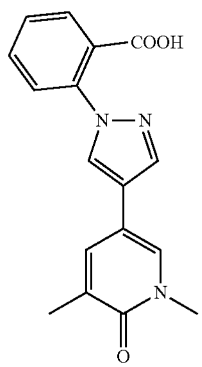 [SMILES: Cc1cc(-c2cnn(-c3ccccc3C(=O)O)c2)cn(C)c1=O] | 2-[4-1,5-Dimethyl-6-oxo-1,6-dihydro-pyridin-3-yl)-pyrazol-1-yl]-benzoic acid | A |
| 256 | 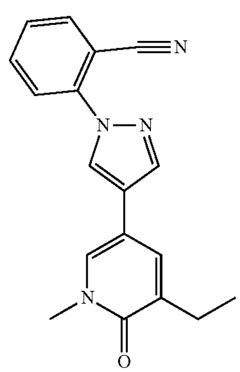 [SMILES: CCc1cc(-c2cnn(-c3ccccc3C#N)c2)cn(C)c1=O] | 2-[4-(5-Ethyl-1-methyl-6-oxo-1,6-dihydro-pyridin-3-yl)-pyrazol-1-yl]-benzonitrile | A |
| 257 | 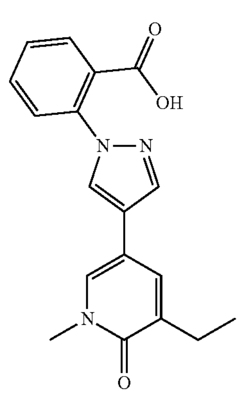 [SMILES: CCc1cc(-c2cnn(-c3ccccc3C(=O)O)c2)cn(C)c1=O] | 2-[4-(5-Ethyl-1-methyl-6-oxo-1,6-dihydro-pyridin-3-yl)-pyrazol-1-yl]-benzoic acid | B |

TABLE 29-continued

| Example | Structure | Name | CBP IC$_{50}$ (μM) |
|---|---|---|---|
| 258 | 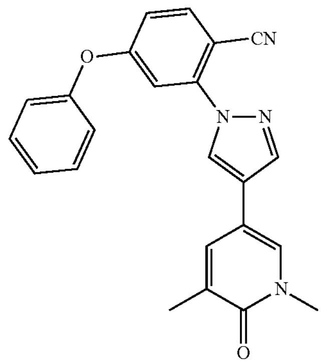 [SMILES: Cc1cc(-c2cnn(-c3cc(Oc4ccccc4)ccc3C#N)c2)cn(C)c1=O] | 2-[4-(1,5-Dimethyl-6-oxo-1,6-dihydro-pyridin-3-yl)-pyrazol-1-yl]-4-phenoxy-benzonitrile | A |
| 259 | 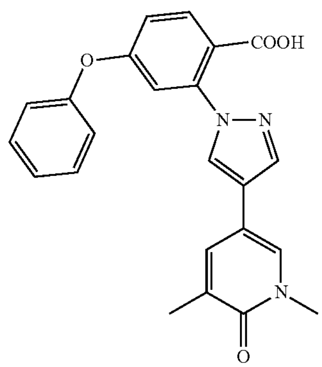 [SMILES: Cc1cc(-c2cnn(-c3cc(Oc4ccccc4)ccc3C(=O)O)c2)cn(C)c1=O] | 2-[4-(1,5-Dimethyl-6-oxo-1,6-dihydro-pyridin-3-yl)-pyrazol-1-yl]-4-phenoxy-benzoic acid | C |
| 260 | 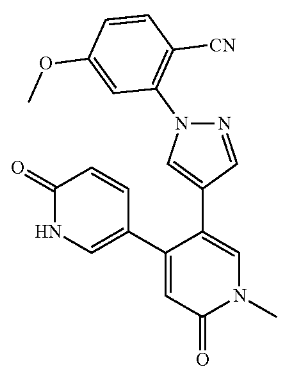 [SMILES: COc1ccc(C#N)c(-n2cc(-c3cn(C)c(=O)cc3-c3ccc(=O)[nH]c3)cn2)c1] | 4-Methoxy-2-[4-(1'-methyl-6,6'-dioxo-1,6,1',6'-tetrahydro-[3,4']bipyridinyl-3'-yl)-pyrazol-1-yl]-benzonitrile | A |
| 261 | 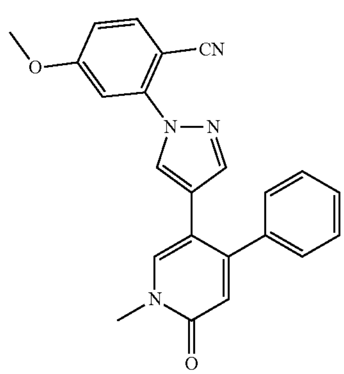 [SMILES: COc1ccc(C#N)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzonitrile | A |

TABLE 29-continued

| Example | Structure | Name | CBP IC$_{50}$ (μM) |
|---|---|---|---|
| 262 | 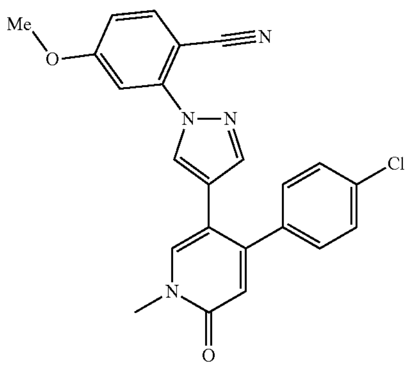 [SMILES: COc1ccc(C#N)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzonitrile | A |
| 263 | 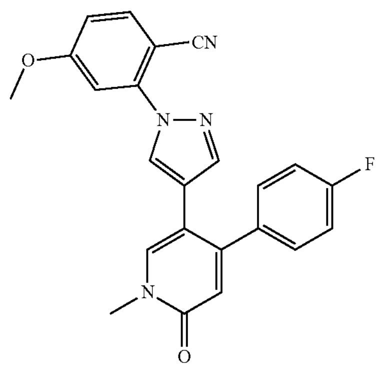 [SMILES: COc1ccc(C#N)c(-n2cc(-c3cn(C)c(=O)cc3-c3ccc(F)cc3)cn2)c1] | 2-{4-[4-(4-Fluoro-phenyl)-1-methyl-6-oxo-1,6-dihydro-pyridin-3-yl]-pyrazol-1-yl}-4-methoxy-benzonitrile | A |
| 264 | 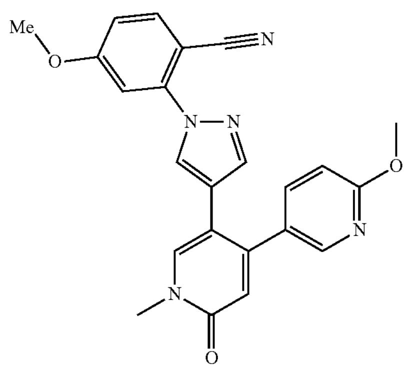 [SMILES: COc1ccc(C#N)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzonitrile | A |
| 265 | 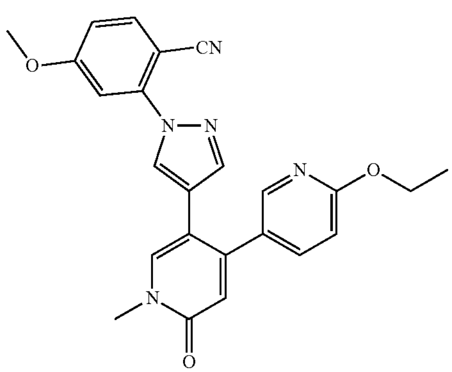 [SMILES: CCOc1ccc(-c2cc(=O)n(C)cc2-c2cnn(-c3cc(OC)ccc3C#N)c2)cn1] | 2-[4-(6-Ethoxy-1'-methyl-6'-oxo-1',6'-dihydro-[3,4']bipyridinyl-3'-yl)-pyrazol-1-yl]-4-methoxy-benzonitrile | A |

TABLE 29-continued

| Example | Structure | Name | CBP IC$_{50}$ (μM) |
|---|---|---|---|
| 266 | 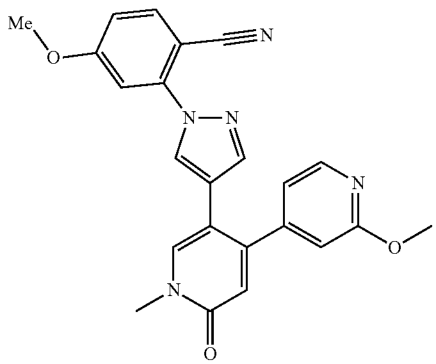 [SMILES: COc1ccc(C#N)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzonitrile | A |
| 267 | 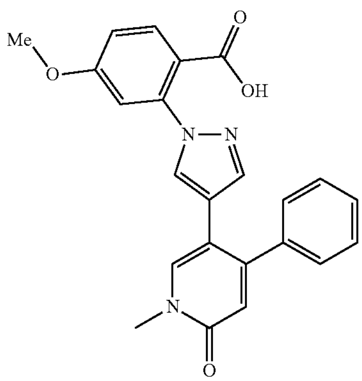 [SMILES: COc1ccc(C(=O)O)c(-n2cc(-c3cn(C)c(=O)cc3-c3ccccc3)cn2)c1] | 4-Methoxy-2-[4-(1-methyl-6-oxo-4-phenyl-1,6-dihydro-pyridin-3-yl)-pyrazol-1-yl]-benzoic acid | A |
| 268 | 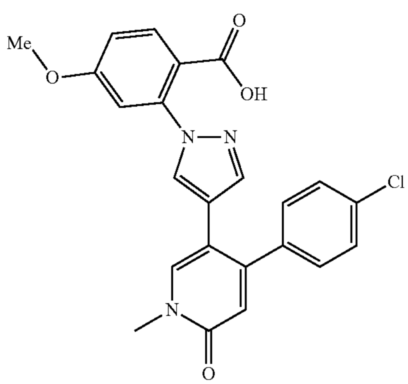 [SMILES: COc1ccc(C(=O)O)c(-n2cc(-c3cn(C)c(=O)cc3-c3ccc(Cl)cc3)cn2)c1] | 2-{4-[4-(4-Chloro-phenyl)-1-methyl-6-oxo-1,6-dihydro-pyridin-3-yl]-pyrazol-1-yl}-4-methoxy-benzoic acid | A |
| 269 | 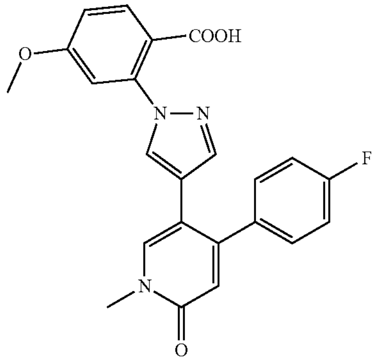 | 2-{4-[4-(4-Fluoro-phenyl)-1-methyl-6-oxo-1,6-dihydro-pyridin-3-yl]-pyrazol-1-yl}-4-methoxy-benzoic acid | A |

TABLE 29-continued

| Example | Structure | Name | CBP IC$_{50}$ (µM) |
|---|---|---|---|
| 270 | 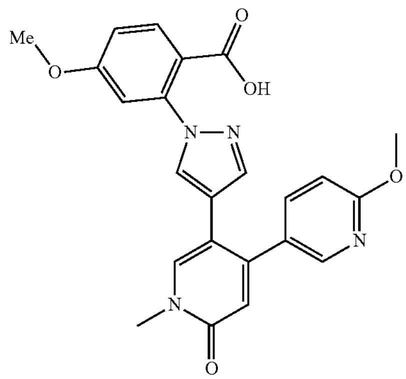 [SMILES: COc1ccc(C(=O)O)c(-n2cc(-c3cn(C)c(=O)cc3-c3ccc(OC)nc3)cn2)c1] | 4-Methoxy-2-[4-(6-methoxy-1'-methyl-6'-oxo-1',6'-dihydro-[3,4']bipyridinyl-3'-yl)-pyrazol-1-yl]-benzoic acid | A |
| 271 | 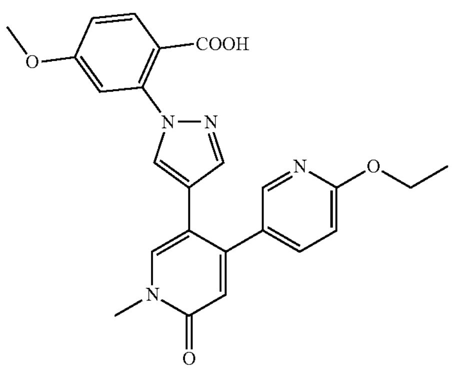 [SMILES: CCOc1ccc(-c2cc(=O)n(C)cc2-c2cnn(-c3cc(OC)ccc3C(=O)O)c2)cn1] | 2-[4-(6-Ethoxy-1'-methyl-6'-oxo-1',6'-dihydro-[3,4']bipyridinyl-3'-yl)-pyrazol-1-yl]-4-methoxy-benzoic acid | A |
| 272 | 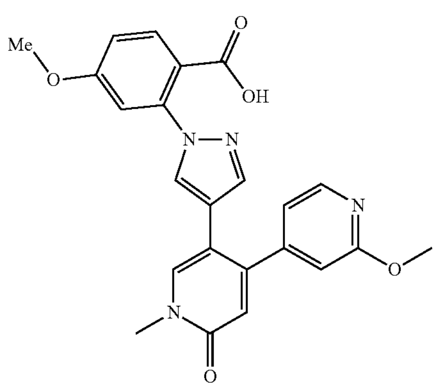 [SMILES: COc1ccc(C(=O)O)c(-n2cc(-c3cn(C)c(=O)cc3-c3ccnc(OC)c3)cn2)c1] | 4-Methoxy-2-[4-(2'-methoxy-1-methyl-6-oxo-1,6-dihydro-[4,4']bipyridinyl-3-yl)-pyrazol-1-yl]-benzoic acid | A |
| 273 | 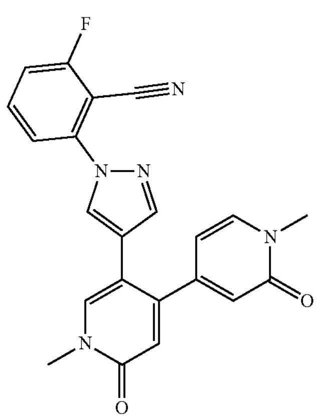 [SMILES: Cn1ccc(-c2cc(=O)n(C)cc2-c2cnn(-c3cccc(F)c3C#N)c2)cc1=O] | 2-[4-(1,1'-Dimethyl-6,2'-dioxo-1,6,1',2'-tetrahydro-[4,4']bipyridinyl-3-yl)-pyrazol-1-yl]-6-fluoro-benzonitrile | A |

TABLE 29-continued

| Example | Structure | Name | CBP IC$_{50}$ (μM) |
|---|---|---|---|
| 274 | 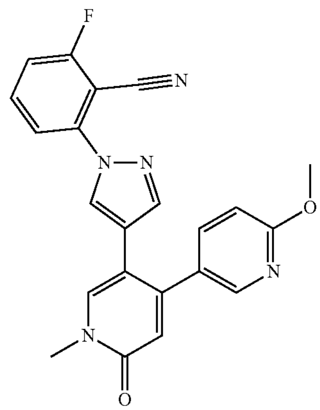 | 2-Fluoro-6-[4-(6-methoxy-1'-methyl-6'-oxo-1',6'-dihydro-[3,4']bipyridinyl-3'-yl)-pyrazol-1-yl]-benzonitrile | A |
| 275 | 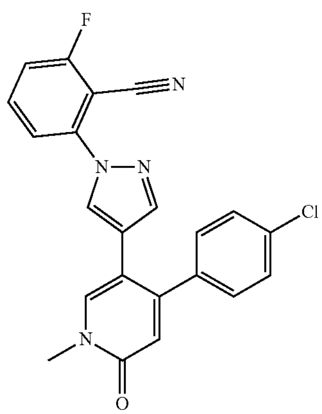 [SMILES: Cn1cc(-c2cnn(-c3cccc(F)c3C#N)c2)c(-c2ccc(Cl)cc2)cc1=O] | 2-{4-[4-(4-Chloro-phenyl)-1-methyl-6-oxo-1,6-dihydro-pyridin-3-yl]-pyrazol-1-yl}-6-fluoro-benzonitrile | A |
| 276 | 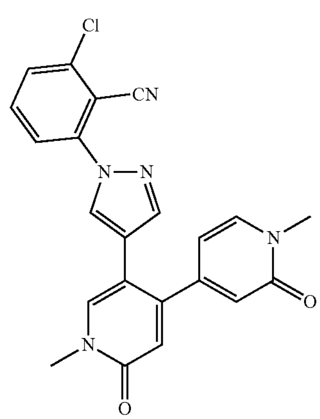 [SMILES: Cn1ccc(-c2cc(=O)n(C)cc2-c2cnn(-c3cccc(Cl)c3C#N)c2)cc1=O] | 2-Chloro-6-[4-(1,1'-dimethyl-6,2'-dioxo-1,6,1',2'-tetrahydro-[4,4']bipyridinyl-3-yl)-pyrazol-1-yl]-benzonitrile | A |

TABLE 29-continued

| Example | Structure | Name | CBP IC$_{50}$ (μM) |
|---|---|---|---|
| 277 | 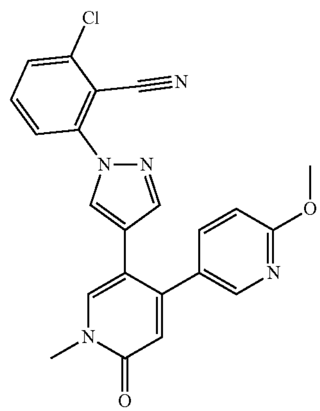 | 2-Chloro-6-[4-(6-methoxy-1'-methyl-6'-oxo-1',6'-dihydro-[3,4']bipyridinyl-3'-yl)-pyrazol-1-yl]-benzonitrile | A |
| 278 | 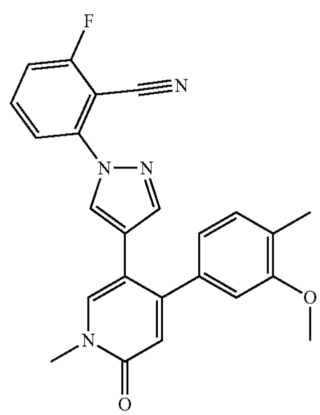 [SMILES: COc1cc(-c2cc(=O)n(C)cc2-c2cnn(-c3cccc(F)c3C#N)c2)ccc1C] | 2-fluoro-6-(4-(4-(3-methoxy-4-methylphenyl)-1-methyl-6-oxo-1,6-dihydropyridin-3-yl)-1H-pyrazol-1-yl)benzonitrile | A |
| 279 | 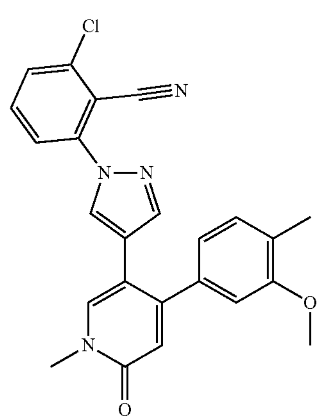 | 2-chloro-6-(4-(4-(3-methoxy-4-methylphenyl)-1-methyl-6-oxo-1,6-dihydropyridin-3-yl)-1H-pyrazol-1-yl)benzonitrile | A |

TABLE 29-continued

| Example | Structure | Name | CBP IC$_{50}$ (µM) |
|---|---|---|---|
| 280 | 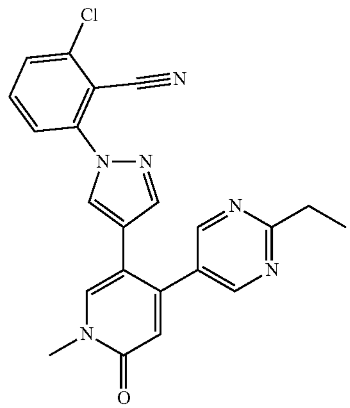 [SMILES: CCc1ncc(-c2cc(=O)n(C)cc2-c2cnn(-c3cccc(Cl)c3C#N)c2)cn1] | 2-chloro-6-(4-(4-(2-ethylpyrimidin-5-yl)-1-methyl-6-oxo-1,6-dihydropyridin-3-yl)-1H-pyrazol-1-yl)benzonitrile | A |
| 281 | 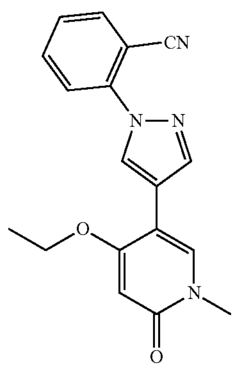 [SMILES: CCOc1cc(=O)n(C)cc1-c1cnn(-c2ccccc2C#N)c1] | 2-(4-(4-ethoxy-1-methyl-6-oxo-1,6-dihydropyridin-3-yl)-1H-pyrazol-1-yl)benzonitrile | A |
| 282 | 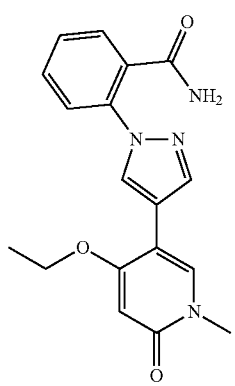 [SMILES: CCOc1cc(=O)n(C)cc1-c1cnn(-c2ccccc2C(N)=O)c1] | 2-(4-(4-ethoxy-1-methyl-6-oxo-1,6-dihydropyridin-3-yl)-1H-pyrazol-1-yl)benzamide | A |
| 283 | 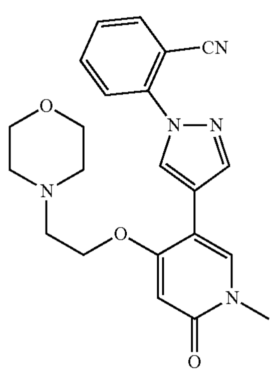 [SMILES: Cn1cc(-c2cnn(-c3ccccc3C#N)c2)c(OCCN2CCOCC2)cc1=O] | 2-(4-(1-methyl-4-(2-morpholinoethoxy)-6-oxo-1,6-dihydropyridin-3-yl)-1H-pyrazol-1-yl)benzonitrile | A |

TABLE 29-continued
| Example | Structure | Name | CBP IC$_{50}$ (μM) |
|---|---|---|---|
| 284 | 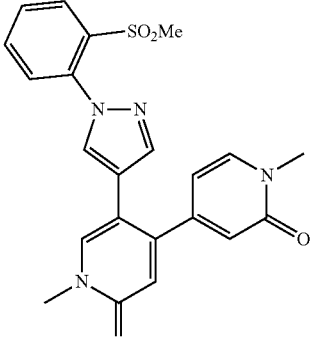 | 5-[1-(2-Methanesulfonyl-phenyl)-1H-pyrazol-4-yl]-1,1'-dimethyl-1H,1'H-[4,4']bipyridinyl-2,2'-dione | A |
| 285 | 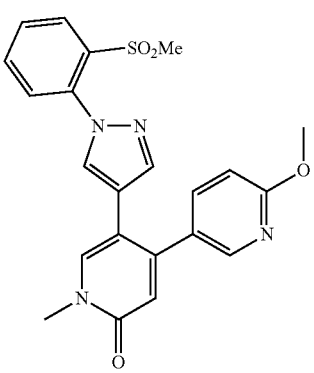 [SMILES: COc1ccc(-c2cc(=O)n(C)cc2-c2cnn(-c3ccccc3S(C)(=O)=O)c2)cn1] | 5'-[1-(2-Methanesulfonyl-phenyl)-1H-pyrazol-4-yl]-6-methoxy-1'-methyl-1'H-[3,4']bipyridinyl-2'-one | A |
| 286 | 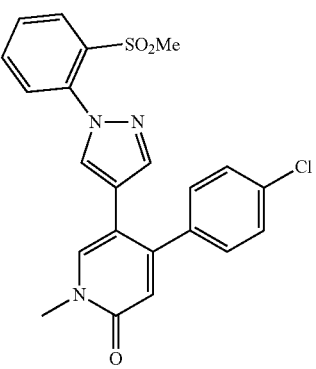 [SMILES: Cn1cc(-c2cnn(-c3ccccc3S(C)(=O)=O)c2)c(-c2ccc(Cl)cc2)cc1=O] | 4-(4-Chloro-phenyl)-5-[1-(2-methanesulfonyl-phenyl)-1H-pyrazol-4-yl]-1-methyl-1H-pyridin-2-one | A |
| 287 | 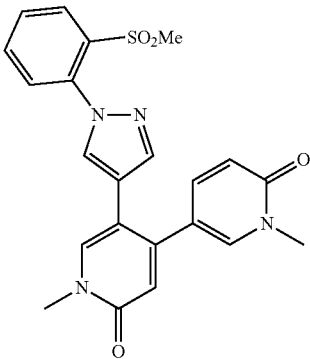 [SMILES: Cn1cc(-c2cc(=O)n(C)cc2-c2cnn(-c3ccccc3S(C)(=O)=O)c2)ccc1=O] | 5'-[1-(2-Methanesulfonyl-phenyl)-1H-pyrazol-4-yl]-1,1'-dimethyl-1H,1'H-[3,4']bipyridinyl-6,2'-dione | B |

TABLE 29-continued

| Example | Structure | Name | CBP IC$_{50}$ (μM) |
|---|---|---|---|
| 288 | 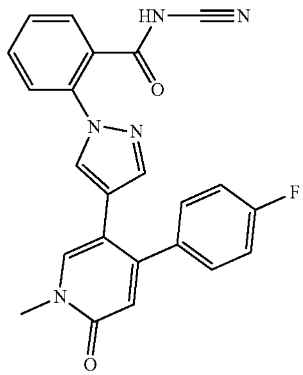 [SMILES: Cn1cc(-c2cnn(-c3ccccc3C(=O)NC#N)c2)c(-c2ccc(F)cc2)cc1=O] | N-cyano-2-(4-(4-(4-fluorophenyl)-1-methyl-6-oxo-1,6-dihydropyridin-3-yl)-1H-pyrazol-1-yl)benzamide | A |
| 289 | 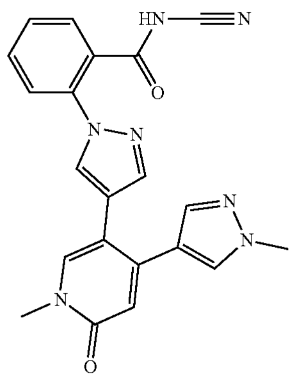 [SMILES: Cn1cc(-c2cc(=O)n(C)cc2-c2cnn(-c3ccccc3C(=O)NC#N)c2)cn1] | N-cyano-2-(4-(1-methyl-4-(1-methyl-1H-pyrazol-4-yl)-6-oxo-1,6-dihydropyridin-3-yl)-1H-pyrazol-1-yl)benzamide | A |
| 290 | 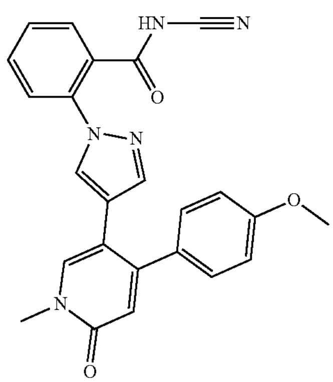 [SMILES: COc1ccc(-c2cc(=O)n(C)cc2-c2cnn(-c3ccccc3C(=O)NC#N)c2)cc1] | N-cyano-2-(4-(4-(4-methoxyphenyl)-1-methyl-6-oxo-1,6-dihydropyridin-3-yl)-1H-pyrazol-1-yl)benzamide | A |
| 291 | 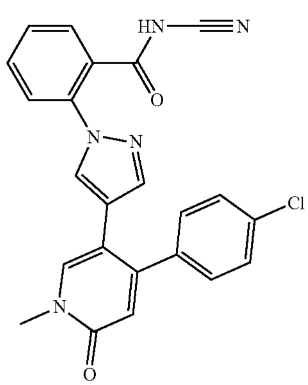 [SMILES: Cn1cc(-c2cnn(-c3ccccc3C(=O)NC#N)c2)c(-c2ccc(Cl)cc2)cc1=O] | 2-(4-(4-(4-chlorophenyl)-1-methyl-6-oxo-1,6-dihydropyridin-3-yl)-1H-pyrazol-1-yl)-N-cyanobenzamide | A |

TABLE 29-continued

| Example | Structure | Name | CBP IC$_{50}$ (µM) |
|---|---|---|---|
| 292 | 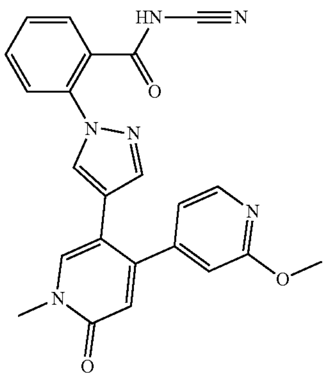 [SMILES: COc1cc(-c2cc(=O)n(C)cc2-c2cnn(-c3ccccc3C(=O)NC#N)c2)ccn1] | N-cyano-2-(4-(2'-methoxy-1-methyl-6-oxo-1,6-dihydro-[4,4'-bipyridin]-3-yl)-1H-pyrazol-1-yl)benzamide | A |
| 293 | 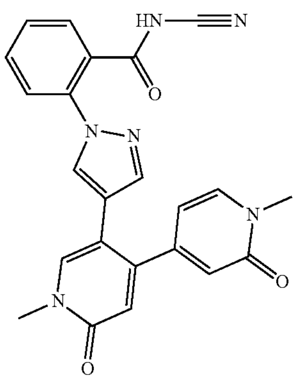 [SMILES: Cn1ccc(-c2cc(=O)n(C)cc2-c2cnn(-c3ccccc3C(=O)NC#N)c2)cc1=O] | N-cyano-2-(4-(1,1'-dimethyl-2',6-dioxo-1,1',2',6-tetrahydro[4,4'-bipyridin]-3-yl)-1H-pyrazol-1-yl)benzamide | A |
| 294 | 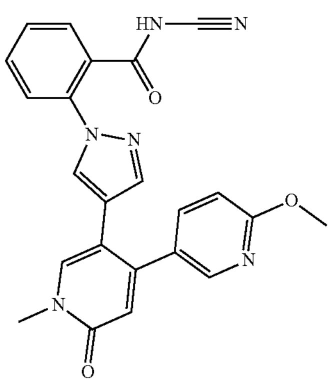 [SMILES: COc1ccc(-c2cc(=O)n(C)cc2-c2cnn(-c3ccccc3C(=O)NC#N)c2)cn1] | N-cyano-2-(4-(6-methoxy-1'-methyl-6'-oxo-1',6'-dihydro-[3,4'-bipyridin]-3'-yl)-1H-pyrazol-1-yl)benzamide | A |
| 295 | 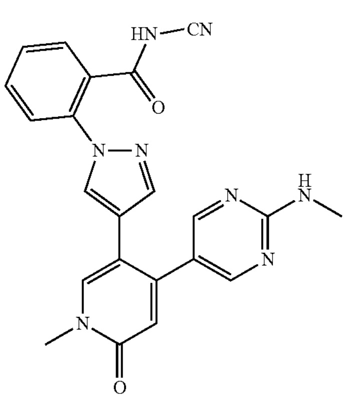 [SMILES: CNc1ncc(-c2cc(=O)n(C)cc2-c2cnn(-c3ccccc3C(=O)NC#N)c2)cn1] | N-cyano-2-(4-(1-methyl-4-(2-(methylamino)pyrimidin-5-yl)-6-oxo-1,6-dihydropyridin-3-yl)-1H-pyrazol-1-yl)benzamide | A |

TABLE 29-continued

| Example | Structure | Name | CBP IC$_{50}$ (µM) |
|---|---|---|---|
| 296 | 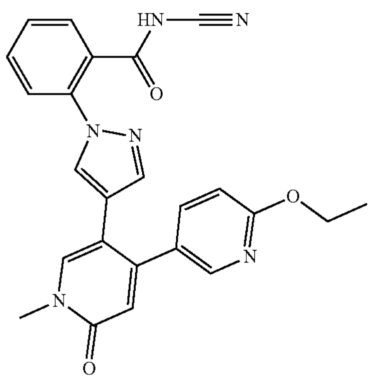 [SMILES: CCOc1ccc(-c2cc(=O)n(C)cc2-c2cnn(-c3ccccc3C(=O)NC#N)c2)cn1] | N-cyano-2-(4-(6-ethoxy-1'-methyl-6'-oxo-1',6'-dihydro-[3,4'-bipyridin]-3'-yl)-1H-pyrazol-1-yl)benzamide | A |
| 297 | 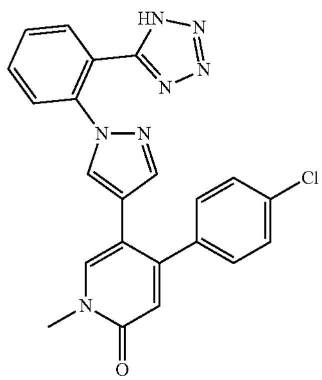 [SMILES: Cn1cc(-c2cnn(-c3ccccc3-c3nnn[nH]3)c2)c(-c2ccc(Cl)cc2)cc1=O] | 5-(1-(2-(1H-tetrazol-5-yl)phenyl)-1H-pyrazol-4-yl)-4-(4-chlorophenyl)-1-methylpyridin-2(1H)-one | A |
| 298 | 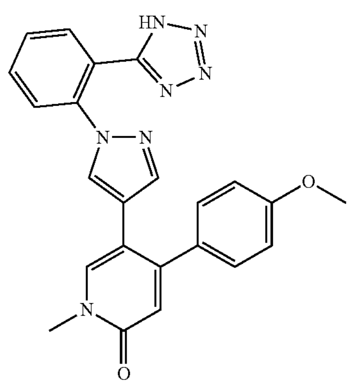 [SMILES: COc1ccc(-c2cc(=O)n(C)cc2-c2cnn(-c3ccccc3-c3nnn[nH]3)c2)cc1] | 4-(4-Methoxy-phenyl)-1-methyl-5-{1-[2-(1H-tetrazol-5-yl)-phenyl]-1H-pyrazol-4-yl}-1H-pyridin-2-one | A |
| 299 | 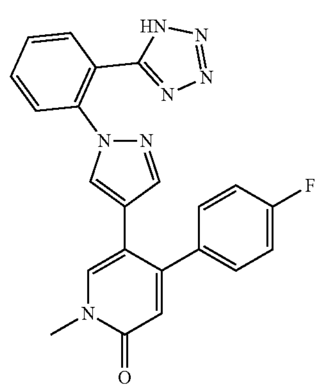 [SMILES: Cn1cc(-c2cnn(-c3ccccc3-c3nnn[nH]3)c2)c(-c2ccc(F)cc2)cc1=O] | 4-(4-Fluoro-phenyl)-1-methyl-5-{1-[2-(1H-tetrazol-5-yl)-phenyl]-1H-pyrazol-4-yl}-1H-pyridin-2-one | A |

TABLE 29-continued

| Example | Structure | Name | CBP IC$_{50}$ (μM) |
|---|---|---|---|
| 300 | 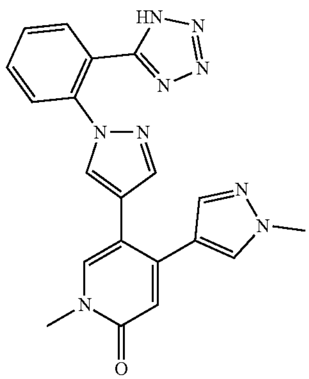 [SMILES: Cn1cc(-c2cc(=O)n(C)cc2-c2cnn(-c3ccccc3-c3nnn[nH]3)c2)cn1] | 1-Methyl-4-(1-methyl-1H-pyrazol-4-yl)-5-{1-[2-(1H-tetrazol-5-yl)-phenyl]-1H-pyrazol-4-yl}-1H-pyridin-2-one | A |
| 301 | 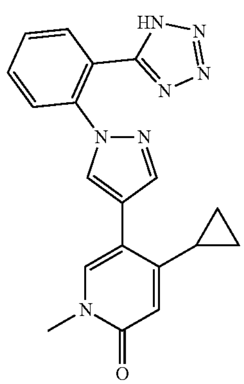 [SMILES: Cn1cc(-c2cnn(-c3ccccc3-c3nnn[nH]3)c2)c(C2CC2)cc1=O] | 4-Cyclopropyl-1-methyl-5-{1-[2-(1H-tetrazol-5-yl)-phenyl]-1H-pyrazol-4-yl}-1H-pyridin-2-one | A |
| 302 | 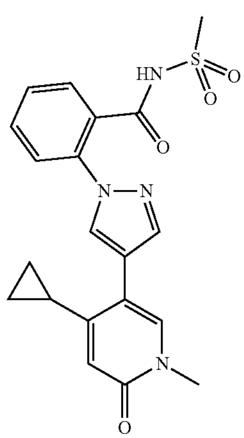 [SMILES: Cn1cc(-c2cnn(-c3ccccc3C(=O)NS(C)(=O)=O)c2)c(C2CC2)cc1=O] | N-{2-[4-(4-Cyclopropyl-1-methyl-6-oxo-1,6-dihydro-pyridin-3-yl)-pyrazol-1-yl]-benzoyl}-methanesulfonamdie | A |

TABLE 29-continued

| Example | Structure | Name | CBP IC$_{50}$ (μM) |
|---|---|---|---|
| 303 | 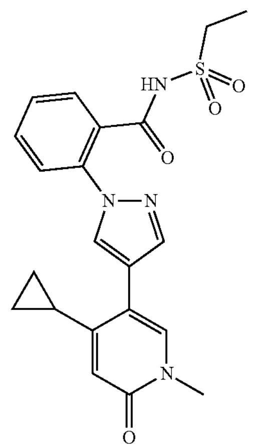 [SMILES: CCS(=O)(=O)NC(=O)c1ccccc1-n1cc(-c2cn(C)c(=O)cc2C2CC2)cn1] | Ethanesulfonic acid 2-[4-(4-cyclopropyl-1-methyl-6-oxo-1,6-dihydro-pyridin-3-yl)-pyrazol-1-yl]-benzoylamide | A |
| 304 | 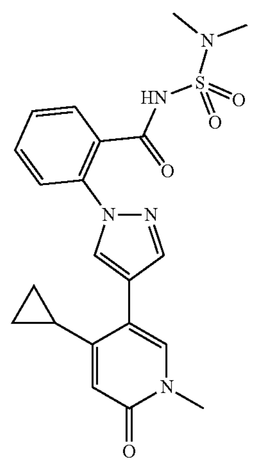 [SMILES: CN(C)S(=O)(=O)NC(=O)c1ccccc1-n1cc(-c2cn(C)c(=O)cc2C2CC2)cn1] | N-[(dimethylamino)sulfonyl]-{2-[4-(4-cyclopropyl-1-methyl-6-oxo(3-hydroxypridyl))pyrazolyl]phenyl}carboxamide | A |
| 305 | 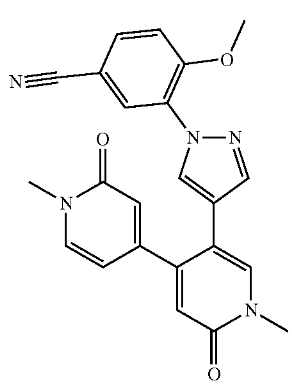 [SMILES: COc1ccc(C#N)cc1-n1cc(-c2cn(C)c(=O)cc2-c2ccn(C)c(=O)c2)cn1] | 3-(4-(1,1'-dimethyl-2',6-dioxo-1,1',2',6-tetrahydro-[4,4'-bipyridin]-3-yl)-1H-pyrazol-1-yl)-4-methoxybenzonitrile | A |

TABLE 29-continued

| Example | Structure | Name | CBP IC$_{50}$ (μM) |
|---|---|---|---|
| 306 | 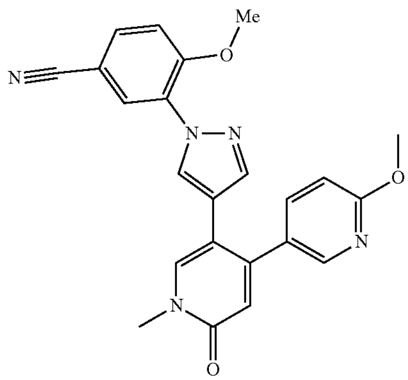 [SMILES: COc1ccc(-c2cc(=O)n(C)cc2-c2cnn(-c3cc(C#N)ccc3OC)c2)cn1] | 4-Methoxy-3-[4-(6-methoxy-1'-methyl-6'-oxo-1',6'-dihydro-[3,4']bipyridinyl-3'-yl)-pyrazol-1-yl]-benzonitrile | A |
| 307 | 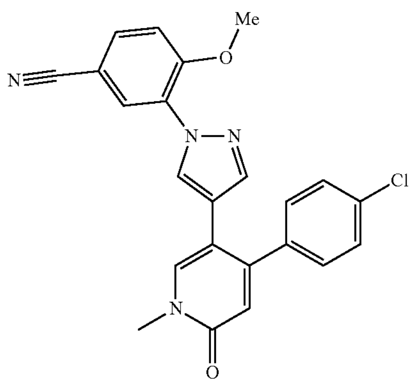 [SMILES: COc1ccc(C#N)cc1-n1cc(-c2cn(C)c(=O)cc2-c2ccc(Cl)cc2)cn1] | 3-{4-[4-(4-Chloro-phenyl)-1-methyl-6-oxo-1,6-dihydro-pyridin-3-yl]-pyrazol-1-yl}-4-methoxy-benzonitrile | A |
| 308 | 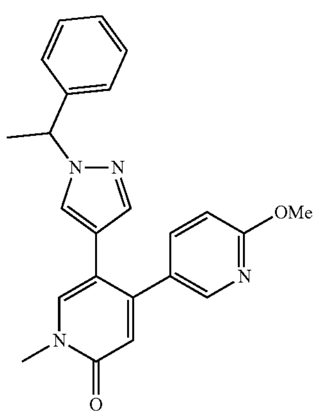 [SMILES: COc1ccc(-c2cc(=O)n(C)cc2-c2cnn(C(C)c3ccccc3)c2)cn1] | 6-methoxy-1'-methyl-5'-(1-(1-phenylethyl)-1H-pyrazol-4-yl)-[3,4'-bipyridin]-2'(1'H)-one. | A |
| 309 | 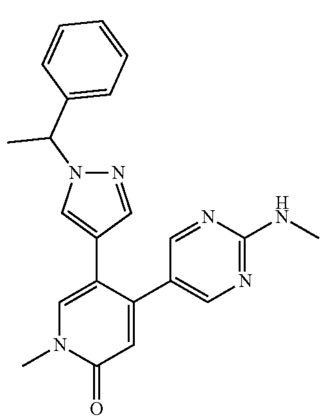 [SMILES: CNc1ncc(-c2cc(=O)n(C)cc2-c2cnn(C(C)c3ccccc3)c2)cn1] | 1-methyl-4-(2-(methylamino)pyrimidin-5-yl)-5-(1-(1-phenylethyl)-1H-pyrazol-4-yl)pyridin-2(1H)-one | A |

TABLE 29-continued

| Example | Structure | Name | CBP IC$_{50}$ (μM) |
|---|---|---|---|
| 310 | 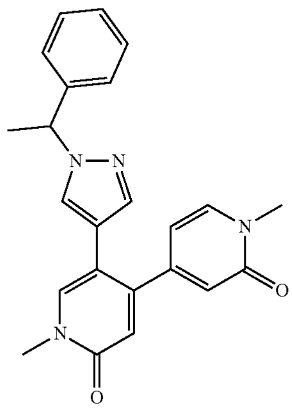 [SMILES: CC(c1ccccc1)n1cc(-c2cn(C)c(=O)cc2-c2ccn(C)c(=O)c2)cn1] | 1,1'-dimethyl-5-(1-(1-phenylethyl)-1H-pyrazol-4-yl)-[4,4'-bipyridine]-2,2'(1H,1'H)-dione | A |
| 311 | 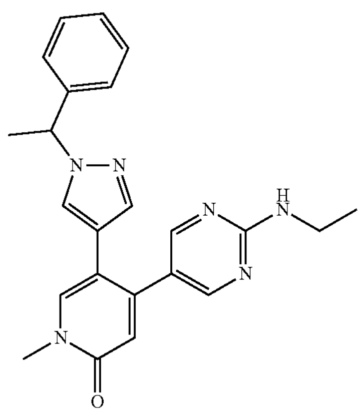 [SMILES: CCNc1ncc(-c2cc(=O)n(C)cc2-c2cnn(C(C)c3ccccc3)c2)cn1] | 4-(2-(ethylamino)pyrimidin-5-yl)-1-methyl-5-(1-(1-phenylethyl)-1H-pyrazol-4-yl)pyridin-2(1H)-one | A |
| 312 | 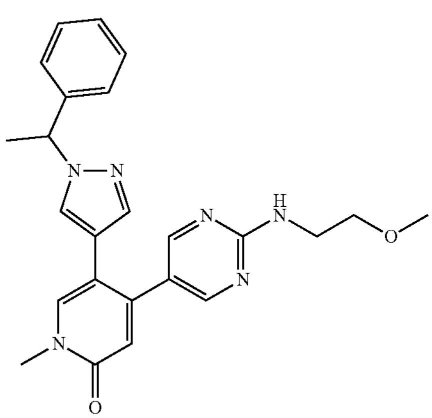 [SMILES: COCCNc1ncc(-c2cc(=O)n(C)cc2-c2cnn(C(C)c3ccccc3)c2)cn1] | 4-(2-((2-methoxyethyl)amino)pyrimidin-5-yl)-1-methyl-5-(1-(1-phenylethyl)-1H-pyrazol-4-yl)pyridin-2(1H)-one | A |

TABLE 29-continued

| Example | Structure | Name | CBP IC$_{50}$ (µM) |
|---|---|---|---|
| 313 | 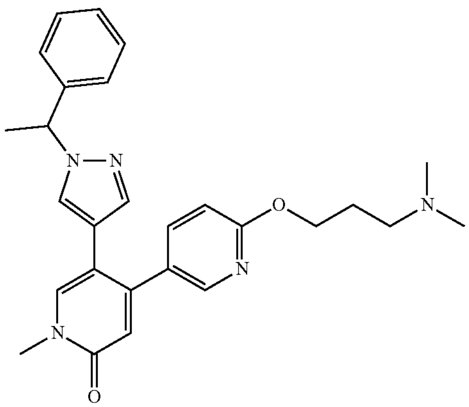 [SMILES: CC(c1ccccc1)n1cc(-c2cn(C)c(=O)cc2-c2ccc(OCCCN(C)C)nc2)cn1] | 6-(3-(dimethylamino)propoxy)-1'-methyl-5'-(1-(1-phenylethyl)-1H-pyrazol-4-yl)-[3,4'-bipyridin]-2'(1'H)-one | A |
| 314 | 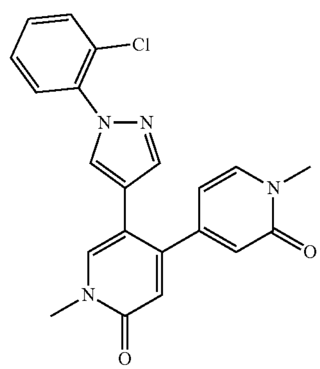 [SMILES: Cn1ccc(-c2cc(=O)n(C)cc2-c2cnn(-c3ccccc3Cl)c2)cc1=O] | 5-(1-(2-chlorophenyl)-1H-pyrazol-4-yl)-1,1'-dimethyl-[4,4'-bipyridine]-2,2'(1H,1'H)-dione | A |
| 315 | 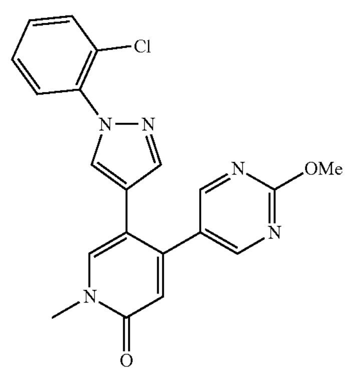 [SMILES: COc1ncc(-c2cc(=O)n(C)cc2-c2cnn(-c3ccccc3Cl)c2)cn1] | 5-(1-(2-chlorophenyl)-1H-pyrazol-4-yl)-4-(2-methoxypyrimidin-5-yl)-1-methylpyridin-2(1H)-one | A |
| 316 | 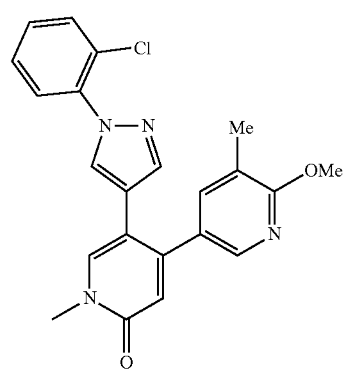 [SMILES: COc1ncc(-c2cc(=O)n(C)cc2-c2cnn(-c3ccccc3Cl)c2)cc1C] | 5'-(1-(2-chlorophenyl)-1H-pyrazol-4-yl)-6-methoxy-1',5-dimethyl-[3,4'-bipyridin]-2'(1'H)-one | A |

TABLE 29-continued

| Example | Structure | Name | CBP IC$_{50}$ (μM) |
|---|---|---|---|
| 317 | 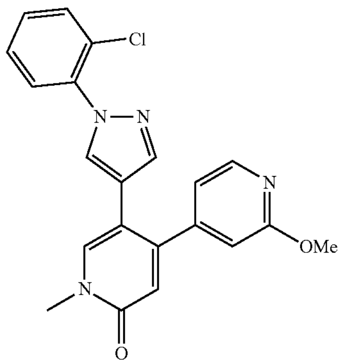 [SMILES: COc1cc(-c2cc(=O)n(C)cc2-c2cnn(-c3ccccc3Cl)c2)ccn1] | 5-(1-(2-chlorophenyl)-1H-pyrazol-4-yl)-2'-methoxy-1-methyl-[4,4'-bipyridin]-2(1H)-one | A |
| 318 | 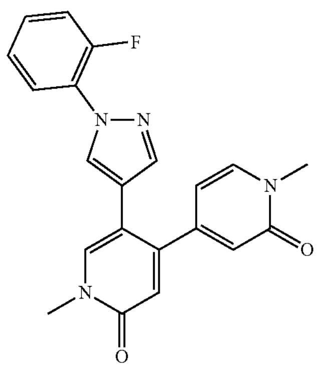 | 5-(1-(2-fluorophenyl)-1H-pyrazol-4-yl)-1,1'-dimethyl-[4,4'-bipyridine]-2,2'(1H,1'H)-dione | A |
| 319 | 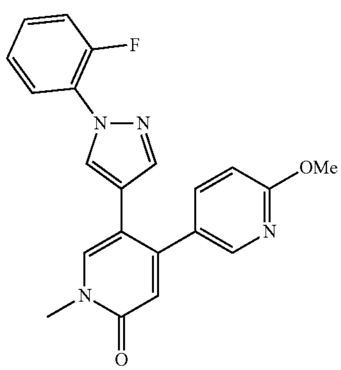 [SMILES: COc1ccc(-c2cc(=O)n(C)cc2-c2cnn(-c3ccccc3F)c2)cn1] | 5'-(1-(2-fluorophenyl)-1H-pyrazol-4-yl)-6-methoxy-1'-methyl-[3,4'-bipyridin]-2'(1'H)-one | A |
| 320 | 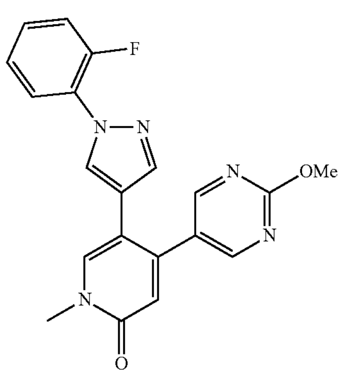 [SMILES: COc1ncc(-c2cc(=O)n(C)cc2-c2cnn(-c3ccccc3F)c2)cn1] | 5-(1-(2-fluorophenyl)-1H-pyrazol-4-yl)-4-(2-methoxypyrimidin-5-yl)-1-methylpyridin-2(1H)-one | A |

TABLE 29-continued

| Example | Structure | Name | CBP IC$_{50}$ (μM) |
|---|---|---|---|
| 321 | 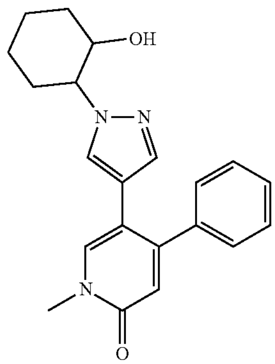 [SMILES: Cn1cc(-c2cnn(C3CCCCC3O)c2)c(-c2ccccc2)cc1=O] | 5-(1-(2-hydroxycyclohexyl)-1H-pyrazol-4-yl)-1-methyl-4-phenylpyridin-2(1H)-one | A |
| 322 | 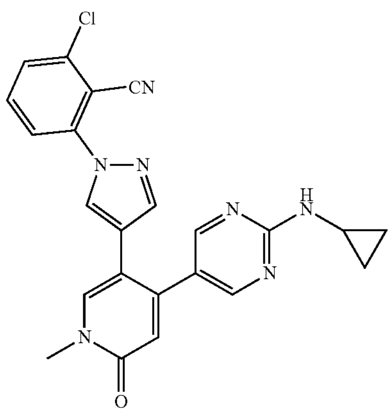 | 2-chloro-6-[4-[4-[2-(cyclopropylamino)pyrimidin-5-yl]-1-methyl-6-oxo-3-pyridyl]pyrazol-1-yl]benzonitrile | A |
| 323 | 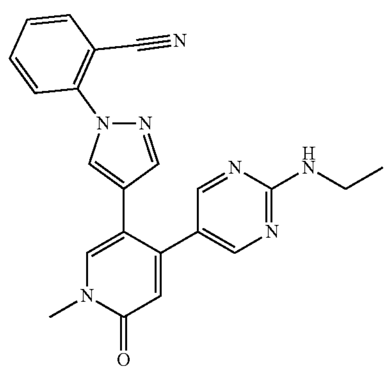 [SMILES: CCNc1ncc(-c2cc(=O)n(C)cc2-c2cnn(-c3ccccc3C#N)c2)cn1] | 2-(4-(4-(2-(ethylamino)pyrimidin-5-yl)-1-methyl-6-oxo-1,6-dihydropyridin-3-yl)-1H-pyrazol-1-yl)benzonitrile | A |
| 324 | 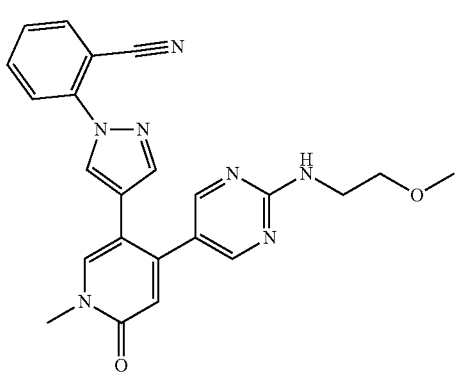 [SMILES: COCCNc1ncc(-c2cc(=O)n(C)cc2-c2cnn(-c3ccccc3C#N)c2)cn1] | 2-(4-(4-(2-((2-methoxyethyl)amino)pyrimidin-5-yl)-1-methyl-6-oxo-1,6-dihydropyridin-3-yl)-1H-pyrazol-1-yl)benzonitrile | A |

TABLE 29-continued

| Example | Structure | Name | CBP IC$_{50}$ (μM) |
|---|---|---|---|
| 325 | 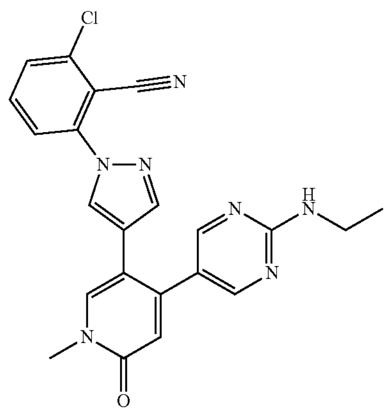 | 2-chloro-6-(4-(4-(2-(ethylamino)pyrimidin-5-yl)-1-methyl-6-oxo-1,6-dihydropyridin-3-yl)-1H-pyrazol-1-yl)benzonitrile | A |
| 326 | 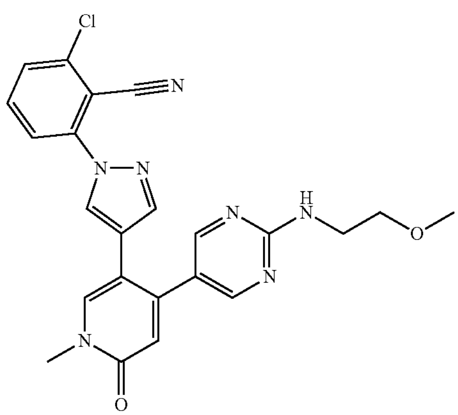 [SMILES: COCCNc1ncc(-c2cc(=O)n(C)cc2-c2cnn(-c3cccc(Cl)c3C#N)c2)cn1] | 2-chloro-6-(4-(4-(2-((2-methoxyethyl)amino)pyrimidin-5-yl)-1-methyl-6-oxo-1,6-dihydropyridin-3-yl)-1H-pyrazol-1-yl)benzonitrile | A |
| 327 | 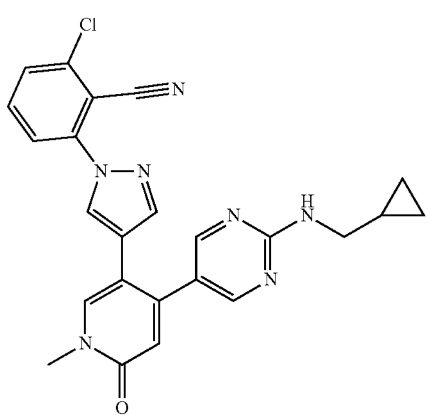 | 2-chloro-6-(4-(4-(2-((cyclopropylmethyl)amino)pyrimidin-5-yl)-1-methyl-6-oxo-1,6-dihydropyridin-3-yl)-1H-pyrazol-1-yl)benzonitrile | A |

TABLE 29-continued

| Example | Structure | Name | CBP IC$_{50}$ (μM) |
|---|---|---|---|
| 328 | 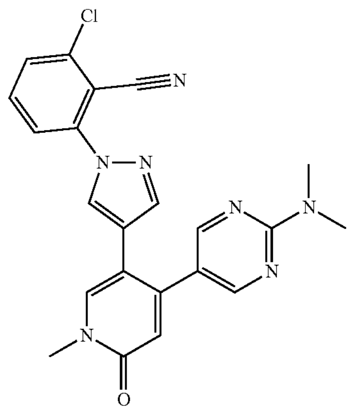 | 2-chloro-6-(4-(4-(2-(dimethylamino)pyrimidin-5-yl)-1-methyl-6-oxo-1,6-dihydropyridin-3-yl)-1H-pyrazol-1-yl)benzonitrile | A |
| 329 | 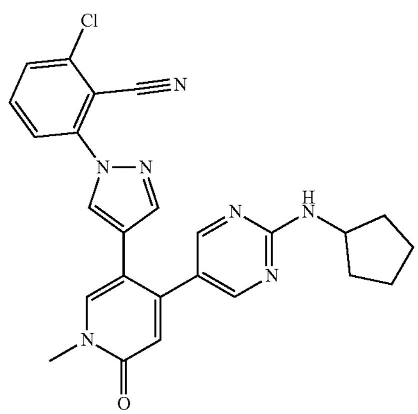 [SMILES: Cn1cc(-c2cnn(-c3cccc(Cl)c3C#N)c2)c(-c2cnc(NC3CCCC3)nc2)cc1=O] | 2-chloro-6-(4-(4-(2-(cyclopentylamino)pyrimidin-5-yl)-1-methyl-6-oxo-1,6-dihydropyridin-3-yl)-1H-pyrazol-1-yl)benzonitrile | A |
| 330 | 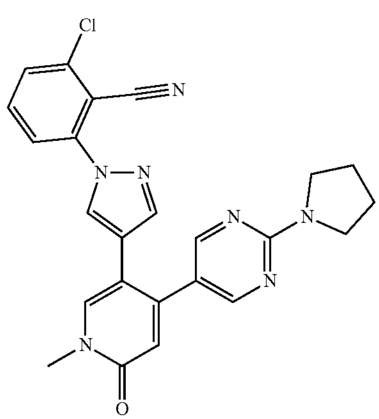 | 2-chloro-6-(4-(1-methyl-6-oxo-4-(2-(pyrrolidin-1-yl)pyrimidin-5-yl)-1,6-dihydropyridin-3-yl)-1H-pyrazol-1-yl)benzonitrile | A |

TABLE 29-continued

| Example | Structure | Name | CBP IC$_{50}$ (μM) |
|---|---|---|---|
| 331 | 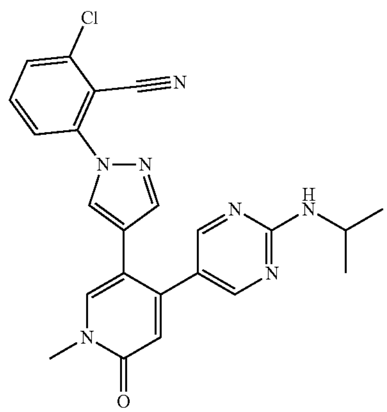 [SMILES: CC(C)Nc1ncc(-c2cc(=O)n(C)cc2-c2cnn(-c3cccc(Cl)c3C#N)c2)cn1] | 2-chloro-6-(4-(4-(2-(isopropylamino)pyrimidin-5-yl)-1-methyl-6-oxo-1,6-dihydropyridin-3-yl)-1H-pyrazol-1-y)benzonitrile | A |
| 332 | 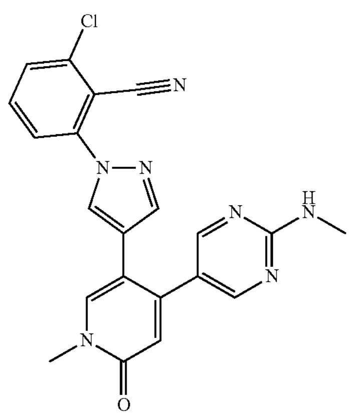 [SMILES: CNc1ncc(-c2cc(=O)n(C)cc2-c2cnn(-c3cccc(Cl)c3C#N)c2)cn1] | 2-chloro-6-(4-(1-methyl-4-(2-(methylamino)pyrimidin-5-yl)-6-oxo-1,6-dihydropyridin-3-yl)-1H-pyrazol-1-yl)benzonitrile | A |
| 333 | 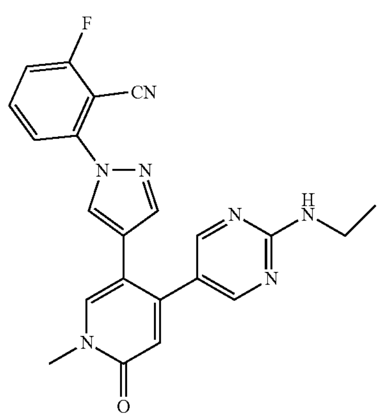 [SMILES: CCNc1ncc(-c2cc(=O)n(C)cc2-c2cnn(-c3cccc(F)c3C#N)c2)cn1] | 2-[4-[4-[2-(ethylamino)pyrimidin-5-yl]-1-methyl-6-oxo-3-pyridyl]pyrazol-1-yl]-6-fluoro-benzonitrile | A |

TABLE 29-continued

| Example | Structure | Name | CBP IC$_{50}$ (μM) |
|---|---|---|---|
| 334 | 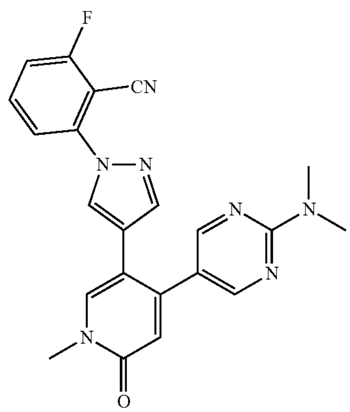 [SMILES: CN(C)c1ncc(-c2cc(=O)n(C)cc2-c2cnn(-c3cccc(F)c3C#N)c2)cn1] | 2-[4-[4-[2-(dimethylamino)pyrimidin-5-yl]-1-methyl-6-oxo-3-pyridyl]pyrazol-1-yl]-6-fluoro-benzonitrile | A |
| 335 | 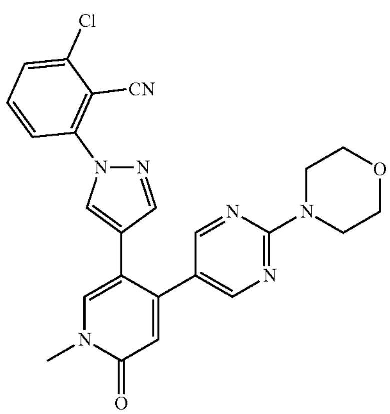 [SMILES: Cn1cc(-c2cnn(-c3cccc(Cl)c3C#N)c2)c(-c2cnc(N3CCOCC3)nc2)cc1=O] | 2-chloro-6-(4-(1-methyl-4-(2-morpholinopyrimidin-5-yl)-6-oxo-1,6-dihydropyridin-3-yl)-1H-pyrazol-1-yl)benzonitrile | A |
| 336 | 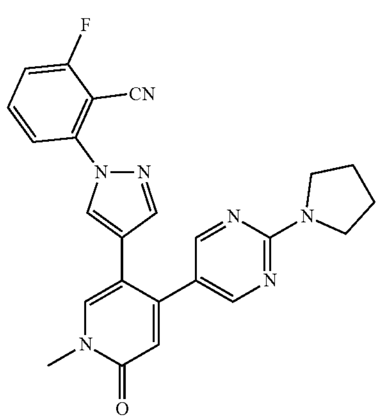 [SMILES: Cn1cc(-c2cnn(-c3cccc(F)c3C#N)c2)c(-c2cnc(N3CCCC3)nc2)cc1=O] | 2-fluoro-6-[4-[1-methyl-6-oxo-4-(2-pyrrolidin-1-ylpyrimidin-5-yl)-3-pyridyl]pyrazol-1-yl]benzonitrile | A |

TABLE 29-continued

| Example | Structure | Name | CBP IC$_{50}$ (μM) |
|---|---|---|---|
| 337 | 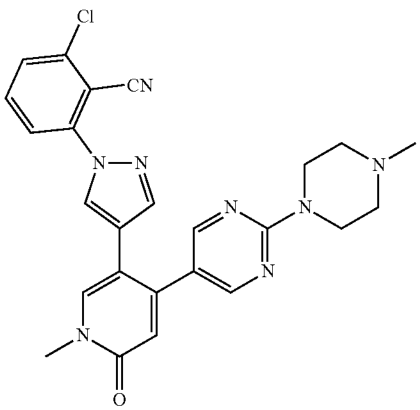 [SMILES: CN1CCN(c2ncc(-c3cc(=O)n(C)cc3-c3cnn(-c4cccc(Cl)c4C#N)c3)cn2)CC1] | 2-chloro-6-(4-(1-methyl-4-(2-(4-methylpiperazin-1-yl)pyrimidin-5-yl)-6-oxo-1,6-dihydropyridin-3-yl)-1H-pyrazol-1-yl)benzonitrile | A |
| 338 | 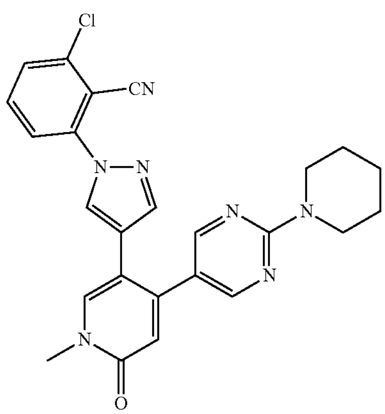 [SMILES: Cn1cc(-c2cnn(-c3cccc(Cl)c3C#N)c2)c(-c2cnc(N3CCCCC3)nc2)cc1=O] | 2-chloro-6-(4-(1-methyl-6-oxo-4-(2-(piperidin-1-yl)pyrimidin-5-yl)-1,6-dihydropyridin-3-yl)-1H-pyrazol-1-yl)benzonitrile | A |
| 339 | 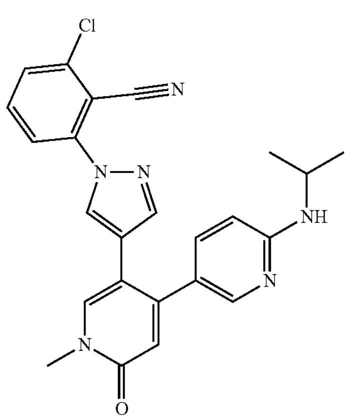 [SMILES: CC(C)Nc1ccc(-c2cc(=O)n(C)cc2-c2cnn(-c3cccc(Cl)c3C#N)c2)cn1] | 2-chloro-6-[4-[4-[6-(isopropylamino)-3-pyridyl]-1-methyl-6-oxo-3-pyridyl]-pyrazol-1-yl]benzonitrile | A |

TABLE 29-continued

| Example | Structure | Name | CBP IC$_{50}$ (μM) |
|---|---|---|---|
| 340 | 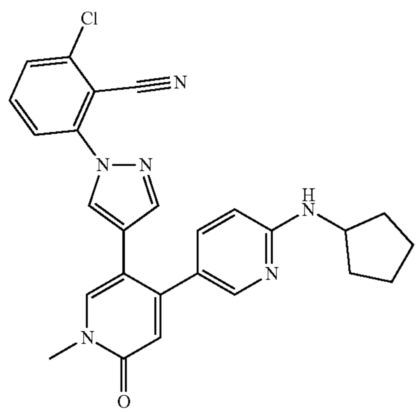 [SMILES: Cn1cc(-c2cnn(-c3cccc(Cl)c3C#N)c2)c(-c2ccc(NC3CCCC3)nc2)cc1=O] | 2-chloro-6-(4-(6-(cyclopentylamino)-1'-methyl-6'-oxo-1',6'-dihydro-[3,4'-bipyridin]-3'-yl)-1H-pyrazol-1-yl)benzonitrile | A |
| 341 | 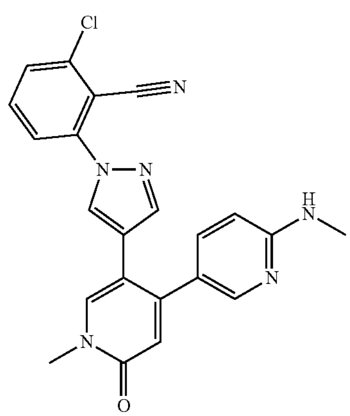 [SMILES: CNc1ccc(-c2cc(=O)n(C)cc2-c2cnn(-c3cccc(Cl)c3C#N)c2)cn1] | 2-chloro-6-(4-(1'-methyl-6-(methylamino)-6'-oxo-1',6'-dihydro-[3,4'-bipyridin]-3'-yl)-1H-pyrazol-1-yl)benzonitrile | A |
| 342 | 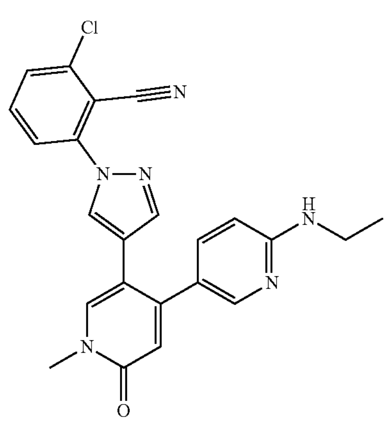 | 2-chloro-6-(4-(6-(ethylamino)-1'-methyl-6'-oxo-1',6'-dihydro-[3,4'-bipyridin]-3'-yl)-1H-pyrazol-1-yl)benzonitrile | A |

TABLE 29-continued

| Example | Structure | Name | CBP IC$_{50}$ (μM) |
|---|---|---|---|
| 343 | 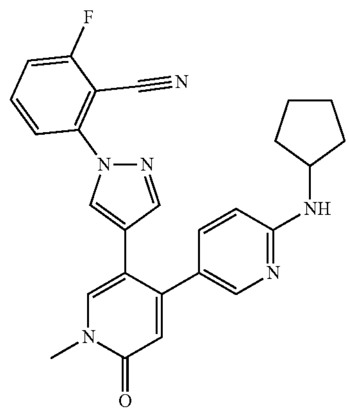 [SMILES: Cn1cc(-c2cnn(-c3cccc(F)c3C#N)c2)c(-c2ccc(NC3CCCC3)nc2)cc1=O] | 2-(4-(6-(cyclopentylamino)-1'-methyl-6'-oxo-1',6'-dihydro-[3,4'-bipyridin]-3'-yl)-1H-pyrazol-1-yl)-6-fluorobenzonitrile | A |
| 344 | 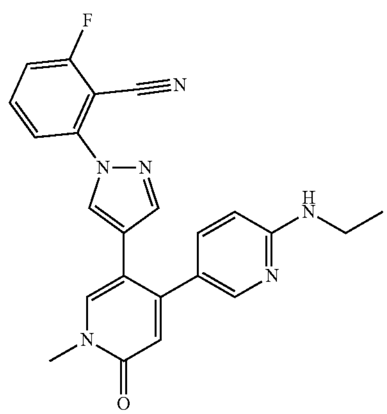 [SMILES: CCNc1ccc(-c2cc(=O)n(C)cc2-c2cnn(-c3cccc(F)c3C#N)c2)cn1] | 2-(4-(6-(ethylamino)-1'-methyl-6'-oxo-1',6'-dihydro-[3,4'-bipyridin]-3'-yl)-1H-pyrazol-1-yl)-6-fluorobenzonitrile | A |
| 345 | 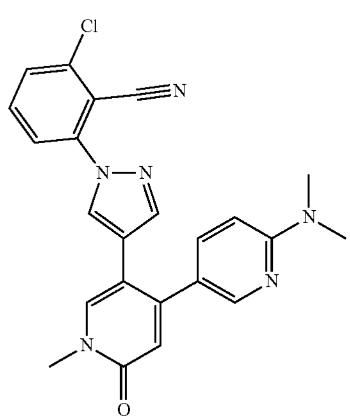 | 2-chloro-6-{4-[6-(dimethylamino)-1'-methyl-6'-oxo-1',6'-dihydro-[3,4'-bipyridin]-3'-yl]-1H-pyrazol-1-yl}benzonitrile | A |

TABLE 29-continued

| Example | Structure | Name | CBP IC$_{50}$ (μM) |
|---|---|---|---|
| 346 | 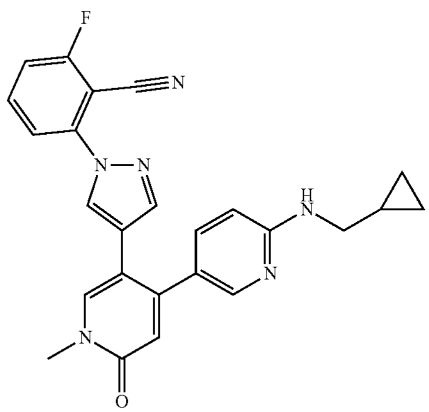 | 2-(4-{6-[(cyclopropylmethyl)amino]-1'-methyl-6'-oxo-1',6'-dihydro-[3,4'-bipyridine]-3'-yl}-1H-pyrazol-1-yl)-6-fluorobenzonitrile | A |
| 347 | 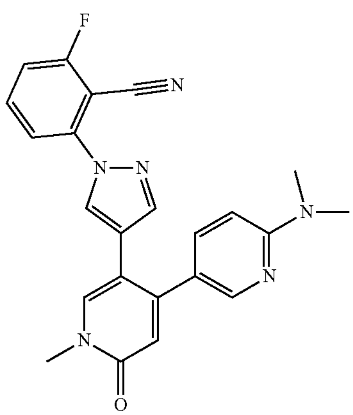 [SMILES: CN(C)c1ccc(-c2cc(=O)n(C)cc2-c2cnn(-c3cccc(F)c3C#N)c2)cn1] | 2-{4-[6-(dimethylamino)-1'-methyl-6'-oxo-1',6'-dihydro-[3,4'-bipyridine]-3'-yl]-1H-pyrazol-1-yl}-6-fluorobenzonitrile | A |
| 348 | 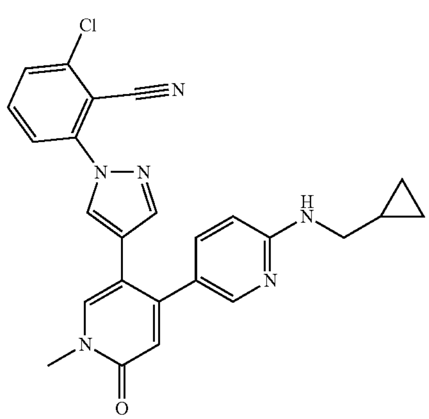 | 2-chloro-6-(4-{6-[(cyclopropylmethyl)amino]-1'-methyl-6'-oxo-1',6'-dihydro-[3,4'-bipyridine]-3'-yl}-1H-pyrazol-1-yl)benzonitrile | A |

TABLE 29-continued

| Example | Structure | Name | CBP IC$_{50}$ (µM) |
|---|---|---|---|
| 349 | 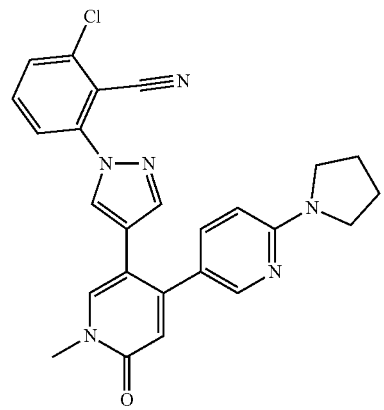 [SMILES: Cn1cc(-c2cnn(-c3cccc(Cl)c3C#N)c2)c(-c2ccc(N3CCCC3)nc2)cc1=O] | 2-chloro-6-[4-([1-methyl-6-oxo-4-(6-pyrrolidin-1-yl)-3-pyridyl)-3-pyridyl]pyrazol-1-yl]benzonitrile | A |
| 350 | 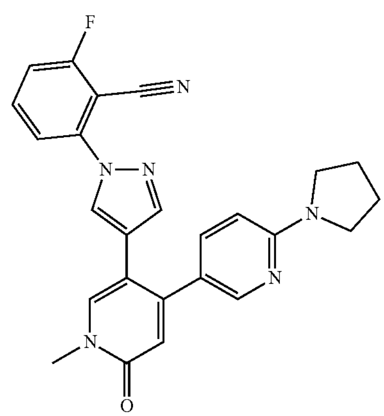 | 2-fluoro-6-[4-[1-methyl-6-oxo-4-(6-pyrrolidin-1-yl-3-pyridyl)-3-pyridyl]pyrazol-1-yl]benzonitrile | A |
| 351 | 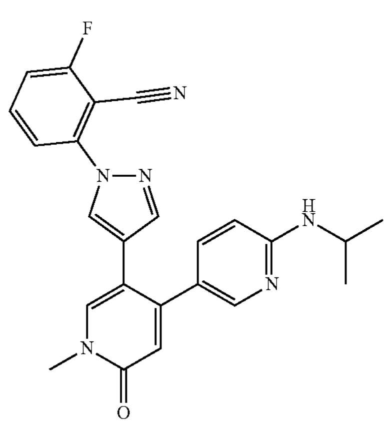 | 2-fluoro-6-(4-(6-(isopropylamino)-1'-methyl-6'-oxo-1',6'-dihydro-[3,4'-bipyridin]-3'-yl)-1H-pyrazol-1-yl)benzonitrile | A |

TABLE 29-continued

| Example | Structure | Name | CBP IC$_{50}$ (μM) |
|---|---|---|---|
| 352 | 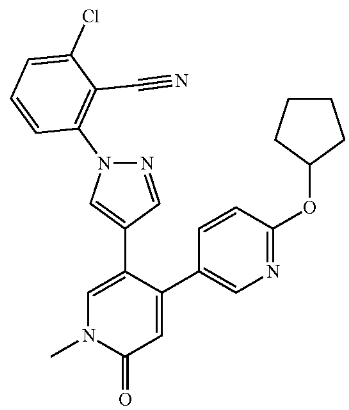 | 2-chloro-6-[4-[4-[6-(cyclopentoxy)-3-pyridyl]-1-methyl-6-oxo-3-pyridyl]pyrazol-1-yl]benzonitrile | A |
| 353 | 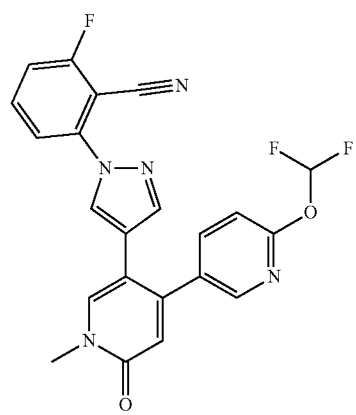 [SMILES: Cn1cc(-c2cnn(-c3cccc(F)c3C#N)c2)c(-c2ccc(OC(F)F)nc2)cc1=O] | 2-(4-(6-(difluoromethoxy)-1'-methyl-6'-oxo-1',6'-dihydro-[3,4'-bipyridin]-3'-yl)-1H-pyrazol-1-yl)-6-fluorobenzonitrile | A |
| 354 | 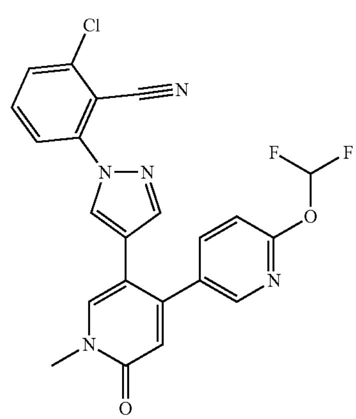 | 2-chloro-6-(4-(6-(difluoromethoxy)-1'-methyl-6'-oxo-1',6'-dihydro-[3,4'-bipyridin]-3'-yl)-1H-pyrazol-1-yl)benzonitrile | A |

TABLE 29-continued
| Example | Structure | Name | CBP IC$_{50}$ (μM) |
|---|---|---|---|
| 355 | 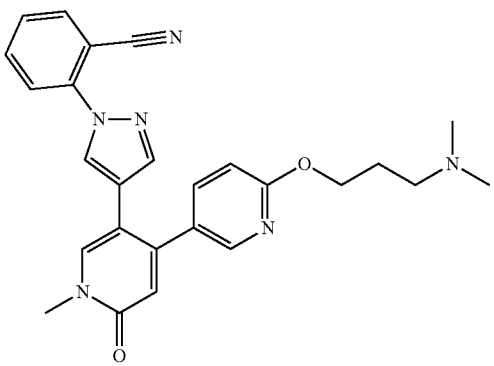 [SMILES: CN(C)CCCOc1ccc(-c2cc(=O)n(C)cc2-c2cnn(-c3ccccc3C#N)c2)cn1] | 2-(4-(6-(3-(dimethylamino)propoxy)-1'-methyl-6'-oxo-1',6'-dihydro-[3,4'-bipyridin]-3'-yl)-1H-pyrazol-1-y)benzonitrile | A |
| 356 | 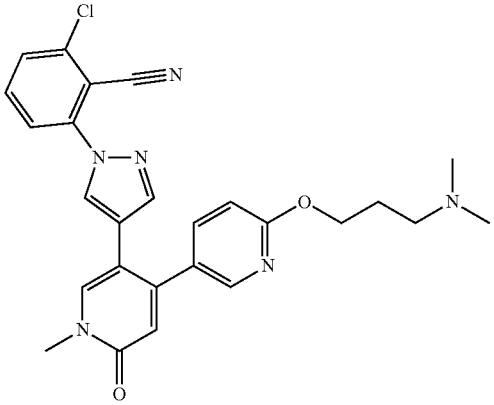 [SMILES: CN(C)CCCOc1ccc(-c2cc(=O)n(C)cc2-c2cnn(-c3cccc(Cl)c3C#N)c2)cn1] | 2-chloro-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile | A |
| 357 | 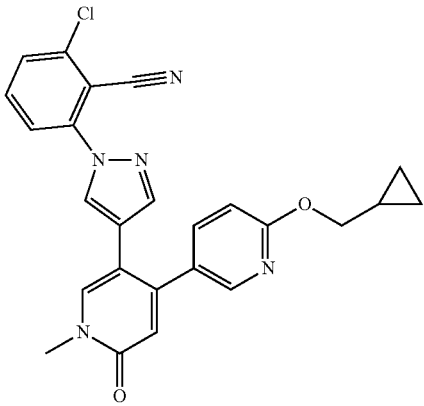 [SMILES: Cn1cc(-c2cnn(-c3cccc(Cl)c3C#N)c2)c(-c2ccc(OCC3CC3)nc2)cc1=O] | 2-chloro-6-[4-[4-[6-(cyclopropylmethoxy)-3-pyridyl]-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 358 | 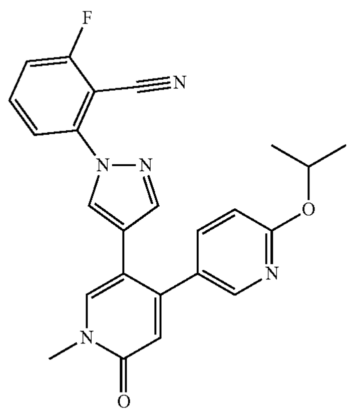 [SMILES: CC(C)Oc1ccc(-c2cc(=O)n(C)cc2-c2cnn(-c3cccc(F)c3C#N)c2)cn1] | 2-fluoro-6-[4-[4-(6-isopropoxy-3-pyridyl)-1-methyl-6-oxo-3-pyridyl]pyrazol-1-yl]benzonitrile | A |
| 359 | 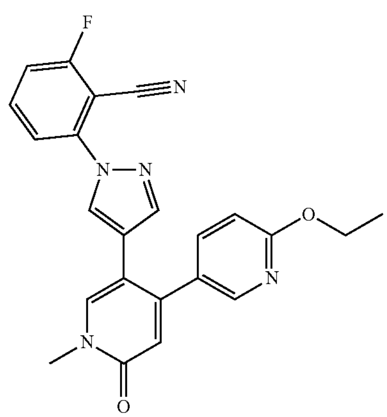 [SMILES: CCOc1ccc(-c2cc(=O)n(C)cc2-c2cnn(-c3cccc(F)c3C#N)c2)cn1] | 2-(4-(6-ethoxy-1'-methyl-6'-oxo-1',6'-dihydro-[3,4'-bipyridin]-3'-yl)-1H-pyrazol-1-yl)-6-fluorobenzonitrile | A |
| 360 | 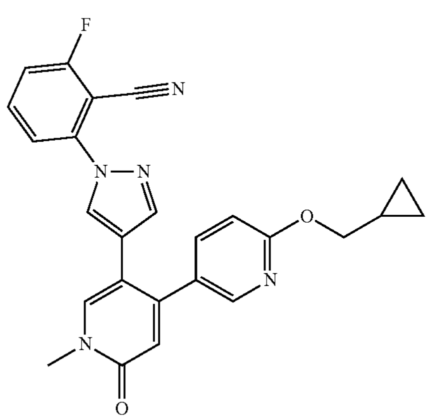 [SMILES: Cn1cc(-c2cnn(-c3cccc(F)c3C#N)c2)c(-c2ccc(OCC3CC3)nc2)cc1=O] | 2-[4-[4-[6-(cyclopropylmethoxy)-3-pyridyl]-1-methyl-6-oxo-3-pyridyl]pyrazol-1-yl]-6-fluoro-benzonitrile | A |

TABLE 29-continued

| Example | Structure | Name | CBP IC$_{50}$ (μM) |
|---|---|---|---|
| 361 | 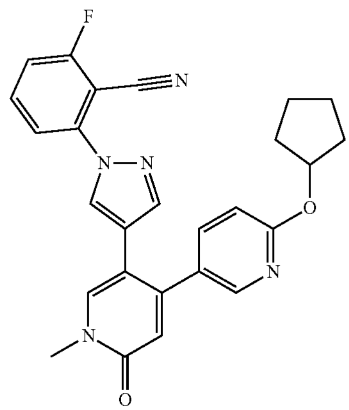 [SMILES: Cn1cc(-c2cnn(-c3cccc(F)c3C#N)c2)c(-c2ccc(OC3CCCC3)nc2)cc1=O] | 2-[4-[4-[6-(cyclopentoxy)-3-pyridyl]-1-methyl-6-oxo-3-pyridyl]pyrazol-1-yl]-6-fluoro-benzonitrile | A |
| 362 | 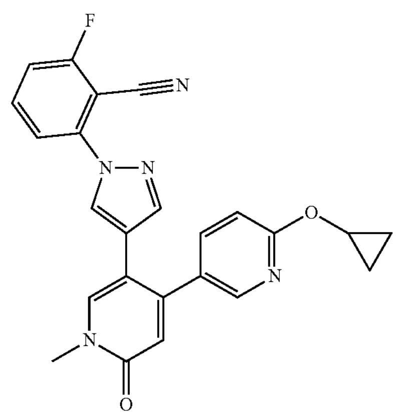 [SMILES: Cn1cc(-c2cnn(-c3cccc(F)c3C#N)c2)c(-c2ccc(OC3CC3)nc2)cc1=O] | 2-[4-[4-[6-(cyclopropoxy)-3-pyridyl]-1-methyl-6-oxo-3-pyridyl]pyrazol-1-yl]-6-fluoro-benzonitrile | A |
| 363 | 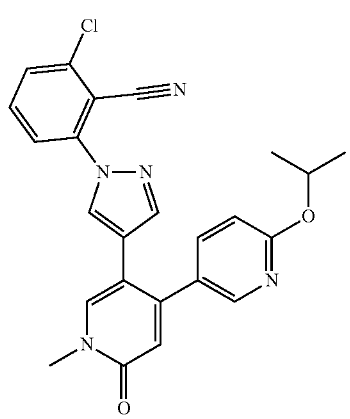 [SMILES: CC(C)Oc1ccc(-c2cc(=O)n(C)cc2-c2cnn(-c3cccc(Cl)c3C#N)c2)cn1] | 2-chloro-6-[4-[4-(6-isopropoxy-3-pyridyl)-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 364 | 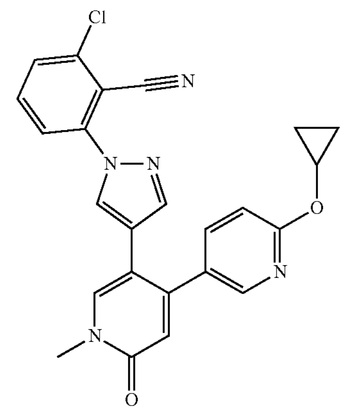 [SMILES: Cn1cc(-c2cnn(-c3cccc(Cl)c3C#N)c2)c(-c2ccc(OC3CC3)nc2)cc1=O] | 2-chloro-6-[4-[4-[6-(cyclopropoxy)-3-pyridyl]-1-methyl-6-oxo-3-pryidyl]pyrazol-1-yl]benzonitrile | A |
| 365 | 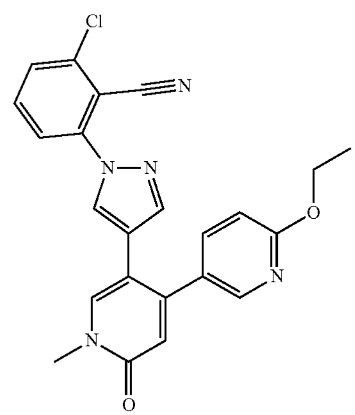 [SMILES: CCOc1ccc(-c2cc(=O)n(C)cc2-c2cnn(-c3cccc(Cl)c3C#N)c2)cn1] | 2-chloro-6-(4-(6-ethoxy-1'-methyl-6'-oxo-1',6'-dihydro-[3,4'-bipyridin]-3'-yl)-1H-pyrazol-1-yl)benzonitrile | A |
| 366 | 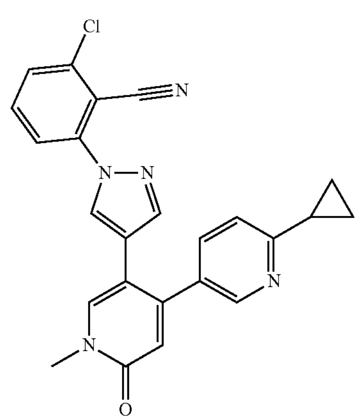 | 2-chloro-6-[4-[4-(6-cyclopropyl-3-pyridyl)-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 367 | 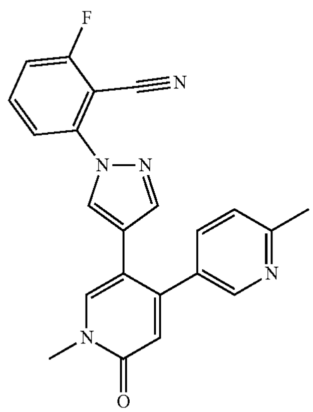 [SMILES: Cc1ccc(-c2cc(=O)n(C)cc2-c2cnn(-c3cccc(F)c3C#N)c2)cn1] | 2-(4-(1',6-dimethyl-6'-oxo-1',6'-dihydro-[3,4'-bipyridin]-3'-yl)-1H-pyrazol-1-yl)-6-fluorobenzonitrile | A |
| 368 | 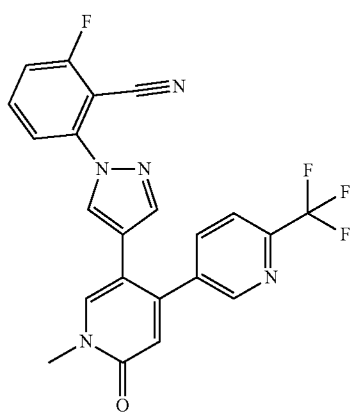 | 2-fluoro-6-(4-(1'-methyl-6'-oxo-6-(trifluoromethyl)-1',6'-dihydro-[3,4'-bipyridin]-3'-yl)-1H-pyrazol-1-yl)benzonitrile | A |
| 369 | 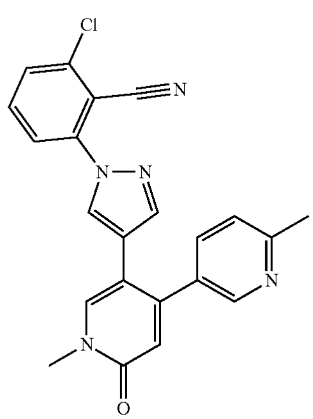 | 2-chloro-6-(4-(1',6-dimethyl-6'-oxo-1',6'-dihydro-[3,4'-bipyridin]-3'-yl)-1H-pyrazol-1-yl)benzonitrile | A |

TABLE 29-continued

| Example | Structure | Name | CBP IC$_{50}$ (μM) |
|---|---|---|---|
| 370 | 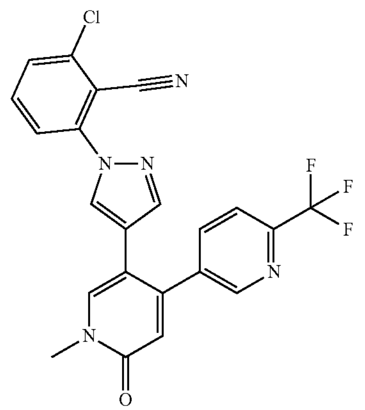 | 2-chloro-6-(4-(1'-methyl-6'-oxo-6-(trifluoromethyl)-1',6'-dihydro-[3,4'-bipyridin]-3'-yl)-1H-pyrazol-1-yl)benzonitrile | A |
| 371 | 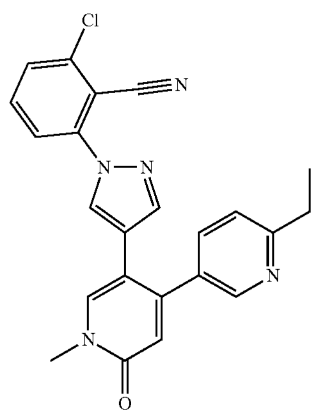 | 2-chloro-6-(4-(6-ethyl-1'-methyl-6'-oxo-1',6'-dihydro-[3,4'-bipyridin]-3'-yl)-1H-pyrazol-1-yl)benzonitrile | A |
| 372 | 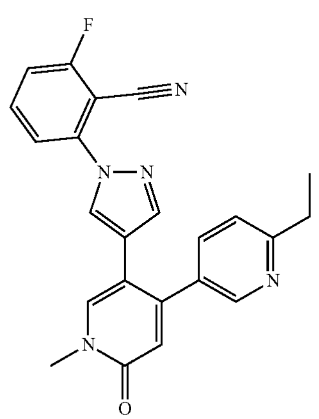 [SMILES: CCc1ccc(-c2cc(=O)n(C)cc2-c2cnn(-c3cccc(F)c3C#N)c2)cn1] | 2-(4-(6-ethyl-1'-methyl-6'-oxo-1',6'-dihydro-[3,4'-bipyridin]-3'-yl)-1H-pyrazol-1-yl)-6-fluorobenzonitrile | A |

TABLE 29-continued

| Example | Name | CBP IC$_{50}$ (μM) |
|---|---|---|
| 373 | 2-(4-(6-ethyl-1'-methyl-6'-oxo-1',6'-dihydro-[3,4'-bipyridin]-3'-yl)-1H-pyrazol-1-yl)benzonitrile | A |
| 374 | 2-[4-[4-(6-cyclopropyl-3-pyridyl)-1-methyl-6-oxo-3-pyridyl]pyrazol-1-yl]-6-fluoro-benzonitrile | A |
| 375 | 2-fluoro-6-[4-[4-(6-isopropyl-3-pyridyl)-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 376 | 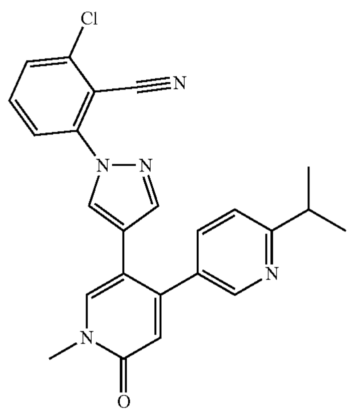 | 2-chloro-6-[4-[4-(6-isopropyl-3-pyridyl)-1-methyl-6-oxo-3-pyridyl]pyrazol-1-yl]benzonitrile | A |
| 377 | 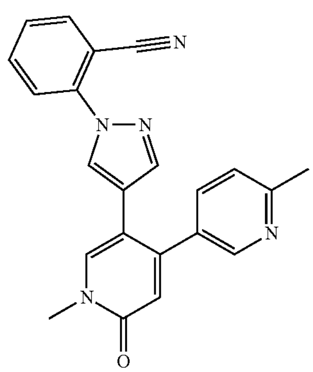 [SMILES: Cc1ccc(-c2cc(=O)n(C)cc2-c2cnn(-c3ccccc3C#N)c2)cn1] | 2-(4-(1',6-dimethyl-6'-oxo-1',6'-dihydro-[3,4'-bipyridin]-3'-yl)-1H-pyrazol-1-yl)benzonitrile | A |
| 378 | 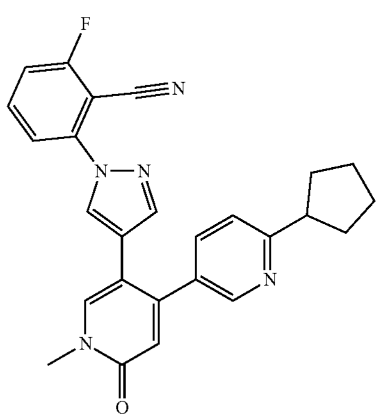 | 2-(4-(6-cyclopentyl-1'-methyl-6'-oxo-1',6'-dihydro-[3,4'-bipyridin]-3'-yl)-1H-pyrazol-1-yl)-6-fluorobenzonitrile | A |

TABLE 29-continued

| Example | Structure | Name | CBP IC$_{50}$ (μM) |
|---|---|---|---|
| 379 | 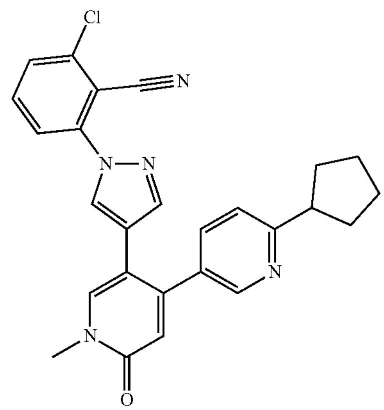 | 2-chloro-6-(4-(6-cyclopentyl-1'-methyl-6'-oxo-1',6'-dihydro-[3,4'-bipyridin]-3'-yl)-1H-pyrazol-1-yl)benzonitrile | A |
| 380 | 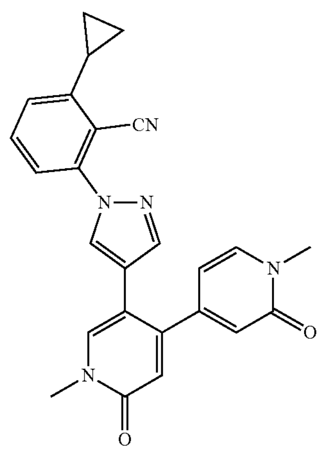 [SMILES: Cn1ccc(-c2cc(=O)n(C)cc2-c2cnn(-c3cccc(C4CC4)c3C#N)c2)cc1=O] | 2-cyclopropyl-6-[4-[1-methyl-4-(1-methyl-2-oxo-4-pyridyl)-6-oxo-3-pyridyl]pyrazol-1-yl]benzonitrile | A |
| 381 | 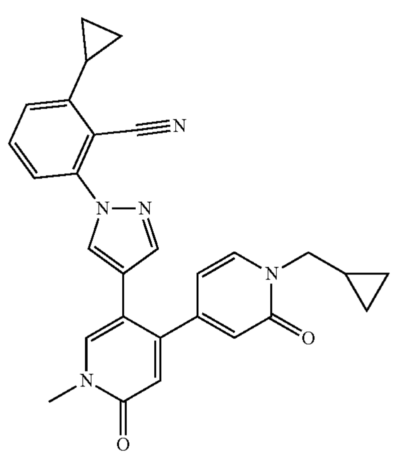 [SMILES: Cn1cc(-c2cnn(-c3cccc(C4CC4)c3C#N)c2)c(-c2ccn(CC3CC3)c(=O)c2)cc1=O] | 2-cyclopropyl-6-[4-[4-[1-(cyclopropylmethyl)-2-oxo-4-pyridyl]-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 382 | 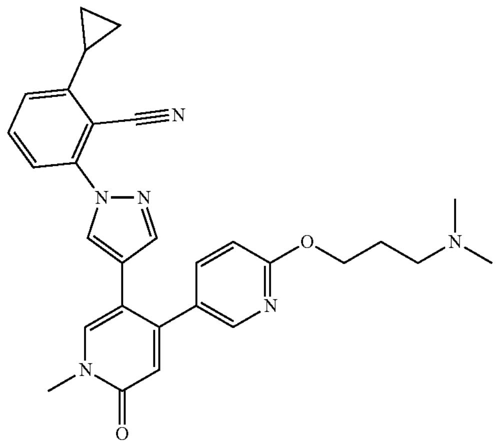 [SMILES: CN(C)CCCOc1ccc(-c2cc(=O)n(C)cc2-c2cnn(-c3cccc(C4CC4)c3C#N)c2)cn1] | 2-cyclopropyl-6-(4-(6-(3-(dimethylamino)propoxy)-1'-methyl-6'-oxo-1',6'-dihydro-[3,4'-bipyridin]-3'-yl)-1H-pyrazol-1-yl)benzonitrile | A |
| 383 | 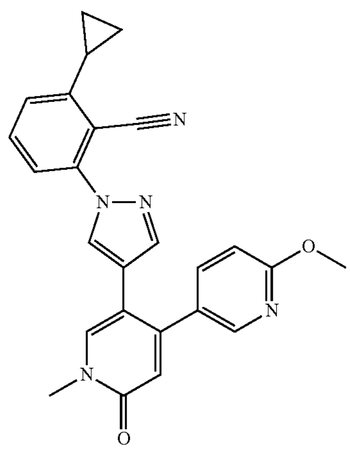 [SMILES: COc1ccc(-c2cc(=O)n(C)cc2-c2cnn(-c3cccc(C4CC4)c3C#N)c2)cn1] | 2-cyclopropyl-6-(4-(6-methoxy-1'-methyl-6'-oxo-1',6'-dihydro-[3,4'-bipyridin]-3'-yl)-1H-pyrazol-1-yl)benzonitrile | A |
| 384 | 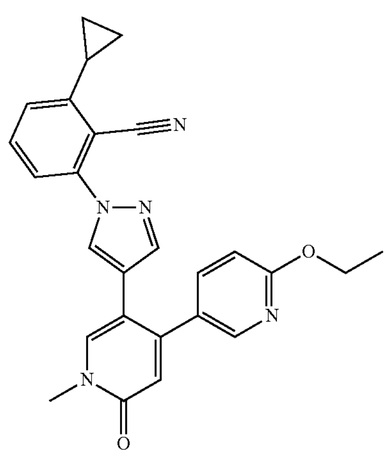 [SMILES: CCOc1ccc(-c2cc(=O)n(C)cc2-c2cnn(-c3cccc(C4CC4)c3C#N)c2)cn1] | 2-cyclopropyl-6-(4-(6-ethoxy-1'-methyl-6'-oxo-1',6'-dihydro-[3,4'-bipyridin]-3'-yl)-1H-pyrazol-1-yl)benzonitrile | A |

TABLE 29-continued

| Example | Structure | Name | CBP IC$_{50}$ (μM) |
|---|---|---|---|
| 385 | 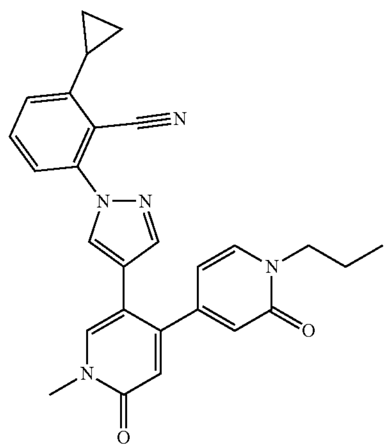 [SMILES: CCCn1ccc(-c2cc(=O)n(C)cc2-c2cnn(-c3cccc(C4CC4)c3C#N)c2)cc1=O] | 2-cyclopropyl-6-[4-[1-methyl-6-oxo-4-(2-oxo-1-propyl-4-pyridyl)-3-pyridyl]pyrazol-1-yl]benzonitrile | A |
| 386 | 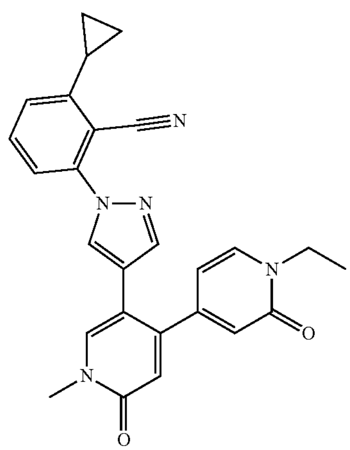 [SMILES: CCn1ccc(-c2cc(=O)n(C)cc2-c2cnn(-c3cccc(C4CC4)c3C#N)c2)cc1=O] | 2-cyclopropyl-6-[4-[4-(1-ethyl-2-oxo-4-pyridyl)-1-methyl-6-oxo-3-pyridyl]pyrazol-1-yl]benzonitrile | A |
| 387 | 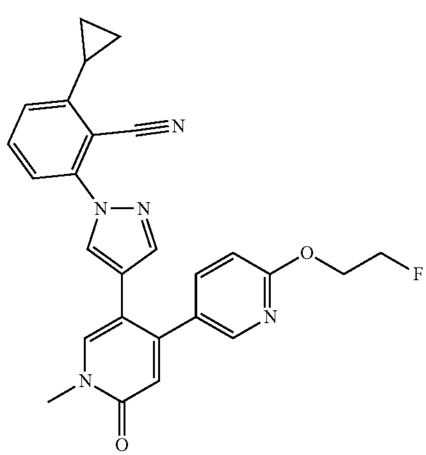 [SMILES: Cn1cc(-c2cnn(-c3cccc(C4CC4)c3C#N)c2)c(-c2ccc(OCCF)nc2)cc1=O] | 2-cyclopropyl-6-[4-[4-[6-(2-fluoroethoxy)-3-pyridyl]-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 388 | 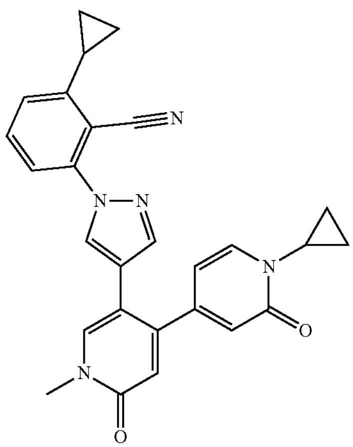 [SMILES: Cn1cc(-c2cnn(-c3cccc(C4CC4)c3C#N)c2)c(-c2ccn(C3CC3)c(=O)c2)cc1=O] | 2-cyclopropyl-6-(4-(1'-cyclopropyl-1-methyl-2',6-dioxo-1,1',2',6-tetrahydro-[4,4'-bipyridin]-3-yl)-1H-pyrazol-1-yl)benzonitrile | A |
| 389 | 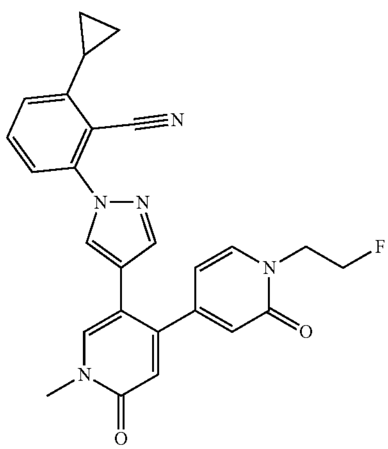 [SMILES: Cn1cc(-c2cnn(-c3cccc(C4CC4)c3C#N)c2)c(-c2ccn(CCF)c(=O)c2)cc1=O] | 2-cyclopropyl-6-[4-[4-[1-(2-fluoroethyl)-2-oxo-4-pyridyl]-1-methyl-6-oxo-3-pyridyl]pyrazol-1-yl]benzonitrile | A |
| 390 | 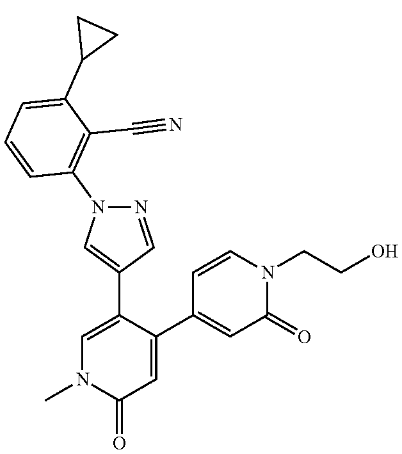 [SMILES: Cn1cc(-c2cnn(-c3cccc(C4CC4)c3C#N)c2)c(-c2ccn(CCO)c(=O)c2)cc1=O] | 2-cyclopropyl-6-[4-[4-[1-(2-hydroxyethyl)-2-oxo-4-pyridyl]-1-methyl-6-oxo-3-pyridyl]pyrazol-1-yl]benzonitrile | A |

TABLE 29-continued

| Example | Structure | Name | CBP IC$_{50}$ (μM) |
|---|---|---|---|
| 391 | 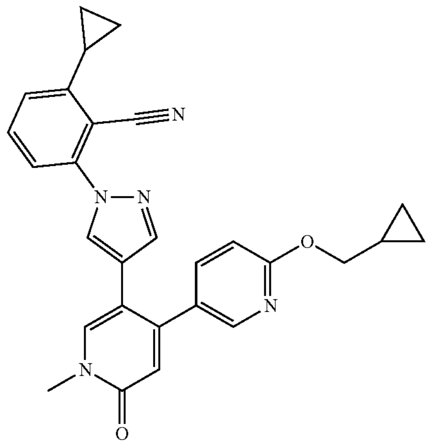 [SMILES: Cn1cc(-c2cnn(-c3cccc(C4CC4)c3C#N)c2)c(-c2ccc(OCC3CC3)nc2)cc1=O] | 2-cyclopropyl-6-(4-(6-(cyclopropylmethoxy)-1'-methyl-6'-oxo-1',6'-dihydro-[3,4'-bipyridin]-3'-yl)-1H-pyrazol-1-yl)benzonitrile | A |
| 392 | 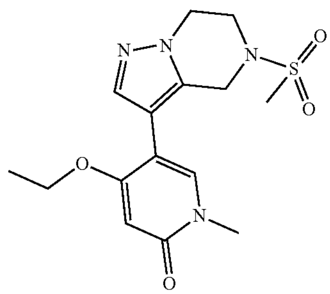 [SMILES: CCOc1cc(=O)n(C)cc1-c1cnn2c1CN(S(C)(=O)=O)CC2] | 4-Ethoxy-5-(5-methanesulfonyl-4,5,6,7-tetrahydro-pyrazolo[1,5-a]pyrazin-3-yl)-1-methyl-1H-pyridin-2-one | A |
| 393 | 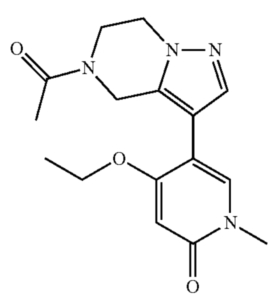 [SMILES: CCOc1cc(=O)n(C)cc1-c1cnn2c1CN(C(C)=O)CC2] | 5-(5-Acetyl-4,5,6,7-tetrahydro-pyrazolo[1,5-a]pyrazin-3-yl)-4-ethoxy-1-methyl-1H-pyridin-2-one | B |
| 394 | 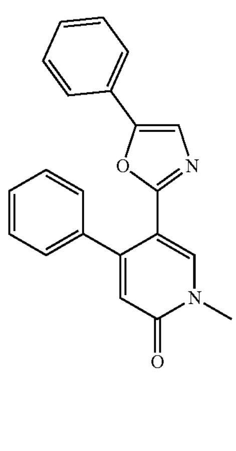 [SMILES: Cn1cc(-c2ncc(-c3ccccc3)o2)c(-c2ccccc2)cc1=O] | 1-methyl-4-phenyl-5-(5-phenyloxazol-2-yl)pyridin-2(1H)-one | B |

TABLE 29-continued

| Example | Structure | Name | CBP IC$_{50}$ (µM) |
|---|---|---|---|
| 395 | 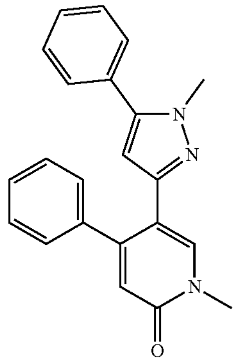 [SMILES: Cn1nc(-c2cn(C)c(=O)cc2-c2ccccc2)cc1-c1ccccc1] | 1-methyl-5-(1-methyl-5-phenyl-1H-pyrazol-3-yl)-4-phenylpyridin-2(1H)-one | A |
| 396 | 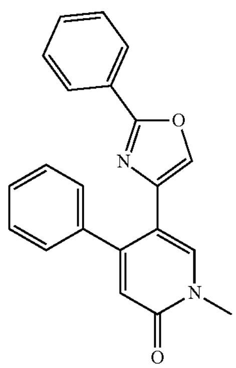 [SMILES: Cn1cc(-c2coc(-c3ccccc3)n2)c(-c2ccccc2)cc1=O] | 1-methyl-4-phenyl-5-(2-phenyloxazol-4-yl)pyridin-2(1H)-one | A |
| 397 | 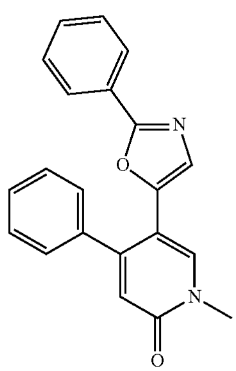 [SMILES: Cn1cc(-c2cnc(-c3ccccc3)o2)c(-c2ccccc2)cc1=O] | 1-methyl-4-phenyl-5-(2-phenyloxazol-5-yl)pyridin-2(1H)-one | B |

Example 2: In Vitro Enzyme Inhibition Assay—BRD4 Inhibition

Inhibition of BRD4 was determined as described previously. See, e.g., U.S. Pat. No. 9,034,900. The IC$_{50}$ values for inhibition of CRREBBP and BRD4 by compounds disclosed herein, as well as two known in the art, are provided in Table 30. The IC$_{50}$ data of CBP and BRD4 were designated within the following ranges: A: ≤0.5 µM; B: >0.5 µM to ≤5.0 µM; and C: >5.0 µM.

TABLE 30

| Example | Structure | Name | CRREBBP IC$_{50}$ (μM) | BRD4 BD1 IC$_{50}$ (μM) |
|---|---|---|---|---|
| 18 | 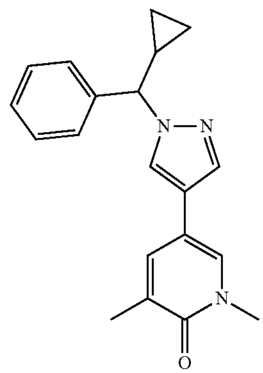 [SMILES: Cc1cc(-c2cnn(C(c3ccccc3)C3CC3)c2)cn(C)c1=O] | 5-(1-(cyclopropyl (phenyl) methyl)-1H-pyrazol-4-yl)-1,3-dimethylpyridin-2(1H)-one | A | B |
| 41 | 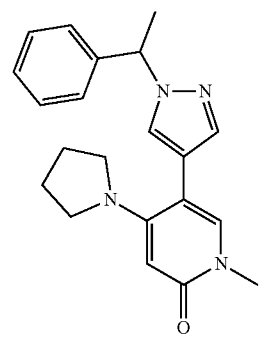 [SMILES: CC(c1ccccc1)n1cc(-c2cn(C)c(=O)cc2N2CCCC2)cn1] | 1-methyl-5-(1-(1-phenylethyl)-1H-pyrazol-4-yl)-4-(pyrrolidin-1-yl) pyridin-2(1H)-one | A | B |
| 43 | 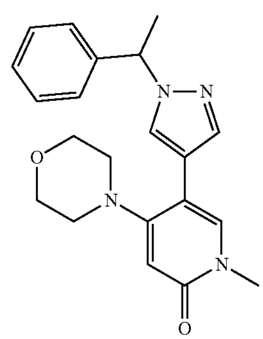 [SMILES: CC(c1ccccc1)n1cc(-c2cn(C)c(=O)cc2N2CCOCC2)cn1] | 1-methyl-4-morpholino-5-(1-(1-phenylethyl)-1H-pyrazol-4-yl)pyridin-2(1H)-one | A | B |
| 74 | 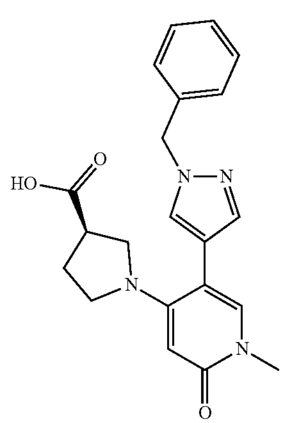 [SMILES: Cn1cc(-c2cnn(Cc3ccccc3)c2)c(N2CC[C@@H](C(=O)O)C2)cc1=O] | (R)-1-(5-(1-benzyl-1H-pyrazol-4-yl)-1-methyl-2-oxo-1,2-dihydropyridin-4-yl)pyrrolidine-3-carboxylic acid | A | C |

TABLE 30-continued

| Example | Structure | Name | CRREBBP IC$_{50}$ (μM) | BRD4 BD1 IC$_{50}$ (μM) |
|---|---|---|---|---|
| 94 | 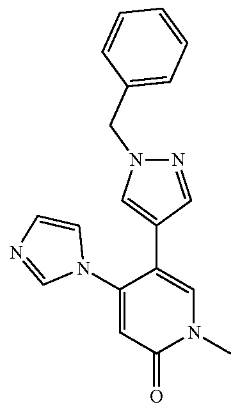 [SMILES: Cn1cc(-c2cnn(Cc3ccccc3)c2)c(-n2ccnc2)cc1=O] | 5-(1-benzyl-1H-pyrazol-4-yl)-4-(1H-imidazol-1-yl)-1-methylpyridin-2(1H)-one | A | C |
| 115 | 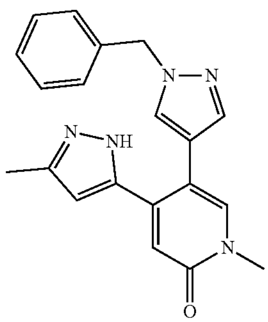 | 5-(1-benzyl-1H-pyrazol-4-yl)-1-methyl-4-(3-methyl-1H-pyrazol-5-yl)pyridin-2(1H)-one | A | C |
| 121 | 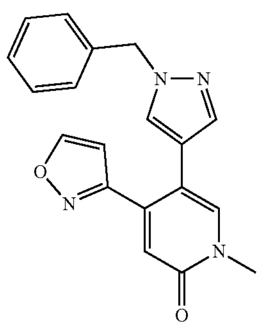 [SMILES: Cn1cc(-c2cnn(Cc3ccccc3)c2)c(-c2ccon2)cc1=O] | 5-(1-benzyl-1H-pyrazol-4-yl)-4-(isoxazol-3-yl)-1-methylpyridin-2(1H)-one | A | C |
| 129 | 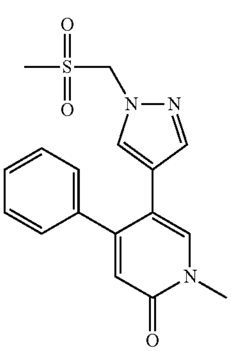 [SMILES: Cn1cc(-c2cnn(CS(C)(=O)=O)c2)c(-c2ccccc2)cc1=O] | 1-methyl-5-(1-((methylsulfonyl)methyl)-1H-pyrazol-4-yl)-4-phenylpyridin-2(1H)-one | A | C |

TABLE 30-continued

| Example | Structure | Name | CRREBBP IC$_{50}$ (μM) | BRD4 BD1 IC$_{50}$ (μM) |
|---------|-----------|------|------------------------|--------------------------|
| 154 | 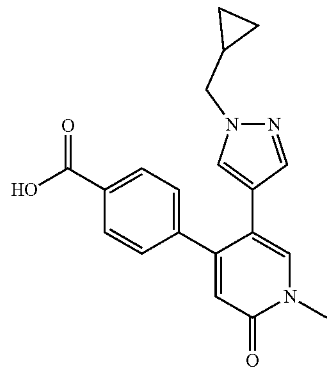 [SMILES: Cn1cc(-c2cnn(CC3CC3)c2)c(-c2ccc(C(=O)O)cc2)cc1=O] | 4-[5-(1-Cyclopropylmethyl-1H-pyrazol-4-yl)-1-methyl-2-oxo-1,2-dihydro-pyridin-4-yl]-benzoic acid | A | C |
| 223 | 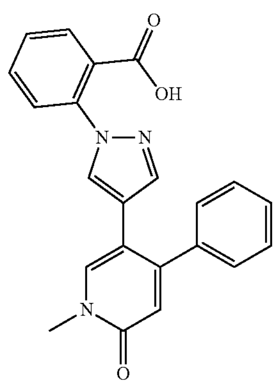 [SMILES: Cn1cc(-c2cnn(-c3ccccc3C(=O)O)c2)c(-c2ccccc2)cc1=O] | 2-[4-(1-Methyl-6-oxo-4-phenyl-1,6-dihydro-pyridin-3-yl)-pyrazol-1-yl]-benzoic acid | A | C |
| 286 | 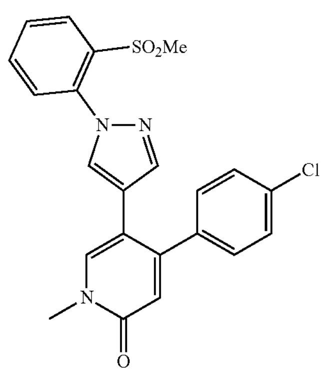 [SMILES: Cn1cc(-c2cnn(-c3ccccc3S(C)(=O)=O)c2)c(-c2ccc(Cl)cc2)cc1=O] | 4-(4-Chloro-phenyl)-5-[1-(2-methanesulfonyl-phenyl)-1H-pyrazol-4-yl]-1-methyl-1H-pyridin-2-one | A | C |
| 323 | 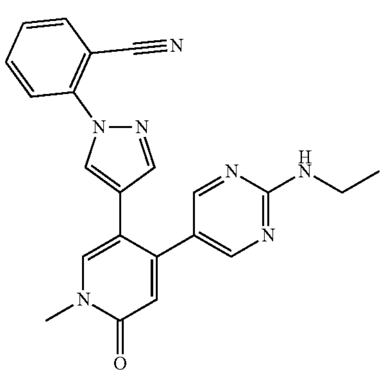 [SMILES: CCNc1ncc(-c2cc(=O)n(C)cc2-c2cnn(-c3ccccc3C#N)c2)cn1] | 2-(4-(4-(2-(ethylamino)pyrimidin-5-yl)-1-methyl-6-oxo-1,6-dihydropyridin-3-yl)-1H-pyrazol-1-yl)benzonitrile | A | B |

TABLE 30-continued

| Example | Structure | Name | CRREBBP IC$_{50}$ (µM) | BRD4 BD1 IC$_{50}$ (µM) |
|---|---|---|---|---|
| | | N-(5-(2,4-difluorophenoxy)-4-(1,5-dimethyl-6-oxo-1,6-dihydropyridin-3-yl)pyrimidin-2-yl) methanesulfonamide | C | A |
| JQ-1 | 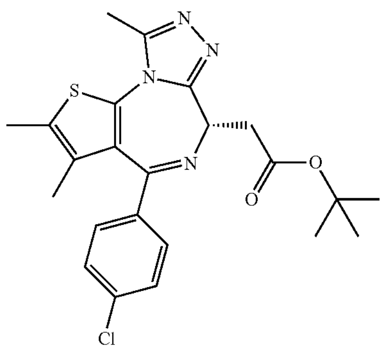 [SMILES: Cc1sc2c(c1C)C(c1ccc(Cl)cc1)=N[C@@H](CC(=O)OC(C)(C)C)c1nnc(C)n1-2] | tert-butyl (S)-2-(4-(4-chloro-phenyl)-2,3,9-trimethyl-6H-thieno[3,2-f][1,2,4]triazolo[4,3-a][1,4]diazepin-6-yl)acetate | C | A |

Example 3: In Vitro Cell-Based Assay—Th17 Differentiation—IL-17A Secretion

100K CD4+ cells per well are plated in a 96-well plate in 1×Th17 differentiation cocktail (0.05 µg/ml IL6, 0.02 µg/ml IL23, 10 µg/ml anti-IFNγ, 10 µg/ml anti-IL4, 0.01 µg/ml IL1β, 0.003 µg/ml TGFβ and 1 bead/cell anti-CD3/CD28) for a total volume of 100 µL/well. The plates are cultured for 96 hr at 37° C. in 5% $CO_2$. Differentiated Th17 cells are pooled, washed and suspended in complete media. 100K Th17 cells per well are plated in a 96-well plate in the presence of IL-23 at a final concentration of 25 ng/mL. Appropriate concentrations of CBP inhibitors are added to the cells for a total volume of 100 µL/well (DMSO and media controls are included). Plates are cultured for 96 hr at 37° C. in 5% $CO_2$. IL-17A levels in cell supernatants are determined using the manufacturer protocol (Meso Scale Discovery #K151ATB-2). Secreted IL-17A levels are interpolated from a standard curve and plotted by % DMSO control.

Example 4: In Vitro Cell-Based Assay—Treg Differentiation and Immune Checkpoints 100K naïve CD4+ cells per well are plated in a 96-well plate and appropriate concentrations of CBP inhibitors are added to the cells. DMSO and media controls are included. Cells are incubated for 1 hr at 37° C. in 5% $CO_2$ and Treg differentiation cocktail (final concentrations: 0.010 µg/ml TGFβ, 10 U/ml IL-2 and 1:1 bead:cell ratio of anti-CD3/CD28) was added for a total volume of 100 µL/well. Plates are cultured for 96 hr at 37° C. in 5% $CO_2$. Tregs are stained for CD4 (562424; BD Biosciences), CTLA4 (563931; BD Biosciences), CD25 (562660; BD Biosciences), LAG-3 (11-2239-42; eBioscience), PD-1 (17-9969-42; eBioscience), Tim3 (eBioscience; #25-3109-42), and FOXP3 (BD Biosciences; #560046). For FOXP3 and CTLA4 intracellular staining cells are fixed and permeabilized using BD Cytofix/Cytoperm solution (BD Biosciences; #554722). Markers are quantified on iQue Screener PLUS flow cytometry analyzer (IntelliCyt) and data analyzed using FCS Express 5 Software (DeNovo Software).

Example III. Preparation of Pharmaceutical Dosage Forms

Example 1: Oral Tablet

A tablet is prepared by mixing 48% by weight of a compound of Formula I, or a pharmaceutically acceptable salt thereof, 45% by weight of microcrystalline cellulose, 5% by weight of low-substituted hydroxypropyl cellulose, and 2% by weight of magnesium stearate. Tablets are prepared by direct compression. The total weight of the compressed tablets is maintained at 250-500 mg.

We claim:
1. A compound having the structure of Formula I:

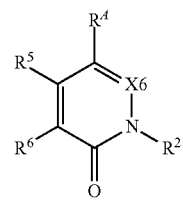

Formula I wherein a compound of Formula I includes a pharmaceutically acceptable salt thereof, and wherein X6 is CR⁷, wherein R⁷ is hydrogen, or alkyl;

R² is CH₃;

R⁵ is halogen, —N(R²²)₂, —NH(R²²), —OW, —SW, or optionally substituted alkyl, aryl, aralkyl, cycloalkyl, or cycloalkylalkyl, wherein W is optionally substituted alkyl, aryl, aralkyl, cycloalkyl, heterocyclyl, or heteroarylalkyl;

R⁶ is methyl;

R⁴ is

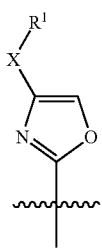

wherein X is a bond, CH₂, CHR, or CRR'; wherein

R and R' are independently halogen, halide, alkyl, cycloalkyl, cycloalkylalkyl, aryl, aralkyl, heterocyclyl, heterocyclylalkyl, heteroaryl, heteroarylalkyl, —SO₂R²¹, or —N(R²²)SO₂R²¹; wherein each R²¹ is independently selected from alkyl, cycloalkyl, cycloalkylalkyl, aryl, aralkyl, heterocyclyl, heterocyclylalkyl, heteroaryl, or heteroarylalkyl;

each R²² is independently selected from hydrogen, alkyl, cycloalkyl, cycloalkylalkyl, aryl, aralkyl, heterocyclyl, heterocyclylalkyl, heteroaryl, or heteroarylalkyl; and R¹ is hydrogen or optionally substituted alkyl, aryl, aralkyl, alkoxy, cycloalkyl, cycloalkylalkyl, heterocyclyl, heterocyclylalkyl, heteroaryl, or heteroarylalkyl.

2. A compound having the structure of Formula I:

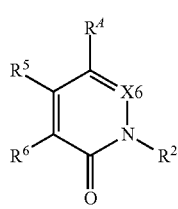

Formula I wherein a compound of Formula I includes a pharmaceutically acceptable salt thereof, and wherein X6 is CR⁷, wherein R⁷ is hydrogen, or alkyl;

R² is CH₃;

R⁵ is optionally substituted alkyl halogen

R⁶ is hydrogen, halogen, alkyl, or —OR²²;

R⁴ is

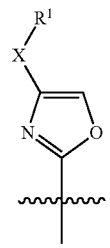

wherein X is a bond, CH₂, CHR, or CRR'; wherein

R and R' are independently halogen, halide, alkyl, cycloalkyl, cycloalkylalkyl, aryl, aralkyl, heterocyclyl, heterocyclylalkyl, heteroaryl, heteroarylalkyl, —SO₂R²¹, or —N(R²²)SO₂R²¹; wherein each R²¹ is independently selected from alkyl, cycloalkyl, cycloalkylalkyl, aryl, aralkyl, heterocyclyl, heterocyclylalkyl, heteroaryl, or heteroarylalkyl;

each R²² is independently selected from hydrogen, alkyl, cycloalkyl, cycloalkylalkyl, aryl, aralkyl, heterocyclyl, heterocyclylalkyl, heteroaryl, or heteroarylalkyl; and R¹ is hydrogen or optionally substituted alkyl, aryl, aralkyl, alkoxy, cycloalkyl, cycloalkylalkyl, heterocyclyl, heterocyclylalkyl, heteroaryl, or heteroarylalkyl.

3. The compound of claim 2, wherein the alkyl is methyl.

4. The compound of claim 1, wherein R⁵ is substituted alkyl.

5. The compound of claim 4, wherein the substituent is methylacetate, methylsulfonyl, propylacetamide, sulfonyl, methylacetamide, or dimethylacetamide.

6. The compound of claim 1, wherein R⁵ is optionally substituted cycloalkyl.

7. The compound of claim 6, wherein the optionally substituted cycloalkyl is cyclobutyl or cycloproplyl.

8. The compound of claim 1, wherein R⁵ is —OW.

9. The compound of claim 8, wherein W is optionally substituted alkyl.

10. The compound of claim 8, wherein W is ethyl.

11. The compound of claim 9, wherein the substituent is carboxylic acid, cyano, hydroxy, or pyridinyl.

12. The compound of claim 1, wherein R⁵ is —SW, and wherein W is optionally substituted alkyl, phenyl, carboxylic acid, alkylacetamide.

13. The compound of claim 1, wherein X is CHR and wherein R is C₁-C₅ alkyl.

14. The compound of claim 13, wherein R is selected from ethyl, methyl, or cyclopropyl.

15. The compound of claim 1, wherein R is —SO₂Me.

16. The compound of claim 1, wherein R¹ is optionally substituted aryl.

17. The compound of claim 1, wherein R¹ is substituted benzyl or phenyl.

18. The compound of claim 17, wherein R¹ is benzyl or phenyl substituted with halo.

19. The compound of claim 18, wherein the halo is bromo, chloro, fluoro, or difluoro.

20. The compound of claim 17, wherein R¹ is benzyl or phenyl substituted with halolkyl.

21. The compound of claim 20, wherein the haloalkyl is difluoromethyl.

22. The compound of claim 17, wherein R¹ is substituted with C₁-C₅ alkyl.

23. The compound of claim 22, wherein the $C_1$-$C_5$ alkyl is ethyl, methyl, propyl, isopropyl, or cyclopropyl.

24. The compound of claim 17, wherein $R^1$ is benzyl or phenyl substituted with cyanyl.

25. The compound of claim 17, wherein $R^1$ is benzyl or phenyl substituted with alkoxy.

26. The compound of claim 25, wherein the alkoxy is methoxy.

27. The compound of claim 17, wherein $R^1$ is benzyl or phenyl substituted with carboxylate.

28. The compound of claim 17, wherein $R^1$ is benzyl or phenyl substituted with optionally substituted heteroaryl.

29. The compound of claim 28, wherein the heteroaryl is pyrazolyl or methylpyrazolyl.

30. The compound of claim 1, wherein $R^1$ is unsubstituted benzyl or phenyl.

31. The compound of claim 1, wherein $R^1$ is optionally substituted cyclyl.

32. The compound of claim 31, wherein the optionally substituted cyclyl is optionally substituted cyclohexyl or cyclopropyl.

33. The compound of claim 1, wherein $R^1$ is substituted cyclyl and the substitution is amino, cyano, dimethylamino, difluoro, hydroxy, methoxy, or methyl.

34. The compound of claim 1, wherein $R^1$ is optionally substituted heterocyclyl.

35. The compound of claim 34, wherein the optionally substituted heterocylcyl is optionally substituted morpholinyl or tetrahydropyranyl.

36. The compound of claim 1, wherein $R^1$ is optionally substituted heteroaryl.

37. The compound of claim 36, wherein the optionally substituted heteroaryl is optionally substituted pyridinyl.

38. The compound of claim 1, wherein $R^1$ is optionally substituted heteroarylalkyl.

39. The compound of claim 38, wherein the optionally substituted heteroarylalkly is pyridinylethyl or piperidinyl.

40. The compound of claim 39, wherein the substitutent is methylsulfonyl or sulfonyl.

41. The compound of claim 1, wherein $R^1$ is optionally substituted $C_1$-$C_5$ alkyl.

42. The compound of claim 41, wherein the optionally substituted $C_1$-$C_5$ alkyl is isobutyl, ethyl, methyl, propyl, cyclopropyl, cyclopropylmethyl, or isopropyl.

43. The compound of claim 42, wherein optionally substituted $C_1$-$C_5$ alkyl is substituted with methylacetate, methylsulfonyl, propylacetamide, sulfonyl, methylacetamide, or dimethylacetamide.

44. The compound of claim 1, wherein the compound has a lower $IC_{50}$ against CBP activity as compared with its $IC_{50}$ against BRD4 activity.

* * * * *